US012674155B2

(12) United States Patent (10) Patent No.: US 12,674,155 B2
Hudalla et al. (45) Date of Patent: Jul. 7, 2026

(54) TARGETED CHONDROITINASE ABC FUSION PROTEINS AND COMPLEXES THEREOF

(71) Applicant: University of Florida Research Foundation, Incorporated, Gainesville, FL (US)

(72) Inventors: Gregory Allan Hudalla, Gainesville, FL (US); Benjamin G. Keselowsky, Gainesville, FL (US); Dillon T. Seroski, Gainesville, FL (US); Shaheen A. Farhadi, Gainesville, FL (US); Christine E. Schmidt, Gainesville, FL (US); Nikunj Kumar Agrawal, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 911 days.

(21) Appl. No.: 17/288,435

(22) PCT Filed: Oct. 25, 2019

(86) PCT No.: PCT/US2019/058230
§ 371 (c)(1),
(2) Date: Apr. 23, 2021

(87) PCT Pub. No.: WO2020/087051
PCT Pub. Date: Apr. 30, 2020

(65) Prior Publication Data
US 2022/0106580 A1 Apr. 7, 2022

Related U.S. Application Data

(60) Provisional application No. 62/751,146, filed on Oct. 26, 2018.

(51) Int. Cl.
*C12N 9/88* (2006.01)
*C12N 9/16* (2006.01)

(52) U.S. Cl.
CPC .................. *C12N 9/88* (2013.01); *C12N 9/16* (2013.01); *C12Y 304/24035* (2013.01); *C12Y 402/02004* (2013.01); *C12Y 402/0202* (2013.01); *C12Y 402/02021* (2013.01)

(58) Field of Classification Search
CPC ..... C12N 9/88; C12N 9/16; C12Y 304/24035
See application file for complete search history.

(56) References Cited

U.S. PATENT DOCUMENTS

| | | | |
|---|---|---|---|
| 11,407,797 B2 | 8/2022 | Hudalla et al. | |
| 11,603,394 B2 * | 3/2023 | Hudalla | C12N 9/0069 |
| 2005/0074865 A1 | 4/2005 | Afeyan et al. | |

| | | | |
|---|---|---|---|
| 2005/0220792 A1 | 10/2005 | Agou et al. | |
| 2005/0260222 A1 | 11/2005 | Gupta et al. | |
| 2007/0098701 A1 | 5/2007 | Okano et al. | |
| 2008/0234177 A1 | 9/2008 | Bremer et al. | |
| 2011/0294983 A1 | 12/2011 | Desmet et al. | |
| 2011/0318372 A1 | 12/2011 | Andersen et al. | |
| 2014/0187487 A1 | 7/2014 | Shoichet et al. | |
| 2017/0335311 A1 * | 11/2017 | Gruskin | C12N 9/96 |
| 2018/0073007 A9 | 3/2018 | Gruskin et al. | |
| 2019/0218264 A1 | 7/2019 | Hudalla et al. | |
| 2020/0262882 A1 | 8/2020 | Hudalla et al. | |
| 2022/0098258 A1 | 3/2022 | Hudalla et al. | |

FOREIGN PATENT DOCUMENTS

| | | |
|---|---|---|
| EP | 1748050 | 1/2007 |
| JP | 2005-537032 A | 12/2005 |
| JP | 2009-515520 A | 4/2009 |
| JP | 2011-520783 A | 7/2011 |
| JP | 2012-514616 A | 6/2012 |
| JP | 2015-528514 A | 9/2015 |
| JP | 2016-040260 A | 3/2016 |
| WO | 1999/012041 A1 | 3/1999 |
| WO | 2003/090780 A1 | 11/2003 |
| WO | 2004/019878 A2 | 3/2004 |
| WO | 2007/058776 A2 | 5/2007 |
| WO | 2009/143843 A1 | 12/2009 |
| WO | 2010/078966 A1 | 7/2010 |
| WO | 2011/034605 A2 | 3/2011 |
| WO | 2014/089267 A1 | 6/2014 |
| WO | 2016/127100 A1 | 8/2016 |

(Continued)

OTHER PUBLICATIONS

Friedberg, Brief. Bioinformatics (2006) 7: 225-242 (Year: 2006).*
Thorton et al. Nature structural biology, structural genomics supplement, Nov. 2000, pp. 991-994 (Year: 2000).*
Chen et al. International Journal of Biological Macromolecules 72 (2015) 6-10 (Year: 2015).*
Pakulska et al. Journal of Controlled Release 171 (2013) 11-16 (Year: 2013).*
Barnes et al. Investigative Ophthalmology & Visual Science Jun. 2013, vol. 54, 1090 (Year: 2013).*
Lee et al., Heme-binding-mediated negative regulation of the tryptophan metabolic enzyme indoleamine 2,3-dioxygenase 1 (IDO1) by IDO2. Exp Mol Med. Nov. 14, 2014;46(11):e121. doi: 10.1038/emm.2014.69.

(Continued)

*Primary Examiner* — Louise W Humphrey
*Assistant Examiner* — Jessica Faye Edwards
(74) *Attorney, Agent, or Firm* — Wolf, Greenfield & Sacks, P.C.

(57) ABSTRACT

Described herein are targeted ChABC fusion proteins, complexes thereof, and uses thereof. The targeted ChABC fusion proteins can include a ChABC polypeptide that can be linked to a Gal-3 polypeptide. Monomer targeted ChABC fusion proteins can form homogeneous or heterogeneous complexes. The targeted ChABC fusion proteins and complexes thereof can be formulated as pharmaceutical formulations. The targeted ChABC fusion proteins, complexes thereof, and formulations thereof can be administered to a subject in need thereof.

12 Claims, 188 Drawing Sheets

Specification includes a Sequence Listing.

(56)                    References Cited

FOREIGN PATENT DOCUMENTS

WO          2016/172319  A1      10/2016
WO          WO-2018067660 A1 *   4/2018     ................ A61P 1/02

OTHER PUBLICATIONS

Extended European Search Report for Application No. EP 17859087. 3, mailed Apr. 8, 2020.

International Search Report and Written Opinion for Application No. PCT/US2017/055076, mailed Feb. 21, 2018.

International Preliminary Report on Patentability for Application No. PCT/US2017/055076, mailed Apr. 18, 2019.

International Search Report and Written Opinion mailed Jan. 4, 2019 for Application No. PCT/US2018/055213.

International Preliminary Report on Patentability mailed Apr. 23, 2020 for Application No. PCT/US2018/055213.

Invitation to Pay Additional Fees for Application No. PCT/US2020/ 020532, mailed May 21, 2020.

International Search Report and Written Opinion for Application No. PCT/US2020/020532, mailed Jul. 24, 2020.

International Preliminary Report on Patentability for Application No. PCT/US2020/020532, mailed Sep. 10, 2021.

[No Author Listed], Plasmid Files. SnapGene. Retrieved from www.snapgene.com/resources/plasmid-files/?set=pgex_vectors_(ge_ healthcare)&plasmid=pGEX-4T-1. Accessed on Nov. 4, 2021. 5 pages.

Brooks et al., Immunomodulatory Factors Galectin-9 and Interferon-Gamma Synergize to Induce Expression of Rate-Limiting Enzymes of the Kynurenine Pathway in the Mouse Hippocampus. Front Immunol. Oct. 17, 2016;7:422. doi: 10.3389/fimmu.2016.00422.

Fettis et al., Engineering Reactive Oxygen Species-Resistant Galectin-1 Dimers with Enhanced Lectin Activity. Bioconjug Chem. Jul. 18, 2018;29(7):2489-2496. doi: 10.1021/acs.bioconjchem.8b00425. Epub Jul. 3, 2018.

Iken et al., Indoleamine 2,3-dioxygenase and metabolites protect murine lung allografts and impair the calcium mobilization of T cells. Am J Respir Cell Mol Biol. Oct. 2012;47(4):405-16. doi: 10.1165/rcmb.2011-0438OC. Epub Apr. 19, 2012.

Inohara et al., Cytoplasmic and serum galectin-3 in diagnosis of thyroid malignancies. Biochem Biophys Res Commun. Nov. 21, 2008;376(3):605-10. doi: 10.1016/j.bbrc.2008.09.041. Epub Sep. 20, 2008.

Krylov et al., Leucine Zipper. Encyclopedia of Life Sciences. 2001. 7 pages.

Li et al., Rate enhancement of an interfacial biochemical reaction through localization of substrate and enzyme by an adaptor domain. J Phys Chem B. Nov. 25, 2010;114(46):15113-8. doi: 10.1021/ jp102820e. Epub Nov. 3, 2010.

Litowski et al., Designing heterodimeric two-stranded alpha-helical coiled-coils. J Biol Chem. Oct. 4, 2002;277(40):37272-9.

Littlejohn et al., Expression and purification of recombinant human indoleamine 2, 3-dioxygenase. Protein Expr Purif. Jun. 2000;19(1):22-9. doi: 10.1006/prep.2000.1214.

Liu et al., Expression of immune checkpoint molecules in endo-metrial carcinoma. Exp. Ther Med. 2015;10(5):1947-52.

Liu et al., Galectins as modulators of tumor progression. Nat. Rev. Cancer. 2005;5(1):29-41.

Nishi et al., Functional and structural bases of a cysteine-less mutant as a long-lasting substitute for galectin-1. Glycobiology. Dec. 2008;18(12):1065-73. doi: 10.1093/glycob/cwn089. Epub Sep. 16, 2008.

Pechar et al., Coiled coil peptides and polymer-peptide conjugates: synthesis, self-assembly, characterization and potential in drug delivery systems. Biomacromolecules. Jul. 14, 2014;15(7):2590-9. doi: 10.1021/bm500436p. Epub Jun. 3, 2014.

Weidle, et al. Fully Human Targeted Cytotoxic Fusion Proteins: New Anticancer Agents on the Horizon. Cancer Genomics Proteomics. 2012;9:119-33.

Weisel et al., Fibrin Formation, Structure and Properties. Subcell Biochem. 2017;82:405-456. doi: 10.1007/978-3-319-49674-0_13. Author Manuscript, 52 pages.

Wheeldon et al., Substrate channeling as an approach to cascade reactions. Nat Chem. Apr. 8, 2016:4;299-309.

International Search Report and Written Opinion for Application No. PCT/US2019/058230, mailed Feb. 5, 2020.

International Preliminary Report on Patentability for Application No. PCT/US2019/058230, mailed May 6, 2021.

Dang, Molecular Approaches to Protein Dimerization: Opportunities for Supramolecular Chemistry. Front Chem. Feb. 8, 2022;10:829312. doi: 10.3389/fchem.2022.829312.

* cited by examiner

Enzyme-G3 fusion protein

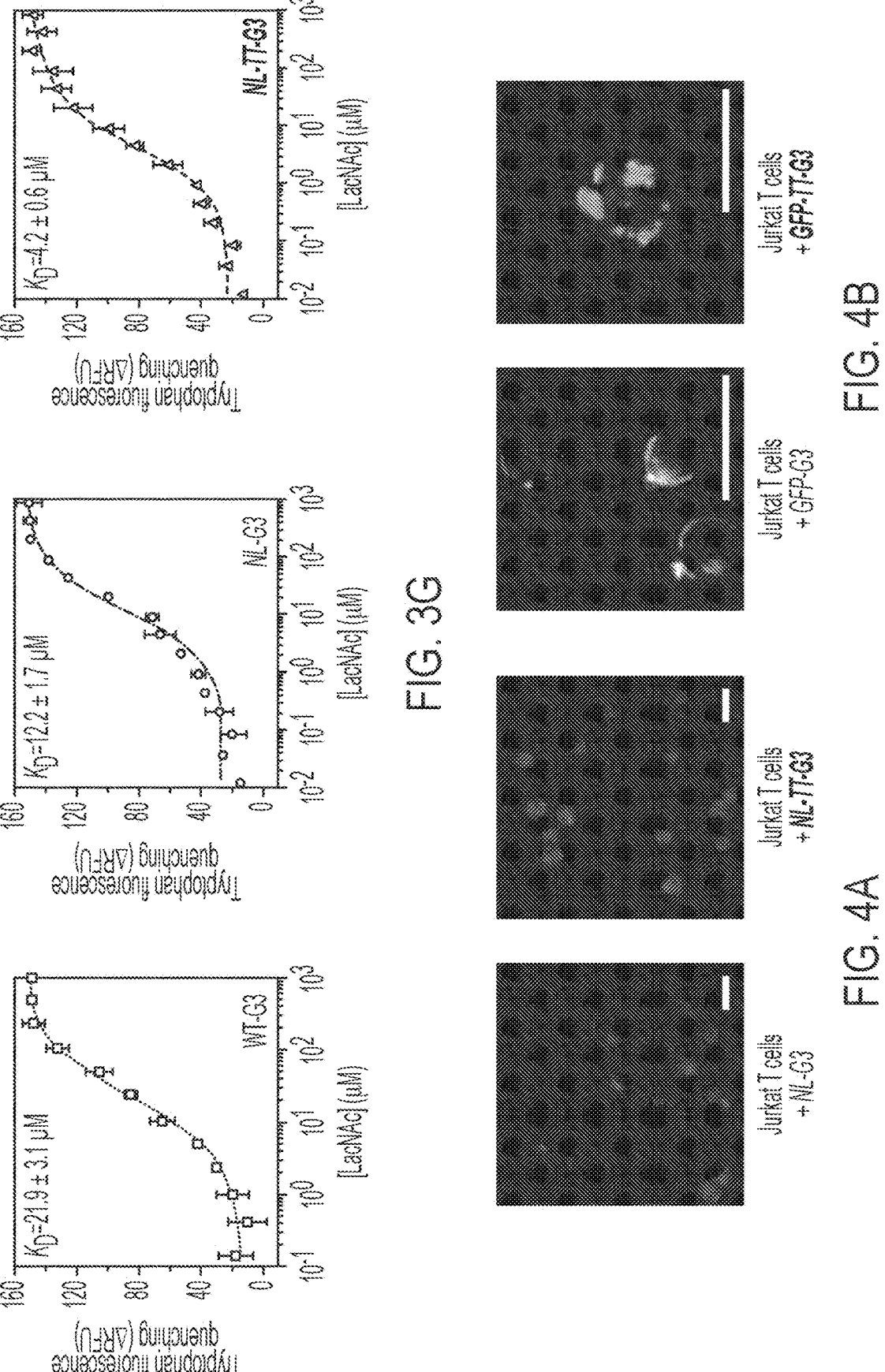

| G3 fusion proteins | Theoretical molecular weights of G3 fusions | |
|---|---|---|
|  | Theoretical denatured molecular weight (kDa) | Theoretical native molecular weight (kDa) |
| NL-G3 | 47.4 | 47.4 |
| GFP-G3 | 54.8 | 54.8 |
| ChABC-G3 | 140.8 | 140.8 |
| NL-TT-G3 | 52.7 | 158.1 |
| GFP-TT-G3 | 60.3 | 180.9 |
| ChABC-TT-G3 | 146.2 | 438.6 |

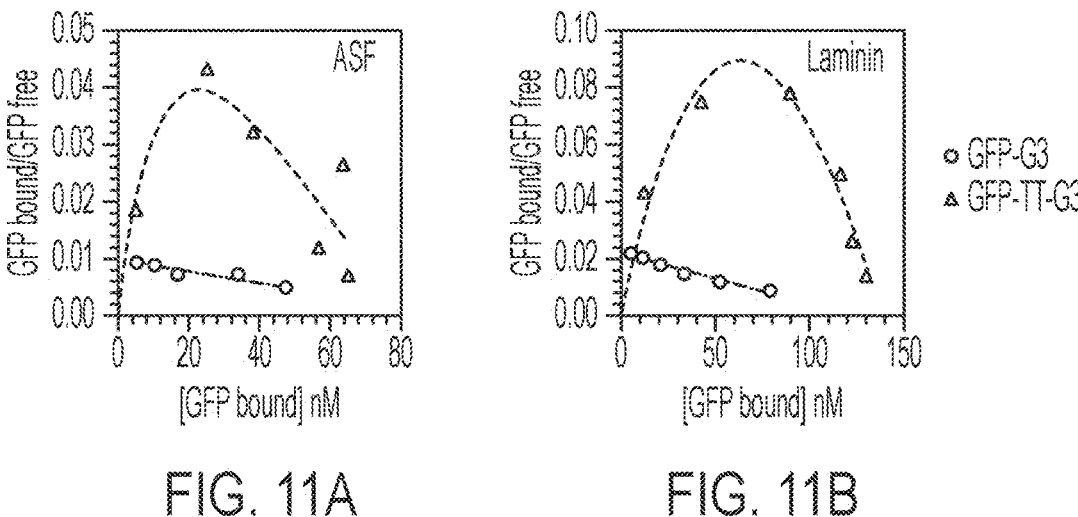
FIG. 11A                    FIG. 11B
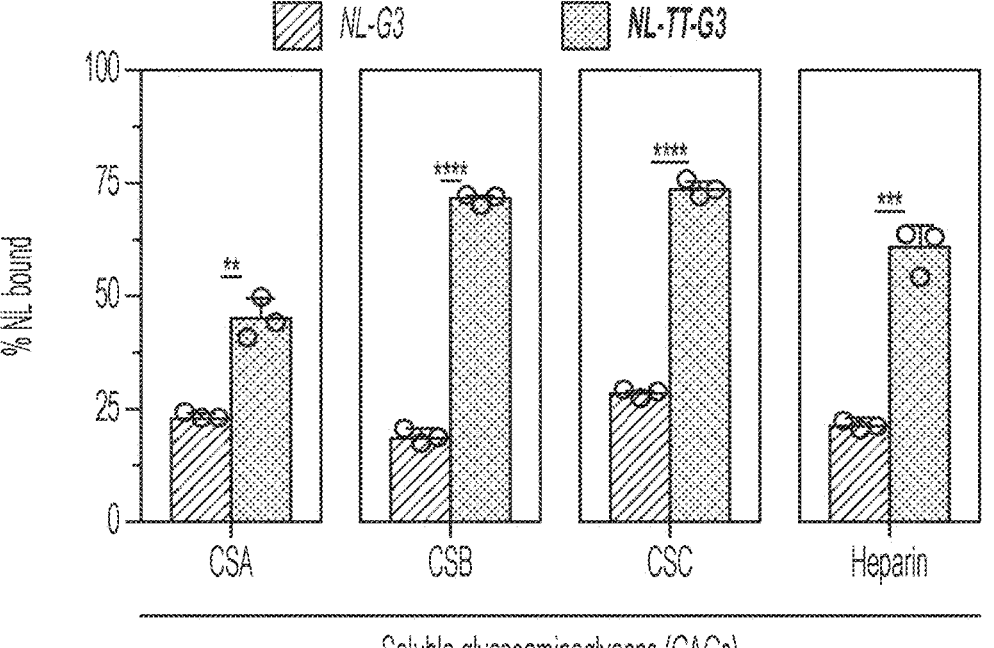
FIG. 12

10 μM WT-G3 +ASF

10 μM NL-TT-G3 +ASF

10 μM NL-G3 +ASF 2.5 μM WT-G3 +ASF 2.5 μM NL-TT-G3 +ASF 2.5 μM NL-G3 +ASF

7 μM ASF

10 μM WT-G3

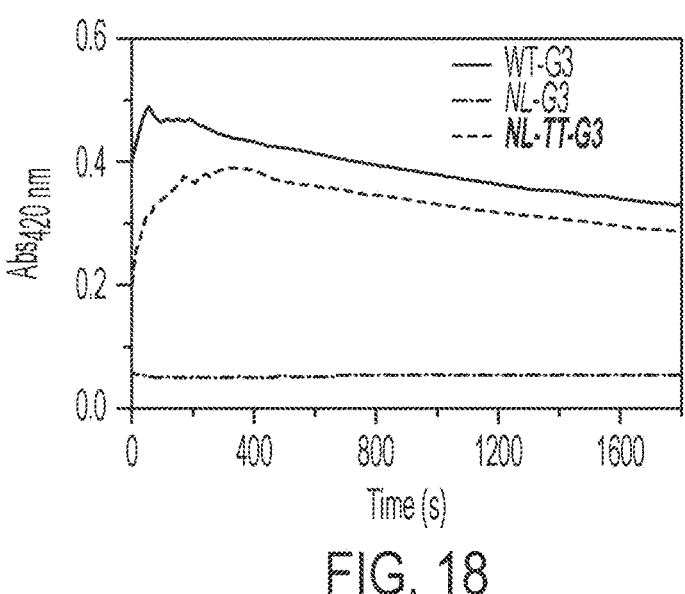
FIG. 18
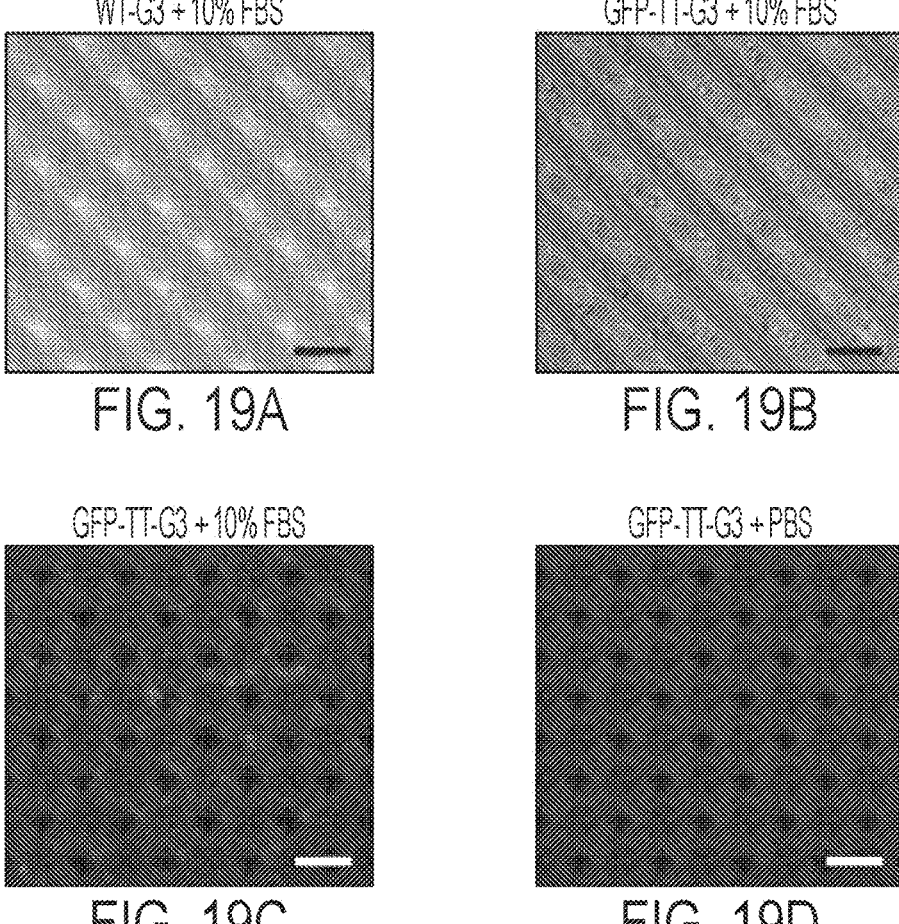
FIG. 19A
FIG. 19B
FIG. 19C
FIG. 19D

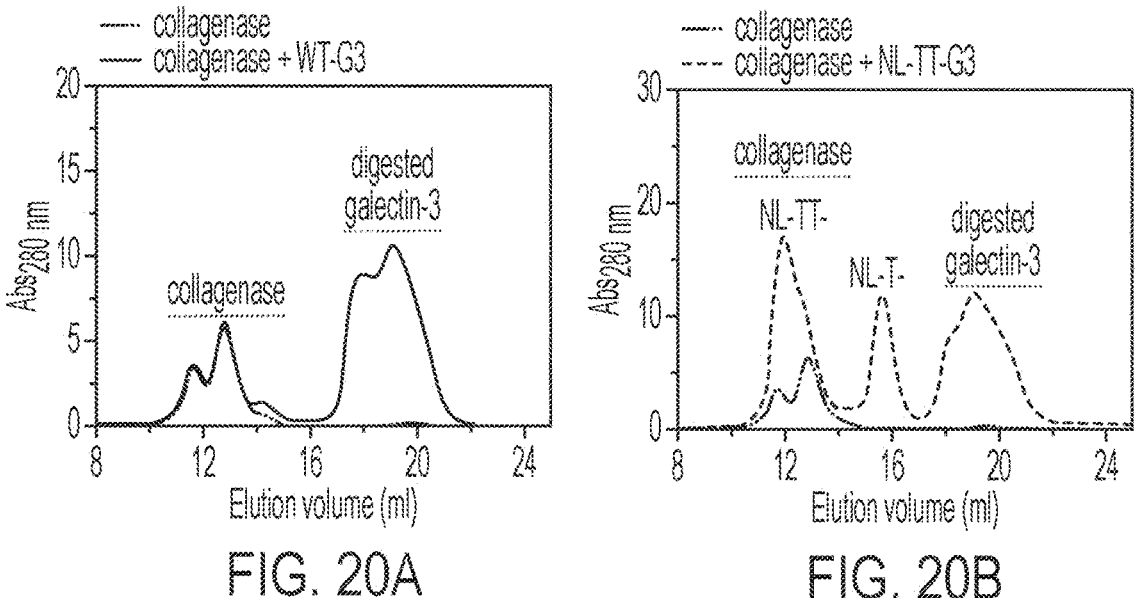
FIG. 20A
FIG. 20B
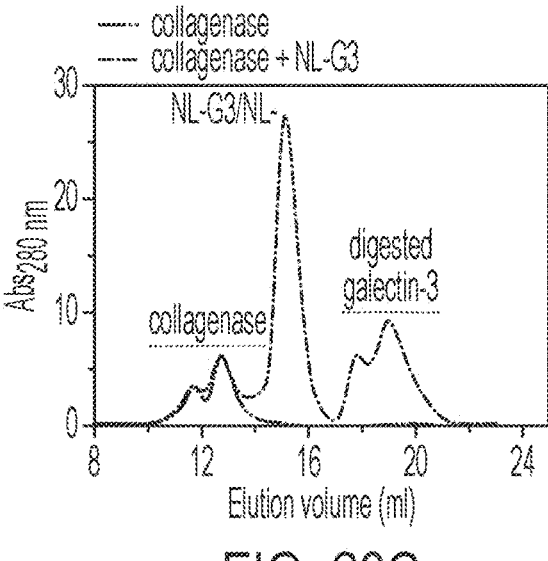
FIG. 20C

NL-TT-G3          NL-G3          WT-NL

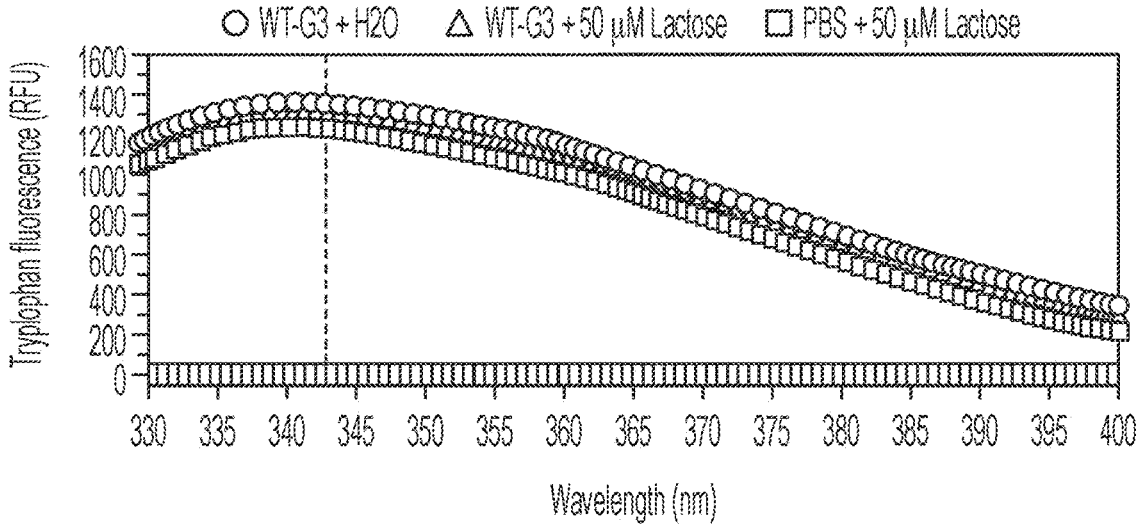
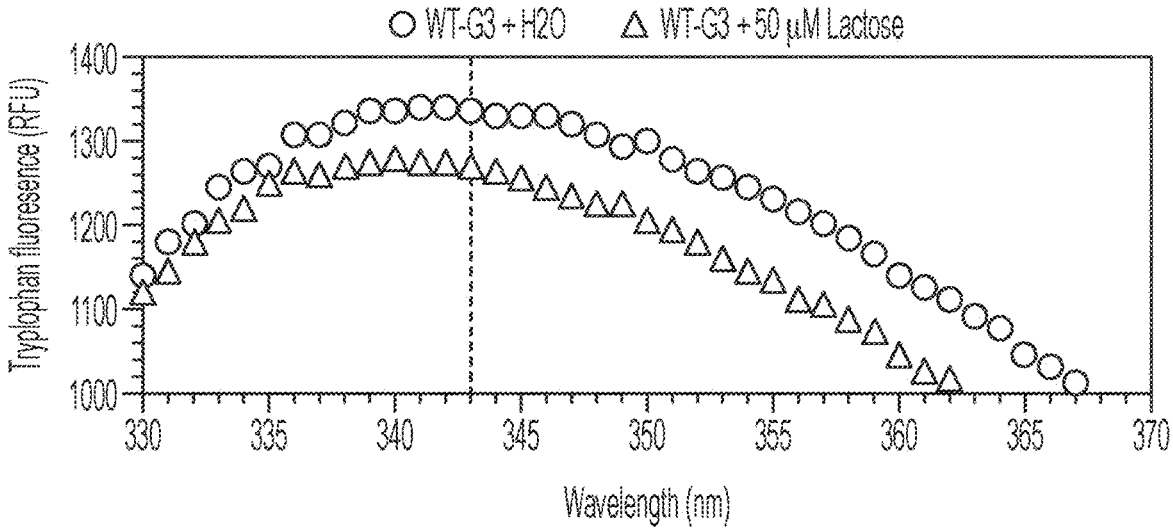
FIG. 27A

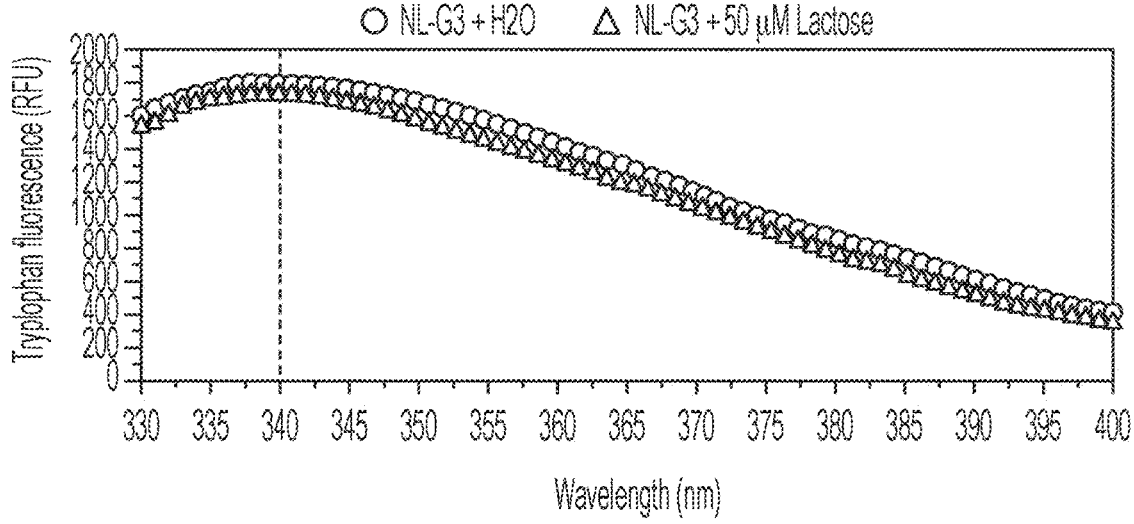
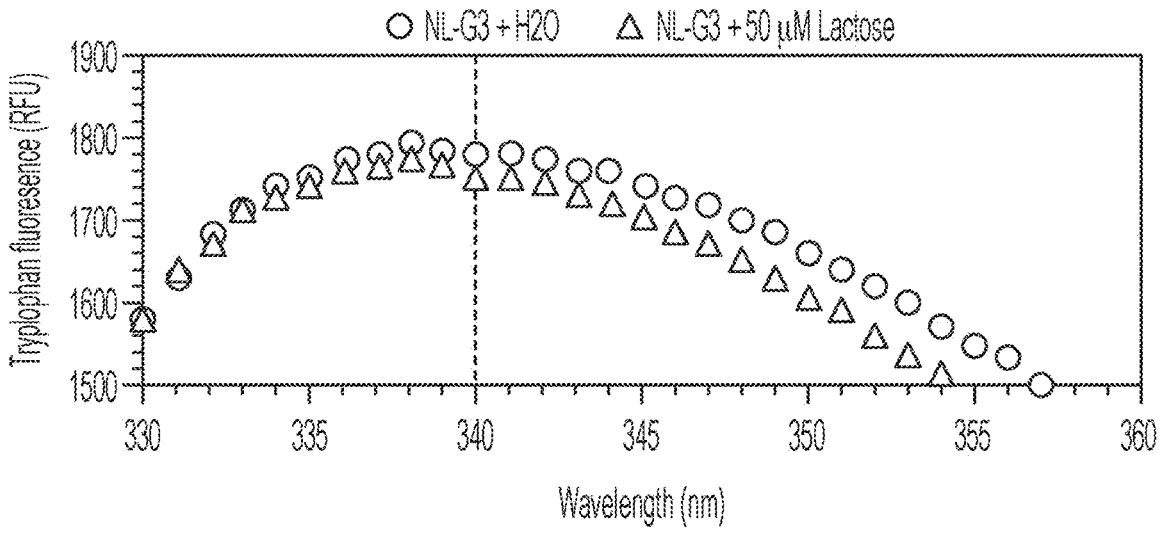
FIG. 27B

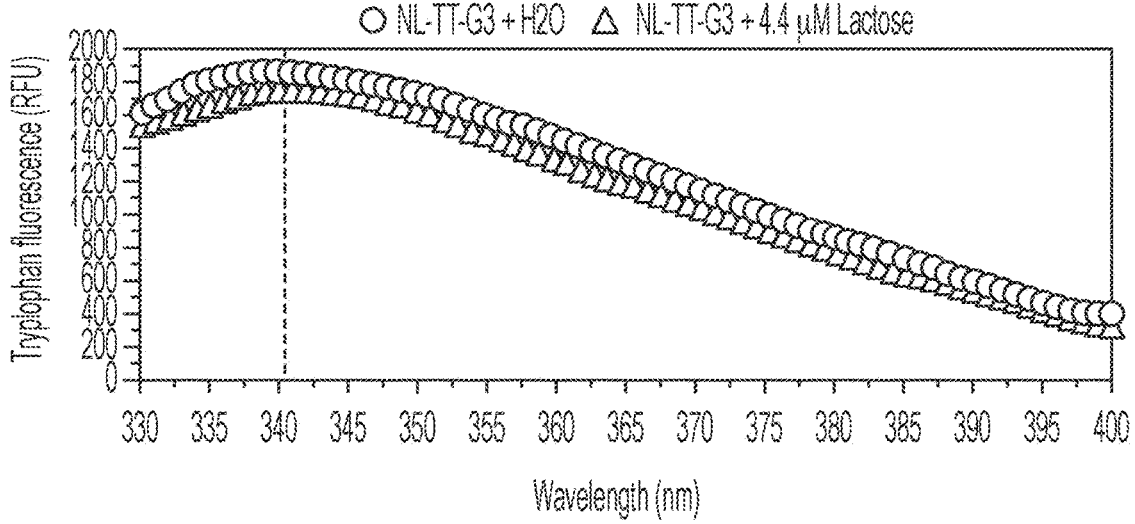
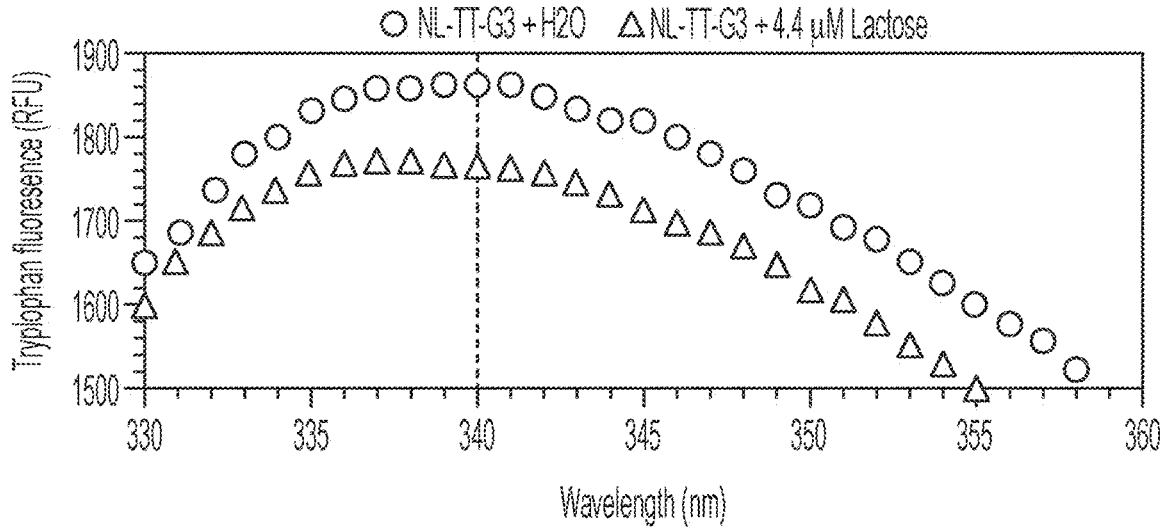
FIG. 27C

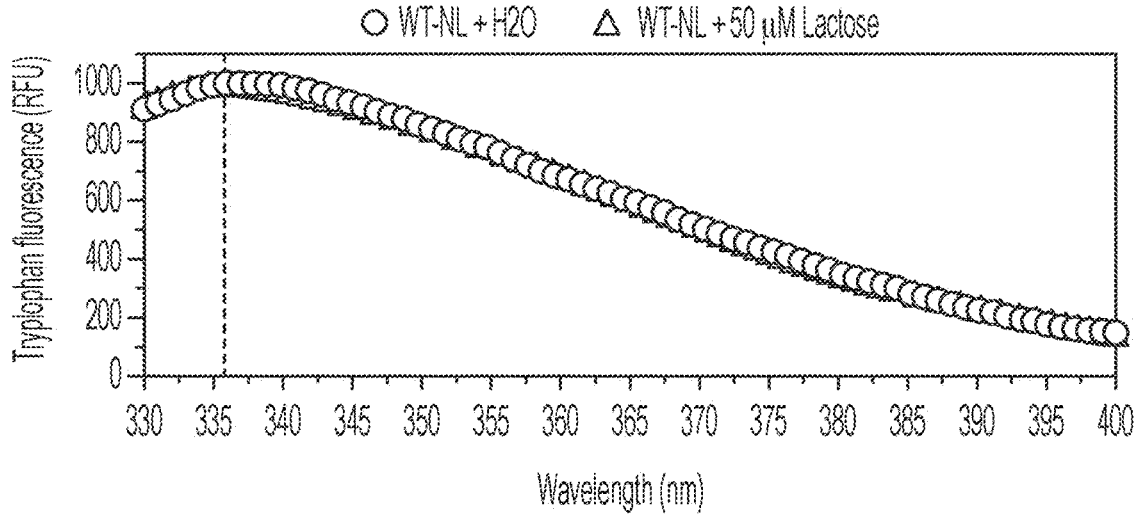
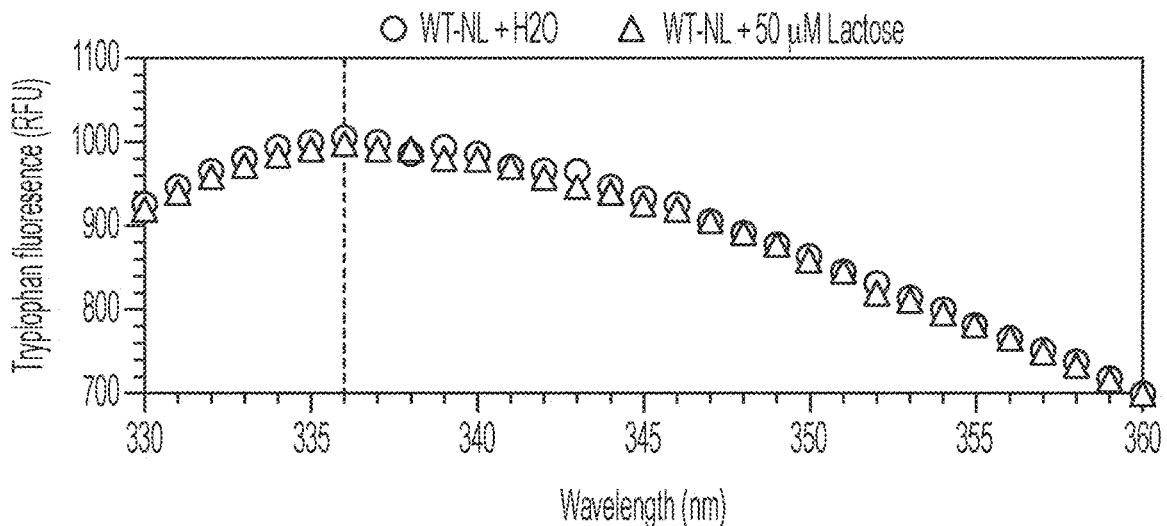
FIG. 27D

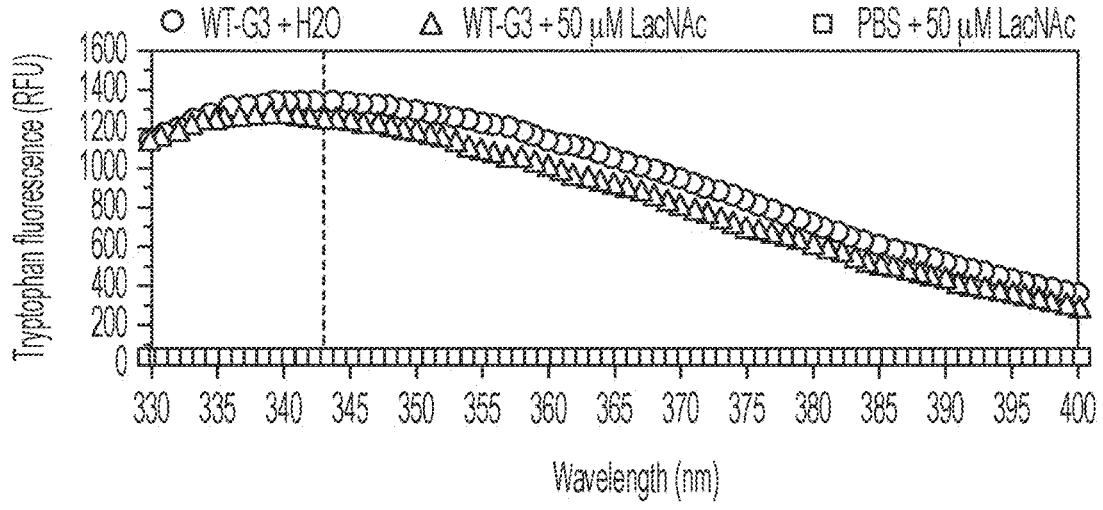
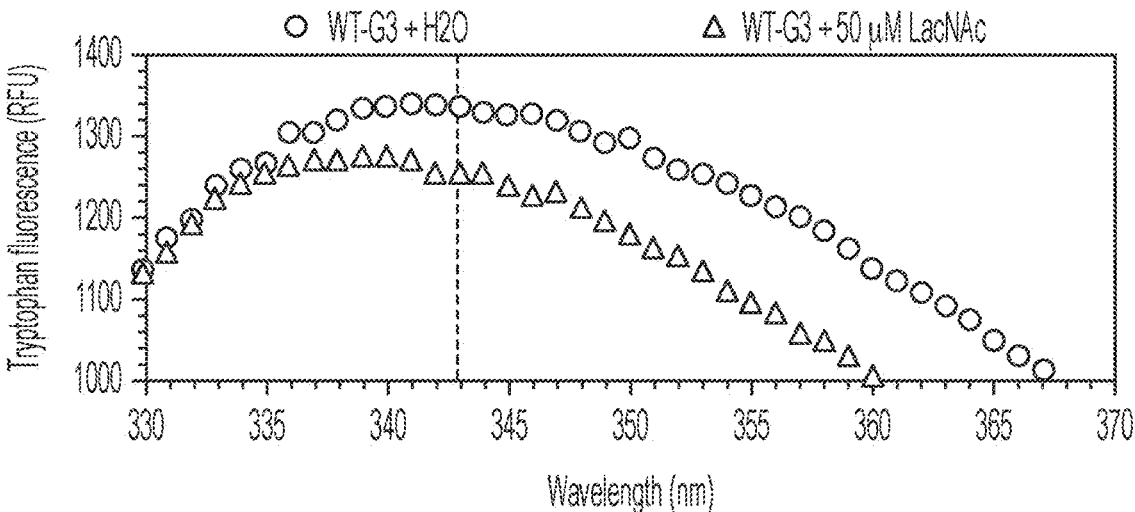
FIG. 28A

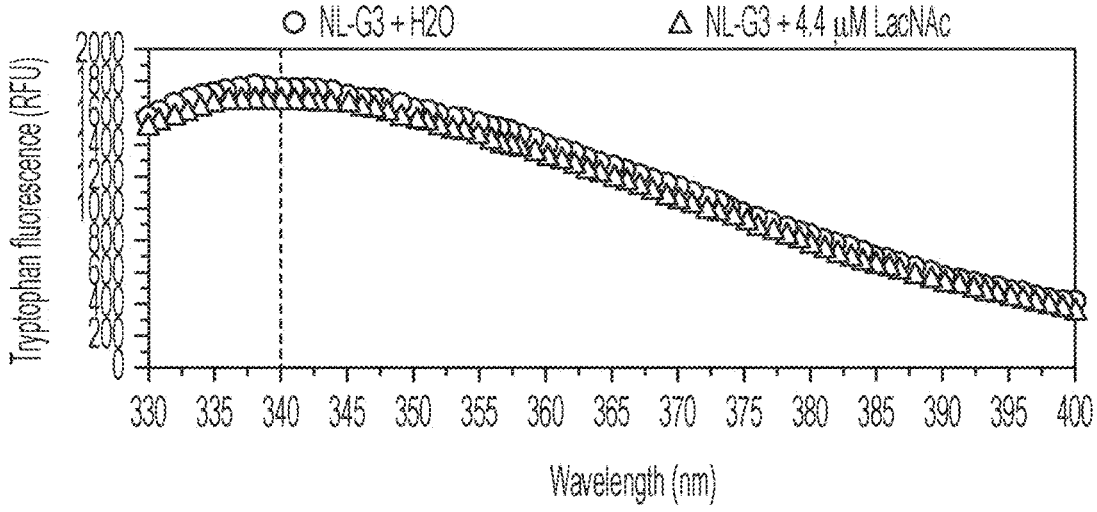
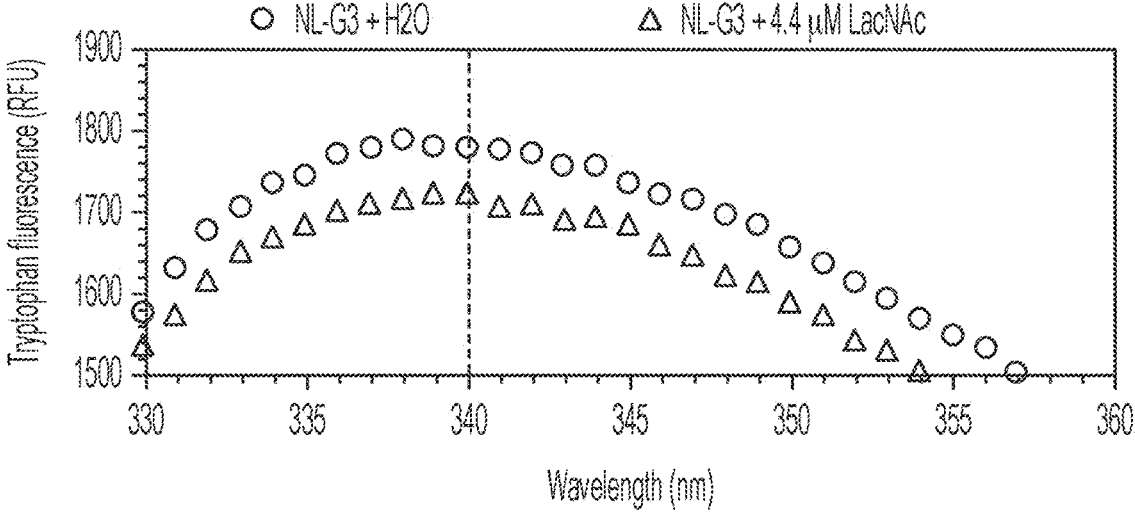
FIG. 28B

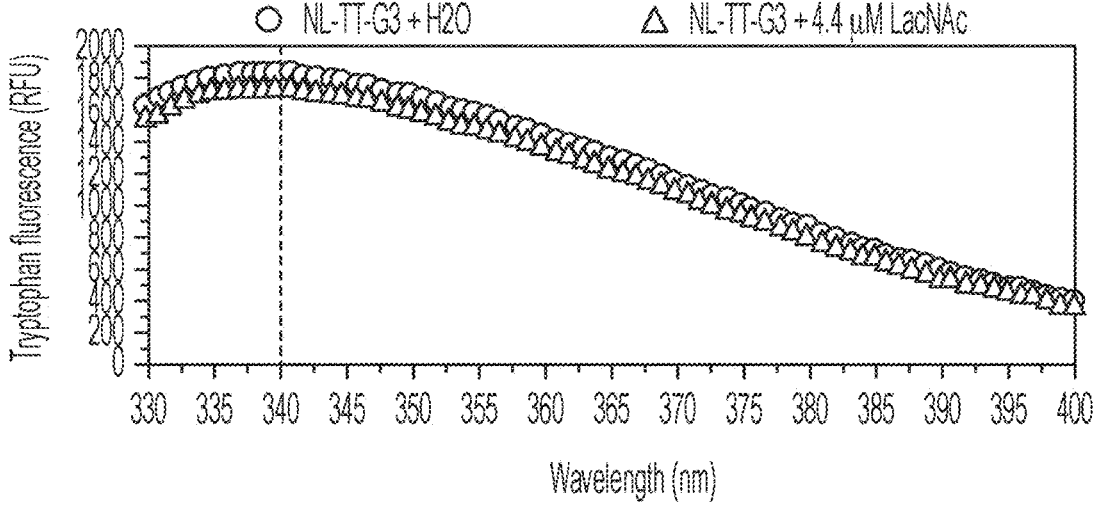
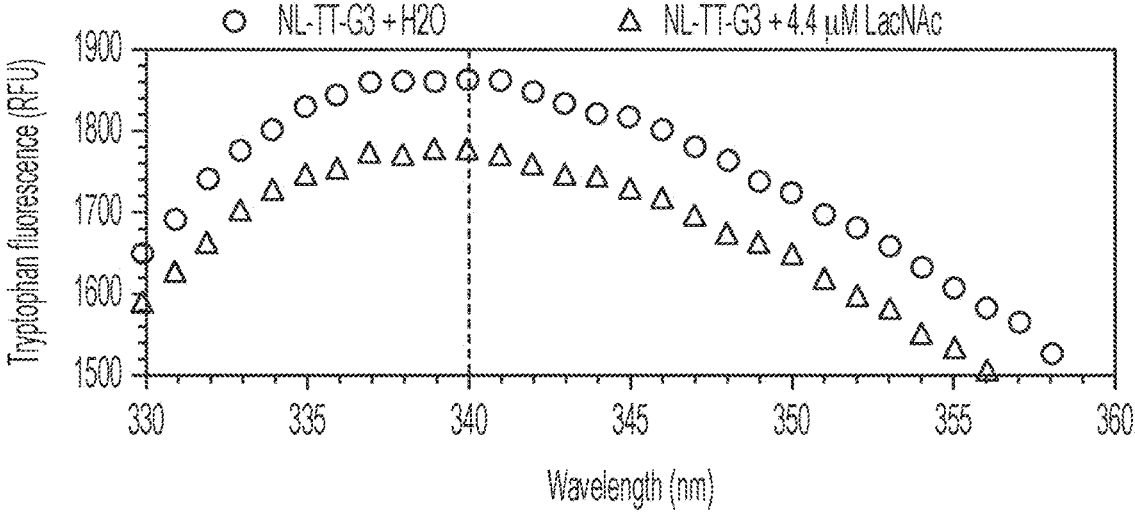
FIG. 28C b

Sample ID    NL-G3 run 3 (Combined)
Date - Time   May 14, 2018 12:35:52
Operator ID  SF
Elapsed Time  00:05:00
Mean Diam.   3.9 nm
Rel. Var.    0.025
Skew         6.077

| d(nm) | G(d) | C(d) | d(nm) | G(d) | C(d) | d(nm) | G(d) | C(d) |
|---|---|---|---|---|---|---|---|---|
| 1.8 | 0 | 0 | 10.0 | 0 | 100 | 55.1 | 0 | 100 |
| 2.1 | 0 | 0 | 11.6 | 0 | 100 | 64.1 | 0 | 100 |
| 2.5 | 0 | 0 | 13.6 | 0 | 100 | 75.2 | 0 | 100 |
| 2.9 | 0 | 0 | 15.9 | 0 | 100 | 87.8 | 0 | 100 |
| 3.4 | 100 | 42 | 18.6 | 0 | 100 | 102.6 | 0 | 100 |
| 3.9 | 85 | 78 | 21.7 | 0 | 100 | 119.8 | 0 | 100 |
| 4.6 | 45 | 96 | 25.3 | 0 | 100 | 140.0 | 0 | 100 |
| 5.4 | 9 | 100 | 29.6 | 0 | 100 | 163.5 | 0 | 100 |
| 6.3 | 0 | 100 | 34.6 | 0 | 100 | 191.0 | 0 | 100 |
| 7.3 | 0 | 100 | 40.4 | 0 | 100 | 223.1 | 0 | 100 |
| 8.5 | 0 | 100 | 47.2 | 0 | 100 | 260.6 | 0 | 100 |

Sample ID    NL-G3 run 2 (Combined)
Date - Time   May 14, 2018 12:35:52
Operator ID   SF
Elapsed Time  00:05:00
Mean Diam.   4.2 nm
Rel. Var.     0.153
Skew         19.771

| d(nm) | G(d) | C(d) | d(nm) | G(d) | C(d) | d(nm) | G(d) | C(d) |
|---|---|---|---|---|---|---|---|---|
| 1.8 | 0 | 0 | 10.0 | 0 | 99 | 55.1 | 0 | 100 |
| 2.1 | 0 | 0 | 11.6 | 0 | 99 | 64.4 | 0 | 100 |
| 2.5 | 0 | 0 | 13.6 | 0 | 99 | 75.2 | 0 | 100 |
| 2.9 | 0 | 0 | 15.9 | 1 | 100 | 57.8 | 0 | 100 |
| 3.4 | 86 | 31 | 18.6 | 0 | 100 | 102.6 | 0 | 100 |
| 3.9 | 100 | 67 | 21.7 | 0 | 100 | 119.8 | 0 | 100 |
| 4.6 | 72 | 92 | 25.3 | 0 | 100 | 140.0 | 0 | 100 |
| 5.4 | 19 | 99 | 29.6 | 0 | 100 | 163.6 | 0 | 100 |
| 6.3 | 0 | 99 | 34.6 | 0 | 100 | 191.0 | 0 | 100 |
| 7.3 | 0 | 99 | 40.4 | 0 | 100 | 223.1 | 0 | 100 |
| 8.5 | 0 | 99 | 47.2 | 0 | 100 | 260.6 | 0 | 100 |

Surface Area

Sample ID      NL-G3 run 3 (Combined)
Date - Time    May 14, 2018 12:35:52
Operator ID    SF
Elapsed Time   00:05:00
Mean Diam.     98.3 nm
Rel. Var.      0.189
Skew           -0.899

| d(nm) | G(d) | C(d) | d(nm) | G(d) | C(d) | d(nm) | G(d) | C(d) |
|---|---|---|---|---|---|---|---|---|
| 1.8 | 0 | 0 | 10.0 | 0 | 4 | 55.1 | 0 | 18 |
| 2.1 | 0 | 0 | 11.6 | 0 | 4 | 64.4 | 0 | 18 |
| 2.5 | 0 | 0 | 13.6 | 7 | 6 | 75.2 | 6 | 19 |
| 2.9 | 0 | 0 | 15.9 | 13 | 9 | 57.8 | 54 | 33 |
| 3.4 | 2 | 1 | 18.6 | 11 | 12 | 102.6 | 87 | 55 |
| 3.9 | 5 | 2 | 21.7 | 11 | 14 | 119.8 | 100 | 80 |
| 4.6 | 6 | 3 | 25.3 | 6 | 16 | 140.0 | 57 | 94 |
| 5.4 | 3 | 4 | 29.6 | 6 | 18 | 163.5 | 23 | 100 |
| 6.3 | 0 | 4 | 34.6 | 0 | 18 | 191.0 | 0 | 100 |
| 7.3 | 0 | 4 | 40.4 | 0 | 18 | 223.1 | 0 | 100 |
| 8.5 | 0 | 4 | 47.2 | 0 | 18 | 260.6 | 0 | 100 |

Intensity

| Sample ID | NL-TT-G3 run 3 (Combined) |
| --- | --- |
| Date - Time | May 14, 2018 15:59:38 |
| Operator ID | SF |
| Elapsed Time | 00:05:00 |
| Mean Diam. | 10.2 nm |
| Rel. Var. | 0.035 |
| Skew | 4.735 |

| d(nm) | G(d) | C(d) | d(nm) | G(d) | C(d) | d(nm) | G(d) | C(d) |
| --- | --- | --- | --- | --- | --- | --- | --- | --- |
| 6.8 | 0 | 0 | 12.1 | 0 | 96 | 21.6 | 0 | 96 |
| 7.2 | 0 | 0 | 12.8 | 0 | 96 | 22.7 | 1 | 97 |
| 7.6 | 0 | 0 | 13.5 | 0 | 96 | 23.9 | 3 | 98 |
| 8.0 | 0 | 0 | 14.2 | 0 | 96 | 25.2 | 4 | 99 |
| 8.4 | 11 | 3 | 15.0 | 0 | 96 | 26.6 | 3 | 100 |
| 8.9 | 52 | 18 | 15.8 | 0 | 96 | 28.0 | 1 | 100 |
| 9.4 | 92 | 45 | 16.6 | 0 | 96 | 29.5 | 0 | 100 |
| 9.9 | 100 | 73 | 17.5 | 0 | 96 | 31.0 | 0 | 100 |
| 10.4 | 61 | 91 | 18.4 | 0 | 96 | 32.7 | 0 | 100 |
| 10.9 | 20 | 96 | 19.4 | 0 | 96 | 34.5 | 0 | 100 |
| 11.5 | 0 | 96 | 20.5 | 0 | 96 | 35.3 | 0 | 100 |

Volume ▼

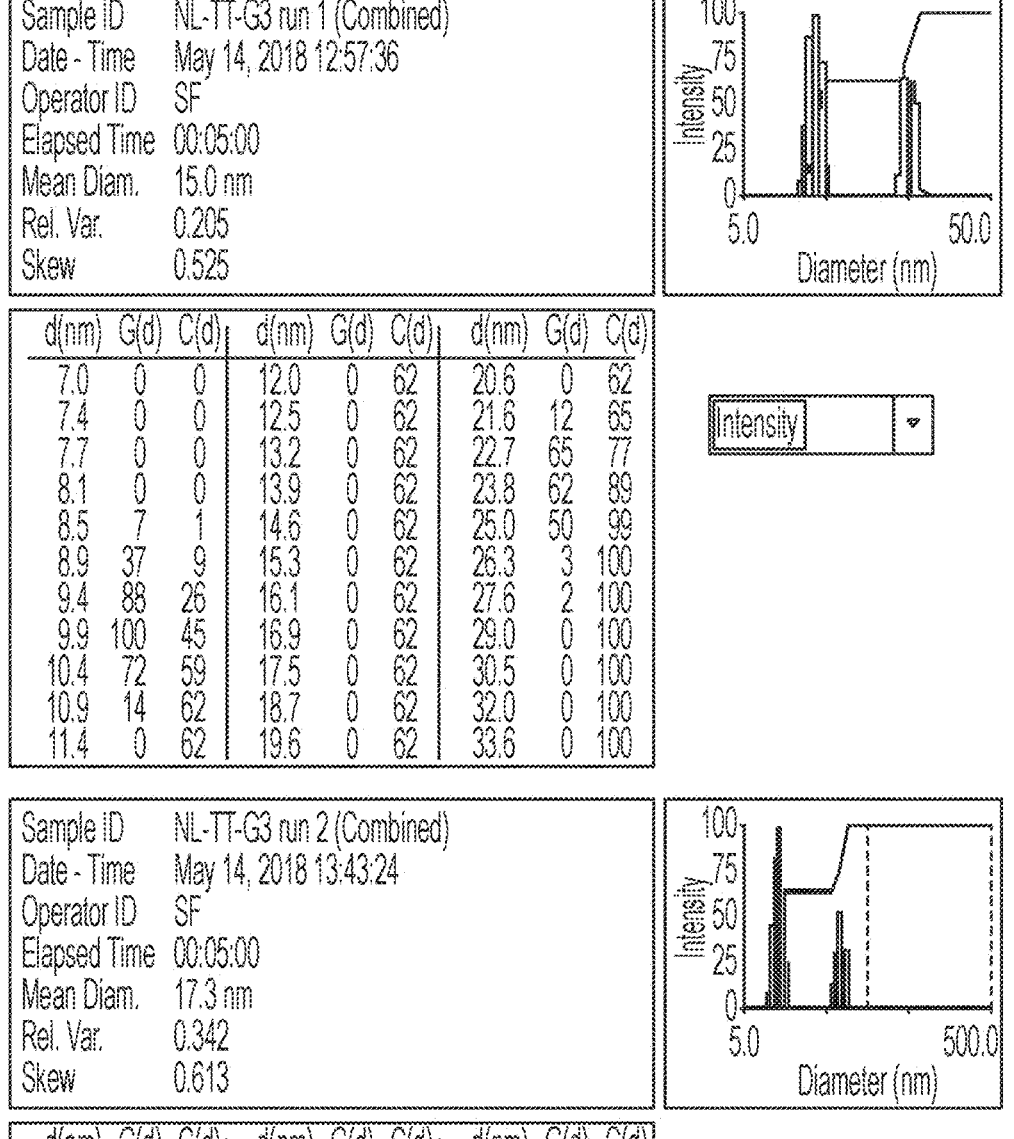
| Sample ID | NL-TT-G3 run 1 (Combined) |
| Date - Time | May 14, 2018 12:57:36 |
| Operator ID | SF |
| Elapsed Time | 00:05:00 |
| Mean Diam. | 15.0 nm |
| Rel. Var. | 0.205 |
| Skew | 0.525 |
| d(nm) | G(d) | C(d) | d(nm) | G(d) | C(d) | d(nm) | G(d) | C(d) |
|---|---|---|---|---|---|---|---|---|
| 7.0 | 0 | 0 | 12.0 | 0 | 62 | 20.6 | 0 | 62 |
| 7.4 | 0 | 0 | 12.5 | 0 | 62 | 21.6 | 12 | 65 |
| 7.7 | 0 | 0 | 13.2 | 0 | 62 | 22.7 | 65 | 77 |
| 8.1 | 0 | 0 | 13.9 | 0 | 62 | 23.8 | 62 | 89 |
| 8.5 | 7 | 1 | 14.6 | 0 | 62 | 25.0 | 50 | 99 |
| 8.9 | 37 | 9 | 15.3 | 0 | 62 | 26.3 | 3 | 100 |
| 9.4 | 88 | 26 | 16.1 | 0 | 62 | 27.6 | 2 | 100 |
| 9.9 | 100 | 45 | 16.9 | 0 | 62 | 29.0 | 0 | 100 |
| 10.4 | 72 | 59 | 17.5 | 0 | 62 | 30.5 | 0 | 100 |
| 10.9 | 14 | 62 | 18.7 | 0 | 62 | 32.0 | 0 | 100 |
| 11.4 | 0 | 62 | 19.6 | 0 | 62 | 33.6 | 0 | 100 |
Intensity ▼
| Sample ID | NL-TT-G3 run 2 (Combined) |
| Date - Time | May 14, 2018 13:43:24 |
| Operator ID | SF |
| Elapsed Time | 00:05:00 |
| Mean Diam. | 17.3 nm |
| Rel. Var. | 0.342 |
| Skew | 0.613 |
| d(nm) | G(d) | C(d) | d(nm) | G(d) | C(d) | d(nm) | G(d) | C(d) |
|---|---|---|---|---|---|---|---|---|
| 7.0 | 0 | 0 | 13.2 | 0 | 64 | 24.9 | 0 | 64 |
| 7.4 | 0 | 0 | 14.0 | 0 | 64 | 26.4 | 12 | 66 |
| 7.8 | 0 | 0 | 14.5 | 0 | 64 | 28.0 | 29 | 72 |
| 8.3 | 7 | 1 | 15.7 | 0 | 64 | 29.7 | 51 | 82 |
| 8.8 | 45 | 10 | 15.5 | 0 | 64 | 31.5 | 50 | 92 |
| 9.3 | 82 | 27 | 17.5 | 0 | 64 | 33.3 | 32 | 98 |
| 9.9 | 100 | 46 | 18.7 | 0 | 64 | 35.3 | 10 | 100 |
| 10.5 | 62 | 59 | 19.5 | 0 | 64 | 37.4 | 0 | 100 |
| 11.1 | 25 | 64 | 21.0 | 0 | 64 | 39.7 | 0 | 100 |
| 11.7 | 0 | 64 | 22.2 | 0 | 64 | 42.0 | 0 | 100 |
| 12.4 | 0 | 64 | 23.5 | 0 | 64 | 44.5 | 0 | 100 |
Intensity ▼
FIG. 44B

| Sample ID | NL-TT-G3 run 3 (Combined) |
|---|---|
| Date - Time | May 14, 2018 15:59:38 |
| Operator ID | SF |
| Elapsed Time | 00:05:00 |
| Mean Diam. | 16.1 nm |
| Rel. Var. | 0.236 |
| Skew | 0.460 |

| d(nm) | G(d) | C(d) | d(nm) | G(d) | C(d) | d(nm) | G(d) | C(d) |
|---|---|---|---|---|---|---|---|---|
| 6.8 | 0 | 0 | 12.1 | 0 | 60 | 21.6 | 0 | 60 |
| 7.2 | 0 | 0 | 12.8 | 0 | 60 | 22.7 | 13 | 63 |
| 7.6 | 0 | 0 | 13.5 | 0 | 60 | 23.9 | 47 | 72 |
| 8.0 | 0 | 0 | 14.2 | 0 | 60 | 25.2 | 65 | 84 |
| 8.4 | 7 | 1 | 15.0 | 0 | 60 | 26.6 | 57 | 94 |
| 8.9 | 38 | 8 | 15.8 | 0 | 60 | 28.0 | 24 | 99 |
| 9.4 | 79 | 23 | 16.6 | 0 | 60 | 29.5 | 0 | 100 |
| 9.9 | 100 | 42 | 17.5 | 0 | 60 | 31.0 | 0 | 100 |
| 10.4 | 71 | 55 | 18.4 | 0 | 60 | 32.7 | 0 | 100 |
| 10.9 | 28 | 60 | 19.4 | 0 | 60 | 34.5 | 0 | 100 |
| 11.5 | 0 | 60 | 20.5 | 0 | 60 | 36.3 | 0 | 100 |

Intensity ▼

| Sample ID | GF-G3 run 3 (Combined) |
| Date - Time | May 14, 2018 13:32:27 |
| Operator ID | SF |
| Elapsed Time | 00:05:00 |
| Mean Diam. | 4.4 nm |
| Rel. Var. | 0.132 |
| Skew | 11.600 |

| d(nm) | G(d) | C(d) | d(nm) | G(d) | C(d) | d(nm) | G(d) | C(d) |
|---|---|---|---|---|---|---|---|---|
| 2.6 | 0 | 0 | 13.2 | 2 | 99 | 68.1 | 0 | 100 |
| 3.0 | 0 | 0 | 15.4 | 1 | 100 | 79.0 | 0 | 100 |
| 3.5 | 100 | 38 | 17.9 | 1 | 100 | 91.6 | 0 | 100 |
| 4.0 | 73 | 68 | 20.7 | 0 | 100 | 106.3 | 0 | 100 |
| 4.7 | 43 | 82 | 24.1 | 0 | 100 | 123.3 | 0 | 100 |
| 5.4 | 25 | 91 | 27.9 | 0 | 100 | 143.1 | 0 | 100 |
| 6.3 | 14 | 97 | 32.4 | 0 | 100 | 166.0 | 0 | 100 |
| 7.3 | 5 | 99 | 37.6 | 0 | 100 | 192.5 | 0 | 100 |
| 8.5 | 0 | 99 | 43.6 | 0 | 100 | 223.4 | 0 | 100 |
| 9.9 | 0 | 99 | 50.6 | 0 | 100 | 258.2 | 0 | 100 |
| 11.4 | 0 | 99 | 58.7 | 0 | 100 | 300.7 | 0 | 100 |

Surface Area ▼

Sample ID    GFP-G3 run 3 (Combined)
Date - Time    May 14, 2018 13:32:27
Operator ID    SF
Elapsed Time    00:05:00
Mean Diam.    120.5 nm
Rel. Var.    0.327
Skew    -1.654

| d(nm) | G(d) | C(d) | d(nm) | G(d) | C(d) | d(nm) | G(d) | C(d) |
|---|---|---|---|---|---|---|---|---|
| 2.6 | 0 | 0 | 13.3 | 24 | 15 | 68.1 | 0 | 26 |
| 3.0 | 0 | 0 | 15.4 | 27 | 21 | 79.0 | 0 | 26 |
| 3.6 | 6 | 1 | 17.9 | 24 | 26 | 91.6 | 0 | 26 |
| 4.0 | 8 | 3 | 20.7 | 0 | 26 | 106.3 | 14 | 29 |
| 4.7 | 8 | 5 | 24.1 | 0 | 26 | 123.3 | 58 | 41 |
| 5.4 | 9 | 7 | 27.9 | 0 | 26 | 143.1 | 93 | 81 |
| 6.3 | 9 | 9 | 32.4 | 0 | 26 | 166.0 | 100 | 83 |
| 7.3 | 5 | 10 | 37.6 | 0 | 26 | 192.5 | 58 | 95 |
| 8.5 | 0 | 10 | 43.6 | 0 | 26 | 223.4 | 22 | 100 |
| 9.9 | 0 | 10 | 50.6 | 0 | 26 | 259.2 | 0 | 100 |
| 11.4 | 0 | 10 | 58.7 | 0 | 26 | 300.7 | 0 | 100 |

| Sample ID | GFP-TT-G3 run 3 (Combined) |
|---|---|
| Date - Time | May 14, 2018 14:44:50 |
| Operator ID | SF |
| Elapsed Time | 00:05:00 |
| Mean Diam. | 12.3 nm |
| Rel. Var. | 0.019 |
| Skew | 1.348 |

| d(nm) | G(d) | C(d) | d(nm) | G(d) | C(d) | d(nm) | G(d) | C(d) |
|---|---|---|---|---|---|---|---|---|
| 6.8 | 0 | 0 | 28.5 | 0 | 100 | 104.0 | 0 | 100 |
| 7.7 | 0 | 0 | 30.0 | 0 | 100 | 117.7 | 0 | 100 |
| 8.7 | 0 | 0 | 34.0 | 0 | 100 | 133.3 | 0 | 100 |
| 9.8 | 21 | 8 | 38.5 | 0 | 100 | 150.9 | 0 | 100 |
| 11.1 | 100 | 45 | 43.6 | 0 | 100 | 170.8 | 0 | 100 |
| 12.6 | 81 | 78 | 49.4 | 0 | 100 | 193.4 | 0 | 100 |
| 14.3 | 47 | 94 | 55.9 | 0 | 100 | 219.0 | 0 | 100 |
| 16.1 | 13 | 99 | 63.3 | 0 | 100 | 247.9 | 0 | 100 |
| 18.3 | 3 | 100 | 71.6 | 0 | 100 | 280.7 | 0 | 100 |
| 20.7 | 0 | 100 | 81.1 | 0 | 100 | 317.8 | 0 | 100 |
| 23.4 | 0 | 100 | 91.8 | 0 | 100 | 359.8 | 0 | 100 |

Number

| Sample ID | GFP-TT-G3 run 3 (Combined) |
|---|---|
| Date - Time | May 14, 2018 14:44:50 |
| Operator ID | SF |
| Elapsed Time | 00:05:00 |
| Mean Diam. | 12.8 nm |
| Rel. Var. | 0.037 |
| Skew | 20.635 |

| d(nm) | G(d) | C(d) | d(nm) | G(d) | C(d) | d(nm) | G(d) | C(d) |
|---|---|---|---|---|---|---|---|---|
| 6.8 | 0 | 0 | 26.5 | 0 | 100 | 104.5 | 0 | 100 |
| 7.7 | 0 | 0 | 30.0 | 0 | 100 | 117.7 | 0 | 100 |
| 8.7 | 0 | 0 | 34.0 | 0 | 100 | 133.3 | 0 | 100 |
| 9.8 | 16 | 5 | 38.5 | 0 | 100 | 150.9 | 0 | 100 |
| 11.1 | 95 | 35 | 43.6 | 0 | 100 | 170.8 | 0 | 100 |
| 12.6 | 100 | 68 | 49.4 | 0 | 100 | 193.4 | 0 | 100 |
| 14.3 | 74 | 83 | 55.9 | 0 | 100 | 219.0 | 0 | 100 |
| 16.1 | 27 | 98 | 63.3 | 0 | 100 | 247.9 | 0 | 100 |
| 18.3 | 7 | 100 | 71.6 | 0 | 100 | 280.7 | 0 | 100 |
| 20.7 | 0 | 100 | 81.1 | 0 | 100 | 317.8 | 0 | 100 |
| 23.4 | 0 | 100 | 91.8 | 0 | 100 | 359.8 | 0 | 100 |

Surface Area

| Sample ID | ChABC-Gal3 (Combined) |
|-----------|----------------------|
| Date - Time | June 1, 2018 12:35:58 |
| Operator ID | DS |
| Elapsed Time | 00:05:00 |
| Mean Diam. | 9.5 nm |
| Rel. Var. | 0.035 |
| Skew | 5.881 |

| d(nm) | G(d) | C(d) | d(nm) | G(d) | C(d) | d(nm) | G(d) | C(d) |
|-------|------|------|-------|------|------|-------|------|------|
| 6.1 | 0 | 0 | 24.0 | 0 | 100 | 93.8 | 0 | 100 |
| 7.0 | 0 | 0 | 27.2 | 0 | 100 | 105.1 | 0 | 100 |
| 7.9 | 100 | 34 | 30.7 | 0 | 100 | 120.1 | 0 | 100 |
| 8.9 | 48 | 51 | 34.8 | 0 | 100 | 136.0 | 0 | 100 |
| 10.1 | 68 | 81 | 39.4 | 0 | 100 | 153.9 | 0 | 100 |
| 11.4 | 37 | 94 | 44.0 | 0 | 100 | 174.2 | 0 | 100 |
| 12.9 | 17 | 100 | 50.5 | 0 | 100 | 197.2 | 0 | 100 |
| 14.6 | 0 | 100 | 57.1 | 0 | 100 | 223.2 | 0 | 100 |
| 16.6 | 0 | 100 | 64.7 | 0 | 100 | 252.8 | 0 | 100 |
| 18.7 | 0 | 100 | 73.2 | 0 | 100 | 285.0 | 0 | 100 |
| 21.2 | 0 | 100 | 82.5 | 0 | 100 | 323.7 | 0 | 100 |

Number

Sample ID        ChaABC-Gal3 (Combined)
Date - Time      Jun 1, 2018 11:08:17
Operator ID      DS
Elapsed Time     00:05:00
Mean Diam.       529.1 nm
Rel. Var.        12.091
Skew             4.138

| d(nm) | G(d) | C(d) | d(nm) | G(d) | C(d) | d(nm) | G(d) | C(d) |
|---|---|---|---|---|---|---|---|---|
| 2.6 | 0 | 0 | 44.5 | 0 | 9 | 758.8 | 0 | 94 |
| 3.4 | 0 | 0 | 57.6 | 41 | 20 | 982.0 | 0 | 94 |
| 4.4 | 0 | 0 | 74.5 | 78 | 41 | 1270.9 | 0 | 94 |
| 5.7 | 6 | 2 | 96.4 | 100 | 68 | 1644.7 | 0 | 94 |
| 7.3 | 10 | 4 | 124.0 | 66 | 85 | 2126.5 | 0 | 94 |
| 9.5 | 12 | 8 | 151.5 | 31 | 94 | 2754.6 | 0 | 94 |
| 12.3 | 4 | 9 | 209.0 | 2 | 94 | 3564.9 | 0 | 94 |
| 15.9 | 0 | 9 | 270.5 | 0 | 94 | 4613.6 | 0 | 94 |
| 20.5 | 3 | 9 | 350.1 | 0 | 94 | 5970.7 | 7 | 94 |
| 26.6 | 0 | 9 | 453.0 | 0 | 94 | 7727.0 | 7 | 94 |
| 34.4 | 0 | 9 | 586.3 | 0 | 94 | 10000.0 | 7 | 94 |

Intensity ▼

Sample ID        ChaABC-Gal3 (Combined)
Date - Time      Jun 1, 2018 11:29:08
Operator ID      DS
Elapsed Time     00:05:00
Mean Diam.       114.9 nm
Rel. Var.        0.187
Skew             -0.928

| d(nm) | G(d) | C(d) | d(nm) | G(d) | C(d) | d(nm) | G(d) | C(d) |
|---|---|---|---|---|---|---|---|---|
| 4.7 | 0 | 0 | 19.5 | 0 | 4 | 81.7 | 0 | 20 |
| 5.3 | 0 | 0 | 21.7 | 8 | 5 | 93.0 | 0 | 20 |
| 6.1 | 0 | 0 | 24.3 | 15 | 9 | 106.9 | 42 | 31 |
| 6.9 | 5 | 1 | 27.2 | 18 | 14 | 120.6 | 77 | 50 |
| 7.9 | 5 | 2 | 30.4 | 15 | 17 | 137.3 | 100 | 75 |
| 9.0 | 5 | 4 | 33.9 | 8 | 19 | 158.4 | 68 | 91 |
| 10.2 | 0 | 4 | 37.9 | 3 | 20 | 178.1 | 31 | 99 |
| 11.6 | 0 | 4 | 42.4 | 0 | 20 | 202.8 | 4 | 100 |
| 13.2 | 0 | 4 | 55.3 | 0 | 20 | 231.0 | 0 | 100 |
| 15.1 | 0 | 4 | 63.0 | 0 | 20 | 263.0 | 0 | 100 |
| 17.2 | 0 | 4 | 71.7 | 0 | 20 | 299.5 | 0 | 100 |

Intensity ▼

| Sample ID | ChaABC-Gal3 (Combined) |
|---|---|
| Date - Time | Jun 1, 2018 12:35:50 |
| Operator ID | DS |
| Elapsed Time | 00:05:00 |
| Mean Diam. | 123.9 nm |
| Rel. Var. | 0.238 |
| Skew | -0.583 |

| d(nm) | G(d) | C(d) | d(nm) | G(d) | C(d) | d(nm) | G(d) | C(d) |
|---|---|---|---|---|---|---|---|---|
| 6.1 | 0 | 0 | 24.0 | 0 | 6 | 93.8 | 0 | 29 |
| 7.0 | 0 | 0 | 27.2 | 0 | 6 | 106.1 | 0 | 29 |
| 7.9 | 2 | 0 | 30.7 | 12 | 9 | 120.1 | 32 | 35 |
| 8.9 | 2 | 1 | 34.8 | 17 | 12 | 136.0 | 74 | 51 |
| 10.1 | 9 | 3 | 39.4 | 28 | 18 | 153.9 | 100 | 72 |
| 11.4 | 8 | 4 | 44.6 | 23 | 23 | 174.2 | 82 | 89 |
| 12.9 | 8 | 6 | 50.5 | 21 | 27 | 197.2 | 42 | 98 |
| 14.6 | 0 | 6 | 57.1 | 7 | 29 | 223.2 | 11 | 100 |
| 16.6 | 0 | 6 | 64.7 | 0 | 29 | 252.6 | 0 | 100 |
| 18.7 | 0 | 6 | 73.2 | 0 | 29 | 286.0 | 0 | 100 |
| 21.2 | 0 | 6 | 82.8 | 0 | 29 | 323.7 | 0 | 100 |

Sample ID    ChABC-TT-Gal3 (Combined)
Date - Time    June 8, 2018 15:05:29
Operator ID    DS
Elapsed Time    00:05:00
Mean Diam.    17.9 nm
Rel. Var.    0.037
Skew    2.894

| d(nm) | G(d) | C(d) | d(nm) | G(d) | C(d) | d(nm) | G(d) | C(d) |
|---|---|---|---|---|---|---|---|---|
| 7.5 | 0 | 0 | 45.7 | 0 | 100 | 279.9 | 0 | 100 |
| 8.8 | 0 | 0 | 53.9 | 0 | 100 | 330.1 | 0 | 100 |
| 10.4 | 0 | 0 | 63.5 | 0 | 100 | 389.2 | 0 | 100 |
| 12.2 | 0 | 0 | 74.9 | 0 | 100 | 459.0 | 0 | 100 |
| 14.4 | 88 | 30 | 88.3 | 0 | 100 | 541.2 | 0 | 100 |
| 17.0 | 100 | 64 | 104.1 | 0 | 100 | 638.2 | 0 | 100 |
| 20.0 | 69 | 88 | 122.8 | 0 | 100 | 752.5 | 0 | 100 |
| 23.8 | 27 | 97 | 144.8 | 0 | 100 | 887.4 | 0 | 100 |
| 27.9 | 7 | 100 | 170.7 | 0 | 100 | 1046.4 | 0 | 100 |
| 32.8 | 1 | 100 | 201.3 | 0 | 100 | 1233.9 | 0 | 100 |
| 38.7 | 0 | 100 | 237.4 | 0 | 100 | 1454.9 | 0 | 100 |

Number

Sample ID    ChABC-TT-Gal3 (Combined)
Date - Time    June 8, 2018 15:33:08
Operator ID    DS
Elapsed Time    00:05:00
Mean Diam.    21.9 nm
Rel. Var.    0.010
Skew    8.439

| d(nm) | G(d) | C(d) | d(nm) | G(d) | C(d) | d(nm) | G(d) | C(d) |
|---|---|---|---|---|---|---|---|---|
| 15.7 | 0 | 0 | 36.9 | 0 | 100 | 96.7 | 0 | 100 |
| 17.0 | 0 | 0 | 39.9 | 0 | 100 | 93.7 | 0 | 100 |
| 18.3 | 18 | 6 | 43.1 | 0 | 100 | 101.3 | 0 | 100 |
| 19.8 | 72 | 28 | 46.6 | 0 | 100 | 109.4 | 0 | 100 |
| 21.4 | 100 | 59 | 50.3 | 0 | 100 | 118.3 | 0 | 100 |
| 23.1 | 53 | 85 | 54.4 | 0 | 100 | 127.0 | 0 | 100 |
| 25.0 | 38 | 97 | 58.8 | 0 | 100 | 138.2 | 0 | 100 |
| 27.0 | 10 | 100 | 63.5 | 0 | 100 | 149.3 | 0 | 100 |
| 29.2 | 0 | 100 | 66.7 | 0 | 100 | 165.4 | 0 | 100 |
| 31.6 | 0 | 100 | 74.2 | 0 | 100 | 174.4 | 0 | 100 |
| 34.1 | 0 | 100 | 80.2 | 0 | 100 | 188.5 | 0 | 100 |

Number

| Sample ID | ChABC-TT-Gal3 (Combined) |
| Date - Time | June 8, 2018 15:38:23 |
| Operator ID | DS |
| Elapsed Time | 00:05:00 |
| Mean Diam. | 25.7 nm |
| Rel. Var. | 2.684 |
| Skew | 11.844 |

| d(nm) | G(d) | C(d) | d(nm) | G(d) | C(d) | d(nm) | G(d) | C(d) |
|---|---|---|---|---|---|---|---|---|
| 7.6 | 0 | 0 | 46.6 | 0 | 97 | 285.7 | 0 | 99 |
| 9.0 | 0 | 0 | 55.0 | 0 | 97 | 336.9 | 0 | 99 |
| 10.6 | 0 | 0 | 54.8 | 0 | 97 | 397.3 | 0 | 99 |
| 12.5 | 0 | 0 | 76.4 | 2 | 98 | 468.5 | 0 | 100 |
| 14.7 | 41 | 12 | 90.1 | 2 | 98 | 552.4 | 1 | 100 |
| 17.3 | 84 | 36 | 106.3 | 2 | 99 | 651.4 | 0 | 100 |
| 20.4 | 100 | 64 | 125.3 | 1 | 99 | 768.1 | 0 | 100 |
| 24.1 | 72 | 85 | 147.8 | 0 | 99 | 905.8 | 0 | 100 |
| 28.4 | 34 | 94 | 174.3 | 0 | 99 | 1068.1 | 0 | 100 |
| 33.5 | 9 | 97 | 205.5 | 0 | 99 | 1259.4 | 0 | 100 |
| 39.5 | 1 | 97 | 242.3 | 0 | 99 | 1485.1 | 0 | 100 |

Volume

| Sample ID | WT-G3 +ASF 2.5 uM (Combined) |
|---|---|
| Date - Time | Jul 16, 2018 17:55:10 |
| Operator ID | SF |
| Elapsed Time | 00:05:00 |
| Mean Diam. | 9.6 nm |
| Rel. Var. | 0.021 |
| Skew | 8.189 |

| d(nm) | G(d) | C(d) | d(nm) | G(d) | C(d) | d(nm) | G(d) | C(d) |
|---|---|---|---|---|---|---|---|---|
| 5.3 | 0 | 0 | 31.5 | 0 | 100 | 188.0 | 0 | 100 |
| 6.2 | 0 | 0 | 37.1 | 0 | 100 | 221.1 | 0 | 100 |
| 7.3 | 0 | 0 | 43.6 | 0 | 100 | 260.1 | 0 | 100 |
| 8.6 | 100 | 54 | 51.3 | 0 | 100 | 305.9 | 0 | 100 |
| 10.1 | 58 | 85 | 60.3 | 0 | 100 | 359.9 | 0 | 100 |
| 11.9 | 22 | 99 | 70.9 | 0 | 100 | 423.3 | 0 | 100 |
| 14.0 | 5 | 100 | 83.5 | 0 | 100 | 497.9 | 0 | 100 |
| 16.5 | 0 | 100 | 98.2 | 0 | 100 | 585.7 | 0 | 100 |
| 19.4 | 0 | 100 | 115.5 | 0 | 100 | 689.0 | 0 | 100 |
| 22.8 | 0 | 100 | 135.8 | 0 | 100 | 810.5 | 0 | 100 |
| 26.8 | 0 | 100 | 159.8 | 0 | 100 | 953.3 | 0 | 100 |

| Sample ID | WT-G3 +ASF 2.5 uM (Combined) |
|---|---|
| Date - Time | Jul 16, 2018 17:55:10 |
| Operator ID | SF |
| Elapsed Time | 00:05:00 |
| Mean Diam. | 15.8 nm |
| Rel. Var. | 8.584 |
| Skew | 9.443 |

| d(nm) | G(d) | C(d) | d(nm) | G(d) | C(d) | d(nm) | G(d) | C(d) |
|---|---|---|---|---|---|---|---|---|
| 5.3 | 0 | 0 | 31.5 | 0 | 97 | 188.0 | 0 | 99 |
| 6.2 | 0 | 0 | 37.1 | 0 | 97 | 221.1 | 0 | 99 |
| 7.3 | 0 | 0 | 43.6 | 1 | 97 | 260.1 | 0 | 99 |
| 8.6 | 100 | 35 | 51.3 | 1 | 98 | 305.9 | 0 | 99 |
| 10.1 | 95 | 69 | 60.3 | 2 | 98 | 359.9 | 0 | 99 |
| 11.9 | 59 | 90 | 70.9 | 1 | 99 | 423.3 | 1 | 99 |
| 14.0 | 20 | 97 | 83.5 | 0 | 99 | 497.9 | 2 | 100 |
| 16.5 | 0 | 97 | 98.2 | 0 | 99 | 585.7 | 0 | 100 |
| 19.4 | 0 | 97 | 115.5 | 0 | 99 | 689.0 | 0 | 100 |
| 22.8 | 0 | 97 | 135.8 | 0 | 99 | 810.5 | 0 | 100 |
| 26.8 | 0 | 97 | 159.8 | 0 | 99 | 953.3 | 0 | 100 |

Volume ▼

Sample ID    WT-G3 +ASF 2.5 uM (Combined)
Date - Time    July 16, 2018 17:55:10
Operator ID    SF
Elapsed Time    00:05:00
Mean Diam.    10.2 nm
Rel. Var.    0.545
Skew    50.288

| d(nm) | G(d) | C(d) | d(nm) | G(d) | C(d) | d(nm) | G(d) | C(d) |
|---|---|---|---|---|---|---|---|---|
| 5.3 | 0 | 0 | 31.5 | 0 | 100 | 188.0 | 0 | 100 |
| 6.2 | 0 | 0 | 37.1 | 0 | 100 | 221.1 | 0 | 100 |
| 7.3 | 0 | 0 | 43.6 | 0 | 100 | 260.1 | 0 | 100 |
| 8.6 | 100 | 42 | 51.3 | 0 | 100 | 305.9 | 0 | 100 |
| 10.1 | 81 | 75 | 60.3 | 0 | 100 | 359.9 | 0 | 100 |
| 11.9 | 43 | 94 | 70.9 | 0 | 100 | 423.3 | 0 | 100 |
| 14.0 | 12 | 100 | 83.5 | 0 | 100 | 497.9 | 0 | 100 |
| 16.5 | 0 | 100 | 98.2 | 0 | 100 | 585.7 | 0 | 100 |
| 19.4 | 0 | 100 | 115.5 | 0 | 100 | 689.0 | 0 | 100 |
| 22.8 | 0 | 100 | 135.8 | 0 | 100 | 810.5 | 0 | 100 |
| 26.8 | 0 | 100 | 159.8 | 0 | 100 | 953.3 | 0 | 100 |

Surface Area ▼

| Sample ID | WT-G3 +ASF 2.5 uM (Combined) |
| Date - Time | July 16, 2018 17:55:10 |
| Operator ID | SF |
| Elapsed Time | 00:05:00 |
| Mean Diam. | 259.0 nm |
| Rel. Var. | 0.355 |
| Skew | -0.347 |

| d(nm) | G(d) | C(d) | d(nm) | G(d) | C(d) | d(nm) | G(d) | C(d) |
|---|---|---|---|---|---|---|---|---|
| 5.3 | 0 | 0 | 31.5 | 0 | 8 | 188.0 | 0 | 32 |
| 6.2 | 0 | 0 | 37.1 | 0 | 8 | 221.1 | 0 | 32 |
| 7.3 | 0 | 0 | 43.6 | 9 | 9 | 260.1 | 46 | 42 |
| 8.6 | 7 | 2 | 51.3 | 18 | 13 | 305.9 | 76 | 59 |
| 10.1 | 11 | 4 | 60.3 | 36 | 21 | 359.9 | 100 | 80 |
| 11.9 | 11 | 6 | 70.9 | 29 | 27 | 423.3 | 62 | 94 |
| 14.0 | 6 | 8 | 83.5 | 24 | 32 | 497.9 | 30 | 100 |
| 16.5 | 0 | 8 | 98.2 | 0 | 32 | 585.7 | 0 | 100 |
| 19.4 | 0 | 8 | 115.5 | 0 | 32 | 689.0 | 0 | 100 |
| 22.8 | 0 | 8 | 135.8 | 0 | 32 | 810.5 | 0 | 100 |
| 26.8 | 0 | 8 | 159.8 | 0 | 32 | 953.3 | 0 | 100 |

| Sample ID | NL-G3+ASF 2.5 uM (Combined) |
|---|---|
| Date - Time | July 16, 2018 19:15:24 |
| Operator ID | SF |
| Elapsed Time | 00:05:00 |
| Mean Diam. | 10.4 nm |
| Rel. Var. | 0.029 |
| Skew | 12.448 |

| d(nm) | G(d) | C(d) | d(nm) | G(d) | C(d) | d(nm) | G(d) | C(d) |
|---|---|---|---|---|---|---|---|---|
| 5.2 | 0 | 0 | 38.2 | 0 | 100 | 282.9 | 0 | 100 |
| 6.2 | 0 | 0 | 45.9 | 0 | 100 | 339.3 | 0 | 100 |
| 7.4 | 0 | 0 | 55.0 | 0 | 100 | 407.0 | 0 | 100 |
| 8.9 | 100 | 45 | 66.0 | 0 | 100 | 488.2 | 0 | 100 |
| 10.7 | 81 | 82 | 79.2 | 0 | 100 | 585.6 | 0 | 100 |
| 12.8 | 32 | 97 | 95.0 | 0 | 100 | 702.5 | 0 | 100 |
| 15.4 | 7 | 100 | 113.9 | 0 | 100 | 842.6 | 0 | 100 |
| 18.5 | 0 | 100 | 136.6 | 0 | 100 | 1010.8 | 0 | 100 |
| 22.2 | 0 | 100 | 183.9 | 0 | 100 | 1212.5 | 0 | 100 |
| 26.5 | 0 | 100 | 196.6 | 0 | 100 | 1454.4 | 0 | 100 |
| 31.9 | 0 | 100 | 235.8 | 0 | 100 | 1744.5 | 0 | 100 |

Sample ID    NL-G3 +ASF 2.5 uM (Combined)
Date - Time    July 16, 2018 19:15:24
Operator ID    SF
Elapsed Time    00:05:00
Mean Diam.    34.3 nm
Rel. Var.    10.355
Skew    5.143

| d(nm) | G(d) | C(d) | d(nm) | G(d) | C(d) | d(nm) | G(d) | C(d) |
|-------|------|------|-------|------|------|-------|------|------|
| 5.2 | 0 | 0 | 38.2 | 0 | 94 | 282.9 | 0 | 96 |
| 6.2 | 0 | 0 | 45.9 | 2 | 95 | 339.3 | 0 | 96 |
| 7.4 | 0 | 0 | 55.0 | 2 | 95 | 407.0 | 0 | 96 |
| 8.9 | 72 | 25 | 66.0 | 1 | 96 | 488.2 | 9 | 98 |
| 10.7 | 100 | 60 | 79.2 | 0 | 96 | 585.6 | 0 | 99 |
| 12.8 | 69 | 85 | 95.0 | 0 | 96 | 702.5 | 0 | 99 |
| 15.4 | 26 | 94 | 113.9 | 0 | 96 | 842.6 | 2 | 100 |
| 18.5 | 0 | 94 | 136.6 | 0 | 96 | 1010.8 | 0 | 100 |
| 22.2 | 0 | 94 | 183.9 | 0 | 96 | 1212.5 | 0 | 100 |
| 26.6 | 0 | 94 | 196.6 | 0 | 96 | 1454.4 | 0 | 100 |
| 31.9 | 0 | 94 | 235.8 | 0 | 96 | 1744.5 | 0 | 100 |

| Sample ID | NL-G3+ASF 2.5 uM (Combined) |
| Date - Time | July 16, 2018 19:15:24 |
| Operator ID | SF |
| Elapsed Time | 00:05:00 |
| Mean Diam. | 11.6 nm |
| Rel. Var. | 1.970 |
| Skew | 33.851 |

| d(nm) | G(d) | C(d) | d(nm) | G(d) | C(d) | d(nm) | G(d) | C(d) |
|---|---|---|---|---|---|---|---|---|
| 5.2 | 0 | 0 | 38.2 | 0 | 100 | 282.9 | 0 | 100 |
| 6.2 | 0 | 0 | 45.9 | 0 | 100 | 339.3 | 0 | 100 |
| 7.4 | 0 | 0 | 55.0 | 0 | 100 | 407.0 | 0 | 100 |
| 8.9 | 88 | 33 | 66.0 | 0 | 100 | 488.2 | 0 | 100 |
| 10.7 | 100 | 71 | 79.2 | 0 | 100 | 585.6 | 0 | 100 |
| 12.8 | 57 | 99 | 95.0 | 0 | 100 | 702.5 | 0 | 100 |
| 15.4 | 18 | 99 | 113.9 | 0 | 100 | 842.6 | 0 | 100 |
| 18.5 | 0 | 99 | 136.6 | 0 | 100 | 1010.8 | 0 | 100 |
| 22.2 | 0 | 99 | 163.9 | 0 | 100 | 1212.5 | 0 | 100 |
| 26.6 | 0 | 99 | 196.6 | 0 | 100 | 1454.4 | 0 | 100 |
| 31.9 | 0 | 99 | 235.8 | 0 | 100 | 1744.5 | 0 | 100 |

Surface Area

| Sample ID | NL-G3 +ASF 2.5 uM (Combined) |
|---|---|
| Date - Time | July 16, 2018 19:15:24 |
| Operator ID | SF |
| Elapsed Time | 00:05:00 |
| Mean Diam. | 436.2 nm |
| Rel. Var. | 0.450 |
| Skew | -0.247 |

| d(nm) | G(d) | C(d) | d(nm) | G(d) | C(d) | d(nm) | G(d) | C(d) |
|---|---|---|---|---|---|---|---|---|
| 5.2 | 0 | 0 | 38.2 | 2 | 10 | 282.9 | 0 | 32 |
| 6.2 | 0 | 0 | 45.9 | 18 | 13 | 339.3 | 0 | 32 |
| 7.4 | 0 | 0 | 55.0 | 37 | 21 | 407.0 | 30 | 38 |
| 8.9 | 6 | 1 | 66.0 | 35 | 28 | 488.2 | 71 | 53 |
| 10.7 | 13 | 4 | 79.2 | 20 | 32 | 585.6 | 100 | 73 |
| 12.8 | 16 | 7 | 95.0 | 0 | 32 | 702.5 | 80 | 90 |
| 15.4 | 10 | 9 | 113.9 | 0 | 32 | 842.6 | 41 | 98 |
| 18.5 | 0 | 9 | 136.6 | 0 | 32 | 1010.8 | 9 | 100 |
| 22.2 | 0 | 9 | 163.9 | 0 | 32 | 1212.5 | 0 | 100 |
| 26.6 | 0 | 9 | 196.6 | 0 | 32 | 1454.4 | 0 | 100 |
| 31.9 | 0 | 9 | 235.8 | 0 | 32 | 1744.5 | 0 | 100 |

Intensity ▼

| Sample ID | NL-TT-G3 +ASF 2.5 uM (Combined) |
|---|---|
| Date - Time | July 15, 2018 18:29:55 |
| Operator ID | SF |
| Elapsed Time | 00:05:00 |
| Mean Diam. | 15.6 nm |
| Rel. Var. | 0.022 |
| Skew | 25.574 |

| d(nm) | G(d) | C(d) | d(nm) | G(d) | C(d) | d(nm) | G(d) | C(d) |
|---|---|---|---|---|---|---|---|---|
| 10.0 | 0 | 0 | 57.5 | 0 | 100 | 331.3 | 0 | 100 |
| 11.7 | 0 | 0 | 67.5 | 0 | 100 | 388.5 | 0 | 100 |
| 13.7 | 100 | 49 | 79.1 | 0 | 100 | 455.5 | 0 | 100 |
| 15.1 | 69 | 52 | 92.5 | 0 | 100 | 534.0 | 0 | 100 |
| 15.9 | 30 | 97 | 106.5 | 0 | 100 | 626.2 | 0 | 100 |
| 22.1 | 7 | 100 | 127.5 | 0 | 100 | 734.2 | 0 | 100 |
| 25.0 | 0 | 100 | 149.5 | 0 | 100 | 860.8 | 0 | 100 |
| 30.4 | 0 | 100 | 175.3 | 0 | 100 | 1009.3 | 0 | 100 |
| 35.7 | 0 | 100 | 205.5 | 0 | 100 | 1183.5 | 0 | 100 |
| 41.9 | 0 | 100 | 241.0 | 0 | 100 | 1387.6 | 0 | 100 |
| 49.1 | 0 | 100 | 282.5 | 0 | 100 | 1527.0 | 0 | 100 |

Number

| Sample ID | NL-TT-G3 +ASF 2.5 uM (Combined) |
|---|---|
| Date - Time | July 16, 2018 18:29:55 |
| Operator ID | SF |
| Elapsed Time | 00:05:00 |
| Mean Diam. | 17.6 nm |
| Rel. Var. | 3.061 |
| Skew | 25.130 |

| d(nm) | G(d) | C(d) | d(nm) | G(d) | C(d) | d(nm) | G(d) | C(d) |
|---|---|---|---|---|---|---|---|---|
| 10.0 | 0 | 0 | 57.5 | 0 | 100 | 331.3 | 0 | 100 |
| 11.7 | 0 | 0 | 67.5 | 0 | 100 | 388.5 | 0 | 100 |
| 13.7 | 100 | 37 | 79.1 | 0 | 100 | 455.5 | 0 | 100 |
| 16.1 | 95 | 72 | 92.8 | 0 | 100 | 534.0 | 0 | 100 |
| 18.9 | 56 | 93 | 136.8 | 0 | 100 | 626.2 | 0 | 100 |
| 22.1 | 18 | 100 | 127.5 | 0 | 100 | 734.2 | 0 | 100 |
| 28.0 | 0 | 100 | 149.5 | 0 | 100 | 888.8 | 0 | 100 |
| 30.4 | 0 | 100 | 175.3 | 0 | 100 | 1009.3 | 0 | 100 |
| 35.7 | 0 | 100 | 205.5 | 0 | 100 | 1183.5 | 0 | 100 |
| 41.9 | 0 | 100 | 241.0 | 0 | 100 | 1387.6 | 0 | 100 |
| 49.1 | 0 | 100 | 232.5 | 0 | 100 | 1627.0 | 0 | 100 |

Surface Area

| Sample ID | NL-TT-G3 +ASF 2.5 uM (Combined) |
|---|---|
| Date - Time | July 16, 2018 18:29:55 |
| Operator ID | SF |
| Elapsed Time | 00:05:00 |
| Mean Diam. | 638.0 nm |
| Rel. Var. | 0.192 |
| Skew | -1.996 |

| d(nm) | G(d) | C(d) | d(nm) | G(d) | C(d) | d(nm) | G(d) | C(d) |
|---|---|---|---|---|---|---|---|---|
| 10.0 | 0 | 0 | 57.5 | 0 | 6 | 331.3 | 0 | 18 |
| 11.7 | 0 | 0 | 67.5 | 0 | 6 | 388.5 | 0 | 16 |
| 13.7 | 4 | 1 | 79.1 | 6 | 8 | 455.5 | 0 | 16 |
| 16.1 | 7 | 3 | 92.8 | 11 | 11 | 534.0 | 37 | 28 |
| 18.9 | 8 | 5 | 136.8 | 13 | 14 | 626.2 | 73 | 45 |
| 22.1 | 5 | 6 | 127.5 | 6 | 16 | 734.2 | 100 | 72 |
| 28.0 | 0 | 6 | 149.5 | 0 | 16 | 880.8 | 67 | 91 |
| 30.4 | 0 | 6 | 175.3 | 0 | 16 | 1009.3 | 32 | 99 |
| 35.7 | 0 | 6 | 205.5 | 0 | 16 | 1183.5 | 3 | 100 |
| 41.9 | 0 | 6 | 241.0 | 0 | 16 | 1387.6 | 0 | 100 |
| 49.1 | 0 | 6 | 282.5 | 0 | 16 | 1627.0 | 0 | 100 |

Intensity ▼

Sample ID    WT-G3 +ASF (Combined)
Date - Time    July 16, 2018 15:20:40
Operator ID    SF
Elapsed Time    00:05:00
Mean Diam.    2359.4 nm
Rel. Var.    0.052
Skew    11.028

| d(nm) | G(d) | C(d) | d(nm) | G(d) | C(d) | d(nm) | G(d) | C(d) |
|---|---|---|---|---|---|---|---|---|
| 1677.3 | 0 | 0 | 3098.5 | 0 | 99 | 5723.9 | 0 | 99 |
| 1773.6 | 0 | 0 | 3276.3 | 0 | 99 | 6052.4 | 0 | 99 |
| 1875.3 | 0 | 0 | 3464.3 | 0 | 99 | 6399.5 | 0 | 99 |
| 1982.9 | 2 | 1 | 3663.1 | 0 | 99 | 6768.8 | 0 | 99 |
| 2096.7 | 80 | 28 | 3873.3 | 0 | 99 | 7155.1 | 0 | 99 |
| 2217.0 | 41 | 42 | 4095.5 | 0 | 99 | 7565.7 | 0 | 99 |
| 2344.2 | 55 | 81 | 4330.5 | 0 | 99 | 7999.8 | 0 | 99 |
| 2478.8 | 100 | 95 | 4579.0 | 0 | 99 | 8458.8 | 0 | 99 |
| 2621.0 | 13 | 99 | 4841.7 | 0 | 99 | 8944.1 | 1 | 100 |
| 2771.4 | 0 | 99 | 5119.6 | 0 | 99 | 9457.3 | 1 | 100 |
| 2930.4 | 0 | 99 | 5413.3 | 0 | 99 | 10000.0 | 1 | 100 |

Volume

| Sample ID | WT-G3 +ASF (Combined) |
|---|---|
| Date - Time | Jul 15, 2018 15:20:40 |
| Operator ID | SF |
| Elapsed Time | 00:05:00 |
| Mean Diam. | 2313.4 nm |
| Rel. Var. | 0.320 |
| Skew | 15.903 |

| d(nm) | G(d) | C(d) | d(nm) | G(d) | C(d) | d(nm) | G(d) | C(d) |
|---|---|---|---|---|---|---|---|---|
| 1677.3 | 0 | 0 | 3098.5 | 0 | 100 | 5723.9 | 0 | 100 |
| 1773.6 | 0 | 0 | 3276.3 | 0 | 100 | 6052.4 | 0 | 100 |
| 1876.3 | 0 | 0 | 3484.3 | 0 | 100 | 6399.6 | 0 | 100 |
| 1982.9 | 2 | 1 | 3563.1 | 0 | 100 | 6766.8 | 0 | 100 |
| 2096.7 | 94 | 31 | 3873.3 | 0 | 100 | 7155.1 | 0 | 100 |
| 2217.0 | 48 | 45 | 4195.5 | 0 | 100 | 7565.7 | 0 | 100 |
| 2344.2 | 59 | 64 | 4330.5 | 0 | 100 | 7999.8 | 0 | 100 |
| 2478.8 | 100 | 96 | 4579.0 | 0 | 100 | 8458.8 | 0 | 100 |
| 2621.0 | 12 | 100 | 4841.7 | 0 | 100 | 8944.1 | 0 | 100 |
| 2771.4 | 0 | 100 | 5119.6 | 0 | 100 | 9457.3 | 0 | 100 |
| 2930.4 | 0 | 100 | 5413.3 | 0 | 100 | 10000.0 | 0 | 100 |

Surface Area

Sample ID   WT-G3 +ASF (Combined)
Date - Time   Jul 16, 2018 14:55:20
Operator ID   SF
Elapsed Time   00:05:00
Mean Diam.   2427.4 nm
Rel. Var.   0.089
Skew   -1.640

| d(nm) | G(d) | C(d) | d(nm) | G(d) | C(d) | d(nm) | G(d) | C(d) |
|---|---|---|---|---|---|---|---|---|
| 615.5 | 0 | 0 | 1155.6 | 0 | 16 | 2169.8 | 0 | 16 |
| 651.8 | 0 | 0 | 1223.7 | 0 | 16 | 2297.7 | 0 | 16 |
| 690.2 | 0 | 0 | 1295.9 | 0 | 16 | 2433.1 | 30 | 24 |
| 730.9 | 4 | 1 | 1372.2 | 0 | 16 | 2576.5 | 75 | 44 |
| 773.9 | 18 | 6 | 1453.1 | 0 | 16 | 2728.4 | 100 | 72 |
| 819.6 | 20 | 11 | 1538.8 | 0 | 16 | 2889.2 | 72 | 91 |
| 867.9 | 17 | 16 | 1629.5 | 0 | 16 | 3059.5 | 30 | 99 |
| 919.0 | 0 | 16 | 1725.5 | 0 | 16 | 3239.8 | 2 | 100 |
| 973.2 | 0 | 16 | 1827.2 | 0 | 16 | 3430.8 | 0 | 100 |
| 1030.5 | 0 | 16 | 1934.9 | 0 | 16 | 3633.0 | 0 | 100 |
| 1091.3 | 0 | 16 | 2049.0 | 0 | 16 | 3847.1 | 0 | 100 |

Sample ID   WT-G3 +ASF (Combined)
Date - Time   Jul 16, 2018 15:05:54
Operator ID   SF
Elapsed Time   00:05:00
Mean Diam.   3018.2 nm
Rel. Var.   0.163
Skew   -0.719

| d(nm) | G(d) | C(d) | d(nm) | G(d) | C(d) | d(nm) | G(d) | C(d) |
|---|---|---|---|---|---|---|---|---|
| 943.1 | 0 | 0 | 1681.3 | 0 | 31 | 2997.5 | 0 | 31 |
| 994.0 | 0 | 0 | 1772.1 | 0 | 31 | 3159.3 | 0 | 31 |
| 1047.6 | 0 | 0 | 1867.7 | 0 | 31 | 3329.8 | 9 | 33 |
| 1104.2 | 10 | 2 | 1968.5 | 0 | 31 | 3509.5 | 53 | 44 |
| 1163.8 | 30 | 8 | 2074.7 | 0 | 31 | 3698.9 | 91 | 63 |
| 1226.6 | 50 | 19 | 2186.7 | 0 | 31 | 3898.5 | 100 | 84 |
| 1292.8 | 42 | 27 | 2304.7 | 0 | 31 | 4108.9 | 58 | 96 |
| 1362.5 | 20 | 31 | 2429.1 | 0 | 31 | 4330.6 | 20 | 100 |
| 1436.1 | 0 | 31 | 2560.2 | 0 | 31 | 4564.4 | 0 | 100 |
| 1513.6 | 0 | 31 | 2698.4 | 0 | 31 | 4810.7 | 0 | 100 |
| 1595.2 | 0 | 31 | 2844.0 | 0 | 31 | 5070.3 | 0 | 100 |

| Sample ID | WT-G3 +ASF (Combined) |
|---|---|
| Date - Time | Jul 16, 2018 15:20:40 |
| Operator ID | SF |
| Elapsed Time | 00:05:00 |
| Mean Diam. | 3085.4 nm |
| Rel. Var. | 0.582 |
| Skew | 2.589 |

| d(nm) | G(d) | C(d) | d(nm) | G(d) | C(d) | d(nm) | G(d) | C(d) |
|---|---|---|---|---|---|---|---|---|
| 1677.3 | 0 | 0 | 3098.5 | 0 | 90 | 5723.9 | 0 | 90 |
| 1773.6 | 0 | 0 | 3276.3 | 0 | 90 | 6051.4 | 0 | 90 |
| 1875.3 | 0 | 0 | 3454.3 | 0 | 90 | 6399.6 | 0 | 90 |
| 1982.9 | 4 | 1 | 3563.1 | 0 | 90 | 6766.8 | 0 | 90 |
| 2096.7 | 35 | 11 | 3873.3 | 0 | 90 | 7155.1 | 0 | 90 |
| 2217.0 | 71 | 31 | 4295.5 | 0 | 90 | 7586.7 | 0 | 90 |
| 2344.2 | 100 | 60 | 4330.5 | 0 | 90 | 7999.8 | 0 | 90 |
| 2478.8 | 70 | 80 | 4579.0 | 0 | 90 | 8458.8 | 0 | 90 |
| 2621.0 | 34 | 90 | 4841.7 | 0 | 90 | 8944.1 | 12 | 93 |
| 2771.4 | 0 | 90 | 5119.6 | 0 | 90 | 9457.3 | 12 | 97 |
| 2930.4 | 0 | 90 | 5413.3 | 0 | 90 | 10000.0 | 12 | 100 |

| Sample ID | NL-G3 +ASF (Combined) |
| Date - Time | Jul 16, 2018 16:22:00 |
| Operator ID | SF |
| Elapsed Time | 00:05:00 |
| Mean Diam. | 13.2 nm |
| Rel. Var. | 0.040 |
| Skew | 9.769 |

| d(nm) | G(d) | C(d) | d(nm) | G(d) | C(d) | d(nm) | G(d) | C(d) |
|---|---|---|---|---|---|---|---|---|
| 7.5 | 0 | 0 | 55.5 | 0 | 100 | 410.4 | 0 | 100 |
| 9.0 | 0 | 0 | 68.5 | 0 | 100 | 492.3 | 0 | 100 |
| 10.8 | 100 | 35 | 79.8 | 0 | 100 | 550.5 | 0 | 100 |
| 12.9 | 100 | 71 | 95.7 | 0 | 100 | 706.3 | 0 | 100 |
| 15.5 | 61 | 92 | 114.8 | 0 | 100 | 849.6 | 0 | 100 |
| 18.6 | 19 | 99 | 137.8 | 0 | 100 | 1019.1 | 0 | 100 |
| 22.3 | 4 | 100 | 165.3 | 0 | 100 | 1222.5 | 0 | 100 |
| 26.8 | 0 | 100 | 198.2 | 0 | 100 | 1456.4 | 0 | 100 |
| 32.1 | 0 | 100 | 237.8 | 0 | 100 | 1759.0 | 0 | 100 |
| 38.5 | 0 | 100 | 285.2 | 0 | 100 | 2109.9 | 0 | 100 |
| 46.2 | 0 | 100 | 342.1 | 0 | 100 | 2530.9 | 0 | 100 |

Number

| Sample ID | NL-G3 +ASF (Combined) |
|---|---|
| Date - Time | Jul 16, 2018 16:01:57 |
| Operator ID | SF |
| Elapsed Time | 00:05:00 |
| Mean Diam. | 42.7 nm |
| Rel. Var. | 11.149 |
| Skew | 5.634 |

Volume

| d(nm) | G(d) | C(d) | d(nm) | G(d) | C(d) | d(nm) | G(d) | C(d) |
|---|---|---|---|---|---|---|---|---|
| 6.4 | 0 | 0 | 47.3 | 1 | 94 | 350.2 | 0 | 97 |
| 7.7 | 0 | 0 | 58.8 | 2 | 95 | 420.1 | 0 | 97 |
| 9.2 | 0 | 0 | 68.1 | 3 | 96 | 504.0 | 2 | 97 |
| 11.0 | 35 | 12 | 81.7 | 2 | 96 | 604.5 | 1 | 98 |
| 13.2 | 100 | 45 | 98.0 | 1 | 97 | 725.1 | 2 | 98 |
| 15.9 | 78 | 72 | 117.6 | 0 | 97 | 859.8 | 4 | 100 |
| 19.1 | 49 | 88 | 141.0 | 0 | 97 | 1043.3 | 1 | 100 |
| 22.9 | 11 | 92 | 169.2 | 0 | 97 | 1251.5 | 0 | 100 |
| 27.4 | 5 | 94 | 202.9 | 0 | 97 | 1501.2 | 0 | 100 |
| 32.9 | 0 | 94 | 243.4 | 0 | 97 | 1800.7 | 0 | 100 |
| 39.5 | 0 | 94 | 292.0 | 0 | 97 | 2180.0 | 0 | 100 |

| Sample ID | NL-G3 +ASF (Combined) |
|---|---|
| Date - Time | Jul 16, 2018 16:10:10 |
| Operator ID | SF |
| Elapsed Time | 00:05:00 |
| Mean Diam. | 27.7 nm |
| Rel. Var. | 14.125 |
| Skew | 6.922 |

Volume

| d(nm) | G(d) | C(d) | d(nm) | G(d) | C(d) | d(nm) | G(d) | C(d) |
|---|---|---|---|---|---|---|---|---|
| 3.9 | 0 | 0 | 33.0 | 3 | 93 | 280.7 | 0 | 97 |
| 4.7 | 0 | 0 | 40.1 | 3 | 95 | 340.9 | 0 | 97 |
| 5.7 | 0 | 0 | 48.7 | 3 | 96 | 414.2 | 0 | 98 |
| 7.0 | 0 | 0 | 59.2 | 1 | 97 | 503.2 | 3 | 99 |
| 8.5 | 100 | 48 | 71.9 | 1 | 97 | 611.3 | 0 | 99 |
| 10.3 | 64 | 76 | 87.3 | 0 | 97 | 742.6 | 1 | 100 |
| 12.5 | 35 | 92 | 106.1 | 0 | 97 | 902.1 | 0 | 100 |
| 15.2 | 0 | 92 | 128.9 | 0 | 97 | 1095.9 | 0 | 100 |
| 18.4 | 0 | 92 | 156.5 | 0 | 97 | 1331.3 | 0 | 100 |
| 22.4 | 0 | 92 | 190.2 | 0 | 97 | 1617.3 | 0 | 100 |
| 27.2 | 0 | 92 | 231.0 | 0 | 97 | 1964.7 | 0 | 100 |

| | | | | | | | | |
|---|---|---|---|---|---|---|---|---|
| Sample ID | NL-G3 +ASF (Combined) | | | | | | | |
| Date - Time | Jul 16, 2018 16:22:00 | | | | | | | |
| Operator ID | SF | | | | | | | |
| Elapsed Time | 00:05:00 | | | | | | | |
| Mean Diam. | 64.2 nm | | | | | | | |
| Rel. Var. | 11.777 | | | | | | | |
| Skew | 4.701 | | | | | | | |

| d(nm) | G(d) | C(d) | d(nm) | G(d) | C(d) | d(nm) | G(d) | C(d) |
|---|---|---|---|---|---|---|---|---|
| 7.5 | 0 | 0 | 55.5 | 1 | 93 | 410.4 | 0 | 95 |
| 9.0 | 0 | 0 | 68.5 | 2 | 94 | 492.3 | 0 | 95 |
| 10.8 | 55 | 16 | 79.8 | 2 | 95 | 550.5 | 0 | 95 |
| 12.9 | 95 | 43 | 95.7 | 1 | 95 | 706.3 | 1 | 95 |
| 15.5 | 100 | 72 | 114.8 | 0 | 95 | 849.6 | 9 | 95 |
| 18.8 | 53 | 88 | 137.8 | 0 | 95 | 1019.1 | 2 | 99 |
| 22.3 | 18 | 93 | 165.3 | 0 | 95 | 1222.5 | 2 | 99 |
| 26.8 | 0 | 93 | 198.2 | 0 | 95 | 1456.4 | 3 | 100 |
| 32.1 | 0 | 93 | 237.8 | 0 | 95 | 1759.0 | 0 | 100 |
| 38.6 | 0 | 93 | 285.2 | 0 | 95 | 2109.9 | 0 | 100 |
| 46.2 | 0 | 93 | 342.1 | 0 | 95 | 2530.9 | 0 | 100 |

| Sample ID | NL-G3+ASF (Combined) |
|---|---|
| Date - Time | Jul 16, 2018 16:22:00 |
| Operator ID | SF |
| Elapsed Time | 00:05:00 |
| Mean Diam. | 656.4 nm |
| Rel. Var. | 0.454 |
| Skew | -0.249 |

| d(nm) | G(d) | C(d) | d(nm) | G(d) | C(d) | d(nm) | G(d) | C(d) |
|---|---|---|---|---|---|---|---|---|
| 7.5 | 0 | 0 | 55.5 | 9 | 11 | 410.4 | 0 | 32 |
| 9.0 | 0 | 0 | 68.5 | 21 | 15 | 492.3 | 0 | 32 |
| 10.8 | 3 | 1 | 79.8 | 39 | 22 | 590.5 | 23 | 36 |
| 12.9 | 8 | 2 | 95.7 | 31 | 28 | 706.3 | 67 | 49 |
| 15.5 | 14 | 5 | 114.8 | 19 | 32 | 849.6 | 100 | 69 |
| 18.6 | 13 | 7 | 137.8 | 0 | 32 | 1019.1 | 93 | 87 |
| 22.3 | 8 | 9 | 165.3 | 0 | 32 | 1222.5 | 51 | 97 |
| 26.8 | 0 | 9 | 198.2 | 0 | 32 | 1456.4 | 16 | 100 |
| 32.1 | 0 | 9 | 237.8 | 0 | 32 | 1759.9 | 0 | 100 |
| 38.6 | 0 | 9 | 285.2 | 0 | 32 | 2109.9 | 0 | 100 |
| 46.2 | 0 | 9 | 342.1 | 0 | 32 | 2530.9 | 0 | 100 |

| Sample ID | NL-TT-G3 +ASF (Combined) |
| Date - Time | Jul 16, 2018 15:38:36 |
| Operator ID | SF |
| Elapsed Time | 00:05:00 |
| Mean Diam. | 254.2 nm |
| Rel. Var. | 3.965 |
| Skew | 4.892 |

| d(nm) | G(d) | C(d) | d(nm) | G(d) | C(d) | d(nm) | G(d) | C(d) |
|---|---|---|---|---|---|---|---|---|
| 120.2 | 0 | 0 | 486.8 | 0 | 96 | 1970.6 | 0 | 96 |
| 136.5 | 0 | 0 | 552.8 | 0 | 96 | 2237.7 | 0 | 96 |
| 155.1 | 0 | 0 | 627.7 | 0 | 96 | 2541.0 | 1 | 97 |
| 176.1 | 100 | 96 | 712.8 | 0 | 96 | 2885.5 | 1 | 98 |
| 199.9 | 0 | 96 | 809.4 | 0 | 96 | 3276.6 | 1 | 99 |
| 227.0 | 0 | 96 | 919.1 | 0 | 96 | 3720.8 | 1 | 100 |
| 257.8 | 0 | 96 | 1043.7 | 0 | 96 | 4225.1 | 0 | 100 |
| 292.8 | 0 | 96 | 1185.2 | 0 | 96 | 4797.8 | 0 | 100 |
| 332.4 | 0 | 96 | 1345.8 | 0 | 96 | 5448.2 | 0 | 100 |
| 377.5 | 0 | 96 | 1528.2 | 0 | 96 | 6186.7 | 0 | 100 |
| 428.7 | 0 | 96 | 1735.4 | 0 | 96 | 7025.3 | 0 | 100 |

| Sample ID | NL-TT-G3 +ASF (Combined) |
| Date - Time | Jul 16, 2018 15:46:35 |
| Operator ID | SF |
| Elapsed Time | 00:05:00 |
| Mean Diam. | 769.8 nm |
| Rel. Var. | 1.501 |
| Skew | 2.038 |

| d(nm) | G(d) | C(d) | d(nm) | G(d) | C(d) | d(nm) | G(d) | C(d) |
|---|---|---|---|---|---|---|---|---|
| 226.7 | 0 | 0 | 833.2 | 0 | 85 | 3062.5 | 14 | 97 |
| 255.2 | 0 | 0 | 937.9 | 0 | 85 | 3447.2 | 7 | 100 |
| 287.2 | 0 | 0 | 1055.7 | 0 | 85 | 3880.3 | 1 | 100 |
| 323.9 | 54 | 21 | 1188.3 | 0 | 85 | 4367.7 | 0 | 100 |
| 363.9 | 64 | 45 | 1337.6 | 0 | 85 | 4916.4 | 0 | 100 |
| 409.6 | 100 | 85 | 1505.6 | 0 | 85 | 5534.0 | 0 | 100 |
| 461.1 | 0 | 85 | 1694.8 | 0 | 85 | 6229.2 | 0 | 100 |
| 519.0 | 0 | 85 | 1907.7 | 0 | 85 | 7011.7 | 0 | 100 |
| 584.2 | 0 | 85 | 2147.3 | 0 | 85 | 7892.5 | 0 | 100 |
| 657.6 | 0 | 85 | 2417.1 | 7 | 87 | 8884.0 | 0 | 100 |
| 740.2 | 0 | 85 | 2720.7 | 11 | 91 | 10000.0 | 0 | 100 |

| Sample ID | NL-TT-G3 + ASF (Combined) |
| Date - Time | Jul 16, 2018 15:53:35 |
| Operator ID | SF |
| Elapsed Time | 00:05:00 |
| Mean Diam. | 328.0 nm |
| Rel. Var. | 2.793 |
| Skew | 5.465 |

| d(nm) | G(d) | C(d) | d(nm) | G(d) | C(d) | d(nm) | G(d) | C(d) |
|---|---|---|---|---|---|---|---|---|
| 125.6 | 0 | 0 | 505.8 | 0 | 97 | 2037.2 | 0 | 97 |
| 142.6 | 0 | 0 | 574.1 | 0 | 97 | 2312.3 | 0 | 97 |
| 161.8 | 0 | 0 | 651.7 | 0 | 97 | 2624.5 | 1 | 97 |
| 183.7 | 0 | 0 | 739.6 | 0 | 97 | 2978.9 | 2 | 98 |
| 208.4 | 100 | 47 | 839.5 | 0 | 97 | 3381.1 | 3 | 99 |
| 236.6 | 68 | 73 | 952.9 | 0 | 97 | 3837.6 | 1 | 100 |
| 268.5 | 40 | 97 | 1081.5 | 0 | 97 | 4355.7 | 0 | 100 |
| 304.8 | 0 | 97 | 1227.5 | 0 | 97 | 4943.8 | 0 | 100 |
| 345.9 | 0 | 97 | 1393.3 | 0 | 97 | 5611.3 | 0 | 100 |
| 392.7 | 0 | 97 | 1581.4 | 0 | 97 | 6368.9 | 0 | 100 |
| 445.7 | 0 | 97 | 1794.9 | 0 | 97 | 7228.8 | 0 | 100 |

| Sample ID | NL-TT-G3 + ASF (Combined) |
| Date - Time | Jul 16, 2018 15:53:35 |
| Operator ID | SF |
| Elapsed Time | 00:05:00 |
| Mean Diam. | 3445.9 nm |
| Rel. Var. | 0.027 |
| Skew | -1.331 |

| d(nm) | G(d) | C(d) | d(nm) | G(d) | C(d) | d(nm) | G(d) | C(d) |
|---|---|---|---|---|---|---|---|---|
| 125.6 | 0 | 0 | 505.8 | 0 | 1 | 2037.2 | 0 | 1 |
| 142.6 | 0 | 0 | 574.1 | 0 | 1 | 2312.3 | 0 | 1 |
| 161.8 | 0 | 0 | 651.7 | 0 | 1 | 2624.5 | 11 | 7 |
| 183.7 | 0 | 0 | 739.6 | 0 | 1 | 2978.9 | 30 | 22 |
| 206.4 | 1 | 0 | 839.5 | 0 | 1 | 3381.1 | 100 | 73 |
| 236.6 | 1 | 1 | 952.9 | 0 | 1 | 3837.6 | 28 | 87 |
| 268.5 | 1 | 1 | 1081.5 | 0 | 1 | 4355.7 | 24 | 99 |
| 304.8 | 0 | 1 | 1227.5 | 0 | 1 | 4943.8 | 2 | 100 |
| 345.9 | 0 | 1 | 1393.3 | 0 | 1 | 5611.3 | 0 | 100 |
| 392.7 | 0 | 1 | 1581.4 | 0 | 1 | 6368.9 | 0 | 100 |
| 445.7 | 0 | 1 | 1794.9 | 0 | 1 | 7228.8 | 0 | 100 |

Volume ▾

Sample ID    NL-TT-G3 +ASF (Combined)
Date - Time    Jul 16, 2018 15:53:35
Operator ID    SF
Elapsed Time    00:05:00
Mean Diam.    3474.6 nm
Rel. Var.    0.054
Skew    -1.692

| d(nm) | G(d) | C(d) | d(nm) | G(d) | C(d) | d(nm) | G(d) | C(d) |
|---|---|---|---|---|---|---|---|---|
| 125.6 | 0 | 0 | 505.8 | 0 | 3 | 2037.2 | 0 | 3 |
| 142.6 | 0 | 0 | 574.1 | 0 | 3 | 2312.3 | 0 | 3 |
| 161.8 | 0 | 0 | 651.7 | 0 | 3 | 2624.5 | 24 | 10 |
| 183.7 | 0 | 0 | 739.6 | 0 | 3 | 2978.9 | 64 | 28 |
| 208.4 | 4 | 1 | 839.5 | 0 | 3 | 3381.1 | 100 | 56 |
| 236.6 | 4 | 2 | 952.9 | 0 | 3 | 3837.6 | 90 | 62 |
| 268.5 | 4 | 3 | 1081.5 | 0 | 3 | 4355.7 | 50 | 96 |
| 304.8 | 0 | 3 | 1227.6 | 0 | 3 | 4943.8 | 14 | 100 |
| 345.9 | 0 | 3 | 1393.3 | 0 | 3 | 5811.8 | 0 | 100 |
| 392.7 | 0 | 3 | 1581.4 | 0 | 3 | 6368.9 | 0 | 100 |
| 445.7 | 0 | 3 | 1794.9 | 0 | 3 | 7228.8 | 0 | 100 |

Intensity ▼

| | | | | | | | | |
|---|---|---|---|---|---|---|---|---|
Sample ID | WT-G3 only (Combined) |
Date - Time | Jul 16, 2018 17:08:55 |
Operator ID | SF |
Elapsed Time | 00:05:00 |
Mean Diam. | 6.0 nm |
Rel. Var. | 0.018 |
Skew | 0.861 |

| d(nm) | G(d) | C(d) | d(nm) | G(d) | C(d) | d(nm) | G(d) | C(d) |
|---|---|---|---|---|---|---|---|---|
| 3.5 | 0 | 0 | 13.7 | 0 | 100 | 53.4 | 0 | 100 |
| 4.0 | 0 | 0 | 15.5 | 0 | 100 | 60.5 | 0 | 100 |
| 4.5 | 0 | 0 | 17.6 | 0 | 100 | 68.4 | 0 | 100 |
| 5.1 | 92 | 30 | 19.9 | 0 | 100 | 77.4 | 0 | 100 |
| 5.8 | 100 | 62 | 22.5 | 0 | 100 | 87.6 | 0 | 100 |
| 6.5 | 80 | 88 | 25.4 | 0 | 100 | 99.1 | 0 | 100 |
| 7.4 | 29 | 97 | 28.8 | 0 | 100 | 112.2 | 0 | 100 |
| 8.4 | 8 | 100 | 32.6 | 0 | 100 | 127.0 | 0 | 100 |
| 9.5 | 0 | 100 | 36.9 | 0 | 100 | 143.7 | 0 | 100 |
| 10.7 | 0 | 100 | 41.7 | 0 | 100 | 162.6 | 0 | 100 |
| 12.1 | 0 | 100 | 47.2 | 0 | 100 | 184.0 | 0 | 100 |

Number

| Sample ID | WT-G3 only (Combined) |
|---|---|
| Date - Time | Jul 16, 2018 17:08:55 |
| Operator ID | SF |
| Elapsed Time | 00:05:00 |
| Mean Diam. | 6.3 nm |
| Rel. Var. | 0.039 |
| Skew | 30.962 |

| d(nm) | G(d) | C(d) | d(nm) | G(d) | C(d) | d(nm) | G(d) | C(d) |
|---|---|---|---|---|---|---|---|---|
| 3.5 | 0 | 0 | 13.7 | 0 | 100 | 53.4 | 0 | 100 |
| 4.0 | 0 | 0 | 15.5 | 0 | 100 | 60.5 | 0 | 100 |
| 4.5 | 0 | 0 | 17.6 | 0 | 100 | 68.4 | 0 | 100 |
| 5.1 | 55 | 17 | 19.9 | 0 | 100 | 77.4 | 0 | 100 |
| 5.8 | 86 | 45 | 22.5 | 0 | 100 | 87.6 | 0 | 100 |
| 6.5 | 100 | 76 | 25.4 | 0 | 100 | 99.1 | 0 | 100 |
| 7.4 | 53 | 93 | 28.8 | 0 | 100 | 112.2 | 0 | 100 |
| 8.4 | 21 | 100 | 32.6 | 0 | 100 | 127.0 | 0 | 100 |
| 9.5 | 0 | 100 | 35.9 | 0 | 100 | 143.7 | 0 | 100 |
| 10.7 | 0 | 100 | 41.7 | 0 | 100 | 162.6 | 0 | 100 |
| 12.1 | 0 | 100 | 47.2 | 0 | 100 | 184.0 | 0 | 100 |

Volume

| Sample ID | WT-G3 only (Combined) |
|---|---|
| Date - Time | Jul 16, 2018 16:49:36 |
| Operator ID | SF |
| Elapsed Time | 00:05:00 |
| Mean Diam. | 12.2 nm |
| Rel. Var. | 0.572 |
| Skew | 0.771 |

| d(nm) | G(d) | C(d) | d(nm) | G(d) | C(d) | d(nm) | G(d) | C(d) |
|---|---|---|---|---|---|---|---|---|
| 3.5 | 0 | 0 | 8.0 | 0 | 66 | 18.4 | 0 | 66 |
| 3.7 | 0 | 0 | 8.6 | 0 | 66 | 19.8 | 0 | 66 |
| 4.0 | 0 | 0 | 9.3 | 0 | 66 | 21.4 | 28 | 72 |
| 4.4 | 0 | 0 | 10.0 | 0 | 66 | 23.0 | 30 | 78 |
| 4.7 | 12 | 2 | 10.8 | 0 | 66 | 24.8 | 53 | 89 |
| 5.1 | 52 | 13 | 11.7 | 0 | 66 | 26.8 | 38 | 95 |
| 5.5 | 96 | 32 | 12.6 | 0 | 66 | 28.9 | 25 | 100 |
| 5.9 | 100 | 52 | 13.6 | 0 | 66 | 31.2 | 2 | 100 |
| 6.4 | 60 | 64 | 14.6 | 0 | 66 | 33.6 | 0 | 100 |
| 6.9 | 13 | 66 | 15.8 | 0 | 66 | 38.3 | 0 | 100 |
| 7.4 | 0 | 66 | 17.0 | 0 | 66 | 39.1 | 0 | 100 |

Intensity ▼

| Sample ID | WT-G3 only (Combined) |
|---|---|
| Date - Time | Jul 16, 2018 16:56:35 |
| Operator ID | SF |
| Elapsed Time | 00:05:00 |
| Mean Diam. | 7.2 nm |
| Rel. Var. | 0.000 |
| Skew | -0.001 |

| d(nm) | G(d) | C(d) | d(nm) | G(d) | C(d) | d(nm) | G(d) | C(d) |
|---|---|---|---|---|---|---|---|---|
| 6.7 | 0 | 0 | 7.2 | 100 | 76 | 7.8 | 0 | 100 |
| 6.7 | 0 | 0 | 7.3 | 51 | 94 | 7.9 | 0 | 100 |
| 6.8 | 0 | 0 | 7.3 | 22 | 100 | 7.9 | 0 | 100 |
| 6.8 | 0 | 0 | 7.4 | 0 | 100 | 8.0 | 0 | 100 |
| 6.9 | 0 | 0 | 7.4 | 0 | 100 | 8.0 | 0 | 100 |
| 6.9 | 0 | 0 | 7.5 | 0 | 100 | 8.1 | 0 | 100 |
| 7.0 | 0 | 0 | 7.5 | 0 | 100 | 8.1 | 0 | 100 |
| 7.0 | 0 | 0 | 7.6 | 0 | 100 | 8.2 | 0 | 100 |
| 7.1 | 16 | 5 | 7.6 | 0 | 100 | 8.3 | 0 | 100 |
| 7.1 | 55 | 20 | 7.7 | 0 | 100 | 8.3 | 0 | 100 |
| 7.2 | 93 | 47 | 7.7 | 0 | 100 | 8.4 | 0 | 100 |

Intensity ▼

| Sample ID | WT-G3 only (Combined) |
| Date - Time | Jul 16, 2018 17:08:55 |
| Operator ID | SF |
| Elapsed Time | 00:05:00 |
| Mean Diam. | 23.2 nm |
| Rel. Var. | 2.113 |
| Skew | 1.659 |

| d(nm) | G(d) | C(d) | d(nm) | G(d) | C(d) | d(nm) | G(d) | C(d) |
|---|---|---|---|---|---|---|---|---|
| 3.5 | 0 | 0 | 13.7 | 0 | 80 | 53.4 | 0 | 80 |
| 4.0 | 0 | 0 | 15.5 | 0 | 80 | 60.5 | 7 | 82 |
| 4.5 | 0 | 0 | 17.6 | 0 | 80 | 68.4 | 7 | 83 |
| 5.1 | 26 | 7 | 19.9 | 0 | 80 | 77.4 | 14 | 87 |
| 5.8 | 59 | 22 | 22.5 | 0 | 80 | 87.6 | 15 | 91 |
| 6.5 | 100 | 48 | 25.4 | 0 | 80 | 99.1 | 21 | 97 |
| 7.4 | 77 | 68 | 28.8 | 0 | 80 | 112.2 | 13 | 100 |
| 8.4 | 44 | 80 | 32.6 | 0 | 80 | 127.0 | 0 | 100 |
| 9.5 | 0 | 80 | 36.9 | 0 | 80 | 143.7 | 0 | 100 |
| 10.7 | 0 | 80 | 41.7 | 0 | 80 | 162.6 | 0 | 100 |
| 12.1 | 0 | 80 | 47.2 | 0 | 80 | 184.0 | 0 | 100 |

Intensity

| Sample ID | ASF only (Combined) |
|---|---|
| Date - Time | Jul 16, 2018 17:30:55 |
| Operator ID | SF |
| Elapsed Time | 00:05:00 |
| Mean Diam. | 1.2 nm |
| Rel. Var. | 0.026 |
| Skew | 3.062 |

| d(nm) | G(d) | C(d) | d(nm) | G(d) | C(d) | d(nm) | G(d) | C(d) |
|---|---|---|---|---|---|---|---|---|
| 0.8 | 0 | 0 | 4.5 | 0 | 100 | 25.2 | 0 | 100 |
| 0.9 | 0 | 0 | 5.2 | 0 | 100 | 29.5 | 0 | 100 |
| 1.1 | 100 | 57 | 6.1 | 0 | 100 | 34.5 | 0 | 100 |
| 1.3 | 43 | 81 | 7.2 | 0 | 100 | 40.4 | 0 | 100 |
| 1.5 | 25 | 96 | 8.4 | 0 | 100 | 47.3 | 0 | 100 |
| 1.7 | 5 | 99 | 9.5 | 0 | 100 | 55.3 | 0 | 100 |
| 2.0 | 2 | 100 | 11.5 | 0 | 100 | 64.8 | 0 | 100 |
| 2.4 | 0 | 100 | 13.4 | 0 | 100 | 75.8 | 0 | 100 |
| 2.8 | 0 | 100 | 15.7 | 0 | 100 | 88.7 | 0 | 100 |
| 3.3 | 0 | 100 | 18.4 | 0 | 100 | 103.8 | 0 | 100 |
| 3.8 | 0 | 100 | 21.5 | 0 | 100 | 121.5 | 0 | 100 |

Number

| Sample ID | ASF only (Combined) |
| --- | --- |
| Date - Time | Jul 16, 2018 17:30:55 |
| Operator ID | SF |
| Elapsed Time | 00:05:00 |
| Mean Diam. | 1.4 nm |
| Rel. Var. | 0.753 |
| Skew | 21.955 |

| d(nm) | G(d) | C(d) | d(nm) | G(d) | C(d) | d(nm) | G(d) | C(d) |
| --- | --- | --- | --- | --- | --- | --- | --- | --- |
| 0.8 | 0 | 0 | 4.5 | 0 | 99 | 25.2 | 0 | 100 |
| 0.9 | 0 | 0 | 5.2 | 0 | 99 | 29.5 | 0 | 100 |
| 1.1 | 100 | 37 | 6.1 | 0 | 99 | 34.5 | 0 | 100 |
| 1.3 | 69 | 62 | 7.2 | 0 | 99 | 40.4 | 0 | 100 |
| 1.5 | 65 | 85 | 8.4 | 0 | 99 | 47.3 | 0 | 100 |
| 1.7 | 22 | 94 | 9.8 | 1 | 99 | 55.3 | 0 | 100 |
| 2.0 | 14 | 99 | 11.5 | 1 | 100 | 64.8 | 0 | 100 |
| 2.4 | 0 | 99 | 13.4 | 1 | 100 | 75.8 | 0 | 100 |
| 2.8 | 0 | 99 | 15.7 | 0 | 100 | 88.7 | 0 | 100 |
| 3.3 | 0 | 99 | 18.4 | 0 | 100 | 103.8 | 0 | 100 |
| 3.8 | 0 | 99 | 21.5 | 0 | 100 | 121.5 | 0 | 100 |

Volume

| Sample ID | ASF only (Combined) |
| Date - Time | Jul 16, 2018 17:30:55 |
| Operator ID | SF |
| Elapsed Time | 00:05:00 |
| Mean Diam. | 1.3 nm |
| Rel. Var. | 0.096 |
| Skew | 27.341 |

| d(nm) | G(d) | C(d) | d(nm) | G(d) | C(d) | d(nm) | G(d) | C(d) |
|---|---|---|---|---|---|---|---|---|
| 0.8 | 0 | 0 | 4.5 | 0 | 100 | 25.2 | 0 | 100 |
| 0.9 | 0 | 0 | 5.2 | 0 | 100 | 29.5 | 0 | 100 |
| 1.1 | 100 | 44 | 6.1 | 0 | 100 | 34.5 | 0 | 100 |
| 1.3 | 59 | 70 | 7.2 | 0 | 100 | 40.4 | 0 | 100 |
| 1.5 | 48 | 91 | 8.4 | 0 | 100 | 47.3 | 0 | 100 |
| 1.7 | 14 | 97 | 9.8 | 0 | 100 | 55.3 | 0 | 100 |
| 2.0 | 7 | 100 | 11.5 | 0 | 100 | 64.8 | 0 | 100 |
| 2.4 | 0 | 100 | 13.4 | 0 | 100 | 75.8 | 0 | 100 |
| 2.8 | 0 | 100 | 15.7 | 0 | 100 | 88.7 | 0 | 100 |
| 3.3 | 0 | 100 | 18.4 | 0 | 100 | 103.8 | 0 | 100 |
| 3.8 | 0 | 100 | 21.5 | 0 | 100 | 121.5 | 0 | 100 |

Surface Area

TARGETED CHONDROITINASE ABC FUSION PROTEINS AND COMPLEXES THEREOF

RELATED APPLICATIONS

This application claims the benefit under 35 U.S.C. 119(e) of United States provisional patent application Ser. No. 62/751,146 filed Oct. 26, 2018 entitled "TARGETED CHONDROITINASE ABC FUSION PROTEINS AND COMPLEXES THEREOF," the entire contents of which are incorporated herein by reference.

This application is a national stage filing under 35 U.S.C. § 371 of International Patent Application No. PCT/US2019/058230, filed Oct. 25, 2019, which claims the benefit under 35 U.S.C. § 119 (e) of U.S. Provisional Patent Application No. 62/751,146, filed Oct. 26, 2018, entitled "TARGETED CHONDROITINASE ABC FUSION PROTEINS AND COMPLEXES THEREOF," each of which is incorporated herein by reference in its entirety.

The instant application contains a Sequence Listing which has been submitted in ASCII format via EFS-Web and is hereby incorporated by reference in its entirety. Said ASCII copy, created on Apr. 23, 2021, is named U119770187US01-SEQ-JOB.txt, and is 76,639 bytes in size.

STATEMENT REGARDING FEDERALLY SPONSORED RESEARCH

This invention was made with Government support EB019684 awarded by the National Institutes of Health. The Government has certain rights in the invention.

BACKGROUND

Glial scar formation is a reactive cellular process that occurs after injury to the central nervous system. It is also referred to as reactive gliosis or glial scarring. Similarly to other scarring in other organs and tissues, glial scarring is meant to guard and start wound healing within an injured central nervous system. Glial scarring can inhibit axon regeneration, inter alia, and thus may influence the ability of the central nervous system to heal in response to injury.

Many attractive enzyme drug candidates fail in clinical trials due to unfavorable pharmacokinetics, pharmacodynamics, and/or safety profiles. The enzyme chondroitinase ABC is currently in veterinary clinical trials for determining its efficacy for neural regeneration. A major drawback of this enzyme and its formulation currently under development and clinical testing is that it is unstable and is rapidly cleared from the tissue injury site. This results in an ineffective retention of the enzyme at a local site and limits its efficacy. In short, due to these stability and clearance issues, the enzyme simply is not retained long enough in an area so as to provide any therapeutic or other benefit or change. As such, there exists an unmet need for improved ChABC compositions.

SUMMARY

Described herein are targeted effector fusion proteins that can include a chondroitinase ABC polypeptide (ChABC) that can be capable of causing a biological effect in a target cell, tissue, and/or organ (e.g., a central nervous system cell, such as a glial cell) and a Galectin 3 (Gal3), which can act as a targeting moiety, that can be capable of directing the ChABC specifically to a desired cell, tissue, and/or organ (also referred to herein as a target cell, tissue or organ). In some aspects, the ChABC can be operatively linked to the Gal3 via a flexible linker or an alpha coil. In some embodiments, the targeted effector fusion proteins can self-assemble into multimers (also referred to herein as targeted effector fusion protein complexes). Also described herein are compositions and formulations of the targeted effector fusion proteins and complexes. The targeted effector fusion proteins, complexes thereof, compositions thereof, and formulations thereof described herein can be administered to a subject in need thereof. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Accordingly, in an aspect, the disclosure relates to a targeted effector fusion protein comprising: a chondroitinase ABC (ChABC) polypeptide; and a galectin-3 (Gal-3) polypeptide, wherein the Gal-3 is operatively linked to the ChABC polypeptide. In some embodiments, the ChABC polypeptide is directly fused to the Gal-3 polypeptide.

In some embodiments, the ChABC polypeptide is operatively linked to the Gal-3 polypeptide via a linker. In some embodiments, the linker is a flexible linker. In some embodiments, the linker is a rigid linker. In some embodiments, the flexible linker is selected from the group consisting of: a peptide, a polypeptide, a cross-linking reagent, and a coupling agent. In some embodiments, the Gal-3 polypeptide is capable of specifically binding to a carbohydrate.

In some embodiments, the linker is an alpha coil polypeptide or a random coil polypeptide. In some embodiments, the alpha coil polypeptide comprises one or more heptads, where each heptad has the general formula of A-B-C-D-E-F-G, wherein the amino acids A and D are each a hydrophobic amino acid, wherein the amino acids B, C, E, F, and G, are each independently selected from a hydrophilic amino acid, a polar amino acid, or a charged amino acid. In some embodiments, the linker comprises a polypeptide sequence that is about 90 to 100% identical to any one of SEQ ID NO: 17-32. In some embodiments, the alpha coil polypeptide is capable of multimerizing with one or more other alpha coils that are integrated in one or more other targeted effector fusion proteins. In some embodiments, the targeted effector fusion protein comprises a polypeptide sequence that is about 90% to 100% identical to any one of SEQ ID NO: 15-16.

In an aspect, the disclosure relates to a multimeric targeted effector fusion protein complex comprising: at least two targeted effector fusion proteins, wherein each of the at least two targeted effector proteins is a targeted effector fusion protein as disclosed herein, and the at least two targeted effector proteins are conjugated to each other by binding between the alpha coil polypeptide or random coil polypeptide in each of the at least two targeted effector proteins. In some embodiments, the multimeric targeted effector fusion protein complex is homogeneous. In some embodiments, the multimeric targeted effector fusion protein complex is heterogeneous.

In an aspect, the disclosure relates to a single fusion polypeptide sequence comprising: a chondroitinase ABC (ChABC) polypeptide; and a galectin-3 (Gal-3) polypeptide, wherein the Gal3 is operatively linked to the effector protein via a linker.

In an aspect, the disclosure relates to a single fusion polypeptide sequence comprising: a chondroitinase ABC (ChABC) polypeptide; and a galectin-3 (Gal-3) polypeptide, wherein the Gal3 is directly fused to the ChABC polypeptide.

In an aspect, the disclosure relates to a polynucleotide that encodes the targeted effector fusion proteins disclosed herein. In some embodiments, the polynucleotide has a sequence that is about 50% to 100% identical to any one of SEQ ID NO: 6-7. In an aspect, the disclosure relates to a vector comprising: a polynucleotide disclosed herein.

In an aspect, the disclosure relates to a single fusion polypeptide sequence comprising: at least two targeted effector fusion proteins as disclosed herein wherein each of the at least two targeted effector fusion proteins are directly fused at the C-terminus, N-terminus, or both the C-terminus and N-terminus of at least one other targeted effector fusion protein of the at least two targeted effector fusion proteins.

In some embodiments, the enzyme (e.g., ChABC polypeptide) is located at the N-terminus of the fusion protein. In some embodiments, the enzyme (e.g., ChABC polypeptide) is located at the C-terminus of the fusion protein. In some embodiments, the Gal3 polypeptide is located at the N-terminus of the fusion protein. In some embodiments, the Gal3 polypeptide is located at the C-terminus of the fusion protein. Accordingly, in some embodiments, the enzyme (e.g., ChABC polypeptide) is located at the N-terminus of the fusion protein and Gal3 polypeptide is located at the C-terminus of the fusion protein and they are either directly connected or via a linker. In other embodiments, the Gal3 polypeptide is located at the N-terminus of the fusion protein and enzyme (e.g., ChABC polypeptide) is located at the C-terminus of the fusion protein and they are either directly connected or via a linker. In an aspect, the disclosure relates to a single fusion polypeptide sequence comprising: at least two targeted effector fusion proteins as disclosed herein, wherein each of the at least two targeted effector fusion proteins are operatively linked at the C-terminus, N-terminus, or both the C-terminus and N-terminus to at least one other targeted effector fusion protein of the at least two targeted effector fusion proteins via one or more additional amino acids.

In some embodiments, a ChABC polypeptide is a full length ChABC. In some embodiments, a ChABC polypeptide is a sequence variant (e.g., containing one or more amino acid truncations and/or substitutions). In some embodiments, a Gal3 polypeptide is a full length Gal3. In some embodiments, a Gal3 polypeptide is a sequence variant (e.g., containing one or more amino acid truncations and/or substitutions). In some embodiments, a ChABC polypeptide is a human, non-human primate, or other mammalian polypeptide or variant thereof. In some embodiments, a Gal3 polypeptide is a human, non-human primate, or other mammalian polypeptide or variant thereof.

In an aspect, the disclosure relates to a vector comprising: a polynucleotide encoding a single fusion polypeptide as disclosed herein. In an aspect, the disclosure relates a pharmaceutical formulation comprising: a targeted effector fusion protein as disclosed herein; and a pharmaceutically acceptable carrier. In some embodiments, the pharmaceutical formulation comprises: a multimeric targeted effector fusion protein complex as disclosed herein; and a pharmaceutically acceptable carrier.

In an aspect, the disclosure relates to a method comprising: administering a targeted effector fusion protein as disclosed herein or a targeted effector fusion protein complex as in disclosed herein. In some embodiments, the subject has a disease. In some embodiments, the subject has a central nervous system injury or symptom thereof. In some embodiments, the subject has glial scarring. In some embodiments, the subject has a ChABC deficiency. In some embodiments, the subject is in need of neuron regeneration.

In some embodiments, the administration is local.

BRIEF DESCRIPTION OF THE DRAWINGS

Further aspects of the present disclosure will be readily appreciated upon review of the detailed description of its various embodiments, described below, when taken in conjunction with the accompanying drawings.

FIGS. 3A-3G show carbohydrate-binding properties of monomeric G3 fusion proteins and trimeric nanoassemblies. a, b NL-G3, NL-TT-G3, GFP-G3, and GFP-TT-G3 binding to asialofetuin (ASF), laminin, collagen IV, aggrecan, and collagen I (negative control) adsorbed onto plastic. c Micrographs taken of NL luminescence or GFP fluorescence localized to a laminin coffee ring adsorbed onto glass. Fusion proteins were mixed with soluble LacNAc to demonstrate inhibition of binding to adsorbed glycoconjugates for a, b, c. d shows cumulative release of GFP and ChABC-gal3 (in monomer and trimer form) as a percentage from luminin extracellular matrix over time. e Competitive inhibition of binding of NL-G3 and NL-TT-G3 to adsorbed ASF by soluble LacNAc. f Saturation binding of GFP-G3 and GFP-TT-G3 to adsorbed ASF and laminin. g Tryptophan fluorescence quenching of wild-type G3 (WT-G3), NLG3, and NL-TT-G3 via binding to soluble LacNAc. N=3, mean±s.d. for a, b, d, e, f. Data points at or above baseline signal are shown as open circles in a and b. Data for WT-G3 appear as squares/traces, for monomeric G3 fusion proteins as bars/circles/traces, and trimeric nanoassemblies as bars/triangles/traces.

FIGS. 4A-4G show extracellular signaling activity of monomeric G3 fusion proteins and trimeric nanoassemblies. a Micrographs demonstrating NL-G3 and NL-TT-G3 bioluminescence on Jurkat T cells using a blue fluorescence filter. b Micrographs demonstrating GFP-G3 and GFP-TT-G3 fluorescence on Jurkat T cells using a green fluorescence filter. c Amount of NL or GFP bound to Jurkat T cells after 4 h incubation with NL-G3, NL-TT-G3, GFP-G3, or GFP-TT-G3. d Bright-field micrographs of Jurkat T cells incubated with PBS (untreated, negative control), WT-G3 (positive control), NL-G3, or NL-TT-G3 for 4 h. e Percent metabolic activity of Jurkat T cells incubated with WT-G3 (positive control), NL-G3, or NL-TT-G3 for 4 h. f hIL-2 produced by Jurkat T cells after incubation with PBS (negative control), WT-G3 (positive control), NL-G3, or NL-TT-G3 for 24 h. Lactose was added as an inhibitor of G3 binding to Jurkat T cells. g Asialofetuin (ASF) (7 M) precipitation with various quantities of WT-G3, NL-G3, or NL-TT-G3 as measured by light scattering and absorption at 420 nm. N=4, mean±s.d., *p<0.001, Student's t-test for c. N=4, mean±s.d., n.s. is no significant differences, **p<0.0001, ANOVA with Tukey's post-hoc for e and f. N=3, mean±s.d. for g. Scale bar=25 m for a, b. Scale bar=50 μm for d. Data points at or above baseline signal are shown as open circles in c, e, and f. Data for WT-G3 appear as bars/squares/traces, for monomeric G3 fusion proteins as bars/circles/traces, and for trimeric nanoassemblies as bars/triangles/traces.

Figure 5A:
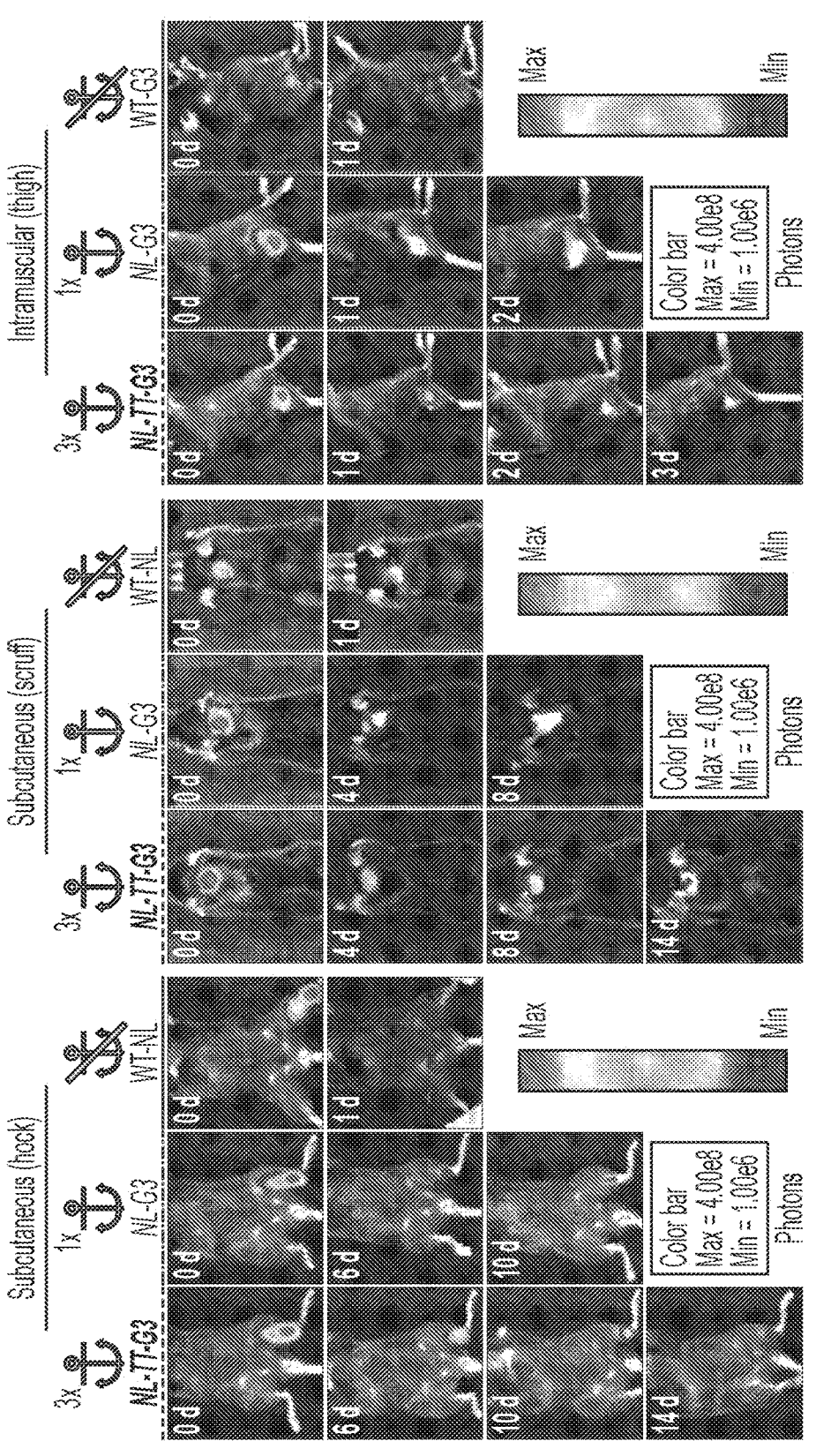
Figures 5B, 5C:
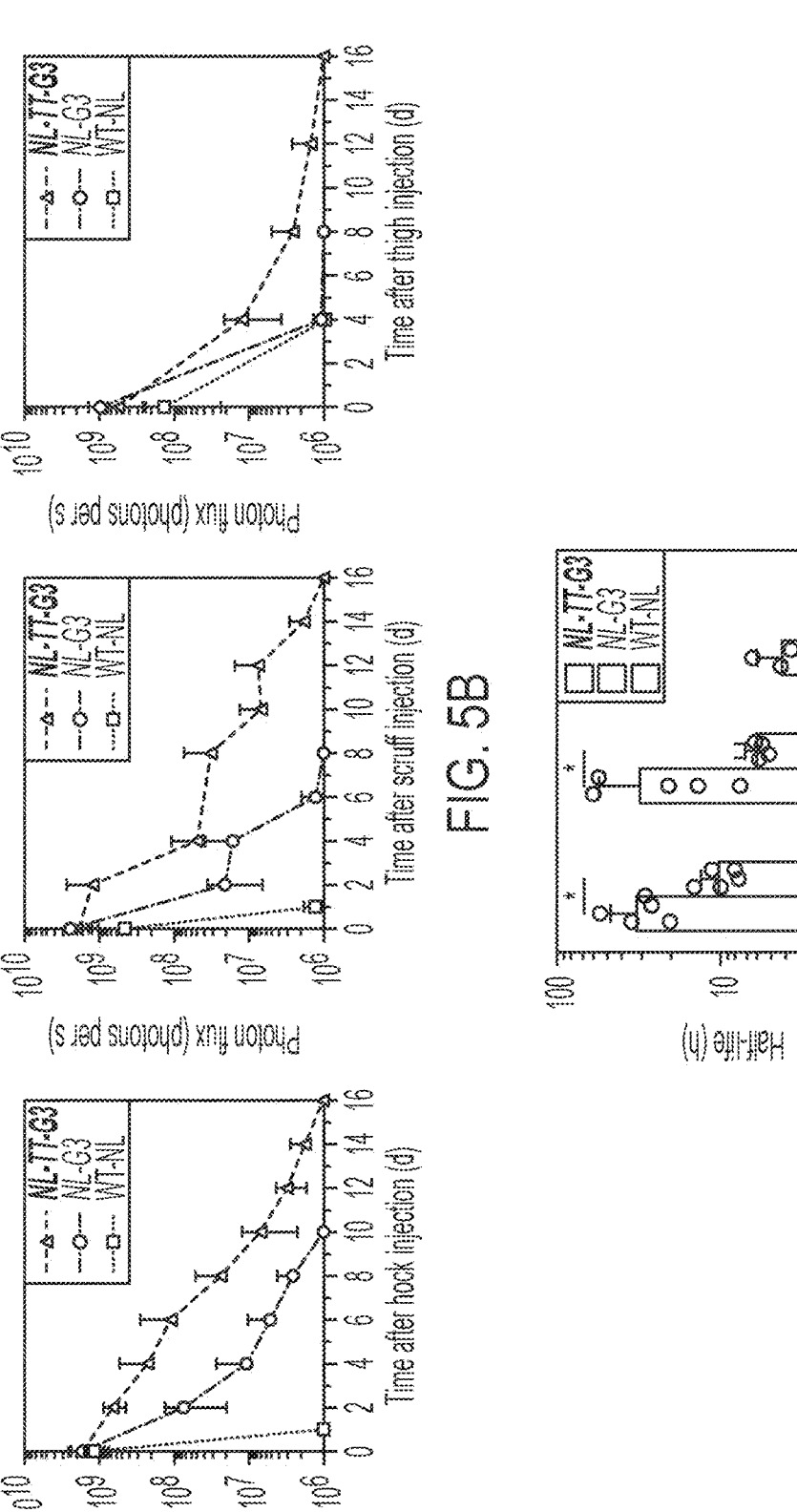

FIGS. 5A-5C show injection site half-life of monomeric G3 fusion proteins and trimeric nanoassemblies. a Bioluminescence images and b photon flux at various time points for mice that received NL-TT-G3, NL-G3, or WT-NL (equivalent moles of NL) in the hock, scruff, or thigh. c Biocatalytic activity half-life of NL-TT-G3, NL-G3, or WT-NL in different tissues. N=5, mean±s.d., *p<0.05, ANOVA with Tukey's post-hoc. In c, open circles represent each half-life calculation, closed circle represents individual animals for which half-life could not be accurately calculated due to rapid enzyme clearance from the injection site, and number sign represents groups for which half-life could not be accurately calculated due to rapid enzyme clearance from the injection site (signal at t=24 was at baseline for 3 or more animals in a cohort). Data for WT-NL appear as bars/squares/traces, NL-G3 as bars/circles/traces, and NL-TT-G3 as bars/triangles/traces.

FIGS. 6A-6D show circulating concentration and proteolysis of monomeric G3 fusion proteins and trimeric nanoassemblies. a Percent of NL, by total mass injected, in blood samples collected over time after subcutaneous injection into the hock. b Percent of NL activity, relative to NL activity at the initial timepoint, in 25% mouse serum in vitro. c Schematic of ECM proteases, such as collagenase and other MMPs, digesting the N-terminal domain (NTD) of G3, thereby separating the carbohydrate-recognition domain (CRD) of G3 from the enzyme fusion partner. d SDS-PAGE analysis of collagenase-mediated digestion of WT-G3, NL-G3, and NL-TT-G3. Uncropped gel image found in FIG. 33. N=5, mean±s.d. for a. N=3, mean±s.d. for b. Data for NL-G3 appear as circles/traces and NL-TT-G3 as triangles/traces.

Figures 7A, 7B, 7C, 8:
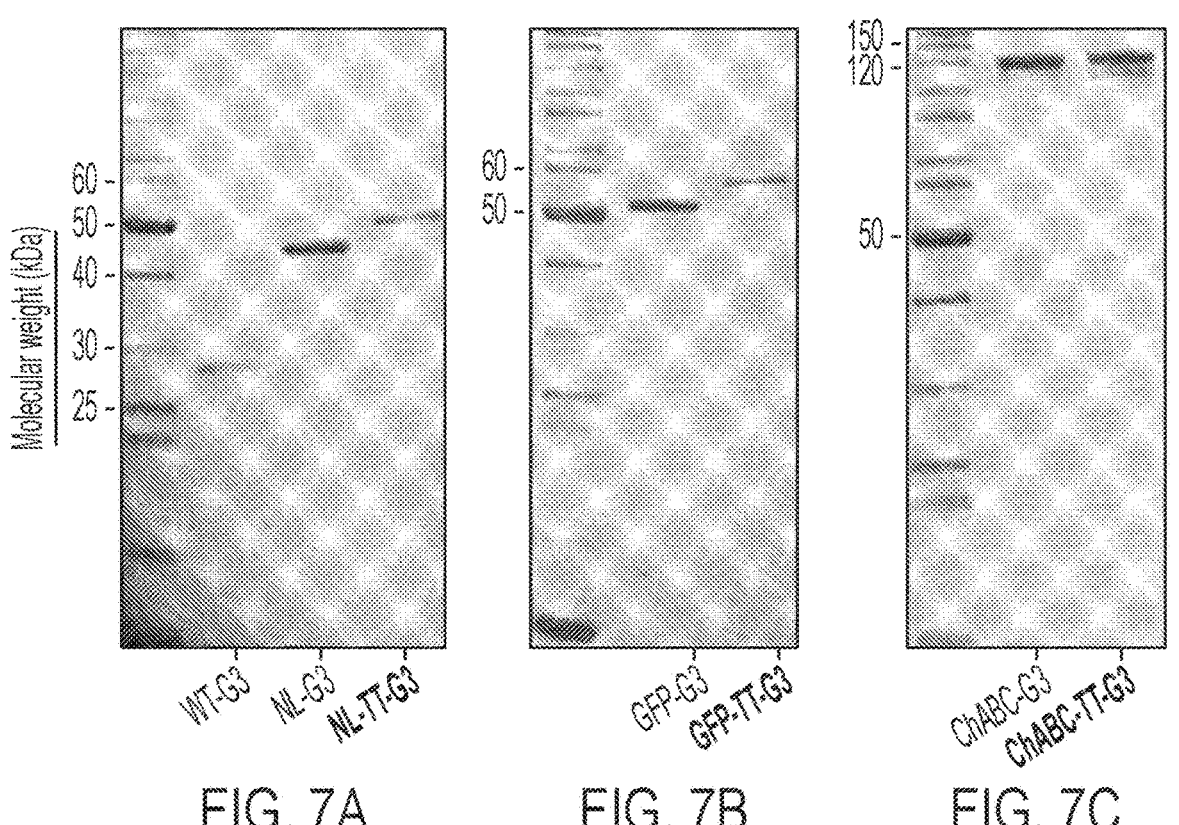

FIGS. 7A-7C show SDS-PAGE gels of monomeric G3 fusion proteins and trimeric nanoassemblies compared to wild-type galectin-3 (WT-G3). a WT-G3, NL-G3, and NL-TT-G3; b GFPG3 and GFP-TT-G3; c ChABC-G3 and ChABC-TT-G3.

FIG. 8 shows a table demonstrating the theoretical molecular weights of G3 fusions.

Figures 9A, 9B, 9C:
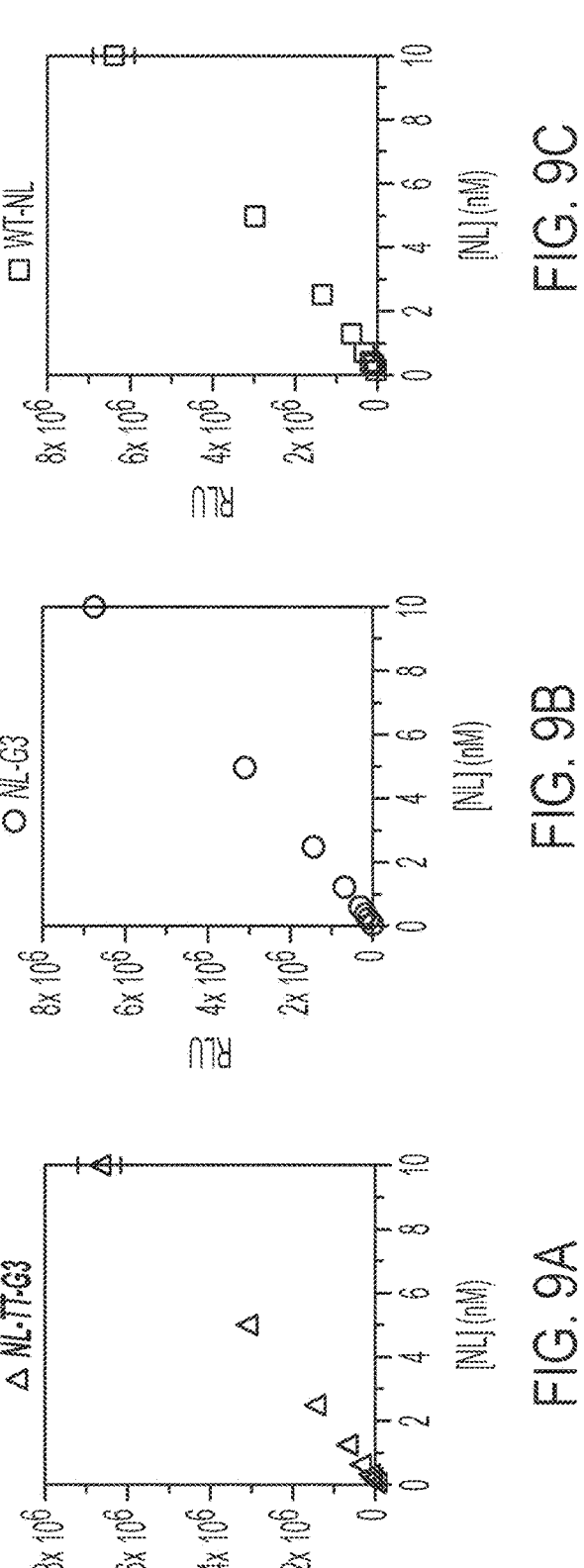

FIGS. 9A-9C show luciferase activity of monomeric G3 fusion proteins and trimeric nanoassemblies compared to wild-type NanoLuc™ (WT-NL). a NL-TT-G3 (triangles), b NL-G3 (circles), and c WT-NL (squares). N=3, mean±s.d.

Figures 10A, 10B, 10C:
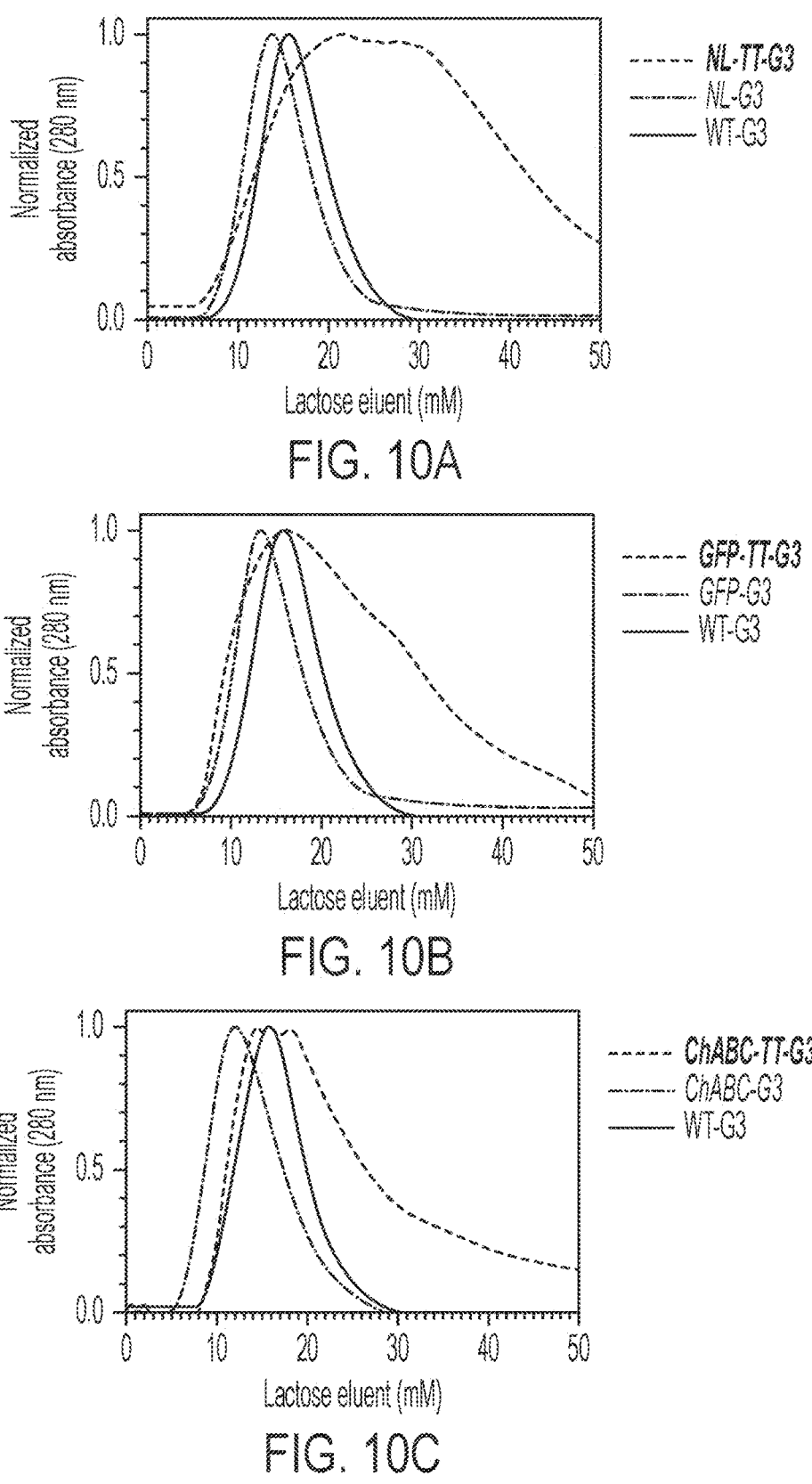
Figure 13A:
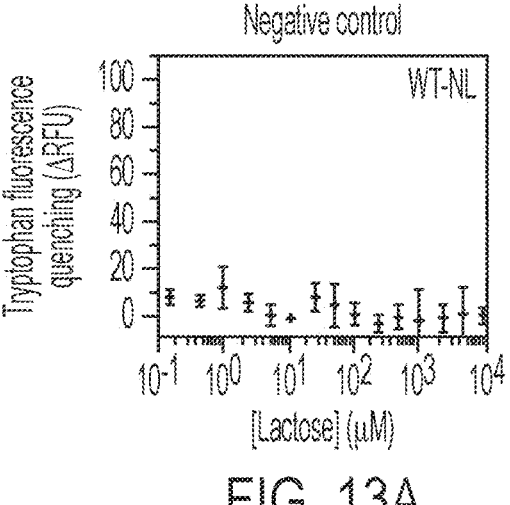
Figure 13B:
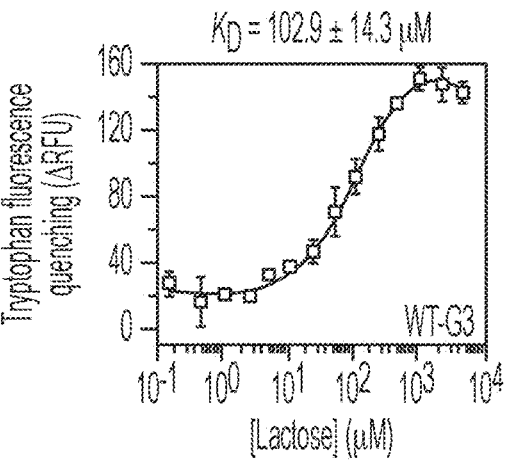
Figure 13C:
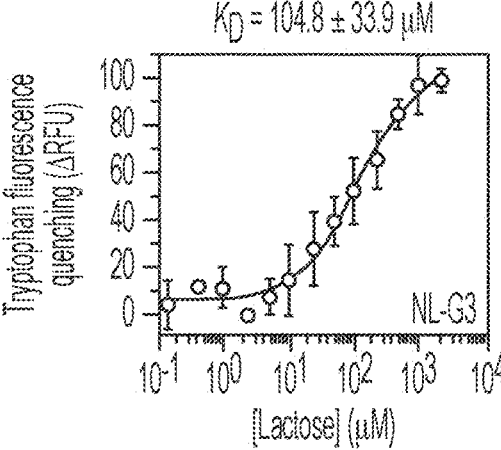
Figure 13D:
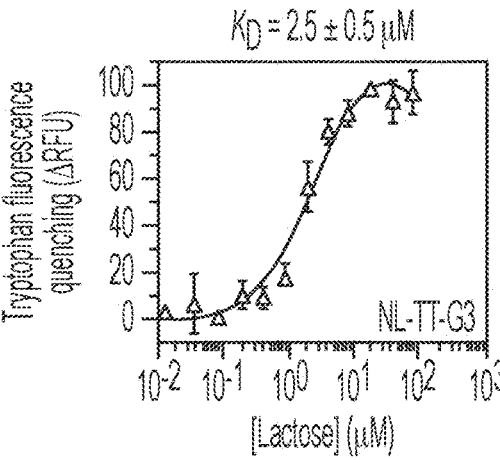
Figures 14A, 14B, 14C, 14D:
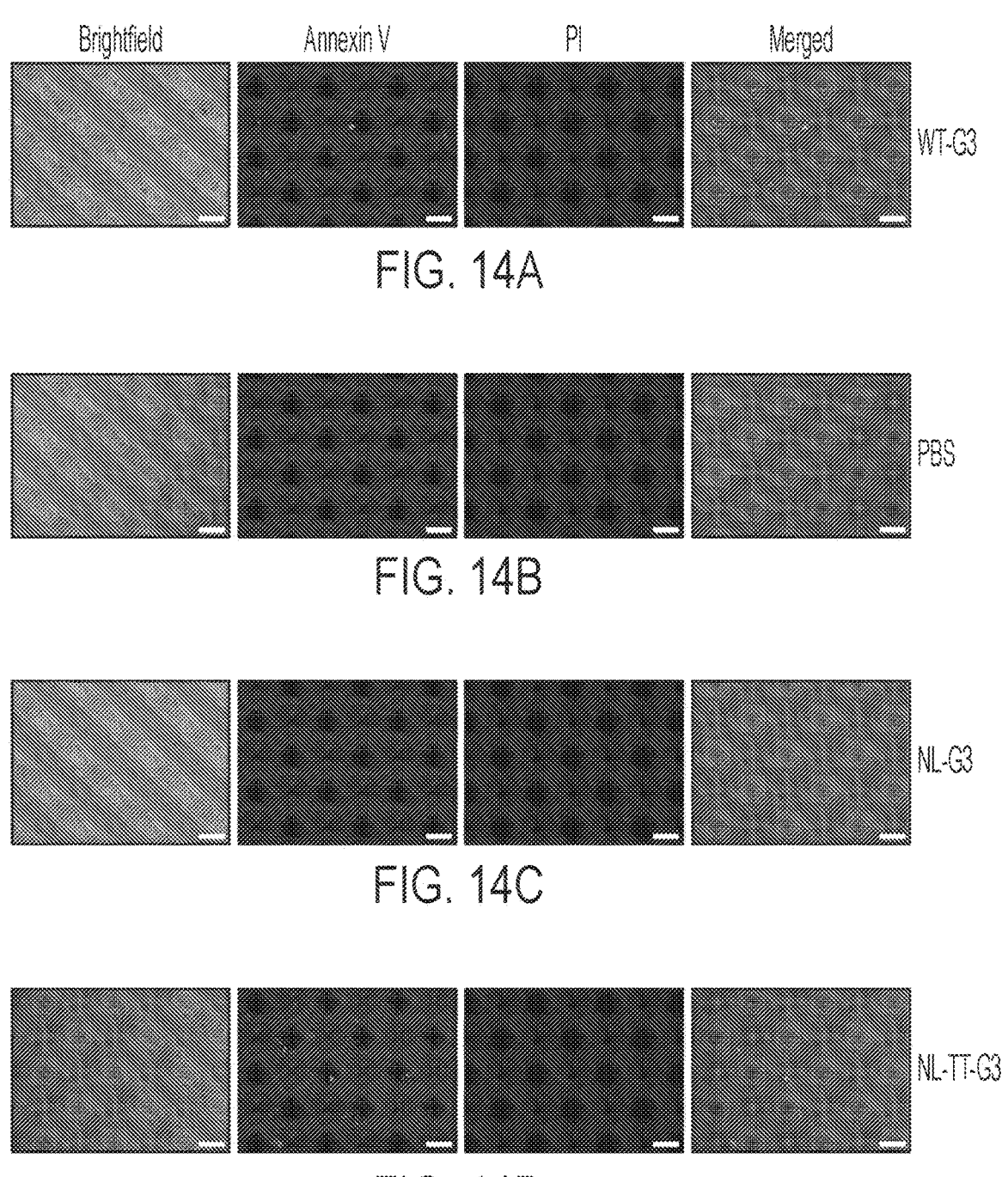
Figures 15A, 15B, 15C, 15D:
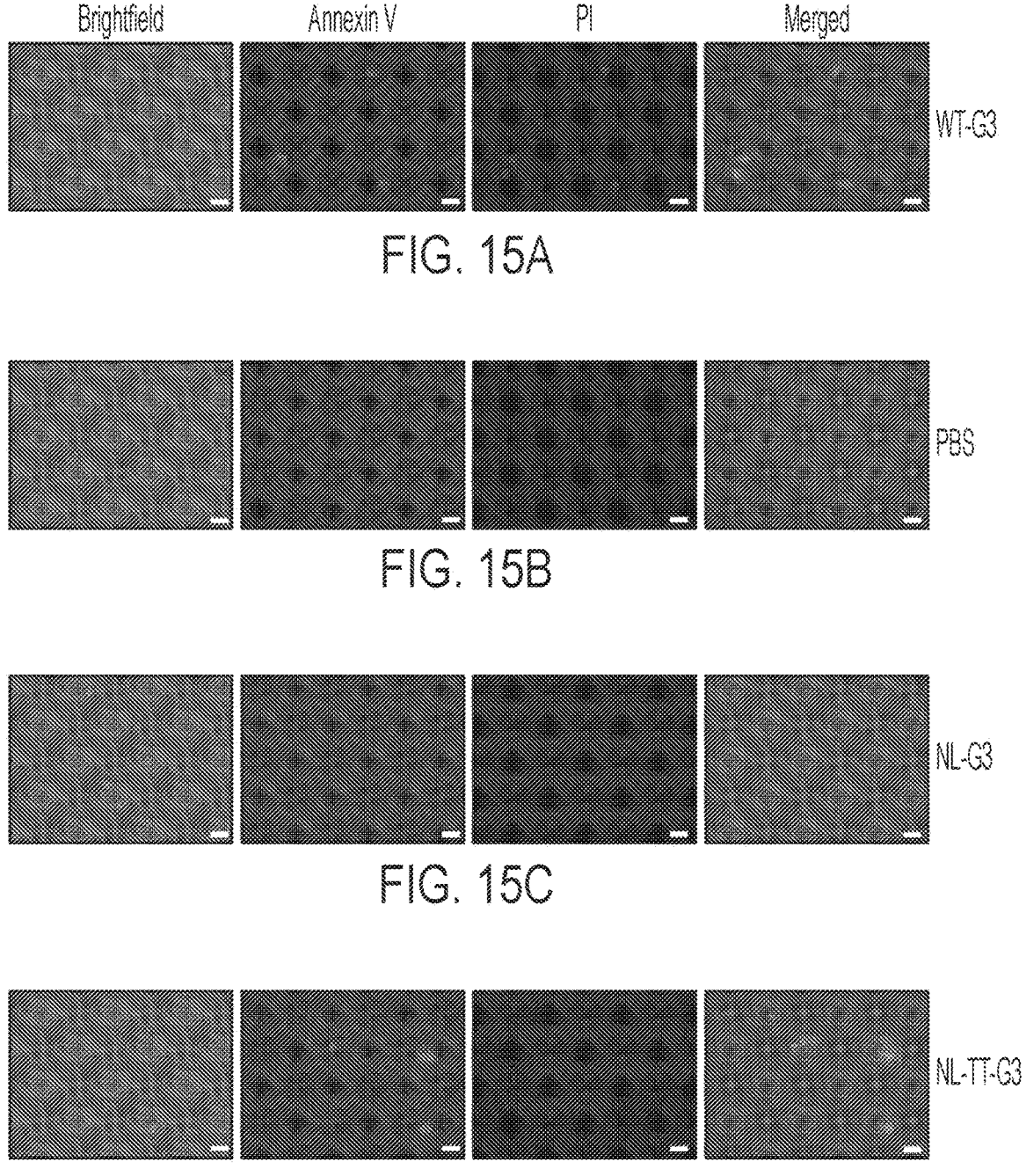
Figures 16A, 16B, 16C, 16D, 16E, 16F, 16G, 16H:
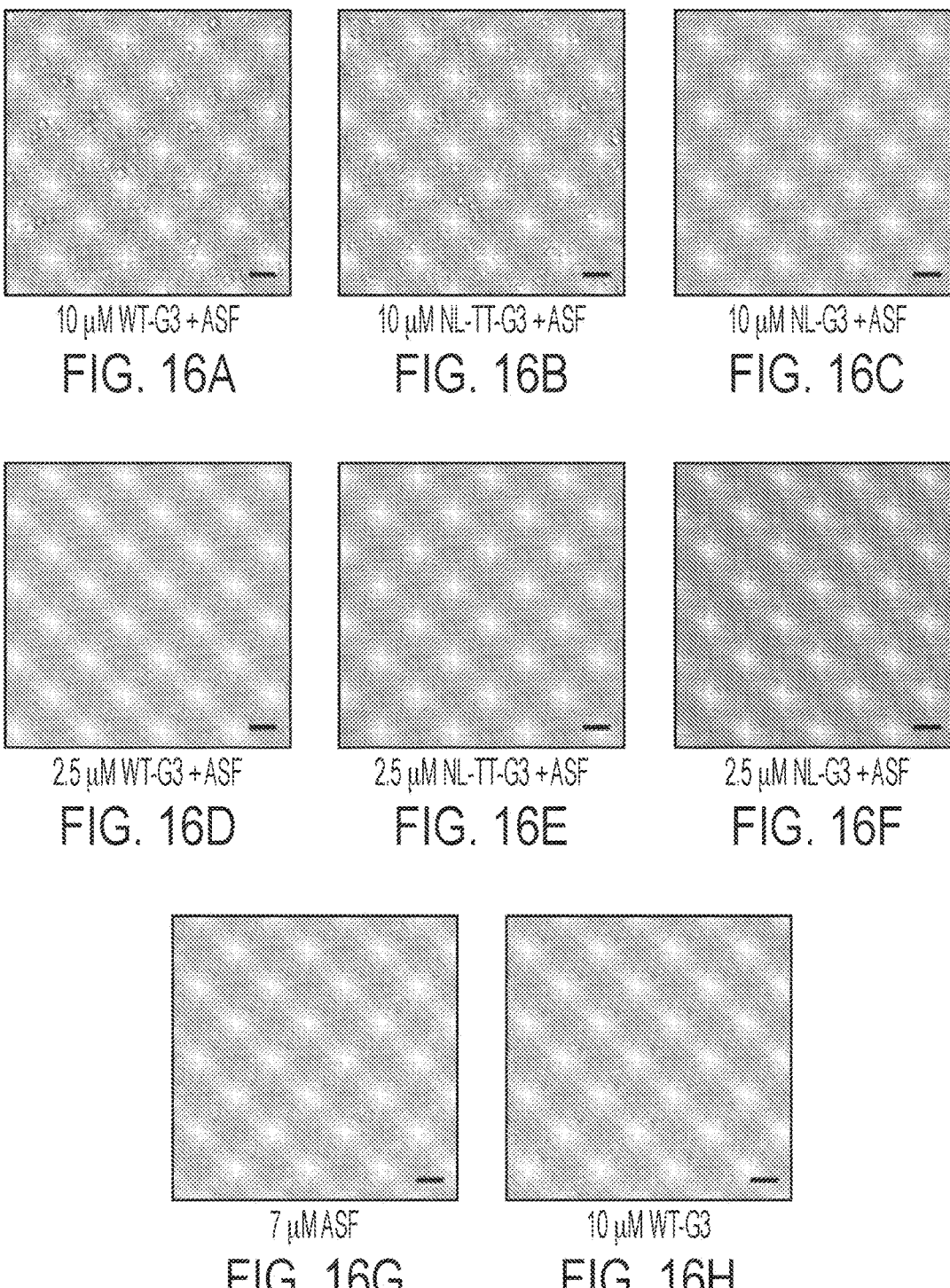
Figure 17A:
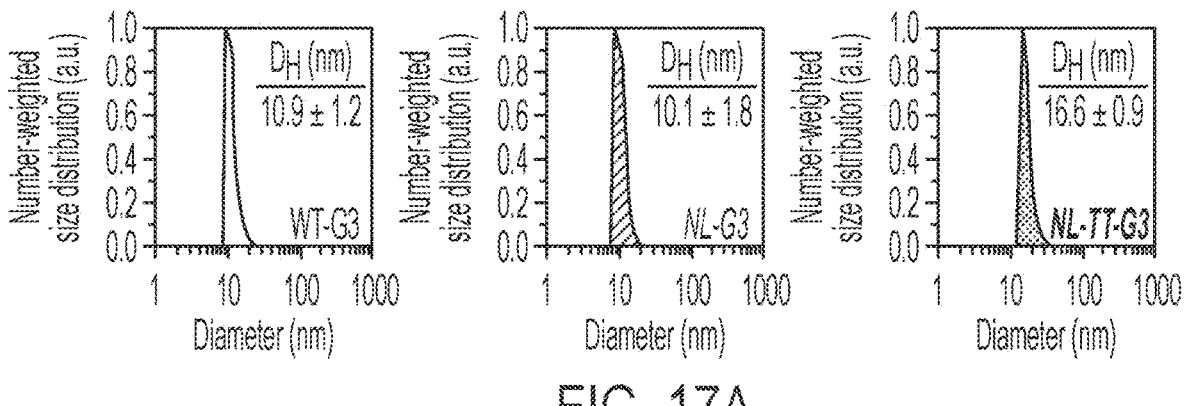
Figure 17B:
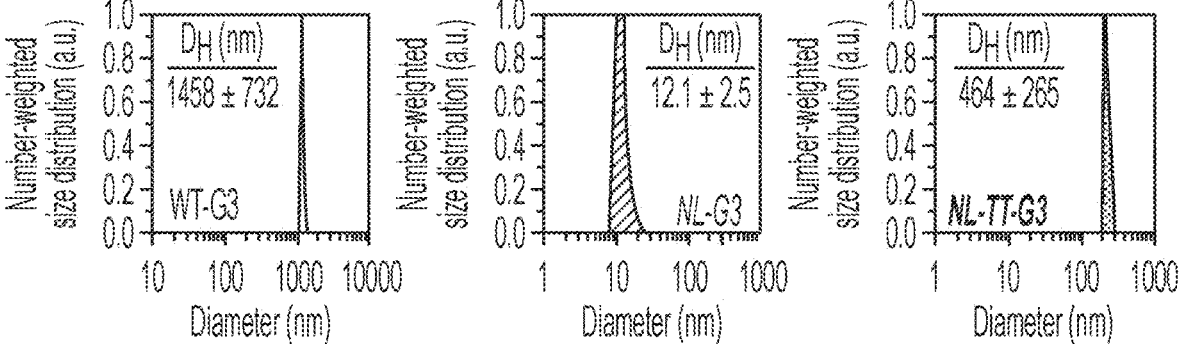
Figures 17C, 17D:
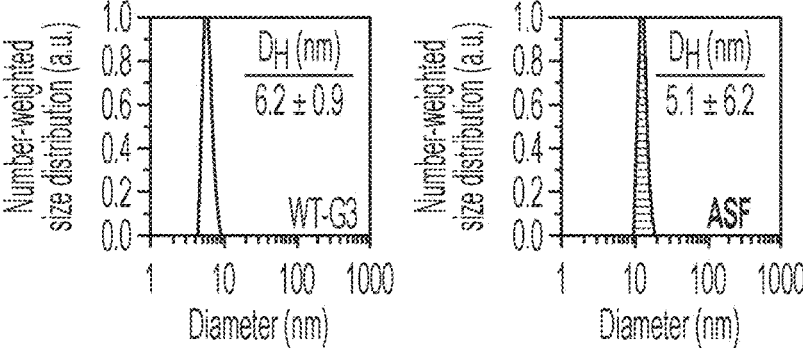

FIGS. 10A-10C show lactose affinity chromatography of monomeric G3 fusion proteins and trimeric nanoassemblies compared to wild-type galectin-3 (WT-G3). a NL-TT-G3, NL-G3, and WTG3; b GFP-TT-G3, GFP-G3, and WT-G3; c ChABC-TT-G3, ChABC-G3, and WT-G3. Trimeric nanoassemblies are presented as dashed lines, monomeric G3 fusion proteins are presented as dashed lines, and WT-G3 is presented as dashed lines.

Figures 3A, 3B:
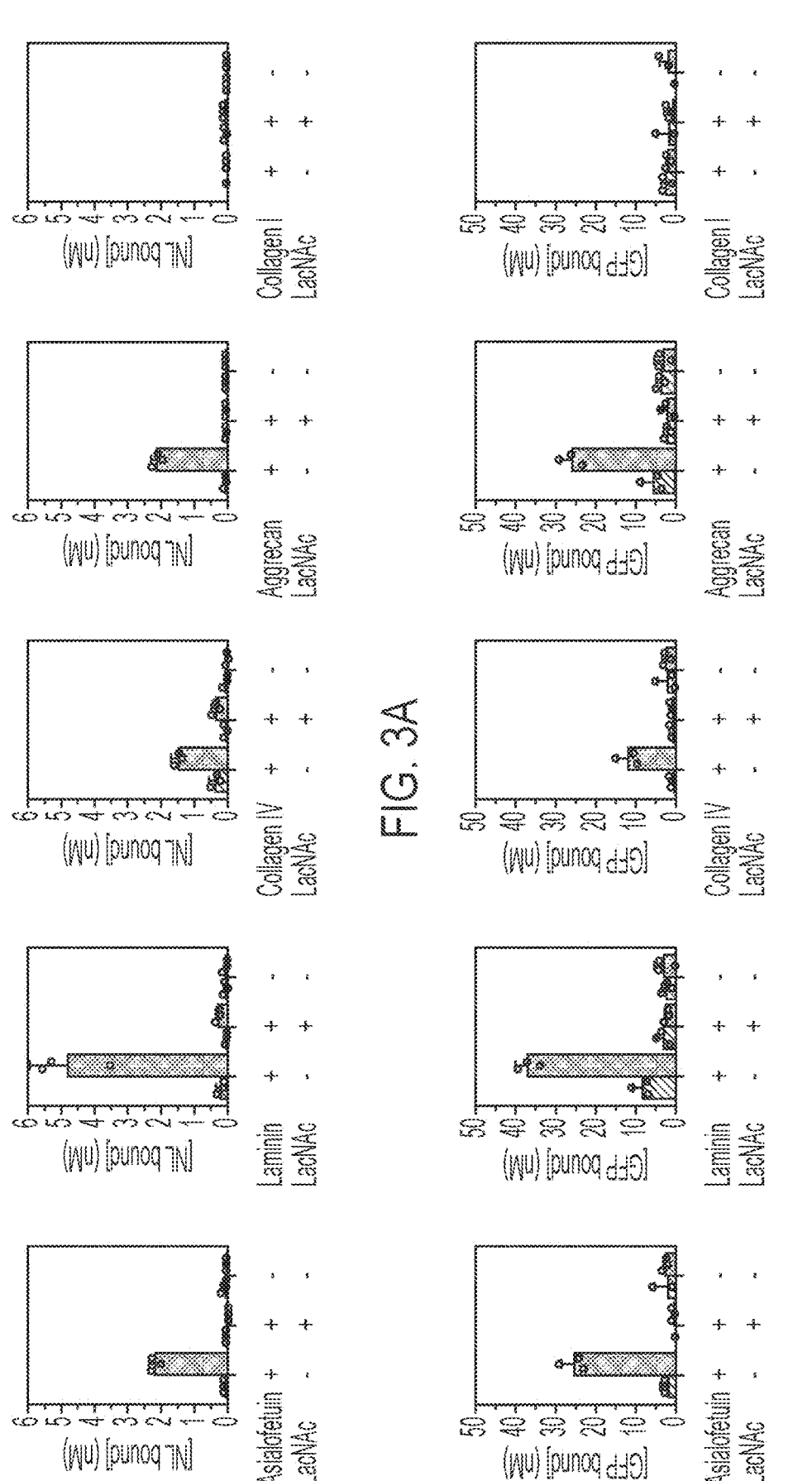
Figure 3C:
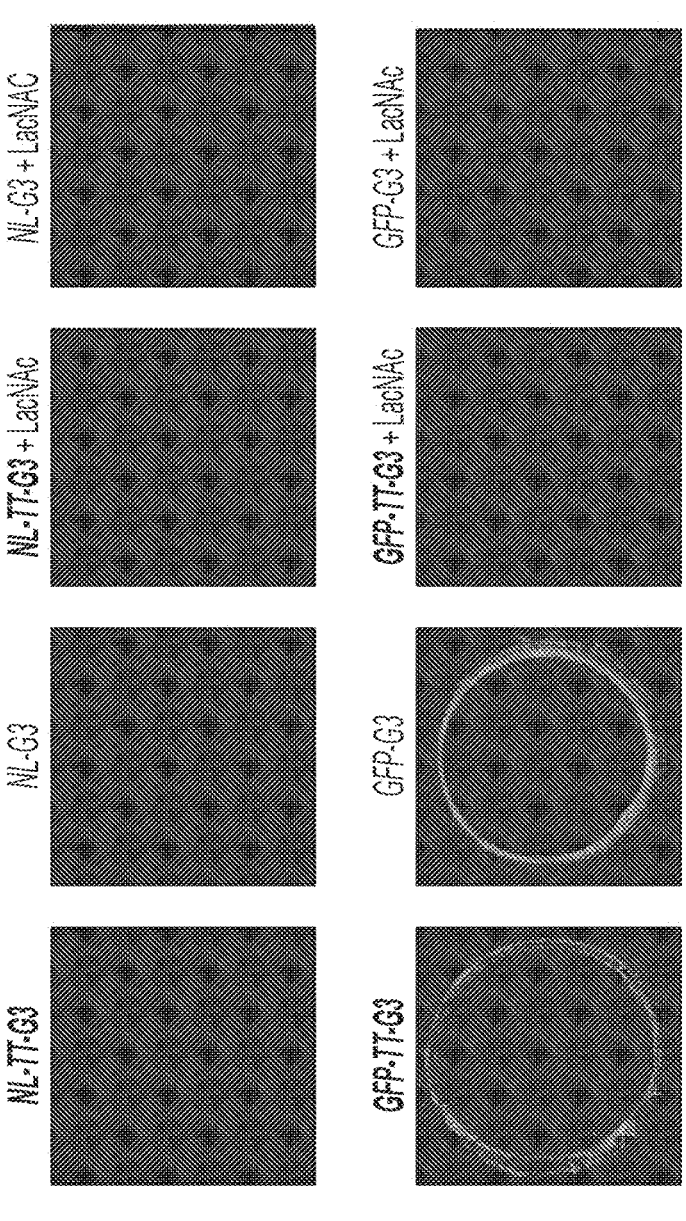
Figure 3D:
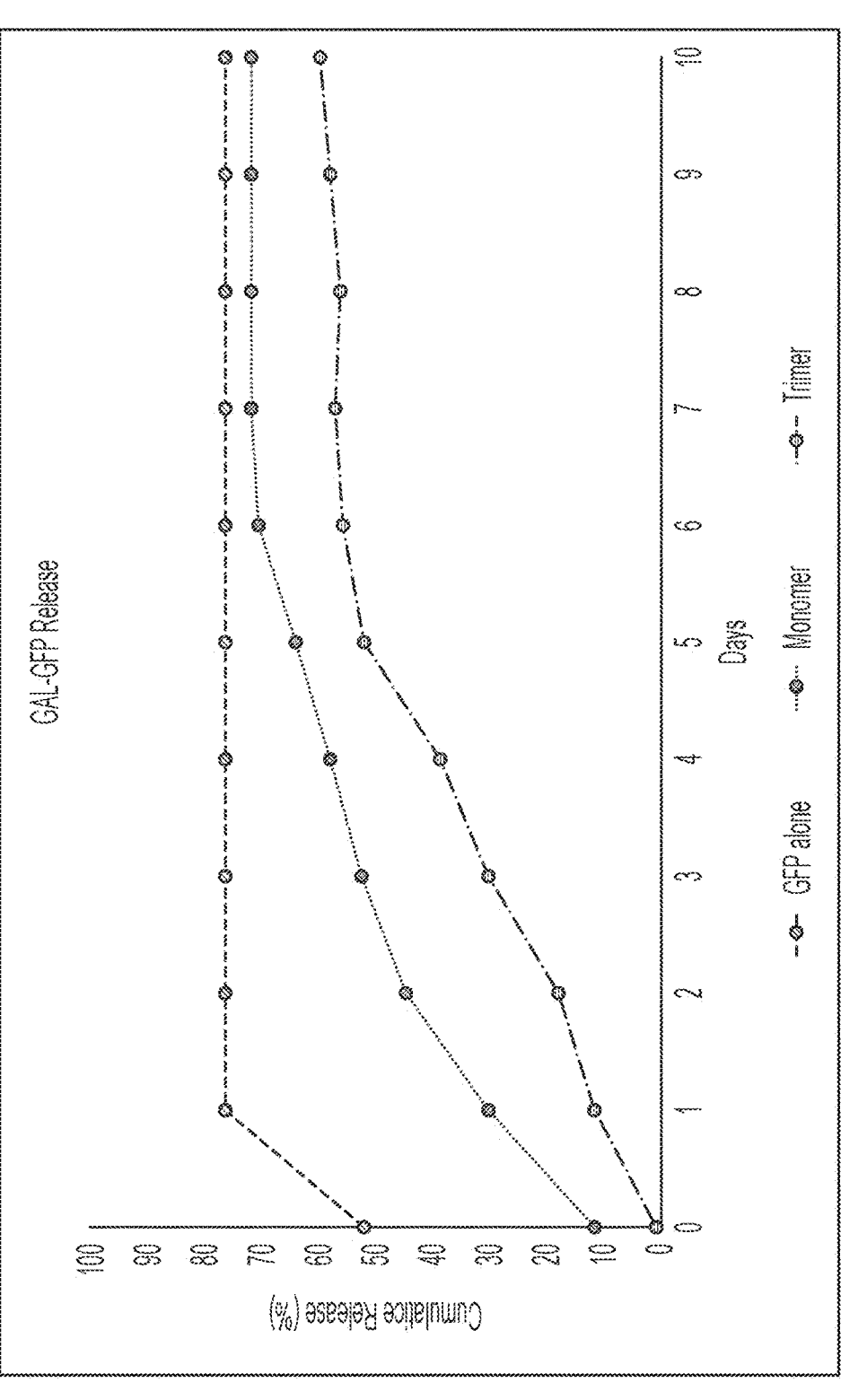
Figures 3E, 3F:
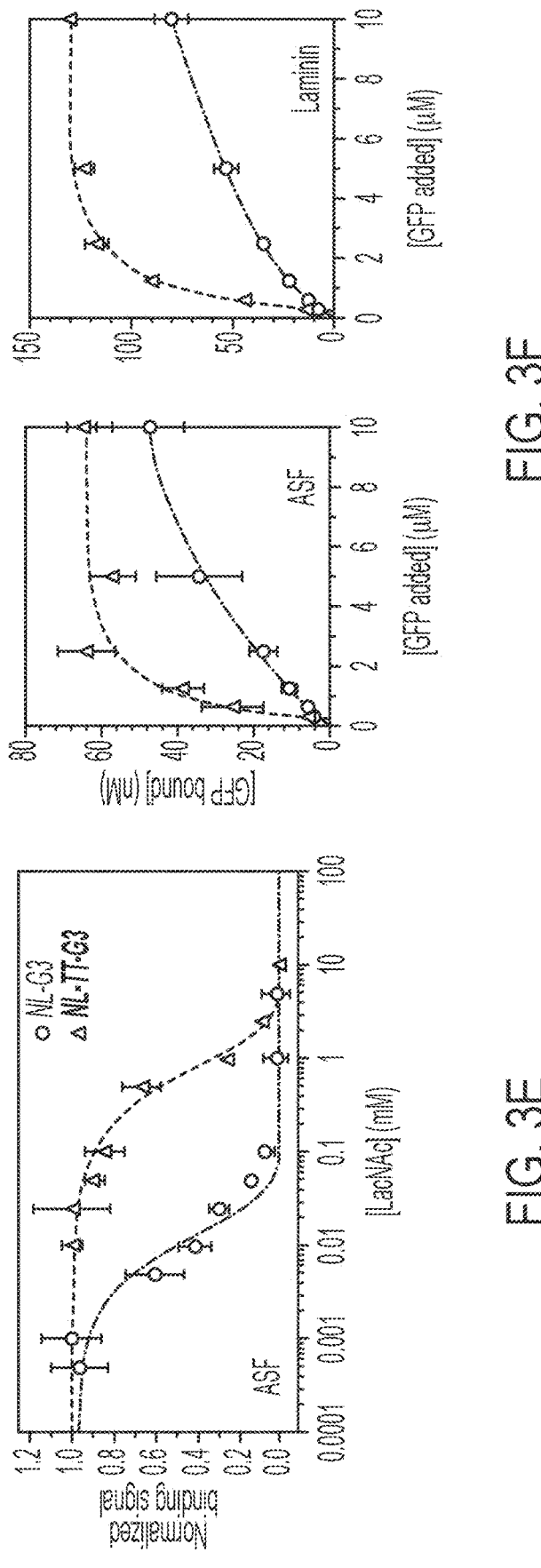

FIGS. 11A-11B show Scatchard analysis of saturating binding data from FIG. 3F for monomeric G3 fusion proteins and trimeric nanoassemblies binding to adsorbed glycoprotein. a GFP-G3 and GFP-TT-G3 binding to asialofetuin (ASF). b GFP-G3 and GFP-TT-G3 binding to laminin. GFP-G3 is presented as circles and GFP-TT-G3 is presented as triangles.

FIG. 12 shows GAG binding competition assay. NL-G3 or NL-TT-G3 were mixed with chondroitin sulfate-A (CSA), chondroitin sulfate-B (CSB), chondroitin sulfate-C(CSC), or heparin and then added to laminin-coated plates. % NL bound represents [NL] bound to laminin versus GAG. N=3, mean±s.d., p<0.01, *p<0.001, ****p<0.0001, Student's t-test between fusions for each GAG group. Data points at or above baseline signal are shown as open circles. NL-G3 is presented as the left column in each pair and NL-TT-G3 is presented as right column in each pair.

FIGS. 13A-13D show tryptophan fluorescence quenching of monomeric G3 fusion proteins and trimeric nanoassemblies due to binding to soluble lactose. a Wild-type NanoLuc™ (WT-NL, diamonds, negative control), b Wild-type galectin-3 (WT-G3, squares), c NL-G3 (circles), and d NL-TT-G3 (triangles). N=3, mean±s.d.

FIGS. 14A-14D show phosphatidylserine exposure and membrane permeability of Jurkat T cells treated with monomeric G3 fusion proteins and trimeric nanoassemblies. Phosphatidylserine exposure was determined via Annexin V staining and membrane permeability was determined via propidium iodide (PI) after Jurkat T cells were treated with a wild-type galectin-3 (WT-G3), b PBS, c NL-G3, or d NL-TT-G3. Scale bar=100 m.

FIGS. 15A-15D show phosphatidylserine exposure and membrane permeability of Jurkat T cells treated with monomeric G3 fusion proteins and trimeric nanoassemblies. Phosphatidylserine exposure was determined via Annexin V staining and membrane permeability was determined via propidium iodide (PI) after Jurkat T cells were treated with a wild-type galectin-3 (WT-G3), b PBS, c NL-G3, or d NL-TT-G3. Scale bar=20 m.

FIGS. 16A-16H show brightfield micrographs of insoluble aggregates formed by asialofetuin (ASF) in the presence of wild-type galectin-3 (WT-G3) and trimeric nanoassemblies in PBS at high concentrations ([G3]=10 μM). 7 μM ASF in the presence of a 10 μM WT-G3, b 10 μM NL-TT-G3, c 10 μM NL-G3, d 2.5 μM WT-G3, e 2.5 μM NL-TT-G3, or f 2.5 μM NL-G3. g 7 μM ASF alone and h 10 μM WT-G3 alone. Scale bar=20 m.

FIGS. 17A-17D shows average hydrodynamic diameter of insoluble aggregates formed by asialofetuin (ASF) in the presence of wild-type galectin-3 (WT-G3) and trimeric nanoassemblies in PBS at high concentrations ([G3]=10 μM), as determined via dynamic light scattering. 7 μM ASF in the presence of a 2.5 μM WT-G3, NL-G3, or NL-TT-G3.

7 μM ASF in the presence of b 10 μM WT-G3, NL-G3, or NL-TT-G3. c 10 μM WT-G3 alone and d 7 μM ASF alone. N=3, mean±s.d. WT-G3 is presented as a the leftmost panel in each of a, b, and c, NL-G3 is presented in the middle panel of each of a and b, NL-TT-G3 is presented in the rightmost panel of a and b, and ASF is presented in d.

FIG. 18 shows a time-course curve for G3-mediated formation of insoluble asialofetuin (ASF) aggregates. 7 μM ASF was added to WT-G3 (uppermost trace), NL-G3 (lowermost trace), or NL-TT-G3 (middle trace) at high concentrations ([G3]=10 μM) and aggregate formation was determined by light scattering (1=420 nm).

FIGS. 19A-19D show brightfield and fluorescent micrographs of insoluble aggregates formed in 10% fetal bovine serum (FBS) in the presence of WT-G3 or GFP-TT-G3. a 10 μM WT-G3 added to FBS. GFP-TT-G3 ([G3]=10 μM) added to b-c FBS or d PBS. Scale bar=m.

FIGS. 20A-20C show results from Size-exclusion chromatography of monomeric G3 fusion proteins and trimeric nanoassemblies digested with collagenase. a Wild-type galectin-3 (WT-G3), b NL-G3, and c NL-TT-G3 fully or partially digested by collagenase (purple trace in a-c). In b, both undigested NL-G3 and digested NL-G3 (i.e., NL-) is present under a broad peak. In c, digested NL-TT-G3 that remained assembled (i.e., NL-TT-) overlaps with the collagenase peaks, while digested and unassembled NL-TT-G3 (i.e., NL-T-) eluted later.

Figure 21A:
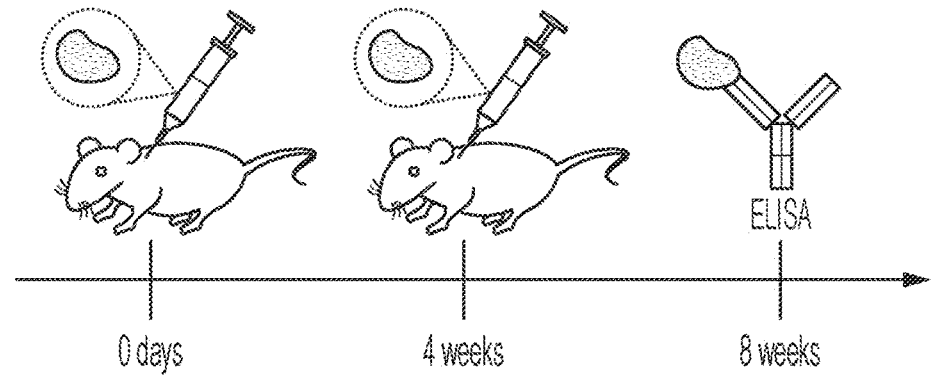
Figure 21B:
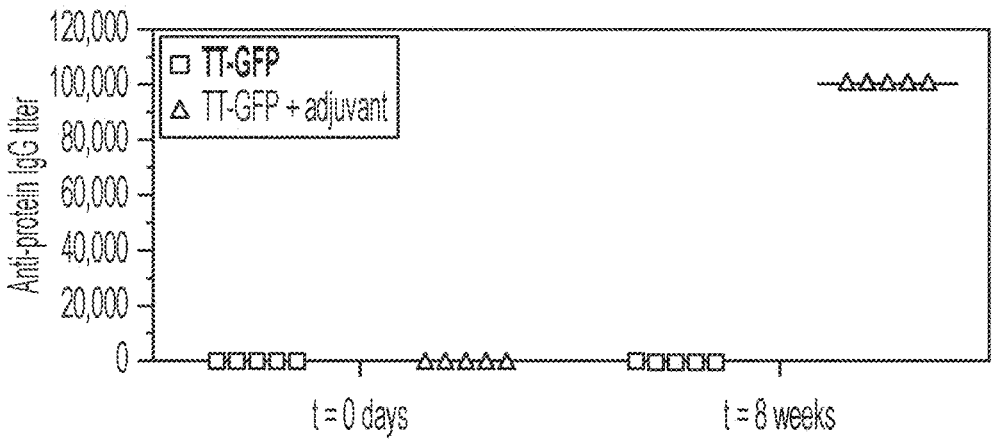
Figure 21C:
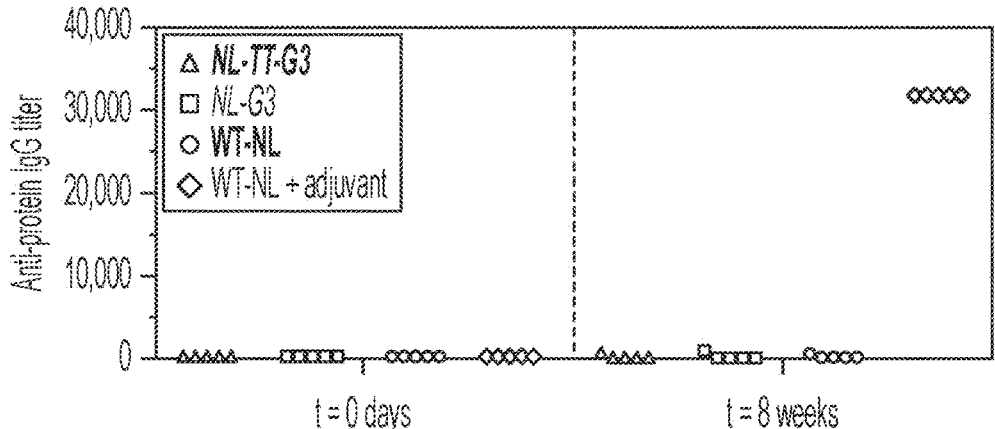

FIGS. 21A-21C show total C57BL/6 serum IgG reactive against monomeric G3 fusion proteins and trimeric nanoassemblies after subcutaneous scruff injection of proteins in PBS or in TiterMax™ adjuvant emulsion. a Timeline for initial protein injection (0 days), boost injection (4 weeks), and analysis of anti-protein IgG antibody response via ELISA (8 weeks). b Anti-protein IgG titer for mice injected with TT-GFP in PBS (squares) or TT-GFP in adjuvant emulsion (TT-GFP+adjuvant, triangles). c Anti-protein IgG titer for mice injected with NL-TT-G3 in PBS (triangles), NL-G3 in PBS (squares), wild-type NanoLuc™ in PBS (WT-NL, circles), and wild-type NanoLuc™ in adjuvant emulsion (WT-NL+adjuvant, diamonds). In b and c, 0 days represents serum from naive, untreated mice, which was collected before the first protein injection. N=5, mean±s.d.

Figure 22A:
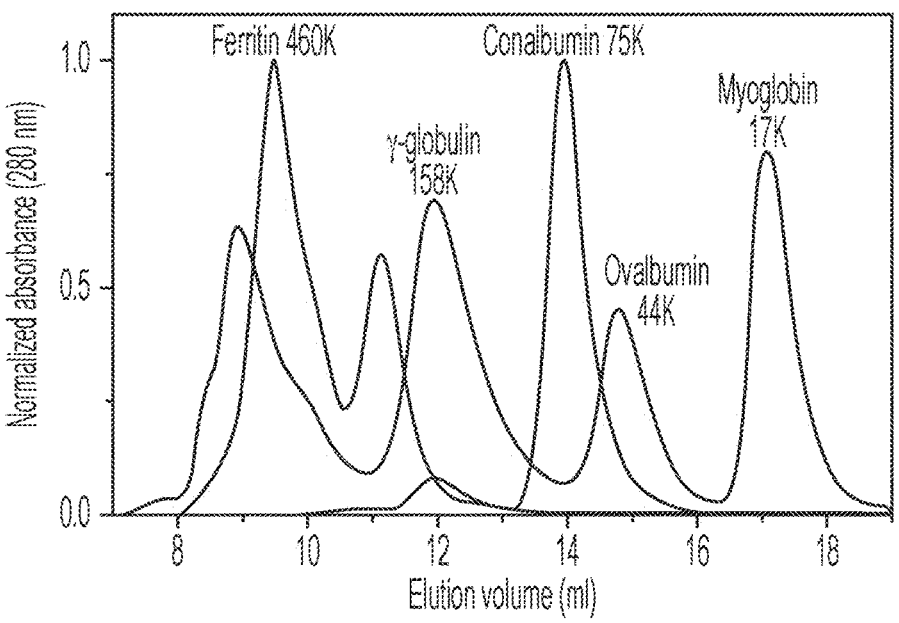
Figure 22B:
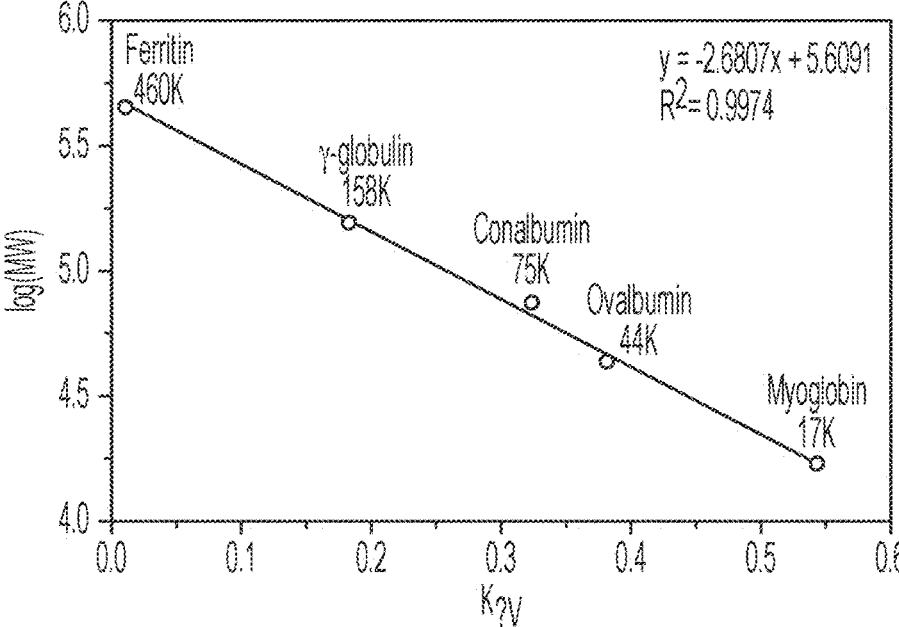
Figure 23A:
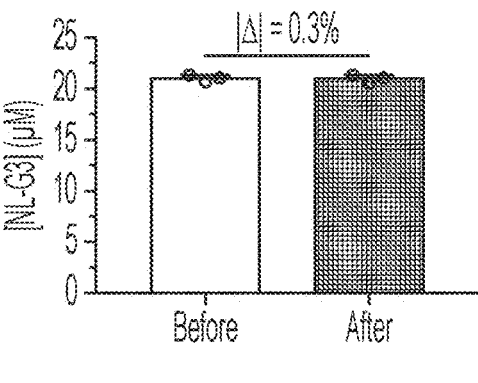
Figure 23B:
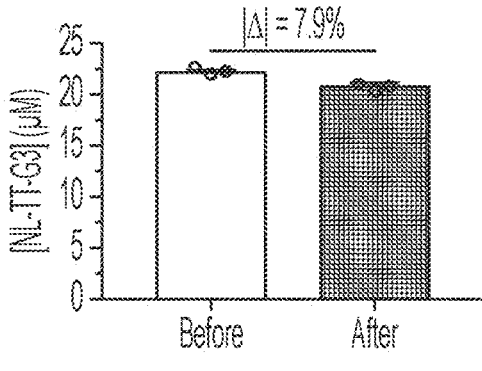
Figure 23C:
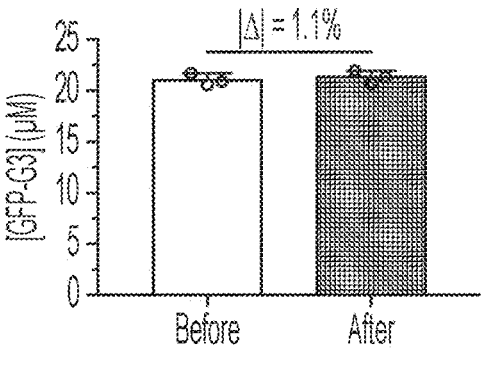
Figure 23D:
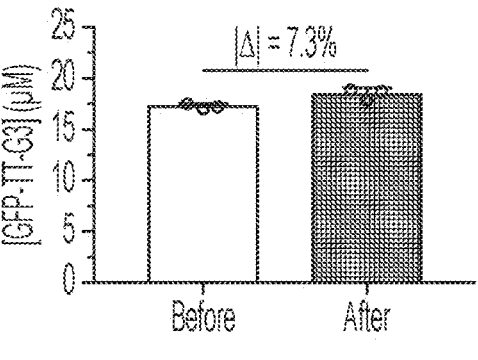
Figure 23E:
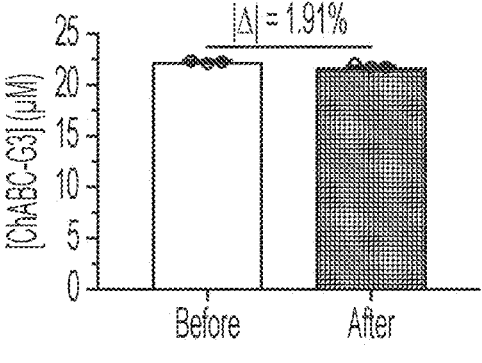
Figure 23F:
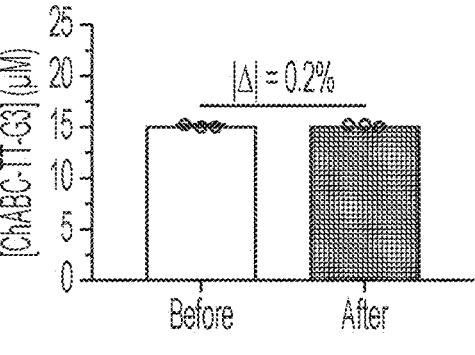

FIGS. 22A-22B show results from size-exclusion chromatography (SEC) calibration. a Overlapped traces of protein standards on a Superdex 200 10/300 GL column. b SEC standard curve plotted as log(MW) vs partition coefficient (Kav). Kav is equal to the protein elution volume (Ve) minus the void volume (Vo, 9.39 mL) and divided by the total column volume (Vt, 23.56 mL) minus the void volume.

FIGS. 23A-23F show molar concentration of monomeric G3 fusion proteins and trimeric nanoassemblies measured before (white bar) and after (gray bar) filtration with a 0.2 micron syringe filter for dynamic light scattering experiments. a NL-G3, b NL-TT-G3, c GFP-G3, d GFP-TTG3, e ChABC-G3, and f ChABC-TT-G3. Δ=percent change in molar concentration. N=3, mean±s.d. Data points at or above baseline signal are shown as open circles.

Figures 24A, 24B, 24C:
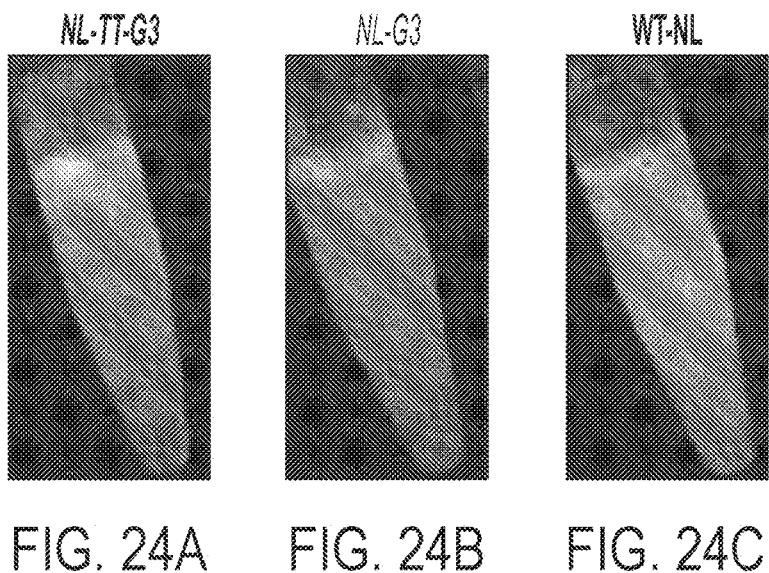

FIGS. 24A-24C show digital photographic images of blue luminescence emitted by monomeric G3 fusion proteins and trimeric nanoassemblies. Luminescence emitted by a NL-TT-G3, b NL-G3, and c wild-type NanoLuc™ (WT-NL).

Figure 25:
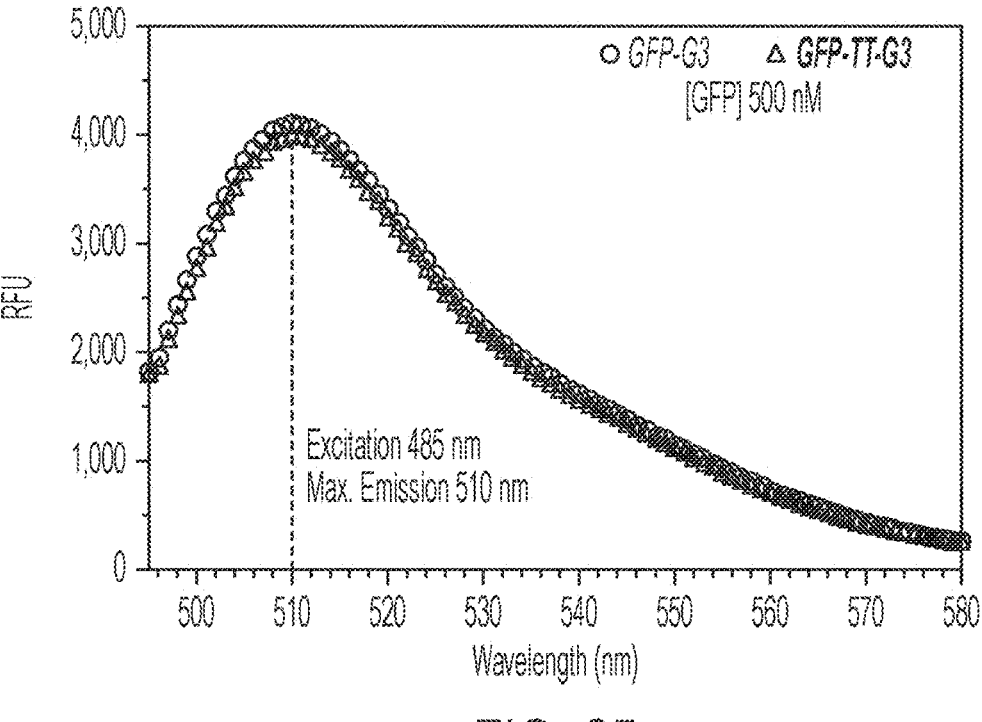

FIG. 25 shows fluorescence spectra of monomeric G3 fusion proteins and trimeric nanoassemblies. Emission spectra of GFP-G3 (circles) and GFP-TT-G3 (triangles) ([GFP] =500 nM) at excitation=485 nm (superfolder GFP). N=3, mean±s.d.

Figure 26:
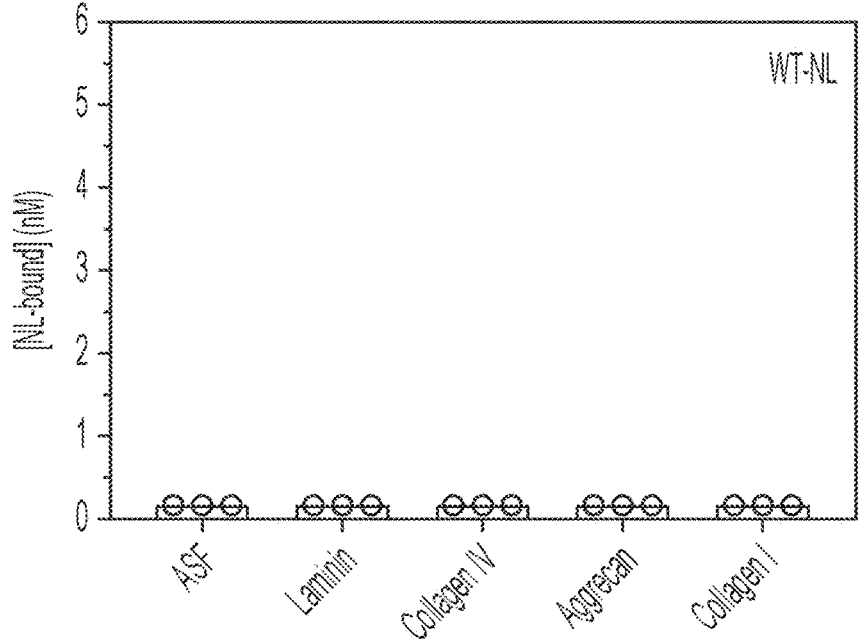

FIG. 26 shows baseline signal produced by non-specific binding of wild-type NanoLuc™ (WT-NL) to various glycoproteins and proteoglycans. N=3, mean±s.d. Data points at baseline signal are shown as open circles.

FIGS. 27A-27D show representative tryptophan fluorescence emission spectra of monomeric G3 fusion proteins and trimeric nanoassemblies in PBS spiked with water (negative control, circles) or soluble lactose in water (triangles). a Wild-type galectin-3 (WT-G3), b NL-G3, c NL-TT-G3, and d wild-type NanoLuc™ (WT-NL). Excitation=280 nm. N=3, mean±s.d.

FIGS. 28A-28C show representative tryptophan fluorescence emission spectra of monmerc G3 fusion proteins and trimeric nanoassemblies in PBS spiked with water (negative control, circles) or soluble LacNAc in water (triangles). A Wild-type galectin-3 (WT-G3), b NL-G3, and c NL-TT-G3. Extcitation=280 nm. N=3, mean±s.d.

Figures 29A, 29B:
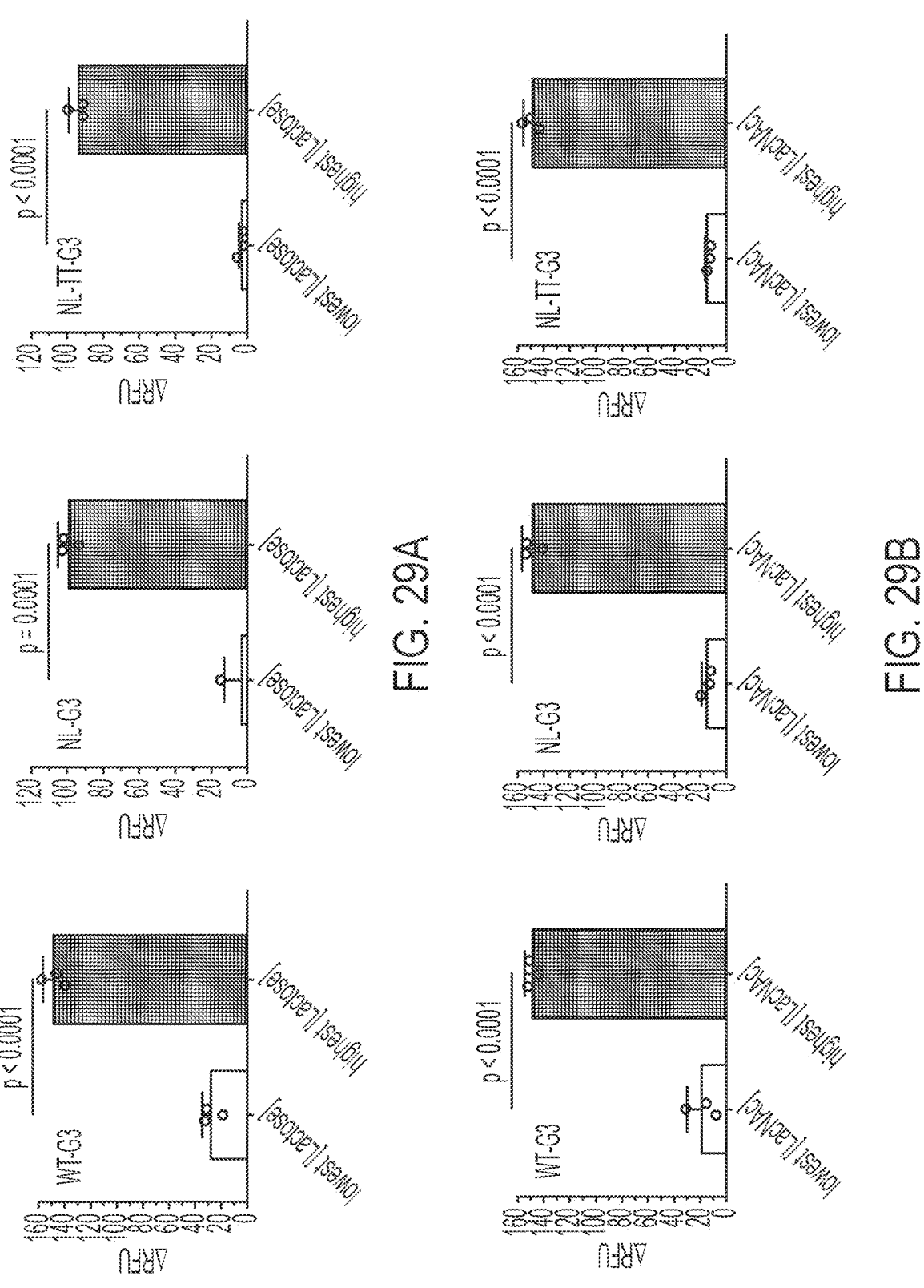

FIGS. 29A-29B show change in fluorescence signal (ΔRFU) for wild-type galectin-3 (WT-G3), NL-G3, and NL-TT-G3 in solution with the lowest (white bar) and highest (gray bar) concentration of soluble carbohydrate used in tryptophan fluorescence quenching experiments. a ΔRFU for lowest and highest [Lactose] extracted from FIGS. 14A-14D. b ΔRFU for lowest and highest [LacNAc] extracted from FIG. 3G. P<0.0001 demonstrates that ΔRFU at the highest carbohydrate concentration tested was significantly greater than ΔRFU at the lowest carbohydrate concentration tested. N=3, mean±s.d. Data points at or above baseline signal are shown as open circles.

Figures 30A, 30B:
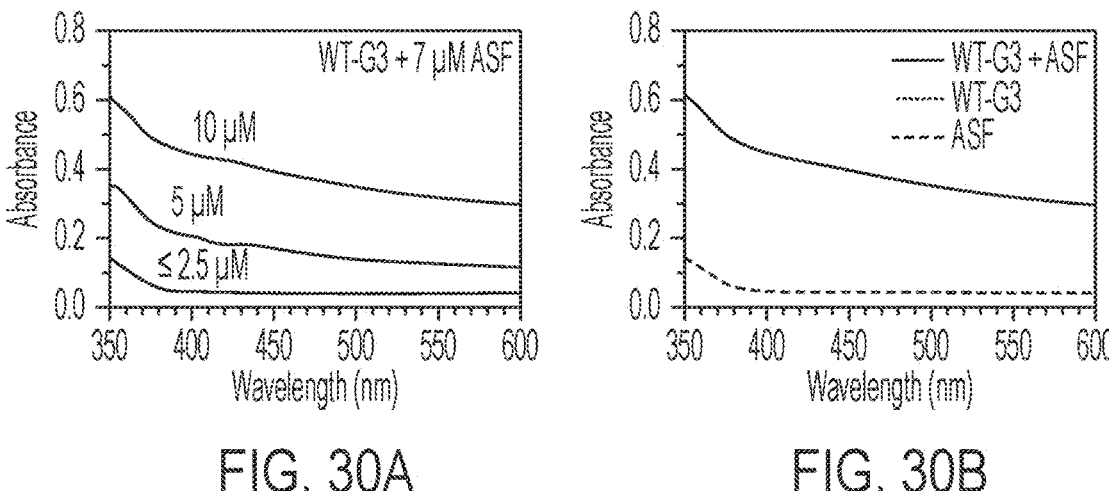
Figure 30C:
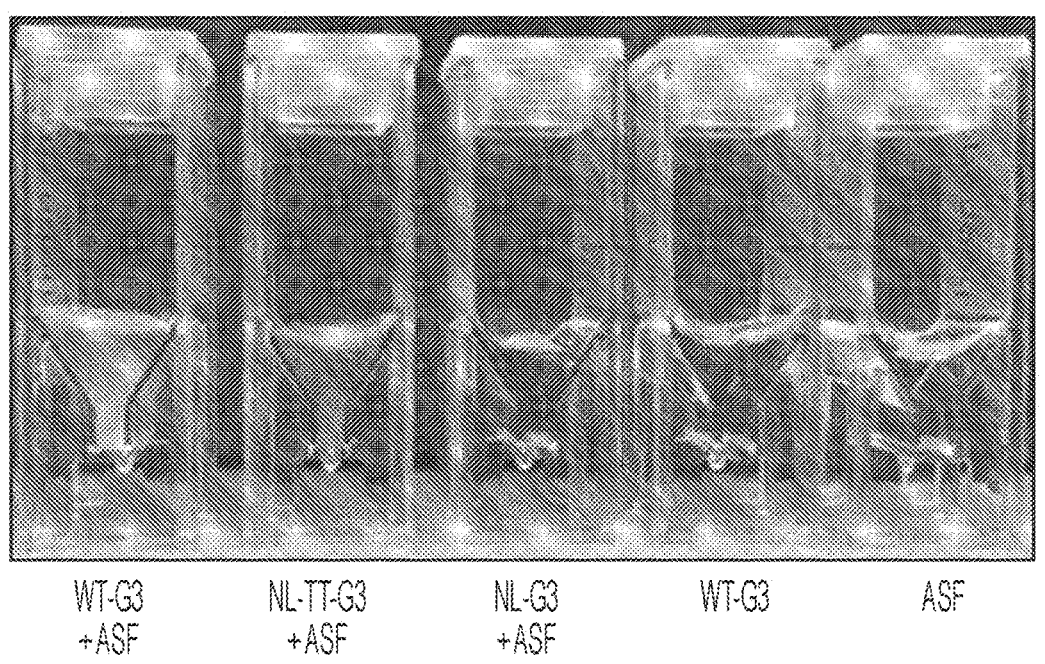

FIGS. 30A-30C show an analysis of insoluble aggregates formed by asialofetuin (ASF) in the presence of WT-G3, NL-G3, and NL-TT-G3. a Absorbance of insoluble aggregates at different concentrations of WT-G3 added to ASF. b Absorbance spectra of 10 μM WT-G3, 7 μM ASF, and insoluble aggregates formed by combining both proteins in solution. c Qualitative digital photographic images of proteins mixed with ASF or proteins alone in PBS. N=3, mean±s.d. for a and b.

Figure 31:
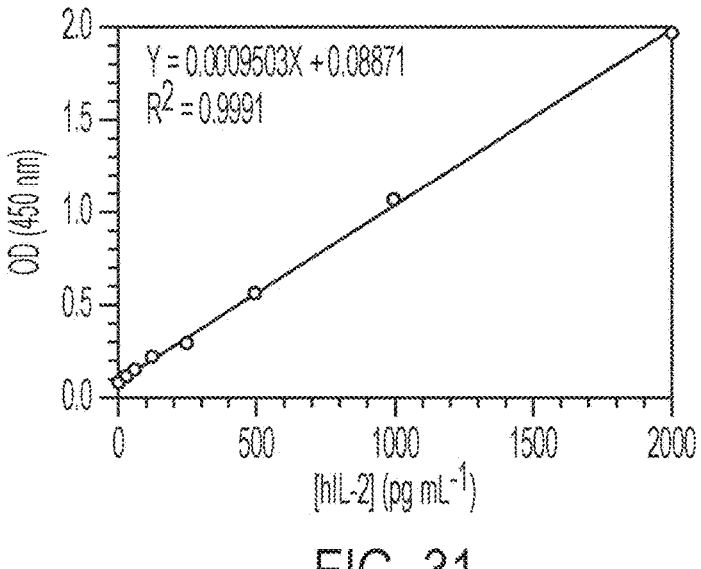

FIG. 31 shows a standard curve of absorbance (450 nm) vs human IL-2 (hIL-2) concentration for the hIL-2 ELISA used to determine the concentration of hIL-2 secreted by Jurkat T cells treated with WT-G3, NL-G3, or NL-TT-G3.

Figures 32A, 32B, 32C:
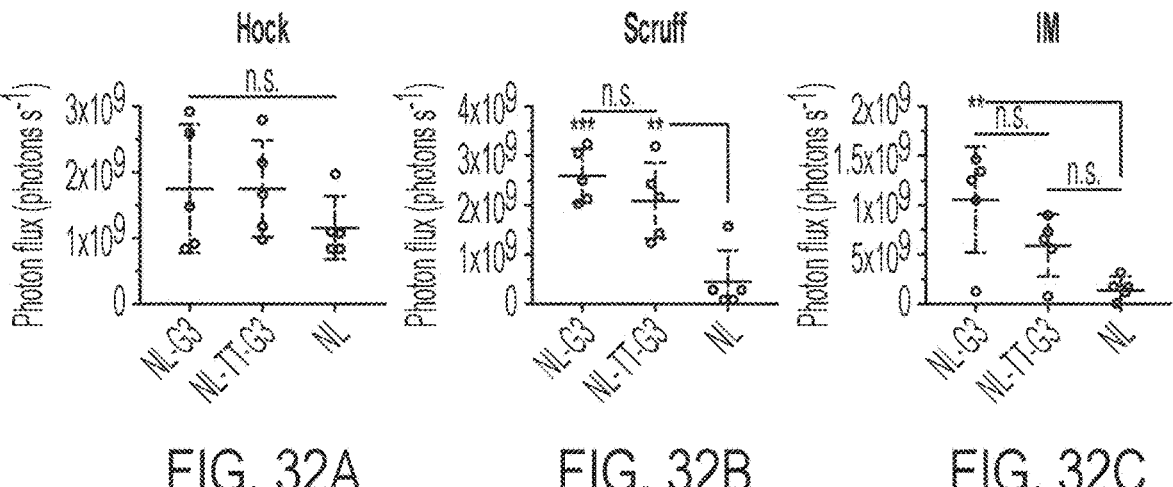

FIGS. 32A-32C show bioluminescence output in terms of photon flux (photon s-1) for NL, NLG3, and NL-TT-G3 at each injection site in female C57BL/6 mice at day 0. a hock, b scruff, and c caudal thigh muscle (intramuscular, IM). N=5, mean±s.d., n.s. is no significant difference, p<0.01, *p<0.001, ANOVA with Tukey's post-hoc. Data points at or above baseline signal are shown as open circles. NL-G3 is presented as the left error bar in each panel, NL-TT-G3 is presented as middle error bar in each panel, and WT-NL is presented as right error bar in each panel.

Figures 6A, 6B, 6C:
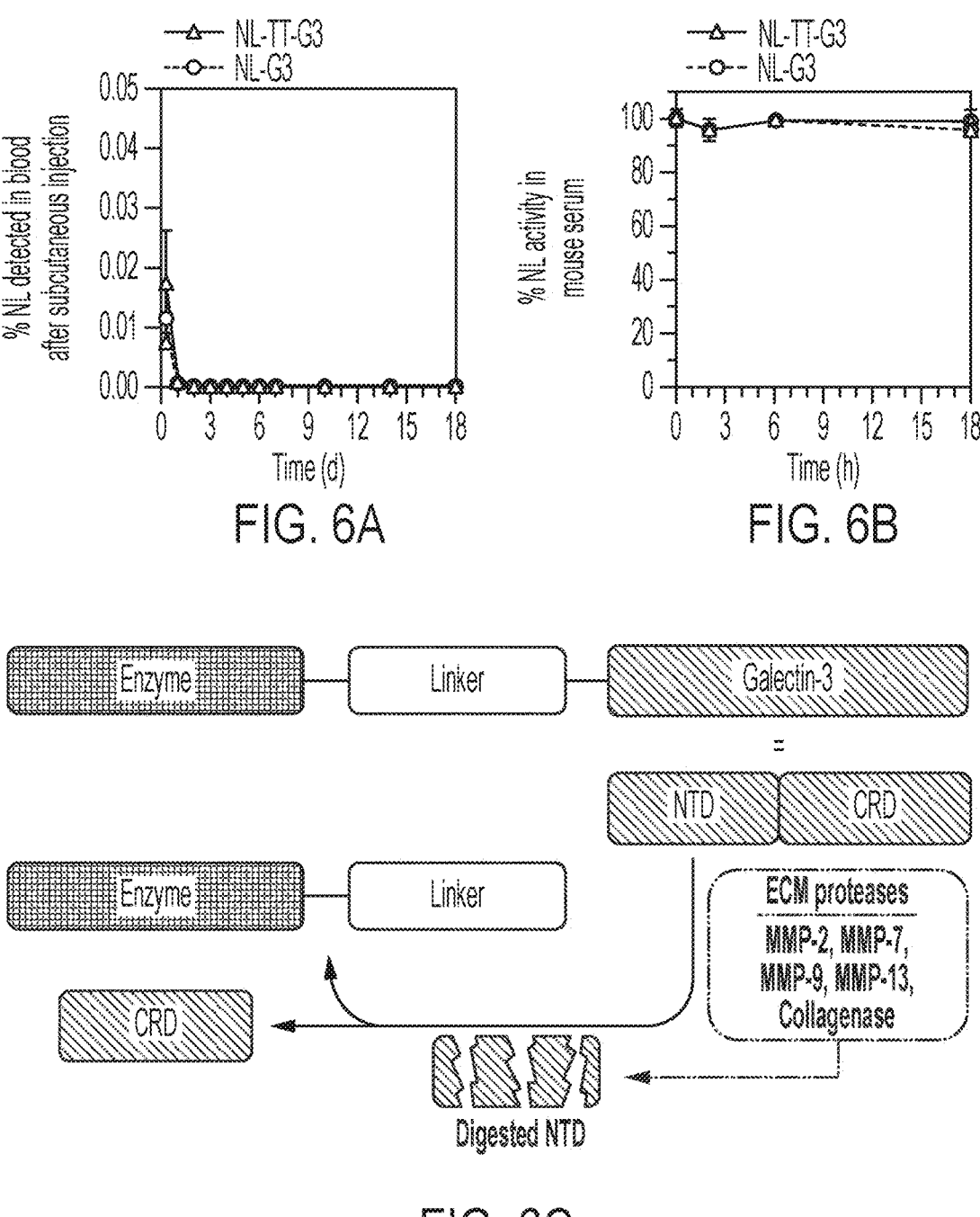
Figure 6D:
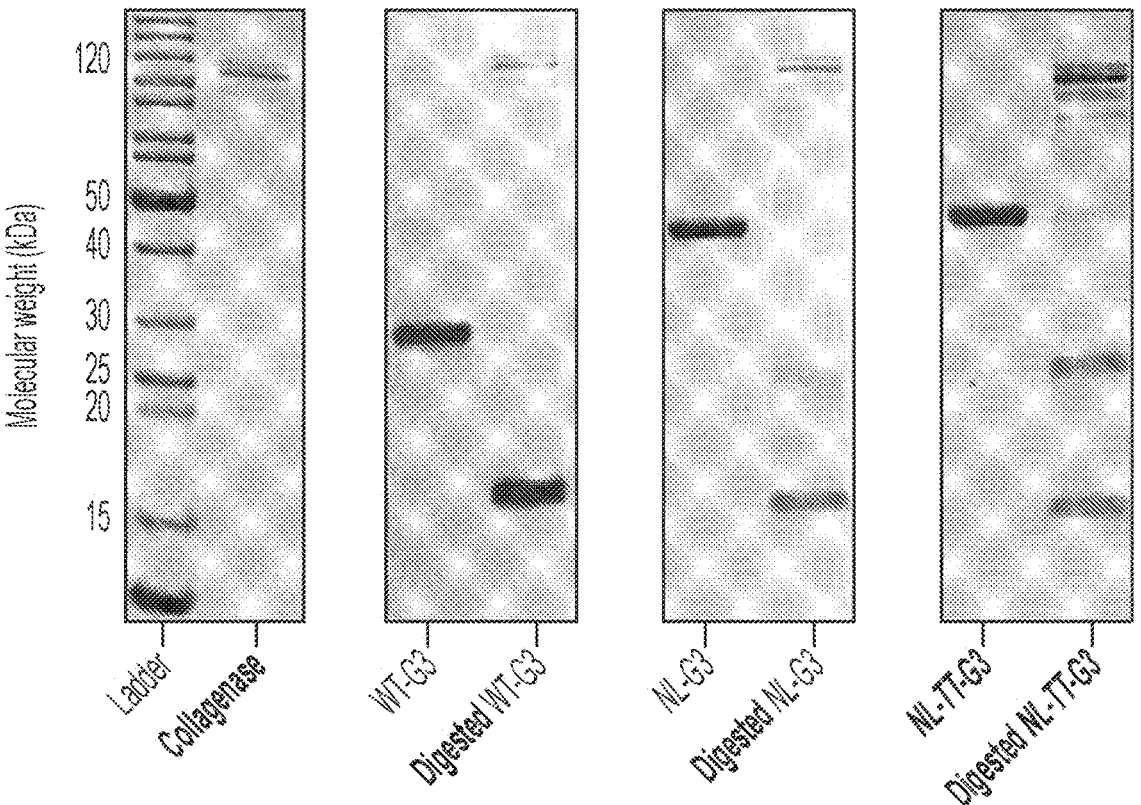
Figure 33:
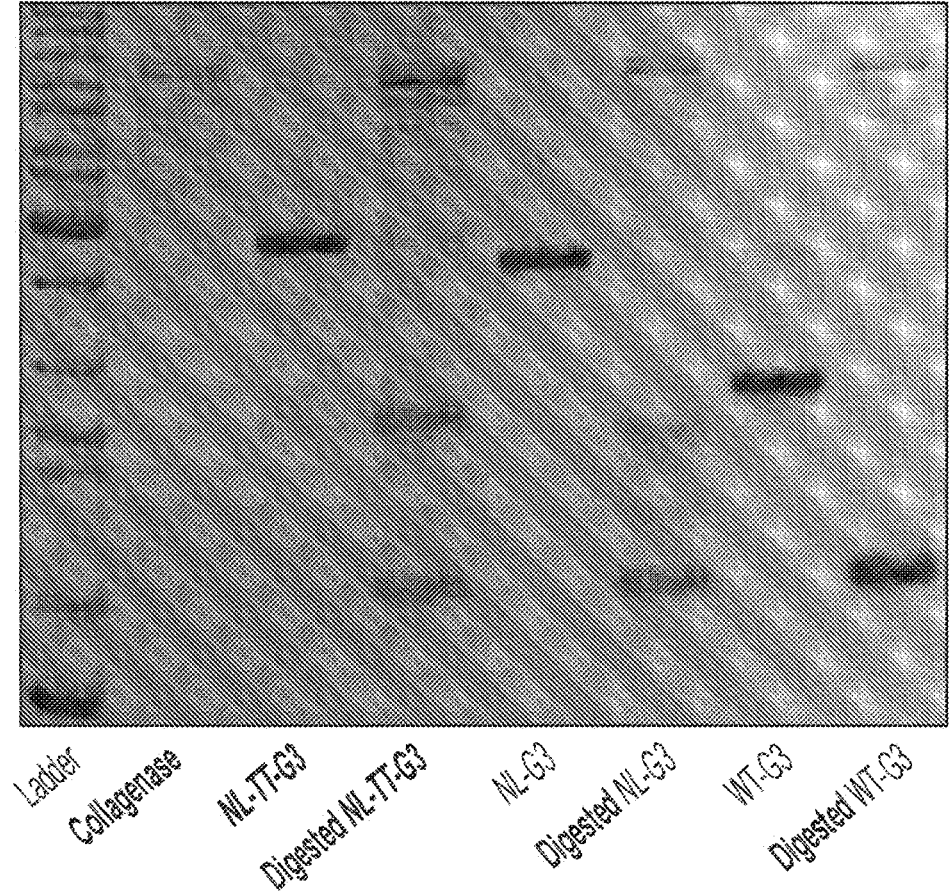

FIG. 33 shows an original SDS-PAGE gel of WT-G3, NL-G3, and NL-TT-G3 before and after treatment with collagenase. This is the same gel as is shown in FIG. 6D, uncropped and without adjusting brightness/contrast to improve printing quality.

Figure 34A:
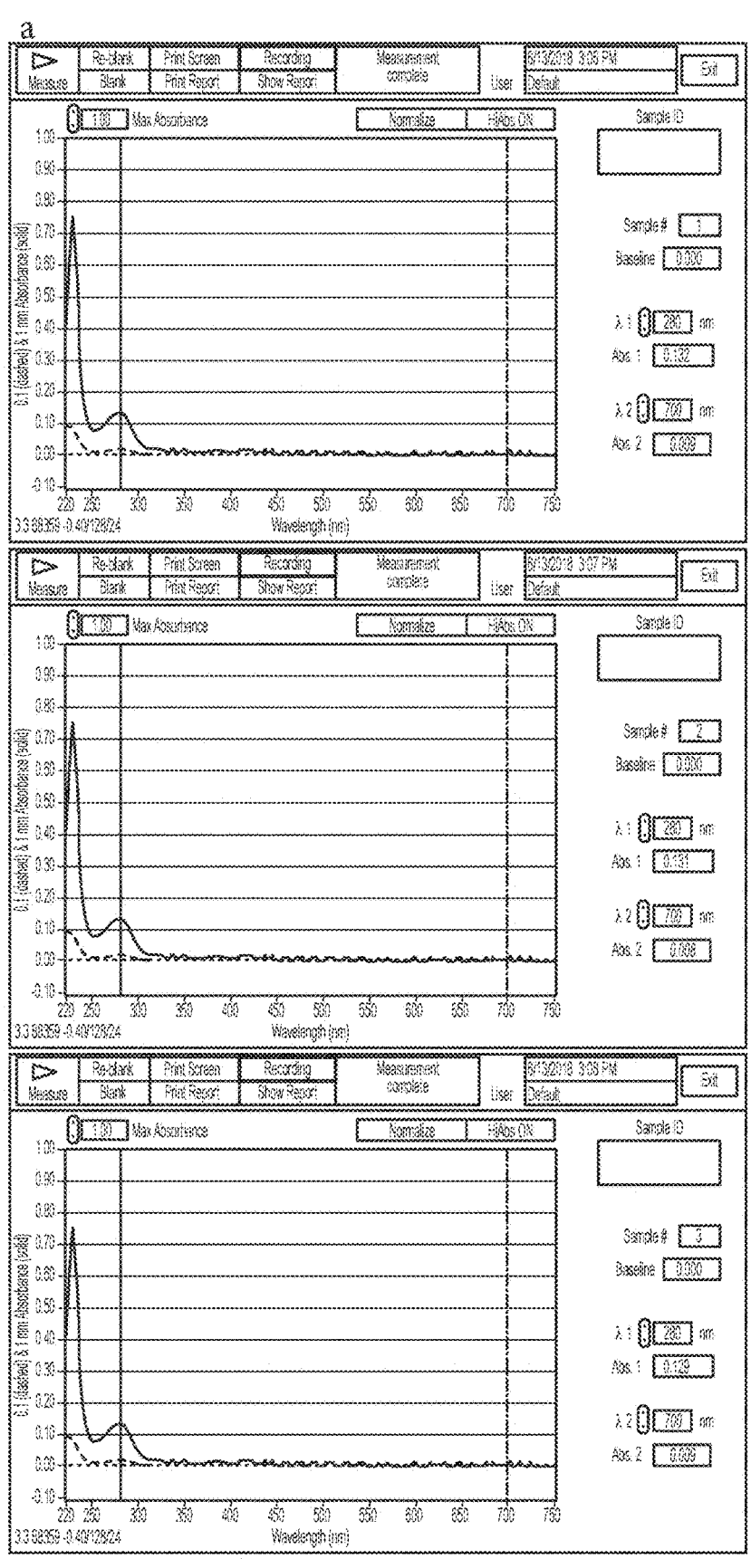
Figure 34B:
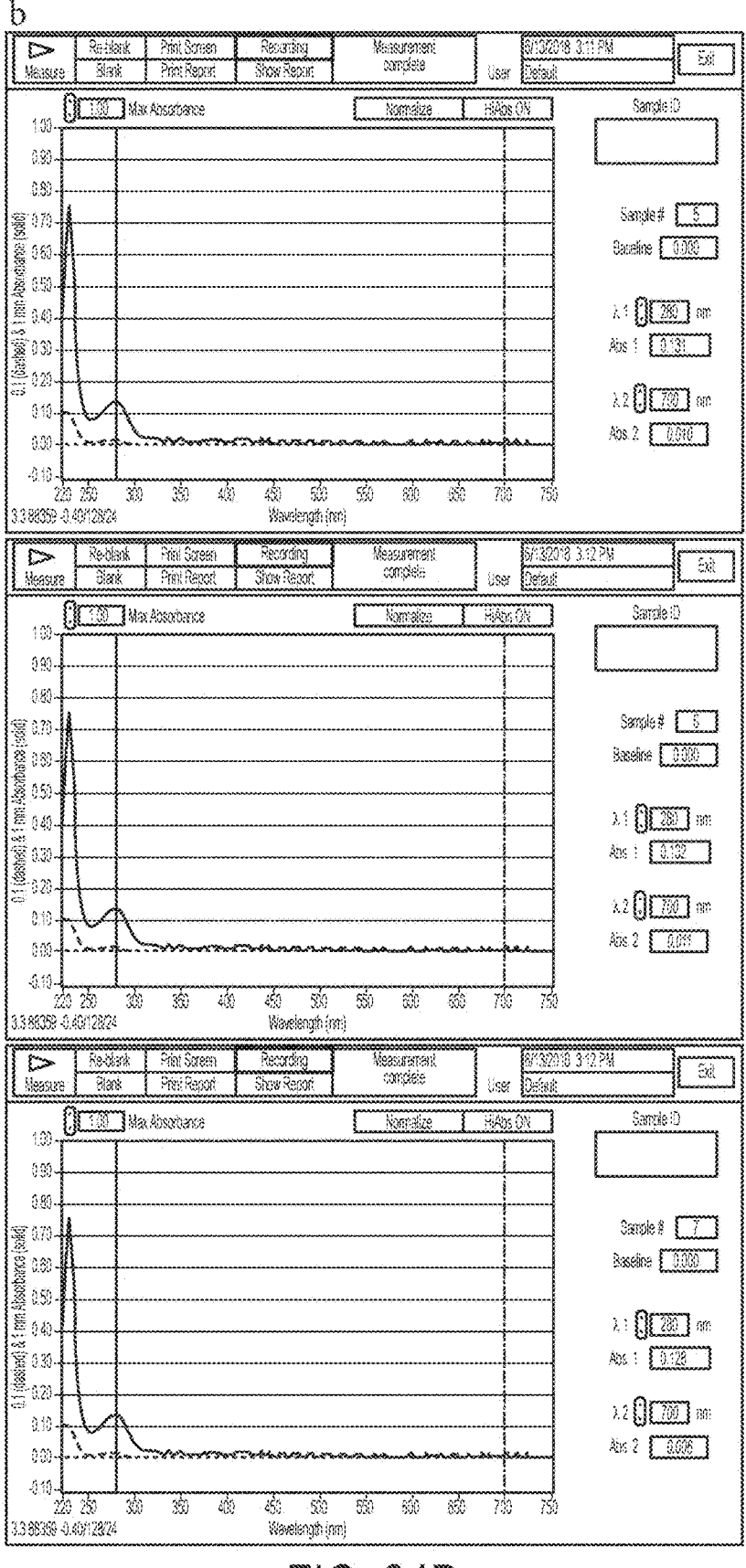

FIGS. 34A-34B show NanoDrop Spectra of 0.2 micron filtered NL-G3 in PBS. a before filtration and b after. Data in columns are technical replicates of a or b.

Figure 35A:
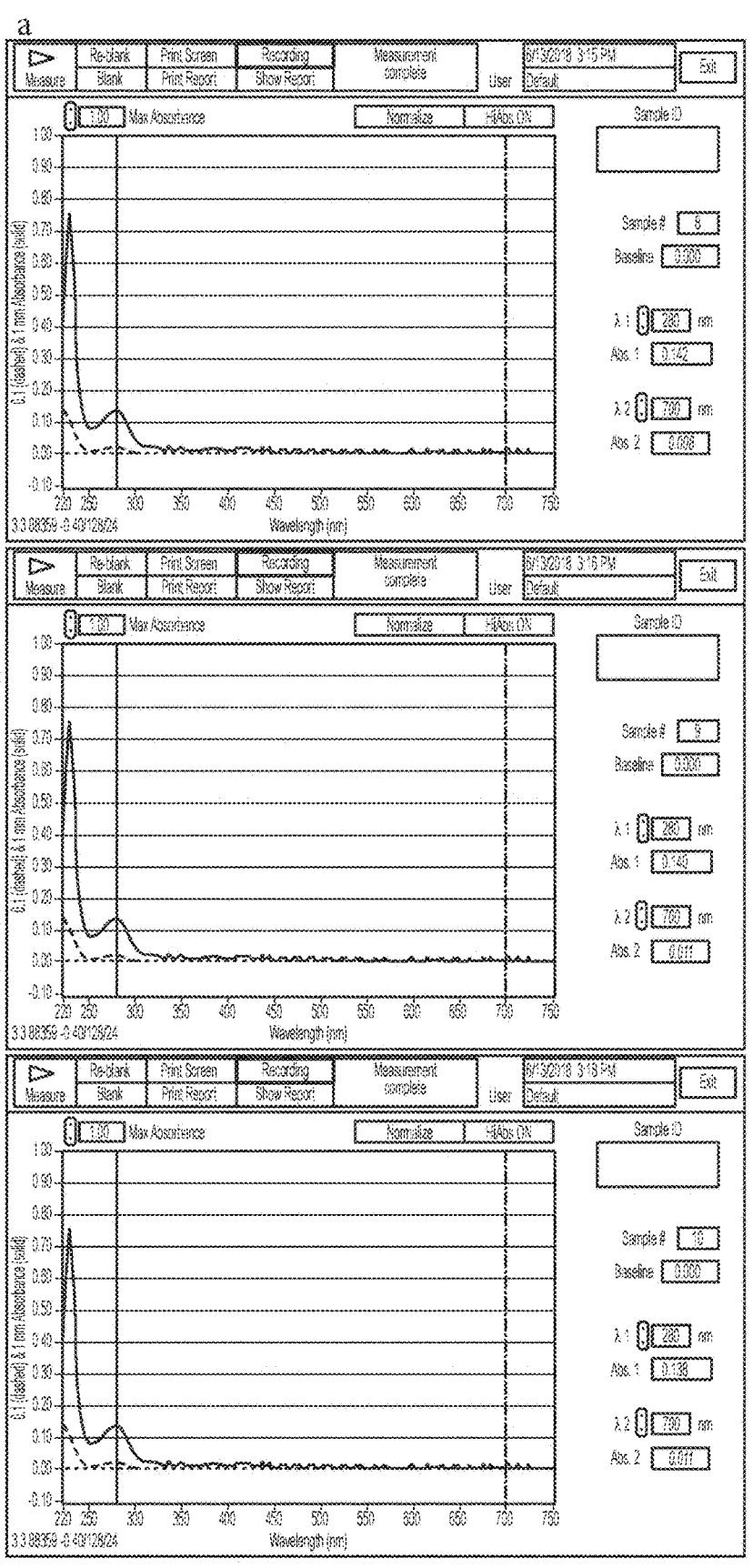
Figure 35B:
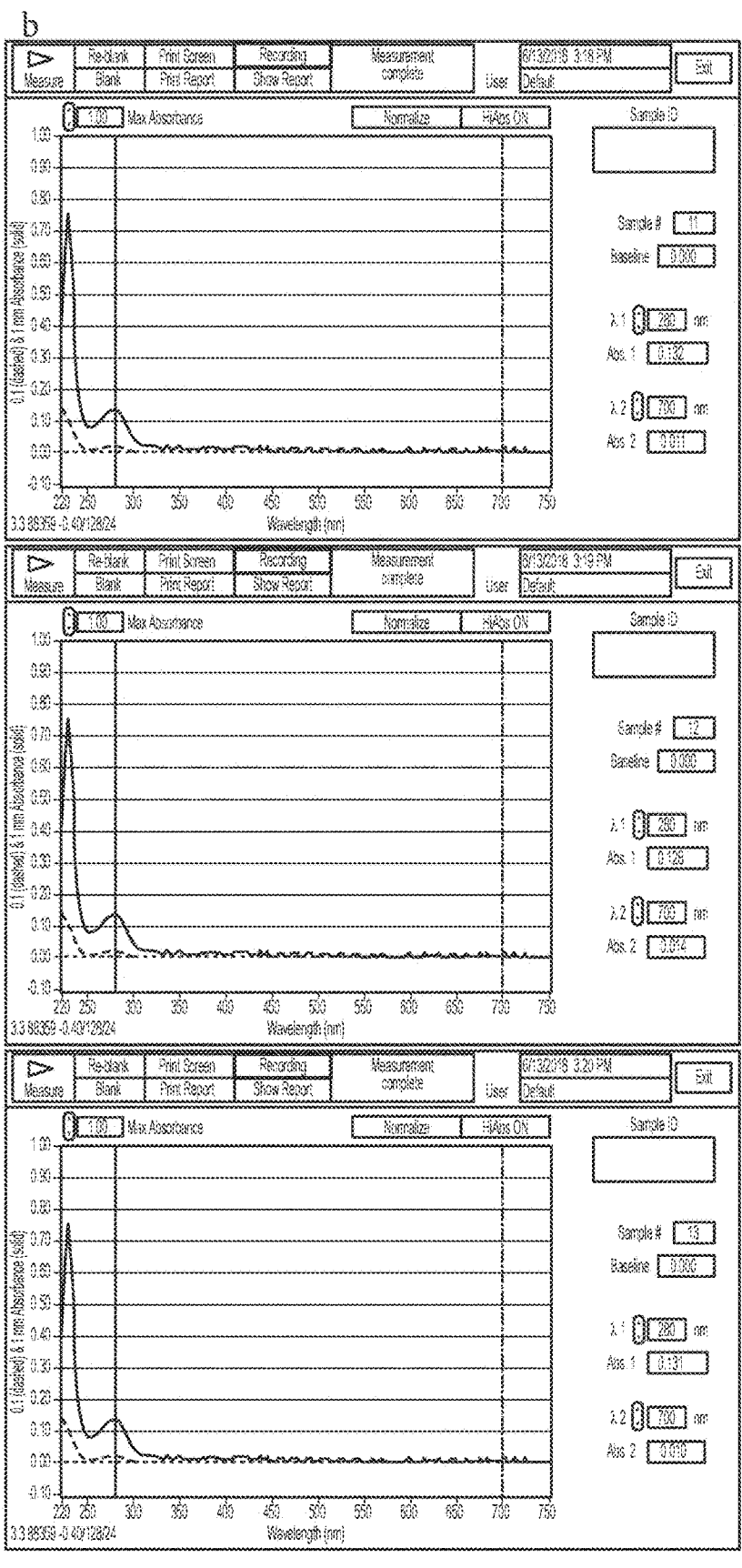

FIGS. 35A-35B show NanoDrop Spectra of 0.2 micron filtered NL-TT-G3 in PBS. a before filtration and b after. Data in columns are technical replicates of a or b.

Figure 36A:
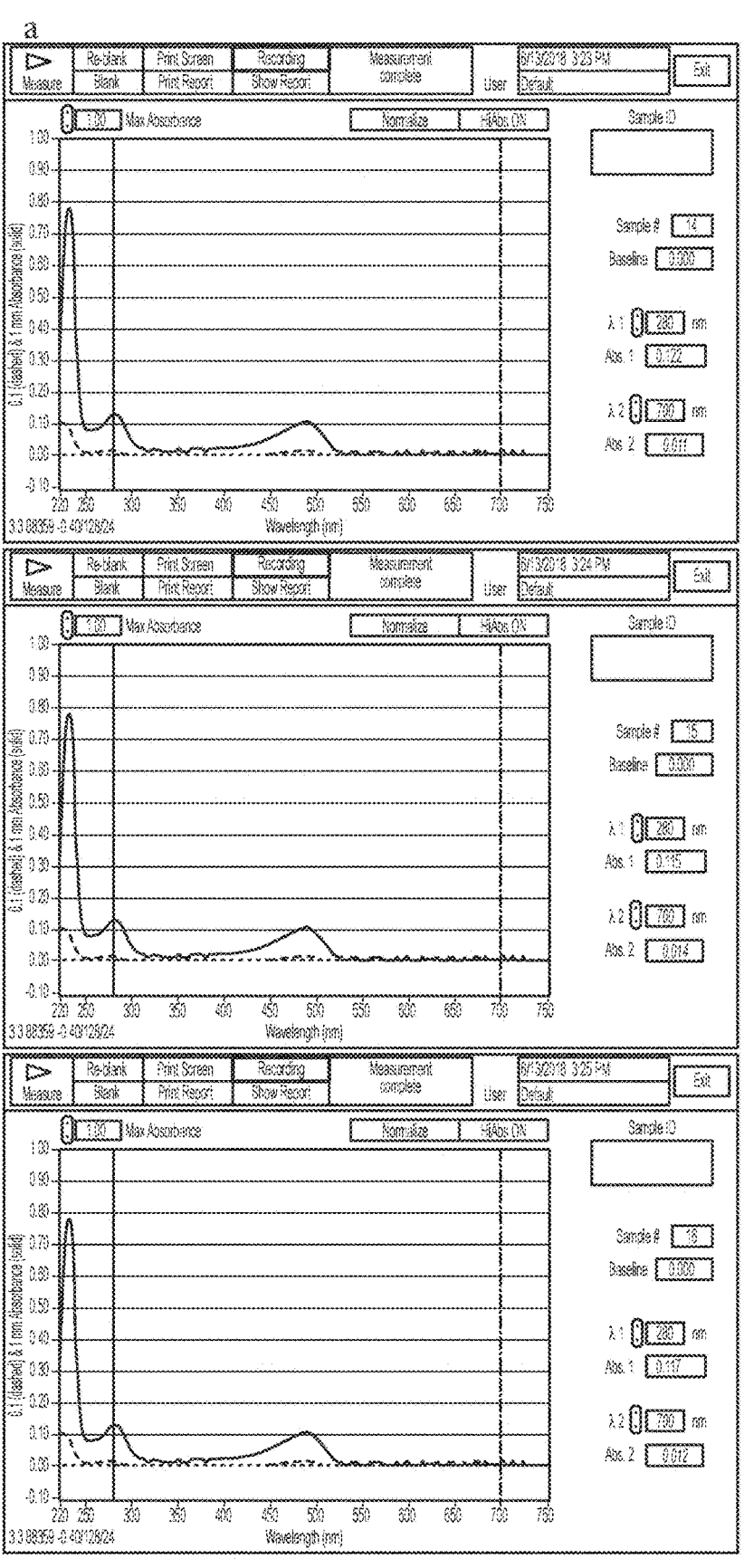
Figure 36B:
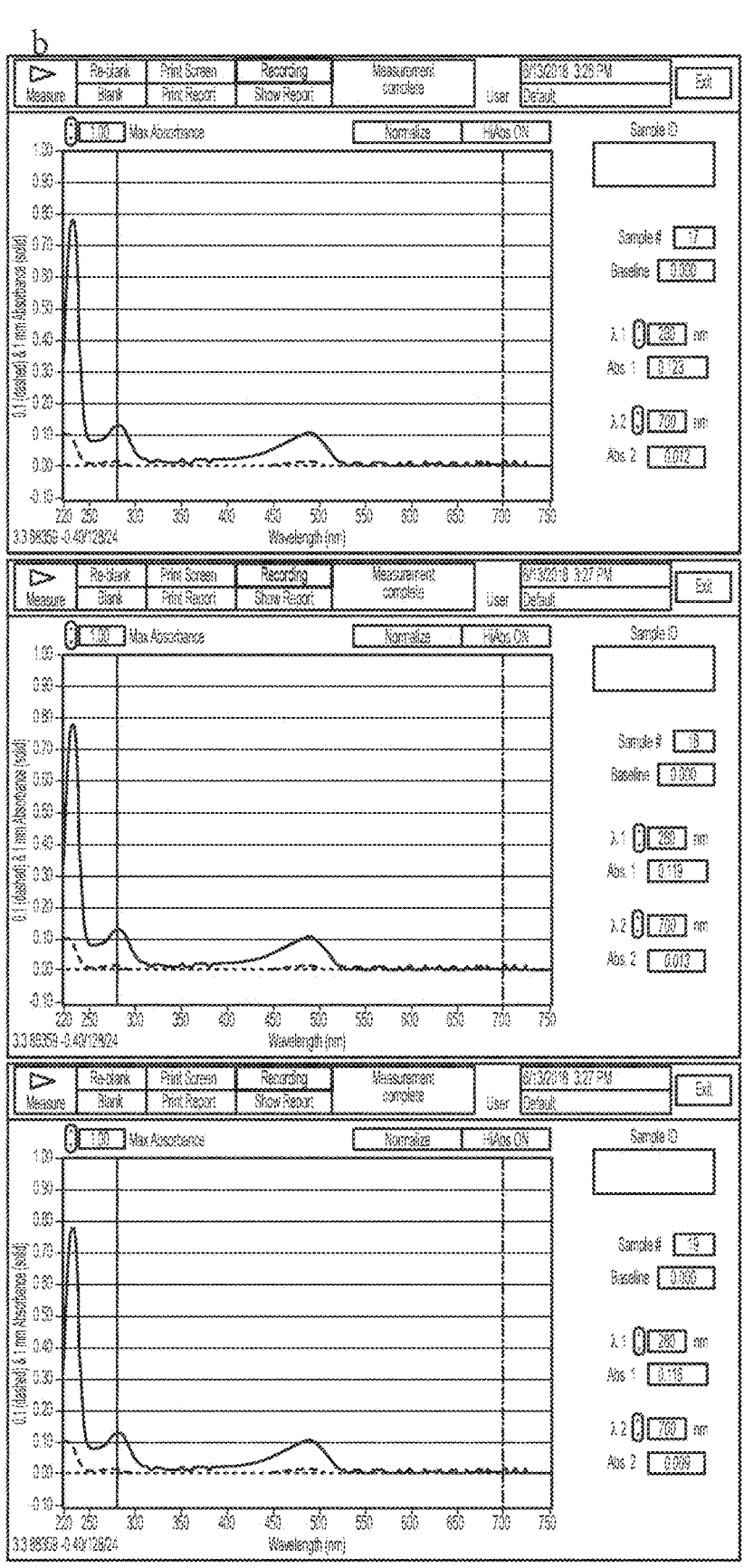

FIGS. 36A-36B show NanoDrop Spectra of 0.2 micron filtered GFP-G3 in PBS. a before filtration and b after. Data in columns are technical replicates of a or b.

Figure 37A:
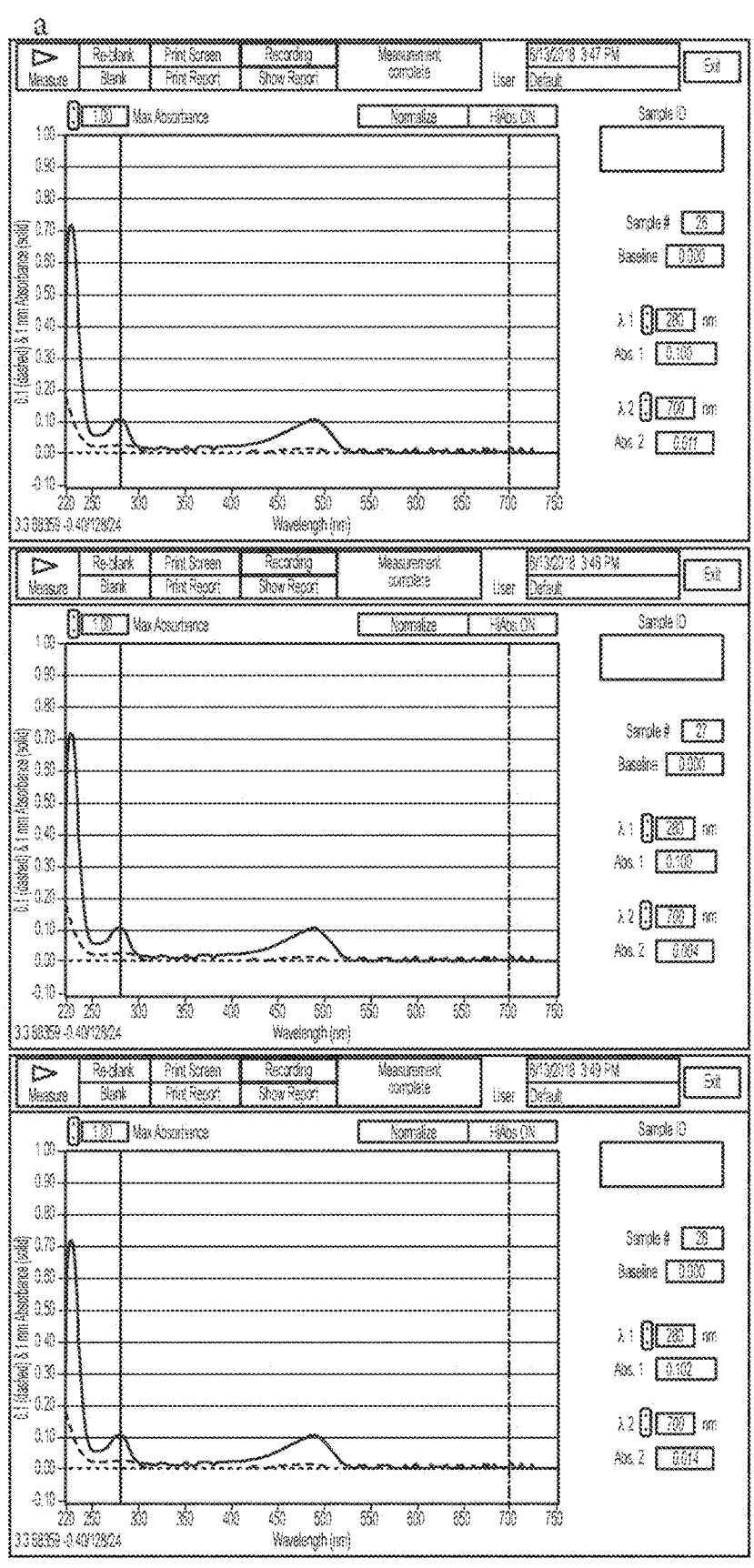
Figure 37B:
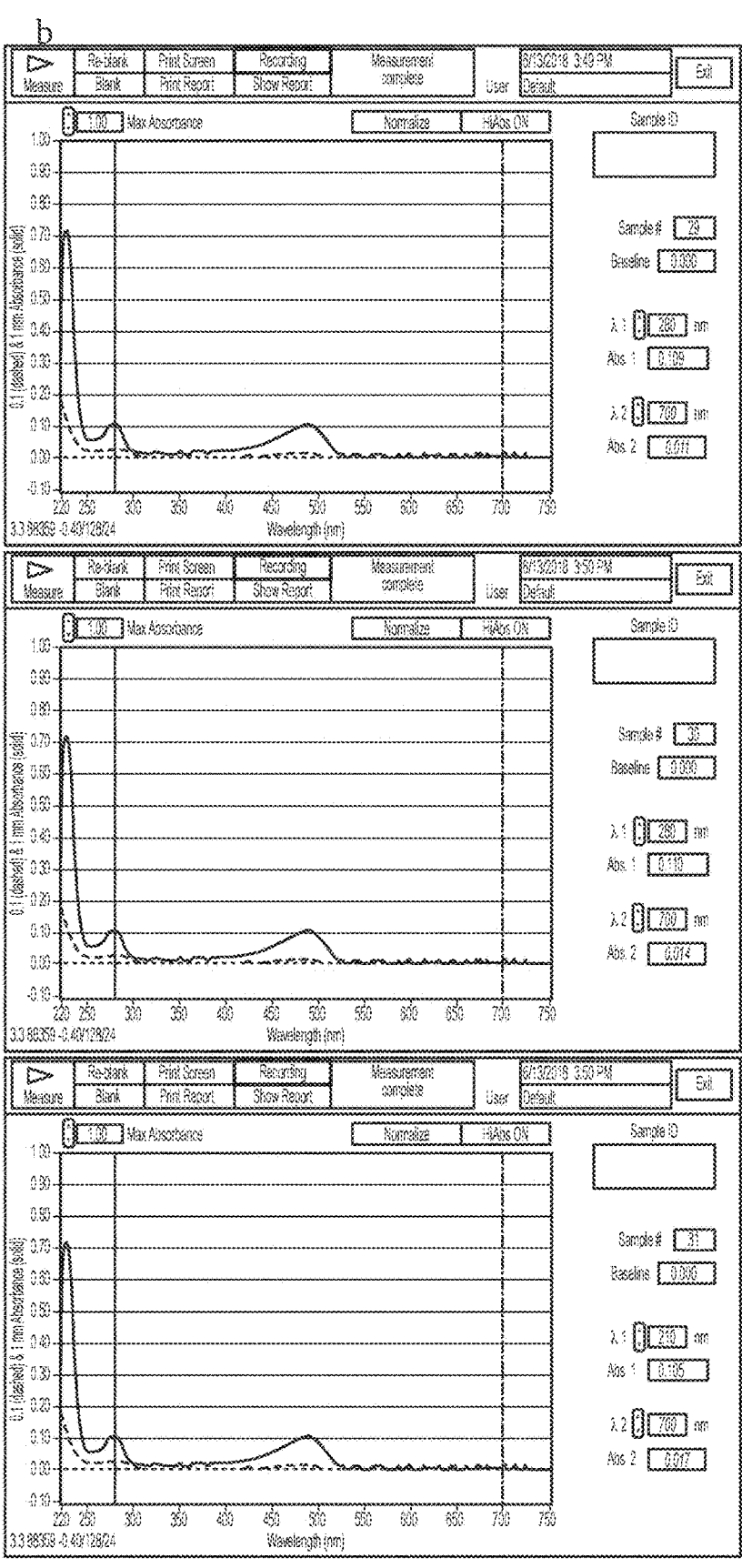

FIGS. 37A-37B show NanoDrop Spectra of 0.2 micron filtered GFP-TT-G3 in PBS. a before filtration and b after. Data in columns are technical replicates of a or b.

Figure 38A:
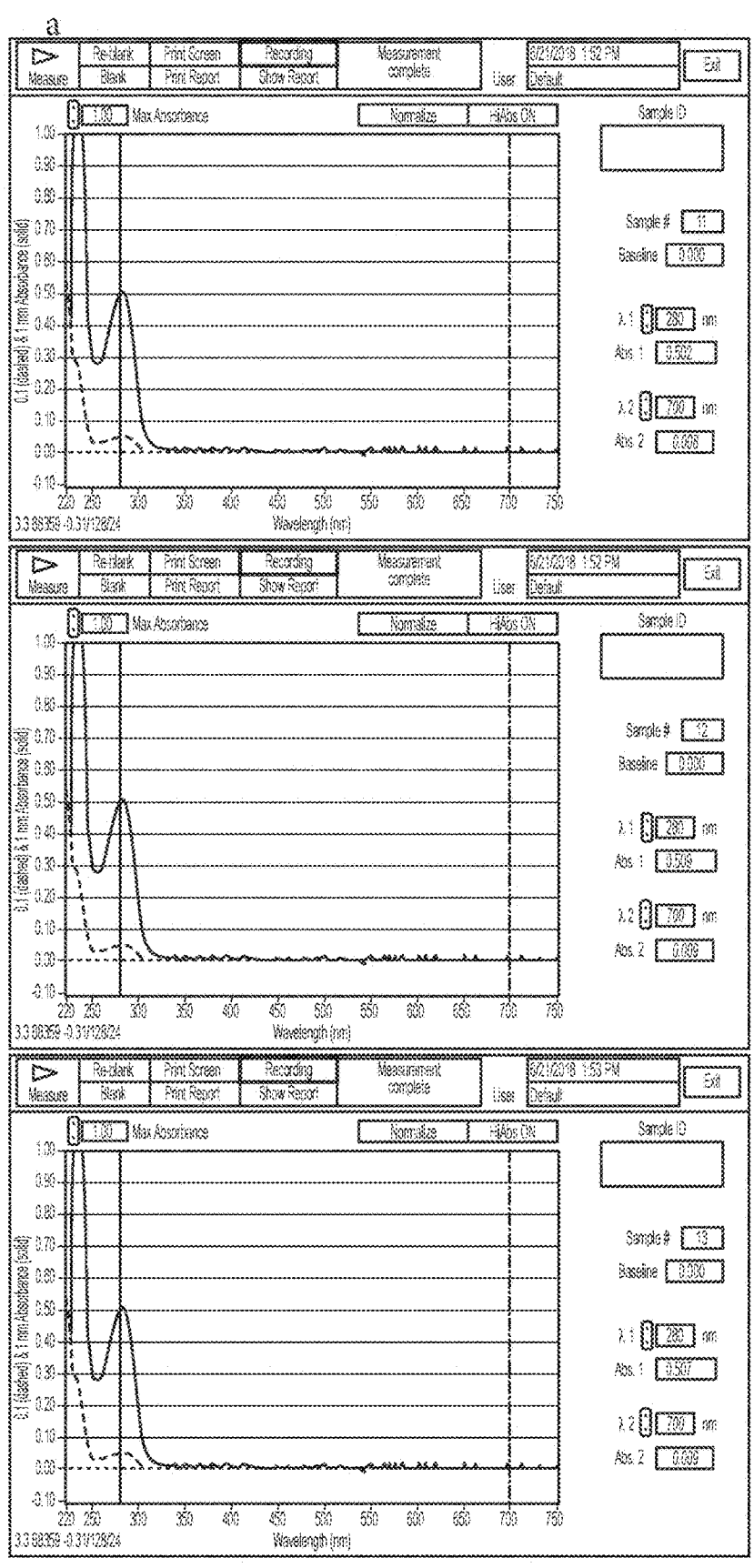
Figure 38B:
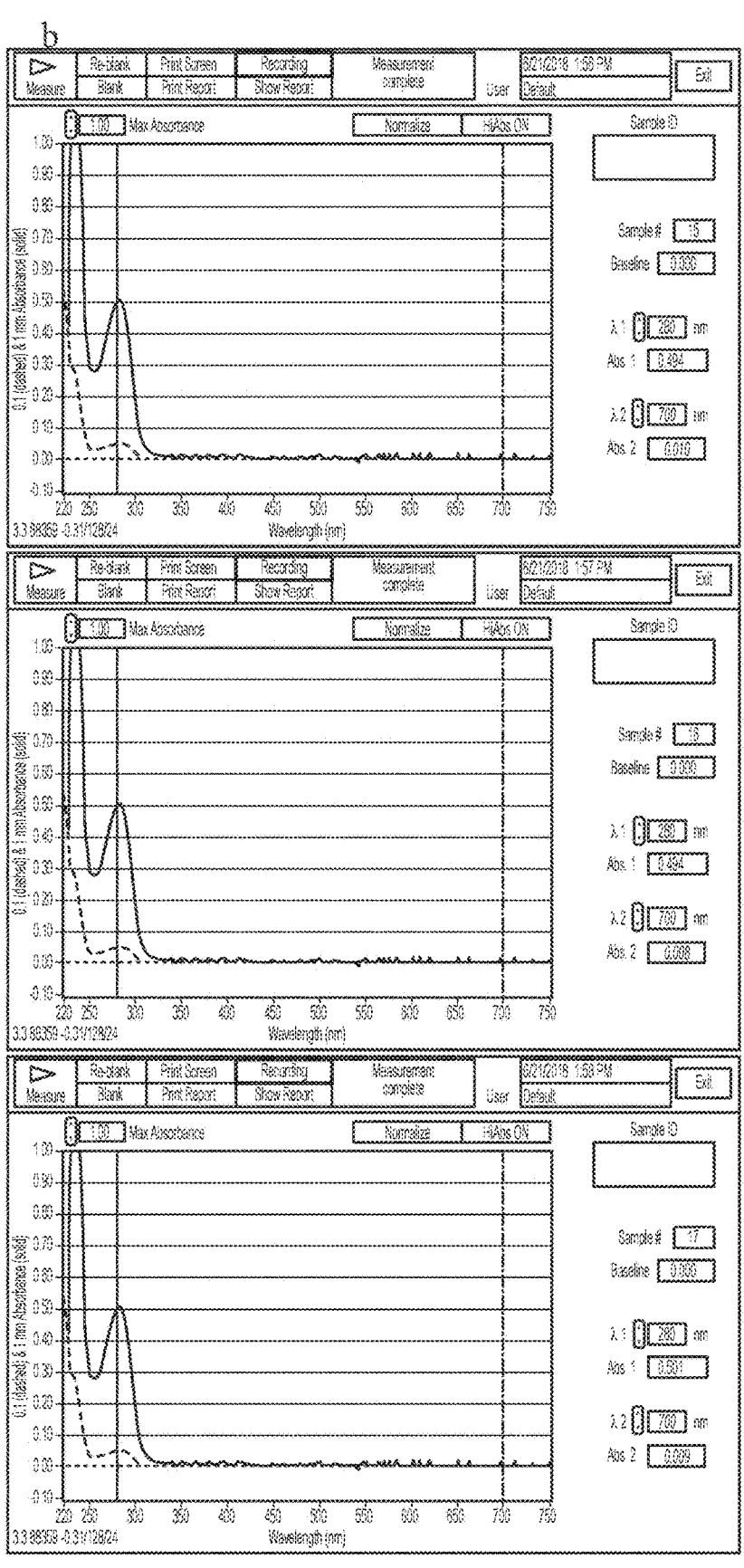

FIGS. 38A-38B show NanoDrop Spectra of 0.2 micron filtered ChABC-G3 in PBS. a before filtration and b after. Data in columns are technical replicates of a or b.

Figure 39A:
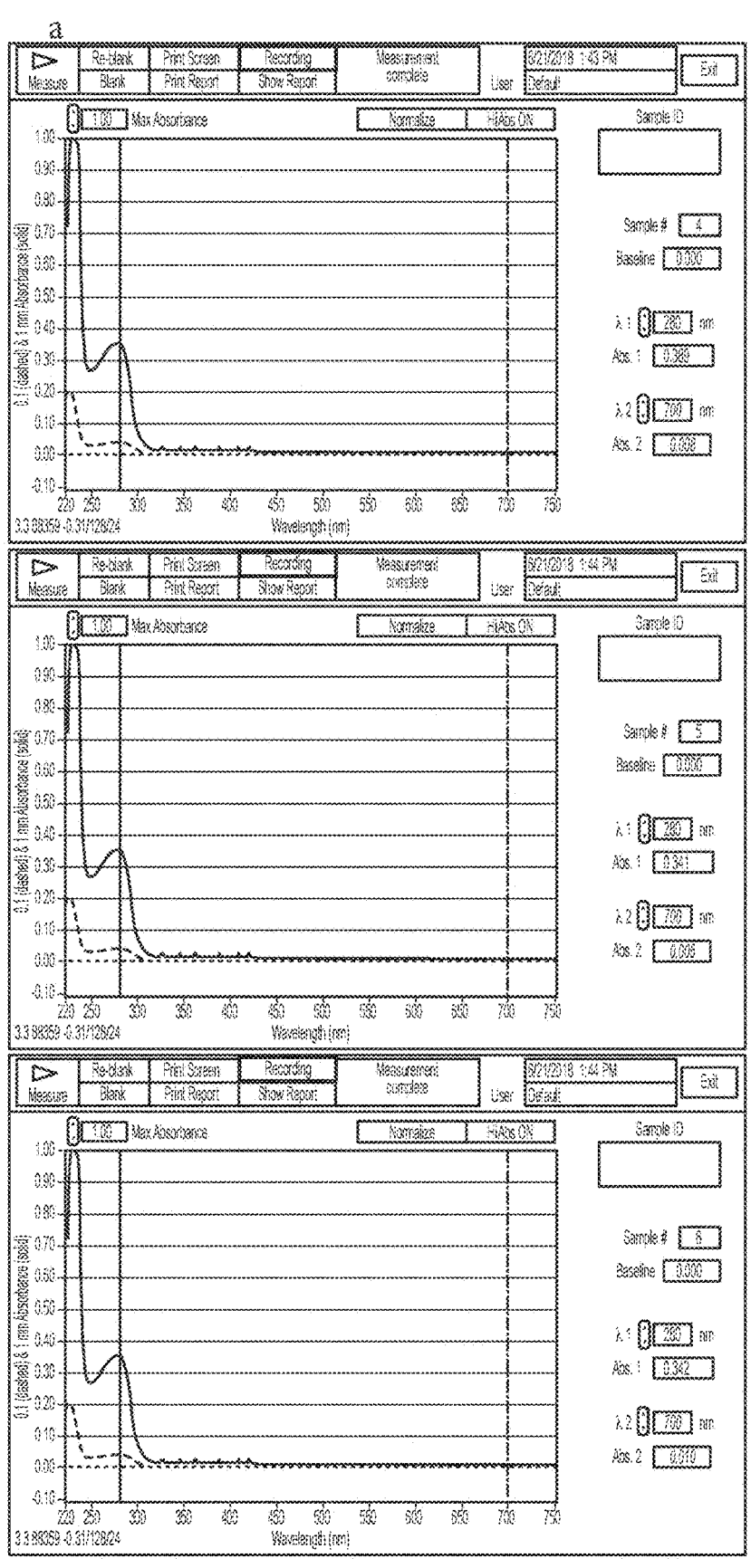
Figure 39B:
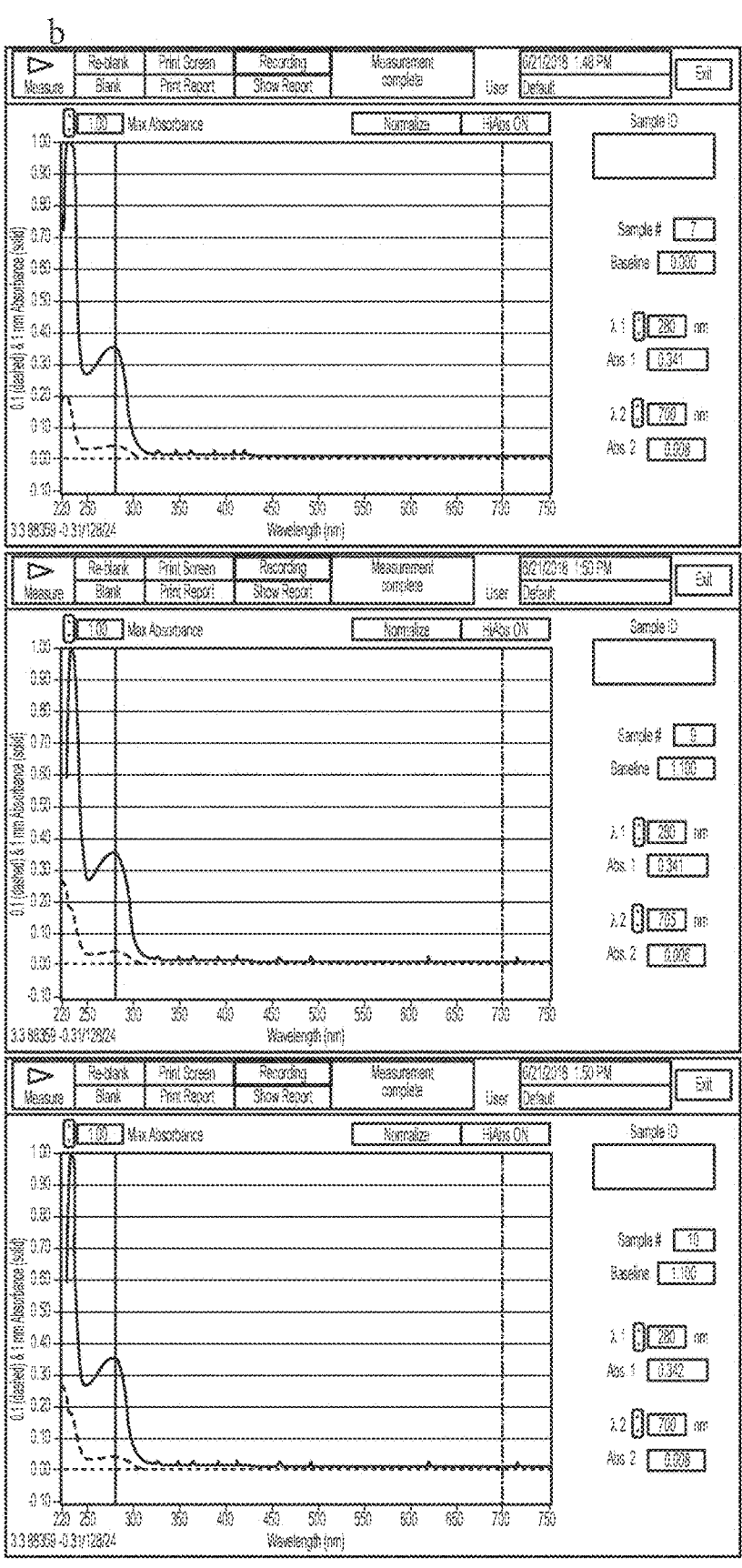

FIGS. 39A-39B show NanoDrop Spectra of 0.2 micron filtered ChABC-TT-G3 in PBS. a before filtration and b after. Data in columns are technical replicates of a or b.

Figure 40A:
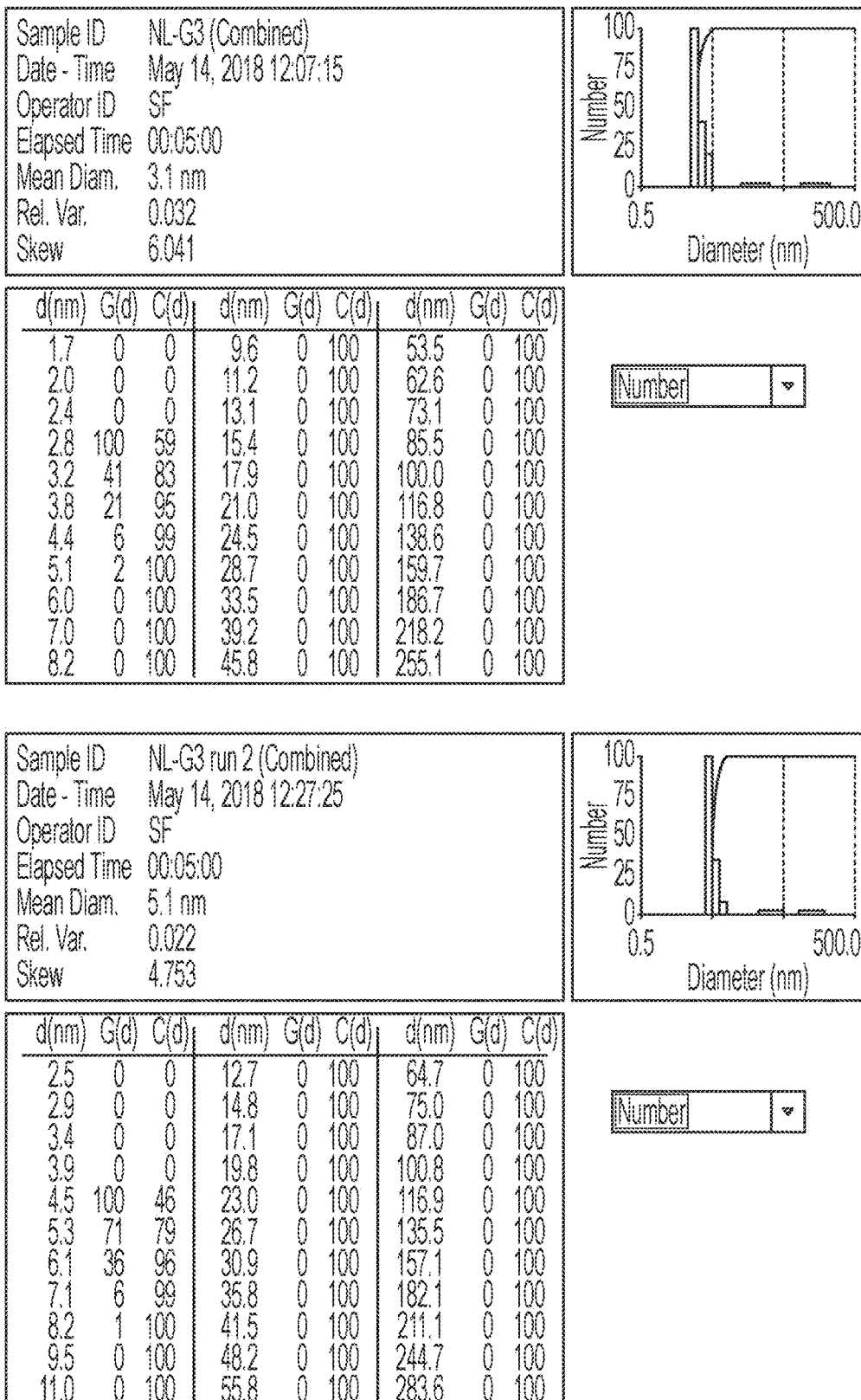
Figure 40A:
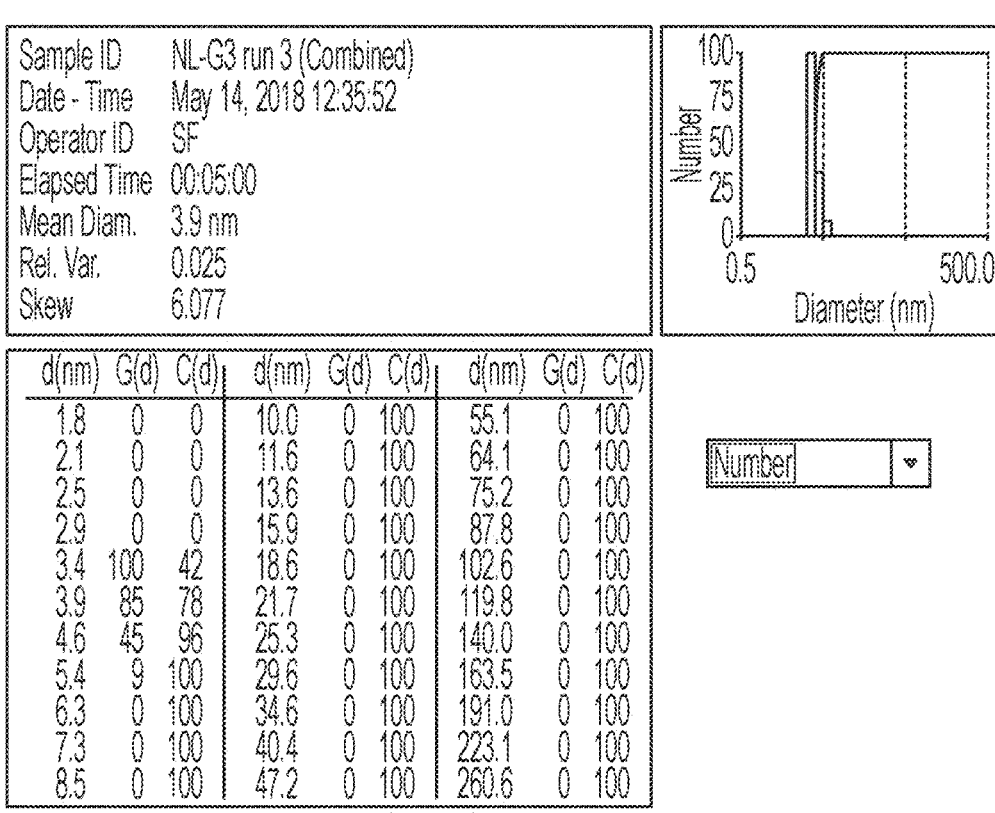
Figure 40B:
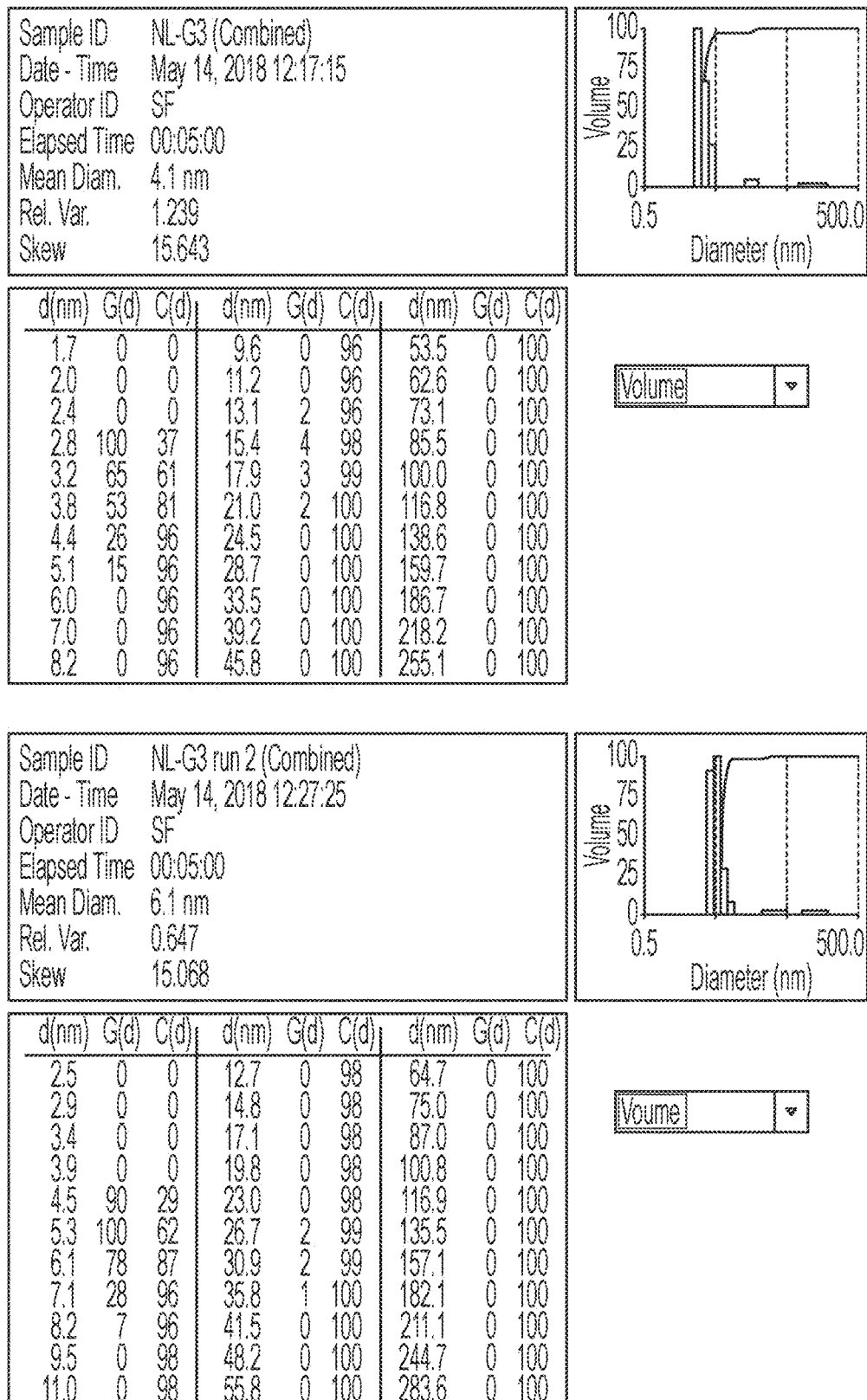
Figure 40B:
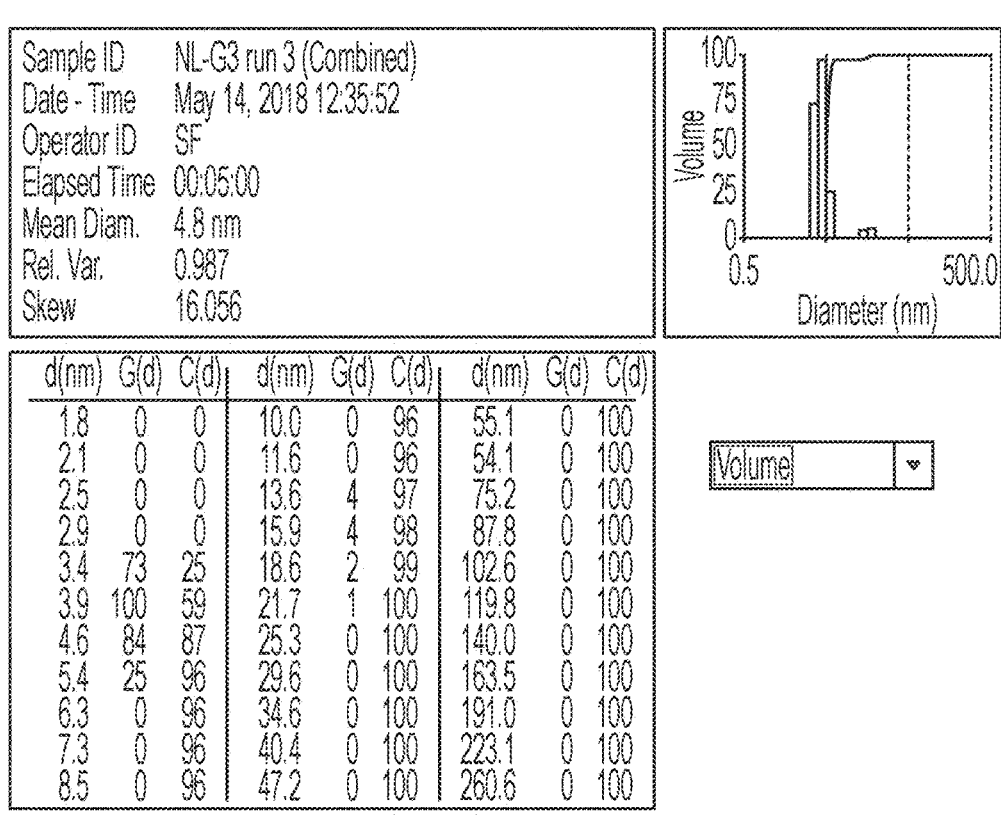

FIGS. 40A-40B show Size distribution of NL-G3 in PBS. a Number- and b volume weighted. Data in columns are technical replicates of a or b.

Figure 41A:
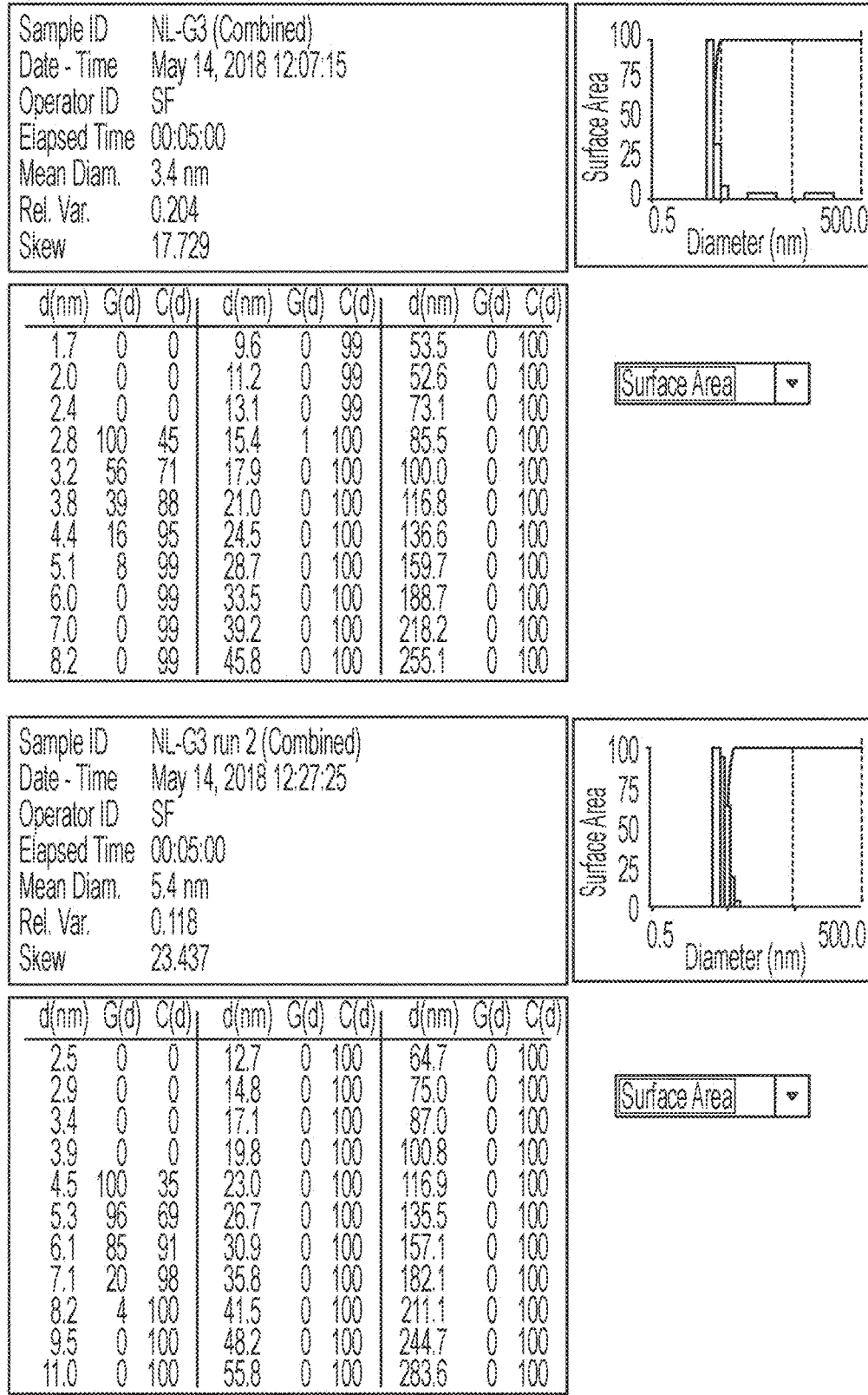
Figure 41A:
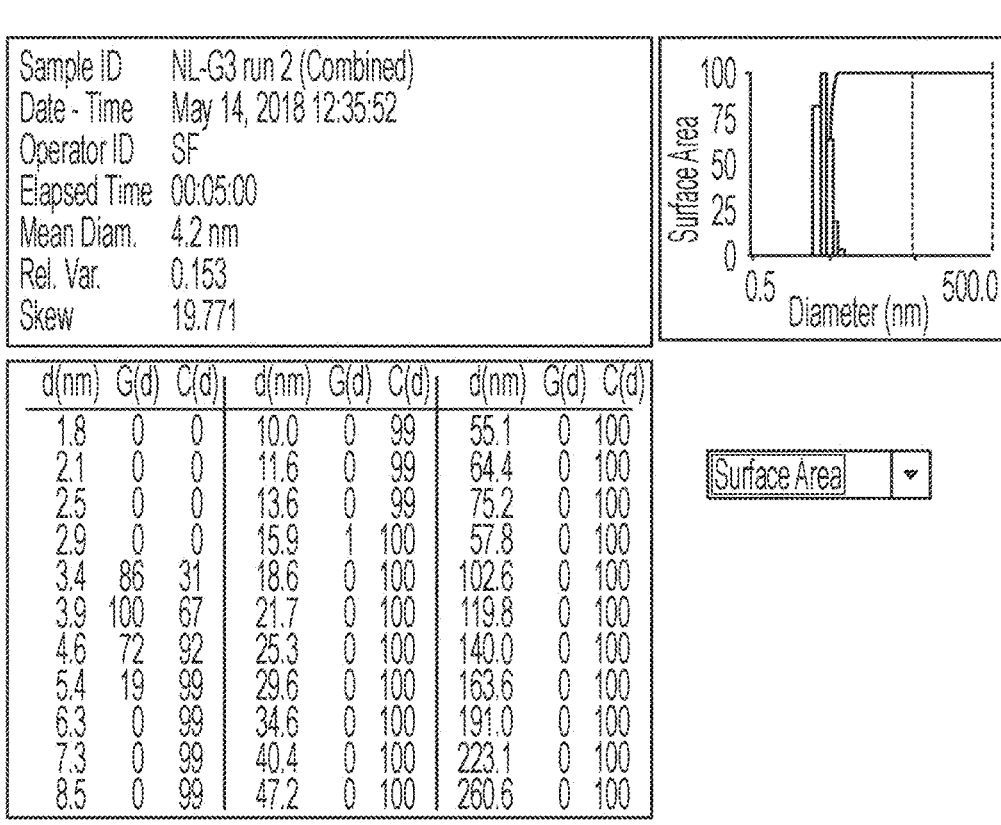
Figure 41B:
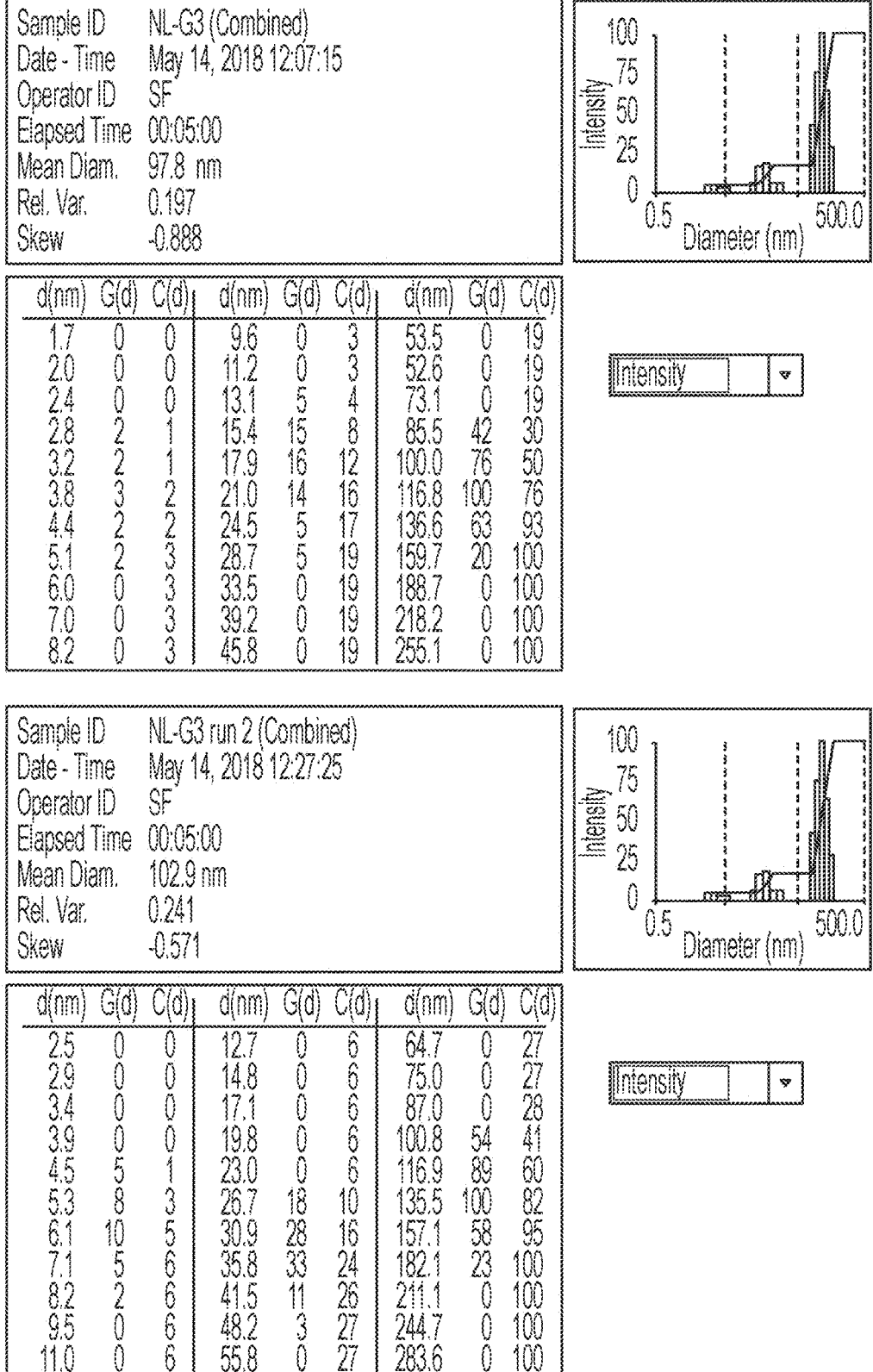
Figure 41B:
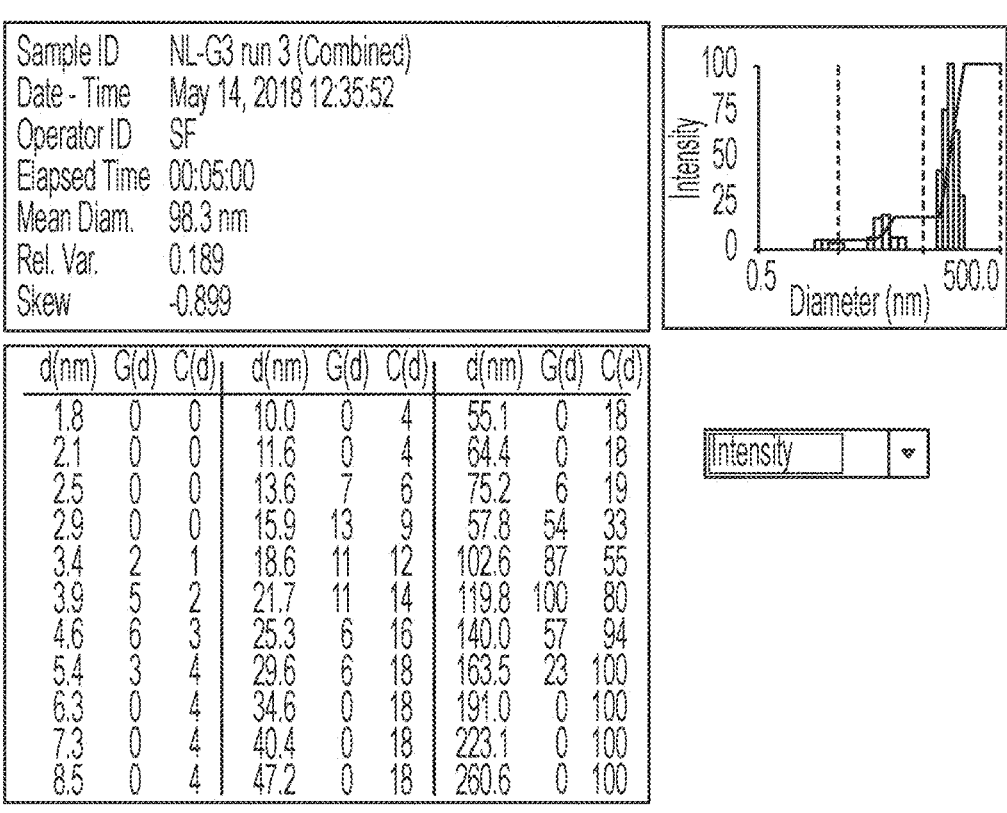

FIGS. 41A-41B show Size distribution of NL-G3 in PBS. a Surface area- and b intensity weighted. Data in columns are technical replicates of a or b.

Figure 42:
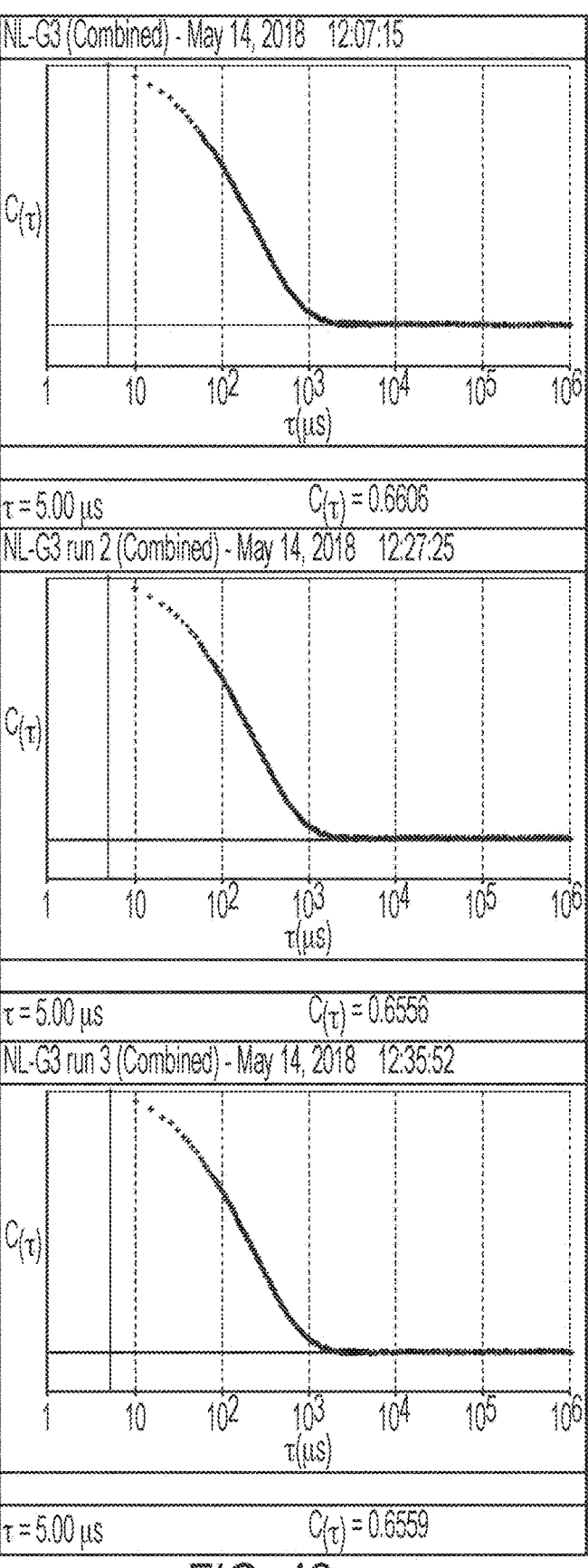

FIG. 42 shows correlation functions for DLS measurements of NL-G3. Data are technical replicates.

Figure 43A:
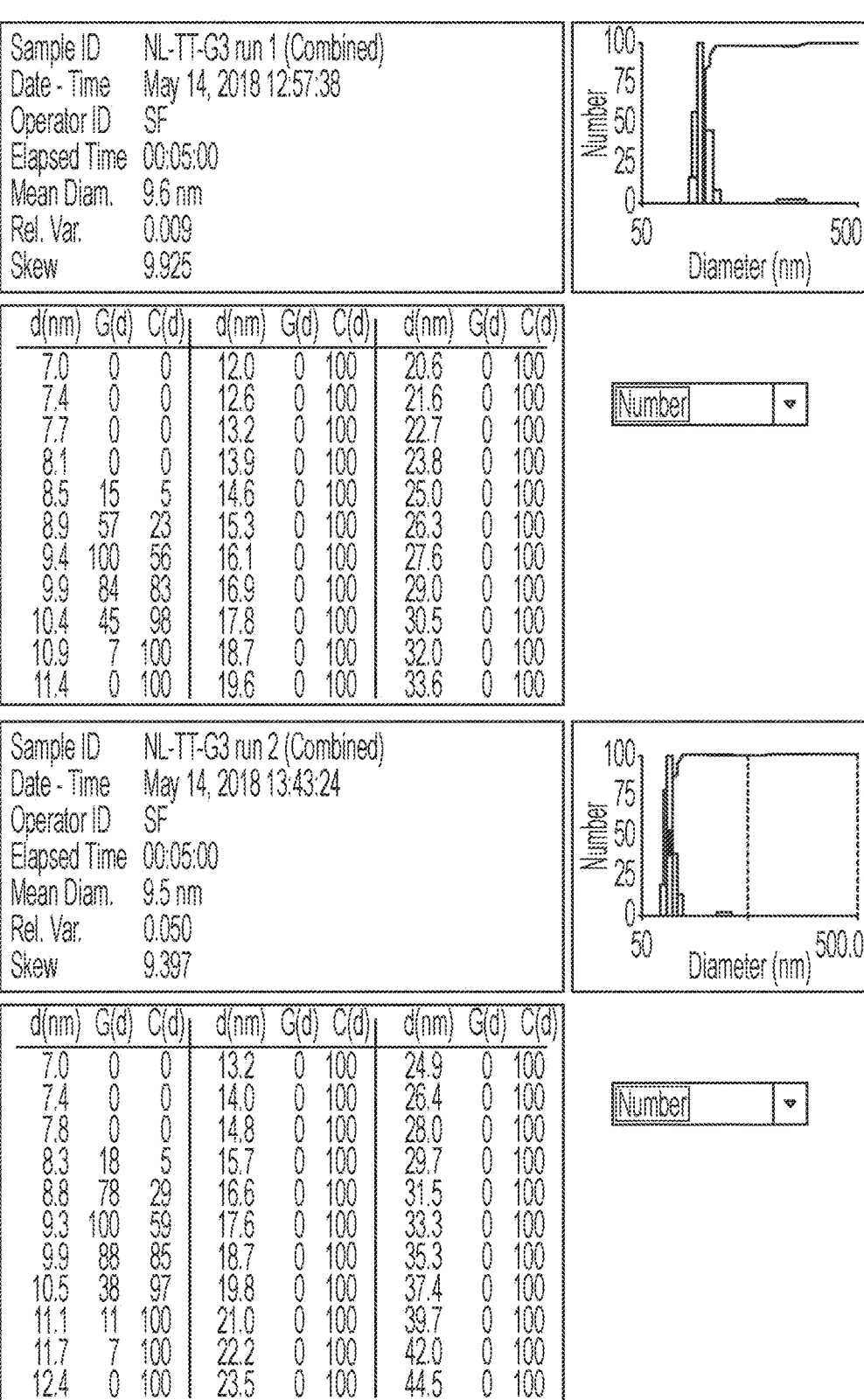
Figure 43A:
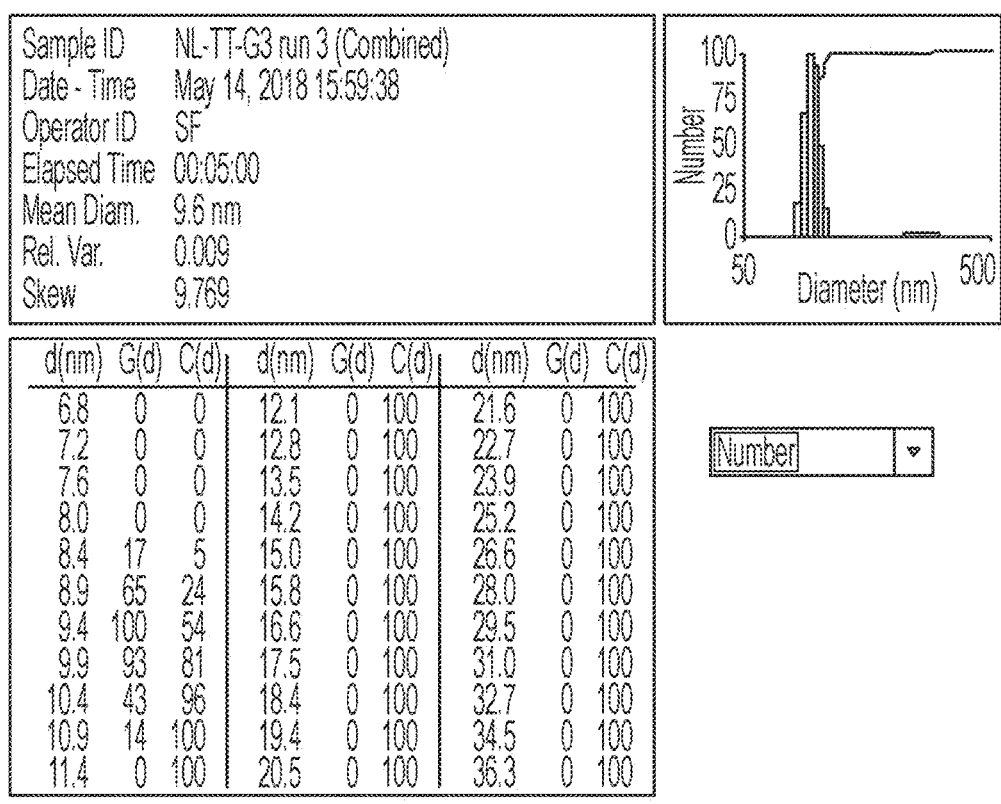
Figure 43B:
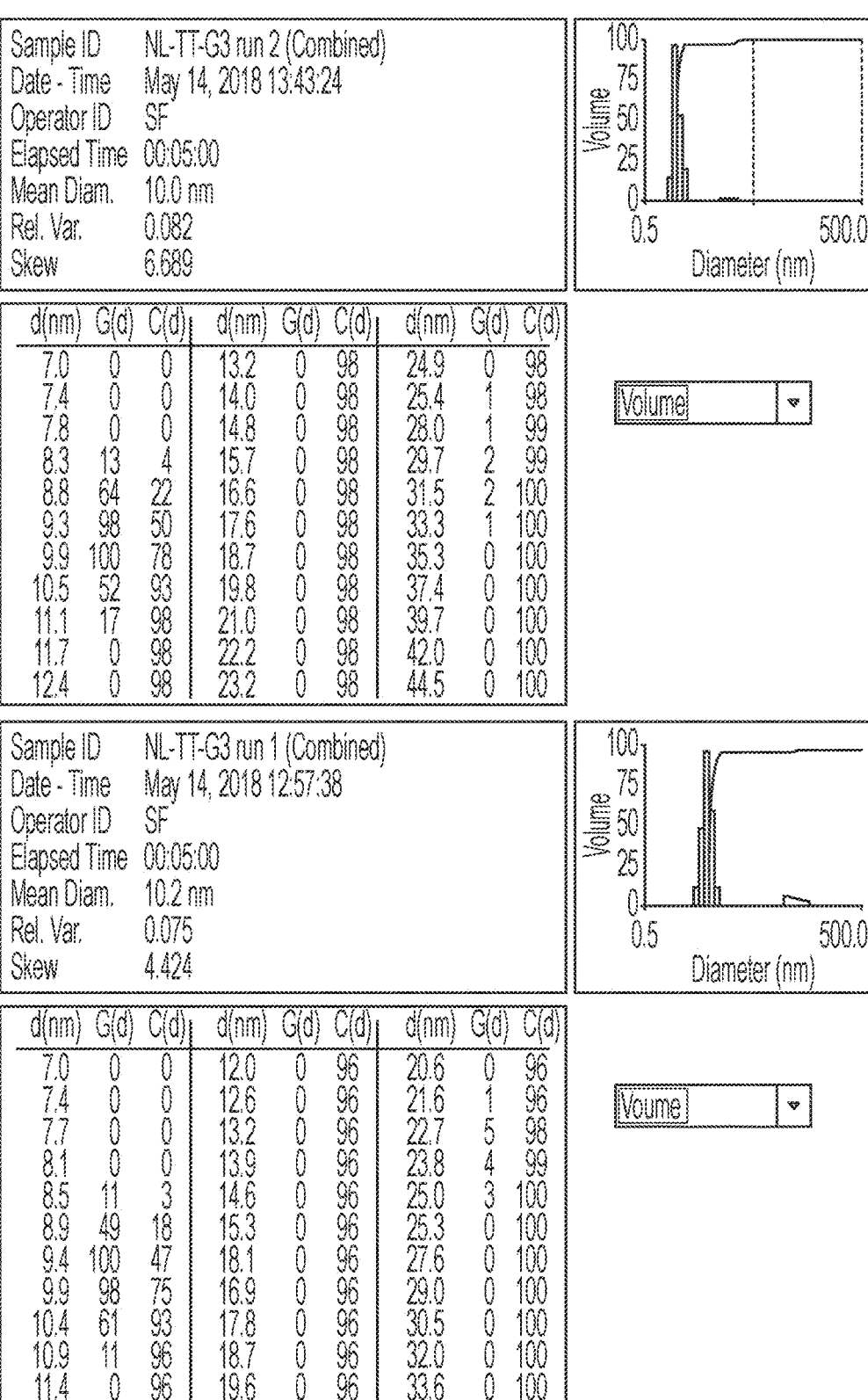
Figure 43B:
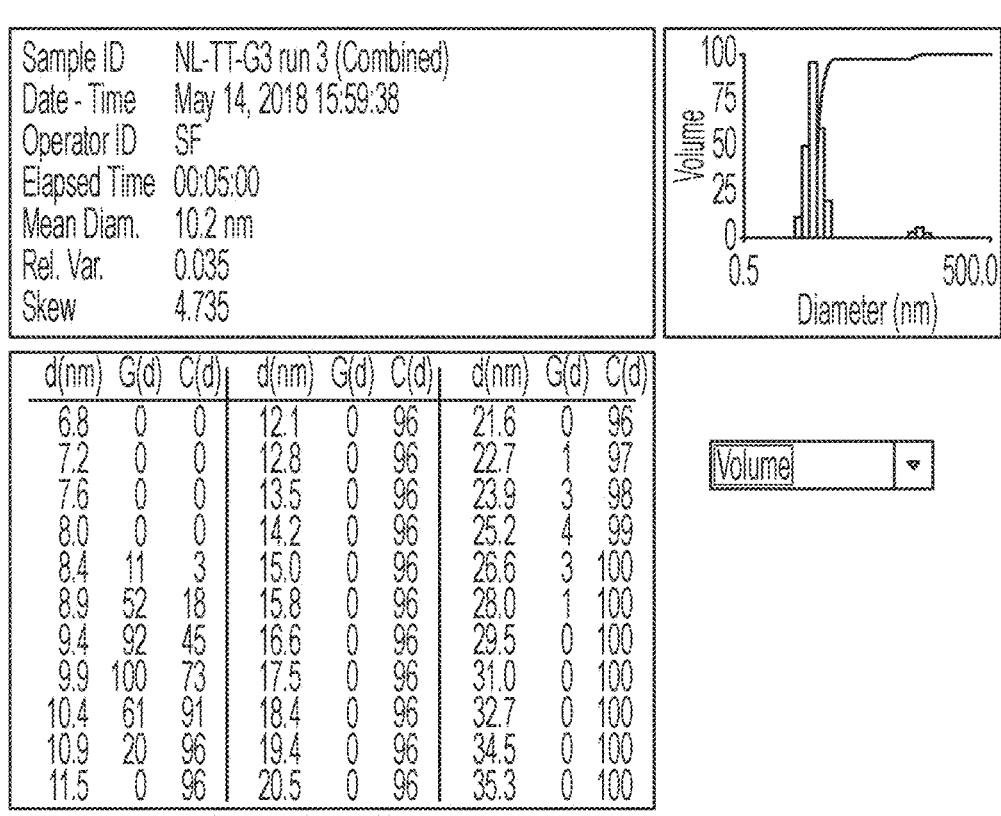

FIGS. 43A-43B show size distribution of NL-TT-G3 in PBS. a Number- and b volume weighted. Data in columns are technical replicates of a or b.

Figure 44A:
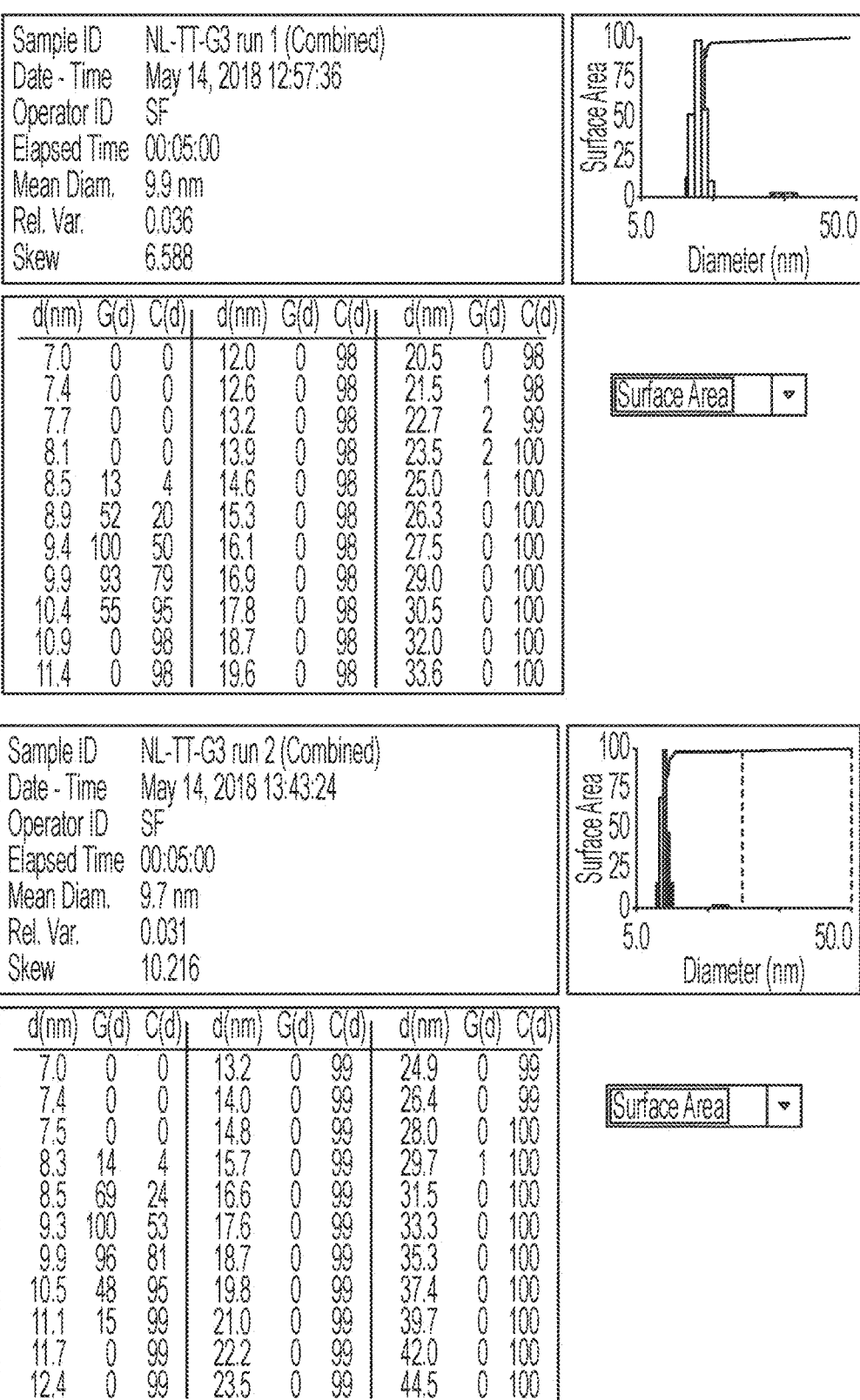
Figure 44A:
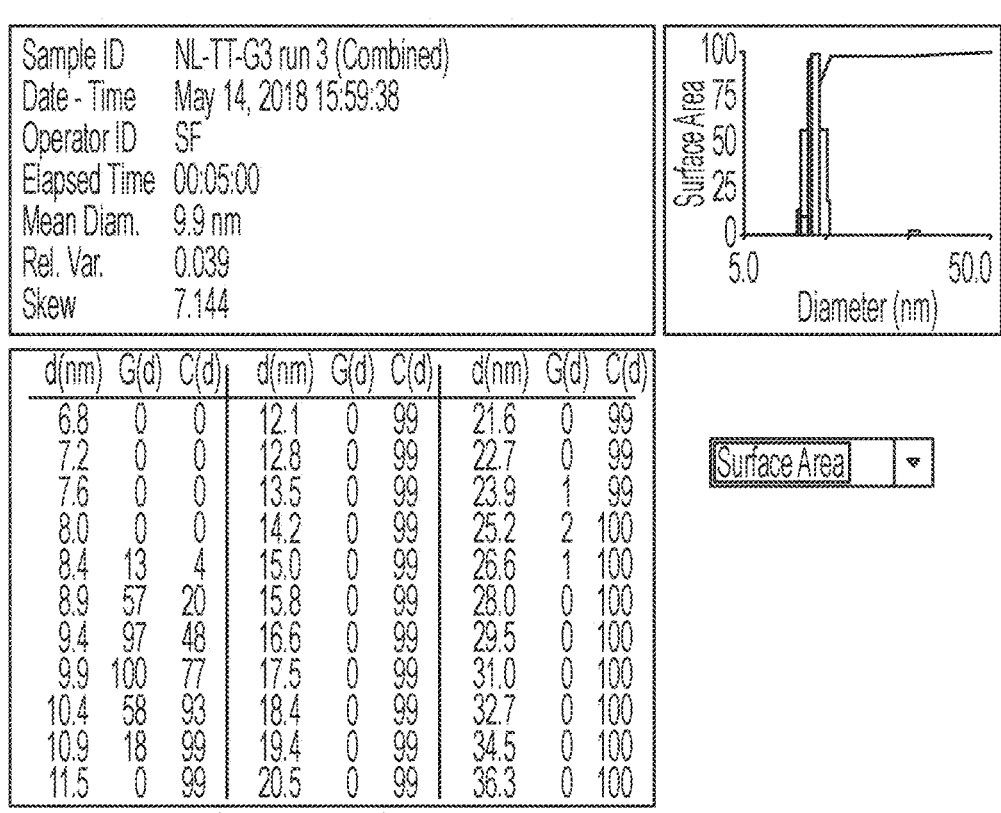
Figure 44B:
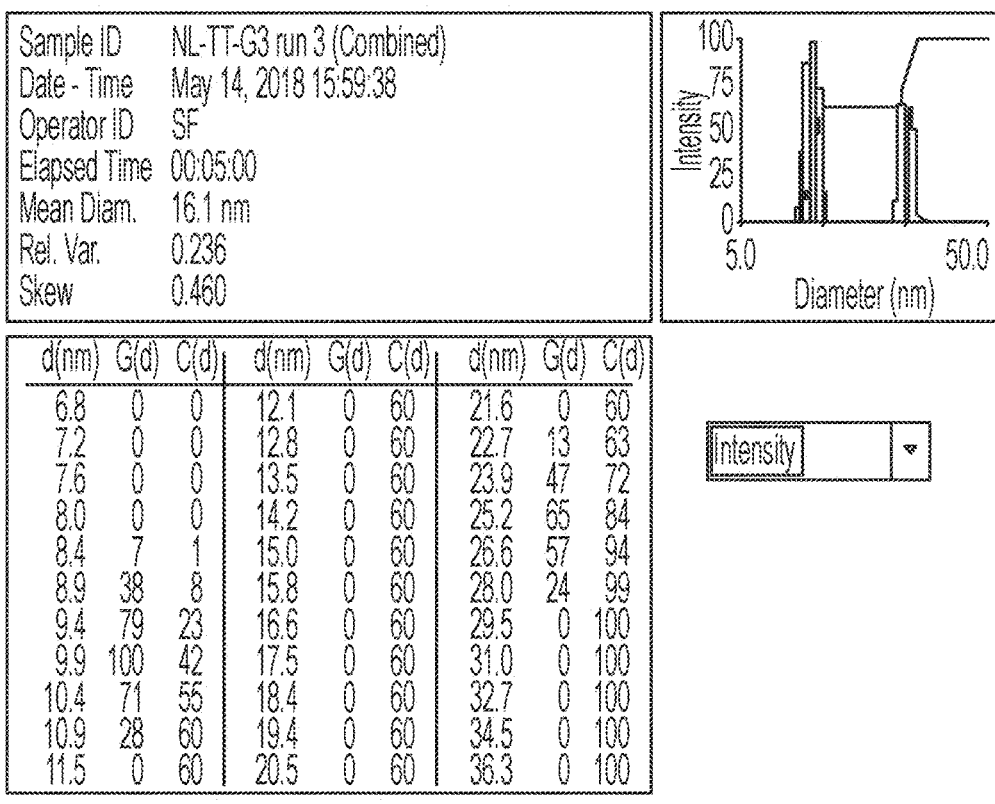

FIGS. 44A-44B show size distribution of NL-TT-G3 in PBS. a Surface area- and b intensity-weighted. Data in columns are technical replicates of a or b.

Figure 45:
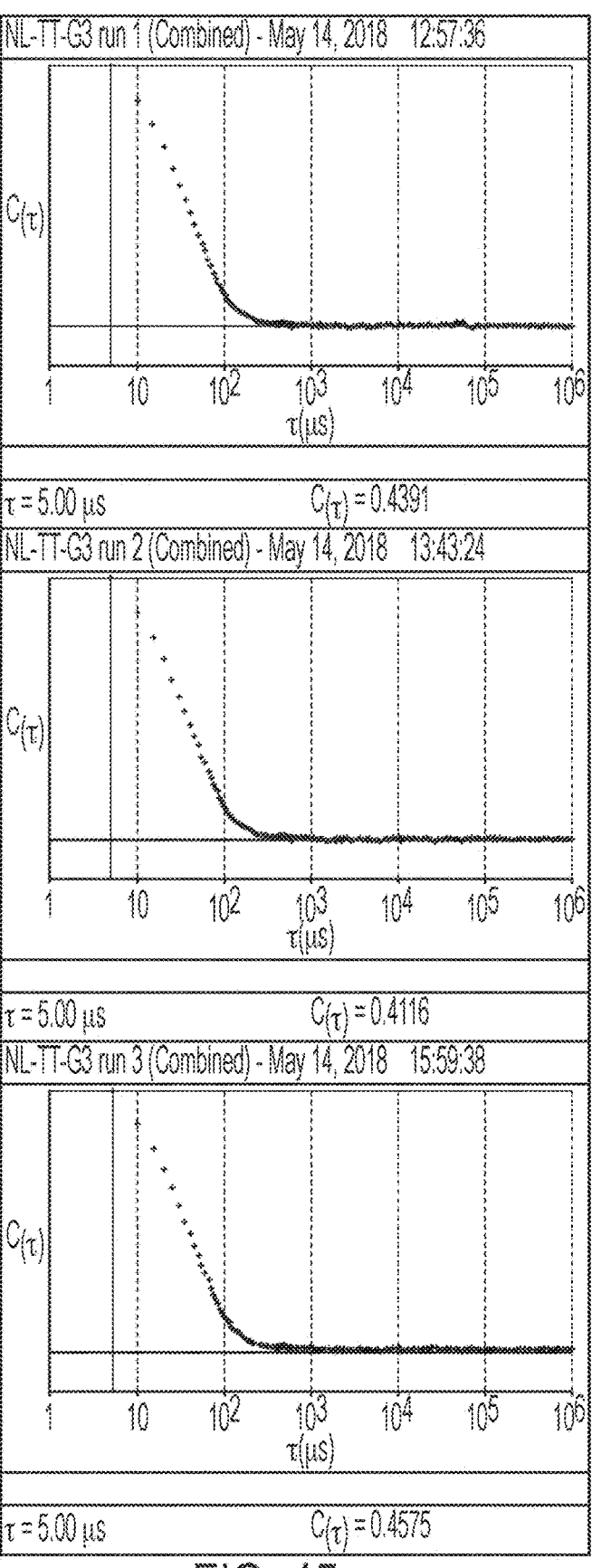

FIG. 45 shows a correlation functions for DLS measurements of NL-TT-G3. Data are technical replicates.

Figure 46A:
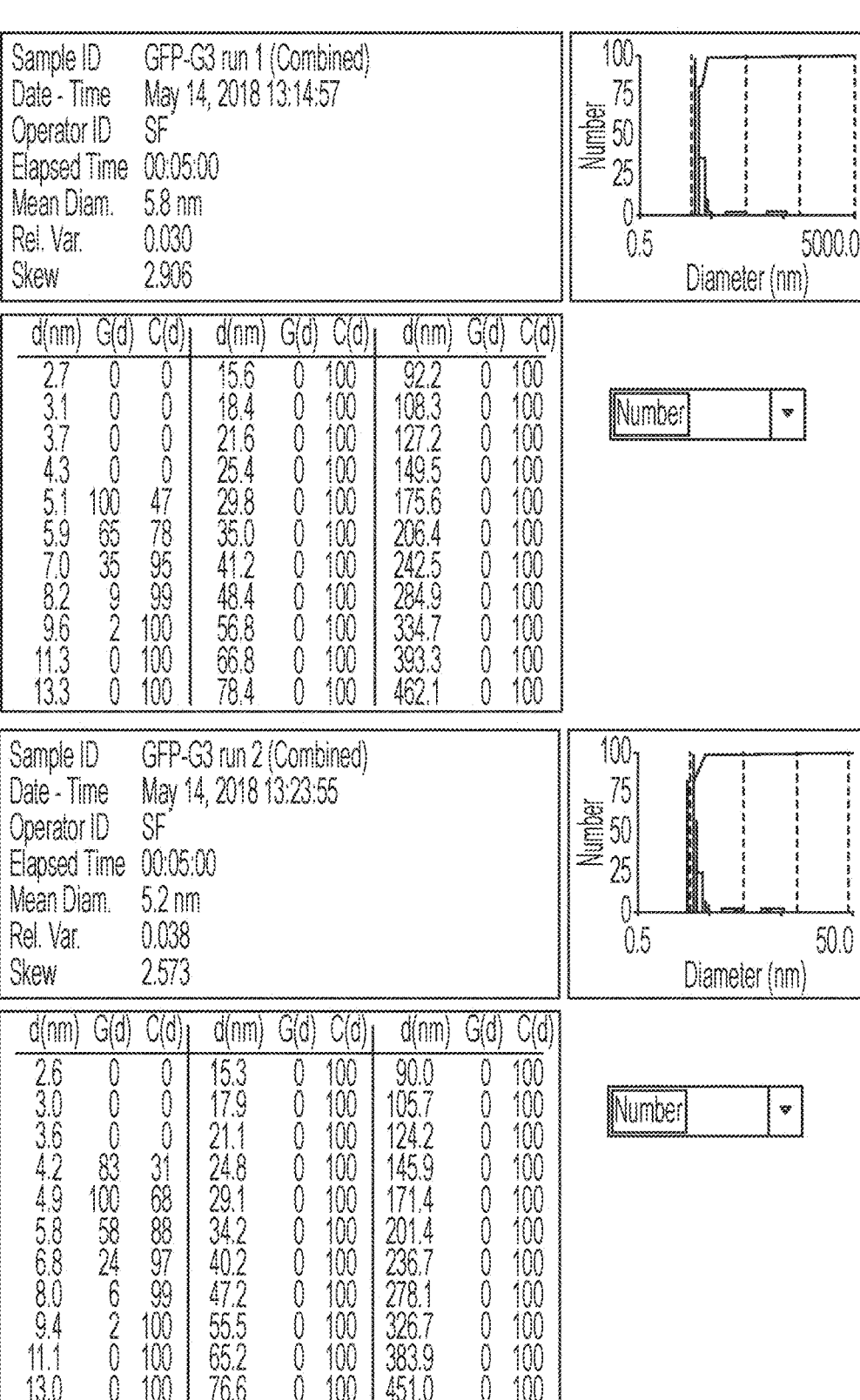
Figure 46A:
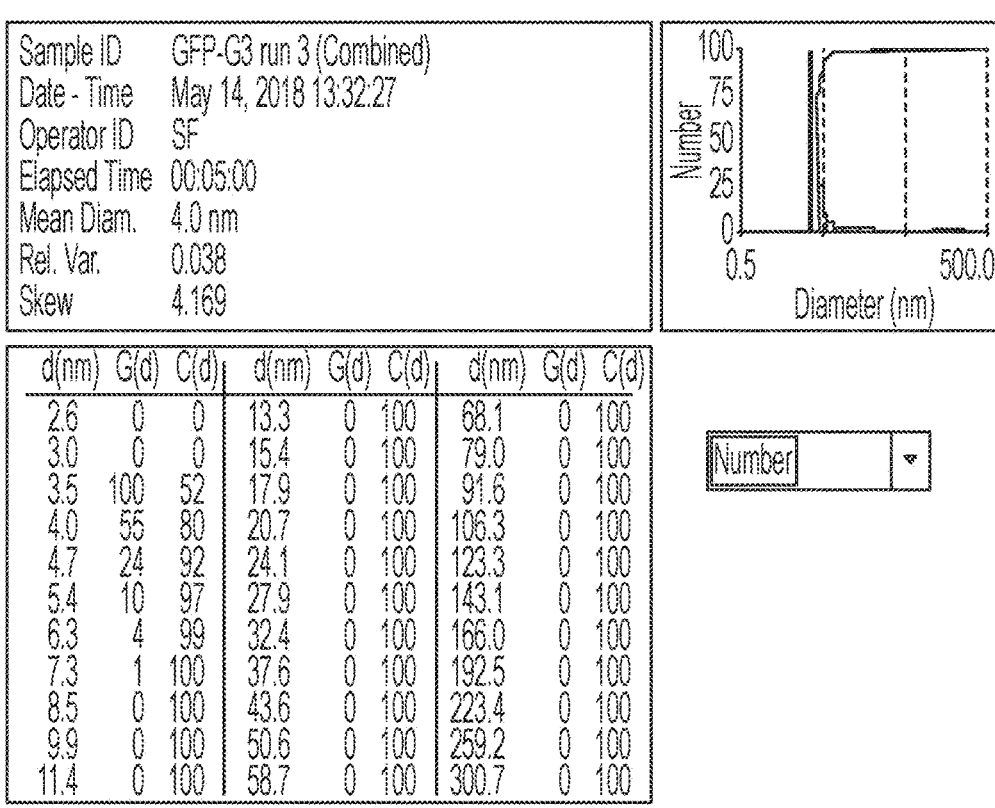
Figure 46B:
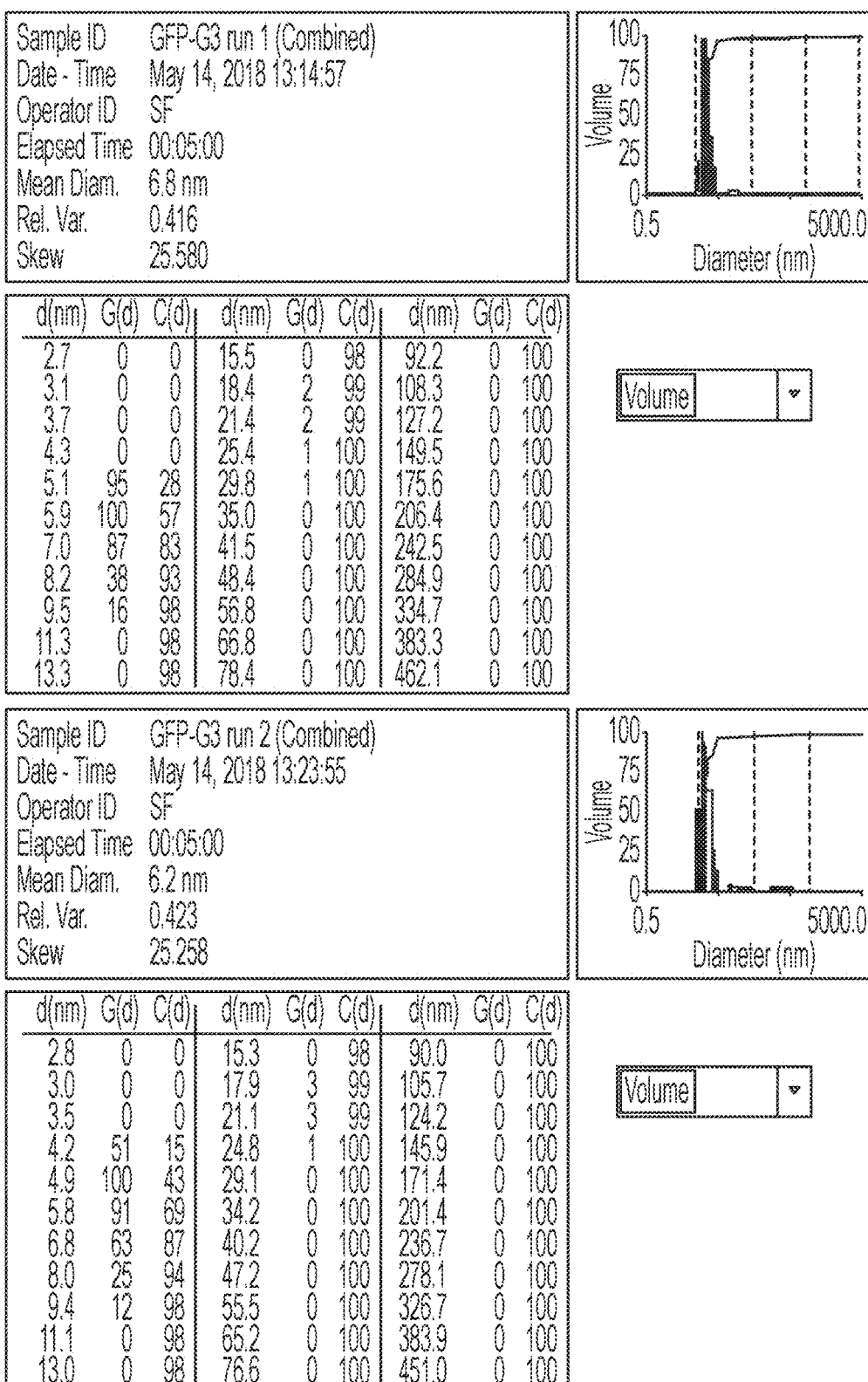
Figure 46B:
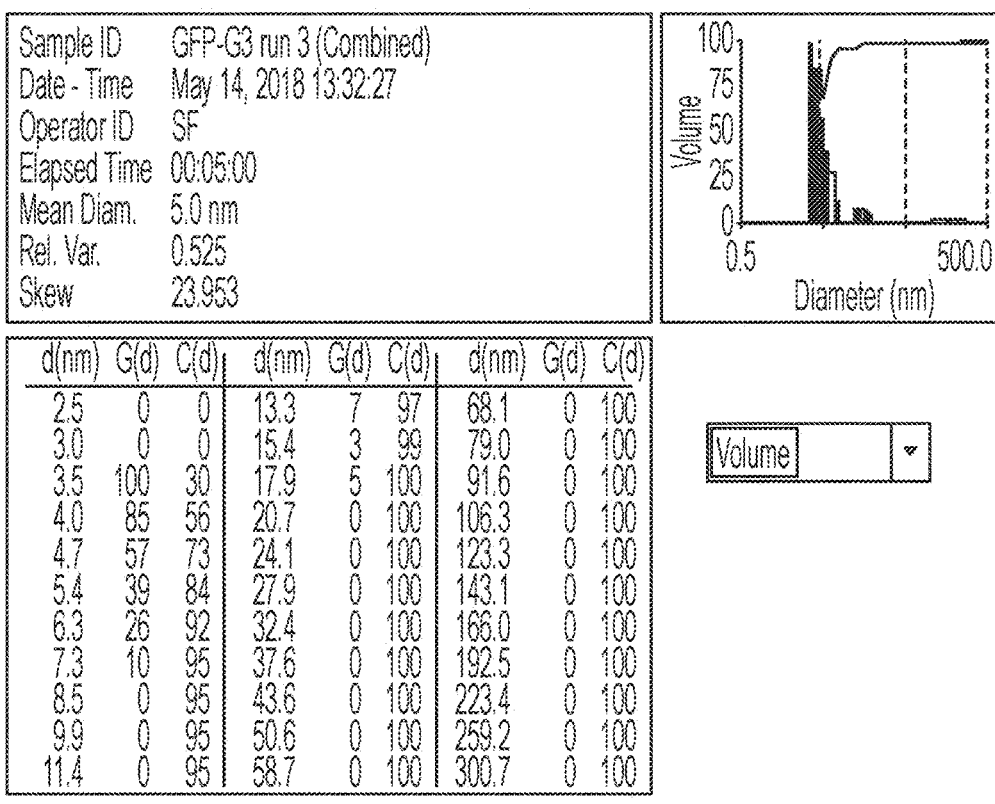

FIGS. 46A-46B show size distribution of GFP-G3 in PBS. a Number- and b volume weighted. Data in columns are technical replicates of a or b.

Figure 47A:
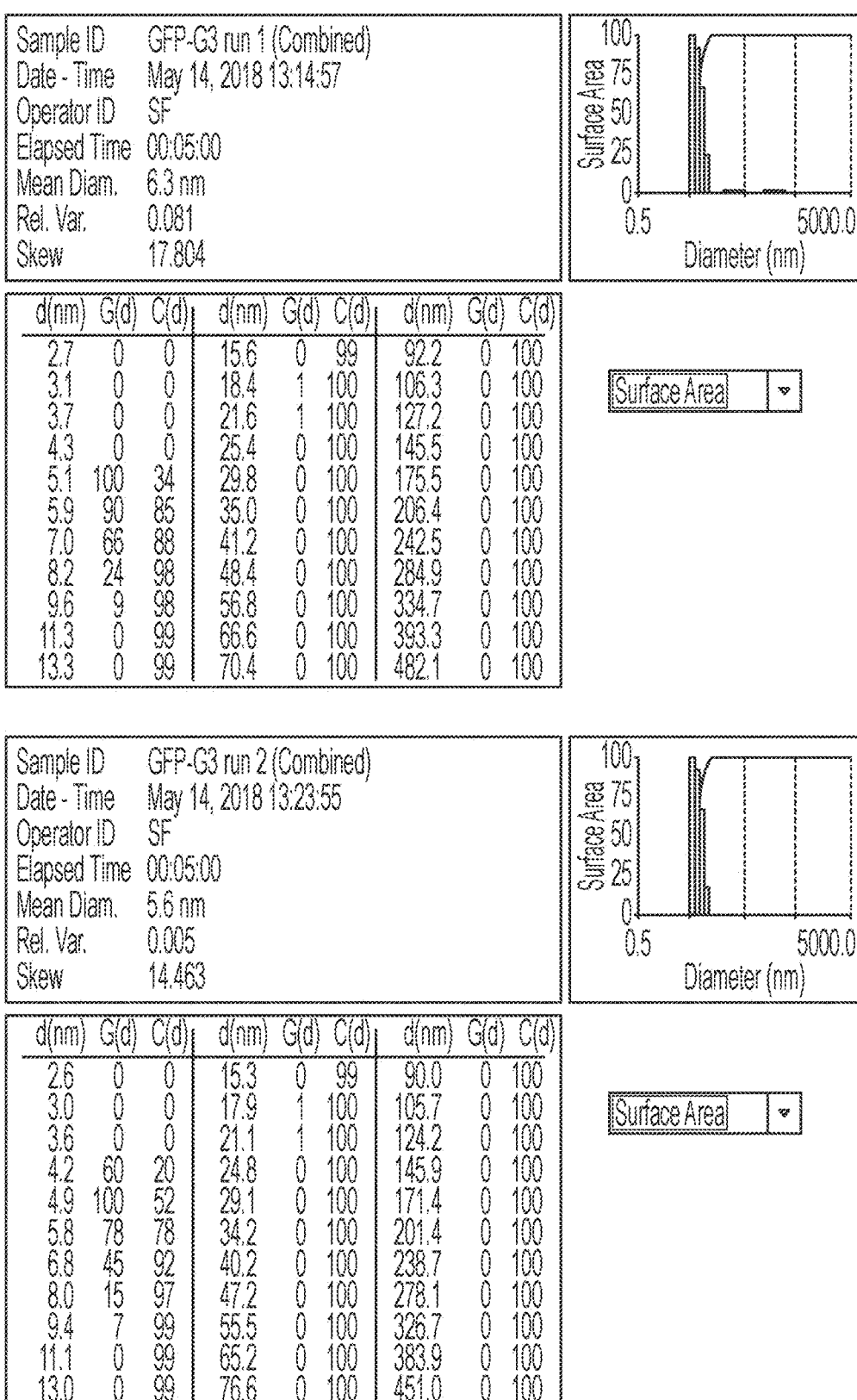
Figure 47A:
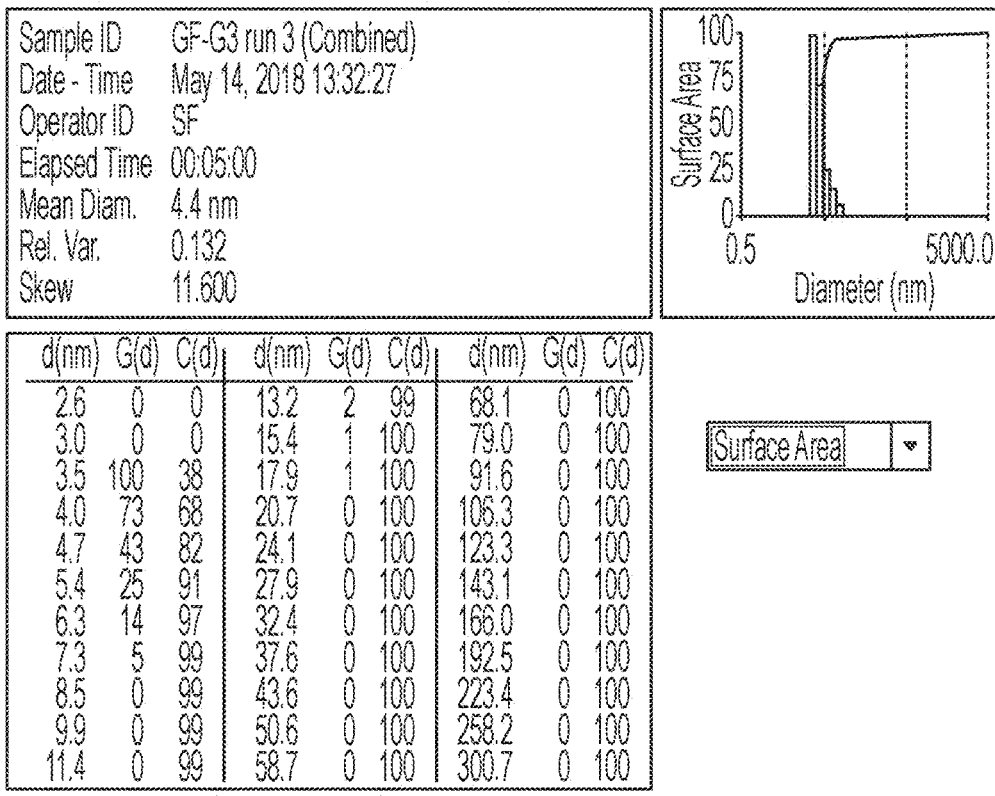
Figure 47B:
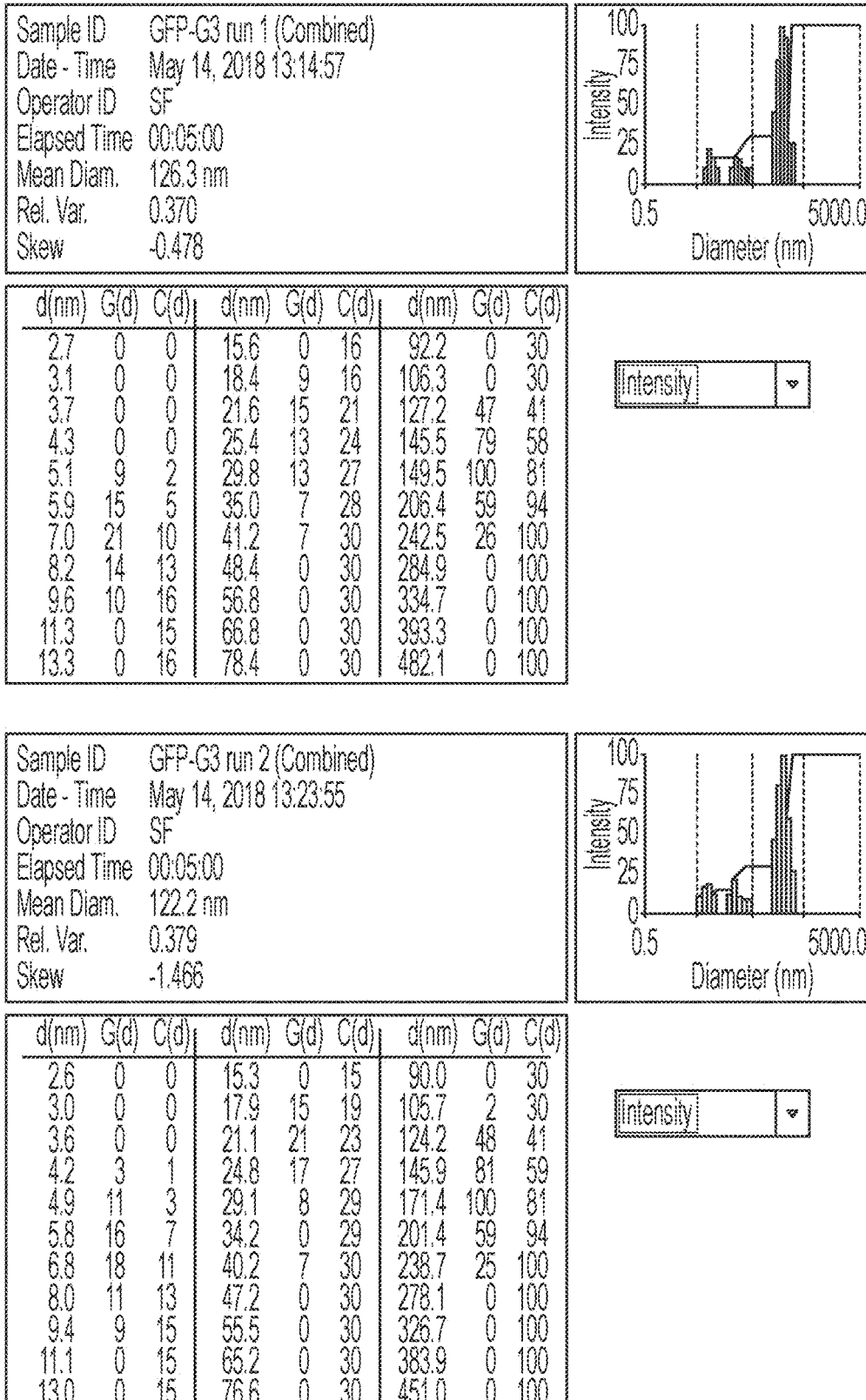
Figure 47B:
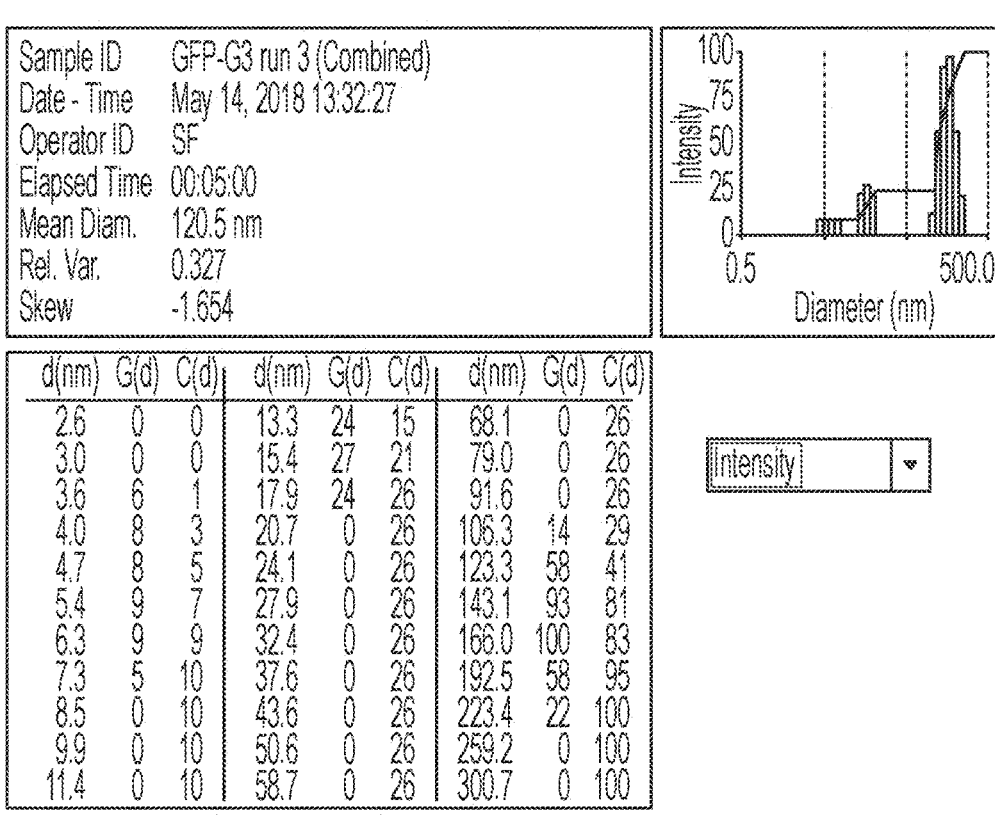

FIGS. 47A-47B show size distribution of GFP-G3 in PBS. a Surface area- and b intensity weighted. Data in columns are technical replicates of a or b.

Figure 48:
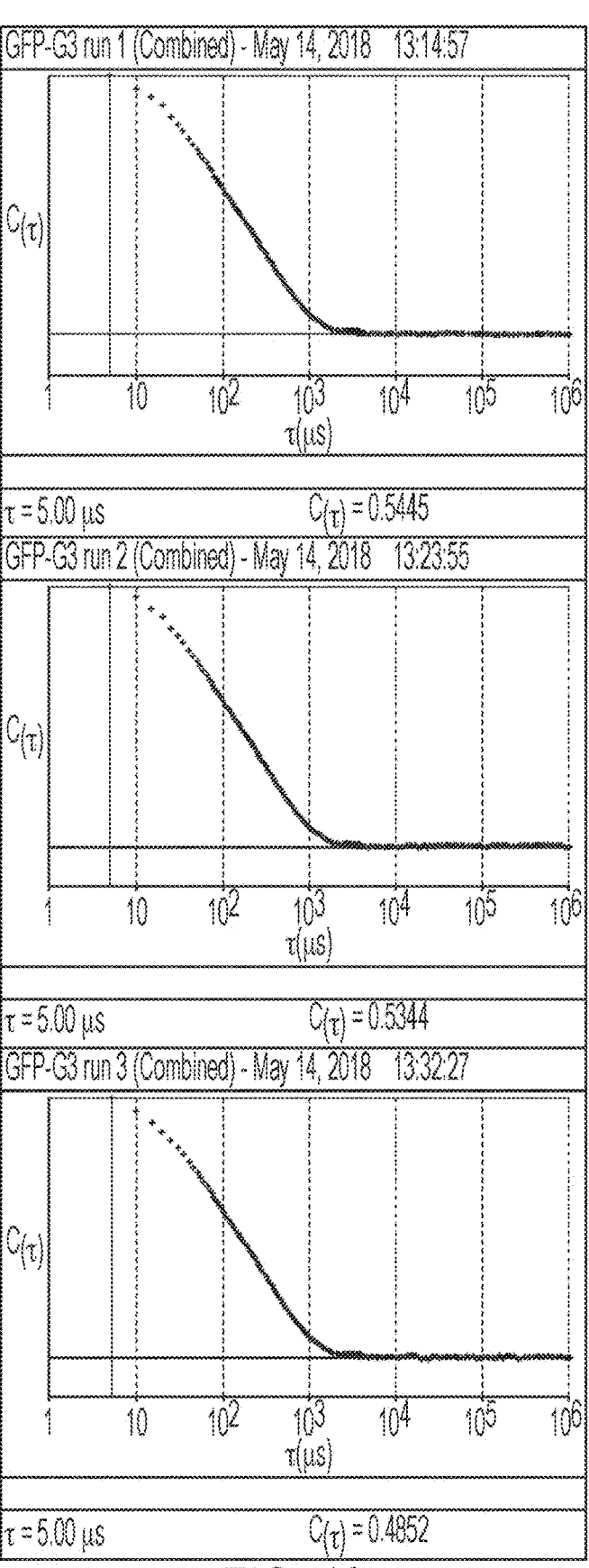

FIG. 48 shows a correlation functions for DLS measurements of GFP-G3. Data are technical replicates.

Figure 49A:
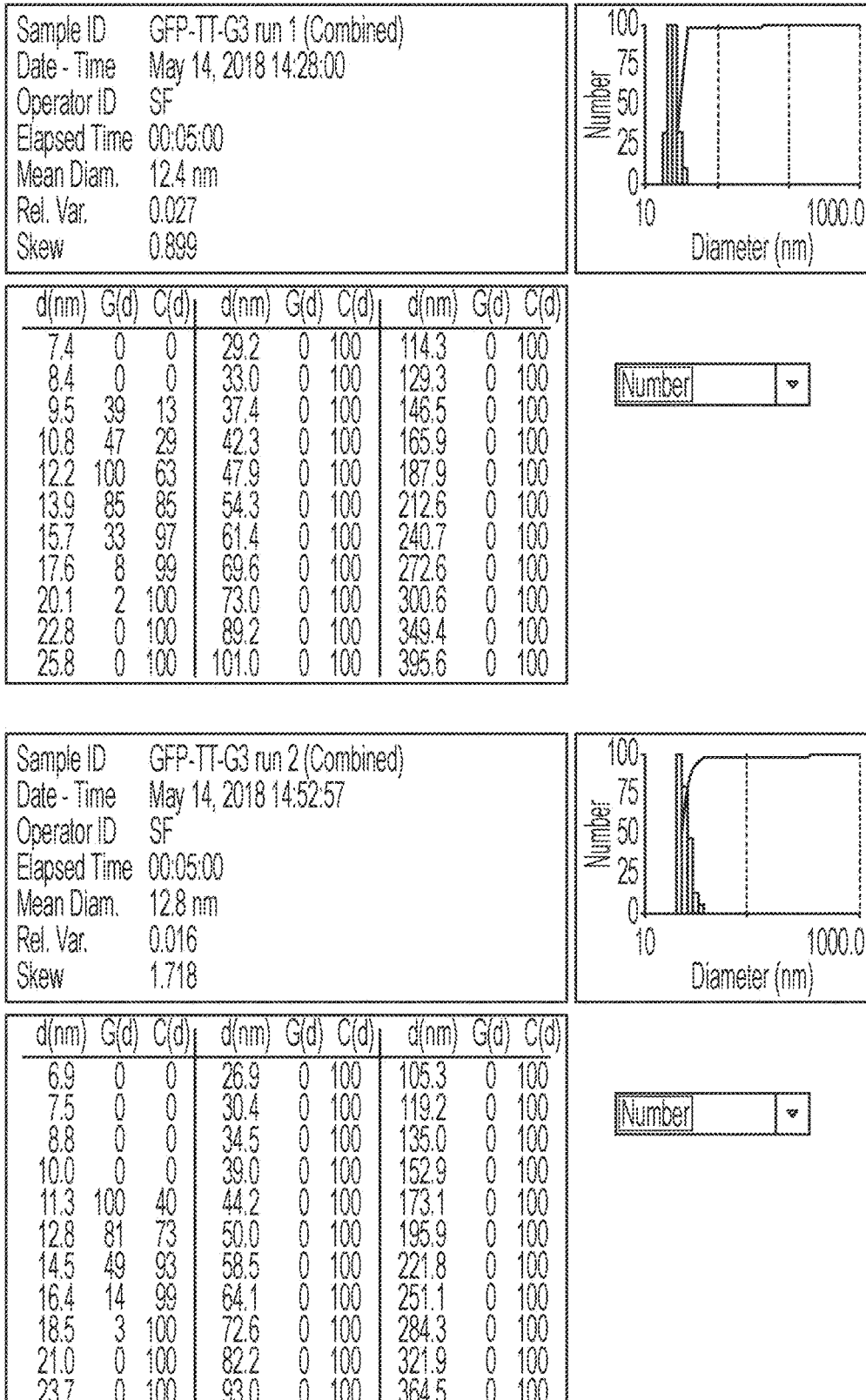
Figure 49A:
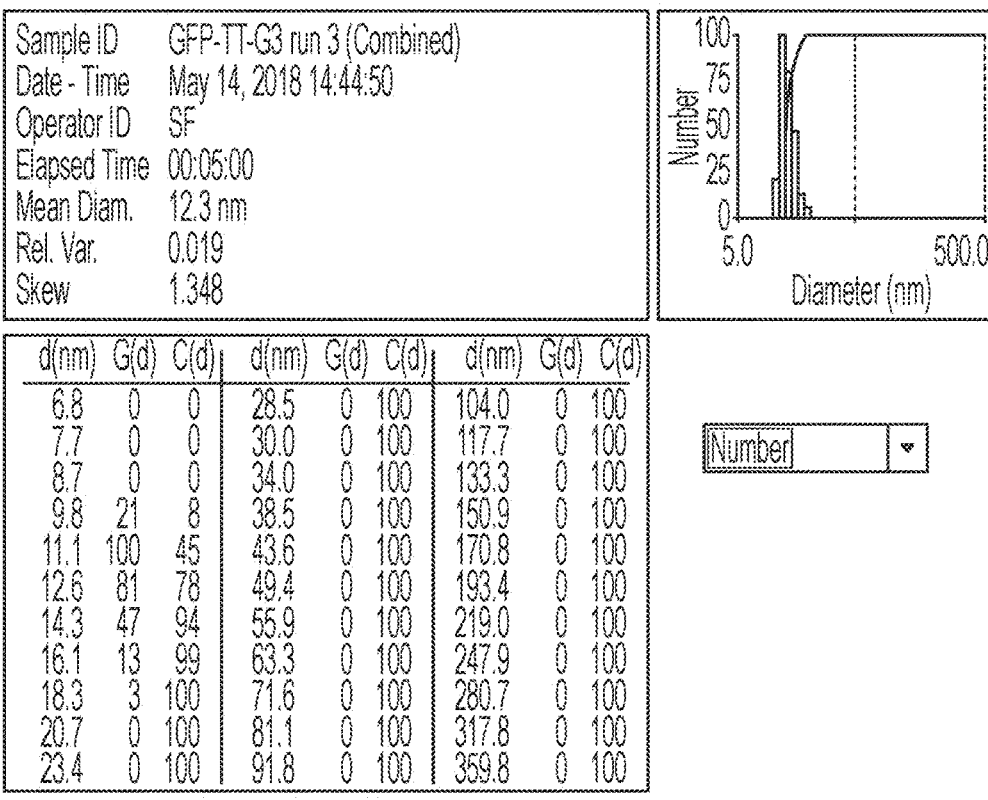
Figure 49B:
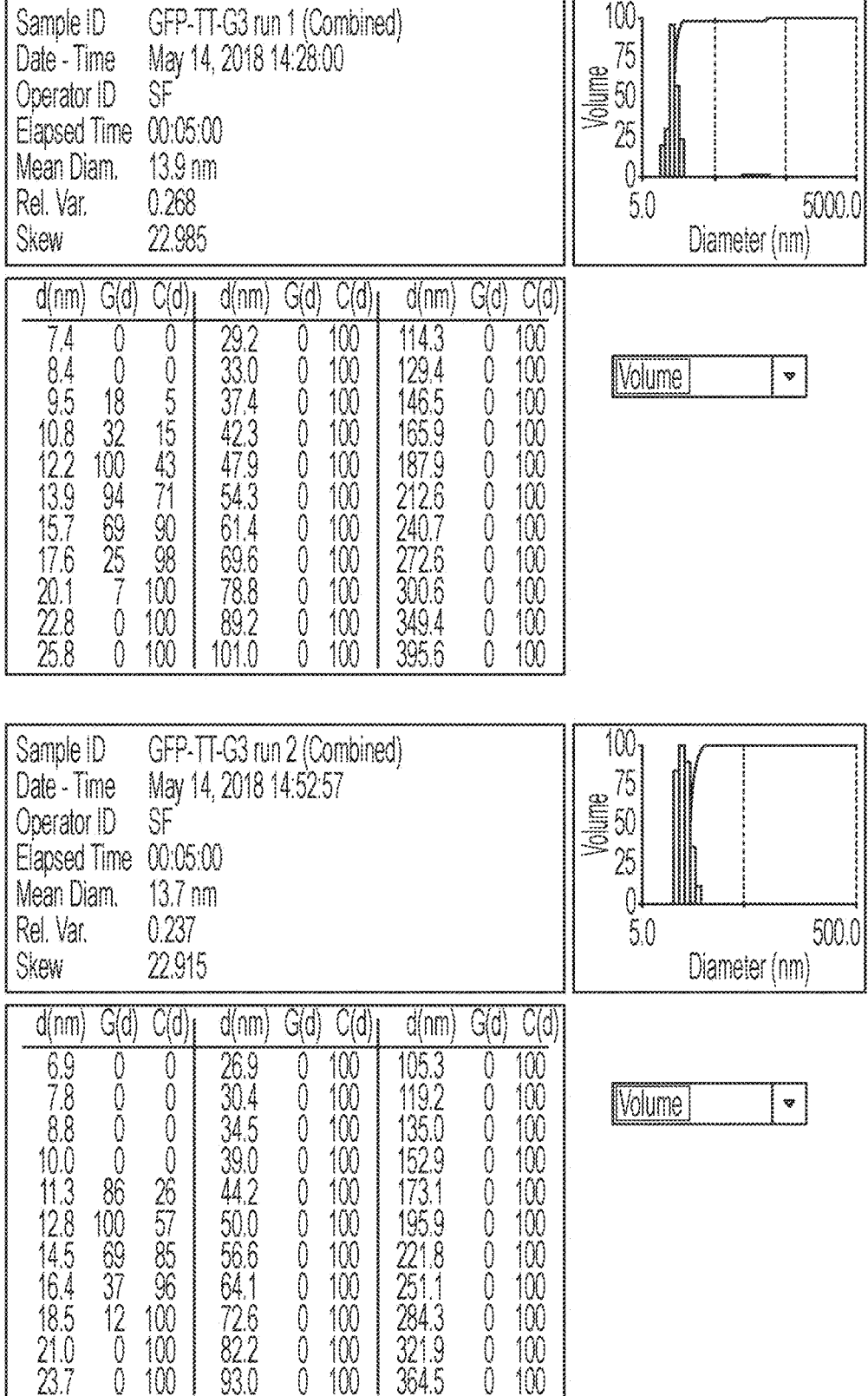
Figure 49B:
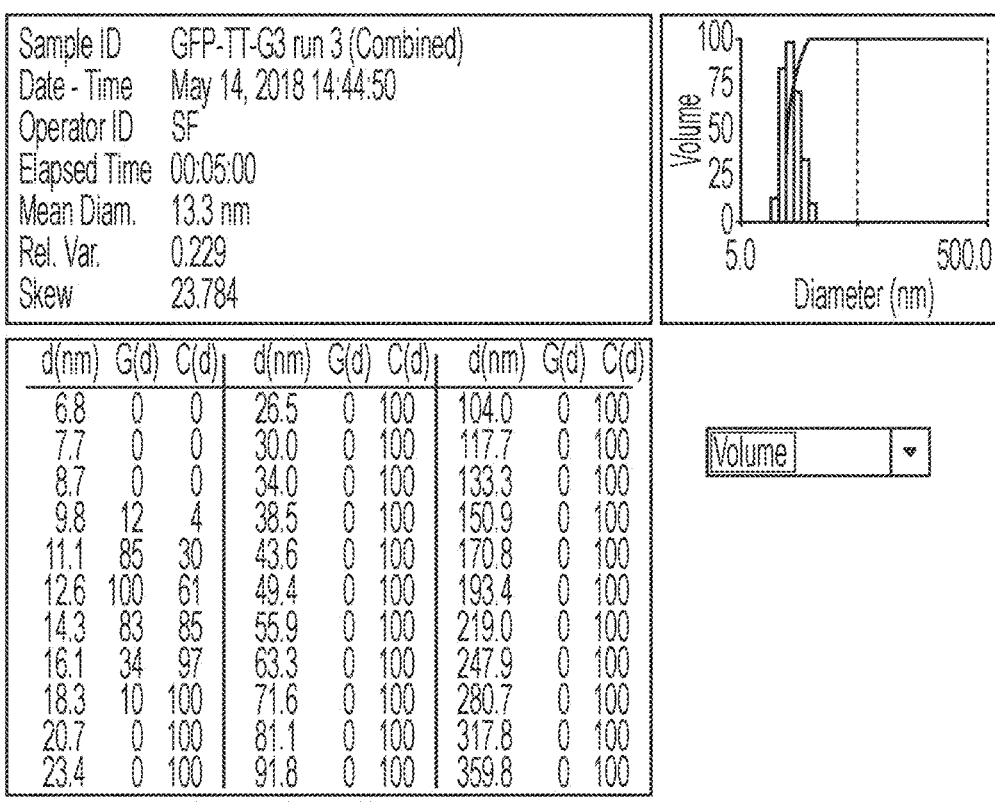

FIGS. 49A-49B show size distribution of GFP-TT-G3 in PBS. a Number- and b volume weighted. Data in columns are technical replicates of a or b.

Figure 50A:
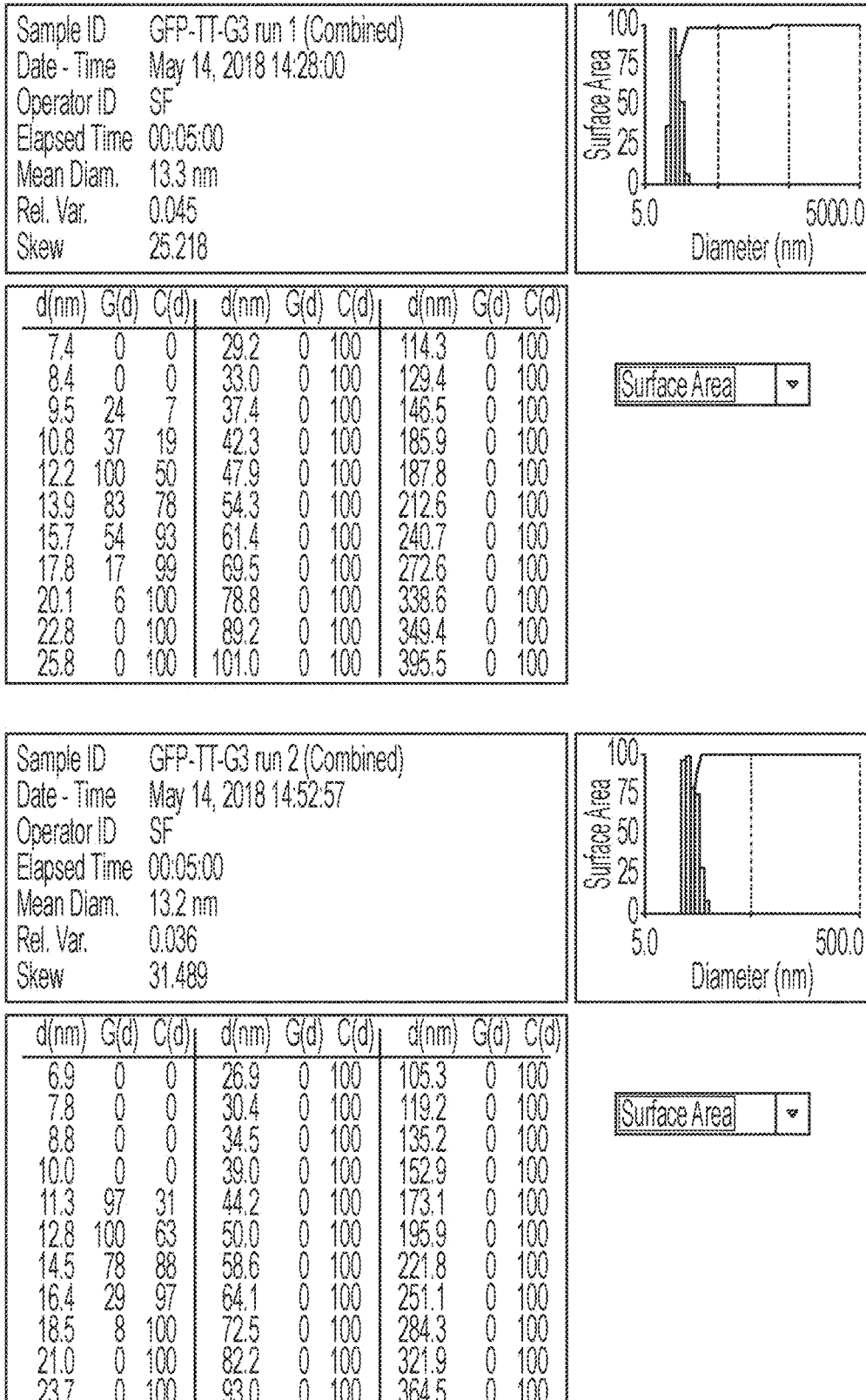
Figure 50A:
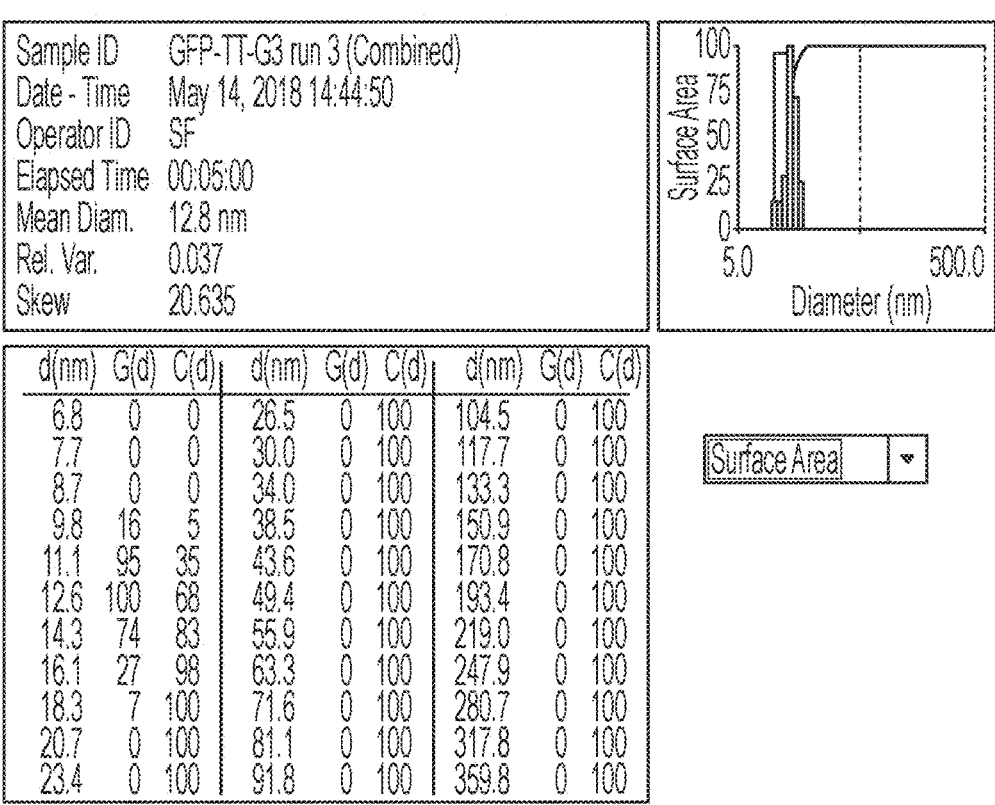
Figure 50B:
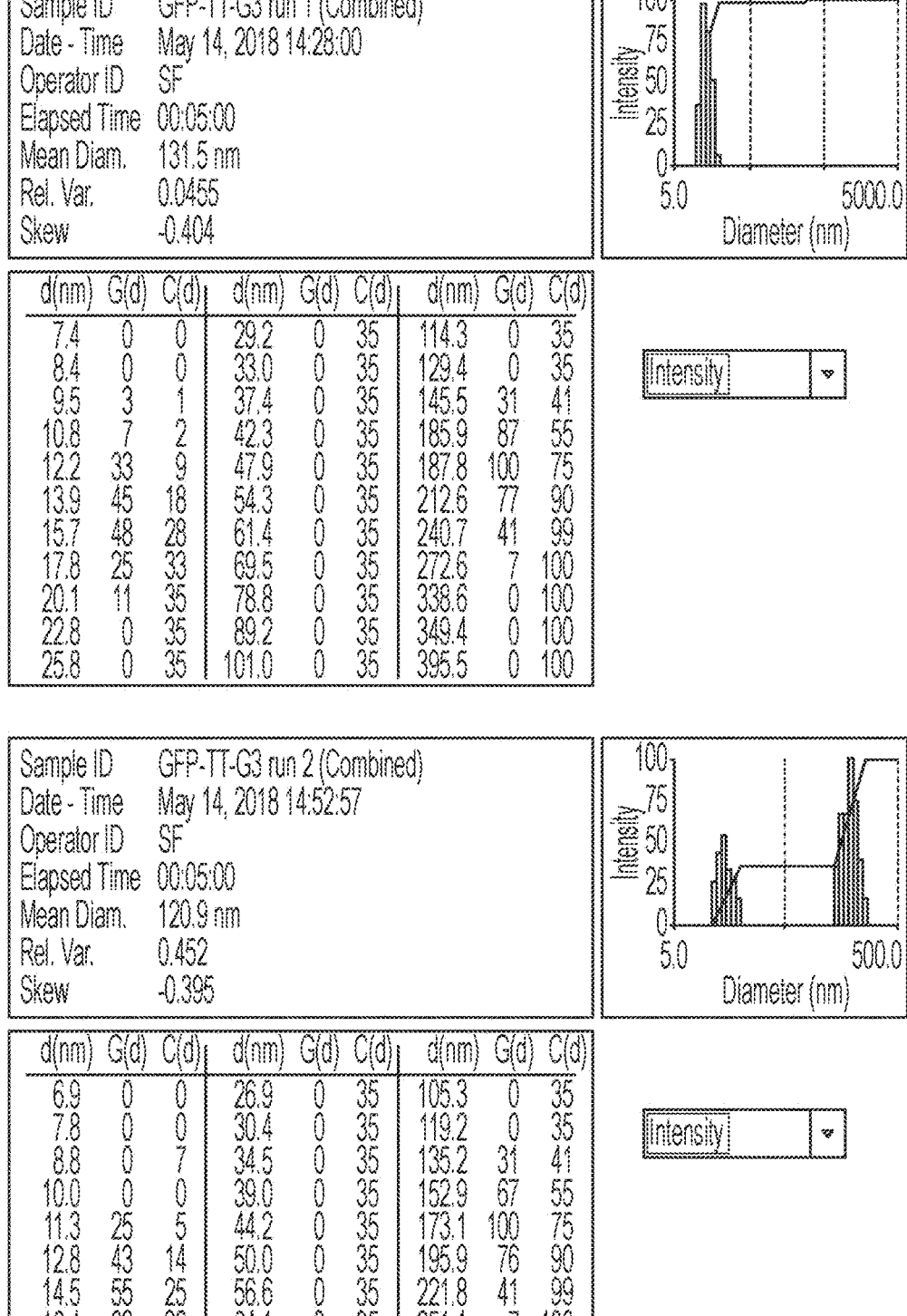
Figure 50B:
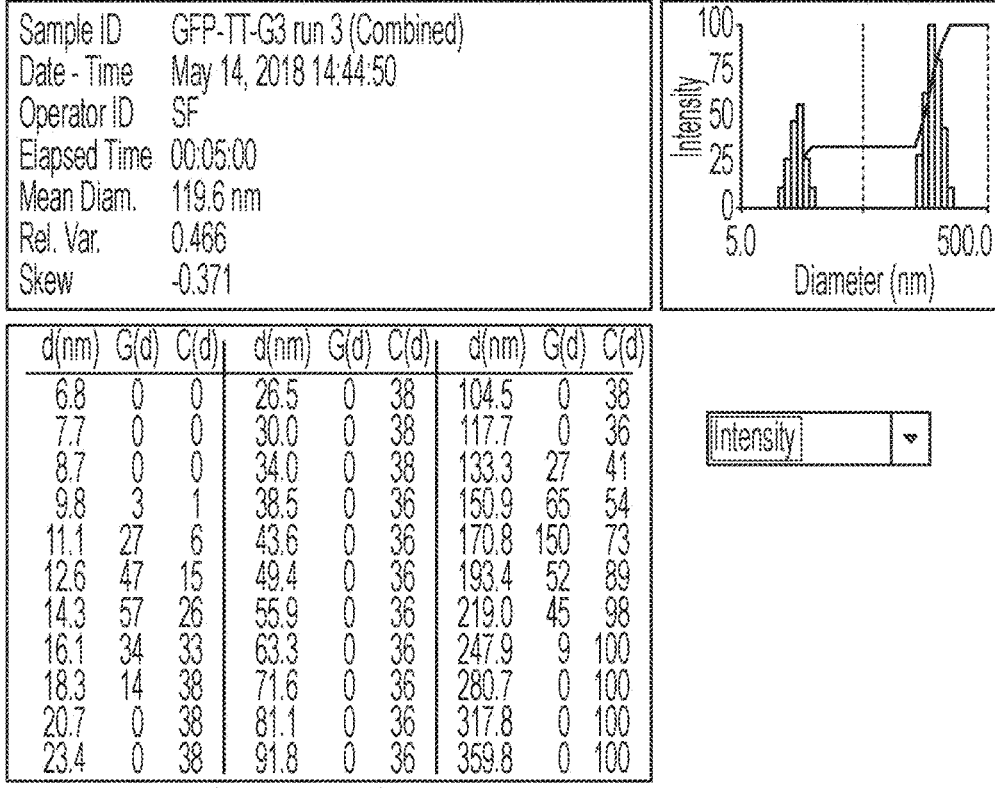

FIGS. 50A-50B show size distribution of GFP-TT-G3 in PBS. a Surface area- and b intensity weighted. Data in columns are technical replicates of a or b.

Figure 51:
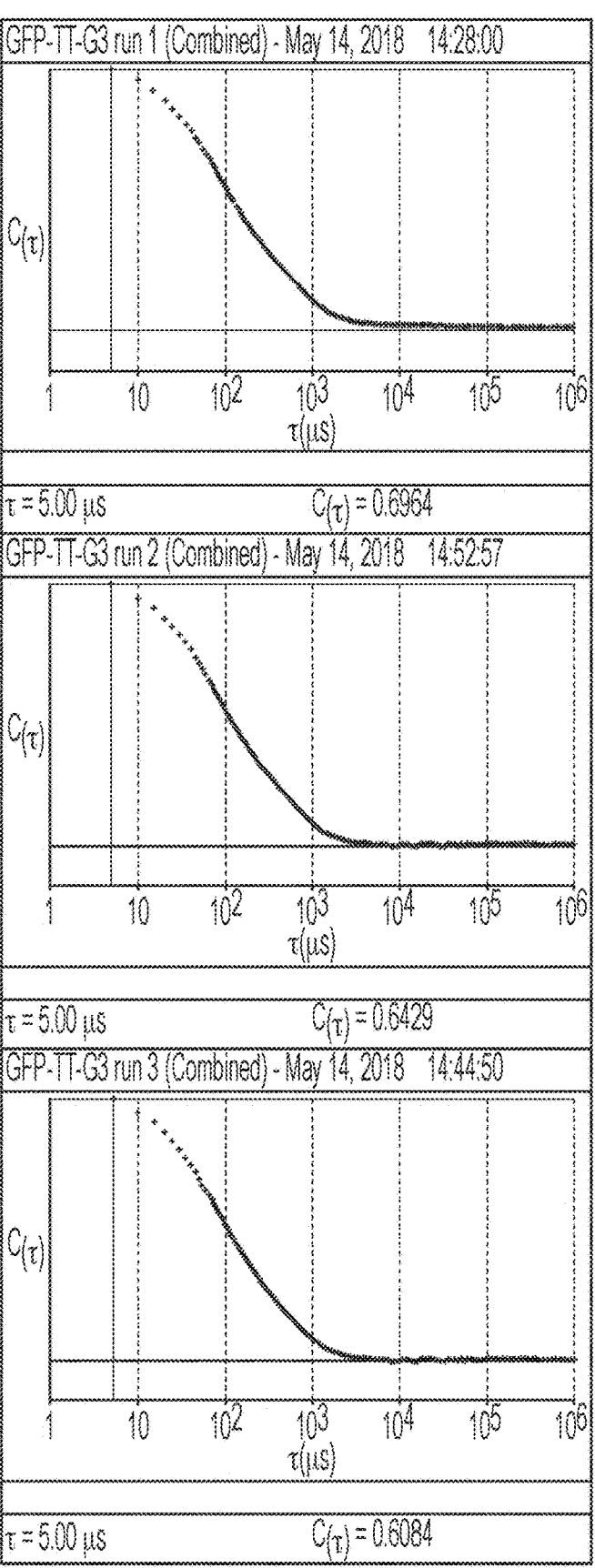

FIG. 51 shows correlation functions for DLS measurements of GFP-TT-G3. Data are technical replicates.

Figure 52:
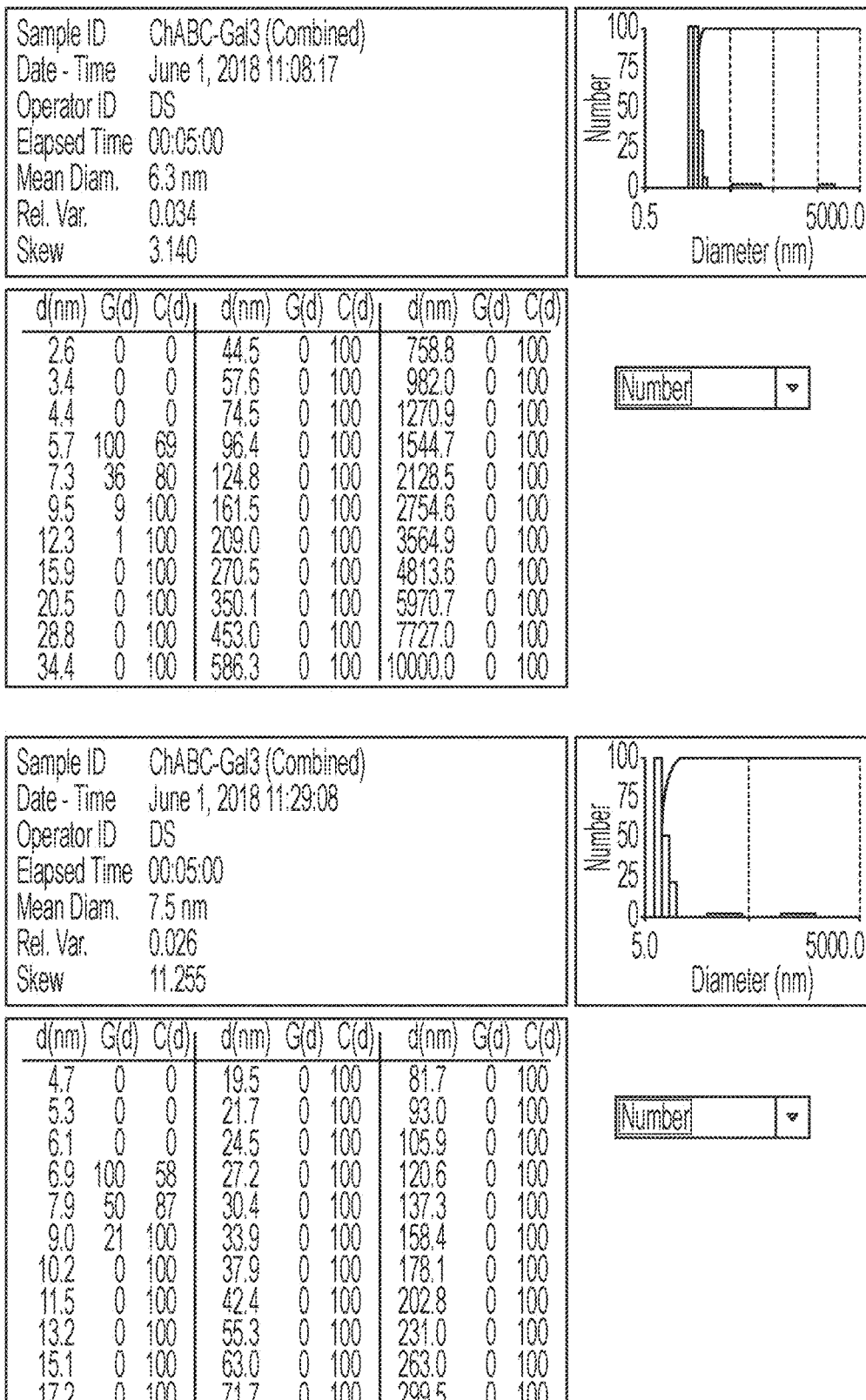
Figure 52:
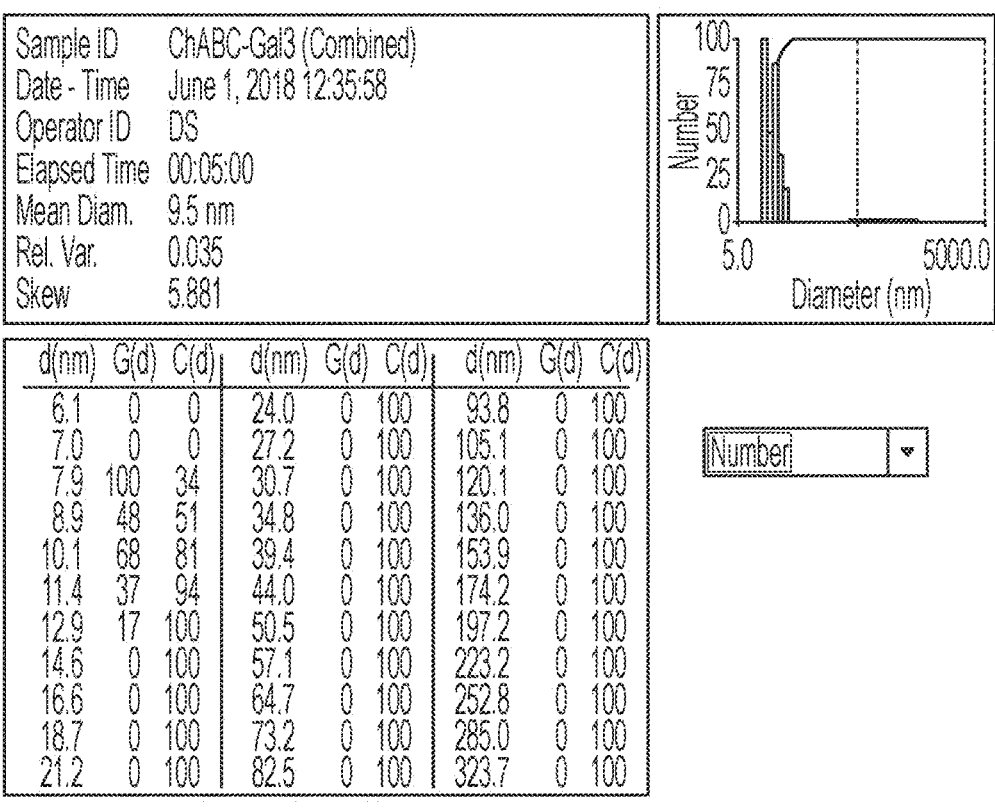
Figure 52:
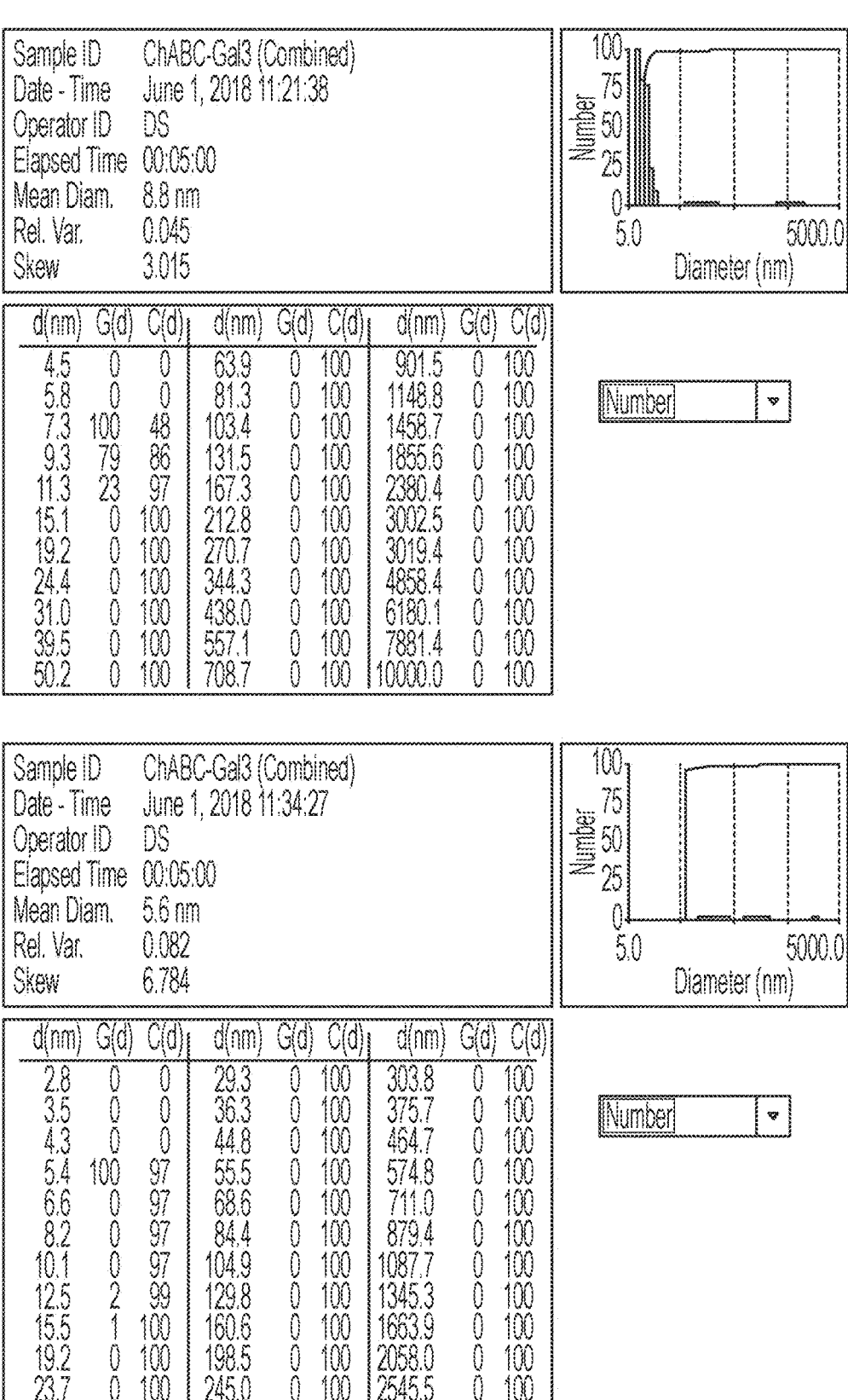

FIG. 52 shows a number-weighted size distribution of ChABC-G3 in PBS. Data are technical replicates.

Figure 53:
Figure 53:
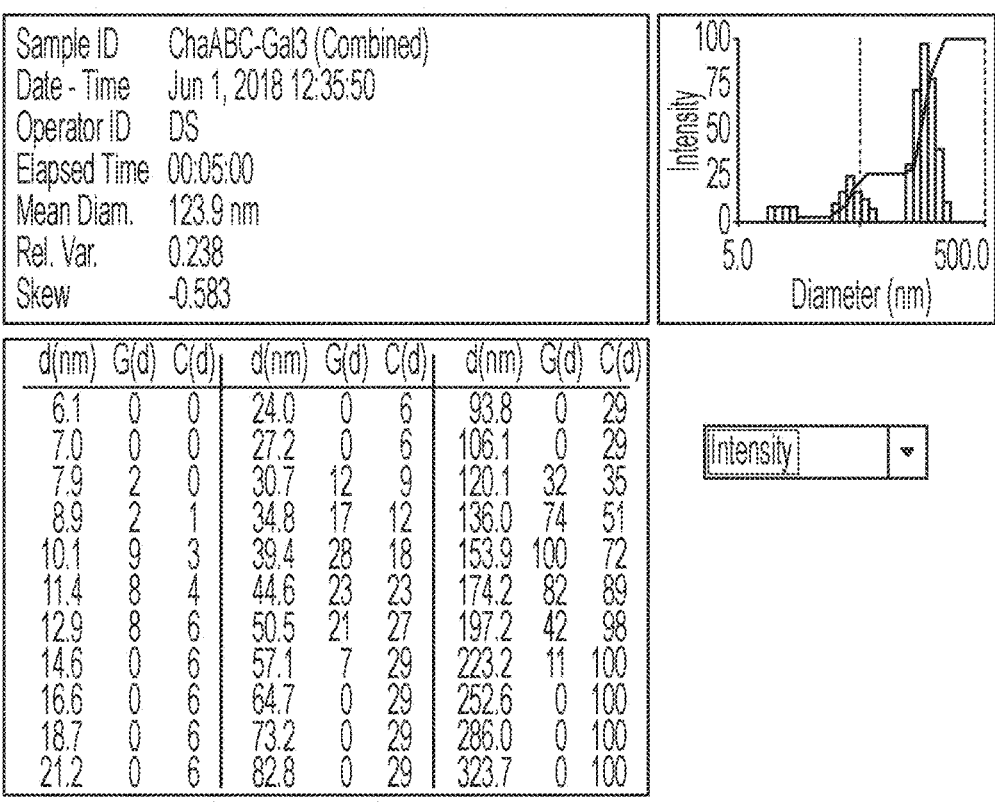
Figure 53:
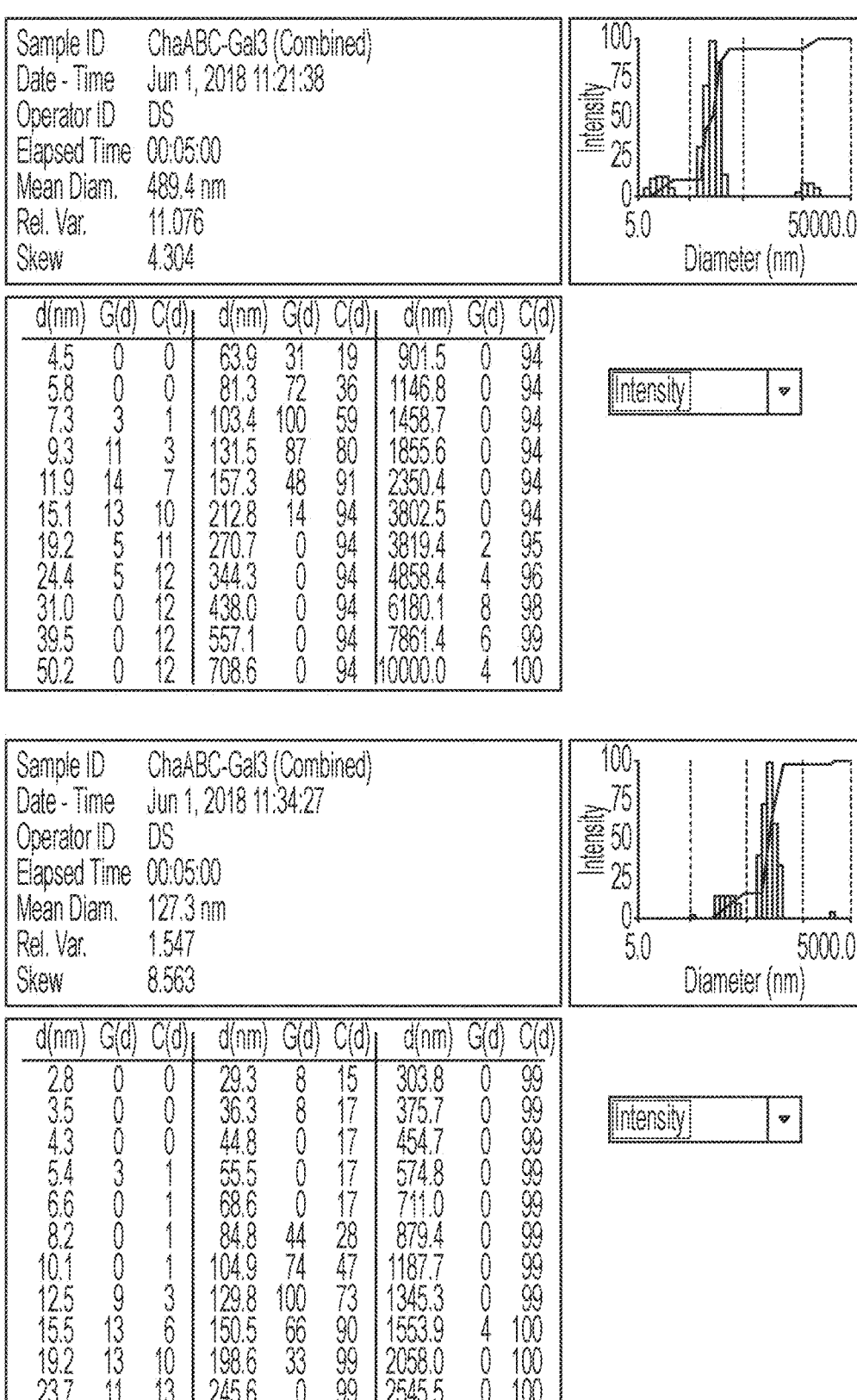

FIG. 53 shows a number-weighted size distribution of ChABC-G3 in PBS. Data are technical replicates.

Figure 54:
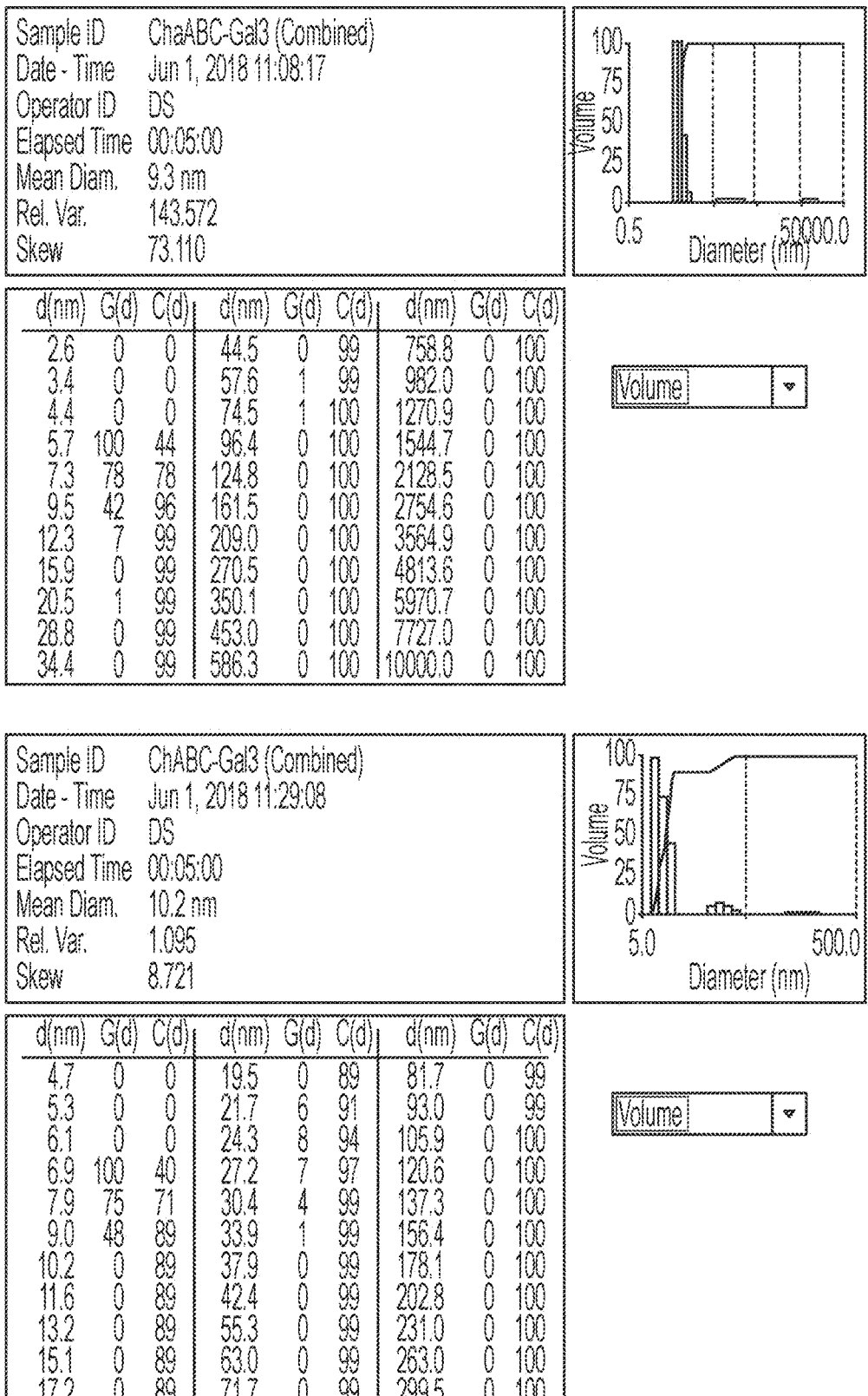
Figure 54:
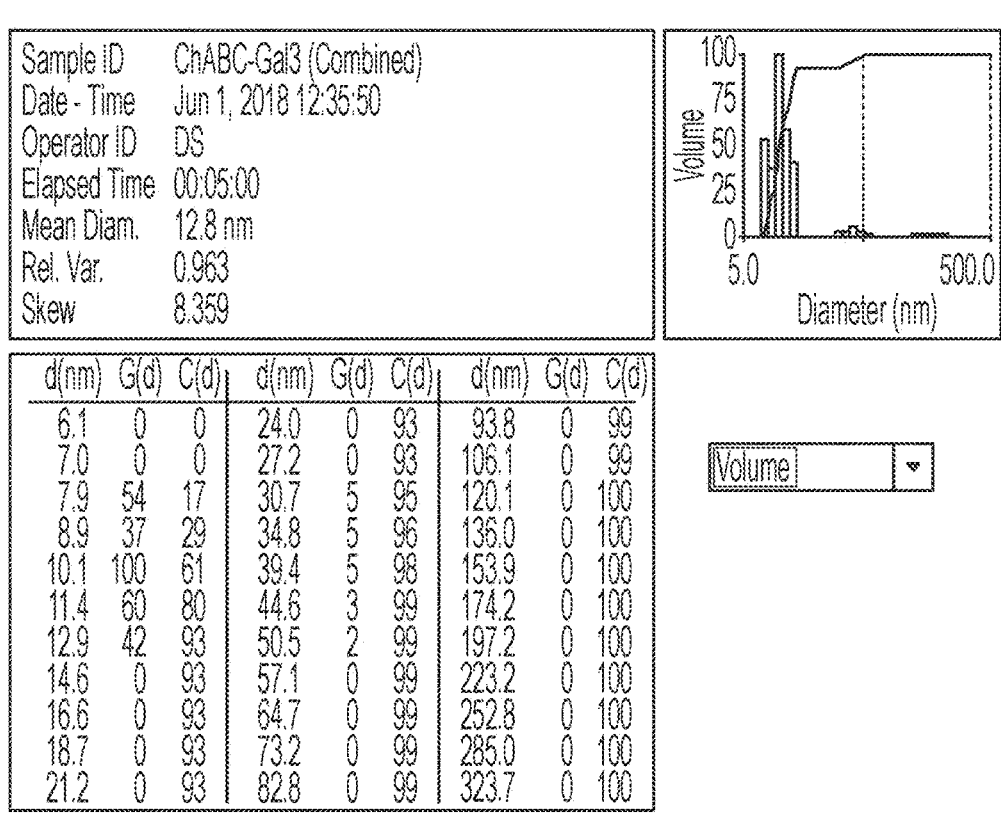
Figure 54:
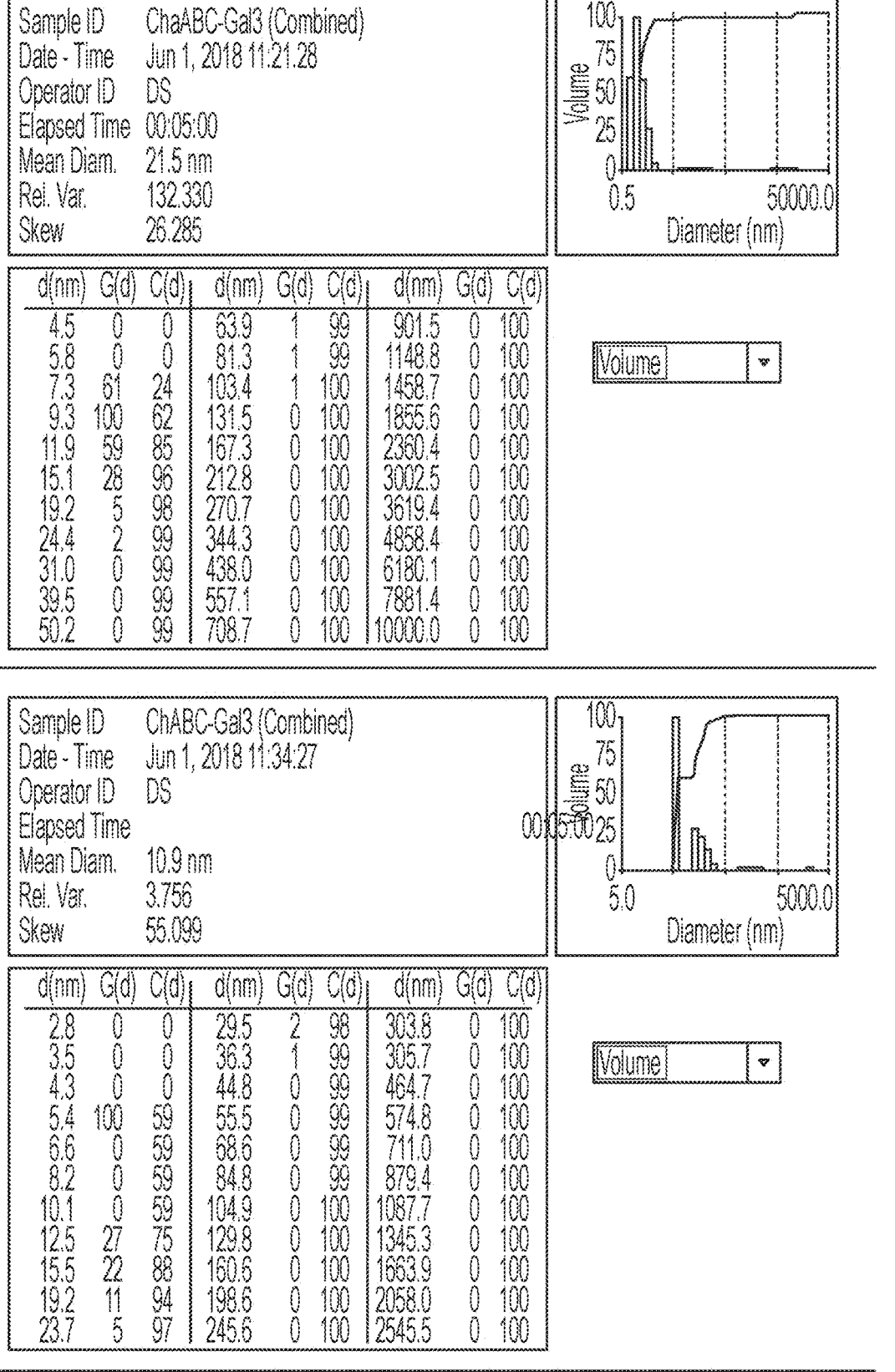

FIG. 54 shows a number-weighted size distribution of ChABC-G3 in PBS. Data are technical replicates.

Figure 55:
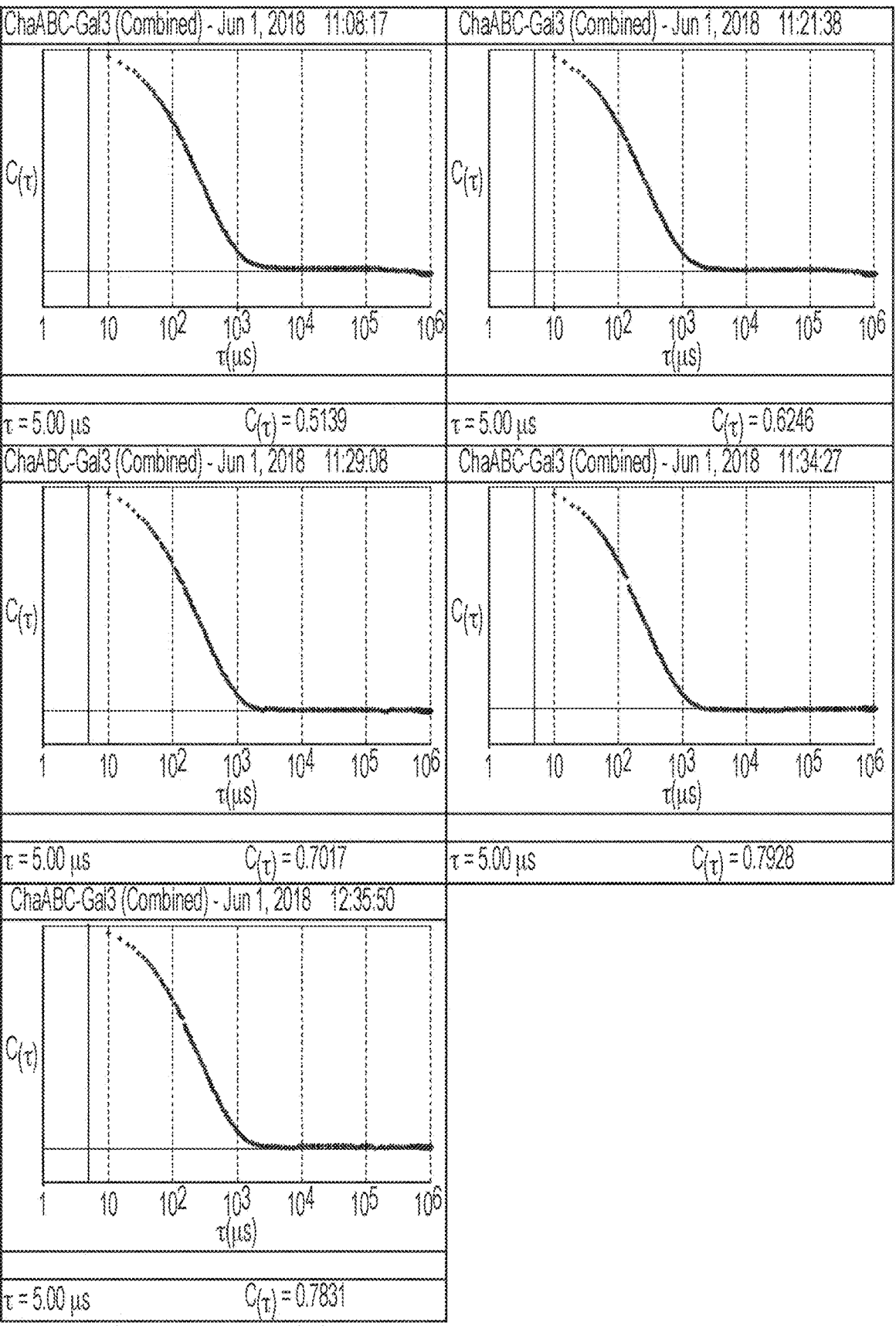

FIG. 55 shows correlation functions for DLS measurements of ChABC-G3. Data are technical replicates.

Figure 56:
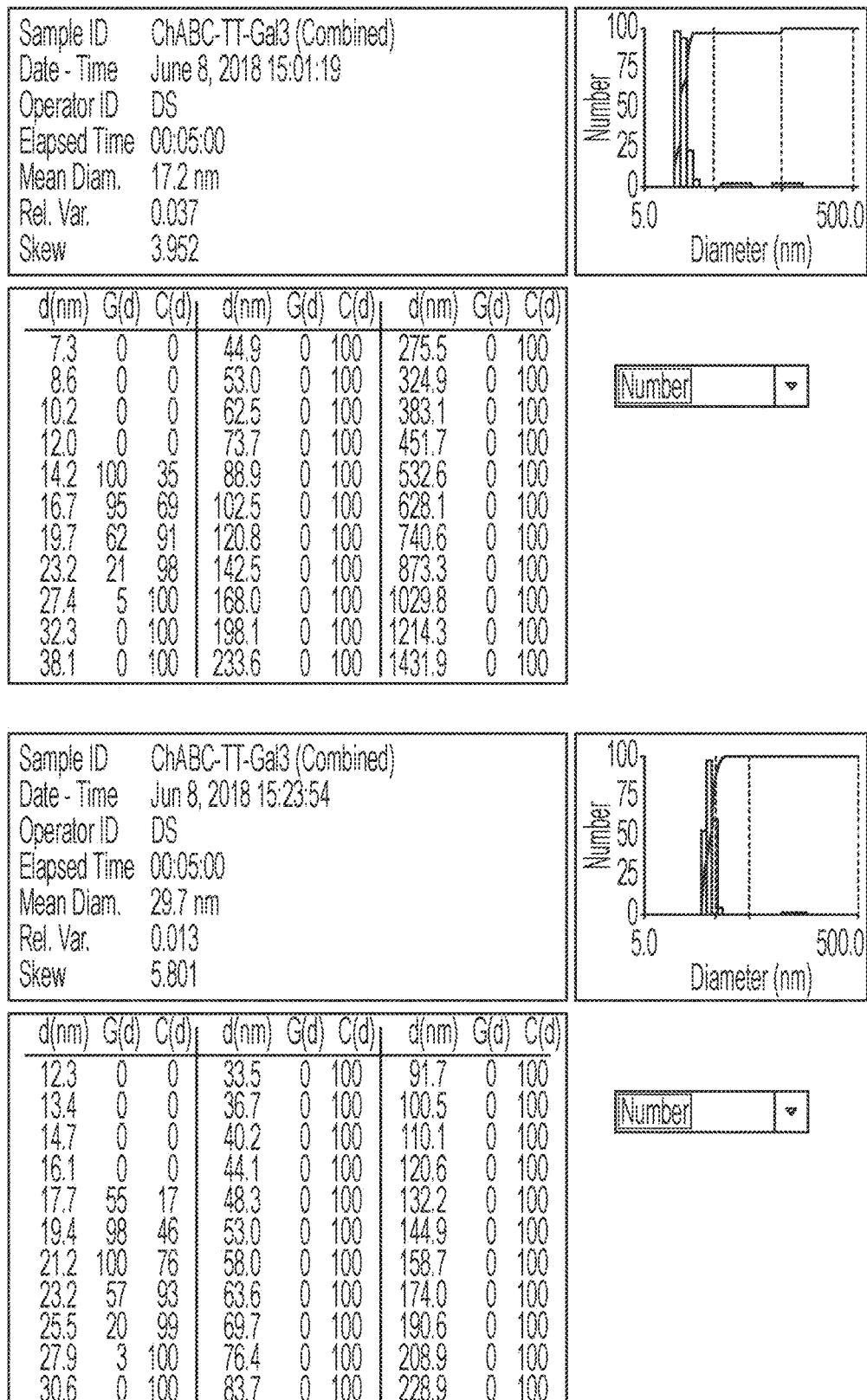
Figure 56:
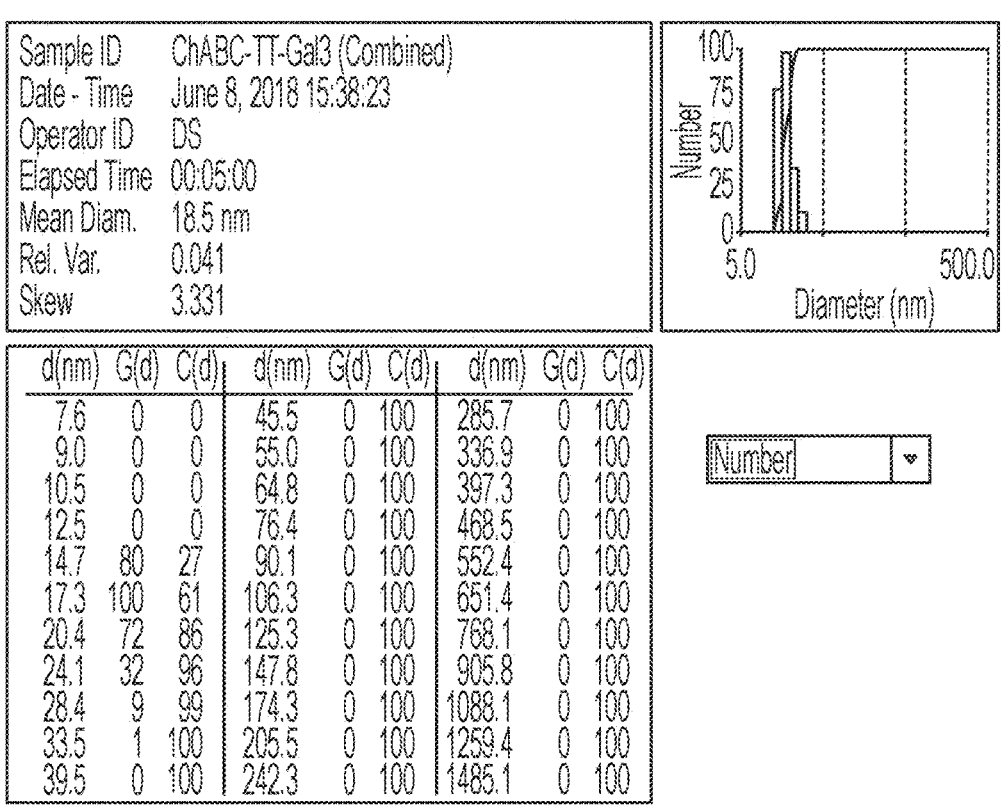
Figure 56:
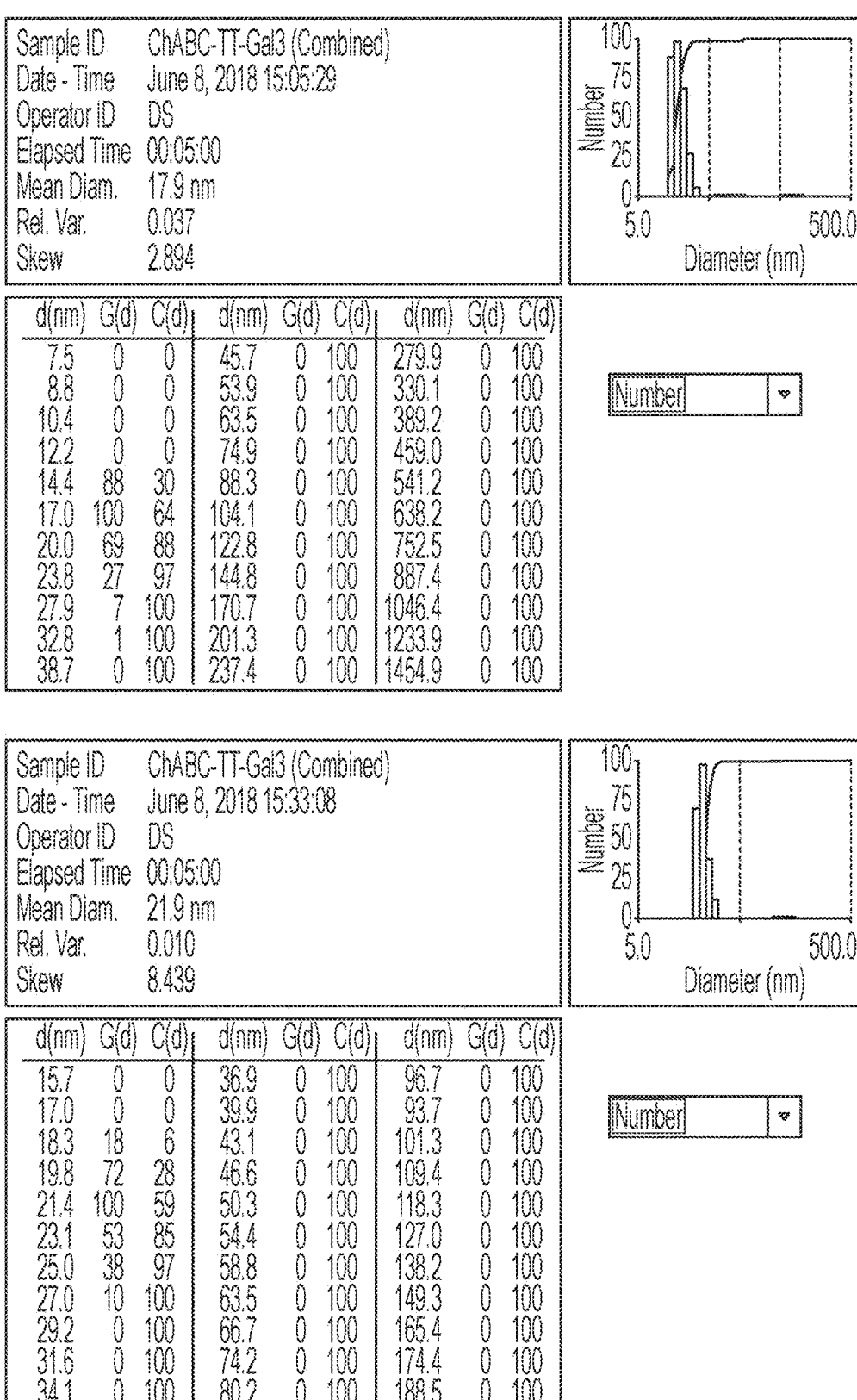
Figure 56:
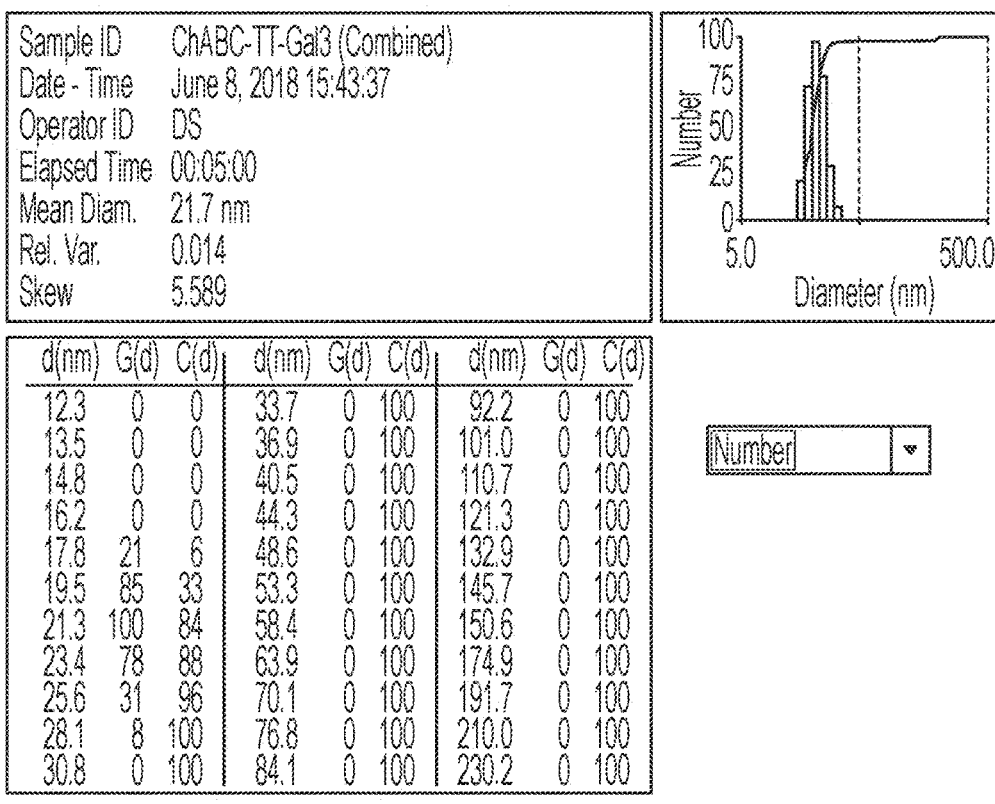

FIG. 56 shows number-weighted size distribution of ChABC-TT-G3 in PBS. Data are technical replicates.

Figure 57:
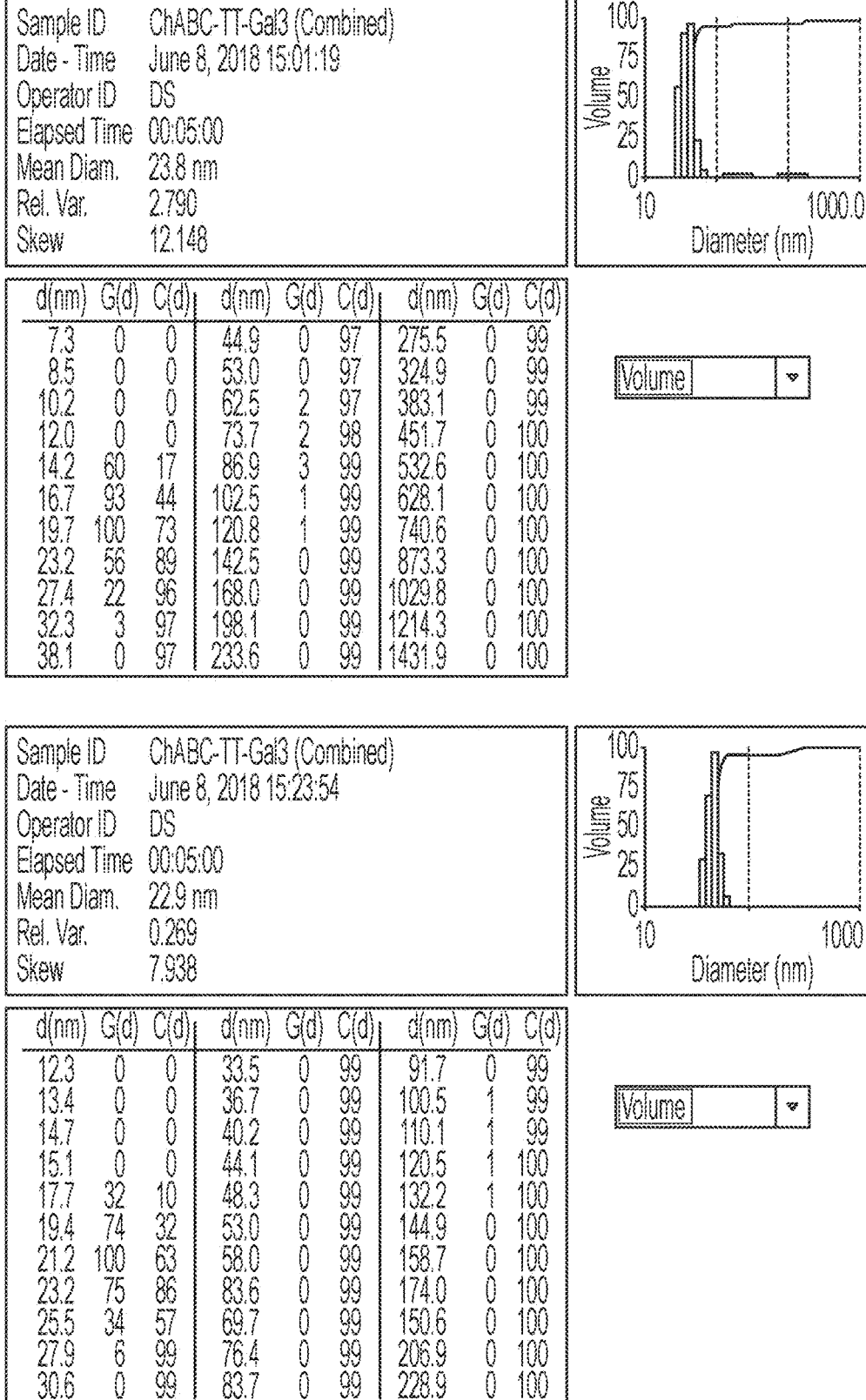
Figure 57:
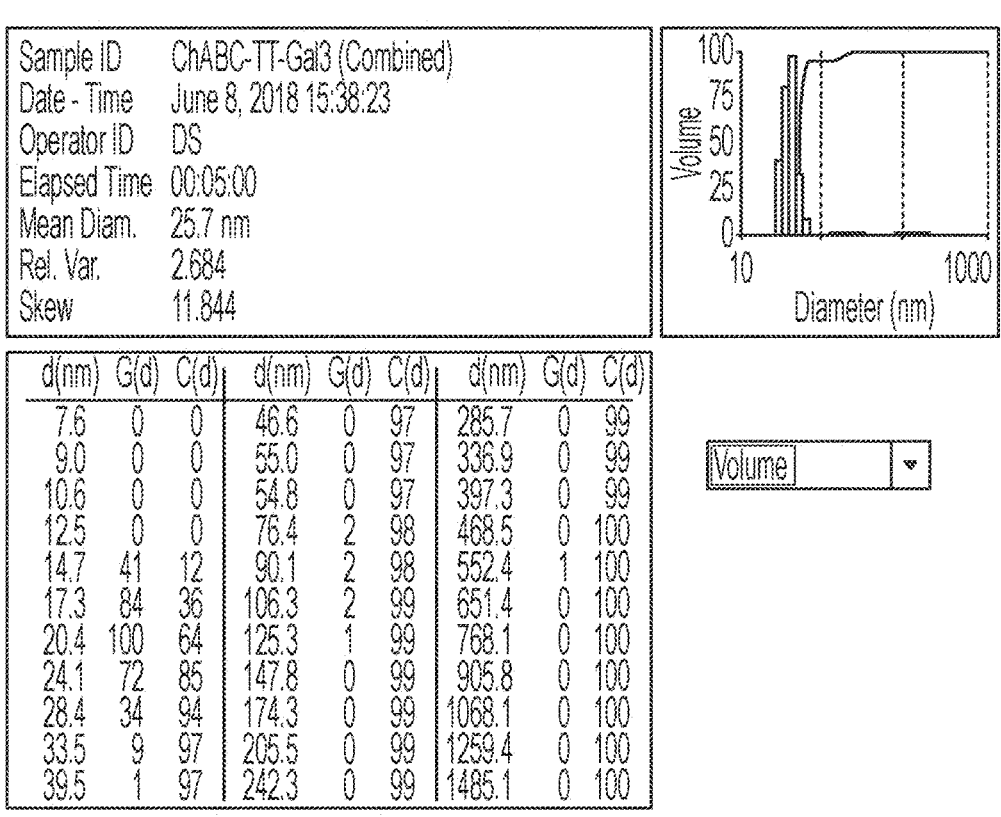
Figure 57:
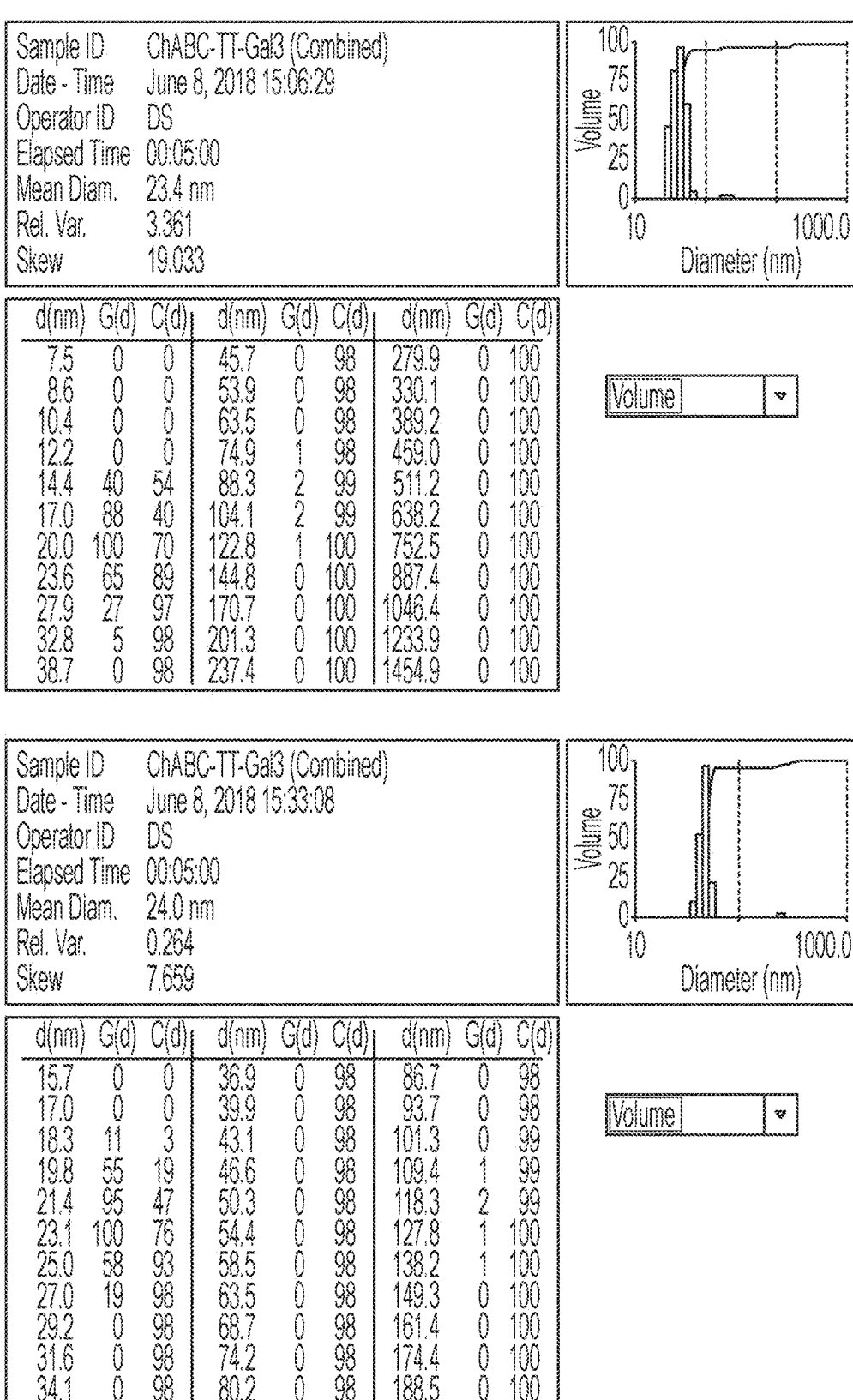
Figure 57:
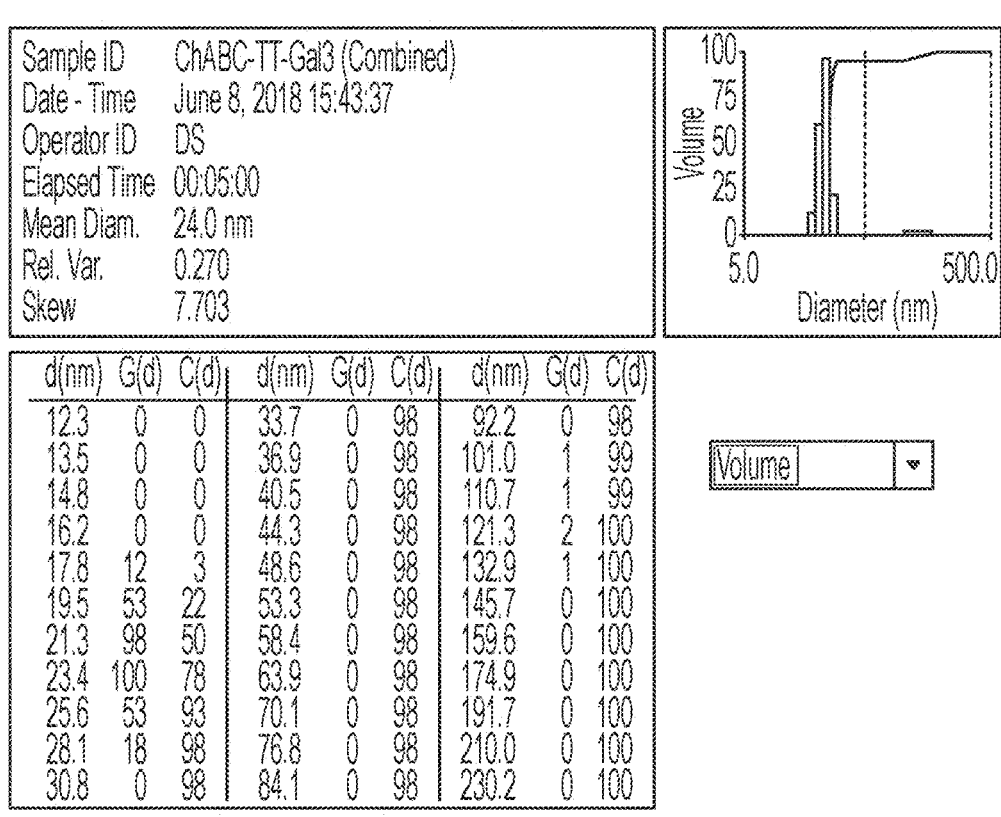

FIG. 57 shows volume-weighted size distribution of ChABC-TT-G3 in PBS. Data are technical replicates.

Figure 58:
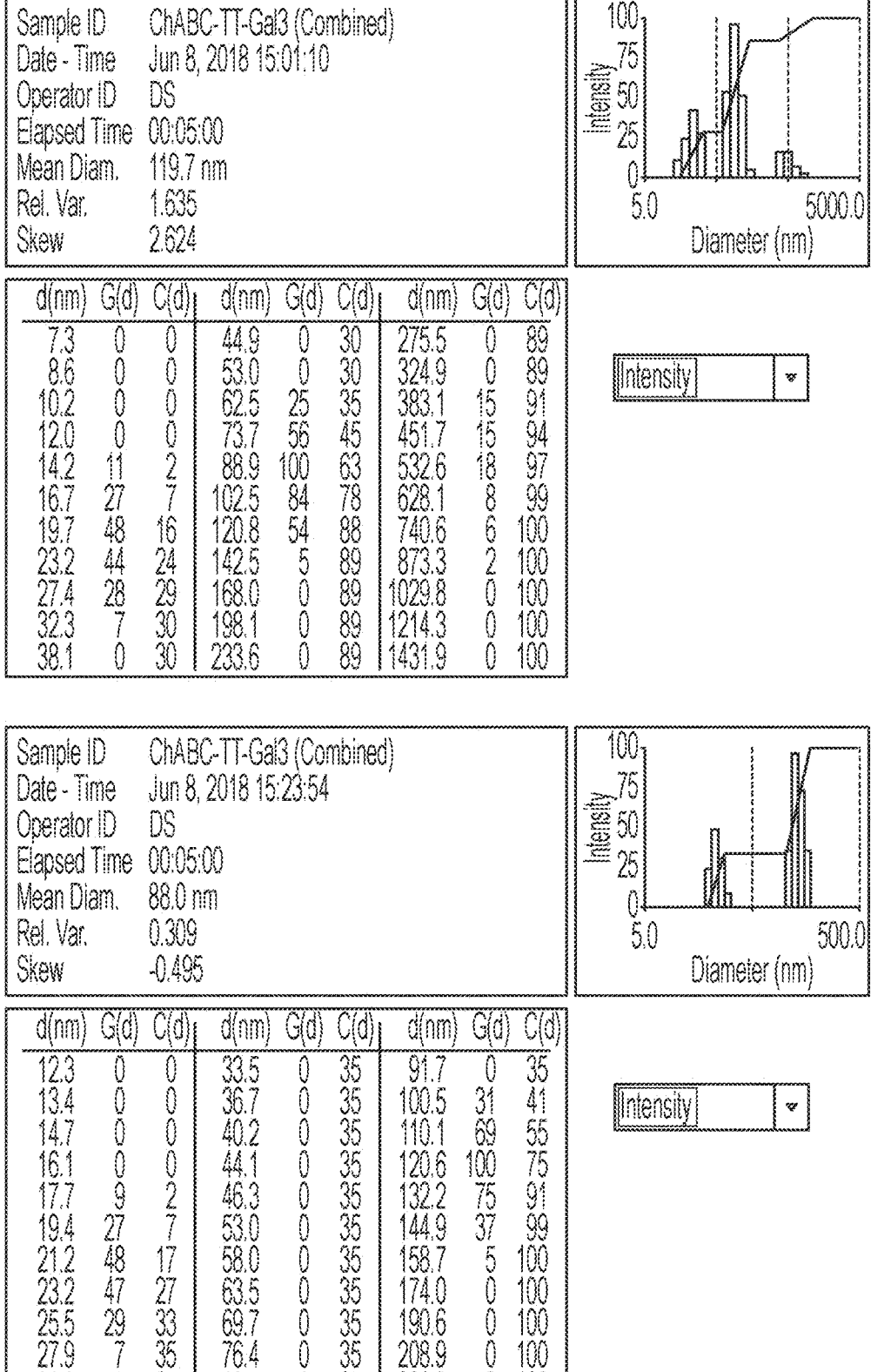
Figure 58:
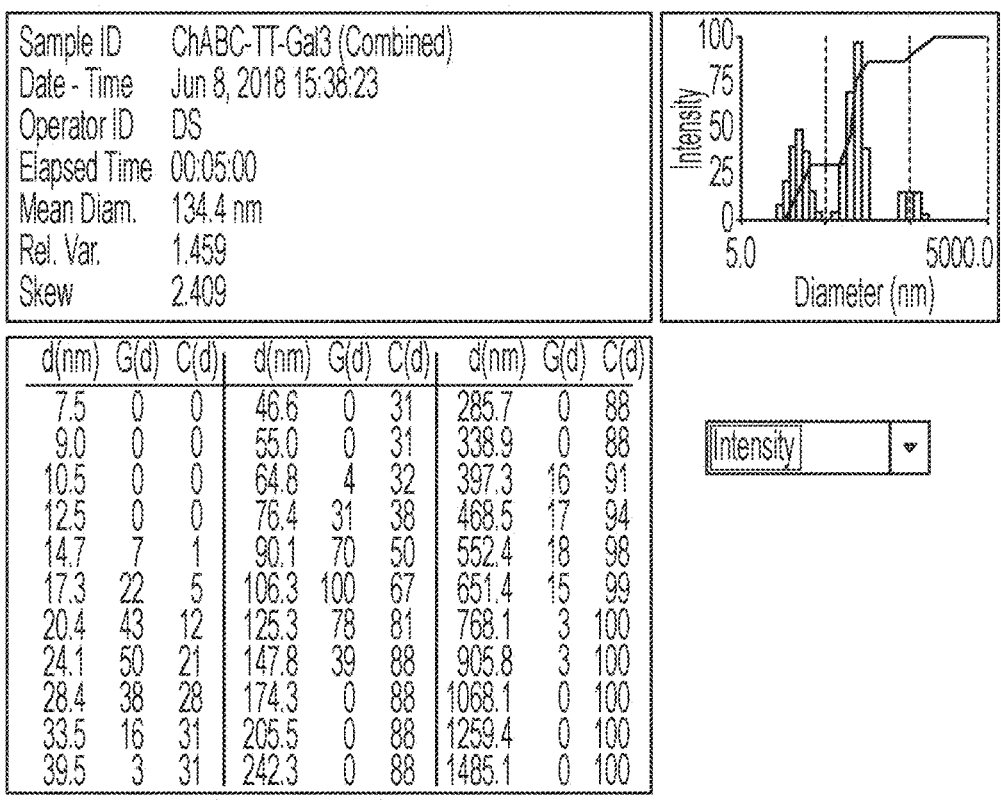
Figure 58:
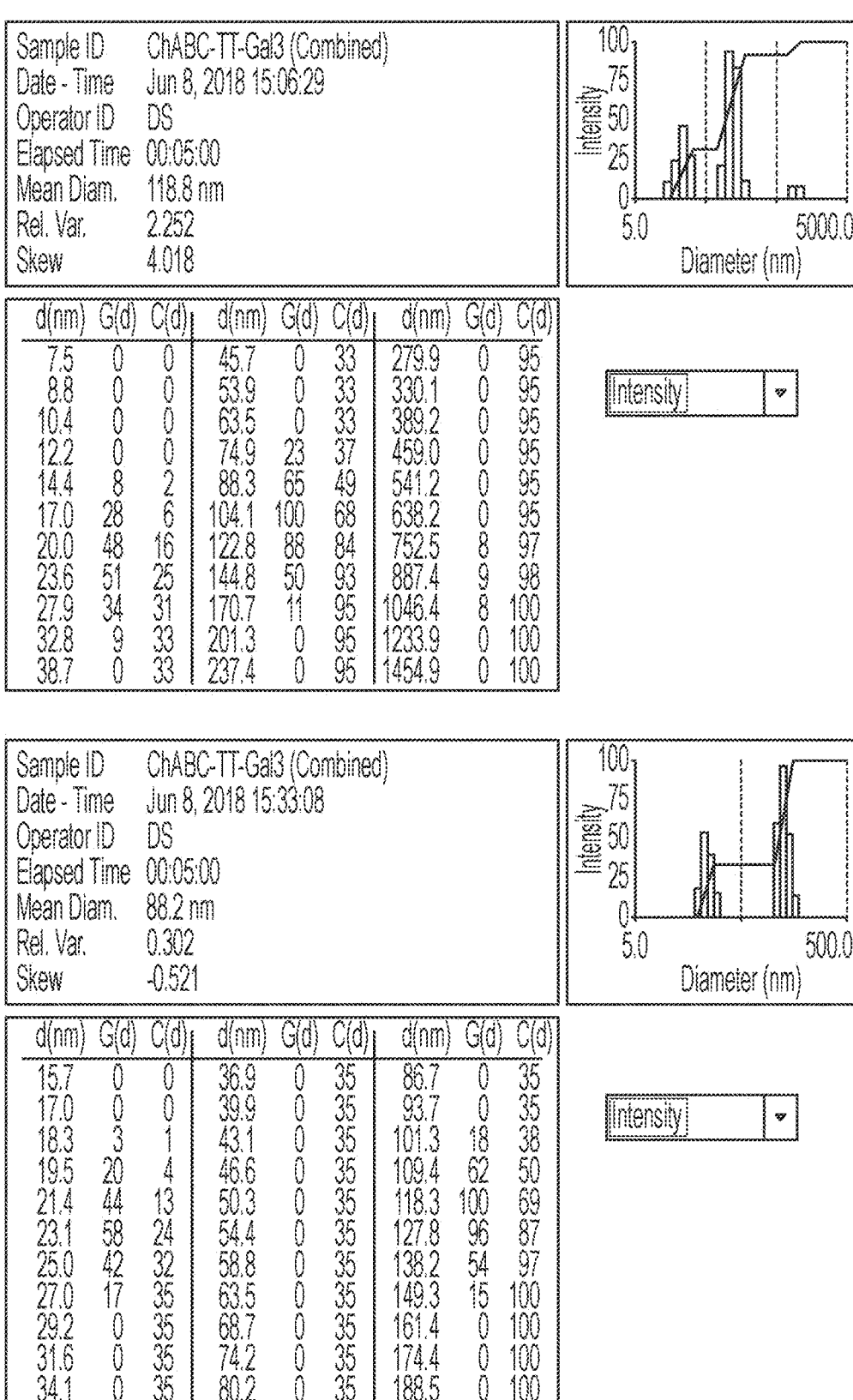
Figure 58:
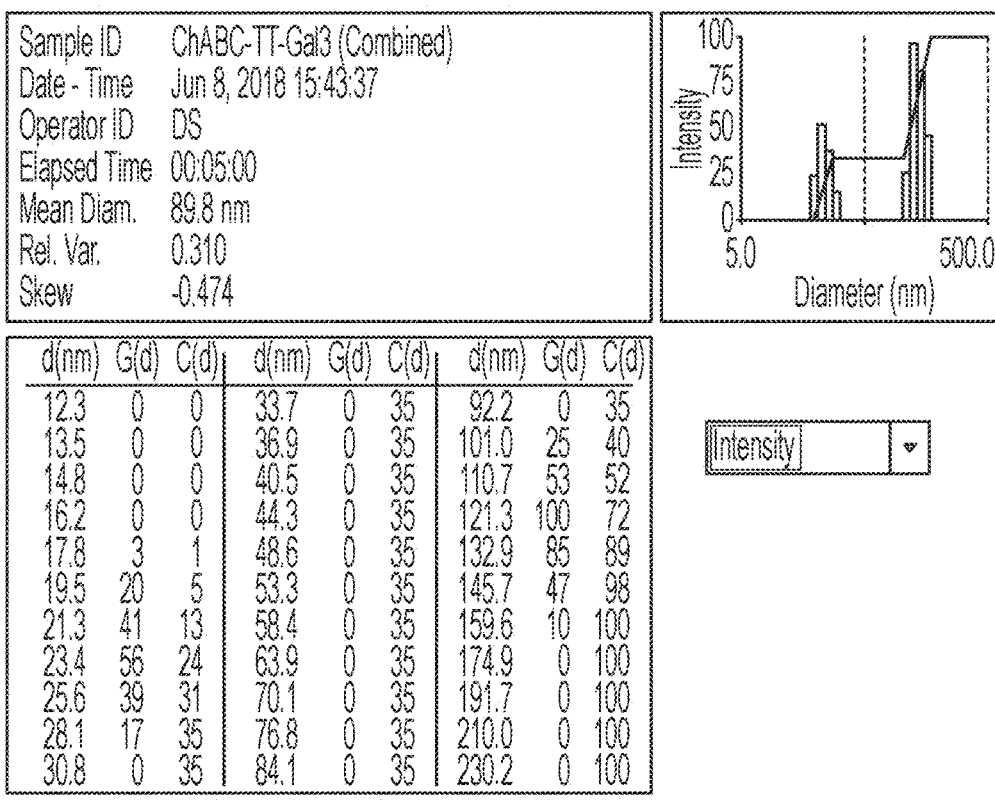

FIG. 58 shows intensity-weighted size distribution of ChABC-TT-G3 in PBS. Data are technical replicates.

Figure 59:
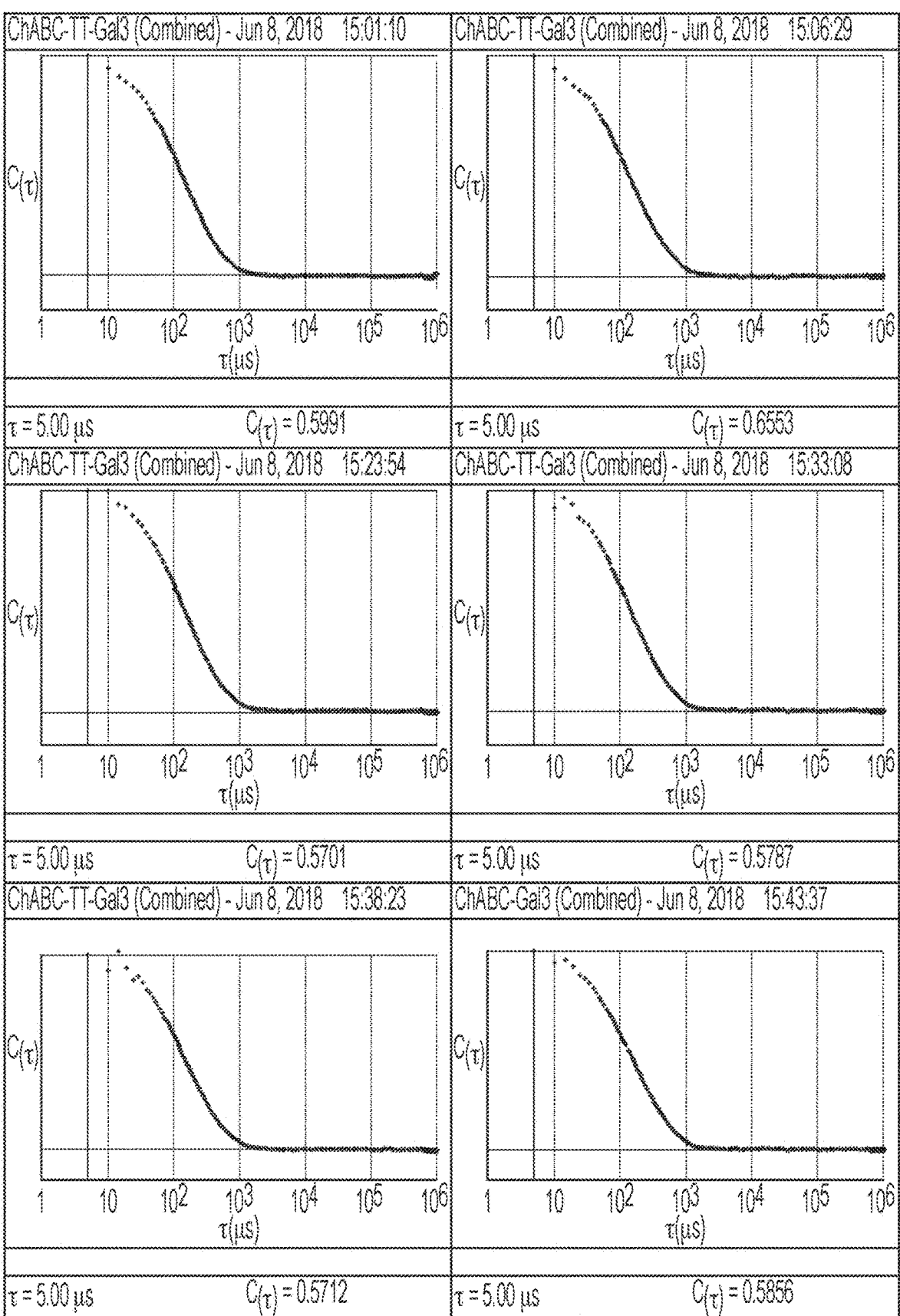

FIG. 59 shows correlation functions for DLS measurements of ChABC-TT-G3. Data are technical replicates.

Figure 60A:
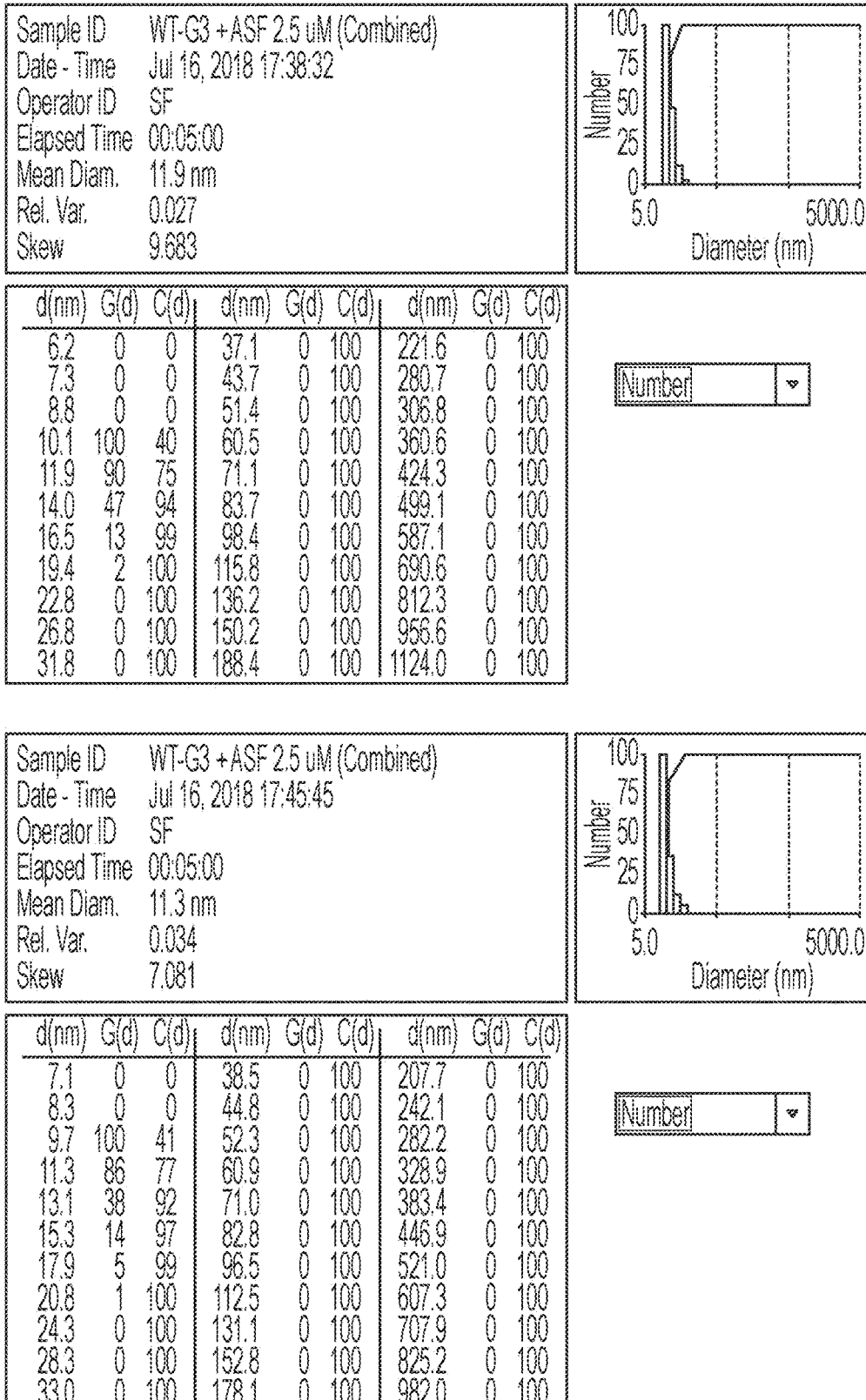
Figure 60A:
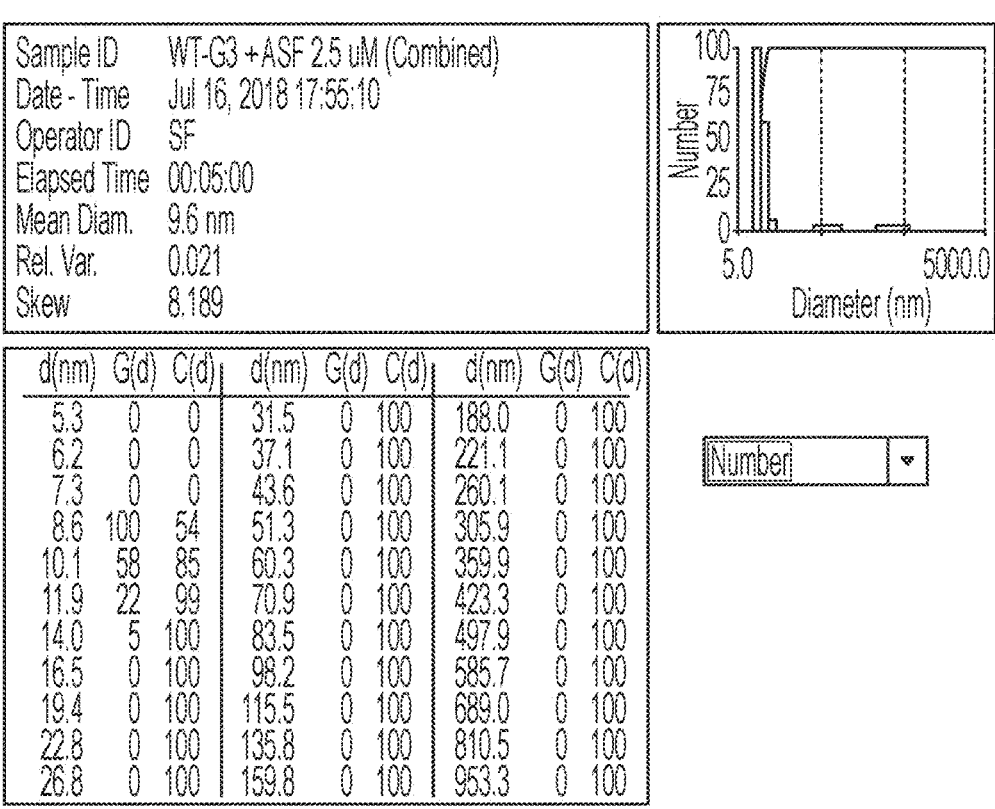
Figure 60B:
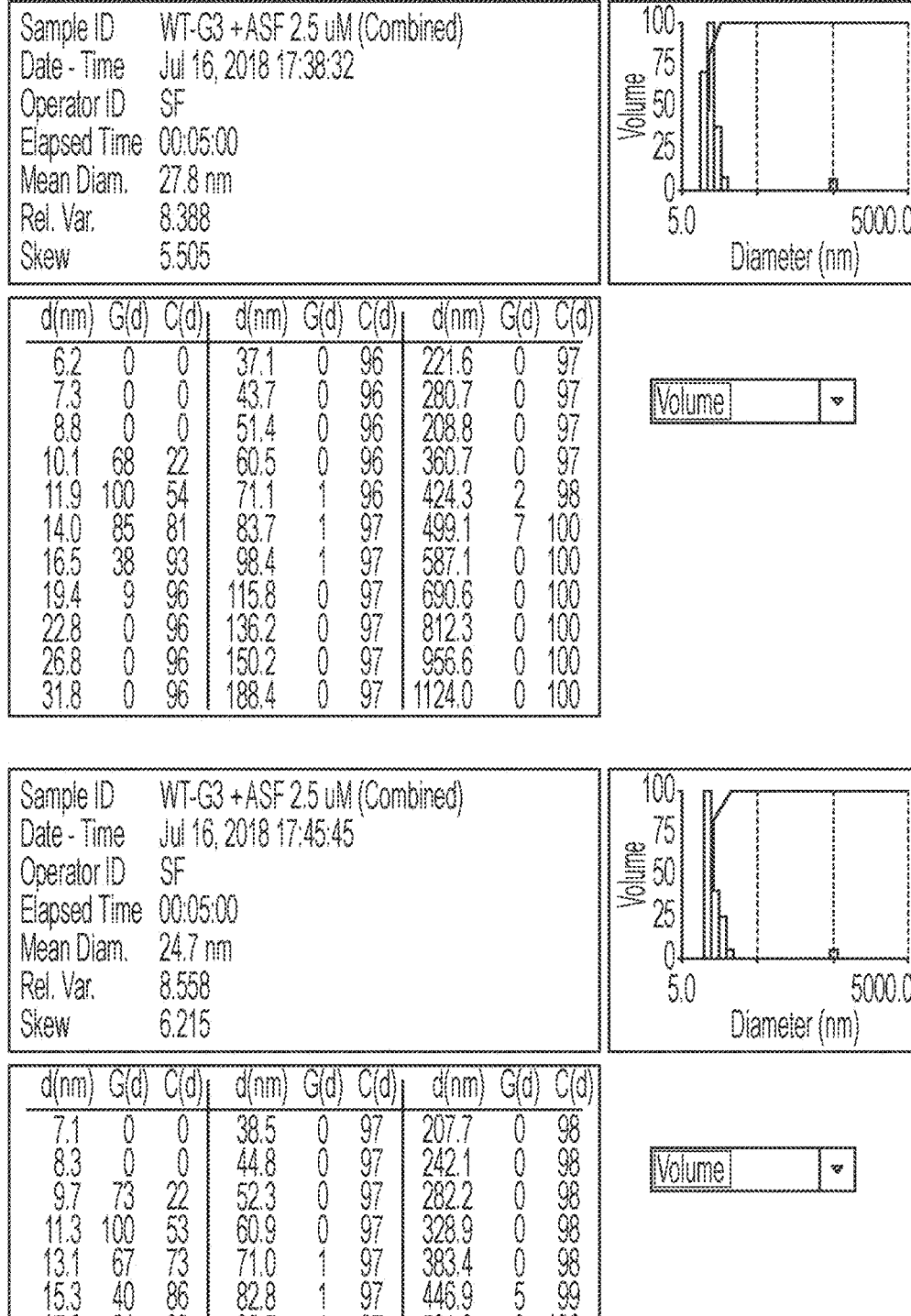
Figure 60B:
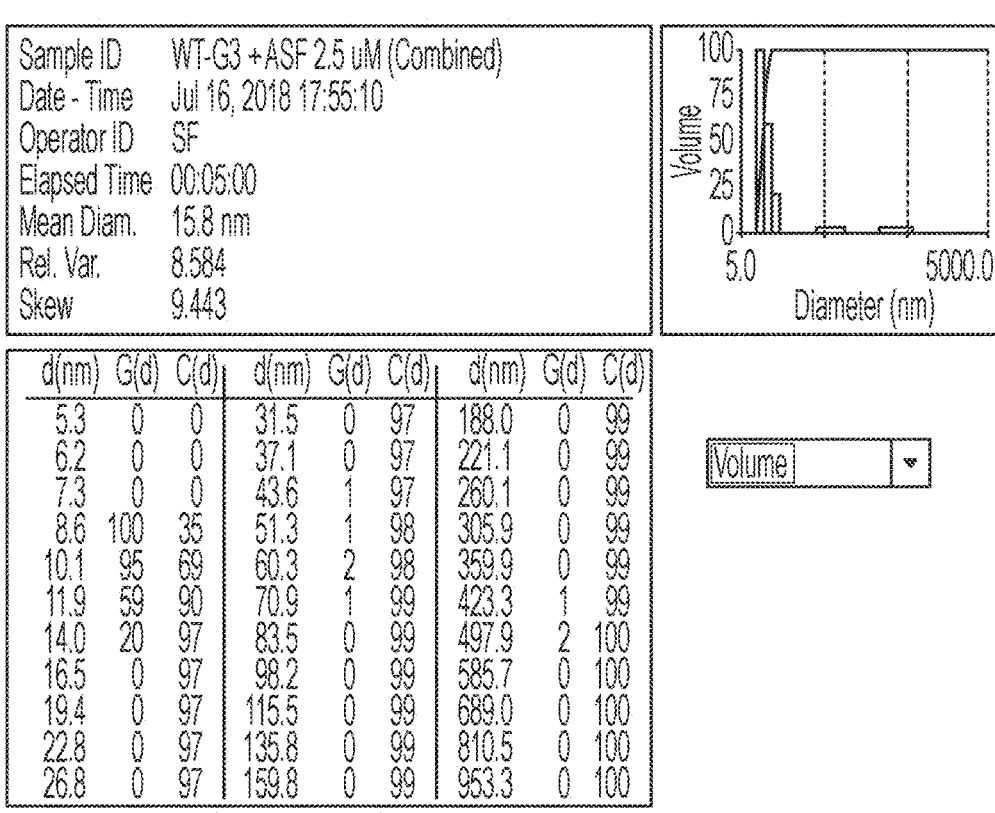

FIGS. 60A-60B show size distribution of 2.5 μM WT-G3 plus 7 μM ASF. a Number- and b volume-weighted. Data in columns are technical replicates of a or b.

Figure 61A:
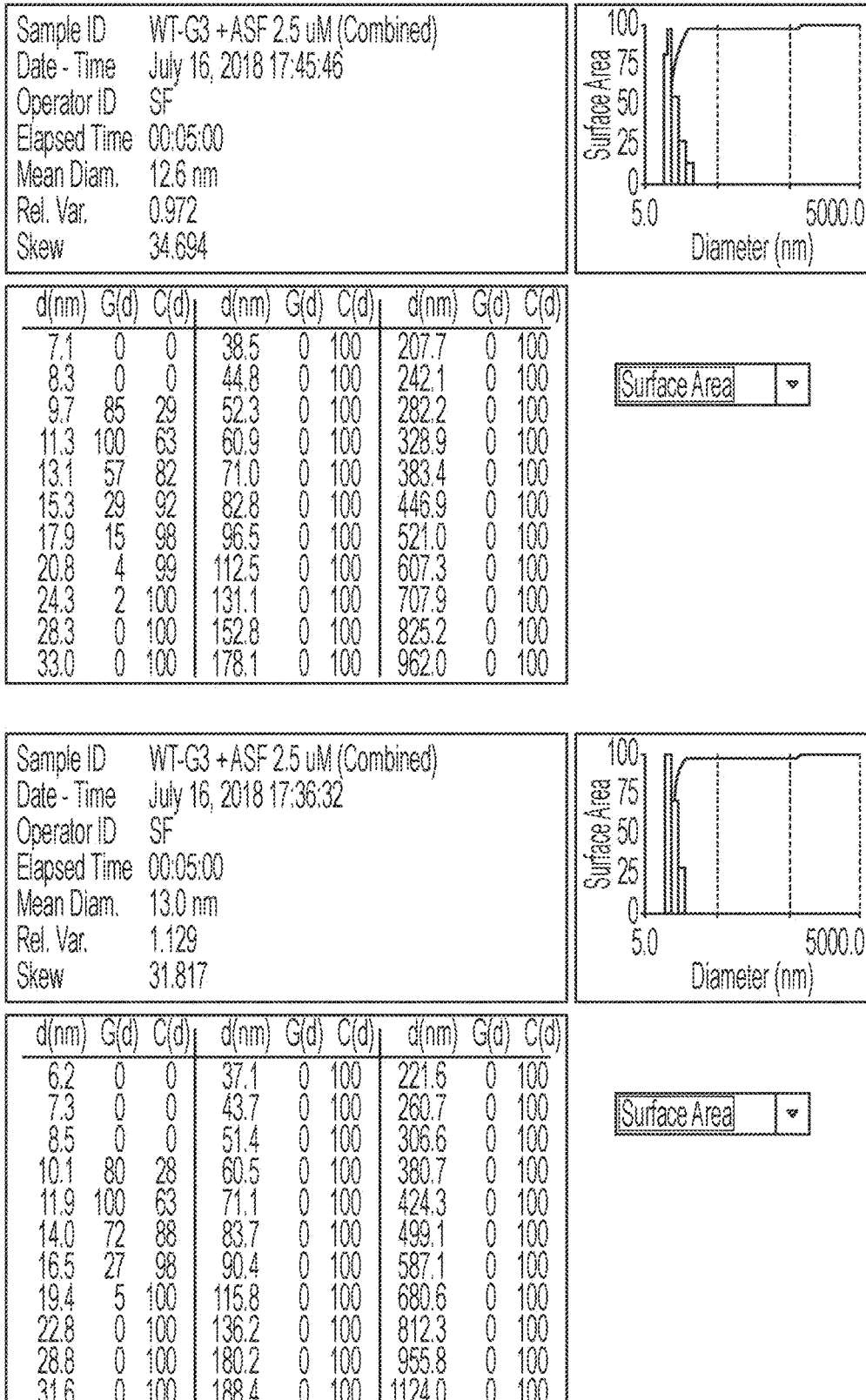
Figure 61A:
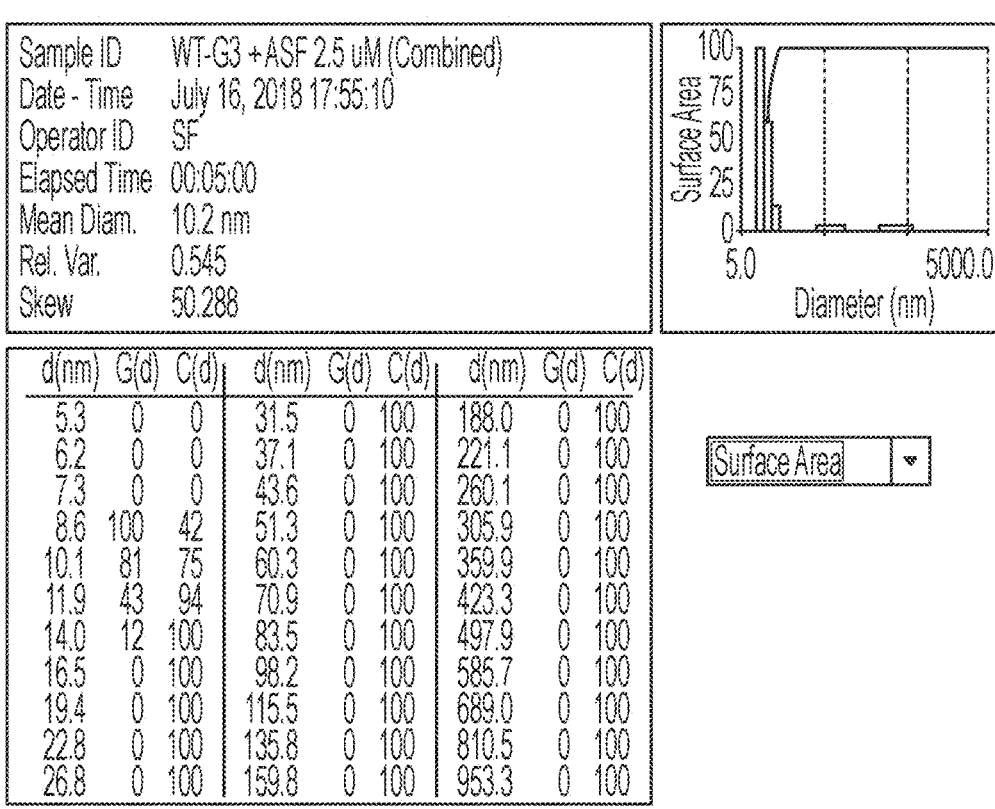
Figure 61B:
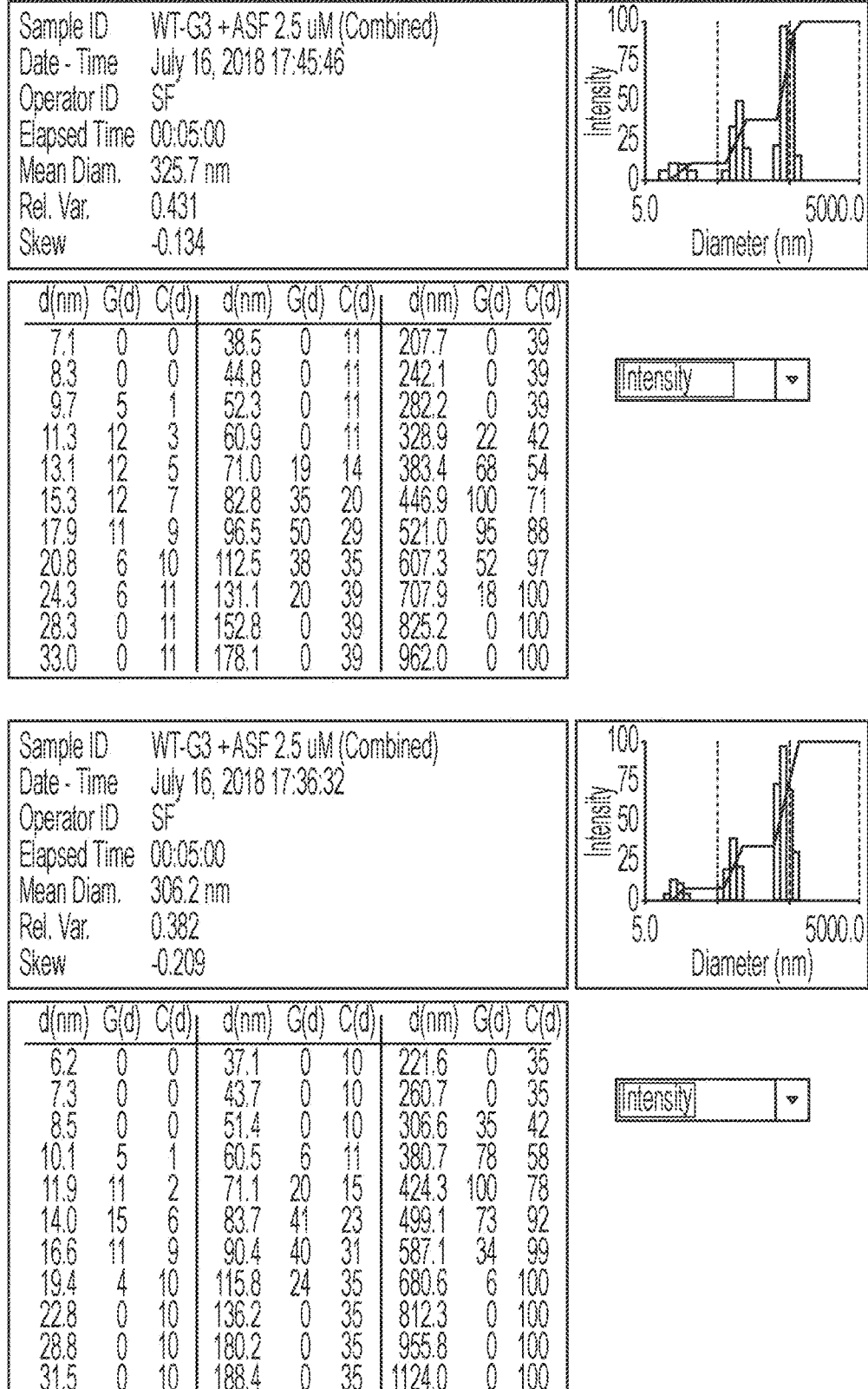
Figure 61B:
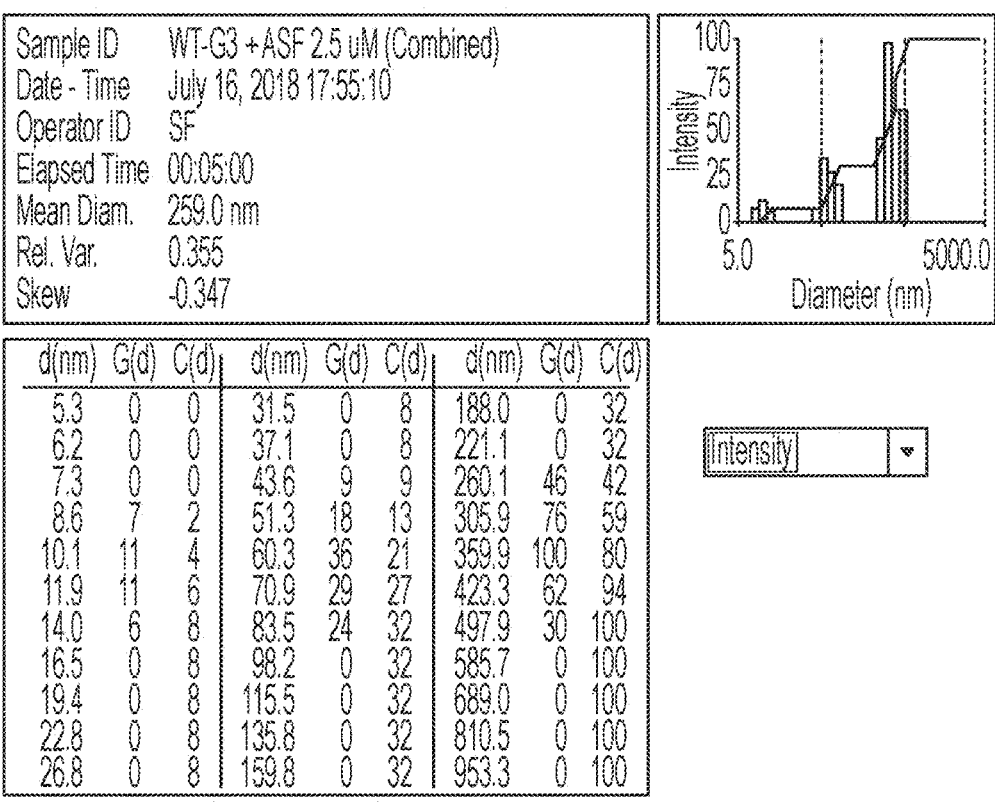

FIGS. 61A-61B show size distribution of 2.5 μM WT-G3 plus 7 μM ASF. a Surface area and b intensity-weighted. Data in columns are technical replicates of a or b.

Figure 62:
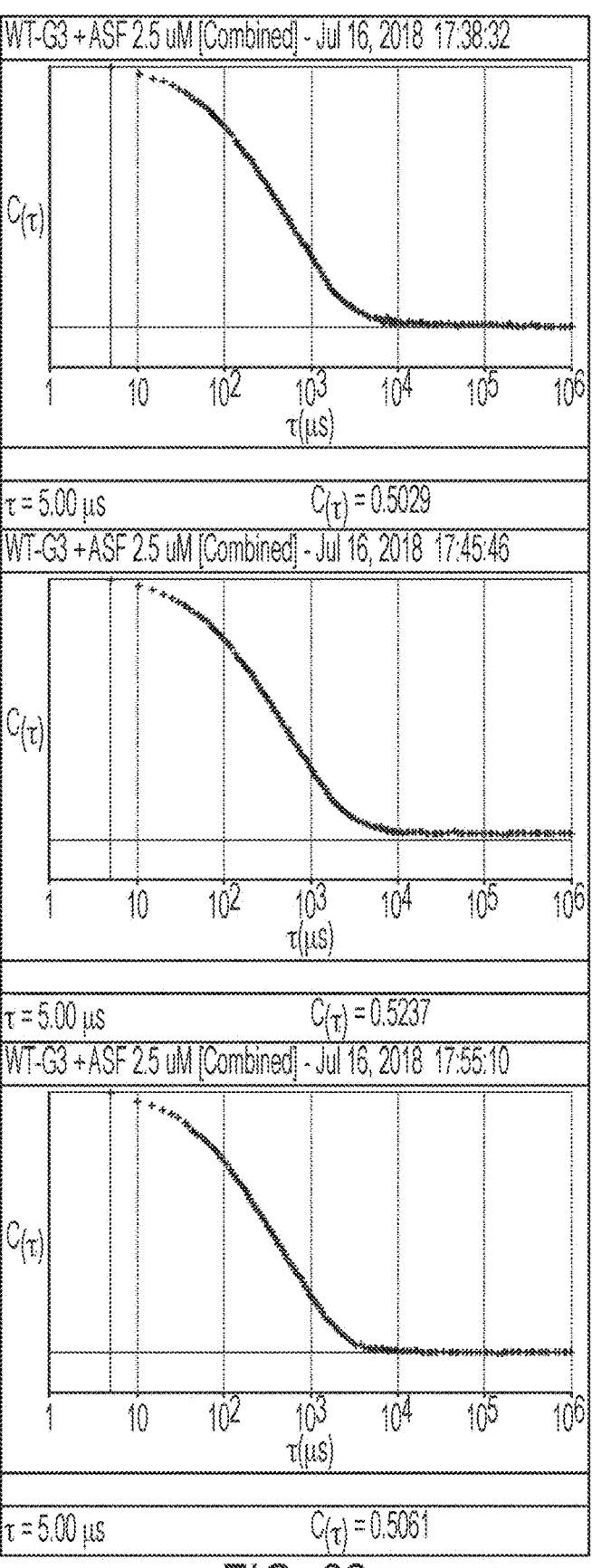

FIG. 62 shows correlation functions for DLS measurements of 2.5 μM WT-G3 plus 7 M ASF. Data are technical replicates.

Figure 63A:
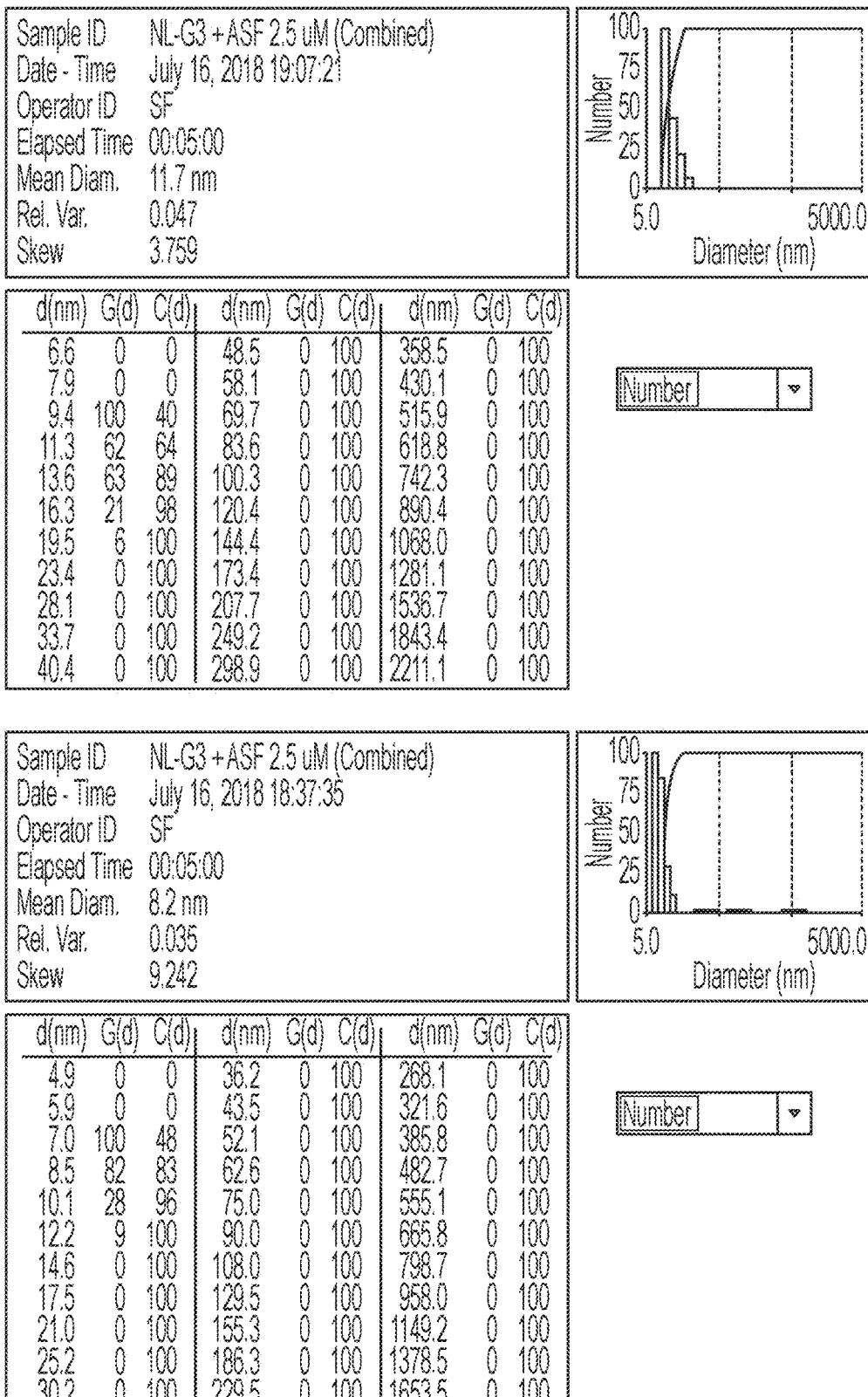
Figure 63A:
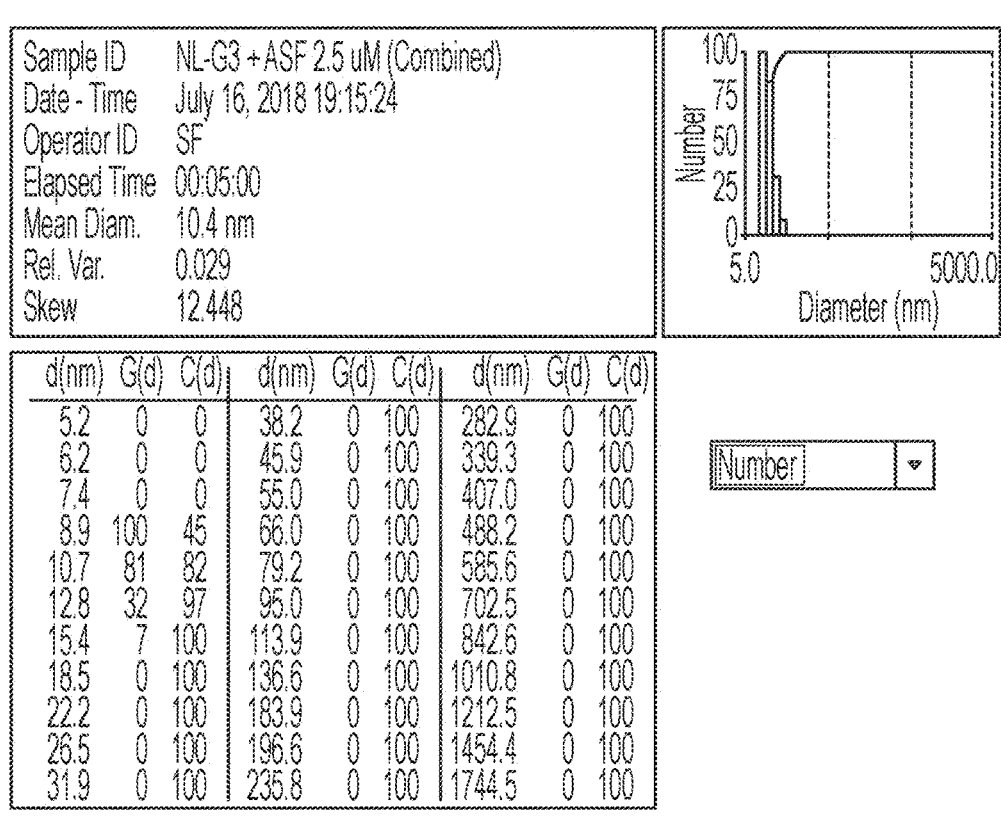
Figure 63B:
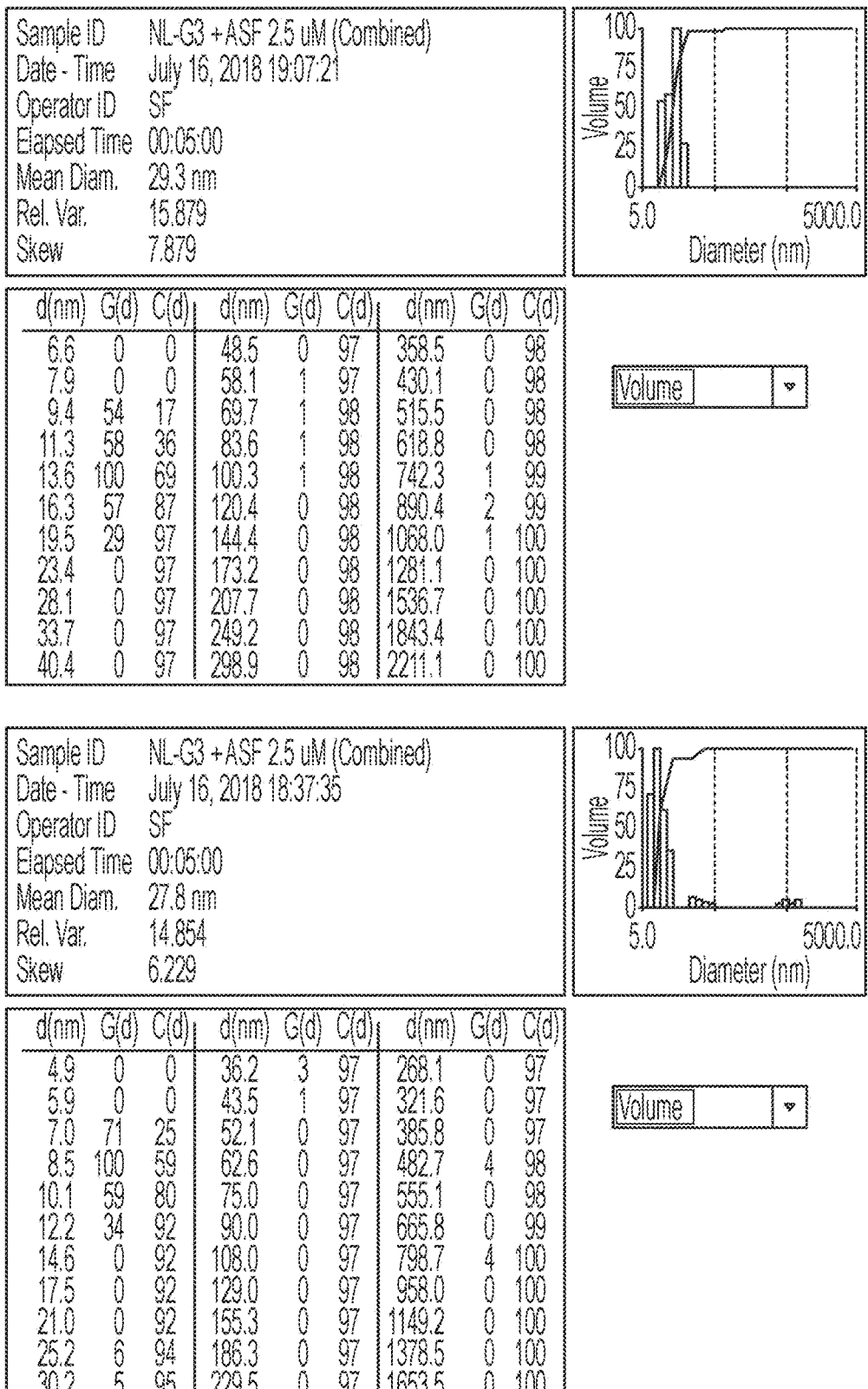
Figure 63B:
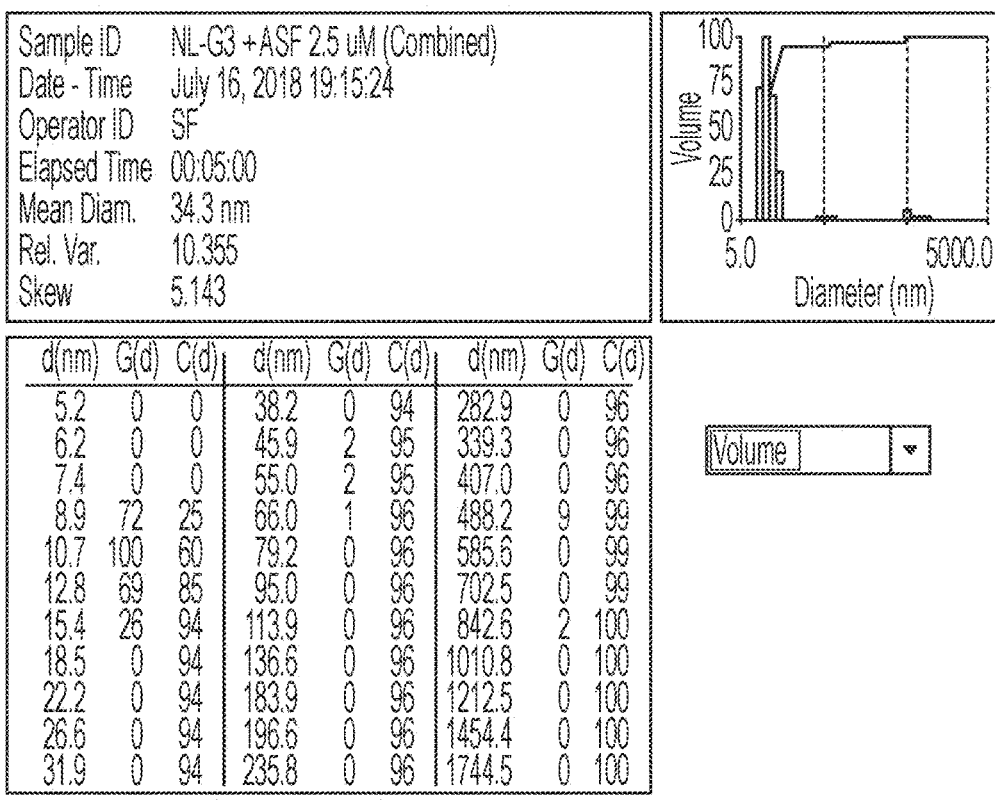

FIGS. 63A-63B show size distribution of 2.5 μM NL-G3 plus 7 μM ASF. a Number- and b volume-weighted. Data in columns are technical replicates of a or b.

Figure 64A:
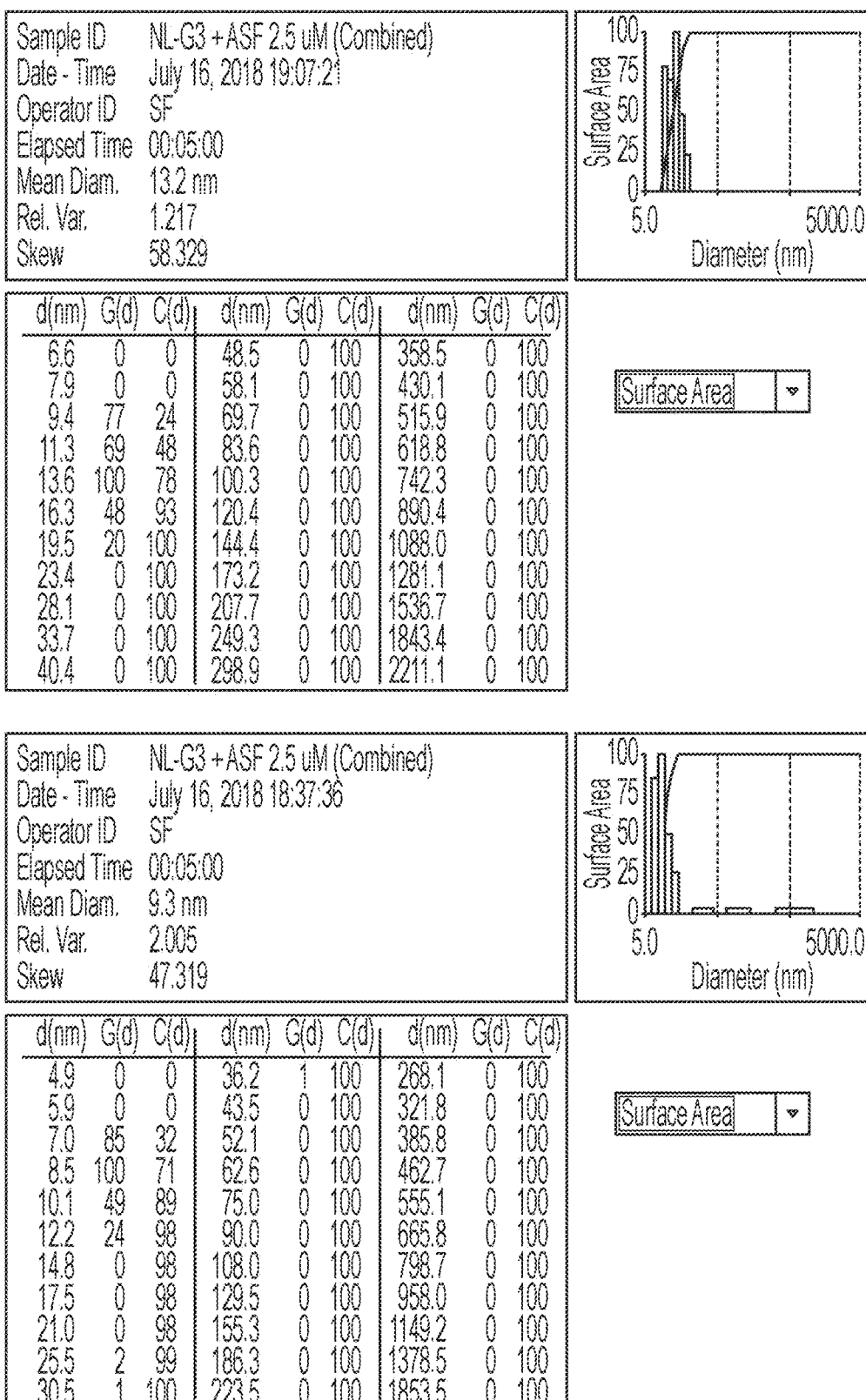
Figure 64A:
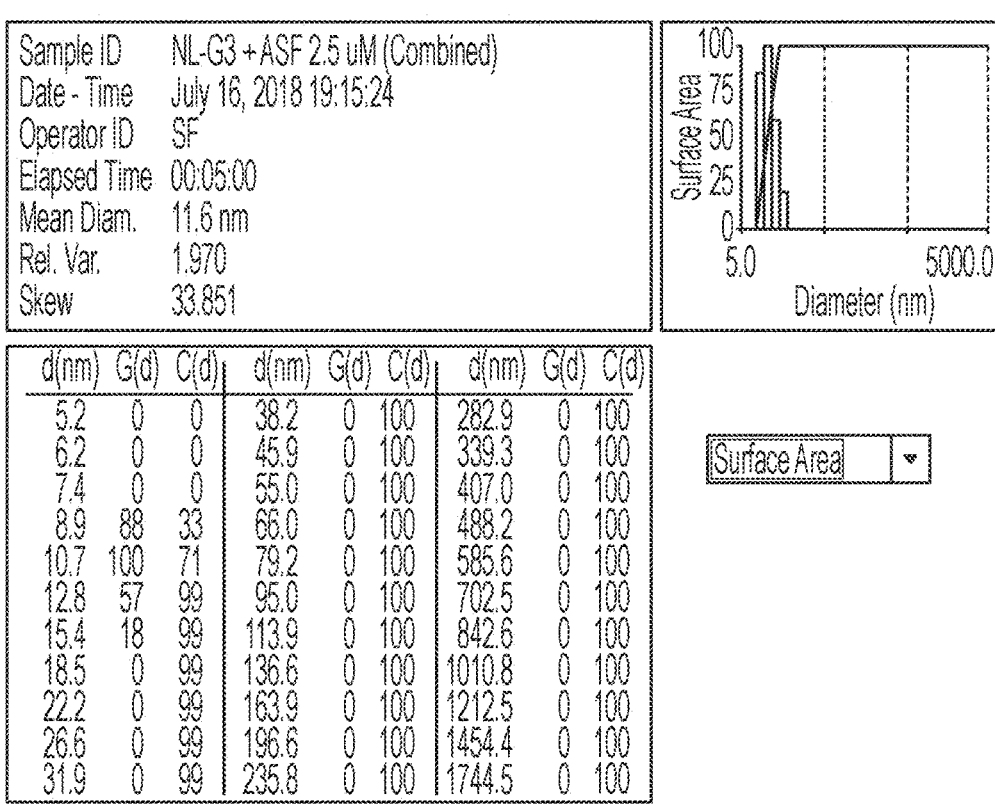
Figure 64B:
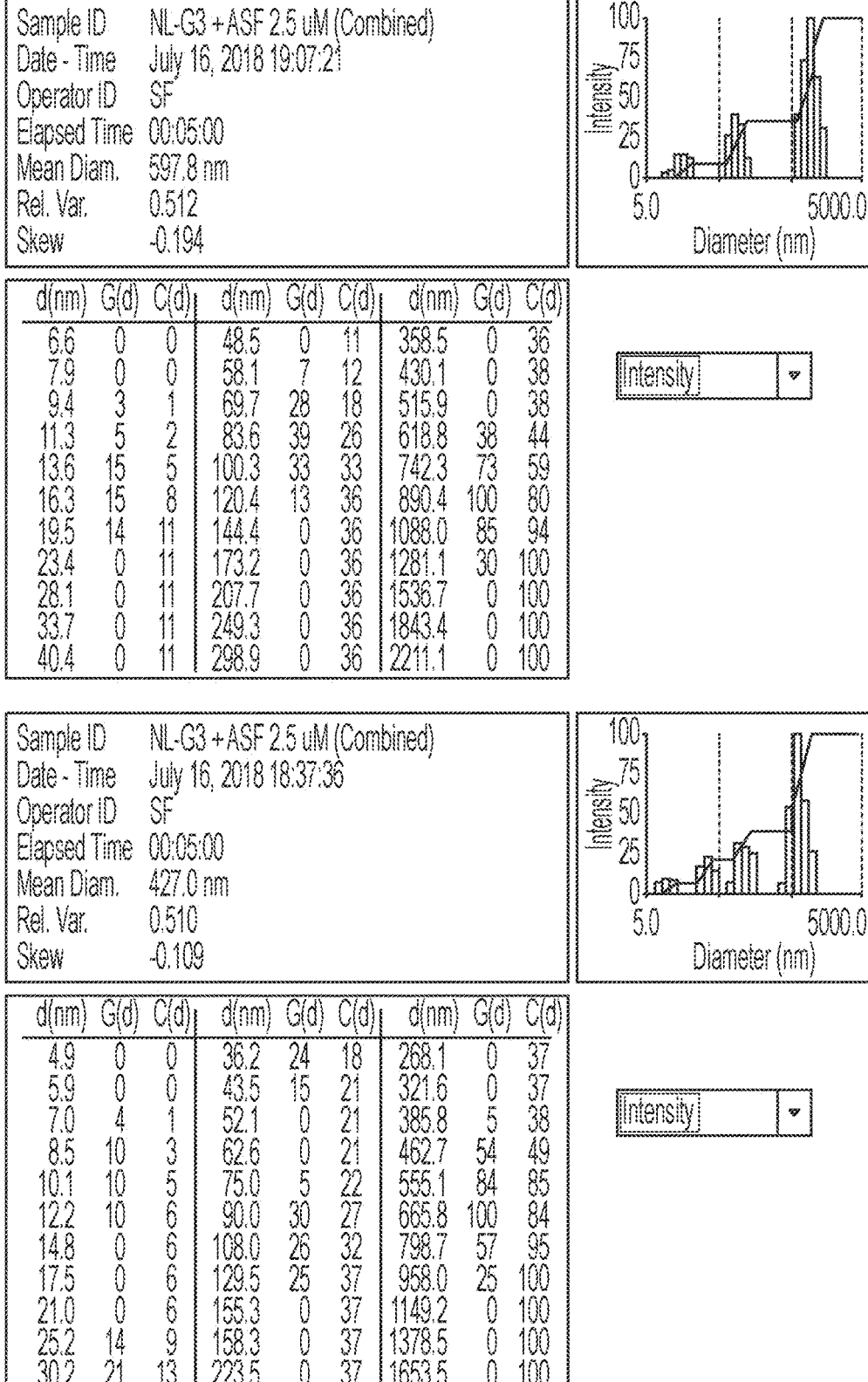
Figure 64B:
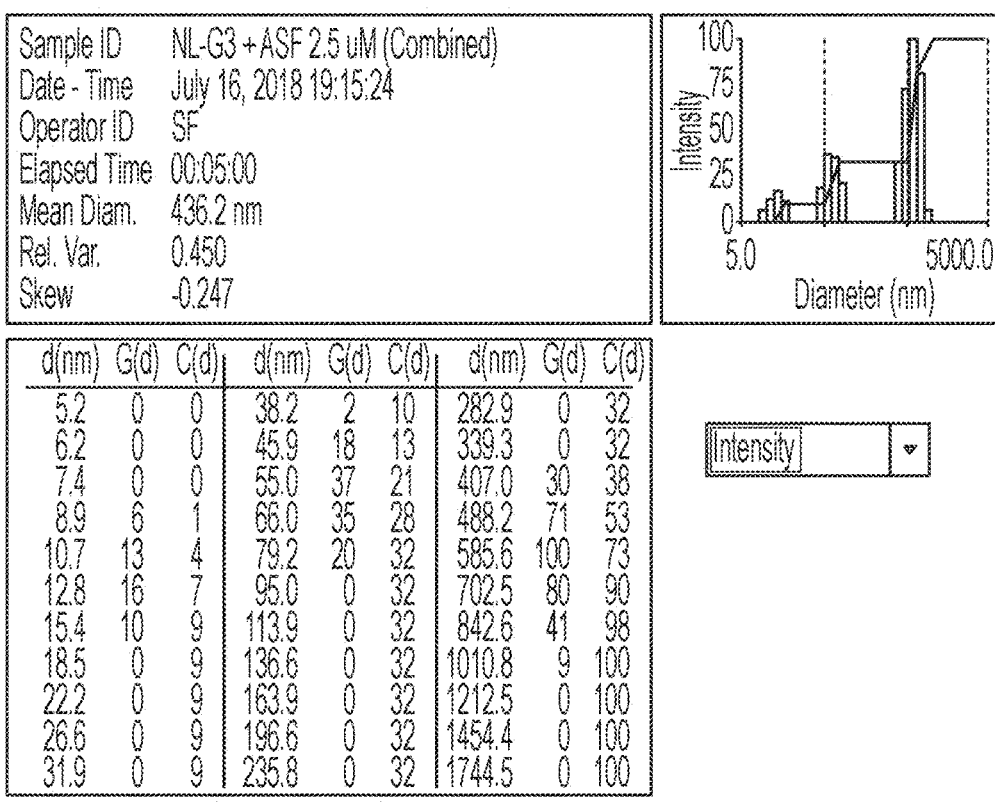

FIGS. 64A-64B show size distribution of 2.5 μM NL-G3 plus 7 μM ASF. a Surface area- and b intensity-weighted. Data in columns are technical replicates of a or b.

Figure 65:
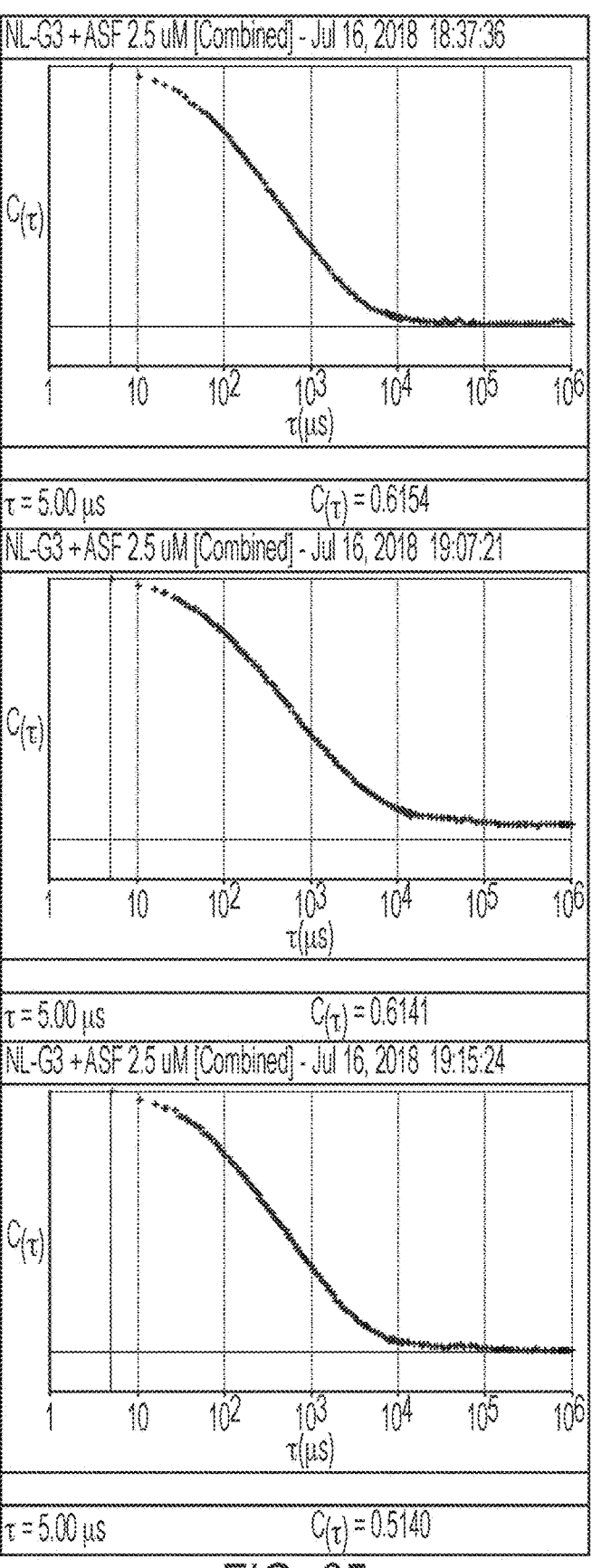

FIG. 65 shows correlation functions for DLS measurements of 2.5 μM NL-G3 plus 7 μM ASF. Data are technical replicates.

Figure 66A:
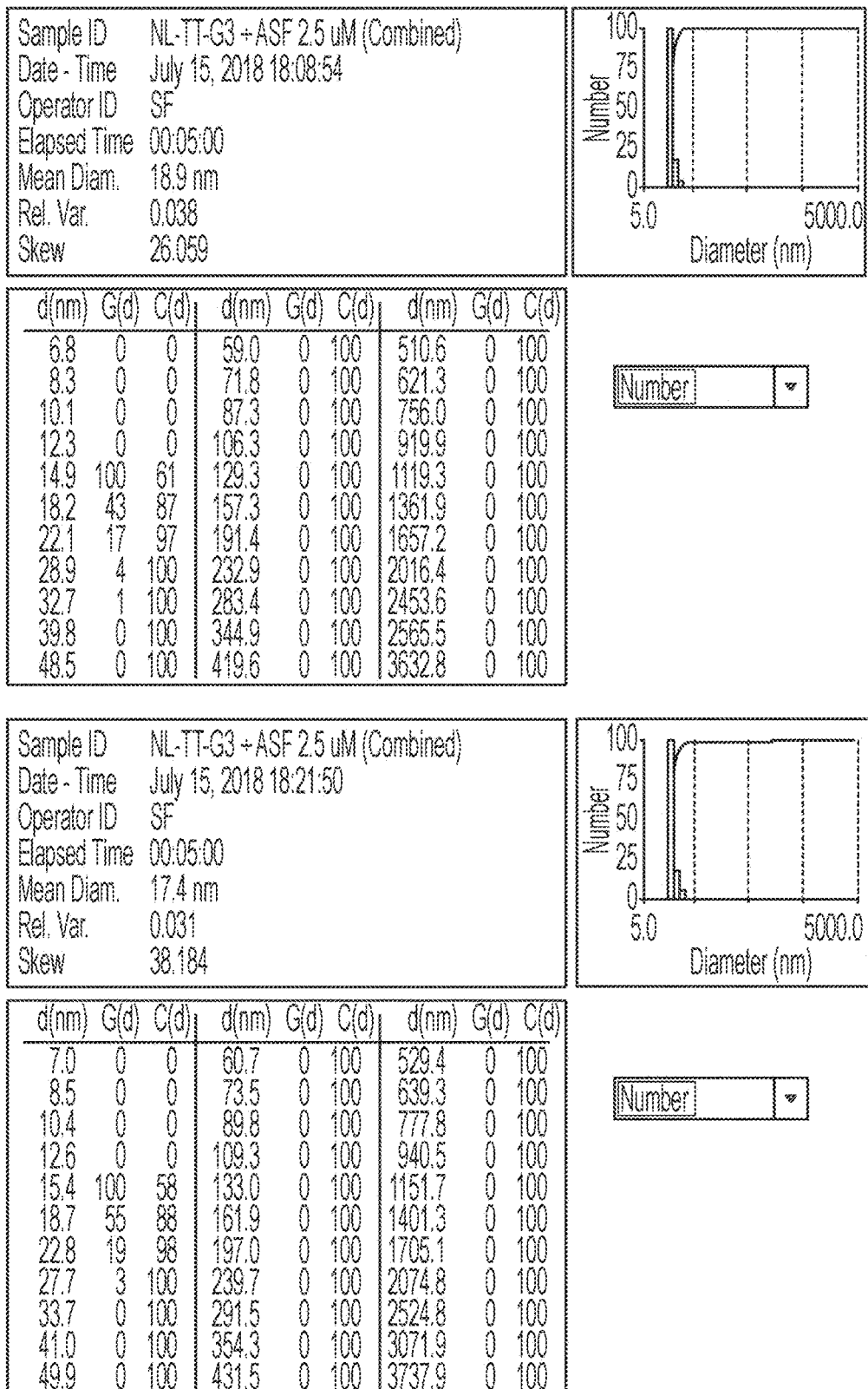
Figure 66A:
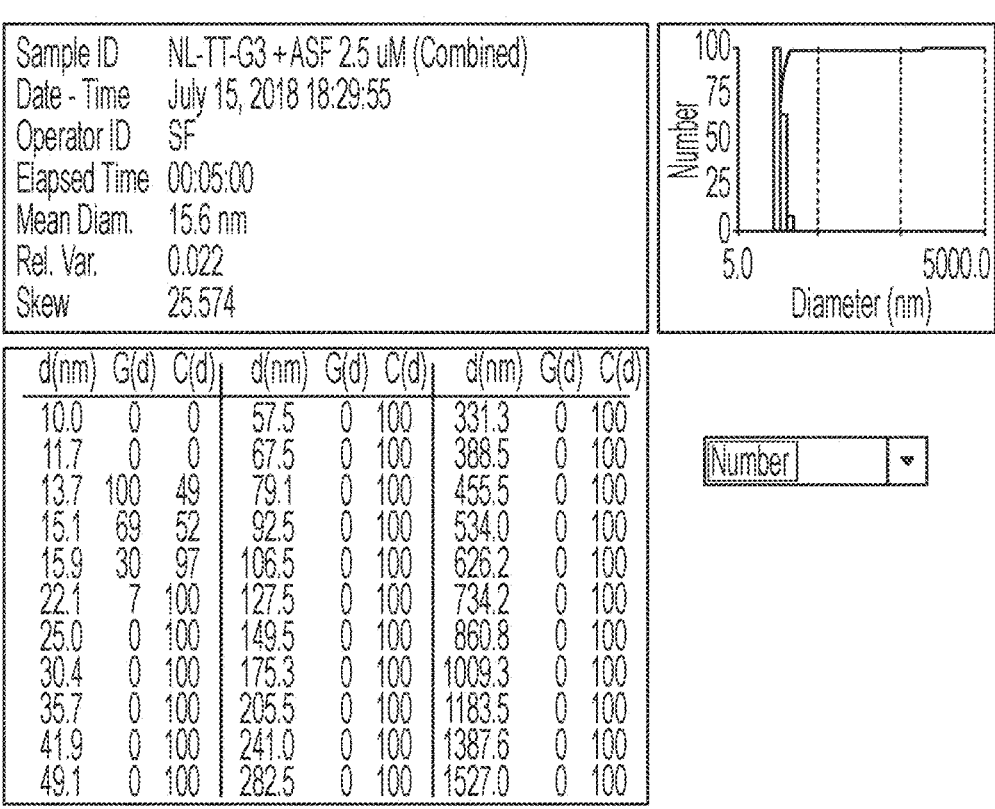
Figure 66B:
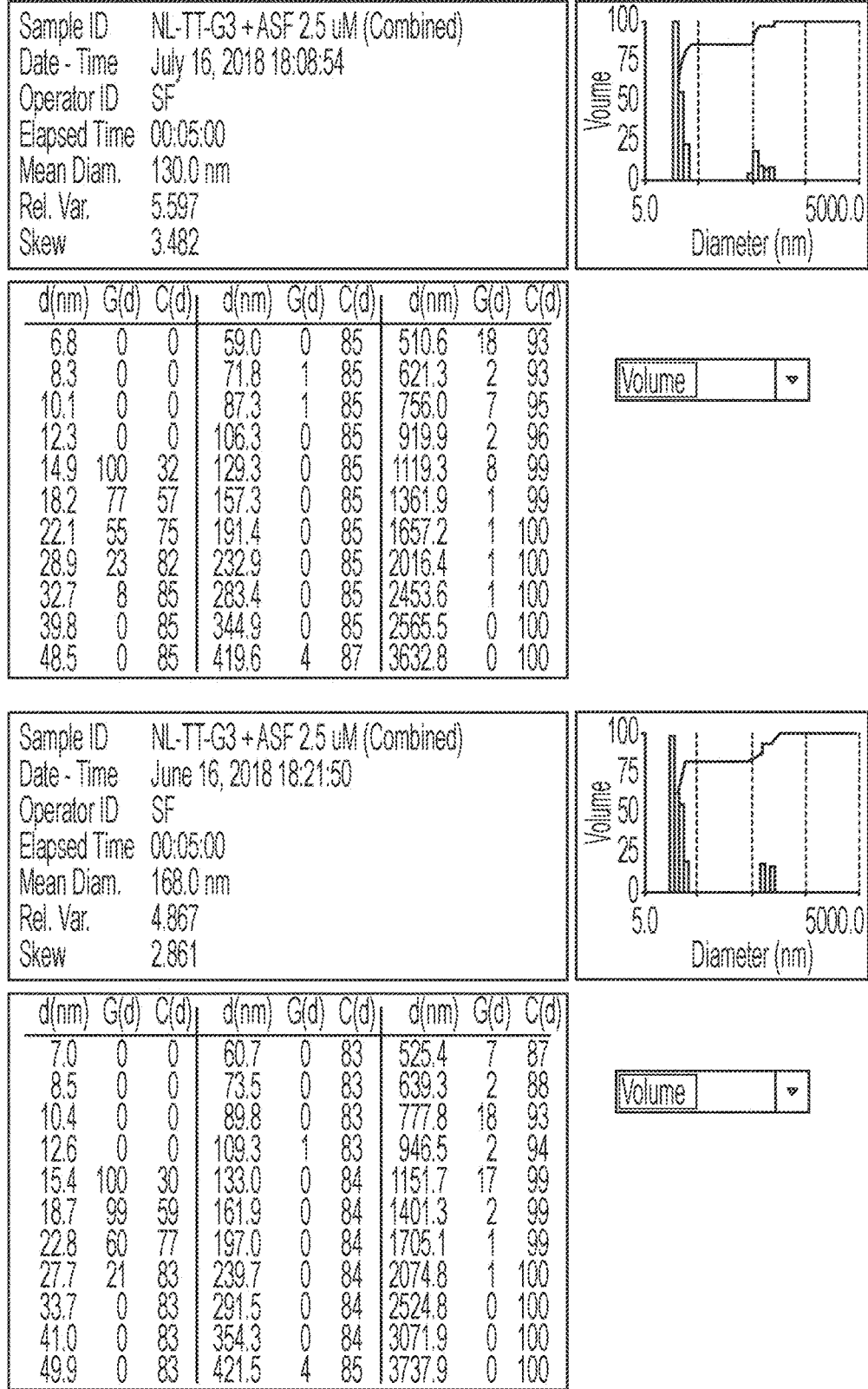
Figure 66B:
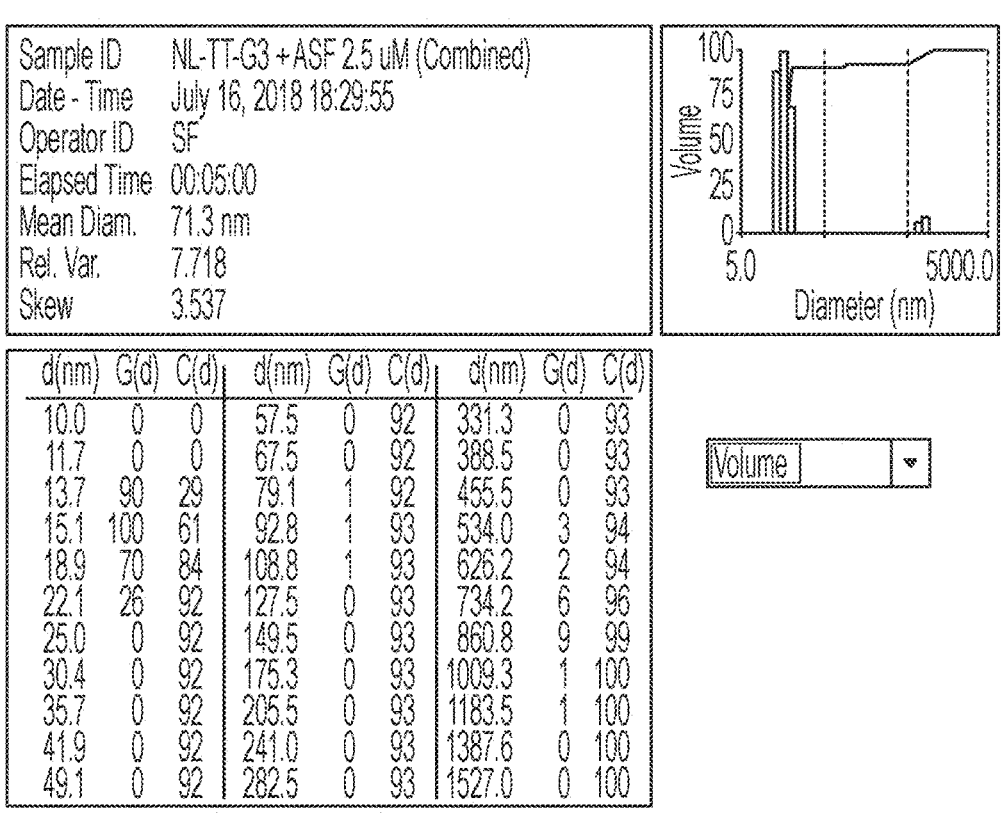

FIGS. 66A-66B show size distribution of 2.5 μM NL-TT-G3 plus 7 μM ASF. a Number and b volume-weighted. Data in columns are technical replicates of a or b.

Figure 67A:
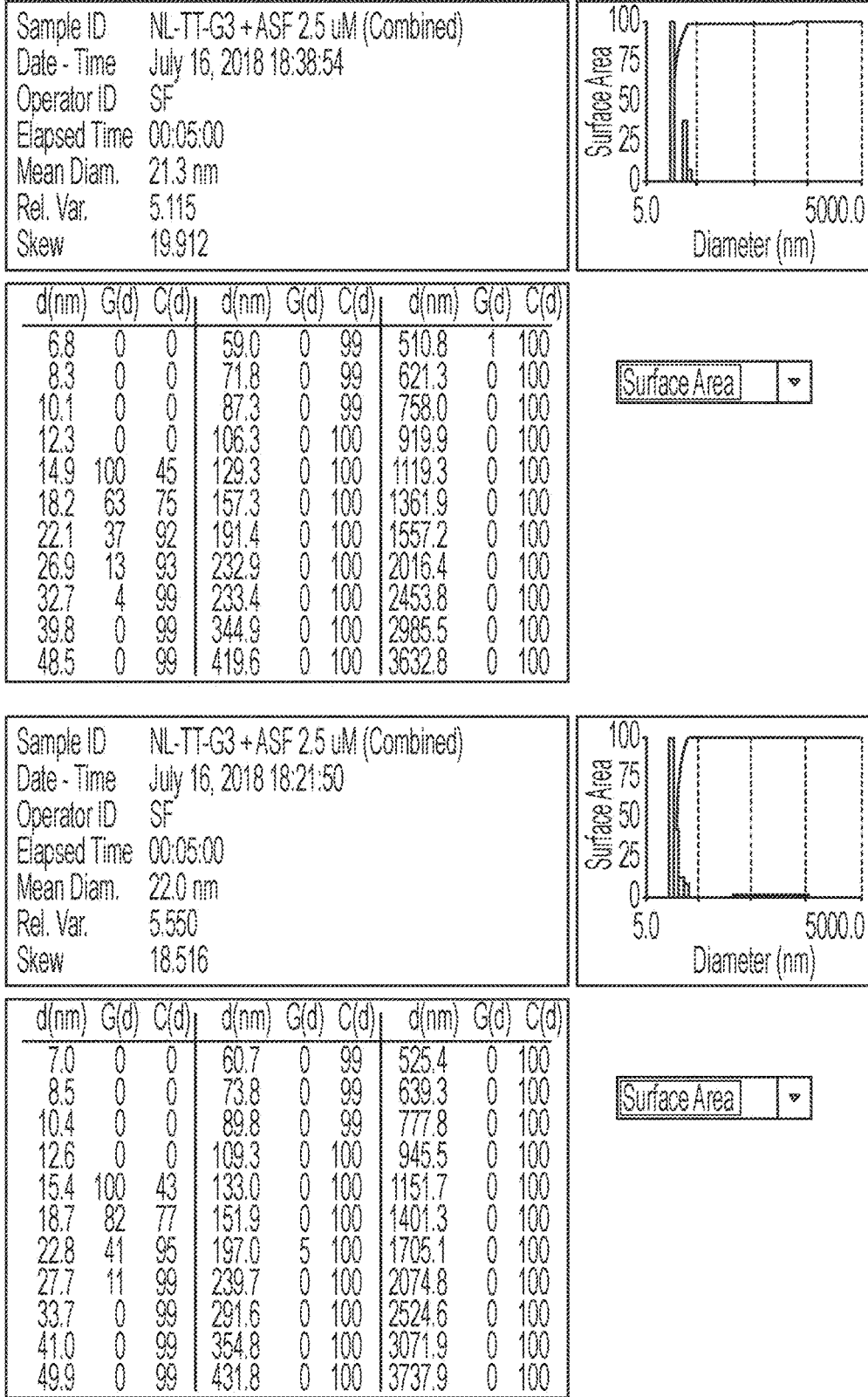
Figure 67A:
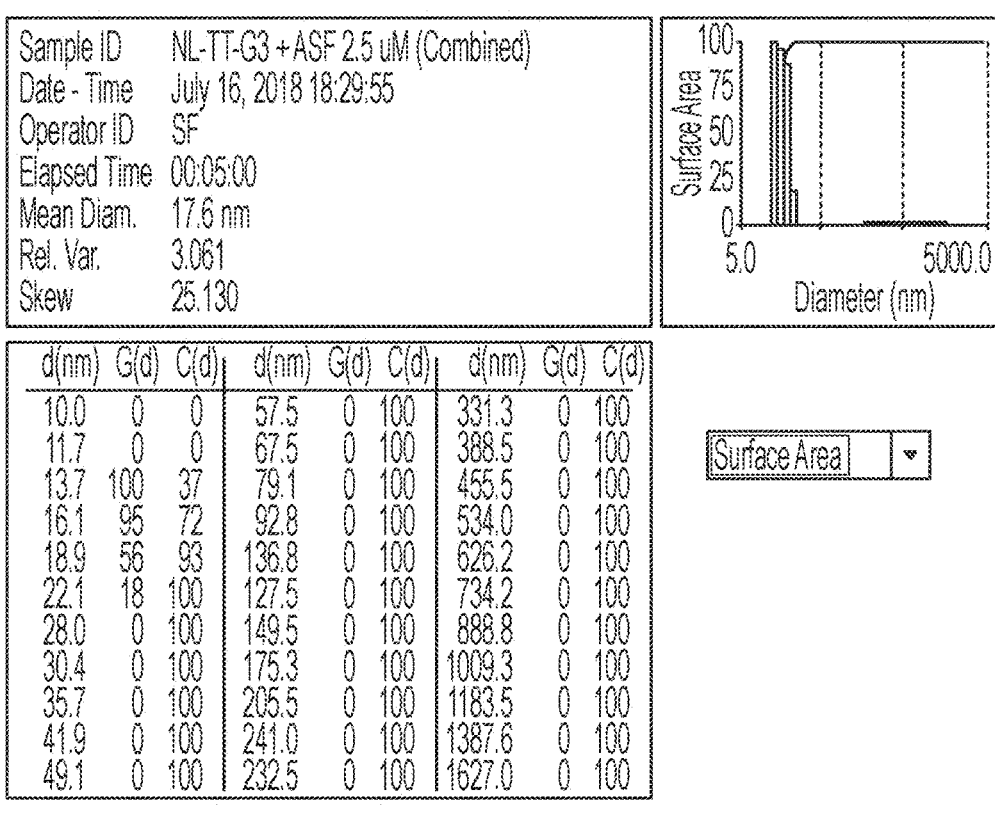
Figure 67B:
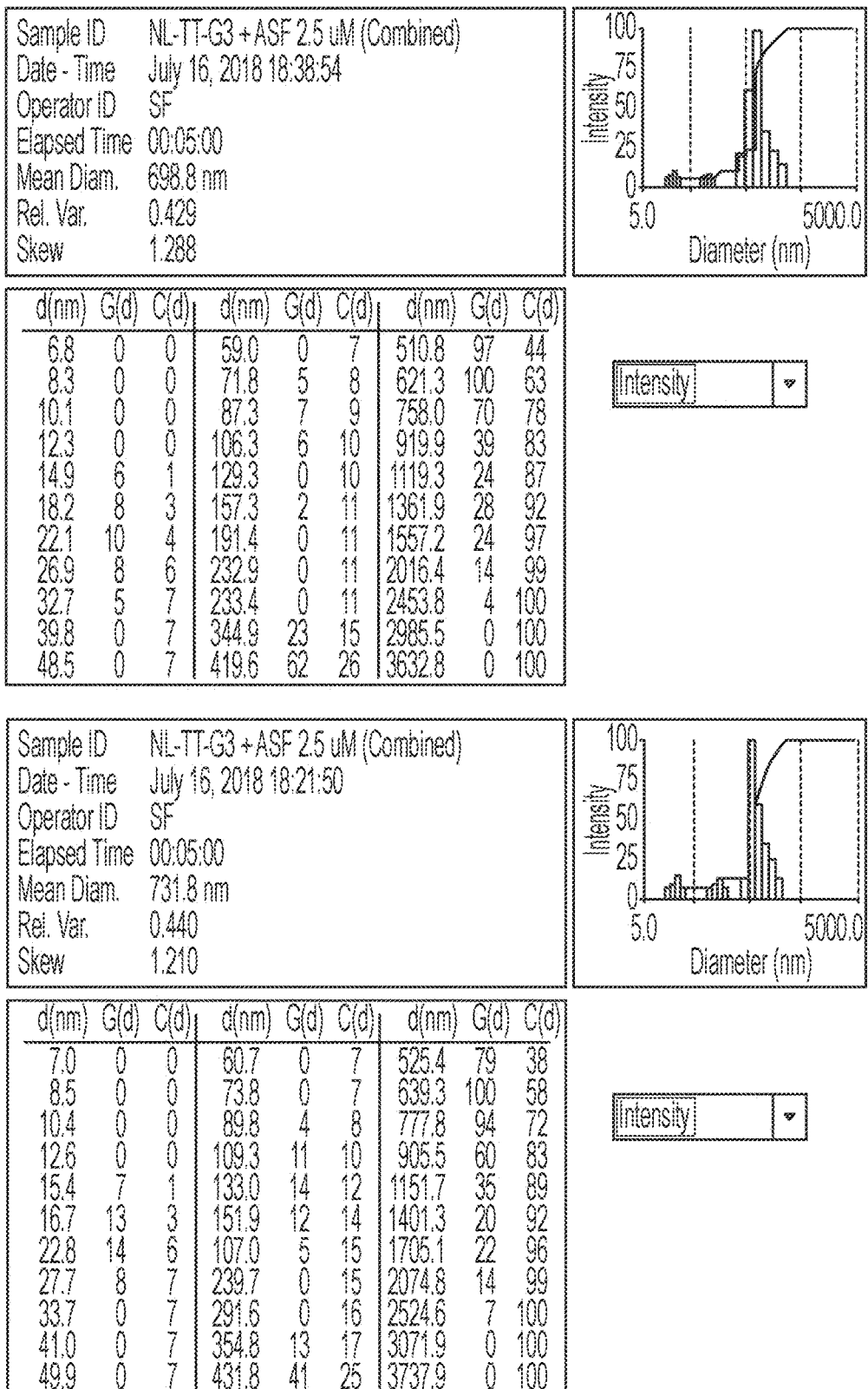
Figure 67B:
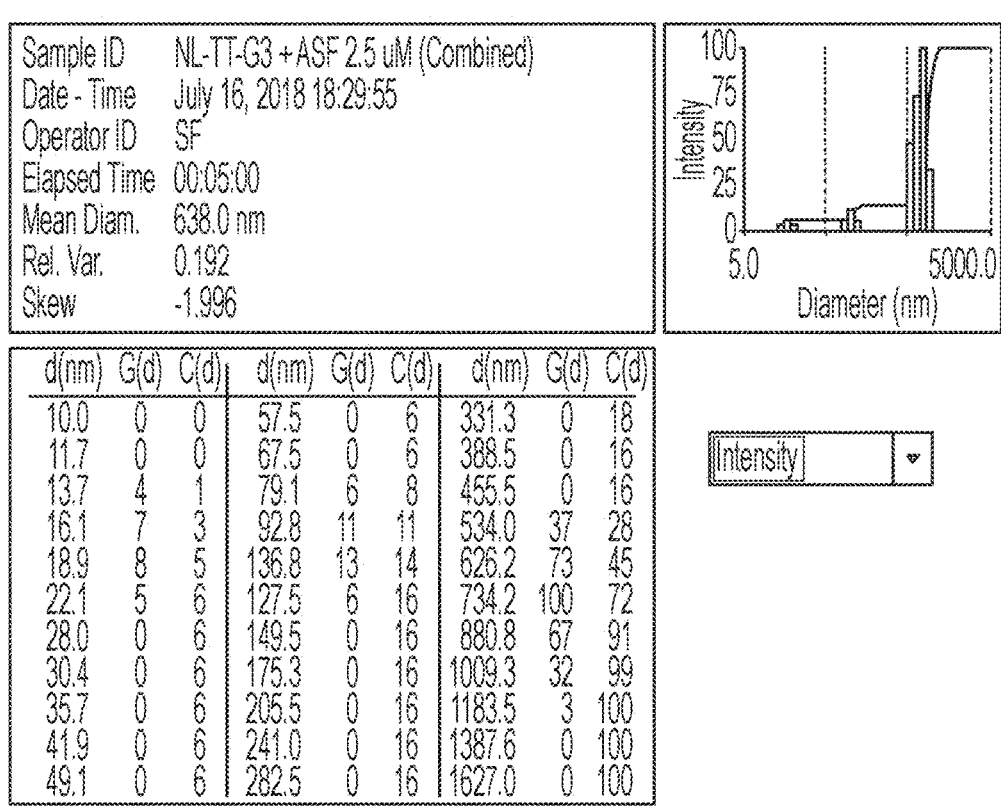

FIGS. 67A-67B show size distribution of 2.5 μM NL-TT-G3 plus 7 μM ASF. a Surface area- and b intensity-weighted. Data in columns are technical replicates of a or b.

Figure 68:
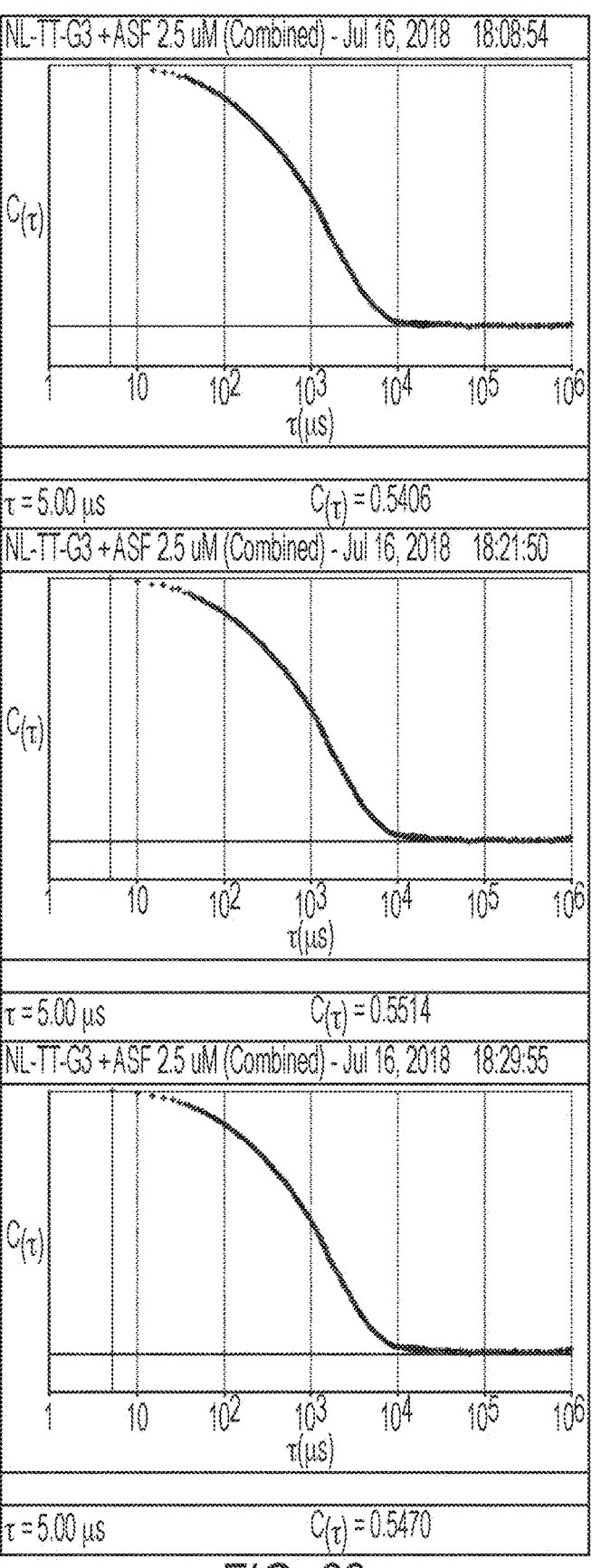

FIG. 68 show correlation functions for DLS measurements of 2.5 μM NL-TT-G3 plus 7 μM ASF. Data are technical replicates.

Figure 69A:
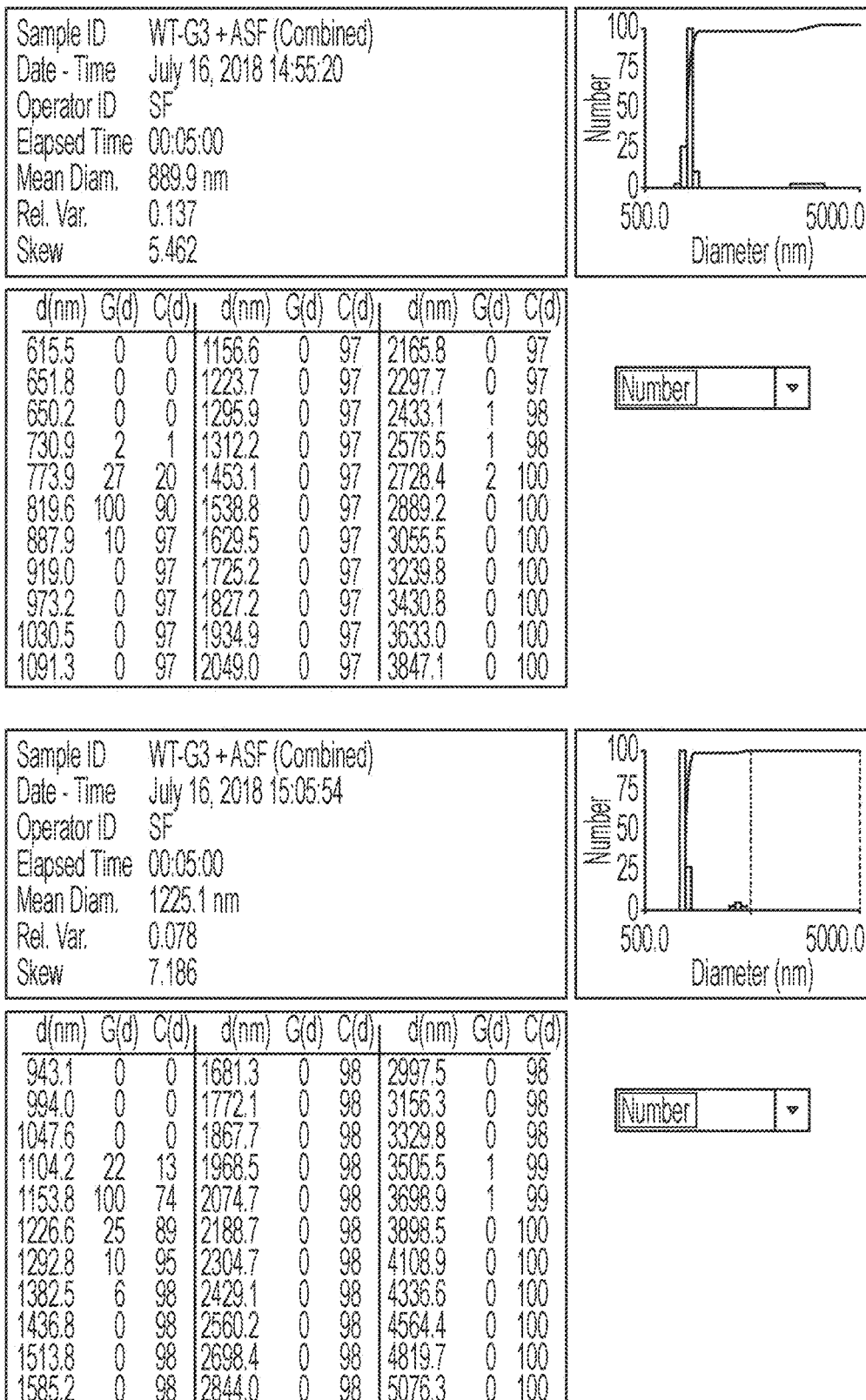
Figure 69A:
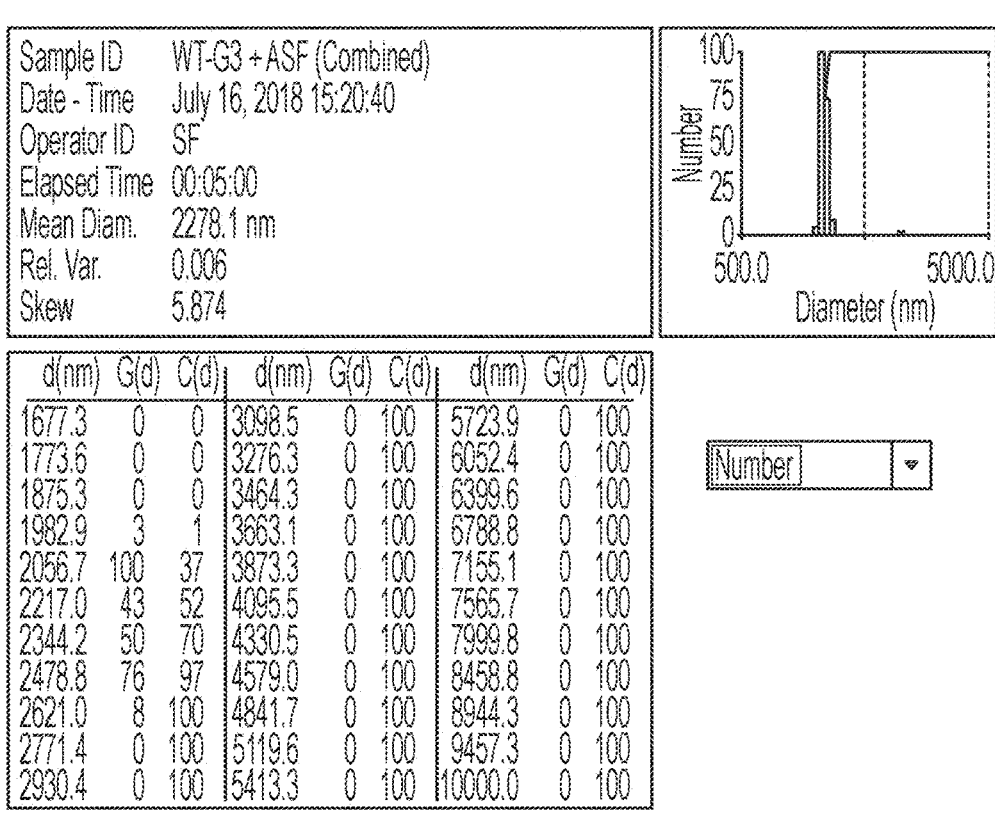
Figure 69B:
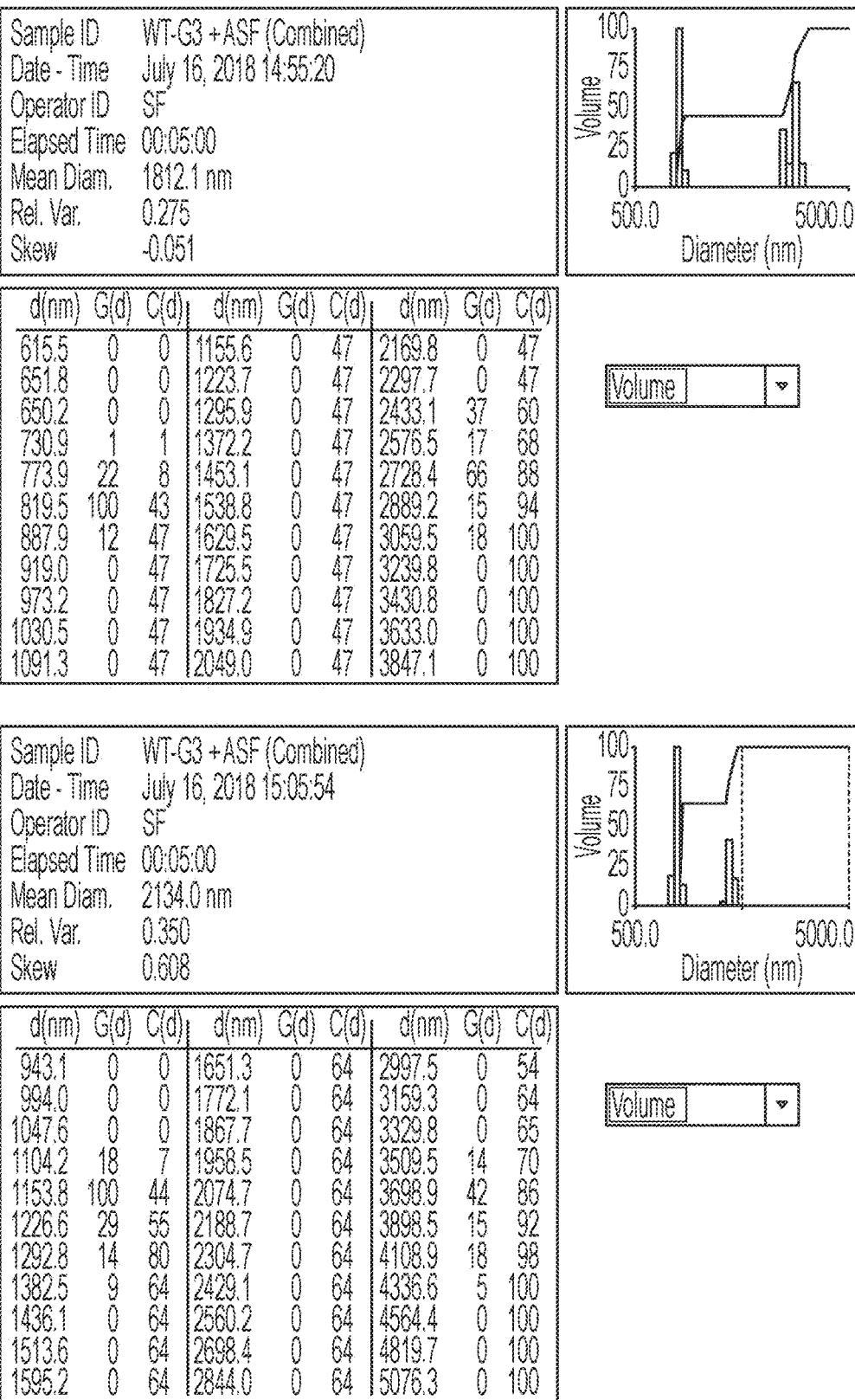
Figure 69B:
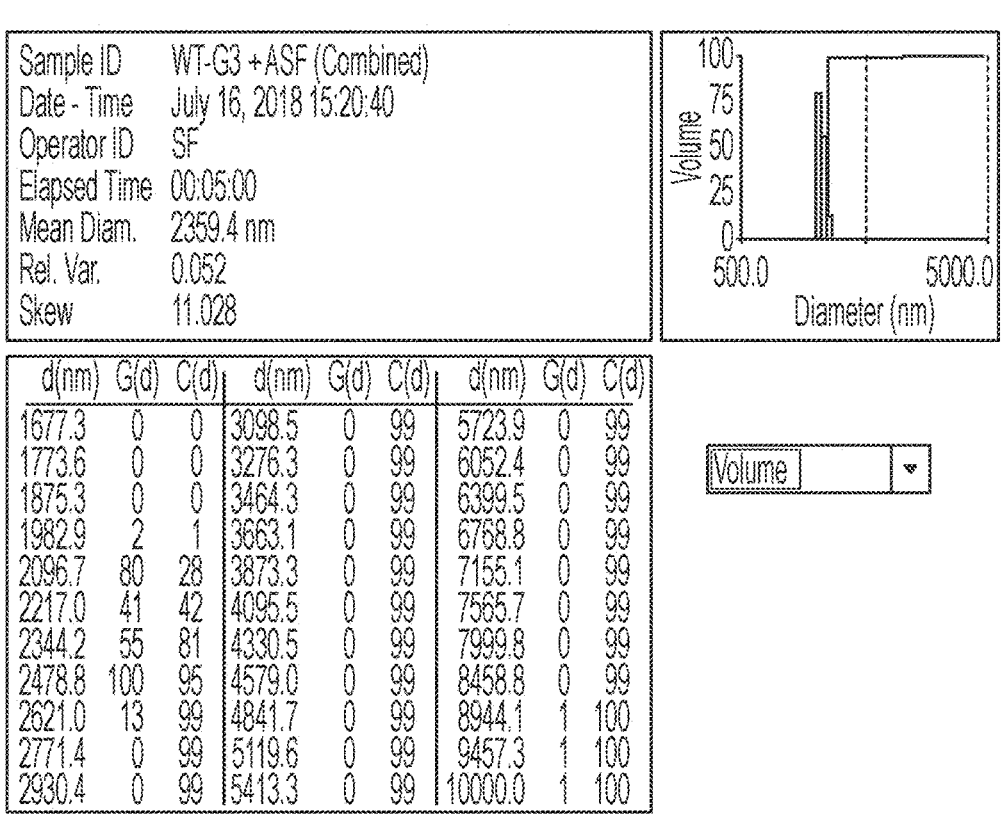

FIGS. 69A-69B show size distribution of 10 μM WT-G3 plus 7 μM ASF. a Number- and b volume-weighted. Data in columns are technical replicates of a or b.

Figure 70A:
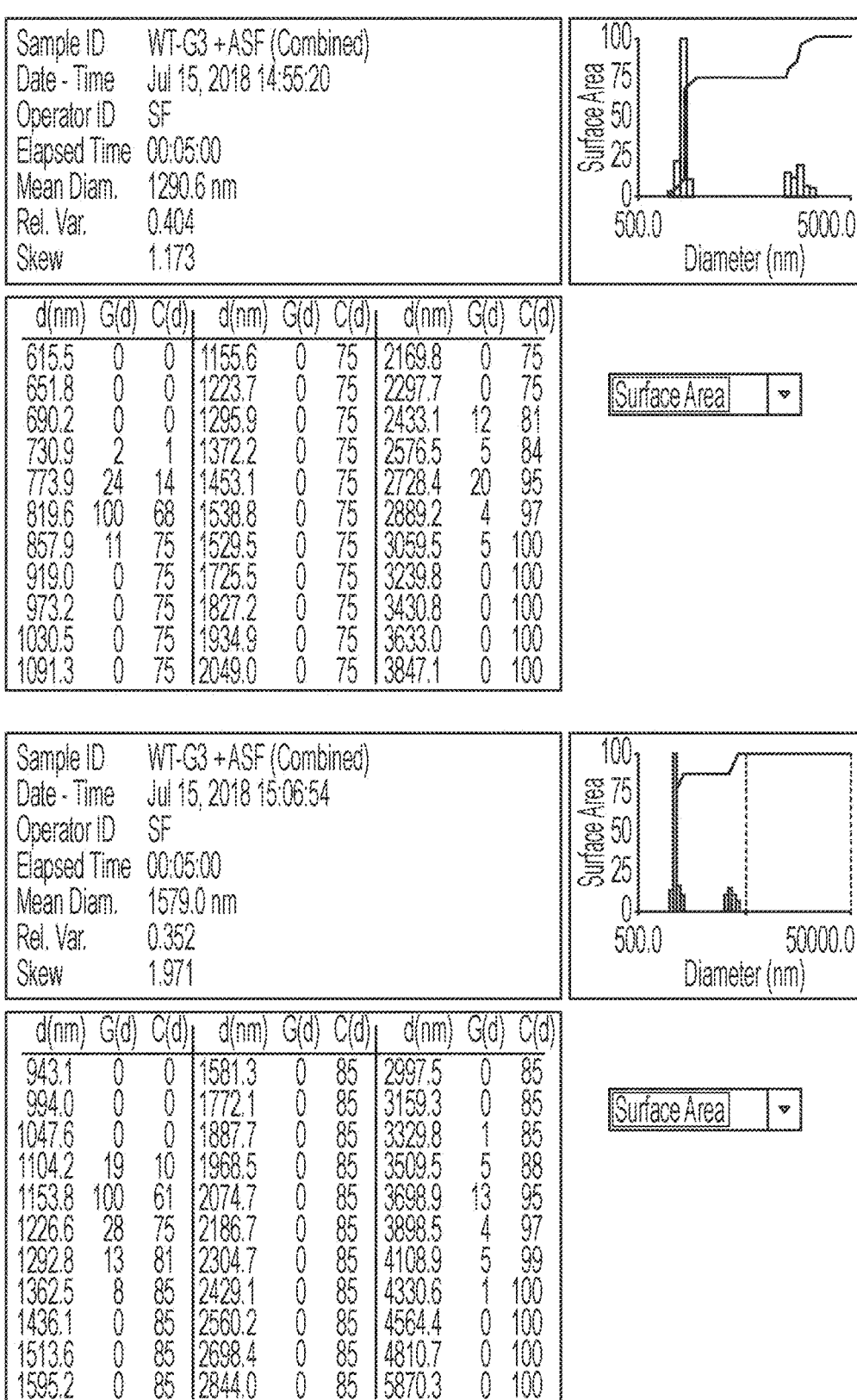
Figure 70A:
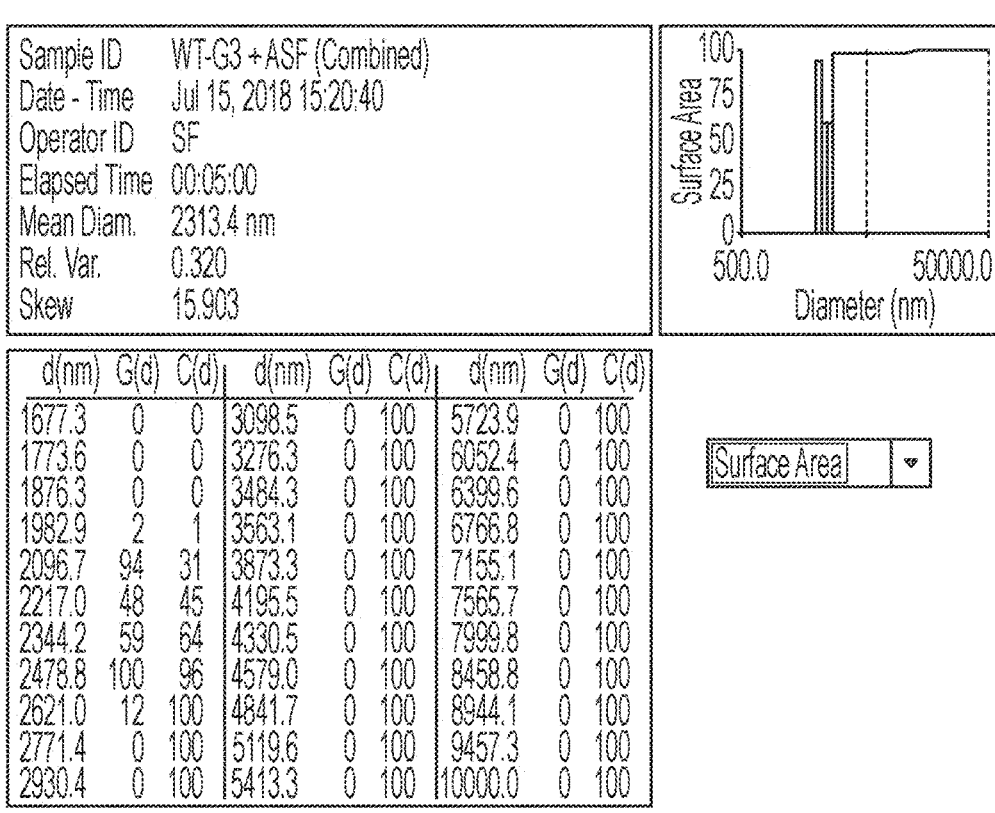
Figure 70B:
Figure 70B:
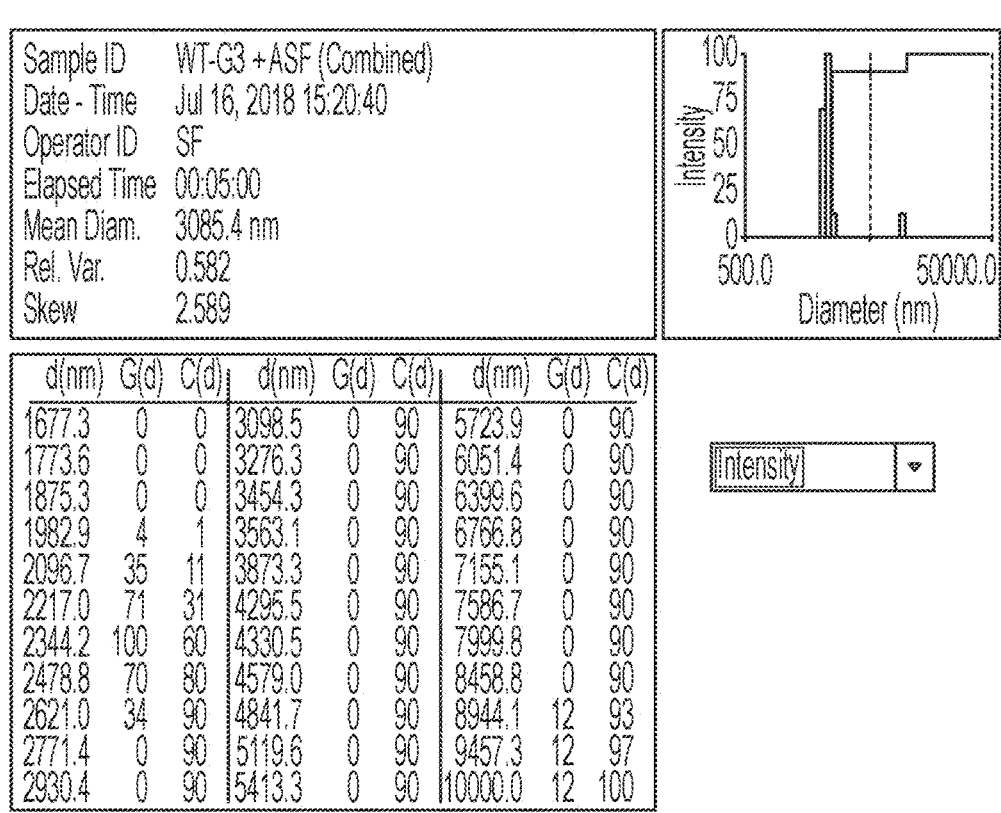

FIGS. 70A-70B show size distribution of 10 μM WT-G3 plus 7 μM ASF. a Surface area and b intensity-weighted. Data in columns are technical replicates of a or b.

Figure 71:
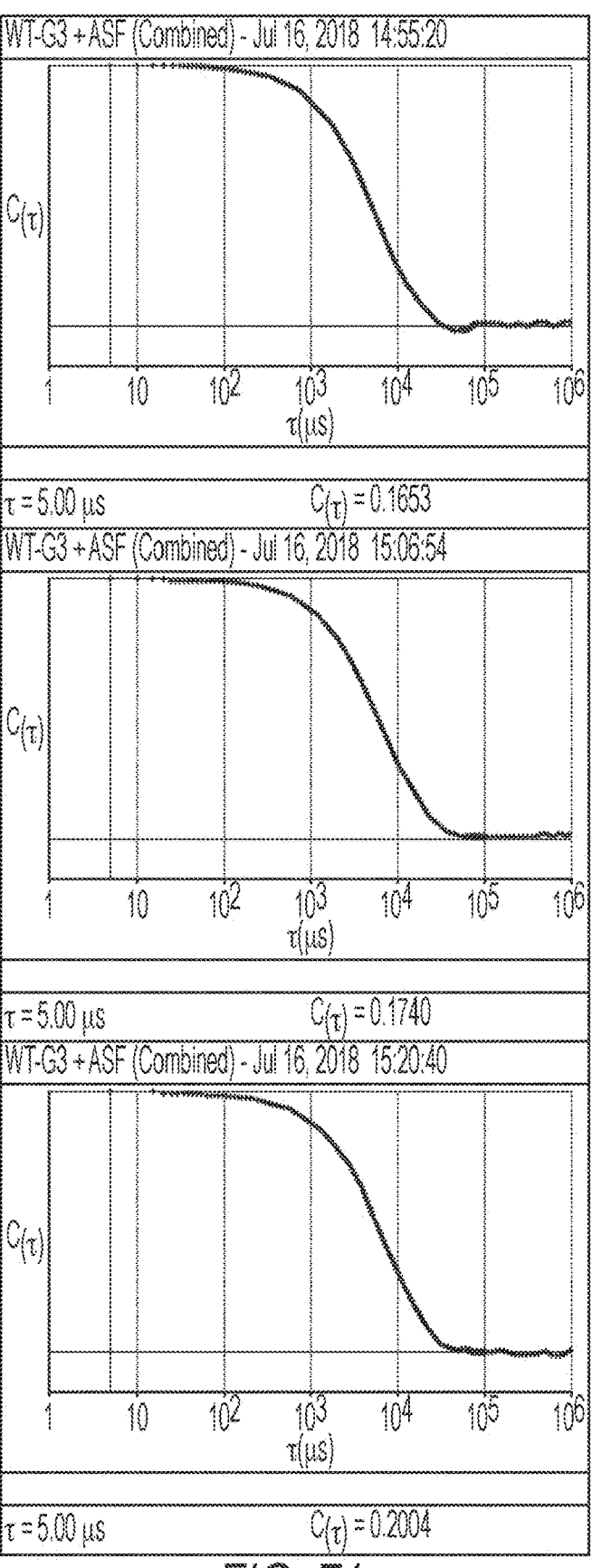

FIG. 71 shows correlation functions for DLS measurements of 10 μM WT-G3 plus 7 μM ASF. Data are technical replicates.

Figure 72A:
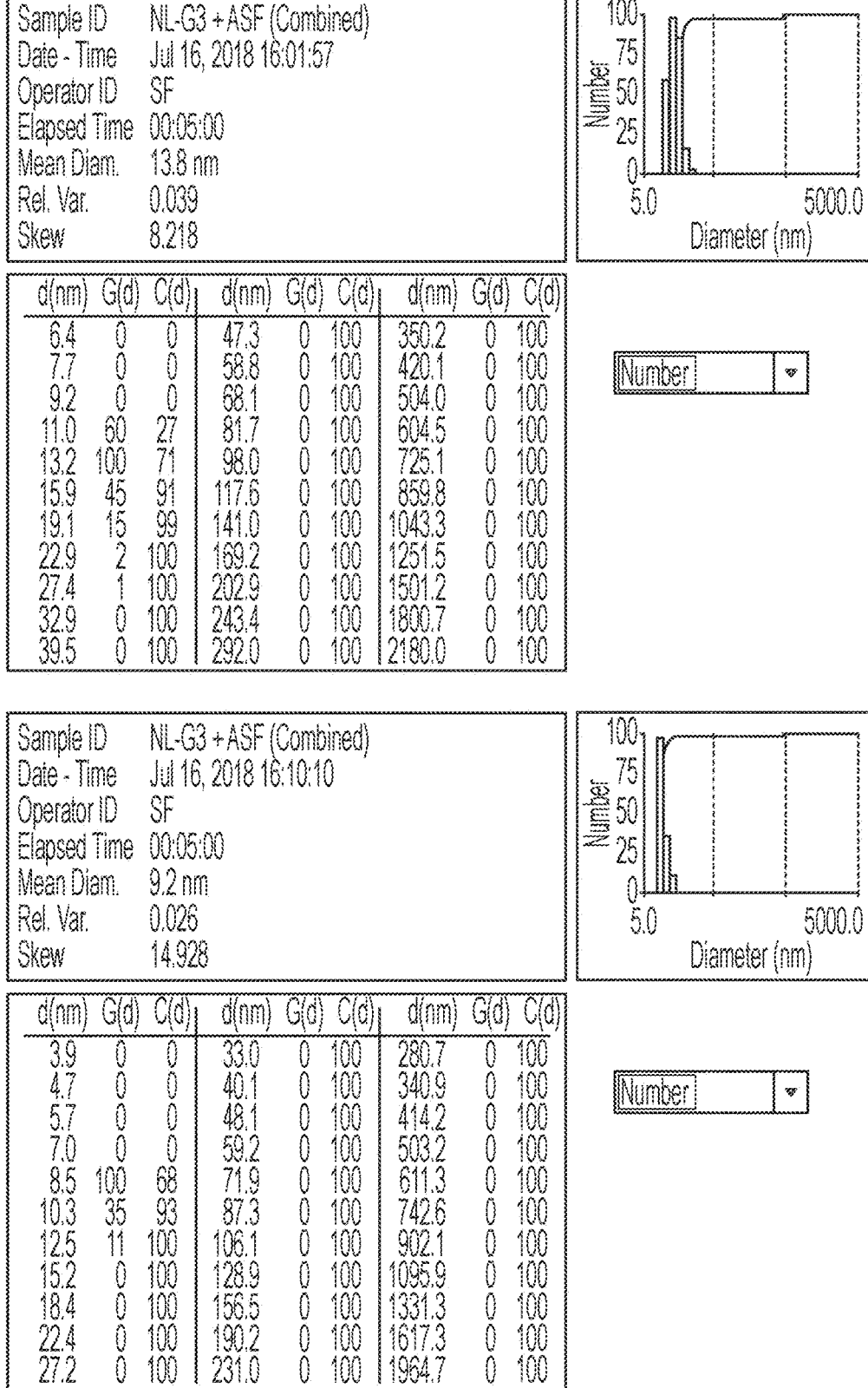
Figure 72A:
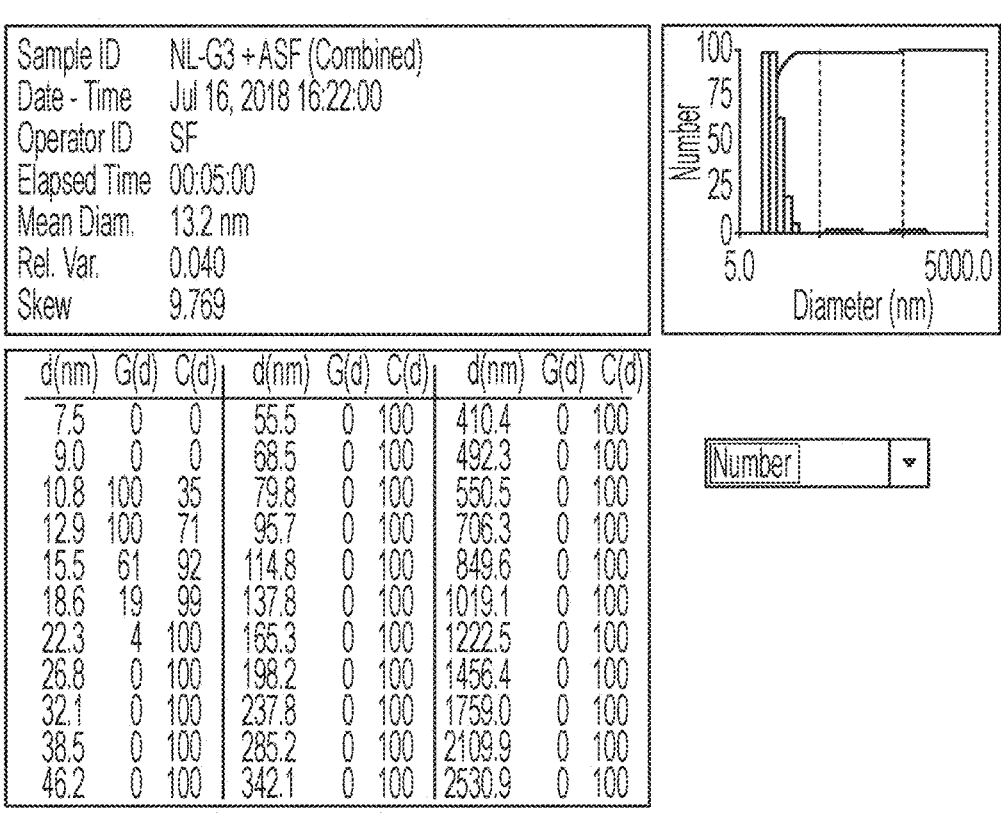
Figure 72B:
Figure 72B:
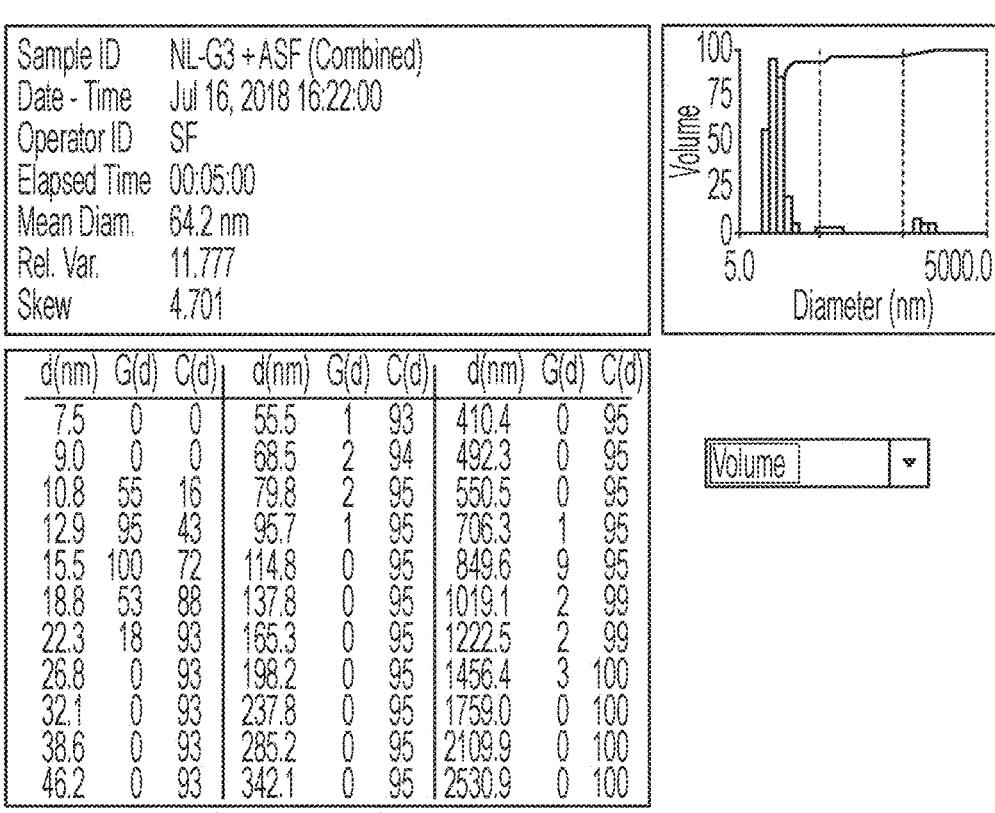

FIGS. 72A-72B show size distribution of 10 μM NL-G3 plus 7 μM ASF. a Number- and b volume-weighted. Data in columns are technical replicates of a or b.

Figure 73A:
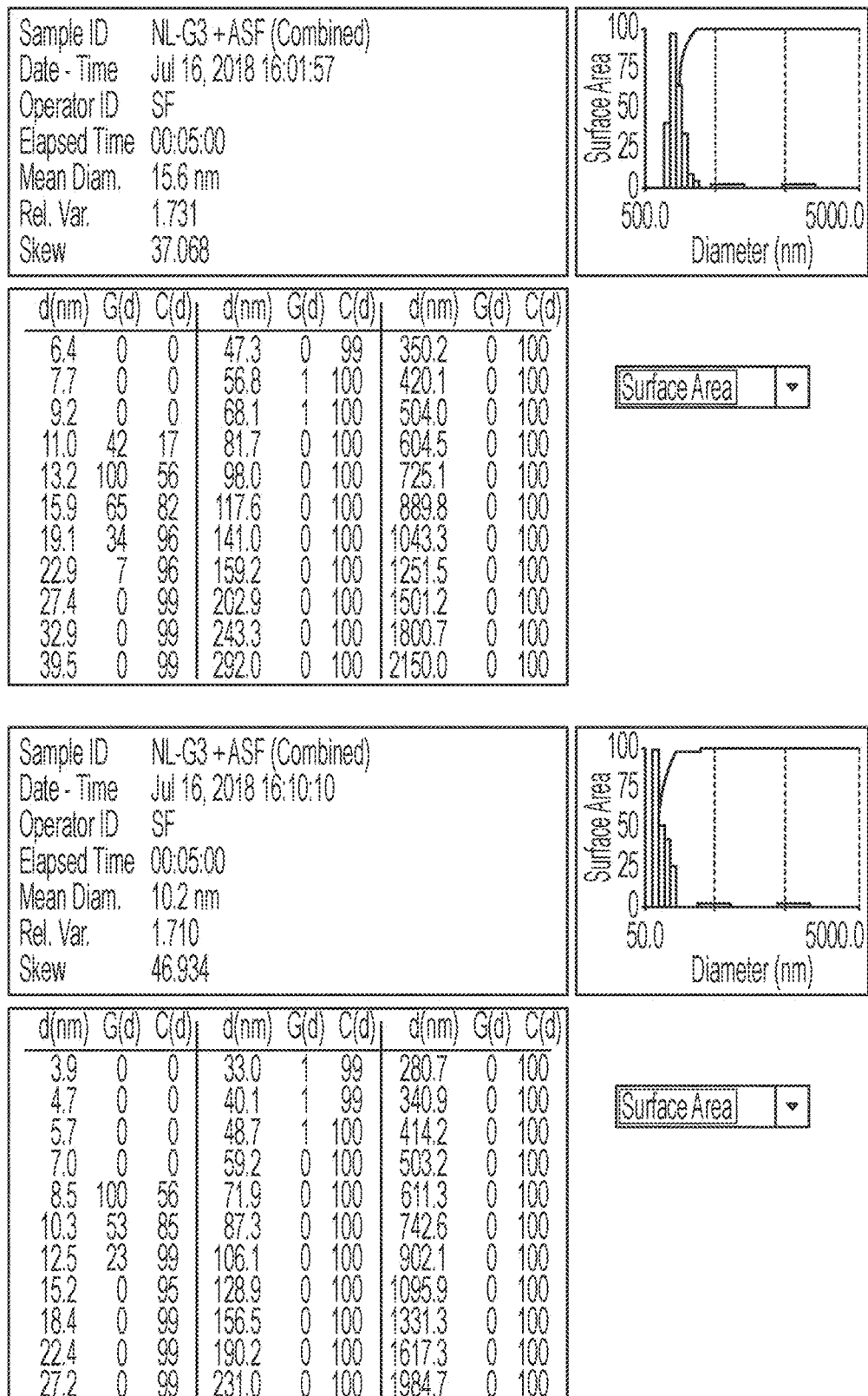
Figure 73A:
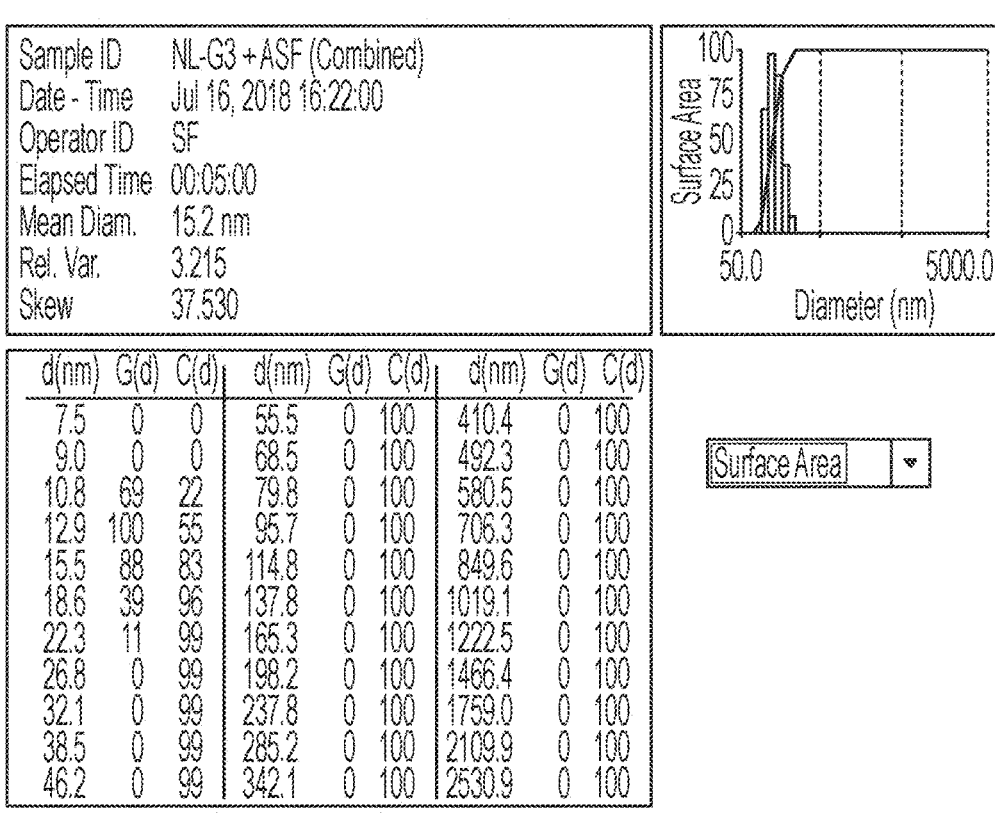
Figure 73B:
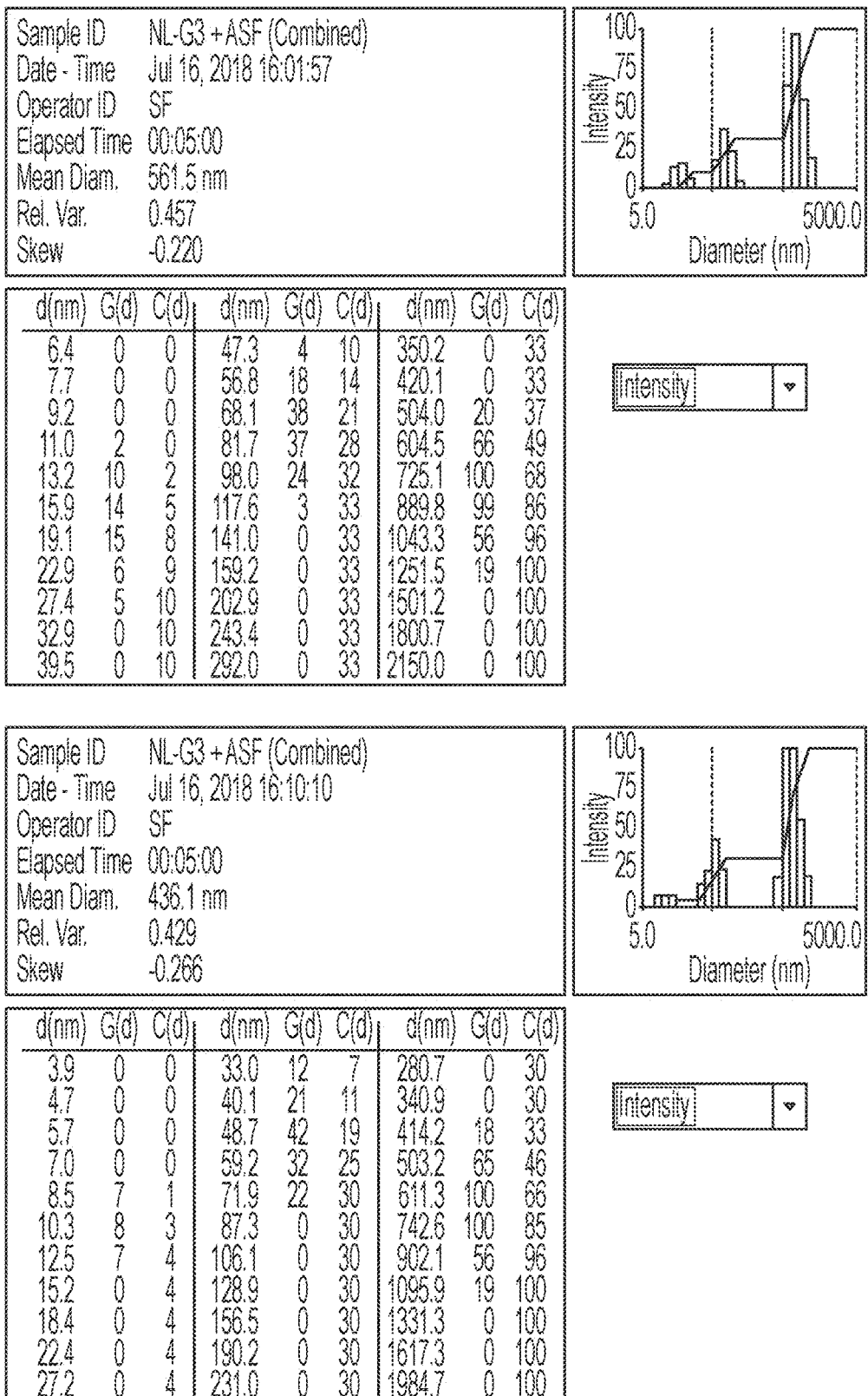
Figure 73B:
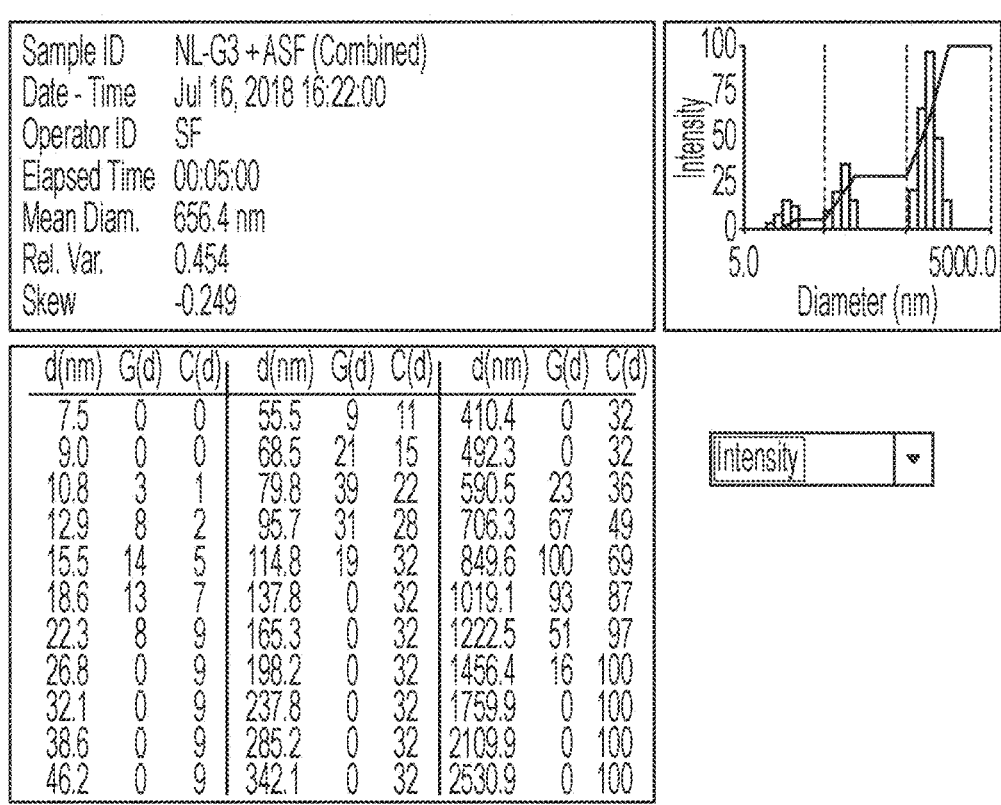

FIGS. 73A-73B show size distribution of 10 μM NL-G3 plus 7 μM ASF. a Surface area and b intensity-weighted. Data in columns are technical replicates of a or b.

Figure 74:
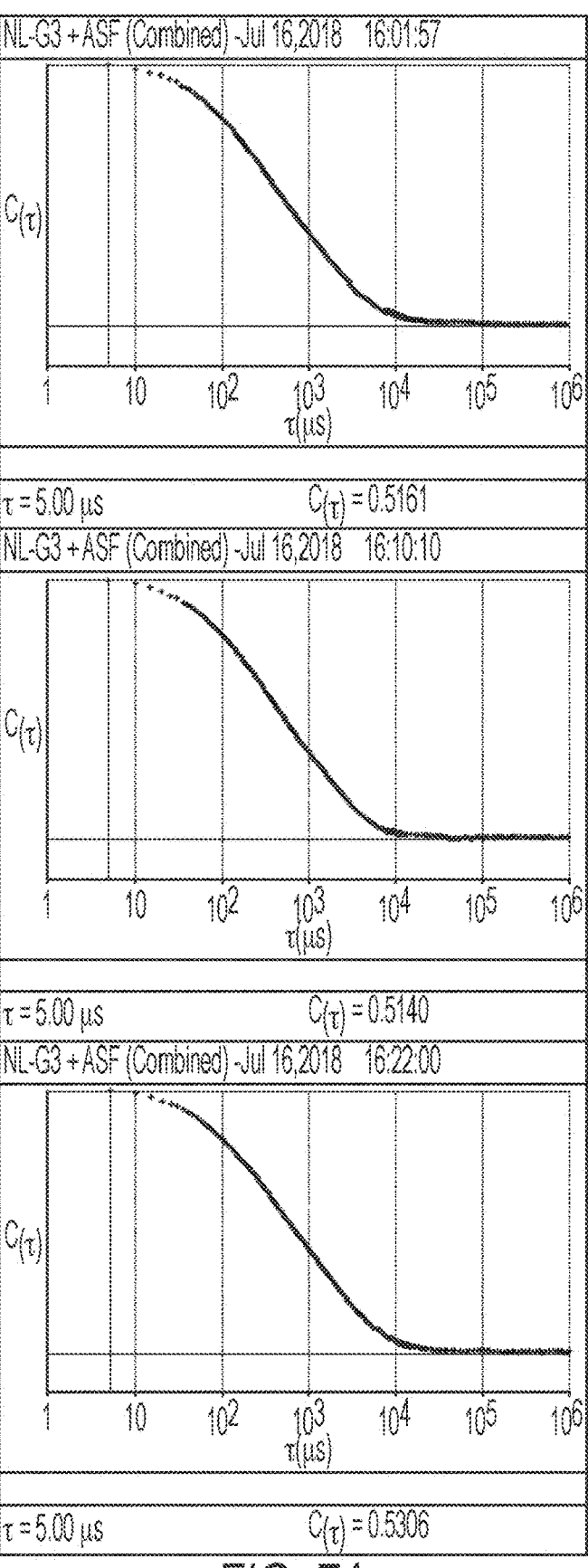

FIG. 74 shows correlation functions for DLS measurements of 10 μM NL-G3 plus 7 μM ASF. Data are technical replicates.

Figure 75A:
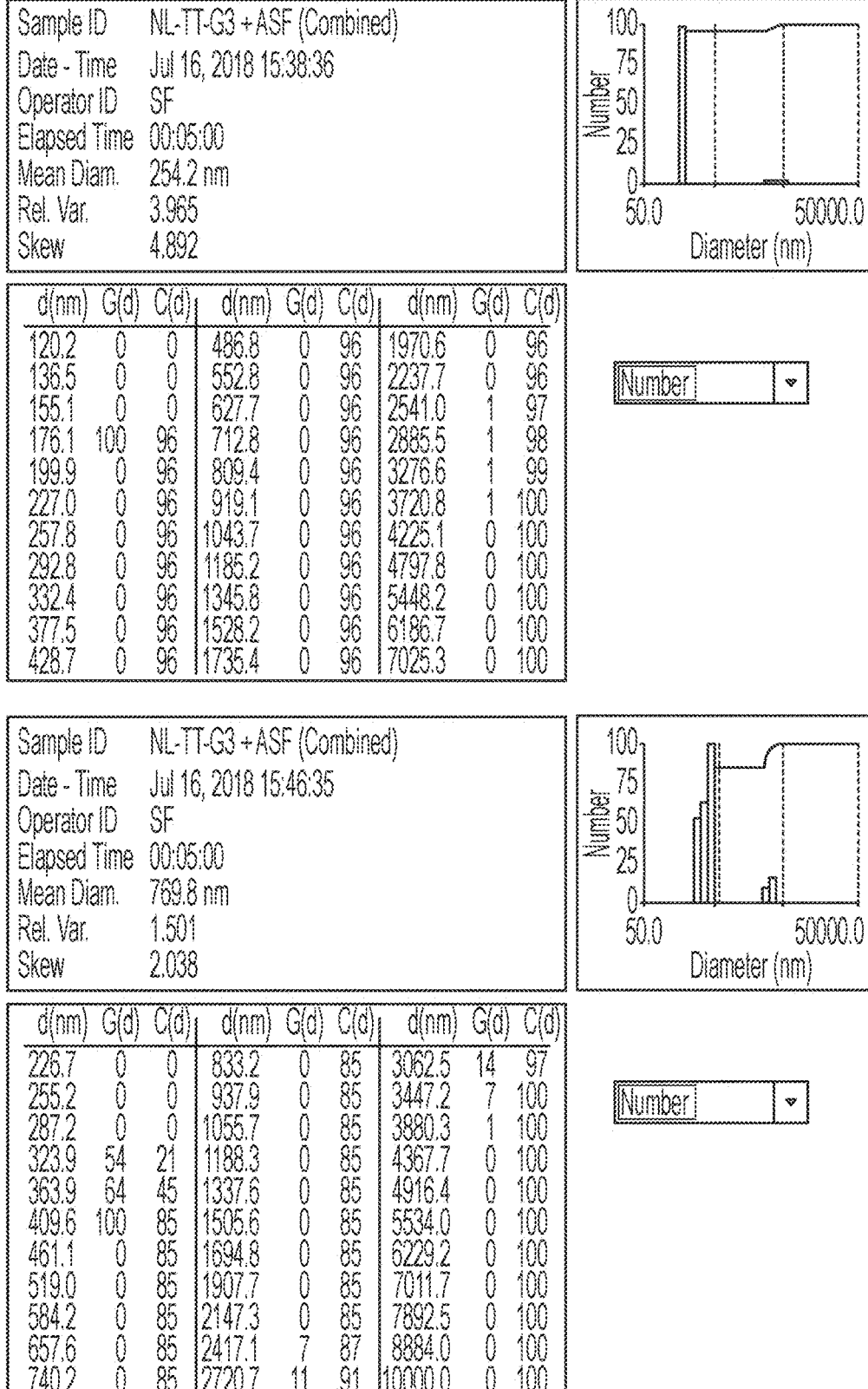
Figure 75A:
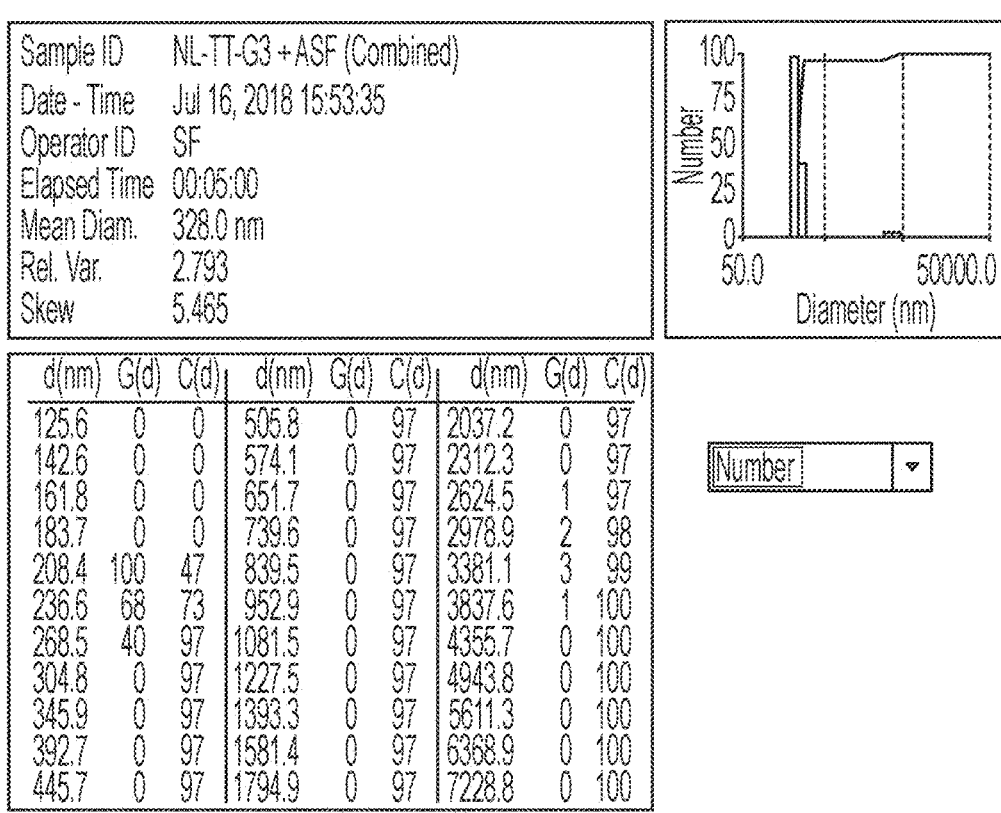
Figure 75B:
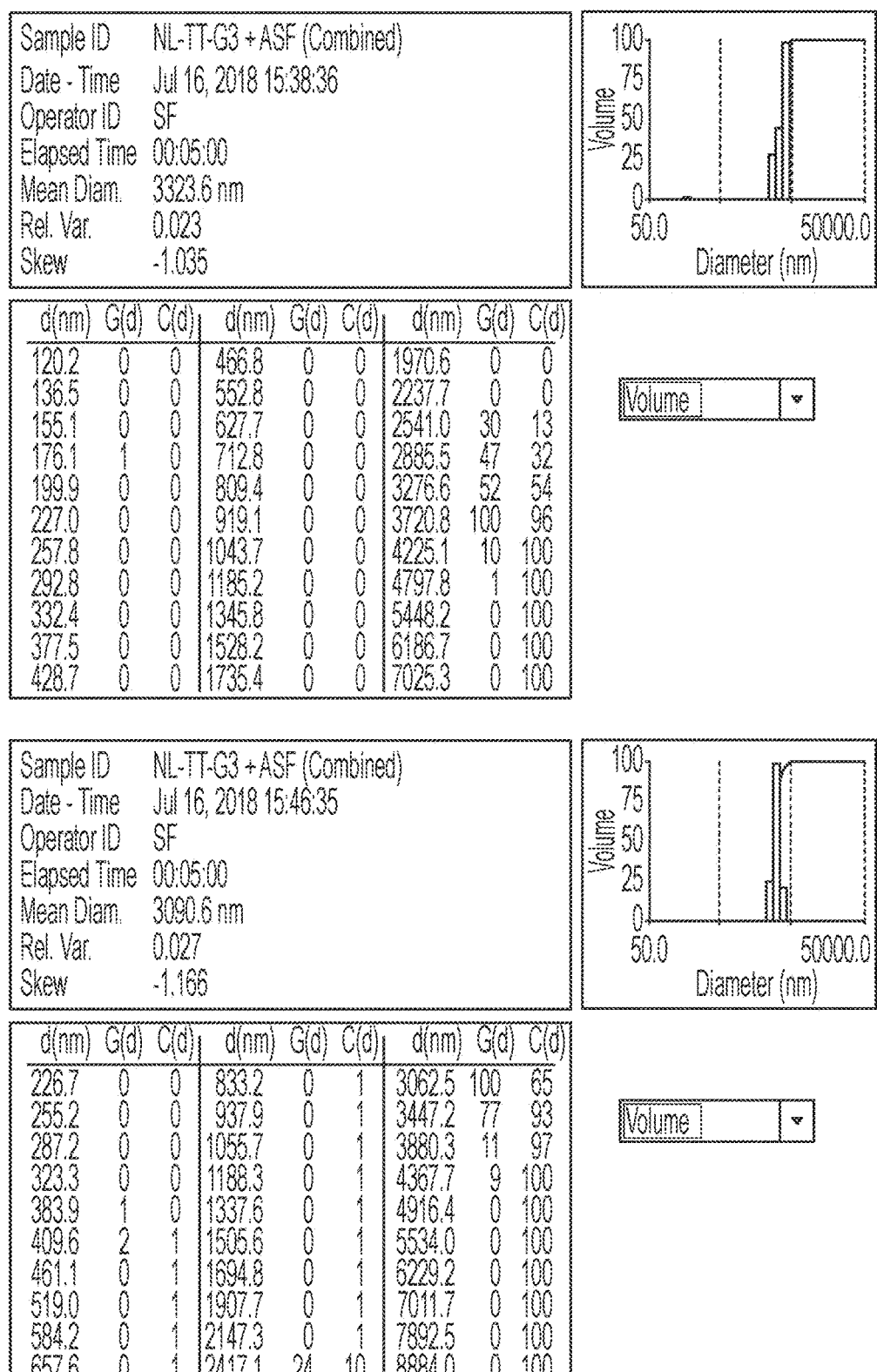
Figure 75B:
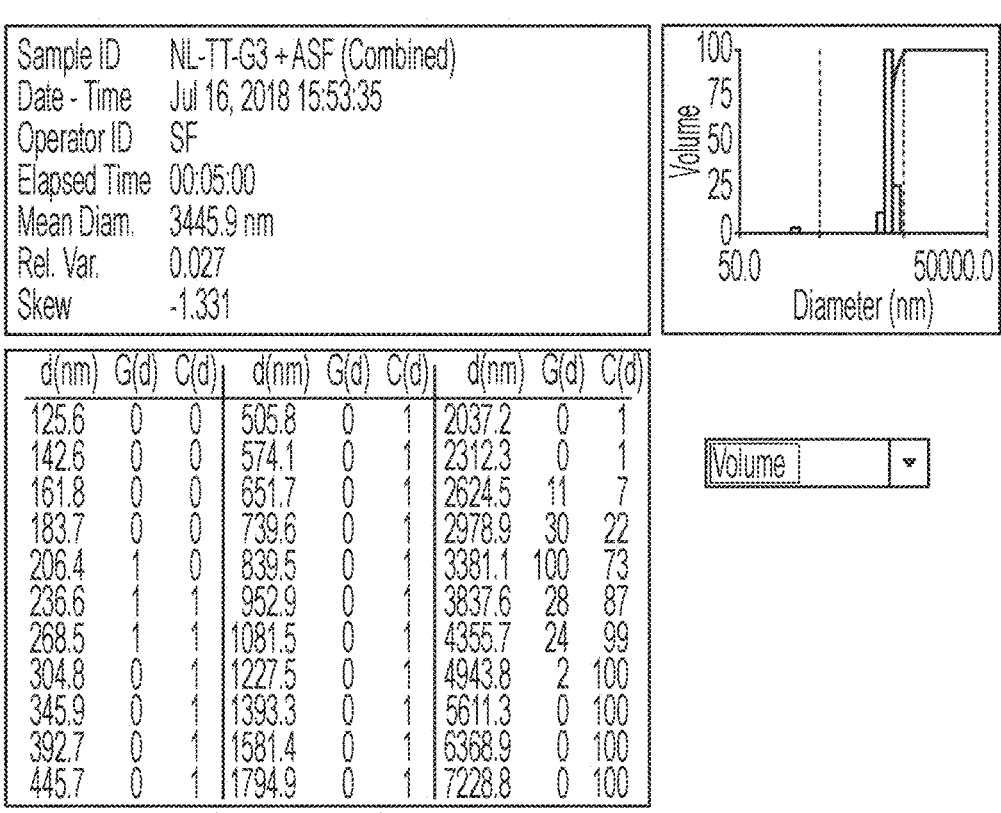

FIGS. 75A-75B show size distribution of 10 μM NL-TT-G3 plus 7 μM ASF. a Number and b volume-weighted. Data in columns are technical replicates of a or b.

Figure 76A:
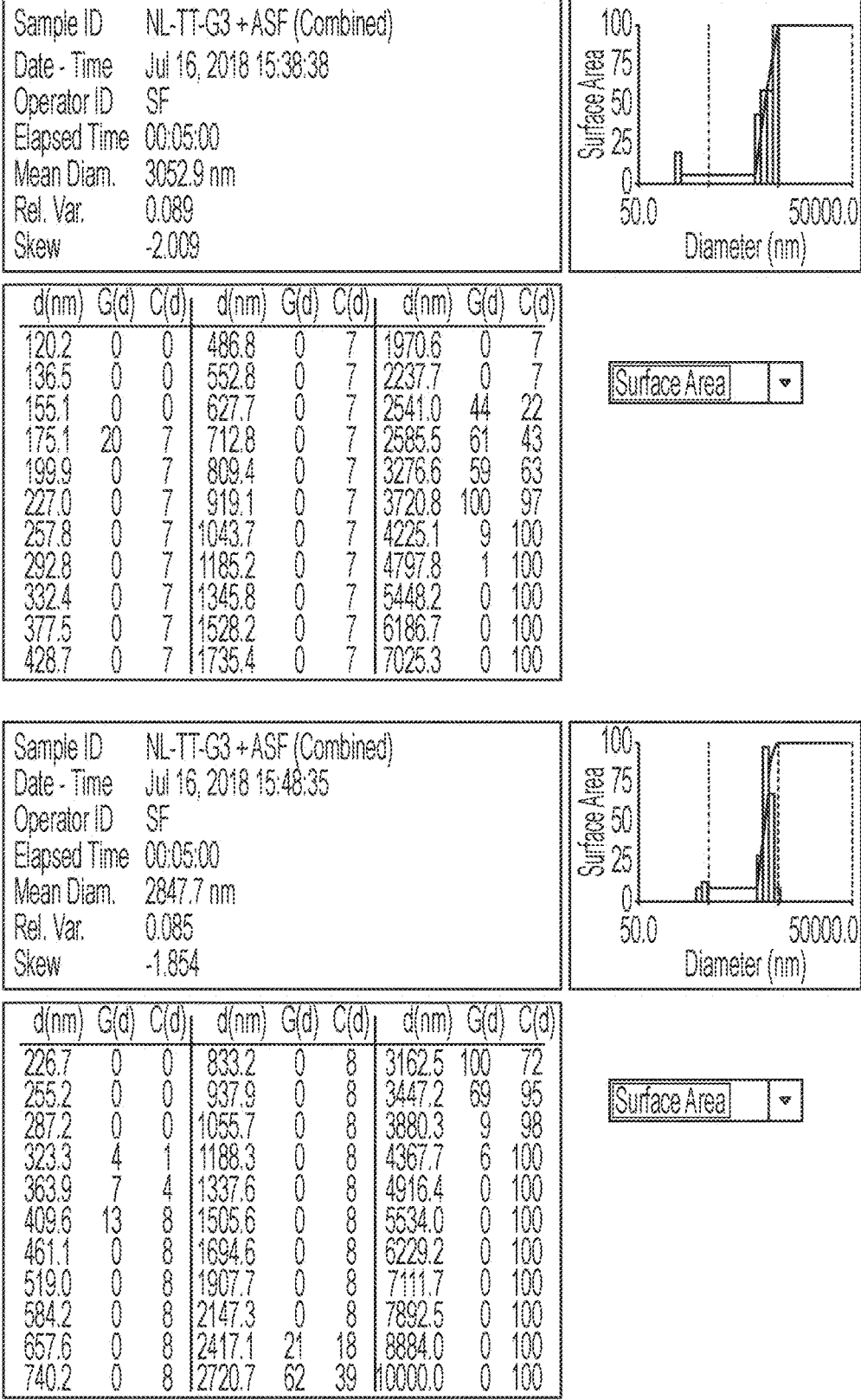
Figure 76A:
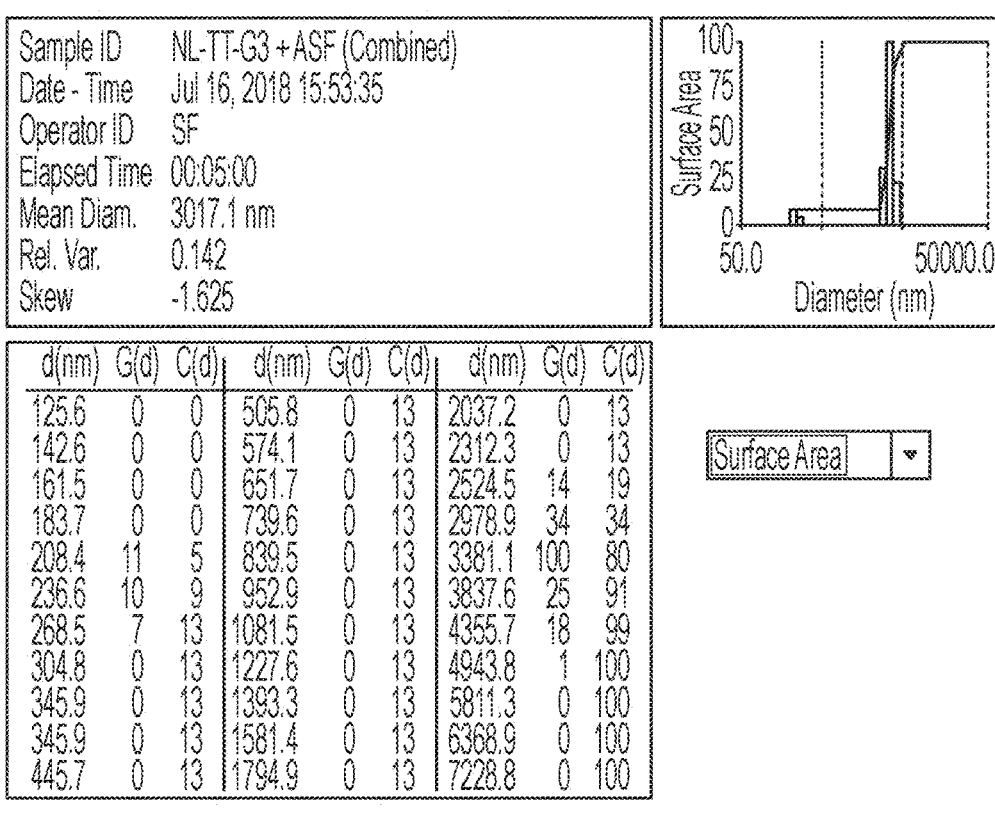
Figure 76B:
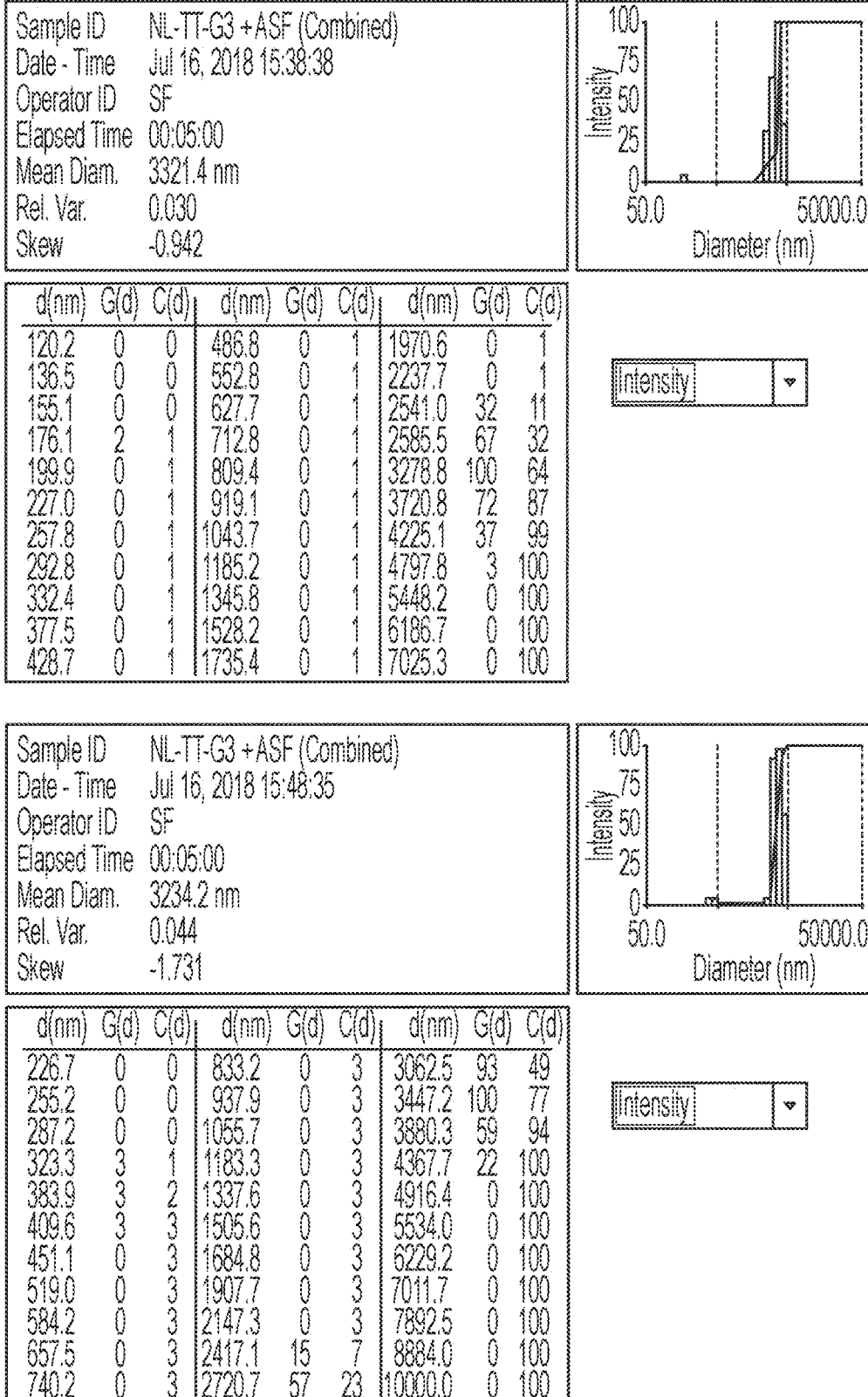
Figure 76B:
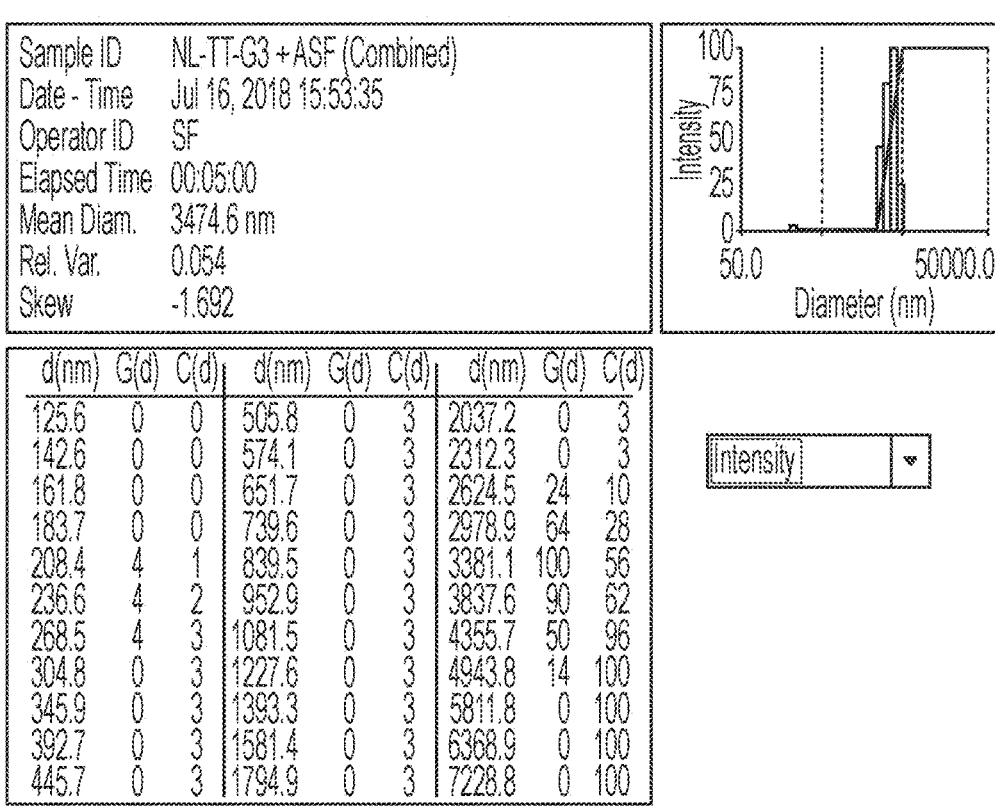

FIGS. 76A-76B show size distribution of 10 μM NL-TT-G3 plus 7 μM ASF. a Surface area- and b intensity-weighted. Data in columns are technical replicates of a or b.

Figure 77:
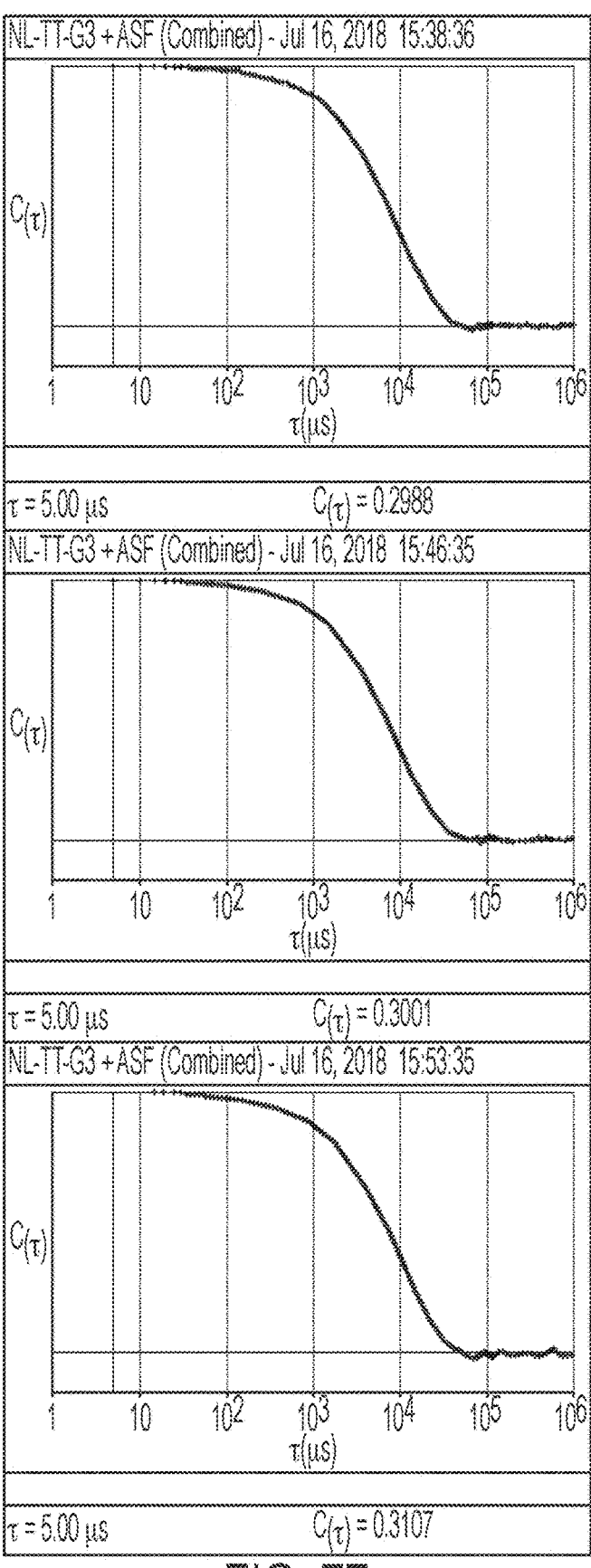

FIG. 77 shows correlation functions for DLS measurements of 10 μM NL-TT-G3 plus 7 μM ASF. Data are technical replicates.

Figure 78A:
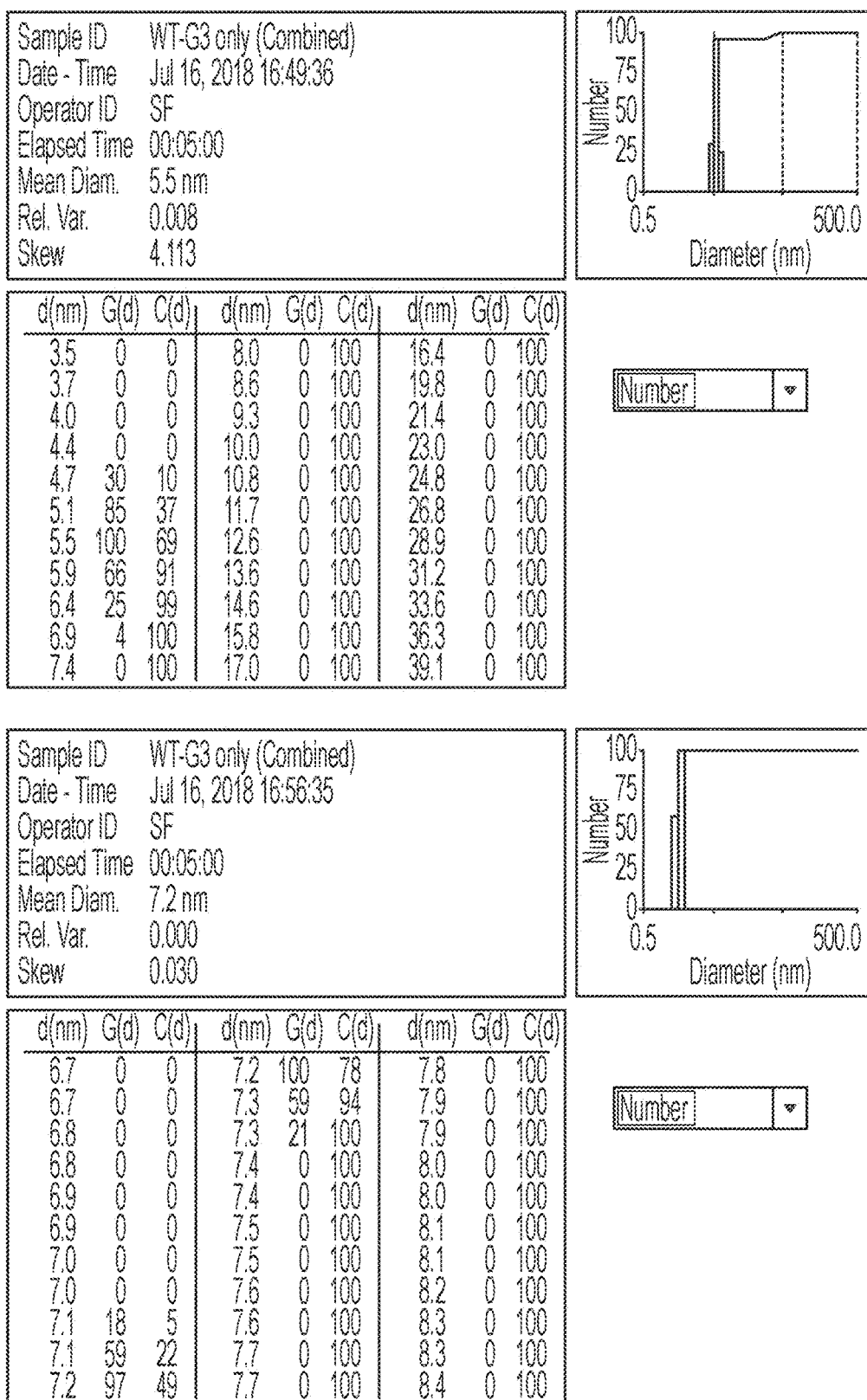
Figure 78A:
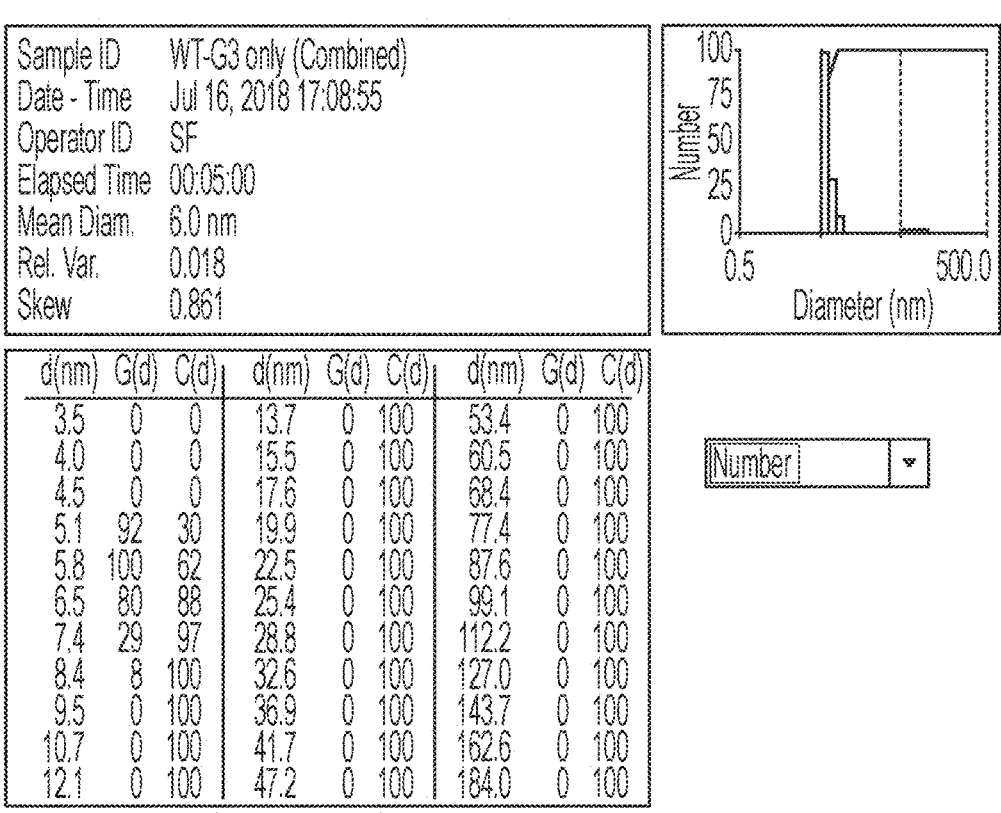
Figure 78B:
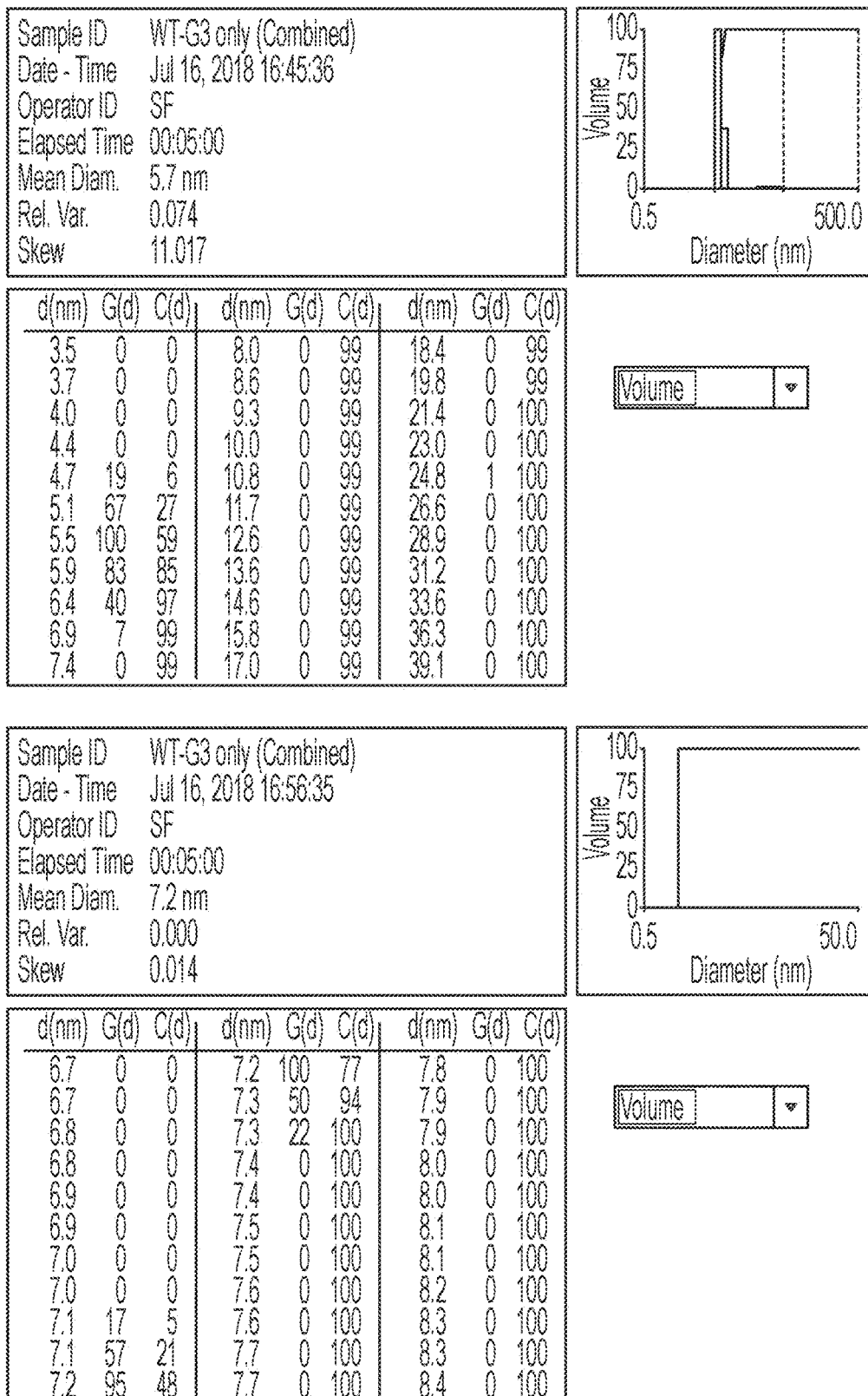
Figure 78B:
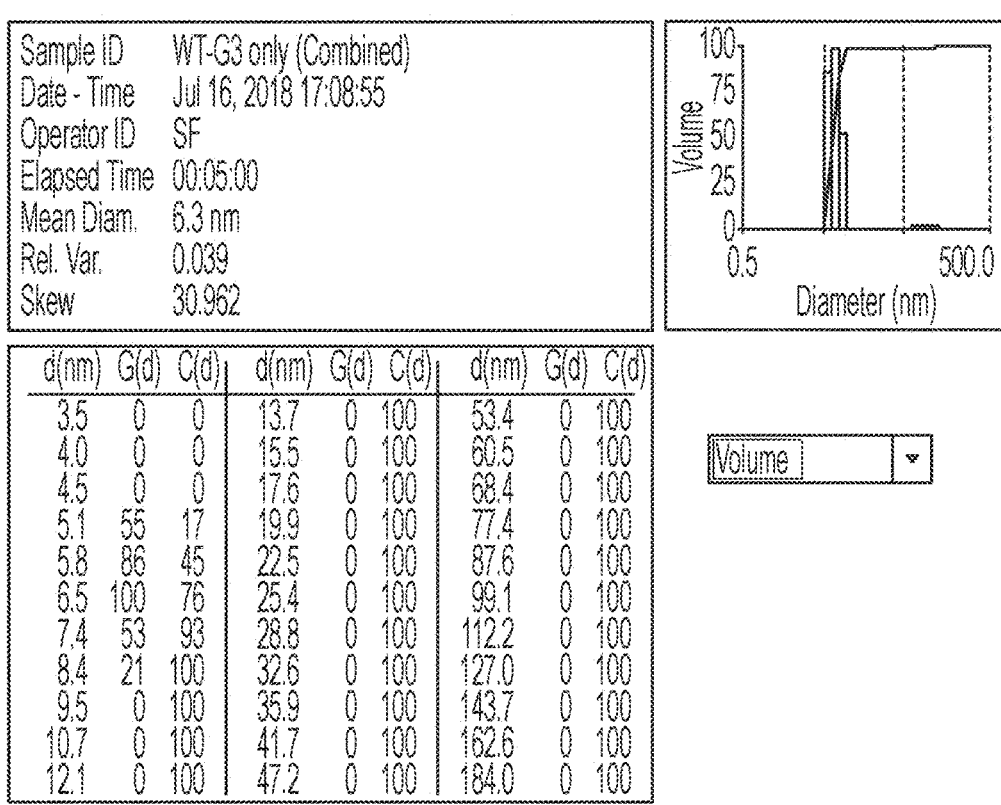

FIGS. 78A-78B show size distribution of 10 μM WT-G3. a Number- and b volume weighted. Data in columns are technical replicates of a or b.

Figure 79A:
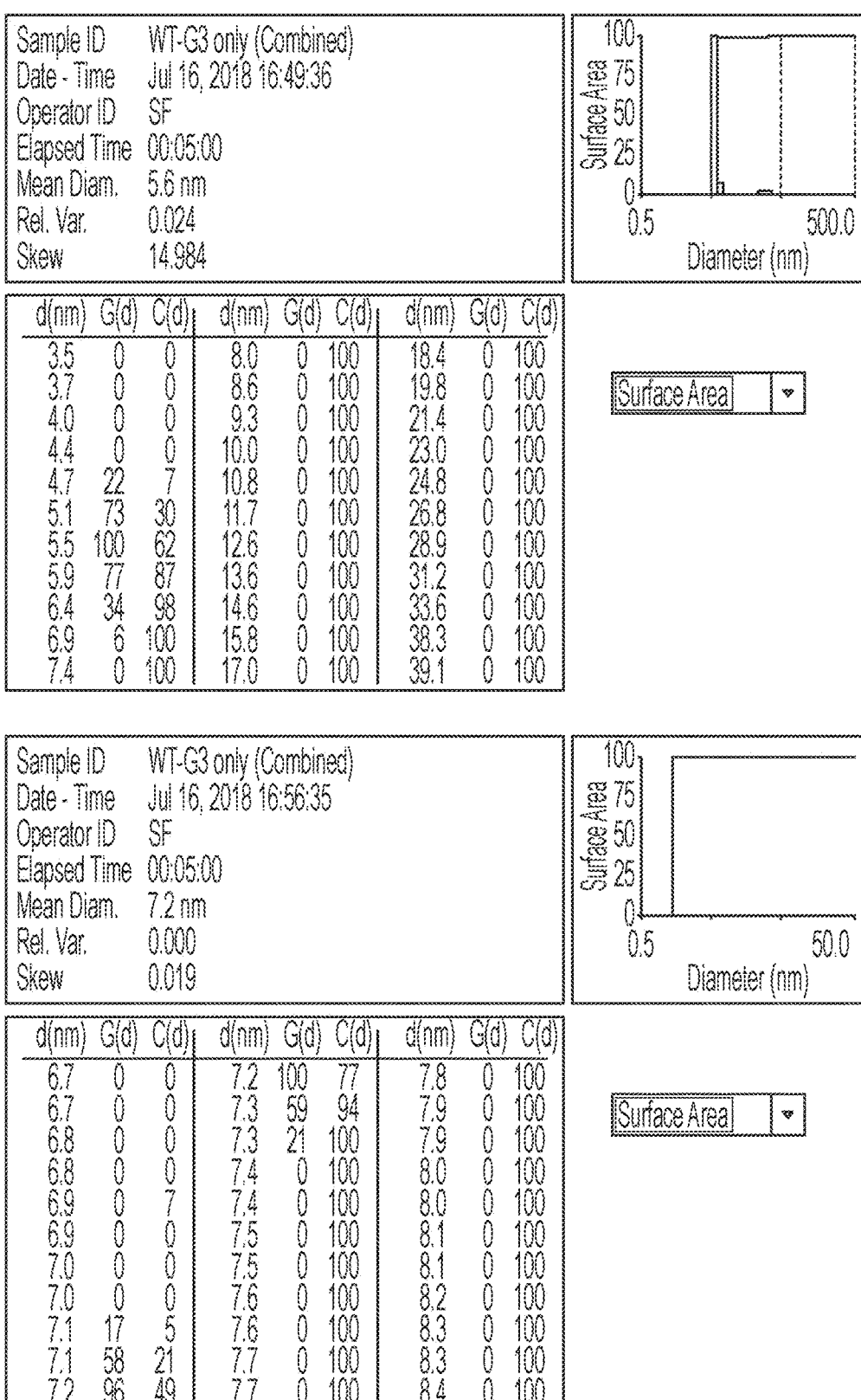
Figure 79A:
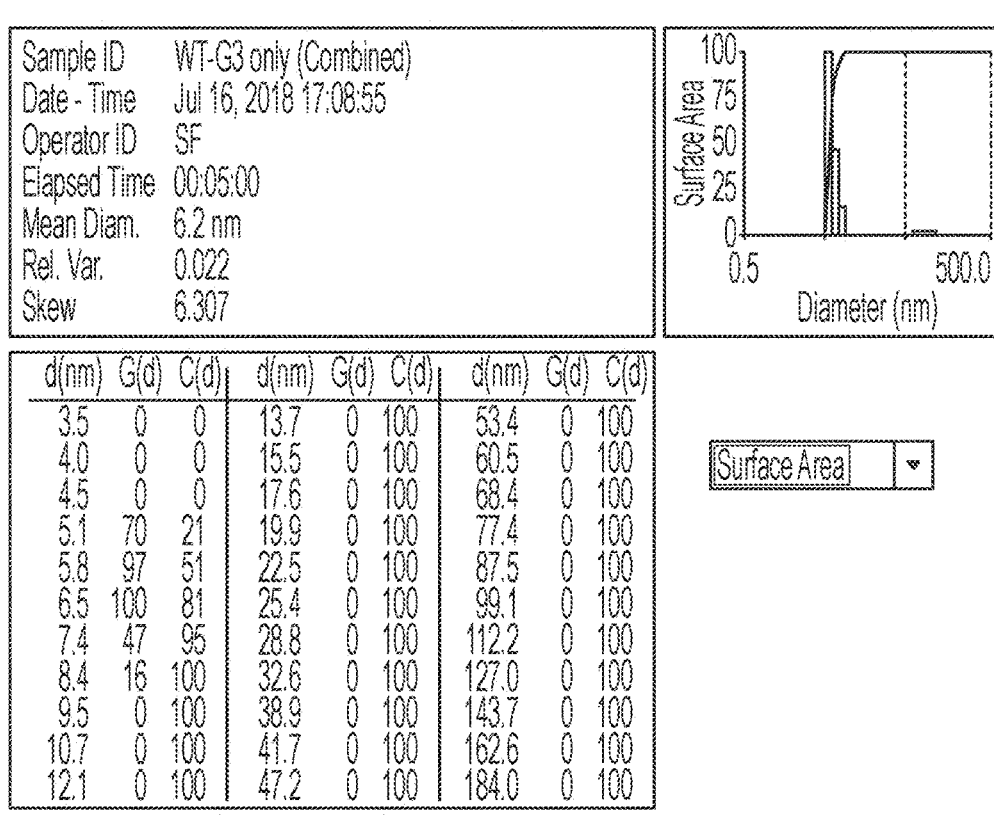
Figure 79B:
Figure 79B:
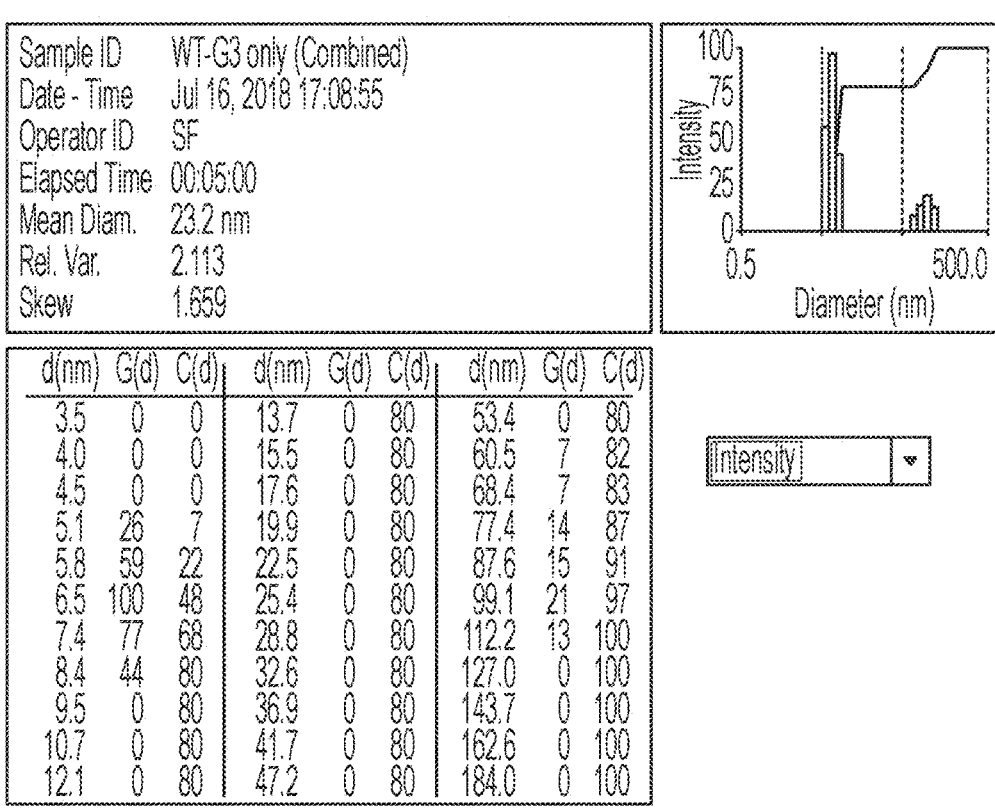

FIGS. 79A-79B show size distribution of 10 μM WT-G3. a Surface area- and b intensity weighted. Data in columns are technical replicates of a or b.

Figure 80:
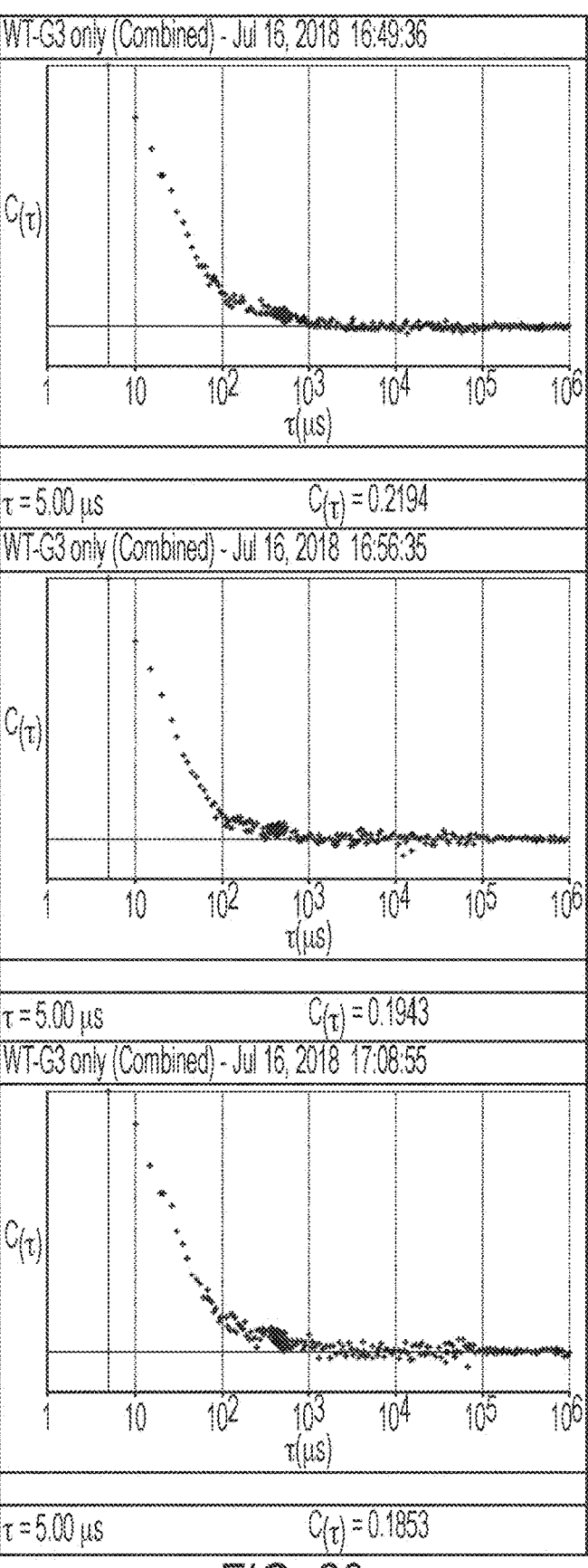

FIG. 80 shows correlation functions for DLS measurements of 10 μM WT-G3. Data are technical replicates.

Figure 81A:
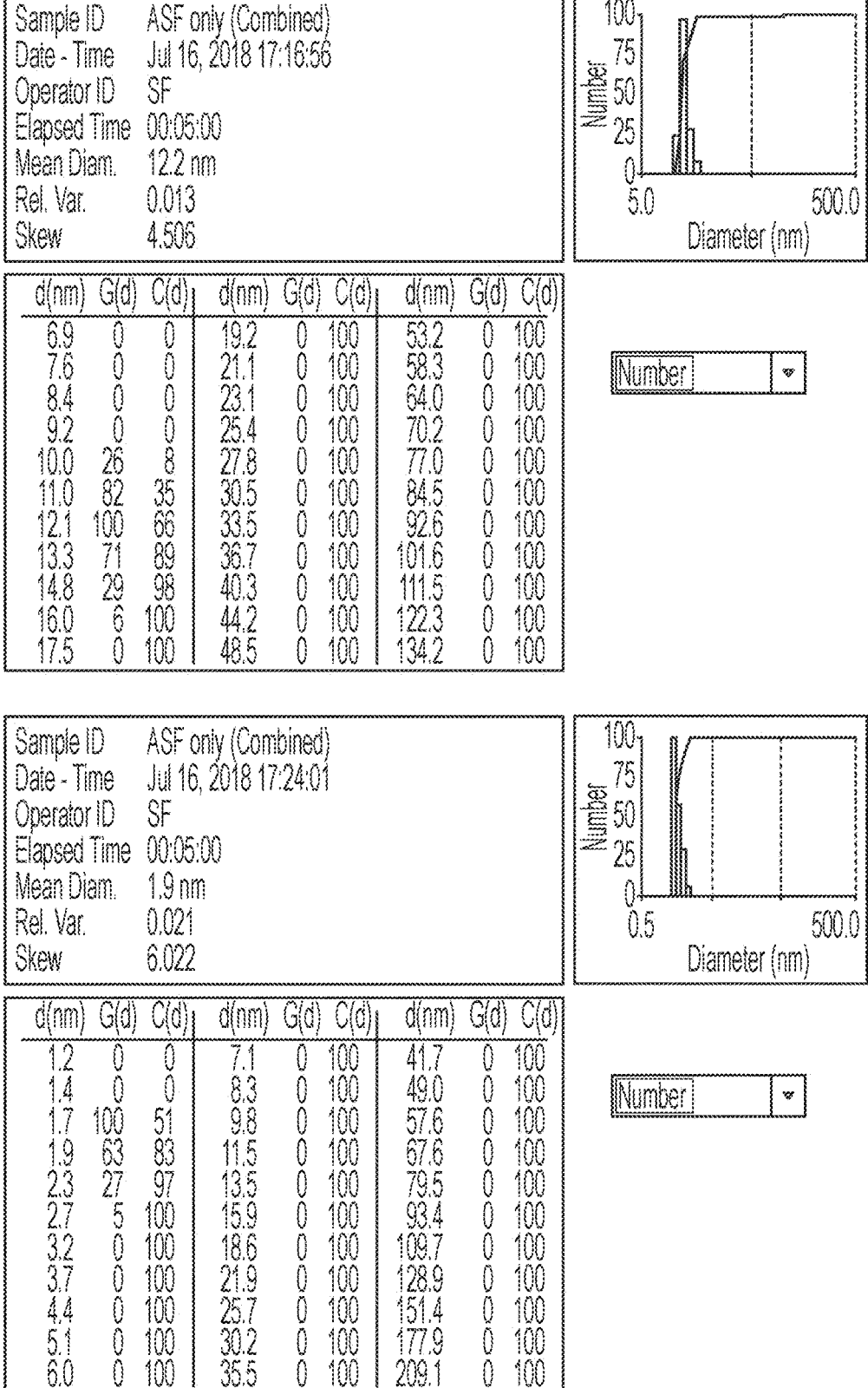
Figure 81A:
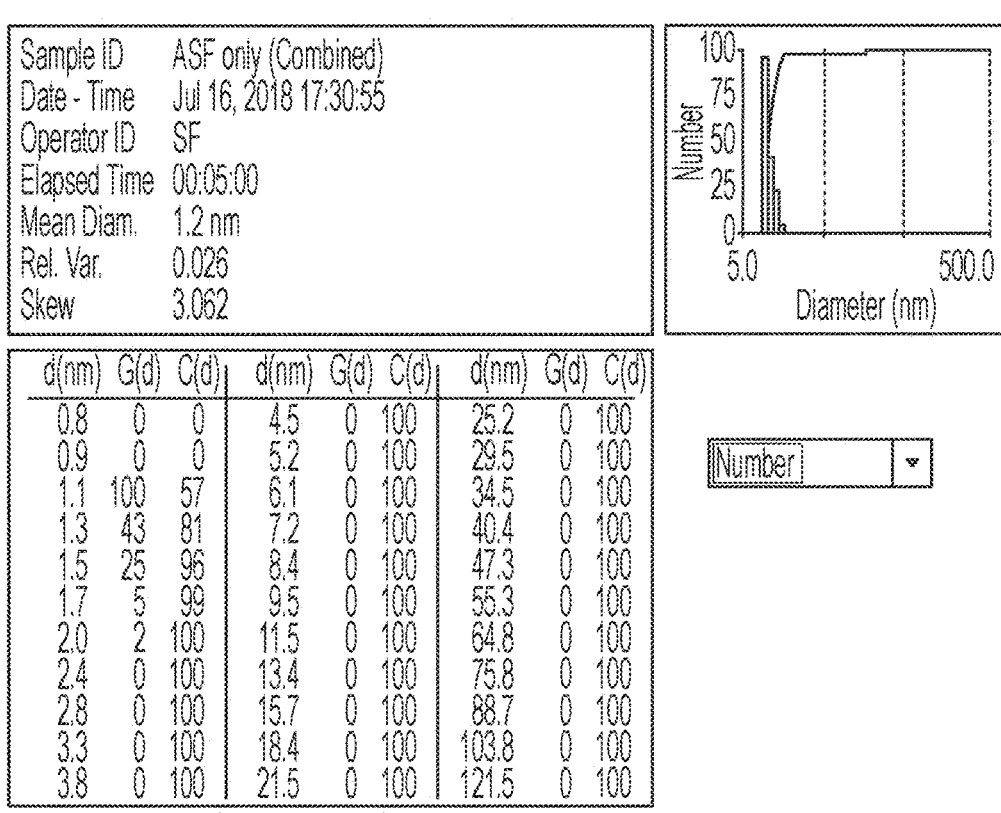
Figure 81B:
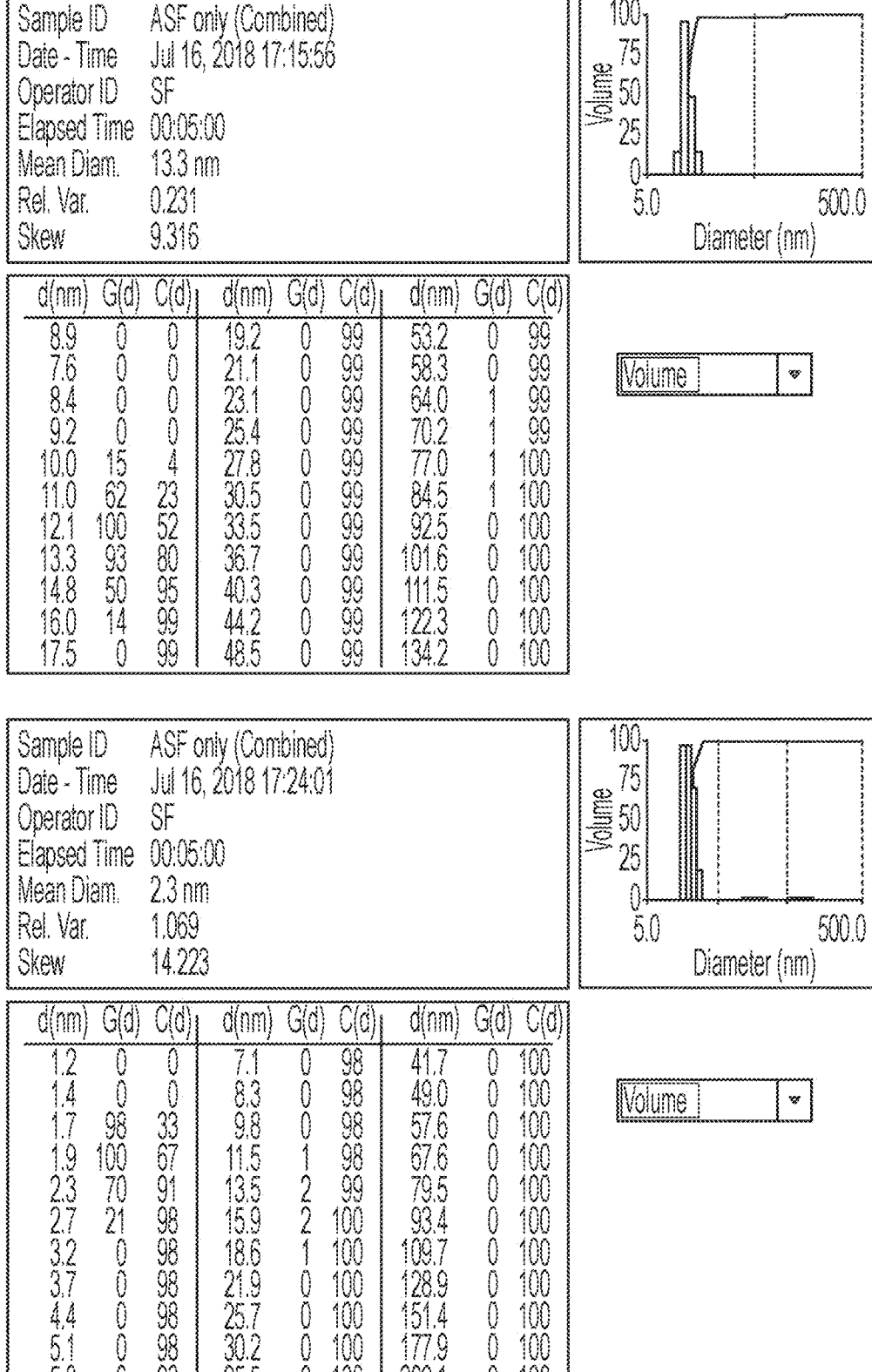
Figure 81B:
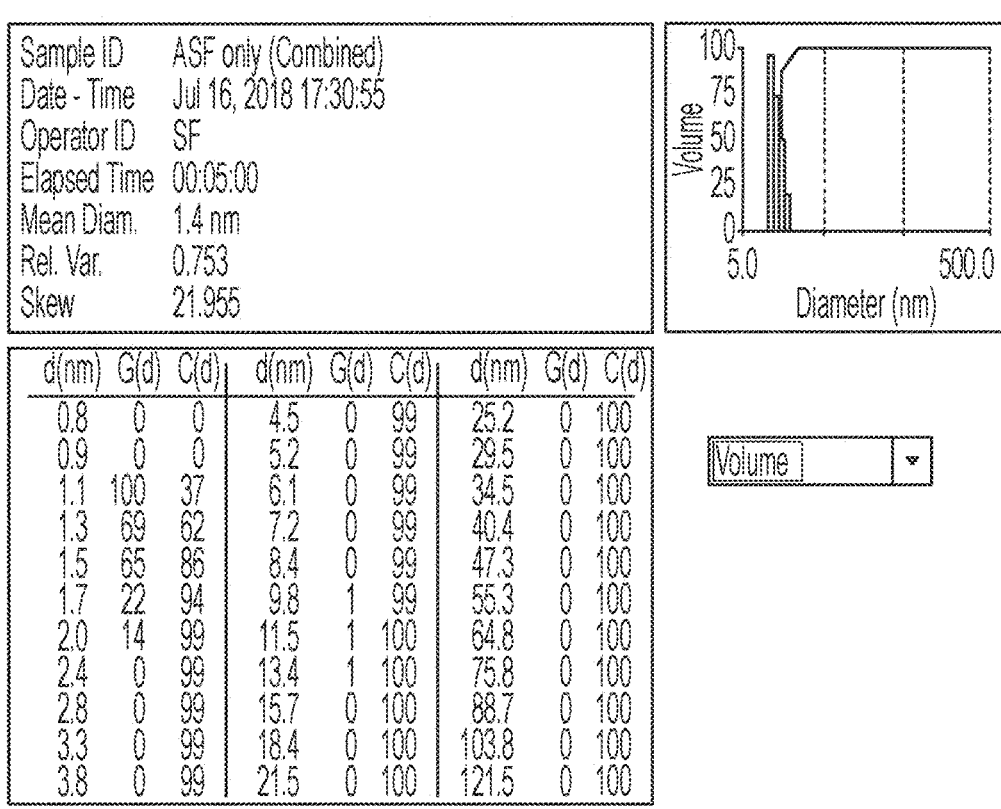

FIGS. 81A-81B show size distribution of 7 μM ASF. a Number- and b volume-weighted. Data in columns are technical replicates of a or b.

Figure 82A:
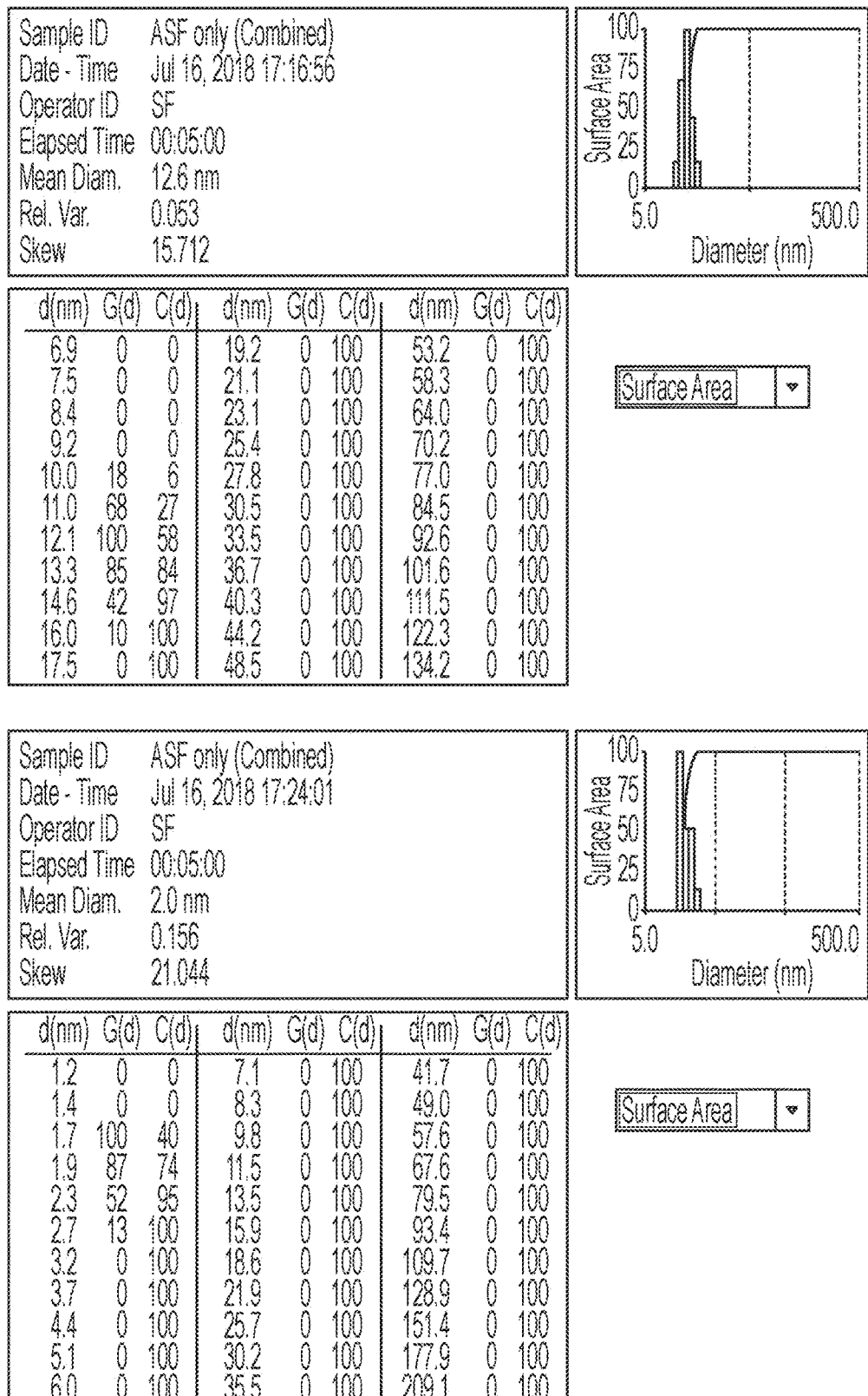
Figure 82A:
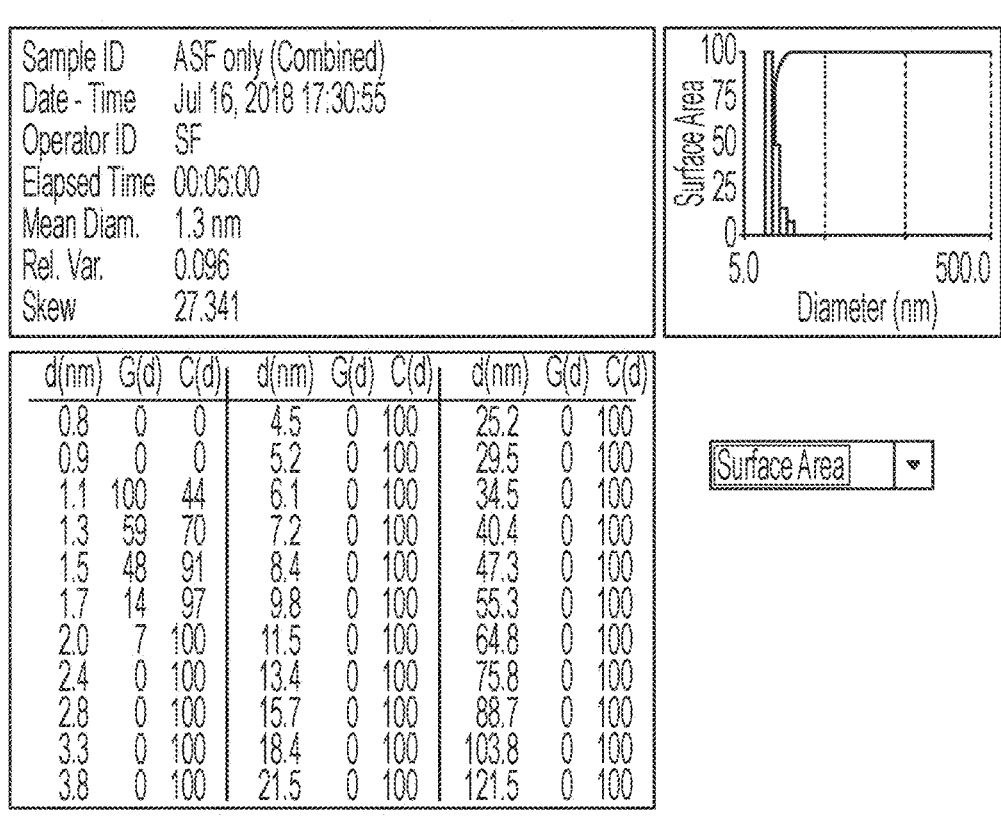
Figure 82B:
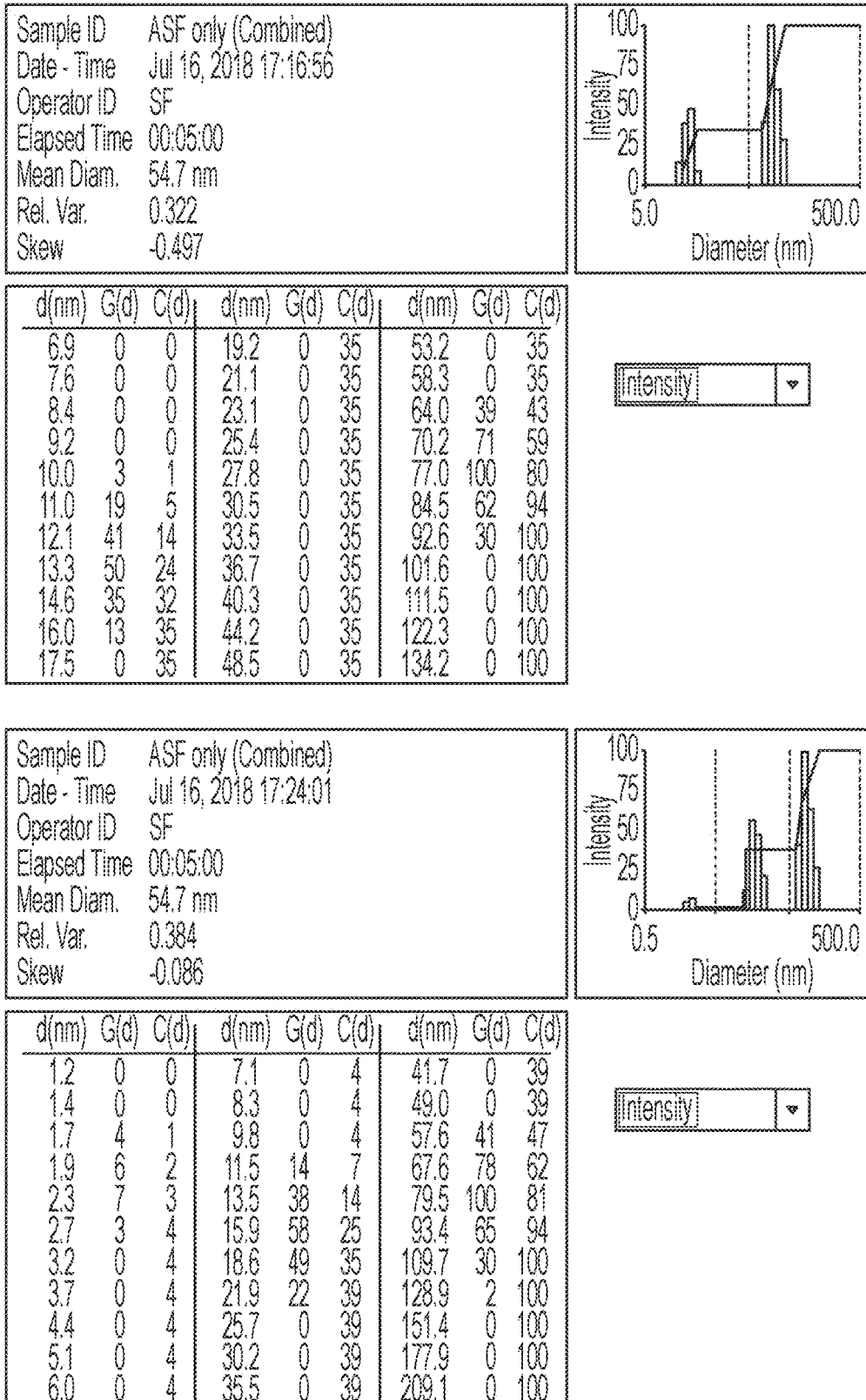
Figure 82B:
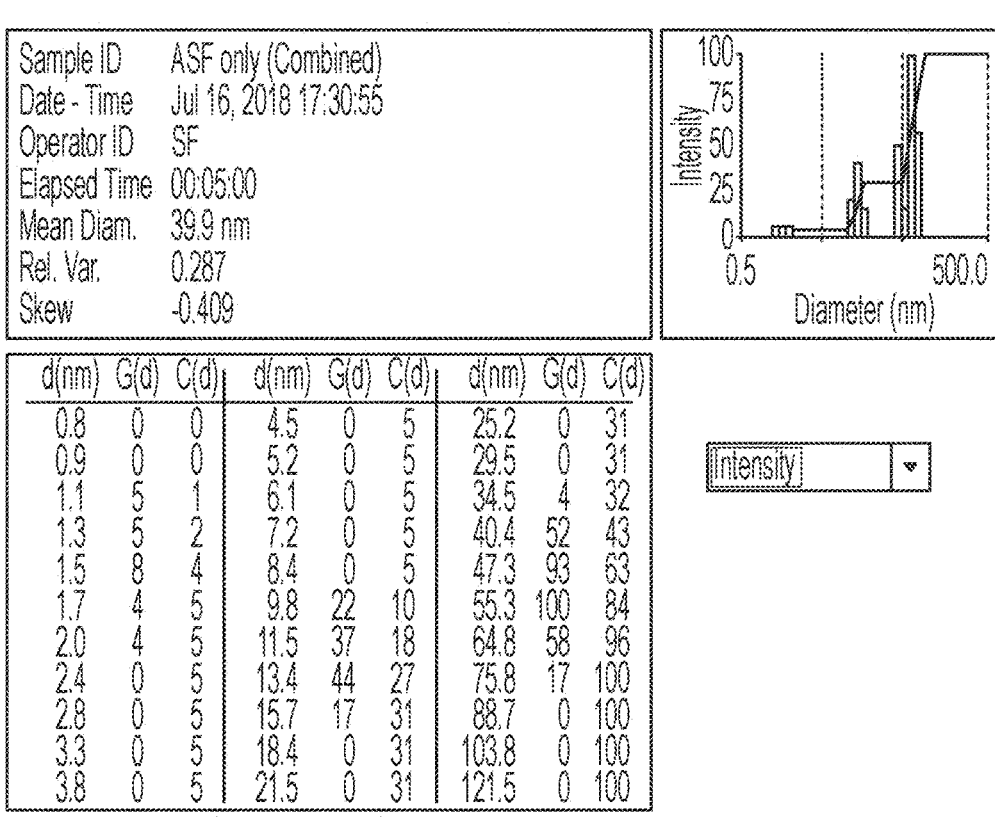

FIGS. 82A-82B show size distribution of 7 μM ASF. a Surface area- and b intensity weighted. Data in columns are technical replicates of a or b.

Figure 83:
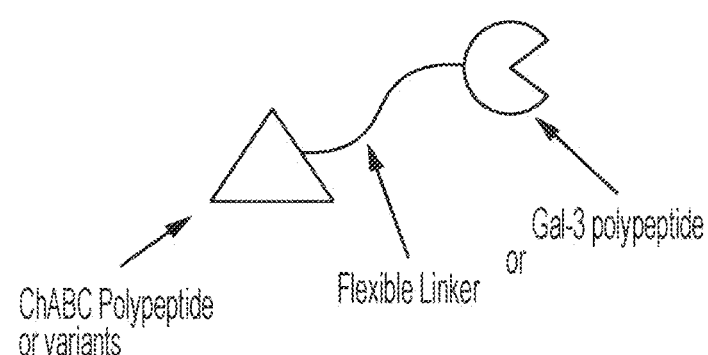

FIG. 83 shows aspects of a ChABC effector fusion protein that can contain a ChABC polypeptide operatively coupled to a Gal-3 polypeptide.

Figure 84A:
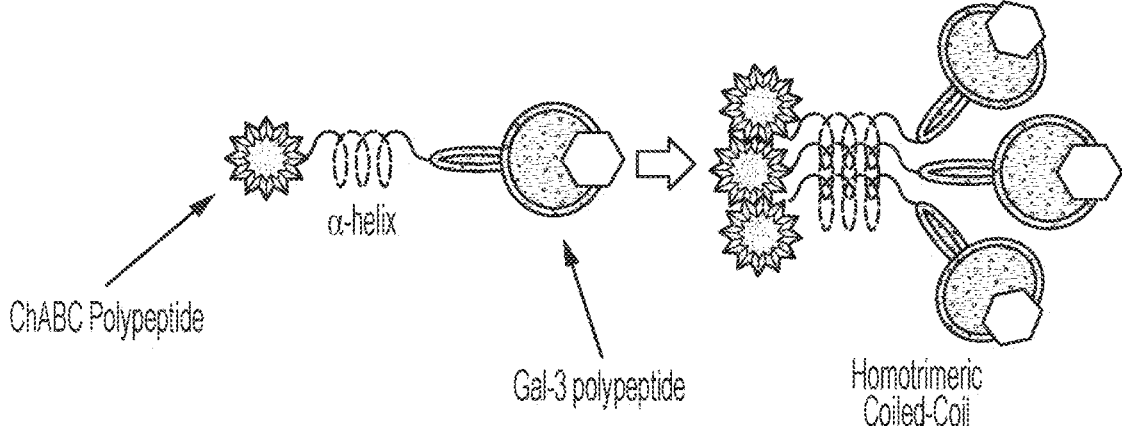
Figure 84B:
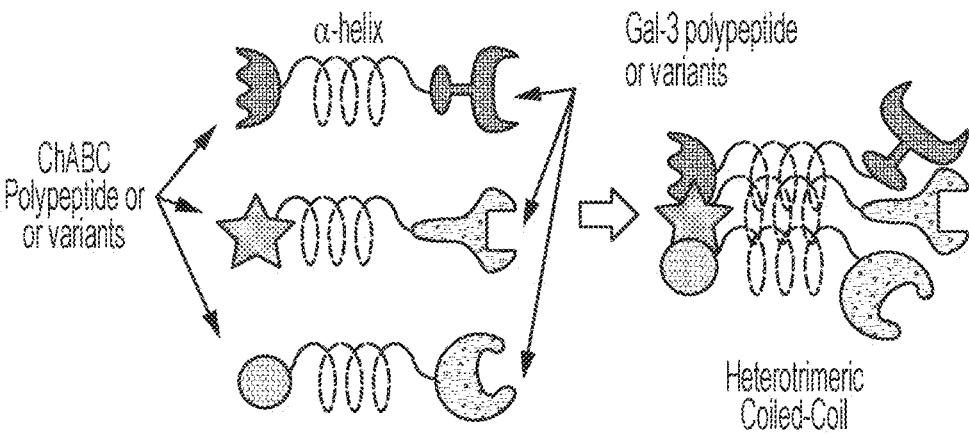

FIGS. 84A-84B show various embodiments of a ChABC effector fusion protein complex as described herein.

FIGS. 85A-85E show graphs demonstrating the thermal sensitivity and stability of Chondoritinase ABC (ChABC)

Figure 85A:
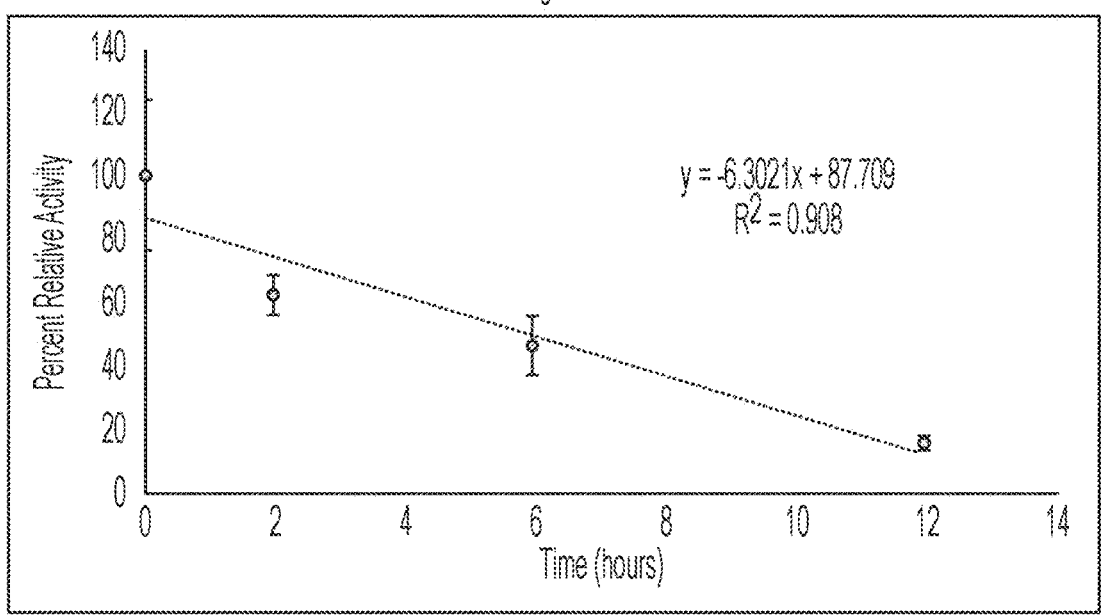
Figure 85B:
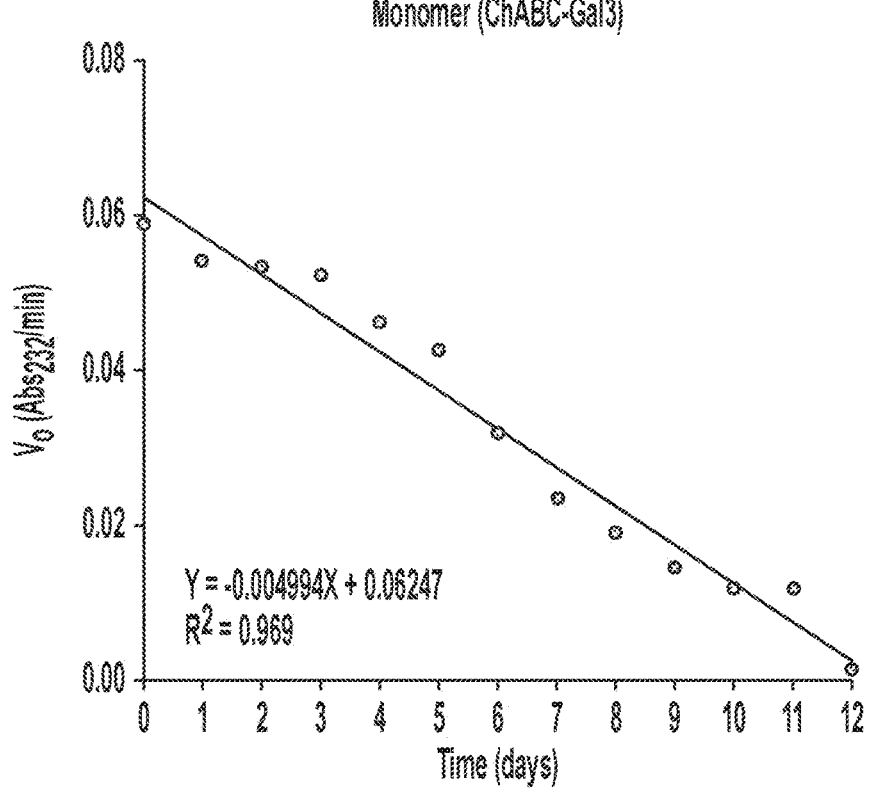
Figure 85C:
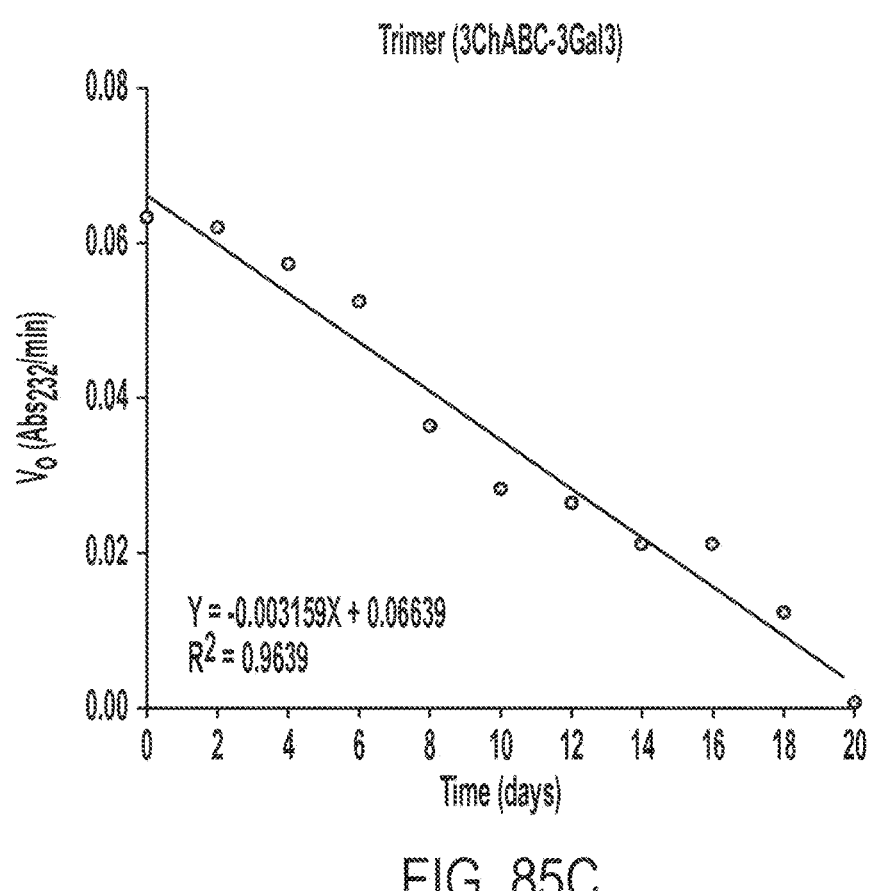
Figure 85D:
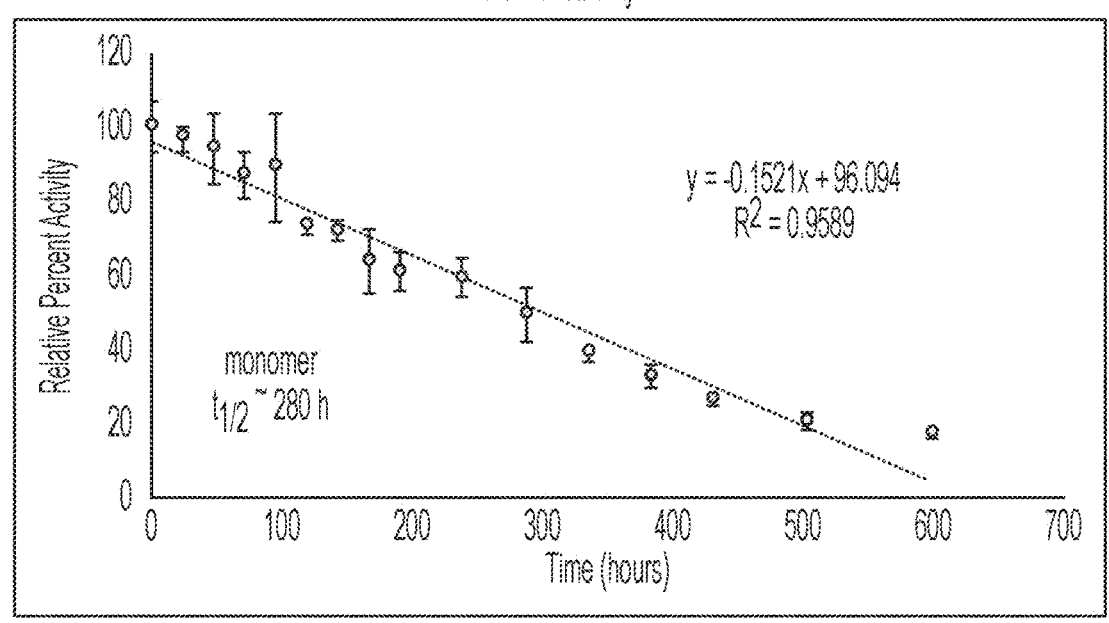
Figure 85E:
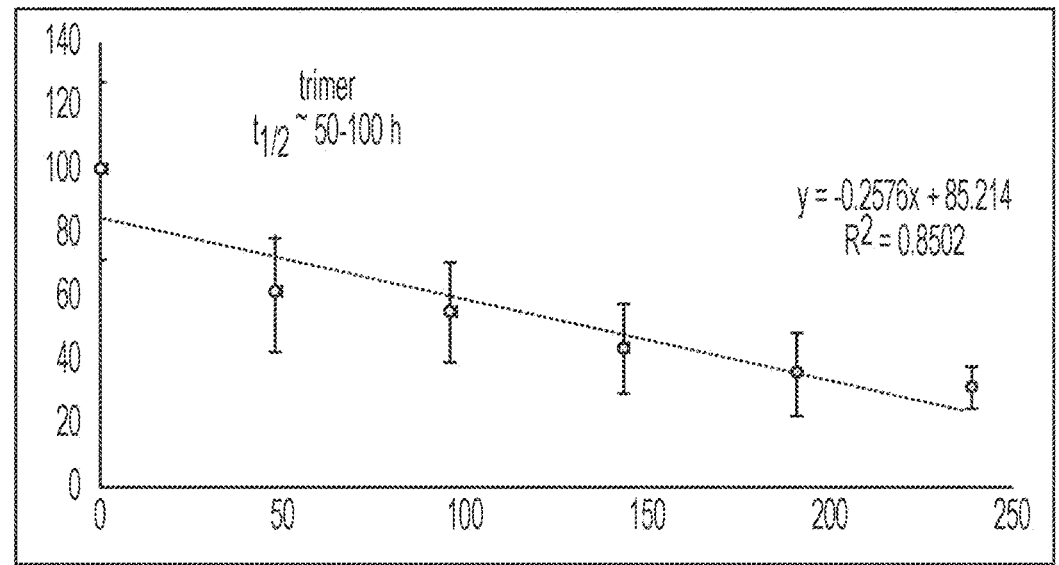

(FIG. 85A), of ChABC fusion enzyme (in monomer form) (FIGS. 85B and 85D), and complex thereof (in trimer form) (FIGS. 85C and 85E).

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g., the phrase "x to y" includes the range from 'x' to 'y' as well as the range greater than 'x' and less than 'y'. The range can also be expressed as an upper limit, e.g., 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used in the specification and the appended claims, the singular forms "a," "an," and "the" include plural referents unless the context clearly dictates otherwise.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

Embodiments of the present disclosure will employ, unless otherwise indicated, techniques of molecular biology, microbiology, organic chemistry, biochemistry, physiology, cell biology, cancer biology, and the like, which are within the skill of the art. Such techniques are explained fully in the literature.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible unless the context clearly dictates otherwise.

Definitions

As used herein, "active agent" or "active ingredient" refers to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed.

As used herein, "additive effect" refers to an effect arising between two or more molecules, compounds, substances, factors, or compositions that is equal to or the same as the sum of their individual effects.

The term "amphiphilic", as used herein, refers to a molecule combining hydrophilic and lipophilic (hydrophobic) properties.

As used herein, "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region and a light chain constant region. The VH and VL regions retain the binding specificity to the antigen and can be further subdivided into regions of hypervariability, termed complementarity determining regions (CDR). The CDRs are interspersed with regions that are more conserved, termed framework regions (FR). Each VH and VL is composed of three CDRs and four framework regions, arranged from amino-terminus to carboxy-terminus in the following order: FR1, CDR1, FR2, CDR2, FR3, CDR3, and FR4. The variable regions of the heavy and light chains contain a binding domain that interacts with an antigen.

As used herein, "anti-infective" refers to compounds or molecules that can either kill an infectious agent or inhibit it from spreading. Anti-infectives include, but are not limited to, antibiotics, antibacterials, antifungals, antivirals, and antiprotozoans.

As used herein, "aptamer" refers to single-stranded DNA or RNA molecules that can bind to pre-selected targets including proteins with high affinity and specificity. Their specificity and characteristics are not directly determined by their primary sequence, but instead by their tertiary structure.

The term "biocompatible", as used herein, refers to a material that along with any metabolites or degradation products thereof that are generally non-toxic to the recipient and do not cause any significant adverse effects to the recipient. Generally speaking, biocompatible materials are materials which do not elicit a significant inflammatory or immune response when administered to a patient.

As used herein "biodegradable" generally refers to a material that will degrade or erode under physiologic conditions to smaller units or chemical species that are capable of being metabolized, eliminated, or excreted by the subject. The degradation time is a function of composition and morphology. Degradation times can be from hours to weeks.

The term "hydrophilic", as used herein, refers to substances that have strongly polar groups that readily interact with water.

As used herein, "cDNA" refers to a DNA sequence that is complementary to a RNA transcript in a cell. It is a man-made molecule. Typically, cDNA is made in vitro by an enzyme called reverse-transcriptase using RNA transcripts as templates.

As used herein, "cell," "cell line," and "cell culture" include progeny. It is also understood that all progeny may not be precisely identical in DNA content, due to deliberate or inadvertent mutations. Variant progeny that have the same function or biological property, as screened for in the originally transformed cell, are included.

As used herein, "composition" refers to a combination of active agent and at least one other compound or molecule, inert (for example, a detectable agent or label) or active, such as an adjuvant.

As used herein, "concentrated" refers to a molecule, including but not limited to a polynucleotide, peptide, polypeptide, protein, antibody, or fragments thereof, that is distinguishable from its naturally occurring counterpart in that the concentration or number of molecules per volume is greater than that of its naturally occurring counterpart.

As used herein, "control" is an alternative subject or sample used in an experiment for comparison purpose and included to minimize or distinguish the effect of variables other than an independent variable.

As used herein, "chemotherapeutic agent" or "chemotherapeutic" refer to a therapeutic agent utilized to prevent or treat cancer.

As used herein, "culturing" refers to maintaining cells under conditions in which they can proliferate and avoid senescence as a group of cells. "Culturing" can also include conditions in which the cells also or alternatively differentiate.

As used herein, "deoxyribonucleic acid (DNA)" and "ribonucleic acid (RNA)" generally refer to any polyribonucleotide or polydeoxribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes.

As used herein, "DNA molecule" includes nucleic acids/polynucleotides that are made of DNA.

As used herein, "derivative" refers to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this may be the case. The term "derivative" can include prodrugs, or metabolites of the parent compound. Derivatives include compounds in which free amino groups in the parent compound have been derivatized to form amine hydrochlorides, p-toluene sulfoamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form methyl and ethyl esters, or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imine, thiones, sulfones, tertiary amides, and sulfides. "Derivatives" also includes extensions of the replacement of the cyclopentane ring with saturated or unsaturated cyclohexane or other more complex, e.g., nitrogen-containing rings, and extensions of these rings with side various groups.

As used herein, "differentiate" or "differentiation," refers to the process by which precursor or progenitor cells (e.g., neuronal progenitor cells) differentiate into specific cell types (e.g., neurons).

As used herein, "differentially expressed," refers to the differential production of RNA, including but not limited to mRNA, tRNA, miRNA, siRNA, snRNA, and piRNA transcribed from a gene or regulatory region of a genome or the protein product encoded by a gene as compared to the level of production of RNA by the same gene or regulator region in a normal or a control cell. In another context, "differentially expressed," also refers to nucleotide sequences or proteins in a cell or tissue which have different temporal and/or spatial expression profiles as compared to a normal or control cell.

As used herein, "diluted" refers to a molecule, including but not limited to a polynucleotide, peptide, polypeptide, protein, antibody, or fragments thereof, that is distinguishable from its naturally occurring counterpart in that the concentration or number of molecules per volume is less than that of its naturally occurring counterpart.

As used herein, "dose," "unit dose," or "dosage" refers to physically discrete units suitable for use in a subject, each unit containing a predetermined quantity of the targeted effector fusion protein, a composition containing the targeted effector fusion protein, and/or a pharmaceutical formulation thereof calculated to produce the desired response or responses in association with its administration.

As used herein, "effective amount" is an amount sufficient to effect beneficial or desired biological, emotional, medical, or clinical response of a cell, tissue, system, animal, or human. An effective amount can be administered in one or more administrations, applications, or dosages. The term also includes within its scope amounts effective to enhance normal physiological function.

As used herein, "expansion" or "expanded" in the context of cell refers to an increase in the number of a characteristic cell type, or cell types, from an initial population of cells, which may or may not be identical. The initial cells used for expansion need not be the same as the cells generated from expansion. For instance, the expanded cells may be produced by ex vivo or in vitro growth and differentiation of the initial population of cells.

As used herein, "expression" refers to the process by which polynucleotides are transcribed into RNA transcripts. In the context of mRNA and other translated RNA species, "expression" also refers to the process or processes by which the transcribed RNA is subsequently translated into peptides, polypeptides, or proteins.

As used herein, "fusion protein" as used herein, refers to a protein formed from the combination of at least two different proteins or protein fragments. In some embodiments, a fusion protein can be a hybrid polypeptide which comprises protein domains from at least two different proteins. One protein may be located at the amino-terminal (N-terminal) portion of the fusion protein or at the carboxy-terminal (C-terminal) protein thus forming an "amino-terminal fusion protein" or a "carboxy-terminal fusion protein," respectively. Any of the proteins provided herein may be produced by any method known in the art. For example, the proteins provided herein may be produced via recombinant protein expression and purification, which is especially suited for fusion proteins comprising a peptide linker. Methods for recombinant protein expression and purification are well known, and include those described by Green and Sambrook, Molecular Cloning: A Laboratory Manual (4th ed., Cold Spring Harbor Laboratory Press, Cold Spring Harbor, N.Y. (2012)), the entire contents of which are incorporated herein by reference. A fusion protein can be encoded by a recombinant DNA molecule. As such, a "targeted effector fusion protein" refers to a recombinant protein having an effector polypeptide or variant thereof operatively linked to a targeting moiety polypeptide and optionally other polypeptide sequences.

As used herein, "gene" refers to a hereditary unit corresponding to a sequence of DNA that occupies a specific location on a chromosome and that contains the genetic instruction for a characteristic(s) or trait(s) in an organism.

As used herein, "green fluorescent protein," "yellow fluorescent protein," "red fluorescent protein" and the like and their abbreviations include, without limitation, all forms of such proteins as they are routinely modified, derivatized, and generally known to those of ordinary skill in the art. For example, "green fluorescent protein" includes, without limitation, enhanced green fluorescent protein (eGFP), redox sensitive GFP (roGFP), superfolder GFP (sfGFP), and all color mutants.

The term "hydrophobic", as used herein, refers to substances that lack an affinity for water; tending to repel and not absorb water as well as not dissolve in or mix with water.

As used herein, "identity," is a relationship between two or more polypeptide or polynucleotide sequences, as determined by comparing the sequences. In the art, "identity" also refers to the degree of sequence relatedness between polypeptide as determined by the match between strings of such sequences. "Identity" can be readily calculated by known methods, including, but not limited to, those described in Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 1970, 48: 443-453,) algorithm (e.g., NBLAST, and XBLAST). The default parameters are used to determine the identity for the polypeptides of the present disclosure.

As used herein, "immunomodulator," refers to an agent, such as a therapeutic agent, which is capable of modulating or regulating one or more immune function or response.

As used herein "induces," "inducing," or "induced" refers to activating or stimulating a process or pathway within a cell, such as endocytosis, secretion, and exocytosis.

As used herein, "isolated" means separated from constituents, cellular and otherwise, in which the polynucleotide, peptide, polypeptide, protein, antibody, or fragments thereof, are normally associated with in nature. A non-naturally occurring polynucleotide, peptide, polypeptide, protein, antibody, or fragments thereof, do not require "isolation" to distinguish it from its naturally occurring counterpart.

The term "linker," as used herein, refers to a molecule linking two other molecules or moieties (e.g., proteins or protein domains or fragments). Linkers are well known in the art and can comprise any suitable combination of nucleic acids or amino acids to facilitate the proper function of the structures they join. The linker can be a series of amino acids. The linker can be an amino acid sequence in the case of a linker joining two fusion proteins. For example, a fusion protein (e.g., targeted effector fusion protein). The linker can also be a nucleotide sequence in the case of joining two nucleotide sequences together. For example, in the instant case, the traditional chondroitinase is linked via or linker to galectin-3. In other embodiments, the linker is an organic molecule, group, polymer, cross-linking agent, coupling agent, or chemical moiety. In some embodiments, the linker is 1-100 amino acids in length, for example: 1; 2; 3; 4; 5; 6; 7; 8; 9; 10; 11; 12; 13; 14; 15; 16; 17; 18; 19; 20; 21; 22; 23; 24; 25; 26; 27; 28; 29; 30; 30-35; 35-40; 40-45; 45-50; 50-60; 60-70; 70-80; 80-90; 90-100; 100-150; or 150-200 amino acids in length. In some embodiments, the linker is 5-1,000 nucleotides in length, for example: 5; 6; 7; 8; 9; 10; 11; 12; 13; 14; 15; 16; 17; 18; 19; 20; 21; 22; 23; 24; 25; 26; 27; 28; 29; 30; 30-35; 35-40; 40-45; 45-50; 50-60; 60-70; 70-80; 80-90; 90-100; 100-150; 150-200; 200-300; 300-500; 500-1,000; 1,000-2,000; or 2,000-5,000 nucleotides. In some embodiments, the linker comprises four amino acids. In some embodiments, the linker is comprises, glycine-glycine-glycine-serine. In some embodiments, the linker comprises (glycine-serine)$_n$, wherein "n" is an interger representing a number of repeats of the sequences (e.g., glycine-serine), for example, (glycine-serine)$_3$, would represent three repeates of glycine-serine, or in other words "glycine-serine-glycine-serine-glycine-serine." In some embodiments, "n" is between 1 and 100. In some embodiments, "n" is between 1 and 50). In some embodiments, "n" is between 7 and 21. In some embodiments, "n" is between 8 and 20. Longer or shorter linkers are also contemplated.

The term "lipophilic", as used herein, refers to compounds having an affinity for lipids.

As used herein, "mammal," for the purposes of treatments, refers to any animal classified as a mammal, including human, domestic and farm animals, nonhuman primates, and zoo, sports, or pet animals, such as, but not limited to, dogs, horses, cats, and cows.

As used herein, "matrix" refers to a material, in which one or more specialized structures, molecules, or compositions, are embedded.

The term "molecular weight", as used herein, generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

As used herein, "multimerizing" can refer to the binding of two or more fusion proteins described herein to each other via binding between the coils (e.g., alpha helix colis and/or random polypeptide coil). In this context, the binding can be non-covalent and/or covalent binding between the two or more fusion proteins.

As used herein, "negative control" refers to a "control" that is designed to produce no effect or result, provided that all reagents are functioning properly and that the experiment is properly conducted. Other terms that are interchangeable with "negative control" include "sham," "placebo," and "mock."

As used herein, "nucleic acid" and "polynucleotide" generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. "Polynucleotide" and "nucleic acids" also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotide" as that term is intended herein.

As used herein, "nucleic acid sequence" and "oligonucleotide" also encompasses a nucleic acid and polynucleotide as defined above.

As used herein, "organism", "host", and "subject" refers to any living entity comprised of at least one cell. A living organism can be as simple as, for example, a single isolated eukaryotic cell or cultured cell or cell line, or as complex as a mammal, including a human being, and animals (e.g., vertebrates, amphibians, fish, mammals, e.g., cats, dogs, horses, pigs, cows, sheep, rodents, rabbits, squirrels, bears, primates (e.g., chimpanzees, gorillas, and humans). "Subject" may also be a cell, a population of cells, a tissue, an organ, or an organism, preferably to human and constituents thereof.

As used herein, "overexpressed" or "overexpression" refers to an increased expression level of an RNA or protein product encoded by a gene as compared to the level of expression of the RNA or protein product in a normal or control cell.

As used herein, "operatively linked" can indicate that the regulatory sequences useful for expression of the coding sequences of a nucleic acid are placed in the nucleic acid molecule in the appropriate positions relative to the coding sequence so as to effect expression of the coding sequence. This same definition is sometimes applied to the arrangement of coding sequences and/or transcription control elements (e.g., promoters, enhancers, and termination elements), and/or selectable markers in an expression vector. The term "operatively linked" can also refer to the arrangement of polypeptide segments within a single polypeptide chain, where the individual polypeptide segments can be, without limitation, a protein, fragments thereof, linking peptides, and/or signal peptides. The term operatively linked can refer to direct fusion of different individual polypeptides within the single polypeptides or fragments thereof where there are no intervening amino acids between the different segments as well as when the individual polypeptides are connected to one another via one or more intervening amino acids.

As used herein, "patient" refers to an organism, host, or subject in need of treatment.

As used herein "peptide" refers to chains of at least 2 amino acids that are short, relative to a protein or polypeptide.

The "percent identity," "sequence identity," "% identity," "% sequence identity," or "% identical" (as they may be interchangeably used herein) of sequences (e.g., nucleic acid or amino acid) refers to a quantitative measurement of the similarity between two sequences (e.g., nucleic acid or amino acid). The percent identity of genomic DNA sequence, intron and exon sequence, and amino acid sequence between humans and other species varies by species type, with chimpanzee having the highest percent identity with humans of all species in each category. Percent identity can be determined using the algorithms of Karlin and Altschul, Proc. Natl. Acad. Sci. USA 87:2264-68, 1990, modified as in Karlin and Altschul, Proc. Natl. Acad. Sci. USA 90:5873-77, 1993. Such algorithms is incorporated into the NBLAST and XBLAST programs (version 2.0) of Altschul et al., J. Mol. Biol. 215:403-10, 1990. BLAST protein searches can be performed with the XBLAST program, score=50, word length=3, to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used. When a percent identity is stated, or a range thereof (e.g., at least, more than, etc.), unless otherwise specified, the endpoints shall be inclusive and the range (e.g., at least 70% identity) shall include all ranges within the cited range (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) and all increments thereof (e.g., tenths of a percent (i.e., 0.1%), hundredths of a percent (i.e., 0.01%), etc.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" refers to any acid or base addition salt whose counter-ions are non-toxic to the subject to which they are administered in pharmaceutical doses of the salts.

As used herein, "plasmid" as used herein refers to a non-chromosomal double-stranded DNA sequence including an intact "replicon" such that the plasmid is replicated in a host cell.

As used herein, "positive control" refers to a "control" that is designed to produce the desired result, provided that all reagents are functioning properly and that the experiment is properly conducted.

As used herein, "preventative" and "prevent" refers to hindering or stopping a disease or condition before it occurs, even if undiagnosed, or while the disease or condition is still in the sub-clinical phase.

As used herein, "protein" as used herein refers to a large molecule composed of one or more chains of amino acids in a specific order. The term protein is used interchangeable with "polypeptide." The order is determined by the base sequence of nucleotides in the gene coding for the protein. Proteins are required for the structure, function, and regulation of the body's cells, tissues, and organs. Each protein has a unique function. The term protein as used herein can also include peptides. Thus, for example, an "effector protein" can include both effector proteins and effector peptides.

As used herein, "purified" or "purify" is used in reference to a nucleic acid sequence, peptide, or polypeptide that has increased purity relative to the natural environment.

As used herein, the term "recombinant" generally refers to a non-naturally occurring nucleic acid, nucleic acid construct, or polypeptide. Such non-naturally occurring nucleic acids may include natural nucleic acids that have been modified, for example that have deletions, substitutions, inversions, insertions, etc., and/or combinations of nucleic acid sequences of different origin that are joined using molecular biology technologies (e.g., a nucleic acid sequences encoding a fusion protein (e.g., a protein or polypeptide formed from the combination of two different proteins or protein fragments), the combination of a nucleic acid encoding a polypeptide to a promoter sequence, where the coding sequence and promoter sequence are from different sources or otherwise do not typically occur together naturally (e.g., a nucleic acid and a constitutive promoter), etc.). Recombinant also refers to the polypeptide encoded by the recombinant nucleic acid. Non-naturally occurring nucleic acids or polypeptides include nucleic acids and polypeptides modified by man.

As used herein, "separated" refers to the state of being physically divided from the original source or population such that the separated compound, agent, particle, or molecule can no longer be considered part of the original source or population.

As used herein, "specifically binds" or "specific binding" refers to binding that occurs between such paired species such as enzyme/substrate, receptor/agonist or antagonist, antibody/antigen, lectin/carbohydrate, oligo DNA primers/DNA, enzyme or protein/DNA, and/or RNA molecule to other nucleic acid (DNA or RNA) or amino acid, which may be mediated by covalent or non-covalent interactions or a combination of covalent and non-covalent interactions. When the interaction of the two species produces a non-covalently bound complex, the binding that occurs is typically electrostatic, hydrogen-bonding, or the result of lipophilic interactions. Accordingly, "specific binding" occurs between a paired species where there is interaction between the two which produces a bound complex having the characteristics of an antibody/antigen, enzyme/substrate, DNA/DNA, DNA/RNA, DNA/protein, RNA/protein, RNA/amino acid, receptor/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins.

As used herein, "specific binding partner" or "binding partner" is a compound or molecule to which a second compound or molecule binds with a higher affinity than all other molecules or compounds.

As used interchangeably herein, "subject," "individual," or "patient" refers to a vertebrate organism.

As used herein, "substantially pure" means an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used herein, "substantially pure cell population" refers to a population of cells having a specified cell marker characteristic and differentiation potential that is about 50%, preferably about 75-80%, more preferably about 85-90%, and most preferably about 95% of the cells making up the total cell population. Thus, a "substantially pure cell population" refers to a population of cells that contain fewer than about 50%, preferably fewer than about 20-25%, more preferably fewer than about 10-15%, and most preferably fewer than about 5% of cells that do not display a specified marker characteristic and differentiation potential under designated assay conditions.

The terms "sufficient" and "effective", as used interchangeably herein, refer to an amount (e.g., mass, volume, dosage, concentration, and/or time period) needed to achieve one or more desired result(s). For example, a therapeutically effective amount refers to an amount needed to achieve one or more therapeutic effects.

As used herein, "synergistic effect," "synergism," or "synergy" refers to an effect arising between two or more molecules, compounds, substances, factors, or compositions that is greater than or different from the sum of their individual effects.

As used herein, "therapeutic" refers to treating, healing, and/or ameliorating a disease, disorder, condition, or side effect, or to decreasing in the rate of advancement of a disease, disorder, condition, or side effect. The term also includes within its scope enhancing normal physiological function, palliative treatment, and partial remediation of a disease, disorder, condition, side effect, or symptom thereof. The disease or disorder can be central nervous system injury or damage. The disease or disorder can be or involve glial scarring. "Therapeutic" can also refer to the ability of the compositions, formulations and/or methods described herein to promote axonal plasticity by degrading perineuronal nets, improve and/or maintain neurological function following stroke and/or ischemic brain injury, promote the repair of spinal cord injuries (e.g., contusion) by, for example, facilitating regrowth of axons, increase the efficacy of transplanted cell therapies into the central nervous system (CNS), facilitate decellularization of transplanted nerve grafts, and/or improve patency of implanted neural electrodes.

As used herein, "therapeutically effective amount" refers to the amount of a targeted effector fusion protein, a pharmaceutical formulation thereof, auxiliary agent, or secondary agent described herein that will elicit the biological or medical response of a tissue, system, animal, or human that is being sought by the researcher, veterinarian, medical doctor or other clinician. "Therapeutically effective amount" includes that amount of a targeted effector fusion protein, a composition containing a targeted effector fusion protein, a pharmaceutical formulation thereof that, when administered alone or co-administered with a secondary agent, is sufficient to prevent development of, reduce or alleviate to some extent, one or more of the symptoms of inflammation. "Therapeutically effect amount" includes that amount of targeted effector fusion protein, a composition containing a targeted effector fusion protein, a pharmaceutical formulation thereof that, when administered alone or co-administered with a secondary agent, is sufficient to reduce or alleviate to some extent, one or more of the symptoms of a central nervous system injury, neuron injury, and/or glial scarring. "Therapeuticically effective amount" can also refer to the amount of the compositions and/or formulations described herein that can promote axonal plasticity by degrading perineuronal nets, improve and/or maintain neurological function following stroke and/or ischemic brain injury, promote the repair of spinal cord injuries (e.g., contusion) by facilitating regrowth of axons, increase the efficacy of transplanted cell therapies into the central nervous system (CNS), facilitate decellularization of transplanted nerve grafts, and/or improve patency of implanted neural electrodes.

The terms "treating" and "treatment" as used herein refer generally to obtaining a desired pharmacological and/or physiological effect. The effect may be prophylactic in terms of preventing or partially preventing a disease, symptom or condition thereof, such as a central nervous system injury or disease, neuronal disease or injury, and/or glial scarring, and/or may be therapeutic in terms of a partial or complete cure of a disease, condition, symptom or adverse effect attributed to the disease, disorder, or condition. "Treating" or "treatment" can also refer to the effect of the compositions, formulations and/or methods described herein to promote axonal plasticity by degrading perineuronal nets, improve and/or maintain neurological function following stroke and/or ischemic brain injury, promote the repair of spinal cord injuries (e.g., contusion) by facilitating regrowth of axons, increase the efficacy of transplanted cell therapies into the central nervous system (CNS), facilitate decellularization of transplanted nerve grafts, and/or improve patency of implanted neural electrodes. The term "treatment" as used herein covers any treatment of a central nervous system injury or disease, neuronal disease or injury, and/or glial scarring, and also includes, but is not limited to, promoting axonal plasticity by degrading perineuronal nets, improving and/or maintaining neurological function following stroke/ischemic brain injury, promoting repair of spinal cord injuries (e.g., contusion) by, for example, facilitating the regrowth of axons, increasing the efficacy of transplanted cell therapies into the CNS, facilitating decellularization of transplanted nerve grafts, and/or improving patency of implanted neural electrodes. The terms "treat" and "treating" can include (a) preventing the disease from occurring in a subject which may be predisposed to the disease but has not yet been diagnosed as having it; (b) inhibiting the disease, i.e., arresting its development; or (c) relieving the disease, i.e., mitigating or ameliorating the disease and/or its symptoms or conditions.

As used herein, "tangible medium of expression" refers to a medium that is physically tangible and is not a mere abstract thought or an unrecorded spoken word. Tangible medium of expression includes, but is not limited to, words on a cellulosic or plastic material or data stored on a suitable device such as a flash memory or CD-ROM.

As used herein, "transduced" refers to the direct introduction of a protein into a cell.

As used herein, the term "transfection" refers to the introduction of an exogenous and/or recombinant nucleic acid sequence into the interior of a membrane enclosed space of a living cell, including introduction of the nucleic acid sequence into the cytosol of a cell as well as the interior space of a mitochondria, nucleus, or chloroplast. The nucleic acid may be in the form of naked DNA or RNA, it may be associated with various proteins or regulatory elements (e.g., a promoter and/or signal element), or the nucleic acid may be incorporated into a vector or a chromosome. It may be incorporated into a viral particle.

As used herein, "transformation" or "transformed" refers to the introduction of a nucleic acid (e.g., DNA or RNA) into cells in such a way as to allow expression of the coding portions of the introduced nucleic acid.

As used herein, "underexpressed" or "underexpression" refers to decreased expression level of an RNA or protein product encoded by a gene as compared to the level of expression of the RNA or protein product in a normal or control cell.

As used herein, "variant" refers to a polypeptide that differs from a reference polypeptide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally. "Variant" includes functional and structural variants.

As used herein, the term "vector" or is used in reference to a vehicle used to introduce an exogenous nucleic acid sequence into a cell. A vector may include a DNA molecule, linear or circular (e.g., plasmids), which includes a segment encoding a polypeptide of interest operatively linked to additional segments that provide for its transcription and translation upon introduction into a host cell or host cell organelles. Such additional segments may include promoter and terminator sequences, and may also include one or more origins of replication, one or more selectable markers, an enhancer, a polyadenylation signal, etc. Expression vectors are generally derived from yeast or bacterial genomic or plasmid DNA, or viral DNA, or may contain elements of both.

As used herein, "wild-type" is the typical form of an organism, variety, strain, gene, protein, or characteristic as it occurs in nature, as distinguished from mutant forms that may result from selective breeding or transformation with a transgene.

As used herein, "encoding" can refer to the basic biological concept that DNA can be transcribed into RNA, which then can be translated into a polypeptide.

Unless otherwise defined herein, all technical and scientific terms used herein have the same meaning as commonly understood by one of ordinary skill in the art.

Discussion

Glial scar formation is a reactive cellular process that occurs after injury to the central nervous system. It is also referred to as reactive gliosis or glial scarring. Similarly to other scarring in other organs and tissues, glial scarring is meant to guard and start wound healing within an injured central nervous system. Glial scarring can inhibit axon regeneration, inter alia, and thus may influence the ability of the central nervous system to heal in response to injury.

Many attractive enzyme drug candidates fail in clinical trials due to unfavorable pharmacokinetics, pharmacodynamics, and/or safety profiles. The enzyme chondroitinase ABC is currently in veterinary clinical trials for determining its efficacy for neural regeneration. A major drawback of this enzyme and its formulation currently under development and clinical testing is that it is unstable and is rapidly cleared from the tissue injury site. This results in an ineffective retention of the enzyme at a local site and limits its efficacy. In short, due to these stability and clearance issues, the enzyme simply is not retained long enough in an area so as to provide any therapeutic or other benefit or change. As such, there exists an unmet need for improved ChABC compositions.

Described herein are targeted effector fusion proteins that can include a chondroitinase ABC 1 polypeptide (ChABC) that can be capable of causing a biological effect in a target cell, tissue, and/or organ (e.g., a central nervous system cell, such as a glial cell) and a Galectin 3 (Gal3), which can act as a targeting moiety, that can be capable of directing the ChABC specifically to a desired cell, tissue, and/or organ (also referred to herein as a target cell, tissue or organ). Chondroitinase ABC is an enzyme with a systematic name of chondroitin ABC lyase and acts on chondroitin 4-sulfate, chondroitin 6-sulfate, and dermatan sulfate. The enzyme degrades polysaccharides containing 1,4-beta-D-hexosaminyl and 1,3-beta-D-glucuronosyl or 1,3-alpha-L-iduronosyl linkages to disaccharides containing 4-deoxy-beta-D-gluc-4-enuronosyl groups. Galectin-3 (Gal3) is a protein (encoded by the LGALS3 gene in humans) which is known for its ability to bind beta-galactosides. This binding ability, enabled by a carbohydrate-recognition binding domain, facilitates the ability of Gal3 to facilitate various activities, for example cell-cell adhesion, cell-matrix interaction, macrophage activation, angiogenesis, metastasis, and apoptosis. In some aspects, the ChABC can be operatively linked to the Gal3 via a flexible linker or an alpha coil. In some embodiments, the targeted effector fusion proteins can self-assemble into multimers (also referred to herein as targeted effector fusion protein complexes). Also described herein are compositions and formulations of the targeted effector fusion proteins and complexes. The targeted effector fusion proteins, complexes thereof, compositions thereof, and formulations thereof described herein can be administered to a subject in need thereof. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Targeted Chondroitinase ABC Fusion Proteins and Complexes Thereof

Disclosed herein are recombinant cDNA sequences, which can code for various targeted effector fusion proteins containing a ChABC polypeptide and Gal3 polypeptide (also referred to herein as the "targeted effector fusion protein"), where the ChABC polypeptide (also referred to herein as the "effector protein") can be operatively coupled to the Gal3 polypeptide (also referred to herein as the "targeting moiety"). The Gal3 can target the effector fusion protein to a glycan and/or a glycosaminoglycan. In some aspects, the glycan can be a beta-galactoside glycan. In some aspects, the beta-galactoside glycan can be N-acetyllactosamine (LacNAc). The glycan(s) and/or glycosaminoglycan(s) can be contained in an extracellular matrix of a cell.

In some aspects, the ChABC polypeptide can be operatively linked to a Gal3 polypeptide. As shown in FIG. 83, in some embodiments, the ChABC polypeptide can be operatively linked to the Gal3 polypeptide via a linker. In some embodiments, the Gal3 polypeptide consists of an N-terminally truncated Gal3 polypeptide. In some embodiments, the N-terminal truncation comprises a truncation of 1 to about 105 amino acids from the N-terminus of Gal3. In some embodiments, the N-terminal truncation comprises a truncation of about 105 amino acids from the N-terminus of Gal3. In some embodiments, the N-terminal truncation comprises the truncation of the bolded residues shown in SEQ ID NO: 33. In some embodiments, the N-terminally truncated Gal3 comprises a sequence having about 80% or greater sequence identity (e.g., about 80%, about 81%, about 82%, about 83%, about 84%, about 85%, about 86%, about 87%, about 88%, about 89%, about 90%, about 91%, about 92%, about 93%, about 94%, about 95%, about 95.5%, about 96%, about 96.5%, about 97%, about 97.5%, about 98%, about 98.5%, about 99%, about 99.5%, about 99.6%, about 99.7%, about 99.8%, about 99.9% identity) to SEQ ID NO: 34. In some embodiments, the N-terminally truncated Gal3 comprises a sequence according to SEQ ID NO: 34. In some embodiments, the truncation comprises all amino acids excepting the C-terminal carbohydrate-binding domain of Gal3. The linker can be a flexible linker, a rigid linker, or a random coil polypeptide. The flexible linker can be a peptide or polypeptide flexible linker, a cross-linking reagent, and/or coupling agent, including, but not limited to, disulfide bonds, azide linkages, avidin-biotin linkages, ester linkages, thioester linkages, or thioether linkages. In some embodiments, the linker can vary from about 1 to 100 amino acids or more in length. In some embodiments, the linker is between 1 and 50 amino acids in length. In some embodiments, the linker is between 1 and 21 amino acids in length. In some embodiments, the linker is 1-100 amino acids in length, for example: 1; 2; 3; 4; 5; 6; 7; 8; 9; 10; 11; 12; 13; 14; 15; 16; 17; 18; 19; 20; 21; 22; 23; 24; 25; 26; 27; 28; 29; 30; 30-35; 35-40; 40-45; 45-50; 50-60; 60-70; 70-80; 80-90; 90-100; 100-150; or 150-200 amino acids in length. In some embodiments, the linker is 5-1,000 nucleotides in length, for example: 5; 6; 7; 8; 9; 10; 11; 12; 13; 14; 15; 16; 17; 18; 19; 20; 21; 22; 23; 24; 25; 26; 27; 28; 29; 30; 30-35; 35-40; 40-45; 45-50; 50-60; 60-70; 70-80; 80-90; 90-100; 100-150; 150-200; 200-300; 300-500; 500-1,000; 1,000-2,000; or 2,000-5,000 nucleotides. In some embodiments, the linker comprises four amino acids in length. In some embodiments, the linker is comprises, glycine-glycine-glycine-serine. In some embodiments, the linker comprises (glycine-serine)n, wherein "n" is an interger representing a number of repeats of the sequences (e.g., glycine-serine), for example, (glycine-serine)3, would represent three repeates of glycine-serine, or in other words "glycine-serine-glycine-serine-glycine-serine." In some embodiments, "n" is between 1 and 100. In some embodiments, "n" is between 1 and 50). In some embodiments, "n" is between 7 and 21. In some embodiments, "n" is between 8 and 20. Longer or shorter linkers are also contemplated. The linker can be any variation or combination (natural or synthetic) of any naturally or synthetically occurring amino acids. The flexible linker can be operatively linked to the C-terminus, N-terminus or both the C-terminus and the N-terminus of the effector protein and/or the targeting moiety. In some embodiments, the effector protein can be fused directly (e.g., "a zero-length" fusion) to the targeting moiety. In other words, in some embodiments, there is no linker between the effector protein and targeting moiety.

As shown in FIGS. 83 and 84A-84B, in some embodiments, the effector protein can be operatively linked to the targeting moiety via a domain that folds into an alpha-helix. The alpha-helix domain can be operatively linked to the C-terminus, N-terminus or both the C-terminus and the N-terminus of the effector protein and/or the targeting moiety. The alpha-helical coil can have the general structure of one or more 7-amino acid heptads repeats, which can each be denoted by the formula A-B-C-D-E-F-G, where each letter represents an amino acid in the heptad. In some embodiments, A and D can each be a hydrophobic amino acid, and each amino acid B, C, E, F, and G can each be independently selected from a hydrophilic amino acid, a polar amino acid, or a charged amino acid. Hydrophobic amino acids can include glycine, alanine, valine, leucine, isoleucine, proline, phenylalanine, methionine, and tryptophan. Polar amino acids can include serine, threonine, asparagine, glutamine, histidine, and tyrosine. Charged amino acids can include arginine, aspartate, glutamate, and lysine. Hydrophilic amino acids can include arginine, lysine, asparagine, histidine, glutamate. The number of heptad repeats can be 1 (i.e., 1 heptad), 2, 3, 4, 5, 6, 7, 8, 9, 10, or more.

In some embodiments, the targeted ChABC fusion protein can have and/or include a polypeptide sequence that has a about 80% to 100% sequence identity (e.g., about 80%, about 81%, about 82%, about 83%, about 84%, about 85%, about 86%, about 87%, about 88%, about 89%, about 90%, about 91%, about 92%, about 93%, about 94%, about 95%, about 95.5%, about 96%, about 96.5%, about 97%, about 97.5%, about 98%, about 98.5%, about 99%, about 99.5%, about 99.6%, about 99.7%, about 99.8%, about 99.9% identity) to any one of SEQ ID NOS:NO: 15-16. In some embodiments, the C-terminal carbohydrate domain of Gal3 is conserved. In some embodiments, the targeted ChABC fusion protein can have 1 or more mutations (e.g., changed or substituted amino acids, deletions, insertions) as compared to SEQ ID NO: 15-16. In some embodiments, the targeted ChABC fusion protein can have between 1-20 mutations (e.g., changed or substituted amino acids, deletions, insertions) as compared to SEQ ID NO: 15-16. In some embodiments, the targeted ChABC fusion protein can have between 1-200 or more mutations (e.g., changed or substituted amino acids, deletions, insertions) as compared to SEQ ID NO: 15-16. In some embodiments, the targeted ChABC fusion protein can have and/or include a polypeptide sequence that is about 90% to 100% identical to any one of SEQ ID NOS: 15-16. In some embodiments, the targeted effector fusion protein having an alpha-helical coiled-coil domain can have a polypeptide sequence that has about 80%-100% sequence identity (e.g., about 80%, about 81%, about 82%, about 83%, about 84%, about 85%, about 86%, about 87%, about 88%, about 89%, about 90%, about 91%, about 92%, about 93%, about 94%, about 95%, about 95.5%, about 96%, about 96.5%, about 97%, about 97.5%, about 98%, about 98.5%, about 99%, about 99.5%, about 99.6%, about 99.7%, about 99.8%, about 99.9% identity) to SEQ ID NO: 15. In some embodiments, the targeted ChABC fusion protein can have 1 or more mutations (e.g., changed or substituted amino acids, deletions, insertions) as compared to SEQ ID NO: 15. In some embodiments, the targeted ChABC fusion protein can have between 1-20 mutations (e.g., changed or substituted amino acids, deletions, insertions) as compared to SEQ ID NO: 15. In some embodiments, the targeted ChABC fusion protein can have between 1-200 or more mutations (e.g., changed or substituted amino acids, deletions, insertions) as compared to SEQ ID NO: 15. In some embodiments, the targeted effector fusion protein having an alpha-helical coiled-coil domain can have a polypeptide sequence that is about 90-100% identical (e.g., about 90%, about 91%, about 92%, about 93%, about 94%, about 95%, about 95.5%, about 96%, about 96.5%, about 97%, about 97.5%, about 98%, about 98.5%, about 99%, about 99.5%, about 99.6%, about 99.7%, about 99.8%, about 99.9% identity) to SEQ ID NO: 15. As shown in FIGS. 84A-84B, in some embodiments where the linker can be an alpha-helix, the targeted effector fusion protein can form a multimer with one or more other targeted effector proteins provided herein also having the exact same, or otherwise complementary (e.g., charge and/or hydrophobicity, hydrogen bond donor/acceptor, Van der Waals forces) alpha-helix domain. The multimer (also referred to interchangeably herein as a "complex", a "targeted effector fusion protein complex" or "targeted ChABC fusion protein complex") can be formed via interactions between the alpha-helix domains included in the targeted effector fusion proteins thereby forming multimeric alpha-helix coiled-coils. The alpha-helix coiled-coils can facilitate self-assembly of a multimeric targeted effector fusion protein. The multimeric targeted effector fusion protein complex can be a dimer, trimer, tetramer, pentamer, hexamer or heptamer. The multimeric targeted effector fusion protein complex can be homogenous or heterogeneous. In this context the term "homogeneous" can refer to a multimer where each monomer targeted effector protein is the same. In this context, the term "heterogeneous" can refer to a multimer where at least two of the monomer targeted effector proteins are different from each other. In some embodiments, the linker or alpha helix polypeptide of the targeted effector protein can have a polypeptide sequence that has about 80 to 100% sequence identity (e.g., about 80%, about 81%, about 82%, about 83%, about 84%, about 85%, about 86%, about 87%, about 88%, about 89%, about 90%, about 91%, about 92%, about 93%, about 94%, about 95%, about 95.5%, about 96%, about 96.5%, about 97%, about 97.5%, about 98%, about 98.5%, about 99%, about 99.5%, about 99.6%, about 99.7%, about 99.8%, about 99.9% identity) to any one of SEQ ID NOs: 17-32. In some embodiments, the linker or alpha helix polypeptide of the targeted effector protein can have a polypeptide sequence that is about 90 to 100% identical (e.g., about 90%, about 91%, about 92%, about 93%, about 94%, about 95%, about 95.5%, about 96%, about 96.5%, about 97%, about 97.5%, about 98%, about 98.5%, about 99%, about 99.5%, about 99.6%, about 99.7%, about 99.8%, about 99.9% identity) to any one of SEQ ID NOs: 17-32.

In some embodiments, the targeted ChABC fusion protein comprises a ChABC fused to an N-terminally truncated Gal3 as described herein. In some embodiments, ChABC-N-terminally truncated fusion protein comprises a polypeptide sequence that has a about 80% to 100% sequence identity (e.g., about 80%, about 81%, about 82%, about 83%, about 84%, about 85%, about 86%, about 87%, about 88%, about 89%, about 90%, about 91%, about 92%, about 93%, about 94%, about 95%, about 95.5%, about 96%, about 96.5%, about 97%, about 97.5%, about 98%, about 98.5%, about 99%, about 99.5%, about 99.6%, about 99.7%, about 99.8%, about 99.9% identity) to a sequence comprising a native ChABC-Gal3 fusion protein, wherein the Gal3 is N-terminally truncated, wherein the N-terminal truncation is approximately 105 amino acids. In some embodiments, the C-terminal carbohydrate binding domain of Gal3 is conserved. In some embodiments, the targeted ChABC fusion protein comprises a ChABC fused to an N-terminally truncated Gal3 such that the C-terminal carbohydrate binding domain remains. In some embodiments, ChABC-C-terminal carbohydrate binding domain fusion protein comprises a polypeptide sequence that has a about 80% to 100% sequence identity (e.g., about 80%, about 81%, about 82%, about 83%, about 84%, about 85%, about 86%, about 87%, about 88%, about 89%, about 90%, about 91%, about 92%, about 93%, about 94%, about 95%, about 95.5%, about 96%, about 96.5%, about 97%, about 97.5%, about 98%, about 98.5%, about 99%, about 99.5%, about 99.6%, about 99.7%, about 99.8%, about 99.9% identity) to sequence comprising a native ChABC-Gal3 fusion protein, wherein the Gal3 comprises the C-terminal carbohydrate binding domain. In some embodiments, ChABC is fused to a truncated Gal3, wherein the truncated Gal3 has a sequence of about 80% to 100% sequence identity (e.g., about 80%, about 81%, about 82%, about 83%, about 84%, about 85%, about 86%, about 87%, about 88%, about 89%, about 90%, about 91%, about 92%, about 93%, about 94%, about 95%, about 95.5%, about 96%, about 96.5%, about 97%, about 97.5%, about 98%, about 98.5%, about 99%, about 99.5%, about 99.6%, about 99.7%, about 99.8%, about 99.9% identity) to SEQ ID NO: 34. In some embodiments, ChABC is fused to a truncated Gal3, wherein the ChABC-truncated Gal3 has a sequence of about 80% to 100% sequence identity (e.g., about 80%, about 81%, about 82%, about 83%, about 84%, about 85%, about 86%, about 87%, about 88%, about 89%, about 90%, about 91%, about 92%, about 93%, about 94%, about 95%, about 95.5%, about 96%, about 96.5%, about 97%, about 97.5%, about 98%, about 98.5%, about 99%, about 99.5%, about 99.6%, about 99.7%, about 99.8%, about 99.9% identity) to wild-type ChABC fused to SEQ ID NO: 34, utilizing any linkers described herein.

In some embodiments, the enzyme (e.g., ChABC polypeptide) is located at the N-terminus of the fusion protein. In some embodiments, the enzyme (e.g., ChABC polypeptide) is located at the C-terminus of the fusion protein. In some embodiments, the Gal3 polypeptide is located at the N-terminus of the fusion protein. In some embodiments, the Gal3 polypeptide is located at the C-terminus of the fusion protein. Accordingly, in some embodiments, the enzyme (e.g., ChABC polypeptide) is located at the N-terminus of the fusion protein and Gal3 polypeptide is located at the C-terminus of the fusion protein and they are optionally connected via a linker. In other embodiments, the Gal3 polypeptide is located at the N-terminus of the fusion protein and enzyme (e.g., ChABC polypeptide) is located at the C-terminus of the fusion protein and they are optionally connected via a linker.

In some embodiments, the linker or alpha helix polypeptide of the targeted effector protein can have 1 or more mutations (e.g., changed or substituted amino acids, deletions, insertions) as compared to SEQ ID NO: 17-32. In some embodiments, the linker or alpha helix polypeptide of the targeted effector protein can have between 1-20 mutations (e.g., changed or substituted amino acids, deletions, insertions) as compared to SEQ ID NO: 17-32. In some embodiments, the linker or alpha helix polypeptide of the targeted effector protein can have between 1-200 mutations (e.g., changed or substituted amino acids, deletions, insertions) as compared to SEQ ID NO: 17-32.

One of skill in the art will be able to, identify, determine, and generate cDNA and DNA sequences encoding any polypeptide provided herein based on algorithms, computer programs, and general knowledge and techniques used in the art.

The targeted effector fusion proteins and thus complexes thereof can contain one or more protein tags operatively coupled to the targeted effector fusion protein. These types of tags can be amino acid sequences that allow for affinity purification, solubilization, chromatographical separation, and/or immunodetection of the fusion protein. Suitable protein tags include, but are not limited to, chitin binding protein (CBP), maltose binding protein (MBP), glutathione-S-transferase (GST), poly(His), thioredoxin (TRX), poly (NANP), FLAG-tag (including any FLAG-tag variant, e.g., 3× FLAG), V5-tag, Myc-tag, HA-tag, S-tag, SBP-Tag, Sftag 1, Softag 3, Tc tag, Xpress tag, Strep-tag, Isopeptag, Spy Tag, Ty tag, Biotin Carboxyl Carrier Protein (BCCP), and Nus tag. Other tags will be appreciated by those of skill in the art and are within the scope of this disclosure.

The targeted effector fusion protein and thus a complex thereof can contain one or more reporter proteins, which can be the effector protein or in addition to the effector protein, operatively coupled to the effector protein and/or targeting moiety. Suitable reporter genes include, but are not limited to, fluorescent proteins (e.g., green fluorescent protein (GFP), red fluorescent protein (RFP), yellow fluorescent protein (YFP), blue fluorescent protein (BFP), and cyan fluorescent protein (CFP)), beta-galactosidase, luciferase (bacterial, firefly, and renilla luciferase), antibiotic-resistance genes (e.g., chloramphenicol acetyltransferase, neomycin phosphotransferase, and NPT-II), p-glucuronidase, and alkaline phosphatase. Inclusion of a reporter protein allows, inter alia, for direct and/or indirect characterization of the fusion protein and function of the fusion protein, as well as affinity purification of the protein. The reporter protein can be operatively linked to the N-terminus and/or the C-terminus of the effector protein and/or the targeting moiety or other portion of the targeted effector fusion protein.

Recombinant Vectors

The targeted effector fusion protein cDNA sequence can be incorporated into a suitable expression vector. The expression vector can contain one or more regulatory sequences or one or more other sequences used to facilitate the expression of the targeted effector fusion protein cDNA. In some embodiments, the targeted effector fusion protein can be encoded by a DNA sequence or cDNA sequence that can be about 50% to about 60%, 70%, 80%, 90%, or 100% identical to any one of SEQ ID NO: 6-7. The expression vector can contain one or more regulatory sequences or one or more other sequences used to facilitate the replication of the targeted effector fusion protein expression vector. The expression vector can be suitable for expressing the targeted effector fusion protein in a bacterial cell. In other embodiments, the expression vector can be suitable for expressing the targeted effector fusion protein in a yeast cell. In further embodiments, the expression vector can be suitable for expressing the targeted effector fusion protein in a plant cell. In other embodiments, the expression vector can be suitable for expressing the targeted effector fusion protein in a mammalian cell. In another embodiment, the vector can be suitable for expressing the targeted effector fusion protein in a fungal cell. In further embodiments, the vector can be suitable for expressing the targeted effector fusion protein in an insect cell. Suitable expression vectors are generally known to those of ordinary skill in the art.

Targeted ChABC Fusion Protein Production

The targeted ChABC fusion proteins described herein can be produced in a suitable in vitro expression system such as bacterial production system, yeast system, insect system, or mammalian cell system. Such systems can include growing a population of bacterial, yeast, or mammalian cells that express one or more vectors that include a DNA encoding one or more targeted effector fusion proteins described herein. The cells can produce the targeted effector fusion proteins and, in some embodiments secrete the produced protein into the cell media. After the targeted effector protein has been produced the targeted effector fusion protein can be harvested from the cell culture media and/or by lysing the cells to release produced protein contained within the cells.

Compositions and Formulations Containing a Targeted ChABC Fusion Protein and/or Complex Thereof Also within the scope of this disclosure are compositions and formulations containing a targeted effector fusion protein or complex thereof as described herein. The targeted effector fusion protein or complex thereof described herein can be provided to a subject in need thereof alone or as an active ingredient, such as in a pharmaceutical formulation. As such, also described herein are pharmaceutical formulations containing an amount of a targeted effector fusion protein or complex thereof. In some embodiments, the pharmaceutical formulations contain a therapeutically effective amount of a targeted effector fusion protein or complex thereof. The pharmaceutical formulations described herein can be administered to a subject in need thereof. The subject in need thereof can have glial scarring. The subject in need thereof can have or be suspected of having a central nervous system injury. The subject in need thereof can be in need of neuron regeneration. The subject in need thereof can have or be suspected of having a stroke and/or ischemic brain injury. The subject in need thereof can have or be suspected of having a spinal chord injury. The subject in need thereof can be receiving or have received a transplanted cell therapy, where the transplanted cell therapy was delivered to the CNS. The subject in need thereof can have an implanted neural electrode. The subject in need thereof can be in need of axonal plasticity and/or increased axonal plasticity, and/or degredation of perineuronal nets, improved and/or maintained neurological function, and/or decellularization of transplanted nerve grafts, or in need of peripheral nerve repair (for example, nerve transection (e.g., neurotmesis) or nerve crush (e.g., axonotmesis), for example occurring from surgery or inadvertent injury).

Pharmaceutically Acceptable Carriers and Auxiliary Ingredients and Agents

The pharmaceutical formulations containing a therapeutically effective amount of a targeted effector fusion protein or complex thereof described herein can further include a pharmaceutically acceptable carrier. Suitable pharmaceutically acceptable carriers include, but are not limited to, water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active composition.

In addition to the therapeutically effective amount of a targeted effector fusion protein and/or complex thereof described herein, the pharmaceutical formulation can also include an effective amount of an auxiliary active agent, including but not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics.

Suitable hormones include, but are not limited to, amino-acid derived hormones (e.g., e.g., melatonin and thyroxine), small peptide hormones and protein hormones (e.g., thyrotropin-releasing hormone, vasopressin, insulin, growth hormone, luteinizing hormone, follicle-stimulating hormone, and thyroid-stimulating hormone), eicosanoids (e.g., arachidonic acid, lipoxins, and prostaglandins), and steroid hormones (e.g., estradiol, testosterone, tetrahydro testosteron cortisol).

Suitable immunomodulators include, but are not limited to, prednisone, azathioprine, 6-MP, cyclosporine, tacrolimus, methotrexate, interleukins (e.g., IL-2, IL-7, and IL-12), cytokines (e.g., interferons (e.g., IFN-α, IFN-βP, IFN-ε, IFN-κ, IFN-ω, and IFN-γ), granulocyte colony-stimulating factor, and imiquimod), chemokines (e.g., CCL3, CCL26 and CXCL7), cytosine phosphate-guanosine, oligodeoxynucleotides, glucans, antibodies, and aptamers).

Suitable antipyretics include, but are not limited to, non-steroidal anti-inflammants (e.g., ibuprofen, naproxen, ketoprofen, and nimesulide), aspirin and related salicylates (e.g., choline salicylate, magnesium salicylae, and sodium salicaylate), paracetamol/acetaminophen, metamizole, nabumetone, phenazone, and quinine.

Suitable anxiolytics include, but are not limited to, benzodiazepines (e.g., alprazolam, bromazepam, chlordiazepoxide, clonazepam, clorazepate, diazepam, flurazepam, lorazepam, oxazepam, temazepam, triazolam, and tofisopam), serotenergic antidepressants (e.g., selective serotonin reuptake inhibitors, tricyclic antidepresents, and monoamine oxidase inhibitors), mebicar, afobazole, selank, bromantane, emoxypine, azapirones, barbiturates, hydroxyzine, pregabalin, validol, and beta blockers.

Suitable antipsychotics include, but are not limited to, benperidol, bromoperidol, droperidol, haloperidol, moperone, pipaperone, timiperone, fluspirilene, penfluridol, pimozide, acepromazine, chlorpromazine, cyamemazine, dizyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veralipride, amisulpride, amoxapine, aripiprazole, asenapine, clozapine, blonanserin, iloperidone, lurasidone, melperone, nemonapride, olanzaprine, paliperidone, perospirone, quetiapine, remoxipride, risperidone, sertindole, trimipramine, ziprasidone, zotepine, alstonie, befeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, non-steroidal anti-inflammants (e.g., ibuprofen, naproxen, ketoprofen, and nimesulide), COX-2 inhibitors (e.g., rofecoxib, celecoxib, and etoricoxib), opioids (e.g., morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g., choline salicylate, magnesium salicylate, and sodium salicylate).

Suitable antispasmodics include, but are not limited to, mebeverine, papverine, cyclobenzaprine, carisoprodol, orphenadrine, tizanidine, metaxalone, methodcarbamol, chlorzoxazone, baclofen, dantrolene, baclofen, tizanidine, and dantrolene.

Suitable anti-inflammatories include, but are not limited to, prednisone, non-steroidal anti-inflammants (e.g., ibuprofen, naproxen, ketoprofen, and nimesulide), COX-2 inhibitors (e.g., rofecoxib, celecoxib, and etoricoxib), and immune selective anti-inflammatory derivatives (e.g., submandibular gland peptide-T and its derivatives).

Suitable anti-histamines include, but are not limited to, Hi-receptor antagonists (e.g., acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbromapheniramine, dexchlorpheniramine, dimenhydrinate, dimetindene, diphenhydramine, doxylamine, ebasine, embramine, fexofenadine, hydroxyzine, levocetirzine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), H2-receptor antagonists (e.g., cimetidine, famotidine, lafutidine, nizatidine, rafitidine, and roxatidine), tritoqualine, catechin, cromoglicate, nedocromil, and β2-adrenergic agonists.

Suitable anti-infectives include, but are not limited to, amebicides (e.g., nitazoxanide, paromomycin, metronidazole, tinidazole, chloroquine, miltefosine, amphotericin b, and iodoquinol), aminoglycosides (e.g., paromomycin, tobramycin, gentamicin, amikacin, kanamycin, and neomycin), anthelmintics (e.g., pyrantel, mebendazole, ivermectin, praziquantel, abendazole, thiabendazole, oxamniquine), antifungals (e.g., azole antifungals (e.g., itraconazole, fluconazole, posaconazole, ketoconazole, clotrimazole, miconazole, and voriconazole), echinocandins (e.g., caspofungin, anidulafungin, and micafungin), griseofulvin, terbinafine, flucytosine, and polyenes (e.g., nystatin, and amphotericin b), antimalarial agents (e.g., pyrimethamine/sulfadoxine, artemether/lumefantrine, atovaquone/proquanil, quinine, hydroxychloroquine, mefloquine, chloroquine, doxycycline, pyrimethamine, and halofantrine), antituberculosis agents (e.g., aminosalicylates (e.g., aminosalicylic acid), isoniazid/rifampin, isoniazid/pyrazinamide/rifampin, bedaquiline, isoniazid, ethambutol, rifampin, rifabutin, rifapentine, capreomycin, and cycloserine), antivirals (e.g., amantadine, rimantadine, abacavir/lamivudine, emtricitabine/tenofovir, cobicistat/elvitegravir/emtricitabine/tenofovir, efavirenz/emtricitabine/tenofovir, avacavir/lamivudine/zidovudine, lamivudine/zidovudine, emtricitabine/tenofovir, emtricitabine/opinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpivirine, delaviridine, nevirapine, entecavir, lamivudine, adefovir, sofosbuvir, didanosine, tenofovir, avacivr, zidovudine, stavudine, emtricitabine, xalcitabine, telbivudine, simeprevir, boceprevir, telaprevir, lopinavir/ritonavir, fosamprenvir, dranuavir, ritonavir, tipranavir, atazanavir, nelfinavir, amprenavir, indinavir, sawuinavir, ribavirin, valcyclovir, acyclovir, famciclovir, ganciclovir, and valganciclovir), carbapenems (e.g., doripenem, meropenem, ertapenem, and cilastatin/imipenem), cephalosporins (e.g., cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g., vancomycin, dalbavancin, oritavancin, and telvancin), glycylcyclines (e.g., tigecycline), leprostatics (e.g., clofazimine and thalidomide), lincomycin and derivatives thereof (e.g., clindamycin and lincomycin), macrolides and derivatives thereof (e.g., telithromycin, fidaxomicin, erthromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, penicillins (amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxaxillin, dicloxacillin, and nafcillin), quinolones (e.g., lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g., sulfamethoxazole/trimethoprim, sulfasalazine, and sulfasoxazole), tetracyclines (e.g., doxycycline, demeclocycline, minocycline, doxycycline/salicyclic acid, doxycycline/omega-3 polyunsaturated fatty acids, and tetracycline), and urinary anti-infectives (e.g., nitrofurantoin, methenamine, fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, asparginase *Erwinia chrysanthemi*, amifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, aresnic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, and all-trans retinoic acid Effective Amounts of the Targeted Effector Fusion Protein and/or Complex Thereof and Auxiliary Agents The pharmaceutical formulations can contain a therapeutically effective amount of a targeted effector fusion protein or complex thereof. In some embodiments the pharmaceutical formulations can also include a therapeutically effective amount of an auxiliary agent. In some embodiments, the therapeutically effective amount of the targeted effector fusion protein and/or complex thereof can range from about 1 µg/kg to about 10 mg/kg. In further embodiments, the therapeutically effective amount of the targeted effector fusion protein and/or complex thereof can range from 1 ng/g bodyweight to about 0.1 mg/g bodyweight. The therapeutically effective amount of the targeted effector fusion protein and/or complex thereof can range from about 1 µg to about 10 g. In some embodiments, the therapeutically effective amount of the targeted effector fusion protein and/or complex thereof or pharmaceutical composition containing the targeted effector fusion protein and/or complex thereof can range from about 10 nL to about 10 mL. In some embodiments, the therapeutically effective amount of the targeted effector fusion protein and/or complex thereof or pharmaceutical composition is from about 10 nL to about 1 µL. For some embodiments, the therapeutically effective amount can be from about 1 ng to about 50 ng per injection, if administered via injection.

In some embodiments, the therapeutically effective amount can be from about 1 to about 2 micrograms per injection, such as for a systemically administered injection. In additional embodiments, the therapeutically effective amount can be about 200 to about 300 μL per injection, such as for a systemically administered injection. In some embodiments, the therapeutically effective amount can be about 5 ng/μL, such as for systemic injections. For some embodiments, the therapeutically effective amount can be about 1 to about 1.5 μg per 5 g of bodyweight. In some embodiments, the therapeutically effective amount can be from about 200 μg to about 300 μg per kg of bodyweight.

In embodiments where there is an auxiliary active agent contained in the pharmaceutical formulation in addition to the targeted effector fusion protein and/or complex thereof, the therapeutically effective amount of the auxiliary active agent will vary depending on the auxiliary active agent. In some embodiments, the effective amount of the auxiliary active agent ranges from 0.001 micrograms to about 1 milligram. In other embodiments, the effective amount of the auxiliary active agent ranges from about 0.01 IU to about 1000 IU. In further embodiments, the effective amount of the auxiliary active agent ranges from 0.001 mL to about 1 mL. In yet other embodiments, the effective amount of the auxiliary active agent ranges from about 1% w/w to about 50% w/w of the total pharmaceutical formulation. In additional embodiments, the effective amount of the auxiliary active agent ranges from about 1% v/v to about 50% v/v of the total pharmaceutical formulation. In still other embodiments, the effective amount of the auxiliary active agent ranges from about 1% w/v to about 50% w/v of the total pharmaceutical formulation.

Dosage Forms

In some embodiments, the pharmaceutical formulations described herein may be in a dosage form. The dosage forms can be adapted for administration by any appropriate route. The dosage forms can be adapted for system administration. The dosage formas can be adapted for local administration. Appropriate routes include, but are not limited to, oral (including buccal or sublingual), rectal, epidural, intracranial, intraocular, inhaled, intranasal, topical (including buccal, sublingual, or transdermal), vaginal, intraurethral, parenteral, intracranial, subcutaneous, intramuscular, intravenous, intraperitoneal, intradermal, intraosseous, intracardiac, intraarticular, intracavernous, intrathecal, intravitreal, intracerebral, gingival, subgingival, intracerebroventricular, and intradermal. Such formulations may be prepared by any method known in the art.

Dosage forms adapted for oral administration can be discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as foam, spray, or liquid solution. In some embodiments, the oral dosage form can contain about 1 ng to 1000 g of a pharmaceutical formulation containing a therapeutically effective amount or an appropriate fraction thereof of the targeted effector fusion protein and/or complex thereof or composition containing the targeted effector fusion protein and or complex thereof. The oral dosage form can be administered to a subject in need thereof.

Where appropriate, the dosage forms described herein can be microencapsulated. The dosage form can also be prepared to prolong or sustain the release of any ingredient. In some embodiments, the targeted effector fusion protein or complex thereof can be the ingredient whose release is delayed.

In other embodiments, the release of an optionally included auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, MD, 2000, and "Pharmaceutical dosage forms and drug delivery systems", 6th Edition, Ansel et al., (Media, PA: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, the targeted effector fusion protein or complex thereof, auxiliary active ingredient, and/or pharmaceutically acceptable salt thereof can be formulated with a paraffinic or water-miscible ointment base. In some embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, the targeted effector fusion protein and/or complex thereof, the composition or formulation containing a targeted effector fusion protein and/or complex thereof, auxiliary active ingredient, and/or pharmaceutically acceptable salt thereof in a dosage form adapted for inhalation is in a particle-size-reduced form that is obtained or obtainable by micronization. In some embodiments, the particle size of the size reduced (e.g., micronized) compound or salt or solvate thereof, is defined by a D50 value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient (e.g., the targeted effector proteins and/or complexes thereof, compositions thereof, and formulations thereof, and/or auxiliary active agent), which may be generated by various types of metered dose pressurized aerosols, nebulizers, or insufflators.

In some embodiments, the dosage forms can be aerosol formulations suitable for administration by inhalation. In some of these embodiments, the aerosol formulation can contain a solution or fine suspension of the targeted effector fusion protein and/or complex thereof, the composition or formulation containing a targeted effector fusion protein and/or complex thereof, and/or pharmaceutically acceptable salt thereof, and a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g., metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of a targeted effector fusion protein, composition containing a targeted effector fusion protein, or a pharmaceutical formulation thereof. In further embodiments, the aerosol formulation can also contain co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, or 3 doses are delivered each time.

For some dosage forms suitable and/or adapted for inhaled administration, the pharmaceutical formulation is a dry powder inhalable formulation. In addition to the targeted effector fusion protein and/or complex thereof, the composition or formulation containing a targeted effector fusion protein and/or complex thereof, an auxiliary active ingredient, and/or pharmaceutically acceptable salt thereof, such a dosage form can contain a powder base such as lactose, glucose, trehalose, manitol, and/or starch. In some of these embodiments, the targeted effector fusion protein, the composition containing a targeted effector fusion protein, auxiliary active ingredient, and/or pharmaceutically acceptable salt thereof is in a particle-size reduced form. In further embodiments, a performance modifier, such as L-leucine or another amino acid, cellobiose octaacetate, and/or metals salts of stearic acid, such as magnesium or calcium stearate.

In some embodiments, the aerosol dosage forms can be arranged so that each metered dose of aerosol contains a predetermined amount of an active ingredient, such as the one or more of the targeted effector fusion proteins and/or complexes thereof, or compositions containing a targeted effector fusion protein and/or complex thereof described herein.

Dosage forms adapted for vaginal administration can be presented as pessaries, tampons, creams, gels, pastes, foams, or spray formulations. Dosage forms adapted for rectal administration include suppositories or enemas.

Dosage forms adapted for parenteral administration and/or adapted for any type of injection (e.g., intravenous, intraperitoneal, subcutaneous, intramuscular, intradermal, intraosseous, epidural, intracardiac, intraarticular, intracavernous, gingival, subginigival, intrathecal, intravireal, intracerebral, and intracerebroventricular) can include aqueous and/or non-aqueous sterile injection solutions, which can contain anti-oxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and resuspended in a sterile carrier to reconstitute the dose prior to administration. Extemporaneous injection solutions and suspensions can be prepared in some embodiments, from sterile powders, granules, and tablets.

Dosage forms adapted for ocular administration can include aqueous and/or non-aqueous sterile solutions that can optionally be adapted for injection, and which can optionally contain anti-oxidants, buffers, bacteriostats, solutes that render the composition isotonic with the eye or fluid contained therein or around the eye of the subject, and aqueous and non-aqueous sterile suspensions, which can include suspending agents and thickening agents.

For some embodiments, the dosage form contains a predetermined amount of the targeted effector fusion protein and/or complex thereof, or formulation or composition containing a targeted effector fusion protein and/or complex thereof per unit dose. In some embodiments, the predetermined amount of the targeted effector fusion protein and or complex thereof or composition or formulation thereof is a therapeutically effective amount of the targeted effector fusion protein and/or complex thereof, composition thereof, or formulation thereof, effective to treat or prevent a ChABC enzymatic deficiency, glial scarring, and/or a central nervous system injury (including but not limited to a spinal chord injury), stroke, and/or ischemic brain injury. The therapeutically effective amount included in the dosage for can also promote axonal plasticity by, for example, degrading perineuronal nets, improve and/or maintain neurological function following stroke/ischemic brain injury, promote the repair of spinal cord injuries (e.g., contusion) by, for example, facilitating regrowth of axons. Increase efficacy of transplanted cell therapies into CNS, facilitate decellularization of transplanted nerve grafts and/or improve patency of implanted neural electrodes.

In other embodiments, the predetermined amount of the targeted effector fusion protein and/or complex thereof, composition thereof, formulation thereof can be an appropriate fraction of the therapeutically effective amount of the active ingredient (e.g., targeted effector fusion protein and/or complex thereof, composition thereof, formulation thereof and/or auxiliary active agent). Such unit doses may therefore be administered once or more than once a day. Such pharmaceutical formulations may be prepared by any of the methods well known in the art.

Methods of Using the Targeted Effector Proteins

The targeted effector fusion protein(s) and complex(es) thereof and pharmaceutical formulations thereof described herein can be used for the treatment and/or prevention of a disease, disorder, syndrome, or a symptom thereof in a subject. In some embodiments, the targeted effector fusion protein(s) and complex(es) thereof and pharmaceutical formulations thereof described herein can be used to treat and/or prevent a chABC enzyme deficiency, glial scarring, a central nervous system injury, a stroke, peripheral nerve repair (for example, nerve transection (e.g., neurotmesis) or nerve crush (e.g., axonotmesis), for example occurring from surgery or inadvertent injury), an ischemic brain injury and/or a symptom thereof in a subject. The compositions and formulations described herein that can contain a ChABC polypeptide can be used for the stimulation of neuron regeneration, promotion of axonal plasticity by, for example, degrading perineuronal nets, improvement and/or maintenance of neurological function following stroke/ischemic brain injury, promotion of repair of spinal cord injuries (e.g., contusion) by, for example, facilitation of the regrowth of axons, increasing efficacy of transplanted cell therapies into the CNS, facilitation of the decellularization of transplanted nerve grafts, and/or improvement of the patency of implanted neural electrodes.

An amount of the targeted effector fusion protein(s) and complex(es) thereof and compositions and pharmaceutical formulations thereof described herein can be administered to a subject in need thereof one or more times per day, week, month, or year. In some embodiments, the amount administered can be the therapeutically effective amount of the targeted effector fusion protein(s) and complex(es) thereof and compositions and pharmaceutical formulations thereof. For example, the targeted effector fusion protein(s) and complex(es) thereof and compositions and pharmaceutical formulations thereof can be administered in a daily dose. This amount may be given in a single dose per day. In other embodiments, the daily dose may be administered over multiple doses per day, in which each containing a fraction of the total daily dose to be administered (sub-doses). In some embodiments, the amount of doses delivered per day is 2, 3, 4, 5, or 6. In further embodiments, the targeted effector fusion protein(s) and complex(es) thereof and compositions and pharmaceutical formulations thereof can be administered one or more times per week, such as 1, 2, 3, 4, 5, or 6 times per week. In other embodiments, the targeted effector fusion protein(s) and complex(es) thereof and compositions and pharmaceutical formulations thereof can be administered one or more times per month, such as 1 to 5 times per month. In still further embodiments, the targeted effector fusion protein(s) and complex(es) thereof and compositions and pharmaceutical formulations thereof can be administered one or more times per year, such as 1 to 11 times per year.

The targeted effector fusion protein(s) and complex(es) thereof and compositions and pharmaceutical formulations thereof can be co-administered with a secondary agent by any convenient route. The secondary agent is a separate compound and/or formulation from the targeted effector fusion protein(s) and complex(es) thereof and compositions and pharmaceutical formulations thereof. The secondary agent can be administered simultaneously with the targeted effector fusion protein(s) and complex(es) thereof and compositions and pharmaceutical formulations thereof. The secondary agent can be administered sequentially with the targeted effector fusion protein(s) and complex(es) thereof and compositions and pharmaceutical formulations thereof. The secondary agent can have an additive or synergistic effect to the targeted effector fusion protein(s) and complex(es) thereof and compositions and pharmaceutical formulations thereof. Suitable secondary agents include, but are not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics.

In embodiments where the targeted effector fusion protein(s) and complex(es) thereof and compositions and pharmaceutical formulations thereof are simultaneously co-administered with a secondary agent, the targeted effector fusion protein(s) and complex(es) thereof and compositions and pharmaceutical formulations thereof can be administered to the subject at substantially the same time as the secondary agent. As used in this context "substantially the same time" refers to administration of targeted effector fusion protein(s) and complex(es) thereof and compositions and pharmaceutical formulations thereof and a secondary agent where the period of time between administration of the targeted effector fusion protein, composition, or pharmaceutical formulation thereof and the secondary agent is between 0 and 10 minutes.

In embodiments where the targeted effector fusion protein(s) and complex(es) thereof and compositions and pharmaceutical formulations thereof is/are sequentially co-administered with a secondary agent, the targeted effector fusion protein(s) and complex(es) thereof and compositions and pharmaceutical formulations thereof can be administered first, and followed by administration of the secondary agent after a period of time. In other embodiments where the targeted effector fusion protein(s) and complex(es) thereof and compositions and pharmaceutical formulations thereof is/are sequentially co-administered with a secondary agent, the secondary agent can be administered first, and followed by administration of the targeted effector fusion protein, composition, or pharmaceutical formulations thereof after a period of time. The period of time between administration of the targeted effector fusion protein(s) and complex(es) thereof and compositions and pharmaceutical formulations thereof and the secondary agent can range from 10 minutes to about 96 hours. In some embodiments the period of time can be about 10 minutes, about 30 minutes, about 1 hour, about 2 hours, about 4 hours, about 6 hours, about 8 hours, about 10 hours, or about 12 hours. The sequential administration can be repeated as necessary over the course of the period of treatment.

The amount of the targeted effector fusion protein(s) and complex(es) thereof and compositions and pharmaceutical formulations thereof that can be administered are described elsewhere herein. The amount of the secondary agent will vary depending on the secondary agent. The amount of the secondary agent can be a therapeutically effective amount. In some embodiments, the effective amount of the secondary agent ranges from 0.001 micrograms to about 1 milligram. In other embodiments, the amount of the secondary agent ranges from about 0.01 IU to about 1000 IU. In further embodiments, the amount of the secondary agent ranges from 0.001 mL to about 1 mL. In yet other embodiments, the amount of the secondary agent ranges from about 1% w/w to about 50% w/w of the total pharmaceutical formulation. In additional embodiments, the amount of the secondary agent ranges from about 1% v/v to about 50% v/v of the total pharmaceutical formulation. In still other embodiments, the amount of the secondary agent ranges from about 1% w/v to about 50% w/v of the total secondary agent composition or pharmaceutical formulation.

In some embodiments, the composition or formulation containing the targeted effector fusion protein(s) and/or complex(es) thereof can be administered to a patient via an injection. Suitable methods of injection include, but are not limited to. intravenous, intraperitoneal, subcutaneous, intramuscular, intradermal, intraosseous, epidural, intracardiac, intraarticular, intracavernous, intrathecal, intravitreal, intracerebral, gingival, subginigival, intranodal, and intracerebroventricular injection. Other suitable methods of administration of the composition or formulation containing the targeted effector fusion protein include, but are not limited to, topical, transdermal, nasal, or oral delivery. In some embodiments, the dosage of the targeted effector fusion protein ranges from about 0.01 µg/g bodyweight to about 10 mg/g bodyweight. The inject can result in local delivery or systemic delivery of the composition or formulation containing the targeted effector fusion protein(s) and/or complex(es) thereof.

Kits Containing the Targeted Effector Fusion Protein and Formulations Thereof

The targeted effector fusion protein(s) and complex(es) thereof and compositions and pharmaceutical formulations thereof described herein can be presented as a combination kit. As used herein, the terms "combination kit" or "kit of parts" refers to the targeted effector fusion protein, compositions containing any one or more of the targeted effector fusion protein(s) and complex(es) thereof and compositions and pharmaceutical formulations thereof described herein and additional components that are used to package, sell, market, deliver, and/or administer the combination of elements or a single element, such as the active ingredient, contained therein. Such additional components include but are not limited to, packaging, syringes, blister packages, bottles, and the like. When one or more of the components (e.g., active agents) contained in the kit are administered simultaneously, the combination kit can contain the active agents in a single pharmaceutical formulation (e.g., a tablet) or in separate pharmaceutical formulations.

The combination kit can contain each agent, compound, pharmaceutical formulation or component thereof described herein, in separate compositions or pharmaceutical formulations. The separate compositions or pharmaceutical formulations can be contained in a single package or in separate packages within the kit. Also provided in some embodiments, are buffers, diluents, solubilization reagents, cell culture media and other reagents. These additional components can be contained in a single package or in separate packages within the kit.

In some embodiments, the combination kit also includes instructions printed on or otherwise contained in a tangible medium of expression. The instructions can provide information regarding the content of the targeted effector fusion protein, compositions containing the targeted effector fusion protein(s) and complex(es) thereof and compositions and pharmaceutical formulations thereof and/or other auxiliary and/or secondary agent contained therein, safety information regarding the content of the targeted effector fusion protein(s) and complex(es) thereof and compositions and pharmaceutical formulations thereof and/or other auxiliary and/or secondary agent contained therein, information regarding the dosages, indications for use, and/or recommended treatment regimen(s) for the targeted effector fusion protein(s) and complex(es) thereof and pharmaceutical formulations thereof and/or other auxiliary and/or secondary agent contained therein. In some embodiments, the instructions can provide directions for administering the targeted effector fusion protein(s) and/or complex(es) thereof and/or pharmaceutical formulations thereof and/or other auxiliary and/or secondary agent to a subject having or suspected of having a chABC enzyme deficiency, glial scarring, a central nervous system injury, peripheral nerve repair (for example, nerve transection (e.g., neurotmesis) or nerve crush (e.g., axonotmesis), for example occurring from surgery or inadvertent injury), and/or a symptom thereof in a subject. In some embodiments, the instructions can provide directions for administering the targeted effector fusion protein(s) and/or complexes thereof and/or pharmaceutical formulations thereof to a subject in need thereof. The subject in need thereof can have glial scarring, can have or be suspected of having a central nervous system injury, can be in need of neuron regeneration, can have or be suspected of having a stroke and/or ischemic brain injury, can have or be suspected of having a spinal chord injury, can be receiving or have received a transplanted cell therapy, where the transplanted cell therapy was delivered to the CNS, can have an implanted neural electrode, and/or can be in need of axonal plasticity and/or increased axonal plasticity, and/or degredation of perineuronal nets, improved and/or maintained neurological function, can have peripheral nerve repair (for example, nerve transection (e.g., neurotmesis) or nerve crush (e.g., axonotmesis), for example occurring from surgery or inadvertent injury), and/or decellularization of transplanted nerve grafts. In some embodiments, the instructions can provide directions for administering the targeted effector fusion protein(s) and/or complex(es) thereof to stimulate of neuron regeneration in a subject.

Without further elaboration, it is believed that one skilled in the art can, based on the description herein, utilize the present disclosure to its fullest extent. It is emphasized that the embodiments of the present disclosure, particularly any "preferred" embodiments, are merely possible examples of the implementations, merely set forth for a clear understanding of the principles of the disclosure. Many variations and modifications may be made to the disclosed embodiment(s) of the disclosure without departing substantially from the spirit and principles of the disclosure. All such modifications and variations are within the scope of this disclosure.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure. The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Example 1

Introduction

Presently, about 15% of all FDA-approved proteins are enzymes used to treat various diseases, including lysosomal storage disorders[1], immunodeficiency[2], leukemia[3], hemophilia B[4], and thrombosis[5]. Despite these notable successes, however, many attractive enzyme drug candidates fail in clinical trials due to unfavorable pharmacokinetics, pharmacodynamics, and safety profiles. For example, agalsidase alfa demonstrates widely varying pharmacokinetics[6], which requires frequent dosing that can lead to anti-drug antibody production[7]. A tumor-targeting variant of carboxypeptidase G2, a chemoprotective agent and chemotherapeutic pro-drug activator, has not been approved due to its immunogenicity[8]. Likewise, factor IX replacement therapy for hemophilia B is hindered by anti-drug antibodies that increase with the extent of mutation of the patient's factor IX gene[9]. Thus, strategies to improve enzyme pharmacokinetics, pharmacodynamics, and safety profiles by extending half-life, increasing target site accumulation, and minimizing immunogenicity hold promise for increasing the number of FDA-approved enzyme drugs.

Various chemical modifications can extend enzyme half-life or increase accumulation within target tissues. For example, modifying enzymes with hydrophilic polymers (e.g., poly(ethylene glycol), PEG) or dextran) can extend half-life in circulation by increasing drug hydrodynamic radius to prevent renal clearance and by masking proteolytic degradation sites[10, 11], as seen for Pegadamase and Pegaspargase[12]. However, modification with hydrophilic polymers does not promote enzyme accumulation at target sites within solid tissues, and therefore is largely limited to enzymes that are effective in systemic circulation. Additionally, PEG and dextran conjugates may be immunogenic and can dramatically reduce enzyme drug activity[13,14]. Encapsulating enzymes within controlled-release vehicles or immobilizing them onto solid phase carriers that can be introduced into a target tissue can extend the duration of localized biocatalysis, although the fabrication processes and degradation products of carriers and vehicles often greatly diminish enzyme catalytic activity[15]. Linking enzymes to antibodies or fragments thereof can increase accumulation within target tissues[16]. However, successful antibody-mediated targeting requires an antigen that is exclusively expressed by the target tissue, such as tumor antigens[17], as well as effective transport of relatively large antibody-enzyme conjugates over endothelial barriers, which is facilitated by the enhanced permeability and retention effect of tumor vasculature. Additionally, recombinant fusions of enzymes and single-chain antibodies are limited by weak binding affinity due to the lack of multivalent avidity effects, poor production efficiency, and potential immunogenicity[16, 17]. In contrast, covalent conjugation of enzymes to whole antibodies affords limited control of drug stoichiometry and orientation, which together can diminish activit[18, 19]. Finally, modifying enzymes with carbohydrates that recognize specific cell surface receptors has proven effective for increasing drug accumulation within target cell populations, as exemplified with Cerezyme used to treat Gaucher disease[20]. However, carbohydrate-mediated targeting can also lead to accumulation within non-target tissues, such as the liver and spleen, as seen for α-galactosidase A used to treat Fabry disease[6]. New strategies to enhance enzyme retention within tissues that address the practical limitations of targeted- or vehicle-mediated delivery would afford significant opportunities to improve the therapeutic efficacy of many existing and emerging enzyme drugs.

Figures 1A, 1B, 1C, 1D, 1E:
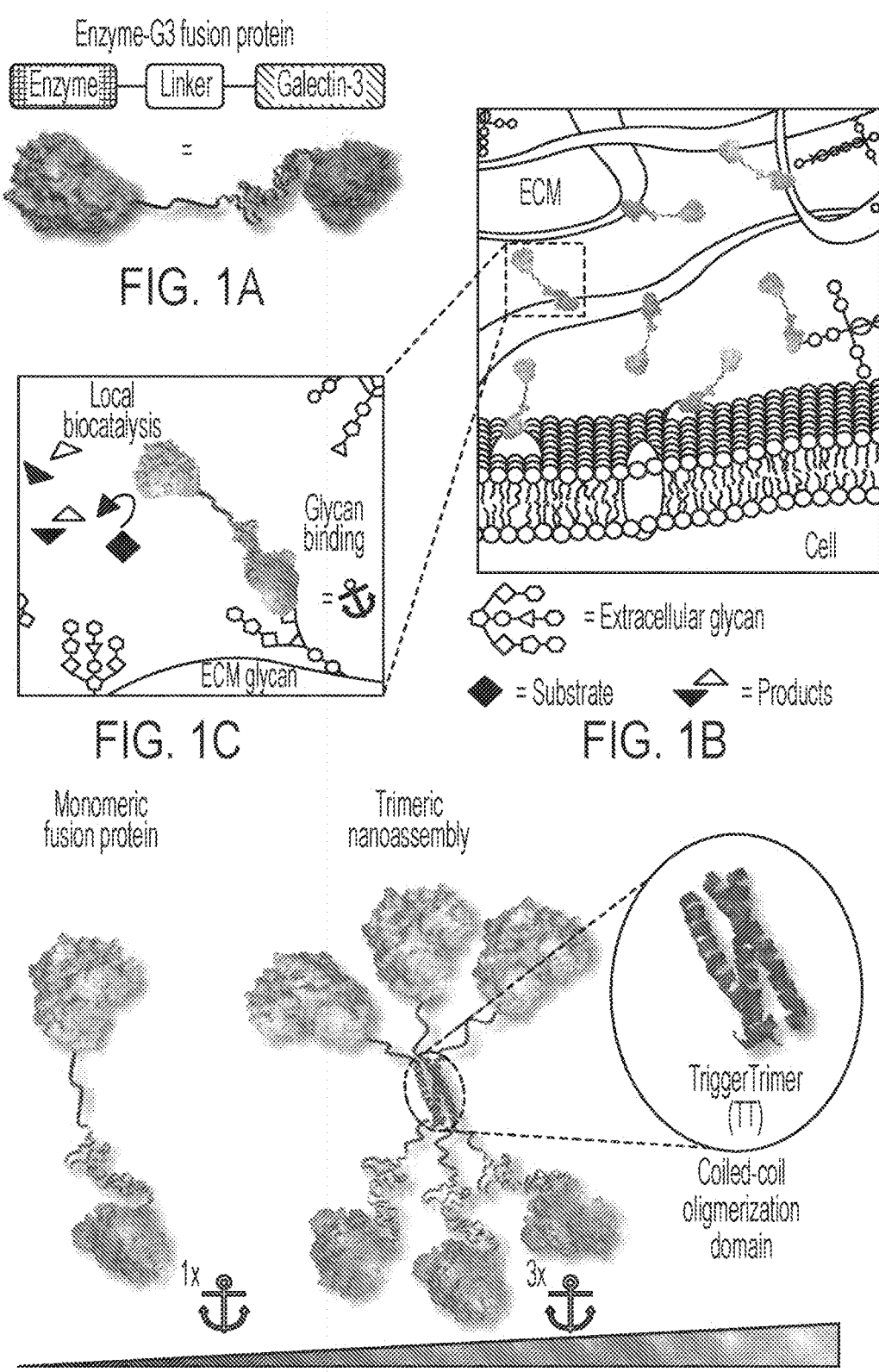
FIGS. 1A-1E show design of G3 fusion proteins to locally anchor enzymes to tissues via extracellular glycan binding. a-c Schematic of recombinant enzymes fused with galectin-3 (i.e., enzyme-G3 fusion protein), which are anchored to an injection site via binding to cell surface and extracellular matrix (ECM) glycans. d Monomeric fusion protein consisting of an enzyme linked to the N-terminal domain of galectin-3 via a flexible peptide linker. e Trimeric nanoassembly formed by inserting the TT domain between the enzyme and G3 domains. The trimeric nanoassembly has higher glycan-binding affinity than the monomeric fusion protein due to multivalent avidity effects. PDB ID: 253L [10.2210/pdb253L/pdb] (generic enzyme), 2O7H [10.2210/pdb2O7H/pdb] (generic coiled-coil), and 5NF7 [10.2210/pdb5NF7/pdb](carbohydraterecognition domain of galectin-3).

Previous reports demonstrate that engineering growth factors or antibodies to bind extracellular matrix proteins can increase their local retention in vitro and in vivo[21-24]. This Example describes an alternative approach to prolong enzyme retention within tissues via recombinant fusion to human galectin-3 (G3). G3 is a protein that binds to b-galactoside glycans, such as N-acetyllactosamine (LacNAc), as well as several glycosaminoglycans (GAGs), which are abundant within the extracellular matrix of mammalian tissues (FIGS. 1A-1B)[25, 26]. Within the extracellular space, G3 can modulate cell adhesion, migration, proliferation, differentiation, and death during various healthy and pathological processes by crosslinking cell surface glycoproteins into lattices[27]. Here, we proposed to use G3 as a fusion domain to endow enzymes with affinity for extracellular carbohydrates to restrict their diffusion through the extracellular space, analogous to growth factor binding to ECM GAGs and proteins[28, 29]. Without being bound by theory, it is believed that enzyme-G3 fusions anchored to an injection site can be retained locally for a longer duration than freely diffusible enzymes, thereby leading to extended pharmacokinetics (FIG. 1C). Fusion to the N-terminus was chosen because the carbohydrate recognition domain (CRD) of G3 is encoded by the C-terminal portion of the protein, while the N-terminal domain (NTD) is an intrinsically disordered domain thought to be involved in G3 self-association into higher ordered oligomers[30]. Notably, G3 variants lacking the NTD retain carbohydrate-binding affinity yet lack wildtype (WT-G3) activity as an extracellular signal[31, 32]. Without being bound by theory, it is believed that fusing an enzyme to the G3 NTD can endow carbohydrate-binding affinity, yet may also inactivate or alter native biological activities of G3 by disrupting its self-association into oligomers. G3 is an ideal fusion partner because it lacks disulfide bridges, does not require post-translational modifications, and is relatively small. Finally, the extracellular carbohydrates recognized by G3 are highly conserved across mammalian species, suggesting that this anchoring strategy will be amenable for human and animal use without requiring significant redesign.

To characterize the carbohydrate-binding properties, bioactivity, and in vivo pharmacokinetics of G3 fusions, we created different constructs in which proteins, such as the bioluminescent reporter NanoLuc™ luciferase (NL)[33], were linked to the N-terminus of G3. The first, which can be defined as a monomeric fusion protein, was composed of a protein connected to G3 via a flexible linker peptide (FIG. 1D). The second consisted of a protein connected to G3 via a linker peptide that forms a three-stranded α-helical coiled-coil, referred to as TriggerTrimer (TT), which was previously developed via site-specific mutation of the GCN4 leucine zipper (i.e., GCN4-pM3)34. Protein-TT-G3 fusions were designed to self-assemble into a nano-scale structure having three protein and three G3 domains via the TT domain, which we define as a trimeric nanoassembly (FIG. 1E). The increased G3 avidity of protein-TT-G3 nanoassemblies confers higher carbohydrate-binding affinity, which anchors the enzyme to an injection site for a longer duration than monomeric G3 fusions.

Results.

Figure 2A:
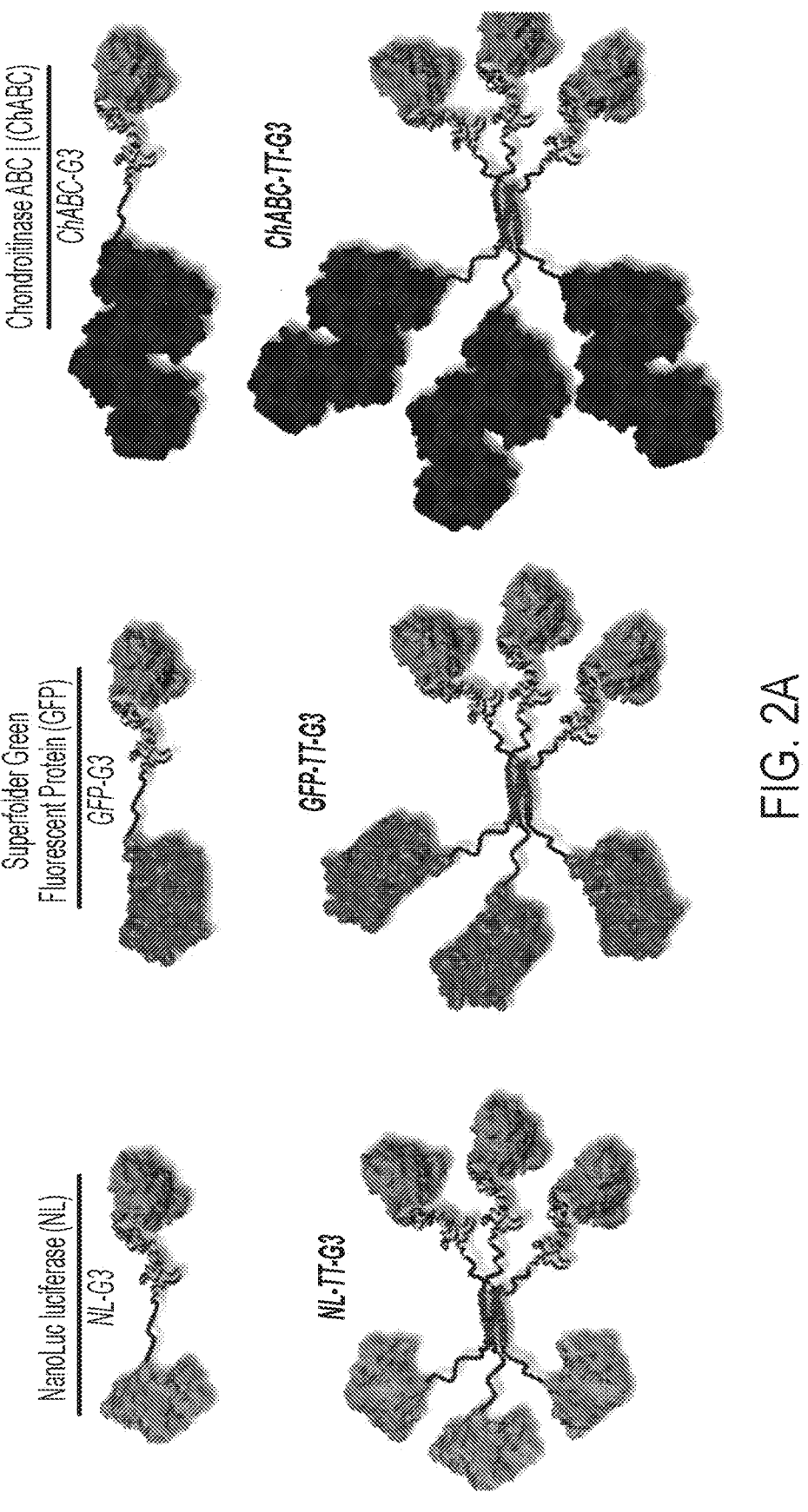
FIGS. 2A-2D show design and characterization of monomeric G3 fusion proteins and trimeric nanoassemblies. a Predicted structure of NanoLuc™ luciferase (NL), superfolder green fluorescent protein (GFP), and chondroitinase ABC I (ChABC) monomeric G3 fusion proteins and trimeric nanoassemblies. b Approximate molecular weight determined under native conditions via size-exclusion chromatography. c Average hydrodynamic diameter estimated via dynamic light scattering. d Quantitative bioluminescence, fluorescence, and reaction velocity of NL, GFP, and ChABC fusions, respectively. PDB ID: 5IBO [10.2210/pdb5IBO/pdb] (NanoLuc™ luciferase), 2B3P [10.2210/pdb2B3P/pdb] (superfolder green fluorescent protein), 1HN0 [10.2210/pdb1HN0/pdb] (chondroitinase ABC I) for a. N≥3, mean±s.d. for c. N=3, mean±s.d. for d. Data for monomeric G3 fusion proteins appear as circles/traces, trimeric nanoassemblies as triangles/traces.
Figures 2B, 2C:
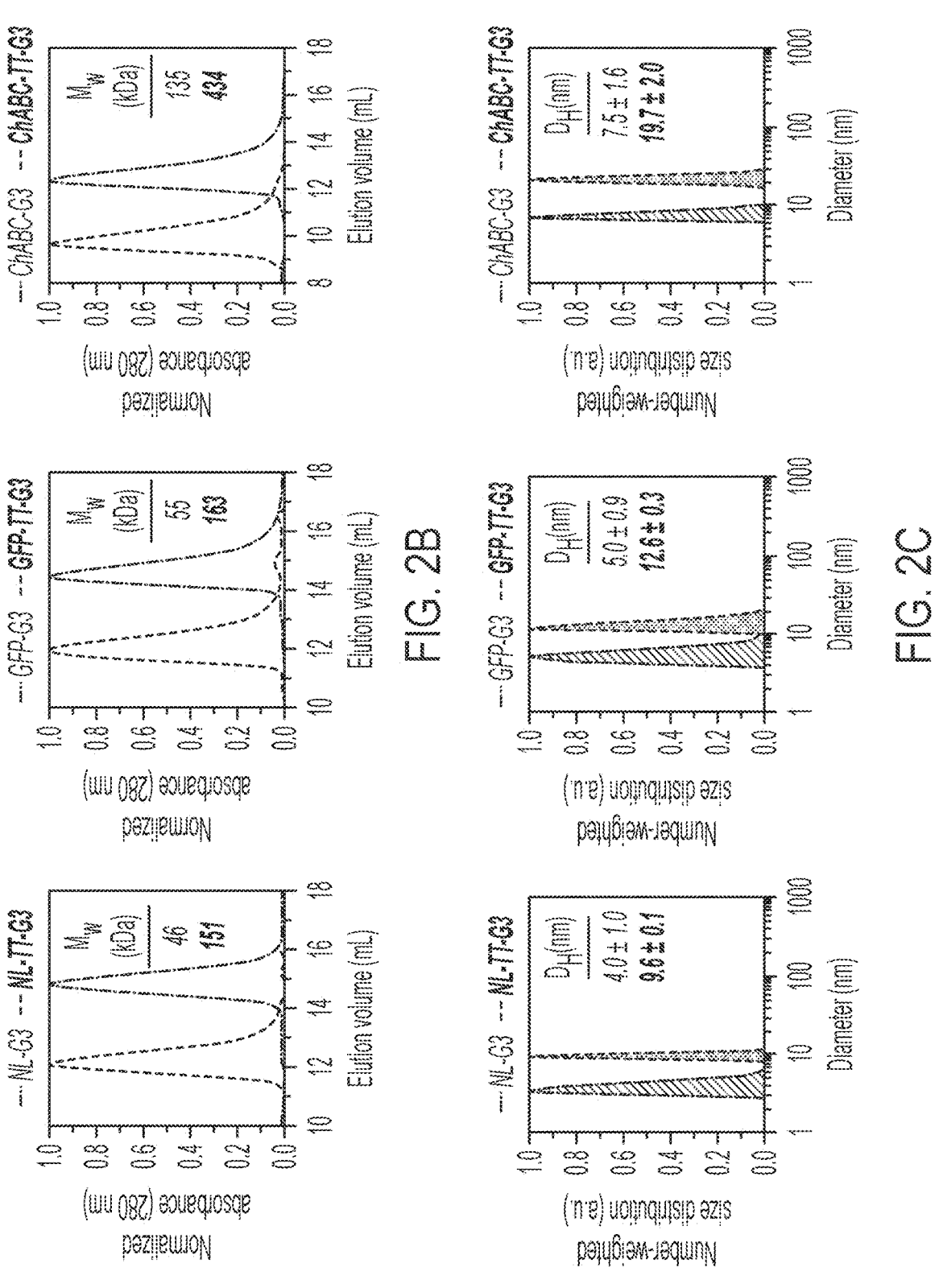
Figure 2D:
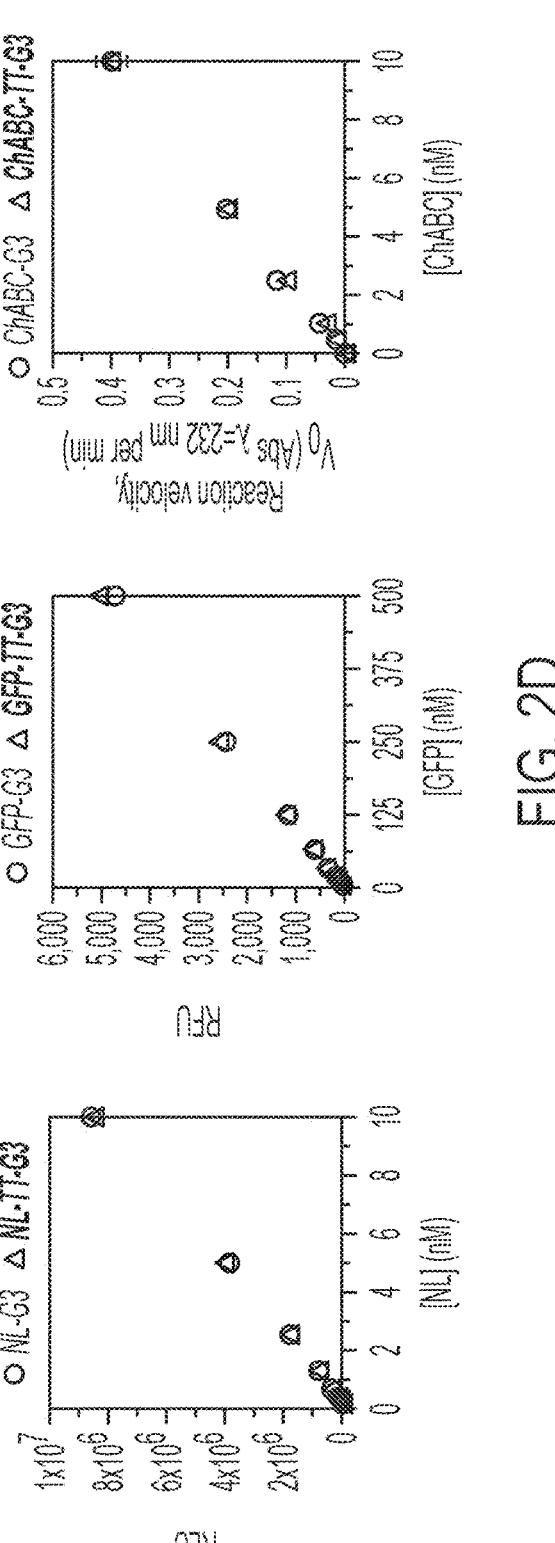

Expression of G3 Fusion Proteins. To characterize the expression, assembly, and activity of G3 fusions, different constructs were constructed in which NanoLuc™ luciferase (NL) (about 19 kDa), superfolder green fluorescentprotein (GFP) (about 27 kDa), or chondroitinase ABC I (ChABC) (about 115 kDa) (e.g., small, medium, and large proteins, respectively) were linked to the N-terminus of G3 or TT (FIG. 2A). All fusion proteins were expressed and recovered from E. coli in the soluble fraction at up to mg per L yields. Electrophoretic mobilities of these proteins under denaturing conditions were consistent with their theoretical denatured molecular weights, which ranged from 47.4 kDa for NL-G3 to 146.2 kDa for ChABC-TT-G3 (FIGS. 7A-7C). The hydrodynamic size of each trimeric nanoassembly determined under native conditions via size-exclusion chromatography was larger than its respective monomeric fusion, as indicated by a smaller elution volume (FIG. 2B). The empirical native molecular weights of each trimeric nanoassembly and fusion protein, which were determined from their elution volume, were consistent with native theoretical molecular weights (FIG. 8). Hydrodynamic diameters, as determined via dynamic light scattering number-weighted size distribution, were larger for each nanoassembly when compared to its respective monomeric fusion protein, and increased as the molecular weight of the enzyme increased (e.g., NL-G3<GFP-G3<ChABC-G3) (FIG. 2C). The DLS distribution demonstrated that monomeric fusion proteins and nanoassemblies were predominantly between 0-20 nm in diameter, suggesting that their tendency for non-specific aggregation in solution was low (FIGS. 40A-59). Consistent with this, protein concentration was similar before and after filtration through a 0.2 micron syringe filter (FIGS. 23A-23F and 34A-39B). Protein activities were evaluated for both monomeric fusion proteins and trimeric nanoassemblies when the concentration of the enzyme or GFP domain was held constant (FIG. 2D). NL-G3 and NL-TT-G3 produced comparable bioluminescence to equimolar quantities of wild-type NL (WT-NL) in the presence of the NL substrate furimazine (FIGS. 9A-9C), similar to previously reported soluble NL fusion proteins35. Likewise, GFP-G3 and GFP-TT-G3 produced comparable fluorescence when the GFP concentration was held constant, while ChABC-G3 and ChABC-TT-G3 demonstrated comparable catalytic activity for degrading chondroitin sulfate A (FIG. 2D). Collectively, these data demonstrated that active proteins with a broad range of molecular weights can be expressed as G3 fusions in microbial hosts and assembled into trimeric nanoassemblies via the TT domain.

Carbohydrate-binding Properties of G3 Fusion Proteins. The lactose binding properties of wild-type G3 (WT-G3), monomeric G3 fusion proteins, and trimeric G3 nanoassemblies were compared using lactose affinity chromatography (FIGS. 10A-10C). WT-G3 and monomeric G3 fusion proteins eluted from the column at a comparable concentration of soluble lactose indicating that they had similar binding affinity for immobilized lactose. In contrast, trimeric G3 nanoassemblies eluted with much broader profiles shifted to higher soluble lactose concentrations, corresponding with a higher apparent binding affinity for immobilized lactose than WT-G3 and monomeric fusions.

Next, NL luminescence and GFP fluorescence was used to characterize binding of monomeric fusion proteins and trimeric nanoassemblies to different surface-adsorbed ECM glycoproteins and proteoglycans, collectively referred to as glycoconjugates. First the fusion protein binding to surface-adsorbed asialofetuin (ASF), laminin, and collagen IV which are decorated with β-galactosides[25, 36] aggrecan which is decorated with G3-binding chondroitin sulfate GAGs[26], and collagen I which is minimally glycosylated and not an observed G3 ligand[25, 37] was compared. More trimeric nanoassemblies bound to surfaces coated with ASF, laminin, collagen IV, and aggrecan than control surfaces lacking adsorbed glycoconjugates, and this binding was inhibited by soluble LacNAc suggesting it was mediated by specific interactions between glycans on adsorbed glycoconjugates and the CRD of G3 (FIGS. 3A-3C). Likewise, no binding of NL-TT-G3 or GFP-TT-G3 to collagen I was observed, further suggesting that binding was specifically mediated by interactions between glycoconjugates and the CRD of G3 (FIGS. 3A-3B). No significant binding was detected for monomeric fusion proteins incubated with adsorbed glycoconjugates at an equivalent concentration of NL or GFP as the trimeric nanoassemblies (FIGS. 3A-3B). However, NL-G3 and GFP-G3 could be visualized bound to laminin at higher concentrations and this binding was also inhibited by soluble LacNAc suggesting it was mediated by specific interactions between laminin glycans and the G3 CRD (FIG. 3C). Additionally, while it was shown the specific binding to laminin, it was observed that the fusion enzyme provided for sustained release (FIG. 3D). Collectively, these data demonstrate that G3 fusion proteins and nanoassemblies specifically recognize glycoconjugates decorated with G3-binding glycans, and that nanoassemblies may have higher binding affinity than monomeric fusions, as reflected by their greater extent of binding.

To further characterize the binding affinity of monomeric fusion proteins and trimeric nanoassemblies for different glycoconjugates, competitive inhibition of their binding to ASF by soluble LacNAc, as well as their saturation binding profile for surface-adsorbed ASF and laminin was evaluated. Higher concentrations of LacNAc were required to inhibit binding of NL-TT-G3 and GFP-TT-G3 to adsorbed ASF when compared to NL-G3 and GFP-G3, respectively (FIG. 3E). Likewise, more GFP-TT-G3 bound to ASF or laminin than GFPG3 over a range of GFP concentrations, with GFP-TT-G3 approaching saturation at about 2 μM while GFP-G3 did not reach saturation up to 10 μM (FIG. 3F). Scatchard analysis of these saturating binding data suggested that GFP-G3 interactions with adsorbed glycoconjugates were non-cooperative, which was likely due to the monomeric fusion protein having only one CRD (FIGS. 11A-11B). The (1:1) dissociation constant (KD) of GFP-G3 for ASF and laminin was predicted to be 11.2 μM and 5.6 μM, respectively, where these differences likely reflect differences in the number of glycans conjugated to ASF versus laminin or the amount of each glycoprotein adsorbed onto the surface. In contrast, Scatchard analysis suggested positive cooperativity for GFP-TT-G3 interactions with ASF and laminin glycans (FIGS. 11A-11B), indicating that two or three CRDs of the trimeric nanoassembly may be bound simultaneously, which precluded accurate estimation of NL-TT-G3 KD for ASF and laminin. Taken together with the apparent binding affinity of monomeric fusions and trimeric nanoassemblies for immobilized lactose (FIGS. 10A-10B), these observations supported our overall hypothesis that multivalent avidity effects can endow trimeric nanoassemblies with higher apparent carbohydrate-binding affinity than monovalent fusion proteins.

Next, binding of NL-G3 and NL-TT-G3 to various sulfated GAGs that are known to bind WTG326 was compared. Specifically, a competition assay in which NL-G3 or NL-TT-G3 was first mixed with chondroitin sulfate-A, chondroitin sulfate-B, chondroitin sulfate-C, or heparin and then added to laminin-coated plates was used. All GAGs competitively inhibited NL-TT-G3 and NL-G3 binding to laminin, albeit to different extents, and the percentage of NL-TT-G3 bound to GAG versus laminin was greater than that for NL-G3 in all cases (FIG. 12). It was expected that NL-G3 and NL-TT-G3 would be resistant to non-specific interactions with anionic GAGs due to their net charges of −6 and −4 at neutral pH, respectively. Likewise, as shown in FIGS. 3A-3B, soluble LacNAc inhibited NL-TT-G3 and GFP-TT-G3 binding to aggrecan, suggesting that trimeric nanoassemblies specifically recognize chondroitin sulfate GAGs. Thus, taken together, these data demonstrated that NL-G3 and NL-TT-G3 recognize various GAGs that are known to bind WT-G3, although with different apparent affinities likely due to differences in their carbohydrate composition or sulfation profile. These data also suggested a propensity for NL-TT- G3 to remain bound to the first ligand it encountered. These results can support, the hypothesis that avidity effects can endow G3 nanoassemblies with higher relative binding affinity for carbohydrates than monomeric fusion proteins.

Finally, to determine if the observed increase in NL-TT-G3 carbohydrate-binding affinity was due solely to avidity effects or was due in part to perturbation of G3 conformation, the binding of soluble, monovalent lactose or LacNAc to NL-TT-G3, NL-G3, and WT-G3 was characterized using tryptophan fluorescence quenching. Unexpectedly, the LacNAc:NL-TT-G3 KD and the LacNAc:NL-G3 KD were approximately 5- and 2-fold lower than the LacNAc:G3 KD, respectively (FIG. 3G). Furthermore, the lactose:NL-TT-G3 KD was significantly lower than that of both NL-G3 and WT-G3, which were not statistically different from each other (FIGS. 13A-13D), and were consistent with previous reports for G3 and G3-fusions[25, 38]. Without being bound by theory, this can be due to regulation of the G3 carbohydrate-recognition domain (CRD) by its N-terminal domain (NTD). Some studies suggest that the NTD can mask the CRD[39-40], while others suggest that transient intramolecular interactions between the NTD and CRD of WT-G3 can diminish carbohydrate binding[41]. Consistent with this, some G3 fragments with truncated NTDs demonstrated significantly higher affinity for carbohydrates than WT-G3[42, 43]. We postulate that NTD fusion to NL or TT may hinder NTD-CRD interactions, thereby increasing G3 affinity for LacNAc. Additionally, steric hindrance imposed by NL-TT-G3 oligomerization may further prevent NTD-CRD interactions, resulting in NL-TT-G3 having higher LacNAc and lactose binding affinity. Although the actual molecular mechanism underlying this phenomenon remains unknown, the observations in this Example can suggest that increased apparent affinity of NL-TT-G3 for extracellular glycoconjugates is likely due to both multivalent avidity effects and increased monovalent carbohydrate-binding affinity.

Figures 4C, 4D:
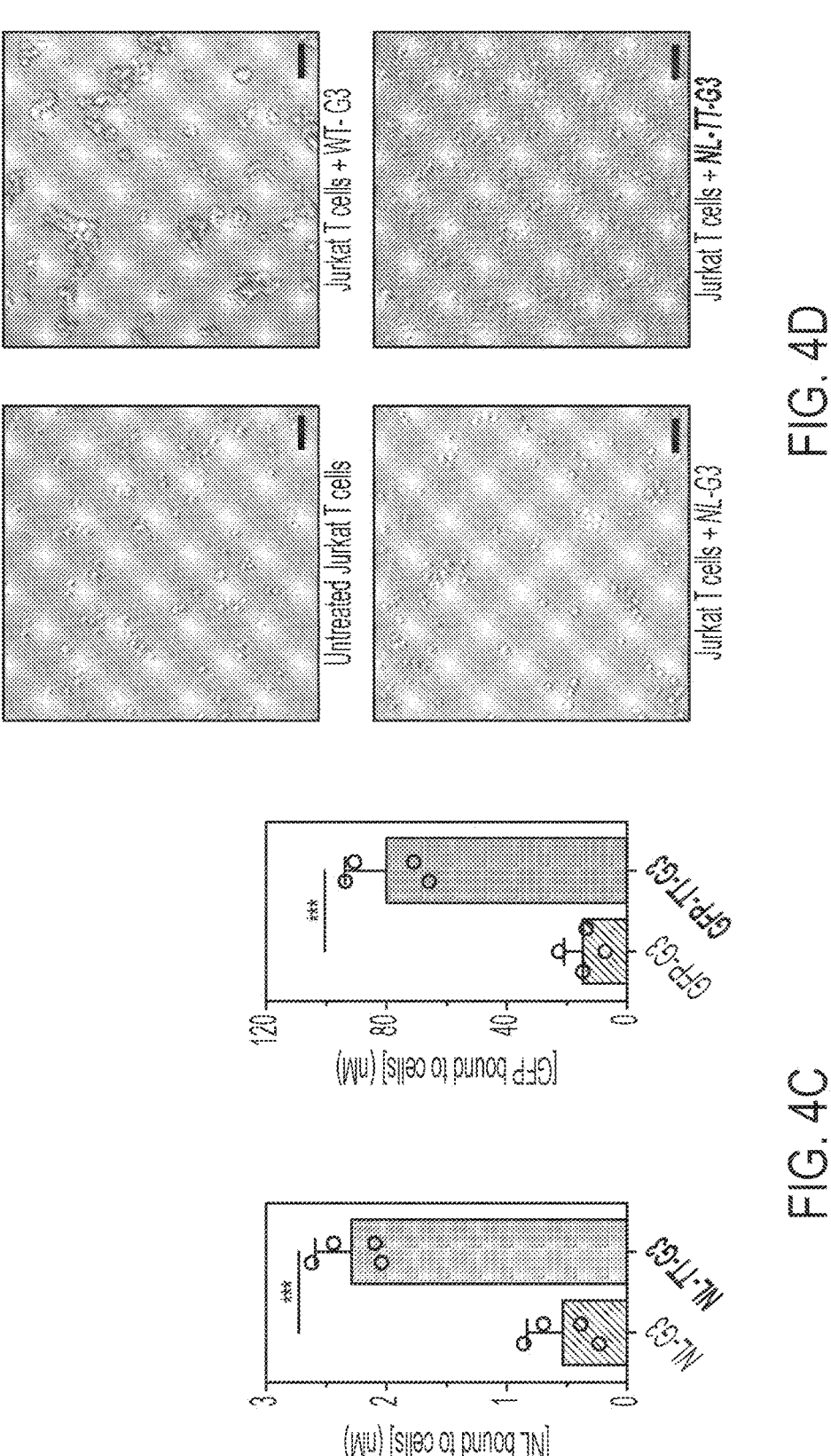
Figure 4F:
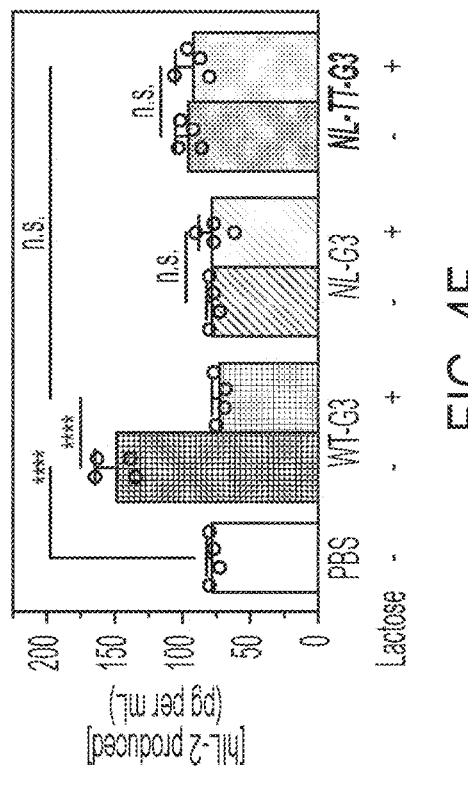
Figure 4E:
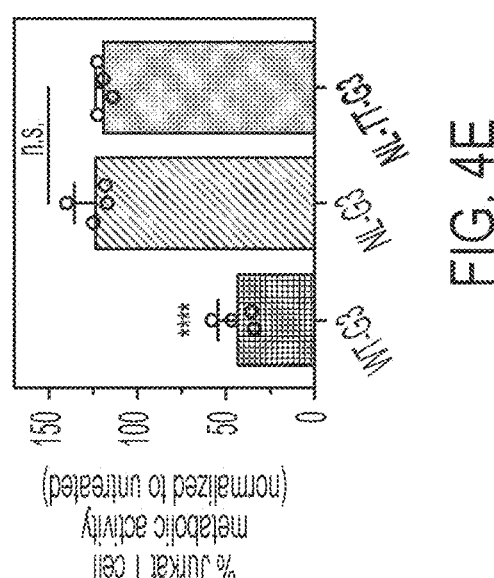
Figure 4G:
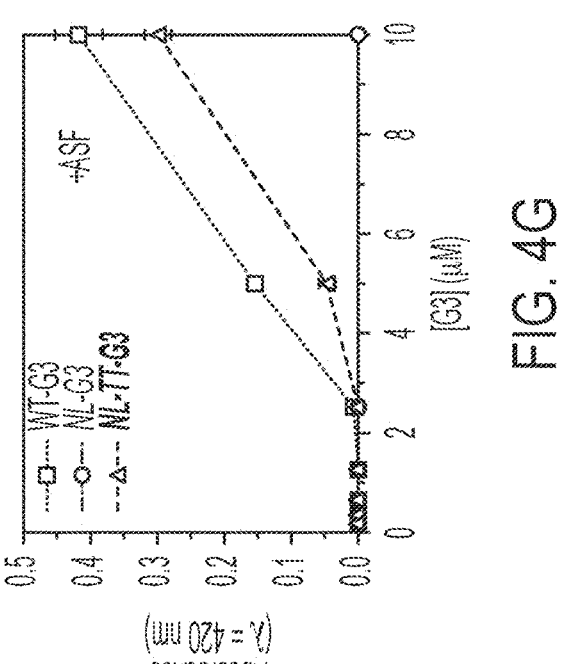

Extracellular Signaling Activity of G3 Fusion Proteins. WT-G3 can induce apoptosis of T cells, indicated by phosphatidylserine exposure, loss of metabolic activity, permeability to propidium iodide, and DNA fragmentation[44], which could be a deleterious immunosuppressive side-effect of enzyme-G3 fusion proteins. A combination of assays was used to compare changes in Jurkat T cell behavior induced by WT-G3, NL-G3, and NL-TT-G3. Jurkat T cells treated with NL-G3 and NL-TT-G3 produced luminescence in the presence of furimazine (FIG. 4A), while cells treated with GFP-G3 and GFP-TT-G3 produced fluorescence (FIG. 4B), demonstrating that both fusion proteins and nanoassemblies bound to cell surface glycans. Notably, significantly more trimeric nanoassemblies bound to Jurkat T cells than monomeric fusion proteins (FIG. 4C), consistent with glycoconjugate binding data (FIGS. 3A-B and 3F). As expected, WT-G3 induced Jurkat T cell agglutination (FIG. 4D), exposure of phosphatidylserine and permeability to propidium iodide (PI) (FIGS. 14A-15D), as well as metabolic activity loss (FIG. 4E), collectively indicating that WT-G3 decreased Jurkat T cell viability. In contrast, neither NL-G3 nor NL-TT-G3 induced Jurkat T cell agglutination nor metabolic activity loss at an equimolar G3 dose (FIGS. 4D-4E). Interestingly, Jurkat T cells treated with NL-G3 were negative for phosphatidylserine exposure and demonstrated comparable PI permeability to untreated cells, whereas cells treated with NL-G3 were positive for phosphatidylserine exposure but also demonstrated comparable PI permeability to untreated cells (FIGS. 14A-15D). Although often taken as an early marker of apoptosis, WT-G3 has been shown to induce non-apoptotic phosphatidylserine exposure on MOLT-4 leukemic T cells44, characterized by Annexin V positive/PI negative cells, and phosphatidylserine exposure independent of apoptosis has been reported for activated CD8+ T cells[45]. The comparable metabolic activity of Jurkat T cells treated with NL-TT-G3 and untreated cells suggests that phosphatidylserine exposure may not be an accurate determinant of early apoptosis in this model. Thus, these data demonstrate that G3 fusions and nanoassemblies do not share WT-G3 activity for inducing Jurkat T cell agglutination, membrane permeability, and loss of metabolic activity, although NL-TTG3 can induce phosphatidylserine exposure.

In addition to inducing apoptosis, lower concentrations of WT-G3 can also induce Jurkat T cell secretion of interleukin (IL)-2[46], a cytokine that can promote differentiation of effector and memory T cell populations upon antigen recognition. Jurkat T cells treated with WT-G3 secreted significantly more IL-2 than untreated cells (PBS) or cells treated with WT-G3 plus lactose inhibitor (FIG. 4F). In contrast, Jurkat T cells treated with NL-G3 and NL-TT-G3 secreted comparable amounts of IL-2 as untreated cells or cells treated with NLG3 or NL-TT-G3 plus lactose inhibitor. Thus, NL-G3 and NL-TT-G3 lacked the activity of WT-G3 for inducing Jurkat T cell IL-2 secretion.

The observation that NL-G3 and NL-TT-G3 bound to Jurkat T cells, yet had diminished activity for inducing cell agglutination, loss of metabolic activity, and IL-2 secretion when compared to WT-G3, may be due to the fused cargo on the NTD of G3. WT-G3 can self-associate into oligomers upon binding glycoproteins via interactions involving its NTD[47, 48], and one proposed mechanism of G3 activation of outside-in signaling is through cell surface glycoprotein clustering via these oligomers49. Prior reports demonstrated that G3 mutants with truncated NTDs failed to induce T cell death, likely because they were unable to self-associate into higher-ordered oligomers[31, 32]. Here, we considered that NL-G3 and NL-TT-G3 may also fail to induce Jurkat T cell agglutination, metabolic activity loss, and cytokine secretion because of a diminished ability to cluster glycoproteins when compared to WT-G3. Regions of punctate staining, suggestive of surface glycoprotein crosslinking, were identified in fluorescent photomicrographs of GFP-TT-G3 bound to Jurkat T cells yet were less pronounced in micrographs of bound GFP-G3 (FIG. 4B). Because G3 crosslinking of cell surface glycoproteins is difficult to evaluate quantitatively, we further characterized glycoprotein crosslinking via WT-G3, NL-G3, and NL-TT-G3 by adapting established precipitation assays based on the model glycoprotein ASF[47, 50]. WT-G3 crosslinked ASF into insoluble precipitates (FIG. 4G and FIGS. 60A-62 and 69A-71), consistent with prior reports[50, 51]. In contrast, NL-G3 failed to crosslink ASF into insoluble precipitates at any concentration tested (FIGS. 4G and 63A-65 and 72A-74). Interestingly, NL-TT-G3 crosslinked ASF into insoluble precipitates (FIGS. 4G and 66A-68 and 75A-77), but the resulting aggregates were smaller and took longer to form than those produced by WT-G3 (FIG. 16A-18). Additionally, NL-TT-G3 and GFP-TT-G3 induced formation of micron-sized particles in the presence of 10% fetal bovine serum (FIG. 4D and FIGS. 19A-19D), likely by interacting with G3-binding serum glycoproteins such as α-2-macroglobulin[52], whereas WT-G3 at an equivalent concentration induced less serum glycoprotein crosslinking (FIG. 4D and FIGS. 19A-19D). Collectively, these data suggest that appending a protein onto the G3 NTD can alter its glycoprotein crosslinking properties, presumably by perturbing its self-association into higher-ordered oligomers. Engineering G3 self-association into a trimer via the TT domain restored some of its glycoprotein crosslinking properties, yet this construct did not induce Jurkat T cell agglutination, PI permeability, loss of metabolic activity, or IL-2 secretion. Thus, WT-G3 activity as an extracellular T cell signal may require a CRD valency greater than 3 or a different CRD organization than that afforded by oligomerization via the TT domain. Alternatively, partitioning of NL-TT-G3 or GFP-TT-G3 into assemblies with serum glycoproteins may decrease the amount of G3 bound to cell surface glycans below the threshold required for activation of signaling mechanisms that lead to agglutination, loss of metabolic activity, PI permeability, or IL-2 secretion. Taken together, these data can suggest that NL-G3 and NL-TT-G3 will have a low likelihood of inducing unwanted changes in T cell behavior in vivo, in part due to an altered ability to crosslink and cluster cell surface glycoproteins.

Local In Vivo Half-Life of G3 Fusion Proteins.

The WT-NL, NL-G3, and NL-TT-G3 pharmacokinetics was evaluated in vivo at different common injection sites in mice by measuring local bioluminescence over time via in vivo imaging. Mice received a single, equivalent enzyme molar dose of WT-NL, NL-G3, or NLTT-G3 subcutaneously into the hock and scruff, as well as intramuscularly (IM) into the caudal thigh muscle, followed by daily local injections of furimazine substrate. Localized bioluminescence was detectable at subcutaneous sites in mice that received NL-TT-G3 for approximately 14 days, whereas catalytic activity persisted for approximately 6-8 days in mice that received NL-G3 (FIGS. 5A-5B). In contrast, no bioluminescence was detectable at 24 h in mice that received WT-NL. Localized bioluminescence was detectable at an IM site for approximately 3 days in mice that received NL-TT-G3, while catalytic activity persisted for approximately 1-2 days in mice that received NL-G3 (FIGS. 5A-5B). Again, no bioluminescence was detectable at an IM site at 24 h in mice that received WT-NL. NL-TT-G3 half-life at subcutaneous sites (mean±standard deviation, 33.5±13.3 h, hock; 31.8±24.4 h, scruff) was significantly longer than that of NL-G3 (mean±standard deviation, 10.4±2.8 h, hock; 6.1±1.0 h, scruff), whereas half-life could not be accurately determined for WT-NL due to rapid signal loss within 24 h (FIG. 5C). Likewise, NL-TT-G3 half-life at an IM site was 4.2±1.8 h (mean±standard deviation) (FIG. 5C), while NL-G3 and WT-NL half-life could not be accurately determined. Taken together, these data demonstrated that fusion to G3 can anchor an enzyme at an injection site for a significantly longer duration than unmodified enzyme, and that nanoassemblies have a longer half-life than monomeric fusion proteins.

Given that NL-G3 and NL-TT-G3 hydrodynamic diameters were smaller than typical ECM pore diameters (10 s of nm-μm)[53], we assumed that prolonged nanoassembly retention was not due to its larger size. Rather, it was inferred from these data that the longer half-life of NL-TT-G3 relative to NL-G3 was primarily due to differences in their apparent carbohydrate-binding affinity, as observed in vitro (FIGS. 3A-3C, 3E-3F, and 4C). The differences in NL-TT-G3 half-life at subcutaneous and IM injections sites may be due to attenuation of blue light emitted by NL at the deeper IM injection site54. The significant differences in NL-TT-G3 half-life at subcutaneous and intramuscular sites may also reflect differences in glycan content of different tissues, which can be a key determinant of G3 fusion protein and nanoassembly pharmacokinetics. Thus, the ability to increase the apparent carbohydrate-binding affinity of enzyme-G3 fusion proteins via self-assembly into multivalent structures may provide a simple route to extend enzyme pharmacokinetics even within tissues having low glycan content.

Clearance of G3 Fusion Proteins. The efficacy of enzymes as drugs is frequently challenged by various clearance mechanisms including phagocytosis by reticuloendothelial cells, antibody neutralization, proteolytic degradation, or renal excretion. To identify possible mechanisms of NL-G3 and NL-TT-G3 clearance, it was first evaluated if NL was present in circulation at various time points after subcutaneous injection into the hock. Less than 0.03% of the total injected mass of NL-TT-G3 or NL-G3 was detected in blood at 6 h, whereas no luminescence was detected in blood at 24 h or daily thereafter (FIG. 6A). This suggested that either the enzyme was not entering circulation, enzyme concentration in blood was too dilute to detect (<pM) as a result of rapid glomerular filtration, or that the enzyme was inactivated by serum proteases. However, NL-TT-G3 and NL-G3 were active for more than 18 h in 25% mouse serum at 37° C. invitro, suggesting that degradation by serum proteases was likely not a clearance mechanism (FIG. 6B). Given that the hydrodynamic diameter of NL-TT-G3 exceeded that of glomerular pores (4.5-5 nm)55, we inferred that the absence of NL in the blood was not due to renal filtration. Rather, these data suggested that NL-G3 and NL-TT-G3 were likely eliminated locally. Matrix metalloproteinases (MMPs), such as collagenase, can cleave the collagen-like NTD of WT-G3, thereby dissociating it from the about 16 kDa CRD (FIG. 6C)[56]. Here, we characterized collagenase degradation of WT-G3, NL-G3, and NL-TT-G3 using denaturing gel electrophoresis and SEC. As expected, collagenasetreated WT-G3 migrated as a single band having a lower molecular weight of about 16 kDa (FIG. 6D), consistent with prior reports[36], and eluted at a higher volume fraction (i.e., lower MW) than untreated WT-G3 via SEC (FIGS. 20A-20C). Similarly, collagenase-treated NL-G3 and NL-TT-G3 migrated to lower molecular weights when compared to untreated protein (FIG. 6D) and eluted at higher volume fractions via SEC (FIGS. 20A-20C). Taken together, these data suggest that the decreasing localized biocatalysis observed over time in vivo may be due to MMP-mediated dissociation of NL from G3, which would lead to enzyme diffusion away from the injection site. Additionally, other proteolytic enzymes not assayed here could also degrade NL or the linker domain, which would also lead to decreased localized biocatalysis over time in vivo. Thus, collectively, these data suggest that enzyme-G3 fusion protein and nanoassembly half-life can depend at least in part on their susceptibility to degradation via local tissue proteases.

Finally, because these fusion proteins are foreign to the host, generation of anti-NL antibodies raised by mice that received subcutaneous NL-G3 or NL-TT-G3 was evaluated twice, four weeks apart. These time points were chosen to ensure that protein injected at the initial time point was completely cleared before the second dose was received and to allow for sufficient time for serum IgG antibody generation. C57BL/6 mice that received NL emulsified in TiterMax Gold™ adjuvant raised significant serum IgG reactive against NL, while mice that received a TT-GFP fusion lacking G3 emulsified in TiterMax Gold™ adjuvant also raised significant serum IgG that were likely reactive against both the TT and GFP domains (FIGS. 21A-21C). In contrast, C57BL/6 mice raised little to no IgG serum antibodies against NL, NL-G3, or NL-TTG3 when the proteins were administered in the absence of an immunostimulatory adjuvant (FIGS. 21A-21C). The lack of antibodies reactive toward G3 fusions after two injections suggested that any depot effect due to the G3 domain did not enhance anti-NL immunogenicity and, therefore, may not be a mechanism of clearance in these studies. However, future efforts can be directed to thoroughly evaluate the immunogenicity of any new G3 fusion proteins on a case-by-case basis, likely by subjecting hosts to repeated injections at doses and over time frames that are relevant for their intended use.

Thermal Sensitivity of ChABC Enzyme and Complexes Thereof. FIGS. 85B-85C show graphs that can demonstrate the thermal sensitivity of the ChABC fusion enzyme and complex thereof. A slow decrease in the activity was observed when the enzymes were reconstityuted in 1×PBS and incubated at about 37° C. (n=1).). FIGS. 85A, 85D, and 85E show graphs of the thermal affects on the stability of various Chondroitinase ABC compositions; Choindroitinase ABC (FIG. 85A), Choindroitinase ABC-galectin-3 fusion enzyme (Monomer ChABC-Gal3) (FIG. 85D), and Choindroitinase ABC-galectin-3 fusion enzyme complex (Trimer ChABC-Gal3) (FIG. 85E). Discussion. In recent years, galectin fusions have gained interest as tools for glycobiology. For example, fusions of G3 with SNAP-tag and fluorescent proteins were developed for ELISA and flow cytometry applications[38, 57], while G3 fusions with bacterial alkaline phosphatase were developed to identify these glycosylation patterns[58]. Likewise, galectin-1 fusion domains are finding use for increasing the solubility of a glycosyltransferase enzyme that is prone to aggregation in *E. coli*, analogous to the application of recombinant maltose-binding fusion proteins[59]. In this Example, these applications were added to by demonstrating that fusing an enzyme to G3 can provide prolonged localized biocatalysis proximal to minimally-invasive injection sites by endowing the enzyme with affinity for extracellular glycans.

Prominent paradigms for therapeutic enzyme delivery extend half-life in circulation or rely on exit from circulation at specific tissue sites through discontinuous, damaged, or dysfunctional vasculature. The approach reported here can establish a delivery modality in which enzymes introduced directly into a desired tissue site persist over a tunable duration of time. Local enzyme activity half-life is dependent on the number of G3 units, which can be varied by engineering enzyme-G3 fusions to self-assemble into multimeric nanoassemblies. Importantly, WT-G3 activity for inducing T cell agglutination, phosphatidylserine exposure, loss of metabolic activity, IL-2 secretion, and death was abolished by fusing an enzyme to its N-terminus, thus potential immunomodulatory side-effects were mitigated. Engineering G3 self-association into a trimeric architecture increased carbohydrate-binding affinity, yet was insufficient to restore G3 activity as an extracellular signal, suggesting that WT-G3 biological activity requires oligomers having a CRD valency greater than 3 or a different CRD orientation than that afforded by assembly via the TT domain. Notably, small, medium, and large G3 fusion proteins and nanoassemblies were expressed and recovered in the soluble fraction from microbial hosts, suggesting that this platform is widely applicable to different functional protein domains and can be readily scaled up using established, cost-effective bioprocess methods. Additionally, in contrast to many conventional drug targeting moieties, G3 recognizes carbohydrate ligands that are highly conserved across mammalian species, suggesting that this anchoring strategy will be translatable across humans and animals. Finally, without being bound to theory, fusion to G3 can likely be applicable for localizing activity of non-enzyme protein drugs within specific tissues. Thus, by providing an attractive general approach to locally anchor proteins within target tissues via minimally-invasive injection routes while also preventing systemic biodistribution, we envision that galectin fusions will be broadly useful for improving local pharmacokinetics of various emerging therapeutic enzymes as well as those that have stalled in the development pipeline.

Methods.

Recombinant protein cloning, expression, and purification. NanoLuc™ is the tradename of an engineered deep sea shrimp luciferase variant developed by Promega Corporation[33]. Genes encoding fusion proteins were inserted into pET-21d(+) vectors between NcoI and XhoI sites. All genetic and protein sequences are provided in the Sequences Section herein. Plasmids were first transformed into One Shot TOP10 Chemically Competent *E. coli* (ThermoFisher) and selected on ampicillin (100 µg per mL) doped LB/agar plates overnight at 37° C. Isolated colonies from the plates were picked and cultured in 5 mL LB broth with ampicillin (100 µg per mL) overnight in an orbital shaker at 37° C., 225 rpm. Recombinant DNA was recovered with a plasmid miniprep kit (Qiagen) and sequenced using the Sanger method. Positive DNA sequences were then transformed into Origami B (DE3) *E. coli* (Novagen) and selected on ampicillin (100 µg per mL) and kanamycin B (50 µg per mL) doped LB/agar plates overnight at 37° C. Positive clones were picked and used to inoculate 5 mL of LB broth containing ampicillin (100 µg per mL) and kanamycin B (50 g per mL). Cultures were grown overnight at 37° C., 225 rpm on an orbital shaker and then sub-cultured into 1 L 2×TY media (16 g tryptone, 10 g yeast extract, 5 g NaCl) with ampicillin (100 µg per mL) and kanamycin B (50 µg per mL) at 37° C., 225 rpm in an orbital shaker until an O.D. at 600 nm=0.6-0.8 was reached. Cultures were then supplemented with 0.5 mM isopropyl β-D-1-thiogalactopyranoside (IPTG) (ThermoFisher) to induce protein expression and incubated for 18 h in an orbital shaker at 18° C., 225 rpm. Bacteria were washed with phosphate buffered saline (PBS) via centrifugation (11,300×g at 4° C. for 10 min) with a Sorvall RC 6 Plus Superspeed Centrifuge (ThermoFisher). Afterwards, the cell pellet was incubated for 20 min at room temperature (RT) with lysis buffer: B-PER bacterial protein extraction reagent (ThermoFisher), 1 Pierce protease inhibitor tablet (ThermoFisher), 2,400 units per mL DNAse I (ThermoFisher), and 50 mg per mL lysozyme (ThermoFisher). The cell pellet was mechanically broken apart with a spatula and further resuspended in wash buffer (PBS, pH 7.4, 20 mM imidazole). The lysate was centrifuged (42,600×g at 4° C. for 15 min) to remove the insoluble fraction and the supernatant was collected by decanting. Metal ion affinity chromatography was used to purify the protein of interest. His-tagged proteins from the soluble fraction were loaded onto HisTrap FF Crude Prepacked Columns (GE Healthcare) connected to an AKTA Pure FPLC system (GE Healthcare). Proteins were eluted from the column using a 0-500 mM imidazole gradient. Imidazole was removed from protein fractions using Amicon Ultra Centrifugal Filters with a 10 kDa cut-off (MilliporeSigma). Protein purity was determined by sodium dodecyl sulfate polyacrylamide gel electrophoresis (SDS-PAGE) and Coomassie staining. Endotoxin content at concentrations used for in vivo experiments was reduced below 1.0 EU per mL, the maximum acceptable allowable dose for pre-clinical drugs[60], using Detoxi-Gel Endotoxin Removing Columns (ThermoFisher). Final endotoxin content was determined with a Pierce LAL Chromogenic Endotoxin Quantitation Kit (ThermoFisher), according to the manufacturer's instructions.

Size Analysis. Fusion protein molecular weights were determined under denaturing conditions using SDSPAGE and protein ladder (BP3602500, ThermoFisher). Size-exclusion chromatography (SEC) was used todetermine fusion protein molecular weight under native conditions. Briefly, a 250 μL solution of protein in PBS was loaded onto a SuperDex-200 10/30 GL column (GE Healthcare) connected to an AKTA pure FPLC system. Eluted proteins were detected at an absorbance of 280 nm, which was normalized based on maximum signal intensity. Fusion protein molecular weight was calculated by fitting protein elution volume to a calibration curve prepared using protein standard markers (Bio-Rad, GE Healthcare, ThermoFisher) (FIG. 22A-22B). Hydrodynamic diameter of fusion proteins was approximated via dynamic light scattering on a NanoBrook 90Plus Particle Size Analyzer and BIC Particle Sizing Software (Brookhaven Instruments). Proteins in PBS were filtered and equilibrated to RT before size measurements. The molar concentration of fusion proteins was measured before and after filtration via UV absorbance at 280 nm using a NanoDrop spectrophotometer (FIGS. 23A-23F and 34A-39B) (ThermoFisher). Extinction coefficients determined using the ExPASy ProtParam tool were: 2,544 M−1 mm-1 for WT-NL; 6,131 M−1 mm-1 for NL-G3; 6,292.5 M−1 mm-1 for NL-TT-G3; 5639.5 M−1 mm-1 for GFP-G3; 5788.5 M−1 mm-1 for GFP-TT-G3; 22,346 M−1 mm-1 for ChABC-G3; 22,495 M−1 mm-1 for ChABC-TT-G3. Hydrodynamic diameter ±standard deviation by number-, volume-, intensity-, and in some cases, surface area-weighted size distribution were determined from ten 30 s runs in triplicate or more (FIGS. 40A-59).

G3 Fusion Partner Activity Assay. Molar concentration of fusion proteins was determined using a NanoDrop spectrophotometer, as described above. Standard curves of relative luminescence units (RLU) versus NL concentration were made by serially diluting NL in white, opaque 96-well microplates (Costar) and adding 50× dilution of stock furimazine (Nano-Glo™ substrate, PRN1120, Promega) in the buffer provided by the manufacturer at a 1:1 volume ratio. Signal was acquired using an open filter (emission=360-630 nm) and 500 ms integration time on a SpectraMax M3 Multi-Mode microplate reader (Molecular Devices) immediately after the addition of the substrate. To obtain mouse serum, institutional guidelines for the care and use of laboratory animals were strictly followed under a protocol approved by the University of Florida's Institutional Animal Care and Use Committee (IACUC). Bioluminescence produced by NL-G3 and NL-TT-G3 (final NL concentration=4 nM) in 25% wild-type female C57BL/6 mouse serum was measured over 18 h at 37° C. by combining NL fusions in PBS with 100% serum (1:1 volume) and then supplementing samples with a 50× dilution of stock furimazine (1:1 volume) at the specified timepoints. Bioluminescence signal was normalized (%) to bioluminescence at the initial time point. Qualitative digital photographic images were taken of blue bioluminescence emitted by WT-NL, NL-G3, and NL-TT-G3 at equal concentrations of enzyme in PBS mixed with 2 μL of stock Nano-Glo substrate (FIGS. 24A-24C).

GFP fusion concentrations were determined via UV absorbance at 280 nm using a NanoDrop spectrophotometer, as described above. Standard curves of relative fluorescence units (RFU) versus GFP concentration were made by serially diluting GFP in black, clear bottom 96-well microplates (Costar) with excitation=485 nm and emission=510 nm using a SpectraMax M3 plate reader. Fluorescence spectra of GFP fusions were measured at 500 nM GFP with the same settings (FIG. 25).

ChABC fusion concentrations were determined via UV absorbance at 280 nm using a NanoDrop spectrophotometer, as described above. ChABC activity was confirmed via absorbance at 232 nm in a glass cuvette (NC9469798, ThermoFisher), based on previous methods[62]. Specifically, ChABC-G3 and ChABC-TTG3 were mixed with their substrate, chondroitin sulfate A (1 mg per mL, C9819 MilliporeSigma), in PBS and their catalytic activity was measured on a SpectraMax M3 plate reader for 15 minutes with a reading every 1 minute. $V_o$ was obtained via linear regression analysis using GraphPad Prism over regions that followed first order enzyme kinetics. The slope, $V_o$, was then plotted versus the concentration of ChABC.

Carbohydrate Binding Assays. Fusion protein lactose binding was evaluated using an α-lactose-agarose affinity column connected to an AKTA pure FPLC system. α-lactose-agarose resin was purchased from a commercial source (L7634, MilliporeSigma) and packed into a column according to manufacturer's instructions (GE). Approximately 400 μL of 20 M protein was applied to the column. Unbound protein was removed by washing with 10 column volumes of PBS. Bound protein was eluted using a gradient of 0-100 mM soluble lactose in PBS. Eluted proteins were detected via absorbance at 280 nm, which was normalized based on maximum signal intensity.

Binding of NL and GFP fusions to ASF, laminin, aggrecan, collagen IV, or collagen I adsorbed onto plastic was determined via luminescence and fluorescence, respectively. For NL fusions, a white 96-well microplate was used, while for GFP fusions a black, clear bottom 96-well plate was used. Microplates were coated with 100 μL of 50 μg per mL ASF (A4781, MilliporeSigma), laminin (23-017-015, ThermoFisher), collagen IV (CB-40233, ThermoFisher), aggrecan (A1960, MilliporeSigma), and collagen I (C3867, MilliporeSigma) or PBS control for 2 h at 37° C. Next, the supernatant was aspirated and wells were washed with PBS followed by blocking with 100 μL of 1% bovine serum albumin (ThermoFisher) for 1 h at RT. Again, the supernatant was removed and wells were washed with PBS. Then, either 50 μL of NL fusions ([NL]=20 nM) or 100 μL of GFP fusions ([GFP]=500 nM) was added to the adsorbed glycoconjugates and incubated for 1 h at RT. As a control, either 50 μL of NL fusions with LacNAc (final [NL]=20 nM and final [LacNAc]=10 mM) or 100 μL of GFP fusions (final [GFP]=500 nM and final [LacNAc]=10 mM) was added to the adsorbed glycoconjugates and incubated for 1 h at RT. Note: different concentrations of NL and GFP fusions were used to account for differences in the detection limit of each protein (NL about 10 pM; GFP about 10 nM). Unbound protein was aspirated and wells were washed three times with PBS. Finally, for GFP fusions, bound protein was soaked in 100 μL PBS, and for NL fusions, bound protein was soaked in 50 μL PBS followed by 50 μL furimazine (50× dilution of stock). Fluorescence or bioluminescence emitted was measured for bound GFP or NL, respectively, using a SpectraMax M3 plate reader with excitation=485 nm and emission=510 nm (GFP) or an open filter with integration time=500 ms, similar to methods described above. Binding of a control protein (WT-NL) was also evaluated, as reported in FIG. 26. Bound GFP and NL concentrations were calculated using a standard curve, as described above.

Micrographs of NL bioluminescence and GFP fluorescence on glass slides coated with laminin (1.2 mg per mL) were obtained by overlaying 50 μL of 5 μM NL or GFP on the slides for 45 minutes at RT. Laminin was previously adsorbed onto glass in a coffee ring shape from a 2 μL droplet for 1 h at 37° C. As a control, proteins were mixed with soluble 10 mM LacNAc prior to addition to adsorbed laminin. Unbound GFP was washed off with 100 μL PBS five times before imaging. Unbound NL was washed off with 100 μL PBS, then soaked in 50 μL furimazine (50× dilution of stock) followed by a second 100 μL PBS wash. Images were taken using a Zeiss Axio Observer inverted microscope using a DAPI filter set for NL (excitation=380 and emission=450 nm) and GFP filter set for GFP (excitation=480 nm and emission=535 nm).

Free GAGs, which lack a hydrophobic protein core, are more challenging to adsorb onto polystyrene surfaces due to their strong hydrophilicity and negative charge[63]. Thus, the percentage of enzyme bound to free GAGs was determined using a competition assay with laminin pre-adsorbed onto polystyrene microplates, as described above. 1 mg per mL chondroitin sulfate (CS) A, B, C, and heparin (C9819, C3788, C4384, and H4784, respectively, MilliporeSigma) or PBS control were first mixed with WT-NL, NL-G3, or NLTT-G3 (final [NL]=4 nM). Then, 50 μL of this solution was added to laminin-coated plates (50 μg per mL laminin) and incubated for 30 min at RT. Unbound enzyme was removed with three PBS washes. 50 μL furimazine (50× dilution of stock) was added to each well and, immediately thereafter, luminescence produced in each well was quantified using a SpectraMax M3 plate reader using an open filter and 500 ms integration time. Baseline signal produced by WT-NL was subtracted from NL-G3 and NL-TT-G3. Bound enzyme concentrations were calculated using a standard curve, as described above. Percent enzyme bound to GAGs was calculated as 1 minus the ratio of [NL] bound to laminin in the GAG group: [NL] bound to laminin in the PBS control.

For competitive inhibition experiments, microplates were coated with ASF, blocked, and washed using the same protocols described above. LacNAc (0-10 mM) was mixed with NL or GFP fusions or nanoassemblies ([NL]=20 nM and [GFP]=500 nM) at a 1:1 volume ratio and then added to adsorbed ASF for 1 h at RT. Unbound protein was aspirated and wells were washed four times with PBS before bound NL or GFP concentration was determined using a Spectra-Max M3 plate reader according to protocols described above. Binding signal was normalized by first subtracting the minimum signal (10 mM LacNAc+protein) and then dividing by maximum signal (0 mM LacNAc+protein). Data were fit via non-linear regression analysis using GraphPad Prism.

Saturation binding curves were generated by adding increasing concentrations of GFP fusions ([GFP]=0-10 μM) to ASF or laminin pre-adsorbed onto microplates, followed by washing of unbound protein, and finally detection of bound protein, using protocols described above. Data were fit via non-linear regression analysis using GraphPad Prism. Scatchard plots from these data were created by calculating the ratio of bound GFP to free GFP at each GFP concentration for each individual replicate, and then plotting the means of these ratios at each GFP concentration vs the mean bound GFP at each concentration. Data for GFP-G3 binding were fit via linear regression and data for GFP-TT-G3 binding were fit via non-linear regression using GraphPad Prism.

WT-G3, NL-G3, and NL-TT-G3 binding affinity for soluble lactose and LacNAc were determined using a tryptophan fluorescence quenching assay, based on previous methods[61]. Specifically, tryptophan fluorescence quenching was detected by mixing in 5 μL increments of 10-2-104 μM soluble lactose or LacNAc in water to 500 μL of WT-G3, NL-G3, or NL-TT-G3 ([G3]=5 μM) in PBS in a quartz cuvette (NC9030411, ThermoFisher), and then measuring tryptophan fluorescence signal at excitation=280 nm and emission=345 nm with a SpectraMax M3 plate reader. As a control, water was mixed in 5 μL increments to 500 μL of WT-G3, NL-G3, or NL-TT-G3 ([G3]=5 μM) in PBS in a quartz cuvette. The change in fluorescence signal (ΔRFU) was calculated by subtracting RFU of bound protein (quenched fluorescence signal) from unbound protein (fluorescence signal of protein alone). Representative spectra are shown in FIGS. 27A-28C. ΔRFU at the lowest and highest concentration of lactose or LacNAc added to G3 proteins were analyzed for statistically significant differences to assess the signal to noise ratio for this assay (FIGS. 29A-29B). Dissociation constants were calculated via non-linear regression using GraphPad Prism.

Quantitative precipitation of ASF with WT-G3, NL-G3, and NL-TT-G3 was measured by light scattering and absorbance at 420 nm[47, 50]. Baseline signal of 7 μM ASF alone had a maximum absorbance of about 0.04. To evaluate assay sensitivity, WT-G3 at different concentrations was mixed with 7 μM ASF and insoluble aggregates that formed were measured by absorbance over a broad wavelength range (FIG. 30A). Aggregates could be detected at 420 nm when [G3]>2.5 μM. Based on these observations, absorbance of samples containing 10 μM WT-G3, 7 μM ASF, or 10 μM WT-G3 plus 7 μM ASF in PBS were then measured over a broad wavelength range (FIG. 30B). WT-G3 and ASF had maximum absorbances of ~0.04, while WT-G3 plus ASF had an absorbance of about 0.4. Based on these observations, WTG3, NL-G3, or NL-TT-G3 ([G3]=0-10 μM) was mixed with ASF (7 μM) at a 1:1 volume ratio in a clear 96-well microplate and absorbance at 420 nm was measured immediately thereafter using a SpectraMax M3 plate reader. Additionally, absorbance at 420 nm was collected every 30 s for 10 min to establish a time-course for insoluble aggregate formation when WT-G3, NL-G3, or NL-TT-G3 was mixed with ASF (FIG. 18). Brightfield micrographs and digital photographs were collected as qualitative representation of insoluble aggregate formation when 2.5 or 10 μM G3 was mixed with 7 μM ASF using a Zeiss Axio Observer inverted microscope or digital camera, respectively (FIGS. 16A-16H and 30C). Hydrodynamic diameter±standard deviation by number-, volume-, intensity-, and in some cases, surface area-weighted size distribution of insoluble aggregates was approximated via dynamic light scattering using a NanoBrook 90Plus Particle Size Analyzer and BIC Particle Sizing Software from ten 30 s runs in triplicate or more (Brookhaven Instruments) (FIGS. 60A-82B). Proteins in PBS were filtered and equilibrated to RT before mixing for size measurements. Brightfield and fluorescent micrographs were taken of WT-G3 and GFP-TT-G3 (final [G3] =10 μM) incubated in PBS with or without 10% fetal bovine serum for 1 h at 37° C. (FIGS. 19A-19D). Images were taken on a Zeiss Axio Observer inverted microscope with the same GFP fluorescence filter set described above.

G3 Fusion Protein and Nanoassembly binding to Jurkat T cells. For all experiments, Jurkat T cells (Clone E6-1, TIB-152, ATCC) were first expanded in complete media (RPMI 1640 supplemented with 10% heatinactivated fetal bovine serum, 1% penicillin-streptomycin, L-glutamine 200 mM, 1% HEPES buffer) at 37° C., 5% $CO_2$. Cells were then aliquoted (20,000 cells per well) into sterile, clear, tissue culture-treated 96-well microplates. Cells were incubated with fusions (final [G3]=5 μM) for 4 h at 37° C. and then transferred to a V-bottom 96-well microplate and collected (400×g for 5 min) using a Jouan CR3i Multifunction Centrifuge equipped with a microplate rotor. The supernatant was carefully pipetted from the wells without disrupting the cell pellet. Cells were resuspended in 50 μL PBS for NL fusions or 100 μL PBS for GFP fusions. Cells were transferred to either a white, opaque 96-well microplate for detection of NL or black, clear bottom 96-well microplate for detection of GFP fusions. Fluorescence from GFP fusions bound to cells was measured directly on a Spectra-Max M3 plate reader (excitation=485 nm, emission=510 nm). For cells treated with NL fusions, 50 μL furimazine (50×dilution of stock) was added to each well and bioluminescence produced in each well was quantified immediately using a SpectraMax M3 plate reader using an open filter and 500 ms integration time. Bound NL or GFP concentrations were calculated using a standard curve, as described above. Micrographs of NL and GFP localized to the surface of Jurkat T cells, using protocols described above, were taken with a Zeiss Axio Observer inverted microscope with DAPI and GFP fluorescent filter sets described before.

Changes in Jurkat T Cell Phenotype and Function. Extracellular activity of WT-G3, NL-G3, and NL-TT-G3 was characterized using Jurkat T cells. For all experiments, cells were first expanded in complete Jurkat T cell media (RPMI 1640 supplemented with 10% heat-inactivated fetal bovine serum, 1% penicillin-streptomycin, L-glutamine 200 mM, 1% HEPES buffer) at 37° C., 5% $CO_2$. Cells were then aliquoted (20,000 cells per well) into sterile, clear, tissue culture-treated 96-well microplates. To evaluate agglutination, cells were incubated with WT-G3, NL-G3, or NL-TT-G3 (final [G3]=5 μM) and then imaged intermittently over 4 h using a Zeiss Axio Observer inverted microscope. To determine changes in cell metabolic activity, Jurkat T cells were incubated with WT-G3, NL-G3, or NL-TT-G3 ([G3]=5 μM) for 4 h followed by incubation with 20 μL per well CellTiter-Blue reagent (PR-G8080, Promega) for 2 h, based on previous methods[61]. Fluorescence produced in each well was then measured using a SpectraMax M3 plate reader (excitation=560 nm, emission=590 nm). Background fluorescence of culture media plus CellTiter-Blue Reagent was subtracted from sample fluorescence. Finally, relative metabolic activity was reported as fluorescence of cells incubated with WT-G3, NL-G3, or NL-TT-G3 normalized to the fluorescence of untreated cells (PBS).

Jurkat T cell phosphatidylserine exposure and PI permeability were evaluated after treating cells with PBS (negative control), WT-G3 (positive control), NL-G3, and NL-TT-G3. Protocols for this experiment were adapted from prior reports64, using a BD Annexin V: FITC Apoptosis Detection Kit I (BD556547, ThermoFisher). Briefly, 500 μL of 2×106 cell per mL was mixed with 500 μL of 10 μM G3 in PBS in a 15 mL conical tube. Cells were then incubated for 4 h at 37° C. in a water bath before being cooled on ice for 10 min. 200 mM ice-cold lactose was added to the cells to remove bound G3, followed by 10 mL of 100 mM lactose and centrifugation at 413×g for 4 min on a Centrifuge 5804 R (Eppendorf). Supernatant was removed thereafter and cells were resuspended in 1 mL 1× Annexin V Binding Buffer (BD556547, ThermoFisher). 100 μL of the cells (~105 cells) were transferred to a 1.5 mL microtube and mixed with 5 μL FITC-Annexin V and 5 μL PI (BD556547, ThermoFisher). Cells were vortexed gently and incubated for 15 min at RT in the dark. 100 μL of 1× Annexin V Binding Buffer was added to the tube and then 100 μL was transferred to a glassbottom microwell (NC9069930, ThermoFisher) for brightfield and fluorescence imaging. Images were taken on a Zeiss Axio Observer inverted microscope with FITC (excitation=470/40 nm and emission=525/50 nm) and rhodamine (excitation=546/12 nm and emission=575-640 nm)

filter set. Individual and overlaid images are available at two magnifications in FIGS. 14A-15D.

To quantify the amount of IL-2 secreted by Jurkat T cells treated with WT-G3, NL-G3, or NL-TT-G3, cells were expanded and aliquoted at the same cell density as above into sterile, clear tissue culture-treated 96-well microplates. Cells were incubated with either PBS, WT-G3 in PBS, NL-G3 in PBS, NL-TT-G3 in PBS, WT-G3+25 mM lactose in PBS, NL-G3+25 mM lactose in PBS, or NL-TT-G3+25 mM lactose in PBS (final [G3]=2.5 μM) for 24 h at 37° C. G3 concentration and incubation time were chosen based on previous reports of WT-G3 induced secretion of IL-2 by Jurkat T cells46. Cells were then centrifuged, as described above, and the supernatant was collected and analyzed for human IL-2 using a commercially-available solid-phase ELISA kit (Quantikine Human IL-2 Immunoassay, D2050, R&D systems), according to manufacturer's instructions. The IL-2 concentration was calculated from the standard curve shown in FIG. 31.

In vivo Imaging and Pharmacokinetics. In all in vivo imaging and pharmacokinetics experiments, institutional guidelines for the care and use of laboratory animals were strictly followed under a protocol approved by the University of Florida's Institutional Animal Care and Use Committee (IACUC). Each injection site had an independent cohort (N=5) of 8-week-old, female wild-type C57BL/6 mice (The Jackson Laboratory). Prior to protein injection, mice were anesthetized with isoflurane and treated with hair removal cream at the injection site. While anesthetized, mice received a single injection of 40 μL WT-NL, NL-G3, or NL-TT-G3 ([NL]=3.27 μM for all formulations) in sterile PBS subcutaneously into the hock or scruff, or intramuscularly (IM) into the caudal thigh muscle. Immediately thereafter, mice received a 40 μL injection of furimazine (50× dilution of stock) in sterile PBS. Mice were then anatomically positioned with injected tissue facing the charge-coupled device (CCD) camera of an IVIS Spectrum In Vivo Imaging System (PerkinElmer) and whole-body bioluminescent images were taken (note: in all experiments this is referred to as t=0). Every 24 h thereafter, mice were anesthetized, and substrate was again injected into the hock, scruff, or thigh. Images were captured immediately thereafter as described for t=0. Bioluminescent images were captured using an open emission filter, subject size 1.5 cm, 1 s exposure time, field-of-view B (6.6 cm), medium binning (factor of 8) resolution, and a 1 F/Stop aperture. Relative light intensities, corresponding with local bioluminescence, were represented by a pseudo color scale ranging from violet (least intense) to red (most intense). Signal produced as color also represented photons, which was then converted to photon flux (photons per s) within a circular region of interest (ROI) using Living Image analysis software. For each injection site, the size of the ROI was manually drawn out to the perimeter of the bioluminescence signal produced at t=0. Color scale limits were adjusted to min=1e6 and max=4e8 manually for all images, and color scale bars are presented in log scale. Subsequently, all bioluminescent images were analyzed using the same size ROI to normalize for background signal and accurately quantify the decay in bioluminescence over time. Data (photon flux versus days) were analyzed on GraphPad Prism software using nonlinear regression to curve fit a one phase exponential decay and calculate a bioluminescence half-life. For samples in which bioluminescence above baseline was only detectable in tissue at t=0, half-life could not be detected because insufficient data points were available for non-linear regression curve fitting. Bioluminescence data for each mouse at t=0 are shown in FIGS. 32A-32C.

To detect the presence of NL in circulation, blood was drawn at 6 h and then daily thereafter from a cohort (N=5) of 8-week-old, female wild-type C57BL/6 mice that received a 40 μL subcutaneous injection of NL-G3 or NL-TT-G3 ([NL]=3.27 μM for both formulations) into the hock. At each time point, about 10 μL of blood was drawn from the tail vein using an 18-gauge needle. Blood samples were immediately mixed with 1 μL of 50 mM EDTA (anticoagulant), according to established methods[65]. 5 μL of blood was mixed with 50x dilution of furimazine (1:10 volume ratio) in a white, opaque 96-well microplate. Luminescence was immediately measured on a SpectraMax M3 plate reader. Background luminescence produced by the blood of mice that did not receive NL-G3 or NL-TT-G3 was subtracted from measured luminescence. NL concentration in blood was then calculated from luminescence using a standard curve, as described above. The amount of NL detected in blood was reported as the percentage of the total protein by mass injected into the hock.

Immunogenicity Assay. In all immunogenicity studies, institutional guidelines for the care and use of laboratory animals were strictly followed under a protocol approved by the University of Florida's Institutional Animal Care and Use Committee (IACUC). 8-week-old, female wild-type C57BL/6 mice (N=5) received scruff injections of 100 μL TT-GFP (control lacking galectin-3), WT-NL, NL-G3, or NL-TT-G3 ([NL]=1 μM for all formulations) in sterile PBS, based on previous methods[66]. For positive control, cohorts of mice were injected with WT-NL or TT-GFP emulsified in TiterMax Gold™ Adjuvant (T2684, MilliporeSigma). Blood was drawn from the submandibular maxillary vein every 2 weeks for 8 weeks. Immediately after blood was collected, sera were isolated via centrifugation and frozen until analysis. At 4 weeks, mice received a second injection of 50 μL of 1 μM protein in PBS or emulsified adjuvant, respectively. Anti-protein antibodies raised in mice were detected with peroxidase-conjugated goat anti-mouse IgG (NC9731556, ThermoFisher) at 450 nm absorbance in ELISA microplates coated with 1 μg per mL protein in PBS or with PBS alone (control), based on previous methods[67].

Collagenase Digestion. To characterize collagenase-mediated degradation, WT-G3, NL-G3, or NL-TT-G3 were treated with collagenase from *Clostridium histolyticum* (C7657, MilliporeSigma) in vitro, based on previous methods[36]. Specifically, collagenase was added to WT-G3, NL-G3, or NL-TT-G3 in PBS at a 3:1 mass ratio. The samples were then incubated at 37° C. for 2 h for SDS-PAGE analysis or 18 h for SEC (FIGS. 33 and 20A-20C, respectively).

Statistical Analysis. All experimental and control groups were n=3 for enzyme and GFP activity and were reported as average±standard deviation. DLS measurements were run at minimum in triplicate, and the data were reported as average±standard deviation. All experimental and control groups were n=3 for glycoconjugate, competitive inhibition, and saturation binding data. Dissociation constants for GFP-G3 from Scatchard curves were calculated by linear regression using GraphPad Prism software. All experimental and control groups were n=3 for tryptophan fluorescence quenching experiments, and the data were reported as average±standard deviation. Dissociation constants from tryptophan fluorescence quenching experiments were calculated by non-linear regression using GraphPad Prism software. All experimental and control groups were n=4 for Jurkat T cell quantitative binding, metabolic activity, and IL-2 expression experiments, and the data were reported as average±standard deviation. All experimental and control groups were n=3 for ASF precipitation experiments, and the data were reported as average±standard deviation. All experimental and control groups were n=5 for animal experiments, and the data were reported as average±standard deviation. Data obtained from DLS and protein concentration measurements are technical replicates. In all other cases, n refers to the number of biological replicates. To calculate bioluminescence half-life, non-linear regression with GraphPad Prism software was used to curve fit a one phase exponential decay. $p=0.0472$ for hock:NL-G3 half-life vs. hock:NL-TT-G3 half-life and $p=0.0219$ for scruff:NL-G3 half-life vs. scruff:NL-TT-G3 half-life. For all other studies, p values are indicated as follows: $*p<0.05$, $p<0.01$, $*p<0.001$, $****p<0.0001$, and n.s. is no significant difference or $p≥0.05$. Statistical differences between groups were analyzed using two-tailed student's t-test (two groups) or ANOVA with Tukey's post-hoc (multiple groups) in GraphPad Prism software.

In GAG binding assays, the t values are $t(4)=8.347$, 47.520, 38.580, 11.680 for CSA, CSB, CSC, and heparin, respectively. For comparison of dissociation constants from tryptophan fluorescence quenching experiments with LacNAC and lactose, the F values are $F(2,6)=54.980$ and 22.770, respectively. For comparison of minimum vs max ΔRFU signal in tryptophan fluorescence quenching experiments, the t values are $t(4)=18.560$, 15.100, and 31.860 for WT-G3, NL-G3, and NL-TT-G3, respectively, treated with lactose. For comparison of minimum vs max ΔRFU signal in tryptophan fluorescence quenching experiments, the t values are $t(4)=18.550$, 27.090, and 38.780 for WT-G3, NL-G3, and NL-TT-G3, respectively, treated with LacNAc. In Jurkat T cell quantitative binding assays, the t values are $t(6)=8.443$ and 8.679 for NL fusions and GFP fusions, respectively. In the Jurkat T cell metabolic activity experiment, the F value is $F(2,9)=105.800$. In the Jurkat T cell IL-2 expression assay, the F value is $F(6,21)=35.710$. For comparison of in vivo half-life, the F value is $F(1,23)=16.510$. For comparison of catalytic activity at initial timepoints in vivo, the F values are $F(2,12)=2.496$, 15.100, and 9.323 for injections into the hock, scruff, and thigh, respectively.

Data Availability. Genetic and amino acid sequences of NL-G3, NL-TT-G3, GFP-G3, GFP-TT-G3, ChABC-G3, ChABC-TTG3, and TT-GFP are not yet available but will be available in GenBank with the accession codes MH92052, MH92053, MH92054, MH92055, MH92056, MH92057, and MH92058, respectively.

References for Example 1

1. Platt, F. M. Emptying the stores: lysosomal diseases and therapeutic strategies. *Nat. Rev. Drug Discov.* 17, 133-150 (2017).
2. Bradford, K. L., Moretti, F. A., Carbonaro-Sarracino, D. A., Gaspar, H. B. & Kohn, D. B. Adenosine deaminase (ADA)-deficient severe combined immune deficiency (SCID): molecular pathogenesis and clinical manifestations. *J. Clin. Immunol.* 37, 626-637 (2017).
3. Lopes, A. M. et al. Therapeutic 1-asparaginase: upstream, downstream and beyond. *Crit. Rev. Biotechnol.* 37, 82-99 (2017).
4. Lyseng-Williamson, K. A. Coagulation factor IX (recombinant), albumin fusion protein (albutrepenonacog alfa; IdelvionR): a review of its use in haemophilia B. *Drugs* 77, 97-106 (2017).

5. Gurman, P. et al. Recombinant tissue plasminogen activators (rtPA): a review. *Clin. Pharmacol. Ther.* 97, 274-285 (2015).

6. Murray, G. J., Anver, M. R., Kennedy, M. A., Quirk, J. M. & Schiffmann, R. Cellular and tissue distribution of intravenously administered agalsidase alfa. *Mol. Genet. Metab.* 90, 307-312 (2007).

7. Vedder, A. C. et al. Treatment of Fabry disease: outcome of a comparative trial with agalsidase alfa or beta at a dose of 0.2 mg/kg. *PLoS One* 2, e598, 10.1371/journal.pone.0000598 (2007).

8. Sharma, S. K. & Bagshawe, K. D. Antibody directed enzyme prodrug therapy (ADEPT): trials and tribulations. *Adv. Drug Deliv. Rev.* 118, 2-7 (2017).

9. Wang, J. et al. Neutralizing antibodies to therapeutic enzymes: considerations for testing, prevention and treatment. *Nat. Biotechnol.* 26, 901-908 (2008).

10. Swierczewska, M., Lee, K. C. & Lee, S. What is the future of PEGylated therapies?Expert Opin. Emerging Drugs 20, 531-536 (2015).

11. van Witteloostuijn, S. B., Pedersen, S. L. & Jensen, K. J. Half-life extension of biopharmaceuticals using chemical methods: alternatives to PEGylation. ChemMedChem 11, 2474-2495 (2016).

12. Farhadi, S. A., Bracho-Sanchez, E. R., Freeman, S. L., Keselowsky, B. & Hudalla, G. A. Enzymes as immunotherapeutics. Bioconjugate Chem. 29, 649-656 (2018).

13. Harris, J. M. & Chess, R. B. Effect of pegylation on pharmaceuticals. Nat. Rev. Drug Discov. 2, 214-221 (2003).

14. Seppala, I., Pelkonen, J. & Makela, O. Isotypes of antibodies induced by plain dextran or a dextran-protein conjugate. Eur. J. Immunol. 15, 827-833 (1985).

15. Mohamad, N. R., Marzuki, N. H. C., Buang, N. A., Huyop, F. & Wahab, R. A. An overview of technologies for immobilization of enzymes and surface analysis techniques for immobilized enzymes. Biotechnol. Biotechnol. Equip. 29, 205-220 (2015).

16. Holliger, P. & Hudson, P. J. Engineered antibody fragments and the rise of single domains. Nat. Biotechnol. 23, 1126-1136 (2005).

17. Attarwala, H. Role of antibodies in cancer targeting. J. Nat. Sci., Biol. Med. 1, 53-56 (2010).

18. Love, T. W. et al. Attachment of an antifibrin antibody to the amino terminus of tissue-type plasminogen activator impairs stimulation by fibrin. Fibrinolysis 8, 326-332 (1994).

19. Tian, F. et al. A general approach to site-specific antibody drug conjugates. Proc. Natl. Acad. Sci. U.S.A 111, 1766-1771 (2014).

20. Brady, R. O., Murray, G. J. & Barton, N. W. Modifying exogenous glucocerebrosidase for effective replacement therapy in Gaucher disease. J. Inherited Metab. Dis. 17, 510-519 (1994).

21. Kitajima, T., Sakuragi, M., Hasuda, H., Ozu, T. & Ito, Y. A chimeric epidermal growth factor with fibrin affinity promotes repair of injured keratinocyte sheets. Acta Biomater. 5, 2623-2632 (2009).

22. Kitajima, T., Terai, H. & Ito, Y. A fusion protein of hepatocyte growth factor for immobilization to collagen. Biomaterials 28, 1989-1997 (2007).

23. Martino, M. M. et al. Growth factors engineered for super-affinity to the extracellular matrix enhance tissue healing. Science 343, 885-888 (2014).

24. Ishihara, J. et al. Matrix-binding checkpoint immunotherapies enhance antitumor efficacy and reduce adverse events. Sci. Transl. Med. 9, eaan0401, 10.1126/scitranslmed.aan0401 (2017).

25. Ochieng, J., Furtak, V. & Lukyanov, P. Extracellular functions of galectin-3. Glycoconjugate J. 19, 527-535 (2002).

26. Talaga, M. L. et al. Multitasking human lectin galectin-3 interacts with sulfated glycosaminoglycans and chondroitin sulfate proteoglycans. Biochemistry 55, 4541-4551 (2016).

27. Cummings, R. D., Liu, F. T. & Vasta, G. R. In Essentials of Glycobiology 2nd edn (eds. Varki, A. et al.) 469-480 (Cold Spring Harbor Press, New York, 2015).

28. Martino, M. M. & Hubbell, J. A. The 12th-14th type III repeats of fibronectin function as a highly promiscuous growth factor-binding domain. FASEB J. 24, 4711-4721 (2010).

29. Hudalla, G. A. & Murphy, W. L. Biomaterials that regulate growth factor activity via bioinspired interactions. Adv. Funct. Mater. 21, 1754-1768 (2011).

30. Lin, Y. H. et al. The intrinsically disordered N-terminal domain of galectin-3 dynamically mediates multisite self-association of the protein through fuzzy interactions. J. Biol. Chem. 292, 17845-17856 (2017).

31. Constance, J. M., Leffler, H., Khal-Knutsson, B., Svensson, I. & Jarvis, G. A. Truncated galectin-3 inhibits tumor growth and metastasis in orthotopic nude mouse model of human breast cancer. Clin. Cancer Res. 9, 2374-2383 (2003).

32. Xue, H. et al. The N-terminal tail coordinates with carbohydrate recognition domain to mediate galectin-3 induced apoptosis in T cells. Oncotarget 8, 49824-49838 (2017).

33. Hall, M. P. et al. Engineered luciferase reporter from a deep sea shrimp utilizing a novel imidazopyrazinone substrate. ACS Chem. Biol. 7, 1848-1857 (2012).

34. Ciani, B. et al. Molecular basis of coiled-coil oligomerization-state specificity. Proc. Natl. Acad. Sci. U.S.A 107, 19850-19855 (2010).

35. England, C. G., Ehlerding, E. B. & Cai, W. NanoLuc: a small luciferase is brightening up the field of bioluminescence. Bioconjugate Chem. 27, 1175-1187 (2016).

36. Massa, S. M., Cooper, D. N., Leffler, H. & Barondes, S. H. L-29, an endogenous lectin, binds to glycoconjugate ligands with positive cooperativity. Biochemistry 32, 260-267 (1993).

37. Terajima, M. et al. Glycosylation and cross-linking in bone type I collagen. J. Biol. Chem. 289, 22636-22647 (2014).

38. Bocker, S. & Elling, L. Binding characteristics of galectin-3 fusion proteins. Glycobiology 27, 457-468 (2017).

39. Birdsall, B. et al. NMR solution studies of hamster galectin-3 and electron microscopic visualization of surface-adsorbed complexes: evidence for interactions between the N- and C-terminal domains. Biochemistry 40, 4859-4866 (2001).

40. Barboni, E. A. M., Bawumia, S., Henrick, K. & Hughes, R. C. Molecular modeling and mutagenesis studies of the N-terminal domains of galectin-3: evidence for participation with the C-terminal carbohydrate recognition domain in oligosaccharide binding. Glycobiology 10, 1201-1208 (2000).

41. Ippel, H. et al. Intra- and intermolecular interactions of human galectin-3: assessment by full-assignment-based NMR. Glycobiology 26, 888-903 (2016).

42. Ochieng, J., Green, B., Evans, S., James, O. & Warfield, P. Modulation of the biological functions of galectin-3 by matrix metalloproteinases. Biochim. Biophys. Acta 1379, 97-106 (1998).

43. Mirandola, L. et al. Galectin-3C inhibits tumor growth and increases the anticancer activity of bortezomib in a murine model of human multiple myeloma. PLoS One 6, e21811, 10.1371/journal.pone.0021811 (2011).

44. Stowell, S. R. et al. Differential roles of galectin-1 and galectin-3 in regulating leukocyte viability and cytokine secretion. J. Immunol. 180, 3091-3102 (2008).

45. Fischer, K. et al. Antigen recognition induces phosphatidylserine exposure on the cell surface of human CD8+ T cells. Blood 108, 4094-4101 (2006).

46. Hsu, D. K., Hammes, S. R., Kuwabara, I., Greene, W. C. & Liu, F. T. Human T lymphotropic virus-I infection of human T lymphocytes induces expression of the beta-galactoside binding lectin, galectin-3. Am. J. Pathol. 148, 1661-1670 (1996).

47. Ahmad, N. et al. Galectin-3 precipitates as a pentamer with synthetic multivalent carbohydrates and forms heterogeneous cross-linked complexes. J. Biol. Chem. 279, 10841-10847 (2004).

48. Nieminen, J., Kuno, A., Hirabayashi, J. & Sato, S. Visualization of galectin-3 oligomerization on the surface of neutrophils and endothelial cells using fluorescence resonance energy transfer. J. Biol. Chem. 282, 1374-1383 (2007).

49. Stillman, B. N. et al. Galectin-3 and galectin-1 bind distinct cell surface glycoprotein receptors to induce T cell death. J. Immunol. 176, 778-789 (2006).

50. Lepur, A., Salomonsson, E., Nilsson, U. J. & Leffler, H. Ligand induced galectin-3 protein self-association. J. Biol. Chem. 287, 21751-21756 (2012).

51. Dam, T. K. et al. Galectins bind to the multivalent glycoprotein asialofetuin with enhanced affinities and a gradient of decreasing binding constants. Biochemistry 44, 12564-12571 (2005).

52. Cederfur, C. et al. Different affinity of galectins for human serum glycoproteins: galectin-3 binds many protease inhibitors and acute phase proteins. Glycobiology 18, 384-394 (2008).

53. Tomasetti, L. & Breunig, M. Preventing obstructions of nanosized drug delivery systems by the extracellular matrix. Adv. Healthcare Mater. 7, DOI:10.1002/adhm.201700739. Epub (2017).

54. Stacer, A. C. et al. NanoLuc reporter for dual luciferase imaging in living animals. Mol. Imaging 12, 1-13 (2013).

55. Longmire, M., Choyke, P. L. & Kobayashi, H. Clearance properties of nano-sized particles and molecules as imaging agents: considerations and caveats. Nanomedicine (London, U. K.) 3, 703-717 (2008).

56. Kopitz, J. et al. Human chimera-type galectin-3: defining the critical tail length for highaffinity glycoprotein/cell surface binding and functional competition with galectin-1 in neuroblastoma cell growth regulation. Biochimie 104, 90-99 (2014).

57. Kupper, C. E. et al. Fluorescent SNAP-tag galectin fusion proteins as novel tools in glycobiology. Curr. Pharm. Des. 19, 5457-5467 (2013).

58. de Melo, F. H. et al. Biological applications of a chimeric probe for the assessment of galectin-3 ligands. J. Histochem. Cytochem. 55, 1015-1026 (2007).

59. Pasek, M., Boeggeman, E., Ramakrishnan, B. & Qasba, P. K. Galectin-1 as a fusion partner for the production of soluble and folded human beta-1,4-galactosyltransferase-T7 in E. coli. Biochem. Biophys. Res. Commun. 394, 679-684 (2010).

60. Malyala, P. & Singh, M. Endotoxin Limits in Formulations for Preclinical Research. J. Pharm. Sci. 97, 2041-2044 (2008).

61. Restuccia, A., Tian, Y. F., Collier, J. H. & Hudalla, G. A. Self-assembled glycopeptide nanofibers as modulators of galectin-1 bioactivity. Cell. Mol. Bioeng. 8, 471-487 (2015).

62. Gu, K., Linhardt, R. J., Laliberte, M., Gu, K. & Zimmermann, J. Purification, characterization and specificity of chondroitin lyases and glycuronidase from Flavobacterium heparinum. Biochem. J. 312 (Pt 2), 569-577 (1995).

63. Vynios, D. H., Vamvacas, S. S., Kalpaxis, D. L. & Tsiganos, C. P. Aggrecan immobilization onto polystyrene plates through electrostatic interactions with spermine. Anal. Biochem. 260, 64-70 (1998).

64. Pace, K. E., Hahn, H. P. & Baum, L. G. Preparation of recombinant human galectin-1 and use in T-cell death assays. Methods Enzymol. 363, 499-518 (2003).

65. Tannous, B. A. Gaussia luciferase reporter assay for monitoring of biological processes in culture and in vivo. Nat. Protoc. 4, 582-591 (2009).

66. Hudalla, G. A. et al. Gradated assembly of multiple proteins into supramolecular nanomaterials. Nat. Mater. 13, 829-836 (2014).

67. Rudra, J. S. et al. Self-assembled peptide nanofibers raising durable antibody responses against a malaria epitope. Biomaterials 33, 6476-6484 (2012).

```
SEQUENCES
(NL-TT-G3 genetic sequence)
(start and stop codons bolded)
                                 SEQ ID NO: 1
CCATGGCGGTCTTCACACTCGAAGATTTCGTTGGG

GACTGGCGACAGACAGCCGGCTACAACCTGGACCA

AGTCCTTGAACAGGGAGGTGTGTCCAGTTTGTTTC

AGAATCTCGGGGTGTCCGTAACTCCGATCCAAAGG

ATTGTCCTGAGCGGTGAAAATGGGCTGAAGATCGA

CATCCATGTCATCATCCCGTATGAAGGTCTGAGCG

GCGACCAAATGGGCCAGATCGAAAAAATTTTTAAG

GTGGTGTACCCTGTGGATGATCATCACTTTAAGGT

GATCCTGCACTATGGCACACTGGTAATCGACGGGG

TTACGCCGAACATGATCGACTATTTCGGACGGCCG

TATGAAGGCATCGCCGTGTTCGACGGCAAAAAGAT

CACTGTAACAGGGACCCTGTGGAACGGCAACAAA

TTATCGACGAGCGCCTGATCAACCCCGACGGCTCC

CTGCTGTTCCGAGTAACCATCAACGGAGTGACCGG

CTGGCGGCTGTGCGAACGCATTCTGGCGGGATCCG

GCGGCGGCAGCGGCGGCAGCGGCGGCAGCGGCGGC

ATGGCGCGCATGAAACAGCTGGAAGATAAAGTGGA

AGAACTGCTGAGCAAAAACTATCATCTGGAAAACC

GCGTGGCGCGCCTGGAAAAACTGGTGGGCGAACGC
```

-continued

GGCGGCGGCAGCGGCGGCAGCGGCGGCGGCGGCAG

CGGCGGCAGCGGCGAATTCGCAGACAATTTTTCGC

TCCATGATGCGTTATCTGGGTCTGGAAACCCAAAC

CCTCAAGGATGGCCTGGCGCATGGGGGAACCAGCC

TGCTGGGGCAGGGGGCTACCCAGGGGCTTCCTCTC

CTGGGGCCTACCCCGGGCAGGCACCCCCAGGGGCT

TATCCTGGACAGGCACCTCCAGGCGCCTACCCTGG

AGCACCTGGAGCTTATCCCGGAGCACCTGCACCTG

GAGTCTACCCAGGGCCACCCAGCGGCCCTGGGGCC

TACCCATCTTCTGGACAGCCAAGTGCCCCCGGAGC

CTACCCTGCCACTGGCCCCTATGGCGCCCCTGCTG

GGCCACTGATTGTGCCTTATAACCTGCCTTTGCCT

GGGGGAGTGGTGCCTCGCATGCTGATAACAATTCT

GGGCACGGTGAAGCCCAATGCAAACAGAATTGCTT

TAGATTTCCAAAGAGGGAATGATGTTGCCTTCCAC

TTTAACCCACGCTTCAATGAGAACAACAGGAGAGT

CATTGTTTGCAATACAAAGCTGGATAATAACTGGG

GAAGGGAAGAAAGACAGTCGGTTTTCCCATTTGAA

AGTGGGAAACCATTCAAAATACAAGTACTGGTTGA

ACCTGACCACTTCAAGGTTGCAGTGAATGATGCTC

ACTTGTTGCAGTACAATCATCGGGTTAAAAAACTC

AATGAAATCAGCAAACTGGGAATTTCTGGTGACAT

AGACCTCACCAGTGCTTCATATAACATGATACTCG

AGCACCACCACCACCACCACTGA

(NL-G3 genetic sequence)
(start and stop codons bolded)

SEQ ID NO: 2

CCATGGCGGTCTTCACACTCGAAGATTTCGTTGGG

GACTGGCGACAGACAGCCGGCTACAACCTGGACCA

AGTCCTTGAACAGGGAGGTGTGTCCAGTTTGTTTC

AGAATCTCGGGGTGTCCGTAACTCCGATCCAAAGG

ATTGTCCTGAGCGGTGAAAATGGGCTGAAGATCGA

CATCCATGTCATCATCCCGTATGAAGGTCTGAGCG

GCGACCAAATGGGCCAGATCGAAAAAATTTTTAAG

GTGGTGTACCCTGTGGATGATCATCACTTTAAGGT

GATCCTGCACTATGGCACACTGGTAATCGACGGGG

TTACGCCGAACATGATCGACTATTTCGGACGGCCG

TATGAAGGCATCGCCGTGTTCGACGGCAAAAAGAT

CACTGTAACAGGGACCCTGTGGAACGGCAACAAAA

TTATCGACGAGCGCCTGATCAACCCCGACGGCTCC

CTGCTGTTCCGAGTAACCATCAACGGAGTGACCGG

CTGGCGGCTGTGCGAACGCATTCTGGCGGGATCCG

-continued

GCGGCGGCAGCGGCGGCAGCGGCGGCAGCGGCGGC

GAATTCGCAGACAATTTTTCGCTCCATGATGCGTT

ATCTGGGTCTGGAAACCCAAACCCTCAAGGATGGC

CTGGCGCATGGGGGAACCAGCCTGCTGGGGCAGGG

GGCTACCCAGGGGCTTCCTATCCTGGGGGCCTACCC

CGGGCAGGCACCCCCAGGGGCTTATCCTGGACAGG

CACCTCCAGGCGCCTACCCTGGAGCACCTGGAGCT

TATCCCGGAGCACCTGCACCTGGAGTCTACCCAGG

GCCACCCAGCGGCCCTGGGGCCTACCCATCTTCTG

GACAGCCAAGTGCCCCCGGAGCCTACCCTGCCACT

GGCCCCTATGGCGCCCCTGCTGGGCCACTGATTGT

GCCTTATAACCTGCCTTTGCCTGGGGGAGTGGTGC

CTCGCATGCTGATAACAATTCTGGGCACGGTGAAG

CCCAATGCAAACAGAATTGCTTTAGATTTCCAAAG

AGGGAATGATGTTGCCTTCCACTTTAACCCACGCT

TCAATGAGAACAACAGGAGAGTCATTGTTTGCAAT

ACAAAGCTGGATAATAACTGGGGAAGGGAAGAAAG

ACAGTCGGTTTTCCCATTTGAAAGTGGGAAACCAT

TCAAAATACAAGTACTGGTTGAACCTGACCACTTC

AAGGTTGCAGTGAATGATGCTCACTTGTTGCAGTA

CAATCATCGGGTTAAAAAACTCAATGAAATCAGCA

AACTGGGAATTTCTGGTGACATAGACCTCACCAGT

GCTTCATATAACATGATACTCGAGCACCACCACCA

CCACCACTGA

(WT-NL genetic sequence)
(start and stop codons bolded)

SEQ ID NO: 3

CCATGGCGGTCTTCACACTCGAAGATTTCGTTGGG

GACTGGCGACAGACAGCCGGCTACAACCTGGACCA

AGTCCTTGAACAGGGAGGTGTGTCCAGTTTGTTTC

AGAATCTCGGGGTGTCCGTAACTCCGATCCAAAGG

ATTGTCCTGAGCGGTGAAAATGGGCTGAAGATCGA

CATCCATGTCATCATCCCGTATGAAGGTCTGAGCG

GCGACCAAATGGGCCAGATCGAAAAAATTTTTAAG

GTGGTGTACCCTGTGGATGATCATCACTTTAAGGT

GATCCTGCACTATGGCACACTGGTAATCGACGGGG

TTACGCCGAACATGATCGACTATTTCGGACGGCCG

TATGAAGGCATCGCCGTGTTCGACGGCAAAAAGAT

CACTGTAACAGGGACCCTGTGGAACGGCAACAAAA

TTATCGACGAGCGCCTGATCAACCCCGACGGCTCC

-continued

CTGCTGTTCCGAGTAACCATCAACGGAGTGACCGG

CTGGCGGCTGTGCGAACGCATTCTGGCGGGATCCC

ACCACCACCACCACCACTGA 5

(GFP-TT-G3 genetic sequence)
(start and stop codons bolded)
SEQ ID NO: 4

CCATGTCCAAAGGAGAAGAGCTGTTCACTGGAGTG
10

GTACCAATACTTGTGGAGTTGGACGGAGATGTGAA

CGGACACAAATTTTCAGTCCGCGGGGAGGGGGAAG

GGGATGCTACTATTGGCAAGCTGACGCTCAAATTC

ATCTGTACCACCGGAAAACTCCCTGTACCCTGGCC 15

CACACTGGTGACAACTCTGACTTACGGCGTGCAAT

GTTTTAGCCGATACCCAGACCACATGAAGAGGCAC

GACTTTTTCAAAAGCGCAATGCCTGAAGGATACGT 20

ACAGGAAAGGACCATTTCTTTTAAAGACGACGGGA

AGTACAAAACCCGGGCAGTGGTGAAGTTTGAGGGC

GATACCCTCGTCAATAGGATCGAATTGAAGGGAAC 25

TGACTTCAAAGAAGATGGCAACATCCTGGGTCACA

AGCTTGAGTATAACTTTAACTCCCACAACGTGTAT

ATTACAGCCGACAAACAGAAGAATGGAATTAAGGC 30

TAACTTCACTGTCAGACACAATGTCGAAGATGGCT

CCGTGCAGCTCGCCGATCACTATCAACAGAATACT

CCTATCGGGGACGGCCCAGTCCTGCTGCCCGACAA 35

CCACTACCTGAGTACCCAGACTGTTCTGAGCAAAG

ATCCGAACGAGAAGCGCGACCACATGGTGCTGCAT

GAGTATGTCAACGCTGCGGGAATTACCCTCGGCAT 40

GGACGAGCTGTACAAGGGATCCGGCGGCGGCAGCG

GCGGCAGCGGCGGCAGCGGCGGCATGGCGCGCATG

AAACAGCTGGAAGATAAAGTGGAAGAACTGCTGAG 45

CAAAAACTATCATCTGGAAAACCGCGTGGCGCGCC

TGGAAAAACTGGTGGGCGAACGCGGCGGCGGCAGC

GGCGGCAGCGGCGGCGGCGGCAGCGGCGGCAGCGG 50

CGAATTCGCAGACAATTTTTCGCTCCATGATGCGT

TATCTGGGTCTGGAAACCCAAACCCTCAAGGATGC

CTGGCGCATGGGGGAACCAGCCTGCTGGGGCAGGG 55

GGCTACCCAGGGGCTTCCTATCCTGGGGCCTACCC

CGGGCAGGCACCCCCAGGGGCTTATCCTGGACAGG

CACCTCCAGGCGCCTACCCTGGAGCACCTGGAGCT 60

TATCCCGGAGCACCTGCACCTGGAGTCTACCCAGG

GCCACCCAGCGGCCCTGGGGCCTACCCATCTTCTG

GACAGCCAAGTGCCCCCGGAGCCTACCCTGCCACT

GGCCCCTATGGCGCCCCTGCTGGGCCACTGATTGT 65

-continued

GCCTTATAACCTGCCTTTGCCTGGGGGAGTGGTGC

CTCGCATGCTGATAACAATTCTGGGCACGGTGAAG

CCCAATGCAAACAGAATTGCTTTAGATTTCCAAAG

AGGGAATGATGTTGCCTTCCACTTTAACCCACGCT

TCAATGAGAACAACAGGAGAGTCATTGTTTGCAAT

ACAAAGCTGGATAATAACTGGGGAAGGGAAGAAAG

ACAGTCGGTTTTCCCATTTGAAAGTGGGAAACCAT

TCAAAATACAAGTACTGGTTGAACCTGACCACTTC

AAGGTTGCAGTGAATGATGCTCACTTGTTGCAGTA

CAATCATCGGGTTAAAAAACTCAATGAAATCAGCA

AACTGGGAATTTCTGGTGACATAGACCTCACCAGT

GCTTCATATAACATGATACTCGAGCACCACCACCA

CCACCACTGA

(GFP-G3 genetic sequence)
(start and stop codons bolded)
SEQ ID NO: 5

CCATGTCCAAAGGAGAAGAGCTGTTCACTGGAGTG

GTACCAATACTTGTGGAGTTGGACGGAGATGTGAA

CGGACACAAATTTTCAGTCCGCGGGGAGGGGGAAG

GGGATGCTACTATTGGCAAGCTGACGCTCAAATTC

ATCTGTACCACCGGAAAACTCCCTGTACCCTGGCC

CACACTGGTGACAACTCTGACTTACGGCGTGCAAT

GTTTTAGCCGATACCCAGACCACATGAAGAGGCAC

GACTTTTTCAAAAGCGCAATGCCTGAAGGATACGT

ACAGGAAAGGACCATTTCTTTTAAAGACGACGGGA

AGTACAAAACCCGGGCAGTGGTGAAGTTTGAGGGC

GATACCCTCGTCAATAGGATCGAATTGAAGGGAAC

TGACTTCAAAGAAGATGGCAACATCCTGGGTCACA

AGCTTGAGTATAACTTTAACTCCCACAACGTGTAT

ATTACAGCCGACAAACAGAAGAATGGAATTAAGGC

TAACTTCACTGTCAGACACAATGTCGAAGATGGCT

CCGTGCAGCTCGCCGATCACTATCAACAGAATACT

CCTATCGGGGACGGCCCAGTCCTGCTGCCCGACAA

CCACTACCTGAGTACCCAGACTGTTCTGAGCAAAG

ATCCGAACGAGAAGCGCGACCACATGGTGCTGCAT

GAGTATGTCAACGCTGCGGGAATTACCCTCGGCAT

GGACGAGCTGTACAAGGGATCCGGCGGCGGCAGCG

GCGGCAGCGGCGGCAGCGGCGGCGAATTCGCAGAC

AATTTTTCGCTCCATGATGCGTTATCTGGGTCTGG

AAACCCAAACCCTCAAGGATGGCCTGGCGCATGGG

GGAACCAGCCTGCTGGGGCAGGGGGCTACCCAGGG

GCTTCCTATCCTGGGGCCTACCCCGGGCAGGCACC

-continued

CCCAGGGGCTTATCCTGGACAGGCACCTCCAGGCG

CCTACCCTGGAGCACCTGGAGCTTATCCCGGAGCA

CCTGCACCTGGAGTCTACCCAGGGCCACCCAGCGG

CCCTGGGGCCTACCCATCTTCTGGACAGCCAAGTG

CCCCCGGAGCCTACCCTGCCACTGGCCCCTATGGC

GCCCCTGCTGGGCCACTGATTGTGCCTTATAACCT

GCCTTTGCCTGGGGGAGTGGTGCCTCGCATGCTGA

TAACAATTCTGGGCACGGTGAAGCCCAATGCAACA

GAATTGCTTTAGATTTCCAAAGAGGGAATGATGTT

GCCTTCCACTTTAACCCACGCTTCAATGAGAACAA

CAGGAGAGTCATTGTTTGCAATACAAAGCTGGATA

ATAACTGGGGAAGGGAAGAAAGACAGTCGGTTTTC

CCATTTGAAAGTGGGAAACCATTCAAAATACAAGT

ACTGGTTGAACCTGACCACTTCAAGGTTGCAGTGA

ATGATGCTCACTTGTTGCAGTACAATCATCGGGTT

AAAAAACTCAATGAAATCAGCAAACTGGGAATTTC

TGGTGACATAGACCTCACCAGTGCTTCATATAACA

TGATACTCGAGCACCACCACCACCACCACTGA

(ChABC-TT-G3 genetic sequence)
(start and stop codons bolded)

SEQ ID NO: 6

CCATGGCCACATCGAATCCGGCTTTCGACCCCAAA

AACTTAATGCAGAGTGAAATCTATCATTTTGCCCA

GAATAACCCATTGGCAGACTTTTCAAGCGATAAAA

ACTCCATTCTGACGTTATCTGACAAGCGTTCCATT

ATGGGAAATCAATCCTTACTTTGGAAATGGAAAGG

CGGCTCCAGTTTTACGTTACATAAAAAATTAATCG

TGCCGACCGATAAGGAAGCATCTAAAGCATGGGGA

CGCAGTAGTACGCCGGTGTTCTCCTTCTGGCTGTA

CAACGAGAAACCTATTGATGGGTACTTGACCATCG

ACTTCGGCGAAAAATTGATTTCAACTAGCGAAGCA

CAAGCTGGCTTTAAGGTTAAATTGGACTTCACCGG

GTGGCGTACGGTCGGAGTCAGCCTTAACAATGACT

TAGAGAATCGCGAAATGACCTTGAATGCTACGAAT

ACGTCCAGCGATGGAACCCAGGATAGCATCGGTCG

TAGTCTGGGAGCAAAGGTGGACAGTATCCGCTTCA

AAGCTCCGAGCAACGTTTCACAGGGGGAAATTTAT

ATCGACCGTATTATGTTCAGTGTCGACGACGCCCG

TTATCAATGGAGTGACTATCAAGTAAAGACCCGTC

TGTCAGAACCTGAGATCCAGTTTCATAATGTGAAG

CCGCAGTTGCCCGTAACGCCCGAAAATTTGGCAGC

TATTGATCTTATCCGCCAGCGCCTGATCAATGAGT

-continued

TTGTCGGCGGGGAGAAAGAAACCAACCTGGCGCTG

GAAGAAAATATCTCAAAACTGAAAAGTGACTTTGA

TGCACTTAATATCCACACGCTGGCGAACGGGGGAA

CCCAAGGACGTCACTTAATTACTGACAAGCAAATT

ATCATCTATCAACCCGAGAATCTTAACTCACAAGA

TAAACAGTTATTTGACAATTATGTCATCTTAGGTA

ACTACACGACCTTGATGTTTAACATCTCTCGCGCC

TATGTTTTGGAAAAAGACCCCACTCAAAAGGCACA

ATTAAAGCAGATGTACCTTCTGATGACCAAACATC

TTTTGGATCAGGGATTCGTGAAAGGTAGTGCGTTA

GTAACAACACACCATTGGGGGTACAGTTCGCGCTG

GTGGTATATCAGTACTTTGTTAATGTCTGATGCAT

TGAAGGAGGCGAATCTTCAGACGCAGGTTTACGAT

TCCCTGCTGTGGTATTCGCGTGAGTTCAAATCTTC

GTTCGATATGAAGGTCAGCGCTGACTCTTCGGATT

TGGATTACTTTAATACCCTTTCGCGCCAGCACTTG

GCCTTGTTACTGCTGGAGCCAGACGACCAGAAACG

CATCAACCTTGTCAACACGTTTAGTCACTATATCA

CAGGAGCGCTTACTCAAGTACCGCCGGGGGGGAAA

GATGGTCTTCGTCCAGATGGTACGGCCTGGCGCCA

TGAGGGTAACTATCCGGGCTATTCCTTTCCGGCAT

TTAAGAATGCGTCCCAACTGATTTACCTTCTGCGT

GATACCCCATTTTCAGTGGGAGAATCTGGATGGAA

CAACTTGAAGAAAGCGATGGTCTCTGCTTGGATTT

ACTCTAACCCAGAAGTTGGATTACCATTAGCAGGC

CGTCACCCATTCAATAGTCCCTCCCTTAAAAGTGT

CGCCCAGGGGTATTATTGGTTAGCTATGTCTGCAA

AGTCGAGTCCTGACAAAACCCTGGCGTCTATCTAC

TTGGCCATCTCCGATAAAACTCAAAACGAATCAAC

CGCCATTTTTGGCGAAACCATCACGCCGGCTTCTT

TGCCGCAGGGGTTCTACGCCTTTAATGGAGGCGCC

TTCGGCATTCATCGTTGGCAGGATAAGATGGTTAC

ATTGAAAGCGTACAATACCAACGTATGGAGTTCCG

AGATCTATAACAAGGATAATCGCTATGGCCGTTAT

CAGTCTCACGGGGTGGCTCAAATTGTCTCTAACGG

TAGTCAATTAAGTCAAGGTTATCAACAGGAGGGAT

GGGACTGGAACCGCATGCCTGGGGCAACAACTATC

CATCTGCCGCTGAAGGATTTAGATAGCCCTAAGCC

ACATACACTGATGCAGCGTGGTGAACGTGGCTTCT

CGGGTACTAGTTCACTGGAGGGGCAATACGGGATG

ATGGCATTTGACTTAATCTATCCAGCTAATTTAGA

-continued

GCGCTTCGACCCCAATTTTACTGCTAAGAAGAGCG

TCCTGGCAGCGGATAACCACCTGATCTTTATTGGA

AGCAATATTAATAGCTCGGACAAGAACAAGAATGT

TGAGACGACACTTTTTCAGCATGCCATCACTCCAA

CTTTGAATACGCTGTGGATCAATGGACAAAAGATC

GAAAATATGCCATACCAGACAACACTTCAGCAGGG

TGACTGGTTGATTGACTCGAATGGGAACGGGTACT

TAATTACACAAGCCGAAAAAGTGAATGTCTCGCGC

CAGCACCAAGTTTCGGCGGAGAATAAAAACCGTCA

ACCTACTGAGGGCAACTTCAGCTCTGCCTGGATTG

ATCACAGTACTCGCCCAAAAGACGCATCATATGAG

TACATGGTATTCTTGGATGCTACGCCTGAGAAAAT

GGGAGAGATGGCTCAAAAGTTCCGTGAGAACAACG

GATTGTACCAAGTTCTGCGCAAGGATAAAGATGTG

CATATCATTTTAGATAAACTTTCCAATGTAACGGG

GTATGCCTTTTATCAACCCGCCAGTATTGAGGATA

AATGGATCAAGAAAGTGAATAAGCCCGCCATCGTA

ATGACTCATCGCCAGAAAGACACTCTTATTGTCTC

GGCGGTAACACCCGATCTTAATATGACTCGCCAGA

AAGCAGCTACTCCCGTAACAATCAACGTTACGATC

AATGGGAAGTGGCAAAGTGCTGATAAGAACAGTGA

GGTTAAATACCAGGTGTCCGGCGATAATACGGAGT

TGACGTTTACATCTTACTTCGGCATCCCACAAGAA

ATTAAGTTGTCCCCTTTGCCGGGATCCGGCGGCGG

CAGCGGCGGCAGCGGCGGCAGCGGCGGCATGGCGC

GCATGAAACAGCTGGAAGATAAAGTGGAAGAACTG

CTGAGCAAAAACTATCATCTGGAAAACCGCGTGGC

GCGCCTGGAAAAACTGGTGGGCGAACGCGGCGGCG

GCAGCGGCGGCAGCGGCGGCGGCGGCAGCGGCGGC

AGCGGCGAATTCGCAGACAATTTTTCGCTCCATGA

TGCGTTATCTGGGTCTGGAAACCCAAACCCTCAAG

GATGGCCTGGCGCATGGGGGAACCAGCCTGCTGGG

GCAGGGGGCTACCCAGGGGCTTCCTATCCTGGGGC

CTACCCCGGGCAGGCACCCCCAGGGGCTTATCCTG

GACAGGCACCTCCAGGCGCCTACCCTGGAGCACCT

GGAGCTTATCCCGGAGCACCTGCACCTGGAGTCTA

CCCAGGGGCCACCCAGCGGCCCTGGGGCCTACCCAT

CTTCTGGACAGCCAAGTGCCCCCGGAGCCTACCCT

GCCACTGGCCCCTATGGCGCCCCTGCTGGGCCACT

GATTGTGCCTTATAACCTGCCTTTGCCTGGGGGAG

-continued

TGGTGCCTCGCATGCTGATAACAATTCTGGGCACG

GTGAAGCCCAATGCAAACAGAATTGCTTTAGATTT

CCAAAGAGGGAATGATGTTGCCTTCCACTTTAACC

CACGCTTCAATGAGAACAACAGGAGAGTCATTGTT

TGCAATACAAAGCTGGATAATAACTGGGGAAGGGA

AGAAAGACAGTCGGTTTTCCCATTTGAAAGTGGGA

AACCATTCAAAATACAAGTACTGGTTGAACCTGAC

CACTTCAAGGTGCAGTGAATGATGCTCACTTGTTG

CAGTACAATCATCGGGTTAAAAAACTCAATGAAAT

CAGCAAACTGGGAATTTCTGGTGACATAGACCTCA

CCAGTGCTTCATATAACATGATACTCGAGCACCAC

CACCACCACCACTGA

(ChABC-G3 genetic sequence)
(start and stop codons bolded)
SEQ ID NO: 7

CCATGGCCACATCGAATCCGGCTTTCGACCCCAAA

AACTTAATGCAGAGTGAAATCTATCATTTTGCCCA

GAATAACCCATTGGCAGACTTTTCAAGCGATAAAA

ACTCCATTCTGACGTTATCTGACAAGCGTTCCATT

ATGGGAAATCAATCCTTACTTTGGAAATGGAAAGG

CGGCTCCAGTTTTACGTTACATAAAAAAATTAATCG

TGCCGACCGATAAGGAAGCATCTAAAGCATGGGGA

CGCAGTAGTACGCCGGTGTTCTCCTTCTGGCTGTA

CAACGAGAAACCTATTGATGGGTACTTGACCATCG

ACTTCGGCGAAAAATTGATTTCAACTAGCGAAGCA

CAAGCTGGCTTTAAGGTTAAATTGGACTTCACCGG

GTGGCGTACGGTCGGAGTCAGCCTTAACAATGACT

TAGAGAATCGCGAAATGACCTTGAATGCTACGAAT

ACGTCCAGCGATGGAACCCAGGATAGCATCGGTCG

TAGTCTGGGAGCAAAGGTGGACAGTATCCGCTTCA

AAGCTCCGAGCAACGTTTCACAGGGGGGAAATTTAT

ATCGACCGTATTATGTTCAGTGTCGACGACGCCCG

TTATCAATGGAGTGACTATCAAGTAAAGACCCGTC

TGTCAGAACCTGAGATCCAGTTTCATAATGTGAAG

CCGCAGTTGCCCGTAACGCCCGAAAATTTGGCAGC

TATTGATCTTATCCGCCAGCGCCTGATCAATGAGT

TTGTCGGCGGGGAGAAAGAAACCAACCTGGCGCTG

GAAGAAAATATCTCAAAACTGAAAGTGACTTTGA

TGCACTTAATATCCACACGCTGGCGAACGGGGGAA

CCCAAGGACGTCACTTAATTACTGACAAGCAAATT

ATCATCTATCAACCCGAGAATCTTAACTCACAAGA

TAAACAGTTATTTGACAATTATGTCATCTTAGGTA

-continued

ACTACACGACCTTGATGTTTAACATCTCTCGCGCC

TATGTTTTGGAAAAAGACCCCACTCAAAAGGCACA

ATTAAAGCAGATGTACCTTCTGATGACCAAACATC

TTTTGGATCAGGGATTCGTGAAAGGTAGTGCGTTA

GTAACAACACACCATTGGGGGTACAGTTCGCGCTG

GTGGTATACAGTACTTTGTTAATGTCTGATGCATT

GAAGGAGGCGAATCTTCAGACGCAGGTTTACGATT

CCCTGCTGTGGTATTCGCGTGAGTTCAAATCTTCG

TTCGATATGAAGGTCAGCGCTGACTCTTCGGATTT

GGATTACTTTAATACCCTTTCGCGCCAGCACTTGG

CCTTGTTACTGCTGGAGCCAGACGACCAGAAACGC

ATCAACCTTGTCAACACGTTTAGTCACTATATCAC

AGGAGCGCTTACTCAAGTACCGCCGGGGGGAAAAG

ATGGTCTTCGTCCAGATGGTACGGCCTGGCGCCAT

GAGGGTAACTATCCGGGCTATTCCTTTCCGGCATT

TAAGAATGCGTCCCAACTGATTTACCTTCTGCGTG

ATACCCCATTTTCAGTGGGAGAATCTGGATGGAAC

AACTTGAAGAAAGCGATGGTCTCTGCTTGGATTTA

CTCTAACCCAGAAGTTGGATTACCATTAGCAGGCC

GTCACCCATTCAATAGTCCCTCCCTTAAAAGTGTC

GCCCAGGGGTATTATTGGTTAGCTATGTCTGCAAA

GTCGAGTCCTGACAAAACCCTGGCGTCTATCTACT

TGGCCATCTCCGATAAAACTCAAAACGAATCAACC

GCCATTTTTGGCGAAACCATCACGCCGGCTTCTTT

GCCGCAGGGGTTCTACGCCTTTAATGGAGGCGCCT

TCGGCATTCATCGTTGGCAGGATAAGATGGTTACA

TTGAAAGCGTACAATACCAACGTATGGAGTTCCGA

GATCTATAACAAGGATAATCGCTATGGCCGTTATC

AGTCTCACGGGGTGGCTCAATTGTCTCTAACGGTA

GTCAATTAAGTCAAGGTTATCAACAGGAGGGATGG

GACTGGAACCGCATGCCTGGGGCAACAACTATCCA

TCTGCCGCTGAAGATTTAGATAGCCCTAAGCCACA

TACACTGATGCAGCGTGGTGAACGTGGCTTCTCGG

GTACTAGTTCACTGGAGGGGCAATACGGGATGATG

GCATTTGACTTAATCTATCCAGCTAATTTAGAGCG

CTTCGACCCCAATTTTACTGCTAAGAAGAGCGTCC

TGGCAGCGGATAACCACCTGATCTTTATTGGAAGC

AATATTAATAGCTCGGACAAGAACAAGAATGTTGA

GACGACACTTTTTCAGCATGCCATCACTCCAACTT

TGAATACGCTGTGGATCAATGGACAAAAGATCGAA

AATATGCCATACCAGACAACACTTCAGCAGGGTGA

-continued

CTGGTTGATTGACTCGAATGGGAACGGGTACTTAA

TTACACAAGCCGAAAAAGTGAATGTCTCGCGCCAG

CACCAAGTTTCGGCGGAGAATAAAAACCGTCAACC

TACTGAGGGCAACTTCAGCTCTGCCTGGATTGATC

ACAGTACTCGCCCAAAAGACGCATCATATGAGTAC

ATGGTATTCTTGGATGCTACGCCTGAGAAAATGGG

AGAGATGGCTCAAAAGTTCCGTGAGAACAACGGAT

TGTACCAAGTTCTGCGCAAGGATAAAGATGTGCAT

ATCATTTTAGATAAACTTTCCAATGTAACGGGGTA

TGCCTTTTATCAACCCGCCAGTATTGAGGATAAAT

GGATCAAGAAAGTGAATAAGCCCGCCATCGTAATG

ACTCATCGCCAGAAAGACACTCTTATTGTCTCGGC

GGTAACACCCGATCTTAATATGACTCGCCAGAAAG

CAGCTACTCCCGTAACAATCAACGTTACGATCAAT

GGGAAGTGGCAAAGTGCTGATAAGAACAGTGAGGT

TAAATACCAGGTGTCCGGCGATAATACGGAGTTGA

CGTTTACATCTTACTTCGGCATCCCACAAGAAATT

AAGTTGTCCCCTTTGCCGGGATCCGGTGGCGGCTC

AGGAGGCAGCGGAGGTTCAGGTGGGGAATTCATGG

CTGACAACTTCAGTTTGCATGATGCTTTAAGTGGC

TCCGGGAACCCGAACCCTCAAGGCTGGCCAGGGGC

ATGGGGTAACCAACCGGCGGGAGCAGGAGGTTATC

CCGGAGCGAGCTACCCTGGAGCCTACCCAGGACAG

GCTCCGCCTGGCGCGTATCCTGGGCAGGCTCCACC

AGGTGCCTACCCGGGGGCACCCGGGGCATATCCGG

GAGCTCCTGCTCCCGGAGTTTATCCGGGTCCTCCT

TCAGGACCGGGAGCGTATCCATCGAGCGGCCAGCC

CAGTGCAACGGGTGCGTACCCAGCCACGGGCCCCT

ATGGAGCCCCAGCGGGACCATTAATTGTACCCTAT

AATCTTCCGCTTCCAGGCGGCGTAGTTCCTCGTAT

GTTAATTACCATTTTAGGAACAGTAAAACCAAATG

CTAATCGTATTGCATTAGACTTTCAACGTGGCAAC

GACGTAGCTTTTCATTTTAACCCACGTTTTAACGA

AAACAATCGTCGTGTCATTGTATGCAATACAAAAC

TGGATAATAATTGGGGACGCGAGGAGCGCCAGAGT

GTGTTCCCATTCGAGTCGGGCAAACCATTCAAAAT

TCAGGTATTGGTCGAGCCAGACCATTTCAAGGTCG

CGGTCAATGACGCTCACTTATTACAGTACAATCAT

CGCGTAAAGAAACTGAATGAGATCAGTAAGTTAGG

AATCTCCGGAGACATTGATCTTACAAGTGCGAGTT

-continued

ACACGATGATTCACCACCACCACCACCACTGAAAG

CTTCTCGAG (TT-GFP genetic sequence)
(start and stop codons bolded)

SEQ ID NO: 8

CCATGGCGCGCATGAAACAGCTGGAAGATAAAGTG

GAAGAACTGCTGAGCAAAAACTATCATCTGGAAAA

CCGCGTGGCGCGCCTGGAAAAACTGGTGGGCGAAC

GCGGATCCGGCGGCGGCAGCGGCGGCAGCGGCGGC

GGCGGCAGCGGCGGCAGCGGCGAATTCTCCAAAGG

AGAAGAGCTGTTCACTGGAGTGGTACCAATACTTG

TGGAGTTGGACGGAGATGTGAACGGACACAAATTT

TCAGTCCGCGGGGAGGGGGAAGGGGATGCTACTAT

TGGCAAGCTGACGCTCAAATTCATCTGTACCACCG

GAAAACTCCCTGTACCCTGGCCCACACTGGTGACA

ACTCTGACTTACGGCGTGCAATGTTTTAGCCGATA

CCCAGACCACATGAAGAGGCACGACTTTTTCAAAA

GCGCAATGCCTGAAGGATACGTACAGGAAAGGACC

ATTTCTTTTAAAGACGACGGGAAGTACAAAACCCG

GGCAGTGGTGAAGTTTGAGGGCGATACCCTCGTCA

ATAGGATCGAATTGAAGGGAACTGACTTCAAAGAA

GATGGCAACATCCTGGGTCACAAGCTTGAGTATAA

CTTTAACTCCCACAACGTGTATATTACAGCCGACA

AACAGAAGAATGGAATTAAGGCTAACTTCACTGTC

AGACACAATGTCGAAGATGGCTCCGTGCAGCTCGC

CGATCACTATCAACAGAATACTCCTATCGGGACGG

CCCAGTCCTGCTGCCCGACAACCACTACCTGAGTA

CCCAGACTGTTCTGAGCAAAGATCCGAACGAGAAG

CGCGACCACATGGTGCTGCATGAGTATGTCAACGC

TGCGGGAATTACCCTCGGCATGGACGAGCTGTACA

AGCTCGAGCACCACCACCACCACCACTGA

(NL-TT-G3 amino acid sequence)
(start Met bolded)

SEQ ID NO: 9

MAVFTLEDFVGDWRQTAGYNLDQVLEQGGVSSLFQ

NLGVSVTPIQRIVLSGENGLKIDIHVIIPYEGLSG

DQMGQIEKIFKVVYPVDDHHFKVILHYGTLVIDGV

TPNMIDYFGRPYEGIAVFDGKKITVTGTLWNGNKI

IDERLINPDGSLLFRVTINGVTGWRLCERILAGS*G*

*GGSGGSGGSGGMARMKQLEDKVEELLSKNYHLENR*

*VARLEKLVGERGGGSGGSGGGGSGGSG*EFADNFSL

HDALSGSGNPNPQGWPGAWGNQPAGAGGYPGASYP

GAYPGQAPPGAYPGQAPPGAYPGAPGAYPGAPAPG

VYPGPPSGPGAYPSSGQPSAPGAYPATGPYGAPAG

-continued

PLIVPYNLPLPGGVVPRMLITILGTVKPNANRIAL

DFQRGNDVAFHFNPRFNENNRRVIVCNTKLDNNWG

REERQSVFPFESGKPFKIQVLVEPDHFKVAVNDAH

LLQYNHRVKKLNEISKLGISGDIDLTSASYNMILE

HHHHHH Stop

(NL-G3amino acid sequence)
(start Met bolded)

SEQ ID NO: 10

MAVFTLEDFVGDWRQTAGYNLDQVLEQGGVSSLFQ

NLGVSVTPIQRIVLSGENGLKIDIHVIIPYEGLSG

DQMGQIEKIFKVVYPVDDHHFKVILHYGTLVIDGV

TPNMIDYFGRPYEGIAVFDGKKITVTGTLWNGNKI

IDERLINPDGSLLFRVTINGVTGWRLCERILAGS*G*

*GGSGGSGGSGG*EFADNFSLHDALSGSGNPNPQGWP

GAWGNQPAGAGGYPGASYPGAYPGQAPPGAYPGQA

PPGAYPGAPGAYPGAPAPGVYPGPPSGPGAYPSSG

QPSAPGAYPATGPYGAPAGPLIVPYNLPLPGGVVP

RMLITILGTVKPNANRIALDFQRGNDVAFHFNPRF

NENNRRVIVCNTKLDNNWGREERQSVFPFESGKPF

KIQVLVEPDHFKVAVNDAHLLQYNHRVKKLNEISK

LGISGDIDLTSASYNMILEHHHHHH Stop

(WT-NL amino acid sequence)
(start Met bolded)

SEQ ID NO: 11

MAVFTLEDFVGDWRQTAGYNLDQVLEQGGVSSLFQ

NLGVSVTPIQRIVLSGENGLKIDIHVIIPYEGLSG

DQMGQIEKIFKVVYPVDDHHFKVILHYGTLVIDGV

TPNMIDYFGRPYEGIAVFDGKKITVTGTLWNGNKI

IDERLINPDGSLLFRVTINGVTGWRLCERILAGSH

HHHHH Stop

(GFP-TT-G3 amino acid sequence)
(start Met bolded)

SEQ ID NO: 12

MSKGEELFTGVVPILVELDGDVNGHKFSVRGEGEG

DATIGKLTLKFICTTGKLPVPWPTLVTTLTYGVQC

FSRYPDHMKRHDFFKSAMPEGYVQERTISFKDDGK

YKTRAVVKFEGDTLVNRIELKGTDFKEDGNILGHK

LEYNFNSHNVYITADKQKNGIKANFTVRHNVEDGS

VQLADDHYQQNTPIGDGPVLLPDNHYLSTQTVLSK

DPNEKRDHMVLHEYVNAAGITLGMDELYKGS*GGGS*

*GGSGGSGGMARMKQLEDKVEELLSKNYHLENRVAR*

*LEKLVGERGGGSGGSGGGGSGGSG*EFADNFSLHDA

LSGSGNPNPQGWPGAWGNQPAGAGGYPGASYPGAY

PGQAPPGAYPGQAPPGAYPGAPGAYPGAPAPGVYP

GPPSGPGAYPS5GQPSAPGAYPATGPYGAPAGPLI

VPYNLPLPGGVV                                    5

PRMLITILGTVKPNANRIALDFQRGNDVAFHFNPR

FNENNRRVIVCNTKLDNNWGREERQSVFPFESGKP

FKIQVLVEPDHFKVAVNDAHLLQYNHRVKKLNEIS          10

KLGISGDIDLTSASTNMILEHHHHHH Stop

(GFP-G3 amino acid sequence)
(start Met bolded)
                                        SEQ ID NO: 13  15
MSKGEELFTGVVPILVELDGDVNGHKFSVRGEGEG

DATIGKLTLKFICTTGKLPVPWPTLVTTLTYGVQC

FSRYPDHMKRHDFFKSAMPEGYVQERTISFKDDGK

YKTRAVVKFEGDTLVNRIELKGTDFKEDGNILGHK          20

LEYNFNSHVVYITADKQKNGIKANFTVRHNVEDGS

VQLADHYQQNTPIGDGPVLLPDNHYLSTQTVLSKD

PNEKRDHMVLHEYVNAAGITLGMDELYKGS*GGGSG*        25

*GSGGSGG*EFADNFSLHDALSGSGNPNPQGWPGAWG

NQPAGAGGYPGASYPGAYPGQAPPGAYPGQAPPGA

YPGAPGAYPGAPAPGVYPGPPSGPGAYPSSGQPSA          30

PGAYPATGPYGAPAGPLIVPYNLPLPGGVVPRMLI

TILGTVKPNANRIALDFQRGNDVAFHFNPRFNENN

RRVIVCNTKLDNNWGREERQSVFPFESGKPFKIQV          35

LVEPDHFKVAVNDAHLLQYNHRVKKLNEISKLGIS

GDIDLTSASYNMILEHHHHH Stop

(TT-GFP amino acid sequence)
(start Met bolded)                           40
                                        SEQ ID NO: 14
_M_ _ARMKQLEDKVEELLSKNYHLENRVARLEKLVGER_

_GSGGGSGGGSGGGSGGGSG_EFSKGEELFTGVVPILV

ELDGDVNGHKFSVRGEGEGDATIGKLTLKFICTTG          45

KLPVPWPTLVTTLTYGVQCFSRYPDHMKRHDFFKS

AMPEGYVQERTISFKDDGKYKTRAVVKFEGDTLVN

RIELKGTDFKEDGNILGHKLEYNFNSHNVYITADK          50

QKNGIKANFTVRHNVEDGSVQLADHYQQNTPIGDG

PVLLPDNHYLSTQTVLSKDPNEKRDHMVLHEYVNA

AGITLGMDELYKLEHHHHHH Stop                 55

(ChABC-TT-G3 amino acid sequence)
(start Met bolded)
                                        SEQ ID NO: 15
MATSNPAFDPKNLMQSEIYHFAQNNPLADFSSDKN

SILTLSDKRSIMGNQSLLWKWKGGSSFTLHKKLIV          60

PTDKEASKAWGRSSTPVFSFWLYNEKPIDGYLTID

FGEKLISTSEAQAGFKVKLDFTGWRTVGVSLNNDL

ENREMTLNATNTSSDGTQDSIGRSLGAKVDSIRFK          65

APSNVSQGEIYIDRIMFSVDDARYQWSDYQVKTRL

SEPEIQFHNVKPQLPVTPENLAAIDLIRQRLINEF

VGGEKETNLALEENISKLKSDFDALNIHTLANGGT

QGRHLITDKQIIIYQPENLNSQDKQLFDNYVILGN

YTTLMFNISRAYVLEKDPTQKAQLKQMYLLMTKHL

LDQGFVKGSALVTTHHWGYSSRWWYISTLLMSDAL

KEANLQTQVYDSLLWYSREFKSSFDMKVSADSSDL

DYFNTLSRQHLALLLLEPDDQKRINLVNTFSHYIT

GALTQVPPGGKDGLRPDGTAWRHEGNYPGYSFPAF

KNASQLIYLLRDTPFSVGESGWNNLKKAMVSAWIY

SNPEVGLPLAGRHPFNSPSLKSVAQGYYWLAMSAK

SSPDKTLASIYLAISDKTQNESTAIFGETITPASL

PQGFYAFNGGAFGIHRWQDKMVTLKAYNTNVWSSE

IYNKDNRYGRYQSHGVAQIVSNGSQLSQGYQQEGW

DWNRMPGATTIHLPLKDLDSPKPHTLMQRGERGFS

GTSSLEGQYGMMAFDLIYPANLERFDPNFTAKKSV

LAADNHLIFIGSNINSSDKNKNVETTLFQHAITPT

LNTLWINGQKIENMPYQTTLQQGDWLIDSNGNGYL

ITQAEKVNVSRQHQVSAENKNRQPTEGNFSSAAWI

DHSTRPKDASYEYMVFLDATPEKMGEMAQKFRENN

GLYQVLRKDKDVHIILDKLSNVTGYAFYQPASIED

KWIKKVNKPAIVMTHRQKDTLIVSAVTPDLNMTRQ

KAATPVTINVTINGKWQSADKNSEVKYQVSGDNTE

LTFTSYFGIPQEIKLSPLPGSGGGSGGSGGSGGMA

RMKQLEDKVEELLSKNYHLENRVARLEKLVGERGG

GSGGSGGGSGGSGEFADNFSLHDALSGSGNPNPQ

GWPGAWGNQPAGAGGYPGASYPGAYPGQAPPGAYP

GQAPPGAYPGAPGAYPGAPAPGVYPGPPSGPGAYP

SSGQPSAPGAYPATGPYGAPAGPLIVPYNLPLPGG

VVPRMLITILGTVKPNANRIALDFQRGNDVAFHFN

PRFNENNRRVIVCNTKLDNNWGREERQSVFPFESG

KPFKIQVLVEPDHFKVAVNDAHLLQYNHRVKKLNE

ISKLGISGDIDLTSASYNMILEHHHHHH Stop

(ChABC-G3 amino acid sequence)
(start Met bolded)
                                        SEQ ID NO: 16
MATSNPAFDPKNLMQSEIYHFAQNNPLADFSSDKN

SILTLSDKRSIMGNQSLLWKWKGGSSFTLHKKLIV

PTDKEASKAWGRSSTPVFSFWLYNEKPIDGYLTID

FGEKLISTSEAQAGFKVKLDFTGWRTVGVSLNNDL

ENREMTLNATNTSSDGTQDSIGRSLGAKVDSIRFK

APSNVSQGEIYIDRIMFSVDDARYQWSDYQVKTRL

-continued

SEPEIQFHNVKPQLPVTPENLAAIDLIRQRLINEF

VGGEKETNLALEENISKLKSDFDALNIHTLANGGT

QGRHLITDKQIIIYQPENLNSQDKQLFDNYVILGN

YTTLMFNISRAYVLEKDPTQKAQLKQMYLLMTKHL

LDQGFVKGSALVTTHHWGYSSRWWYISTLLMSDAL

KEANLQTQVYDSLLWYSREFKSSFDMKVSADSSDL

DYFNTLSRQHLALLLLEPDDQKRINLVNTFSHYIT

GALTQPVPGGKDGLRPDGTAWRHEGNYPGYSFPAF

KNASQLIYLLRDTPFSVGESGWNNLKKAMVSAWIY

SNPEVGLPLAGRHPFNSPSLKSVAQGYYWLAMSAK

SSPDKTLASIYLAISDKTQNESTAIFGETITPASL

PQGFYAFNGGAFGIHRWQDKMVTLKAYNTNVWSSE

IYNKDNRYGRYQSHGVAQIVSNGSQLSQGYQQEGW

DWNRMPGATTIHLPLKDLDSPKPHTLMQRGERGFS

GTSSLEGQYGMMAFDLIYPANLERFDPNFTAKKSV

LAADNHLIFIGSNINSSDKNKNVETTLFQHAITPT

LNTLWINGQKEINMPYQTTLQQGDWLIDSNGNGYL

ITQAEKVNVSRQHQVSAENKNRQPTEGNFSSAWID

HSTRPKDASYEYMVFLDATPEKMGEMAQKFRENNG

LYQVLRKDKDVHIILDKLSNVTGYAFYQPASIEDK

WIKKVNKPAIVMTHRQKDTLIVSAVTPDLNMTRQK

AATPVTINVTINGKWQSADKNSEVKYQVSGDNTEL

TFTSYFGIPQEIKLSPLPGS*GGGSGGSGGSGG*EFM

ADNFSLHD

ALSGSGNPNPQGWPGAWGNQPAGAGGYPGASYPGA

YPGQAPPGAYPGQAPPGAYPGAPGAYPGAPAPGVY

PGPPSGPGAYPSSGQPSATGAYPATGPYGAPAGPL

IVPYNLPLPGGVVPRMLITILGTVKPNANRIALDF

QRGNDVAFHFNPRFNENNRRVIVCNTKLDNNWGRE

ERQSVFPPFESGKPFKIQVLVEPDHFKVAVNDAHLL

QYNHRVKKLNEISKLGISGDIDLTSASYTMIHHHH

HH Stop

An alpha-helix trimer domain
(an alpha-helix coil)
                    SEQ ID NO: 17
MARMKQLEDKVEELLSKNYHLENRVARLEKLVGER An alpha-helix trimer domain
                    SEQ ID NO: 18
XRMKQLEDKVEELLSKNYHLENEVARLKKLVGER An alpha-helix tetramer domain
                    SEQ ID NO: 19
MKVKQLVDKVEELLSKNYHLVNEVARLVKLVGER -continued An alpha-helix tetramer domain
                    SEQ ID NO: 20
MKVKQLEDVVEELLS VNYHLENVVARLKKLVGER An alpha-helix tetramer domain
                    SEQ ID NO: 21
MKVKQLADKVEELLSKNYHLANEVARLAKLVGER An alpha-helix tetramer domain
                    SEQ ID NO: 22
MKVKQLEDAVEELLSANYHLENAVARLKKLVGER An alpha-helix heptamer domain
                    SEQ ID NO: 23
XGEIAQALKEIAKALKEIAWALKEIAQALKG An alpha-helix heptamer domain
                    SEQ ID NO: 24
XGEIAKALREIAKALREXAWAHREEAKALRG An alpha-helix heptamer domain
                    SEQ ID NO: 25
XGEIAKALREIAKALRECAWAHREEAKALRG An alpha-helix heptamer domain
                    SEQ ID NO: 26
XGEIAKALREIAKALRECAWAHREEAKALRG An alpha-helix heptamer domain
                    SEQ ID NO: 27
XGEIAKALREIAKALRECAWAHREIAKALRG An alpha-helix heptamer domain
                    SEQ ID NO: 28
XGEIAKALREIAKALREIAWAHREIAKALRG An alpha-helix heptamer domain
                    SEQ ID NO: 29
XGEIAQALKEIAKALKEIAWACKEIAQALKG An alpha-helix heptamer domain
                    SEQ ID NO: 30
MKVKQLADAVEELASANYHLANAVARLAKAVGER a linker
                    SEQ ID NO: 31
GSGGGSGGSGGSGG a linker
                    SEQ ID NO: 32
GGGSGGSGGGGSGGSG wild-type Gal3 (N-terminal
truncation residues Bolded)
                    SEQ ID NO: 33
ADNFSLHDALSGSGNPNPQGWPGAWGNQPAGAGGY

PGASYPGAYPGQAPPGAYPGQAPPGAYPGAPGAYP

GAPAPGVYPGPPSGPGAYPSSGQPSAPGAYPATGP

YGAPAGPLIVPYNLPLPGGVVPRMLITILGTVKPN

ANRIALDFQRGNDVAFHFNPRFNENNRRVIVCNTK

LDNNWGREERQSVFPPFESGKPFKIQVLVEPDHFKV

AVNDAHLLQYNHRVKKLNEISKLGISGDIDLTSAS

YNMI

-continued

Gal3 C-terminal carbohydrate
binding domain

SEQ ID NO: 34

YGAPAGPLIVPYNLPLPGGVVPRMLITILGTVKPN

ANRIALDFQRGNDVAFHFNPRFNENNRRVIVCNTK

-continued

LDNNWGREERQSVFPFESGKPFKIQVLVEPDHFKV

AVNDAHLLQYNHRVKKLNEISKLGISGDIDLTSAS

YNMI

---

We claim:

1. A targeted effector fusion protein comprising a polypeptide sequence that is identical to any one of SEQ ID NOs: 15-16.

2. A multimeric targeted effector fusion protein complex comprising:

at least two targeted effector fusion proteins, wherein each of the at least two targeted effector proteins is according to claim 1, and the at least two targeted effector proteins are conjugated to each other by binding between an alpha coil polypeptide or a random coil polypeptide in each of the at least two targeted effector proteins.

3. The multimeric targeted effector fusion protein complex of claim 2, wherein the multimeric targeted effector fusion protein complex is homogeneous.

4. The multimeric targeted effector fusion protein complex of claim 2, wherein the multimeric targeted effector fusion protein complex is heterogeneous.

5. A polynucleotide that encodes the targeted effector fusion protein of claim 1.

6. The polynucleotide of claim 5, wherein the polynucleotide sequence is SEQ ID NO: 6 or 7.

7. A vector comprising:

a polynucleotide according to claim 5.

8. A single fusion polypeptide sequence comprising:

at least two targeted effector fusion proteins as in claim 1, wherein each of the at least two targeted effector fusion proteins are directly fused at the C-terminus, N-terminus, or both the C-terminus and N-terminus of at least one other targeted effector fusion protein of the at least two targeted effector fusion proteins.

9. A single fusion polypeptide sequence comprising:

at least two targeted effector fusion proteins as in claim 1, wherein each of the at least two targeted effector fusion proteins are operatively linked at the C-terminus, N-terminus, or both the C-terminus and N-terminus to at least one other targeted effector fusion protein of the at least two targeted effector fusion proteins via one or more additional amino acids.

10. A polynucleotide encoding the single fusion polypeptide of claim 8.

11. A vector comprising:

the polynucleotide according to claim 10.

12. A pharmaceutical formulation comprising:

one or more targeted effector fusion proteins as in claim 1; and a pharmaceutically acceptable carrier.

* * * * *

SEQUENCE LISTING

<160> NUMBER OF SEQ ID NOS: 34

<210> SEQ ID NO 1
<211> LENGTH: 1493
<212> TYPE: DNA
<213> ORGANISM: Artificial Sequence
<220> FEATURE:
<223> OTHER INFORMATION: Synthetic polynucleotide

<400> SEQUENCE: 1

```
ccatggcggt cttcacactc gaagatttcg ttggggactg gcgacagaca gccggctaca      60
acctggacca agtccttgaa cagggaggtg tgtccagttt gtttcagaat ctcggggtgt     120
ccgtaactcc gatccaaagg attgtcctga gcggtgaaaa tgggctgaag atcgacatcc     180
atgtcatcat cccgtatgaa ggtctgagcg gcgaccaaat gggccagatc gaaaaaattt     240
ttaaggtggt gtaccctgtg gatgatcatc actttaaggt gatcctgcac tatggcacac     300
tggtaatcga cggggttacg ccgaacatga tcgactattt cggacggccg tatgaaggca     360
tcgccgtgtt cgacggcaaa aagatcactg taacagggac cctgtggaac ggcaacaaaa     420
ttatcgacga gcgcctgatc aaccccgacg gctccctgct gttccgagta accatcaacg     480
gagtgaccgg ctggcggctg tgcgaacgca ttctggcggg atccggcggc ggcagcggcg     540
gcagcggcgg cagcggcggc atggcgcgca tgaaacagct ggaagataaa gtggaagaac     600
tgctgagcaa aaactatcat ctggaaaacc gcgtggcgcg cctggaaaaa ctggtgggcg     660
aacgcggcgg cggcagcggc ggcagcggcg gcggcggcag cggcggcagc ggcgaattcg     720
cagacaattt ttcgctccat gatgcgttat ctgggtctgg aaacccaaac cctcaaggat     780
ggcctggcgc atgggggaac cagcctgctg gggcagggg ctacccaggg gcttcctctc     840
ctggggccta ccccgggcag gcacccccag gggcttatcc tggacaggca cctccaggcg     900
cctaccctgg agcacctgga gcttatcccg agcacctgc acctggagtc tacccagggc     960
cacccagcgg ccctggggcc tacccatctt ctggacagcc aagtgccccc ggagcctacc    1020
ctgccactgg cccctatggc gccctgctg gccactgat tgtgccttat aacctgcctt    1080
tgcctggggg agtggtgcct cgcatgctga taacaattct gggcacggtg aagcccaatg    1140
caaacagaat tgctttagat ttccaaagag ggaatgatgt tgccttccac tttaacccac    1200
gcttcaatga gaacaacagg agagtcattg tttgcaatac aaagctggat aataactggg    1260
gaagggaaga aagacagtcg gttttcccat ttgaaagtgg gaaaccattc aaaatacaag    1320
tactggttga acctgaccac ttcaaggttg cagtgaatga tgctcacttg ttgcagtaca    1380
atcatcgggt taaaaaactc aatgaaatca gcaaactggg aatttctggt gacatagacc    1440
tcaccagtgc ttcatataac atgatactcg agcaccacca ccaccaccac tga           1493
```

<210> SEQ ID NO 2
<211> LENGTH: 1340
<212> TYPE: DNA
<213> ORGANISM: Artificial Sequence
<220> FEATURE:
<223> OTHER INFORMATION: Synthetic polynucleotide -continued

<400> SEQUENCE: 2

```
ccatggcggt cttcacactc gaagatttcg ttggggactg gcgacagaca gccggctaca      60
acctggacca agtccttgaa cagggaggtg tgtccagttt gtttcagaat ctcggggtgt     120
ccgtaactcc gatccaaagg attgtcctga gcggtgaaaa tgggctgaag atcgacatcc     180
atgtcatcat cccgtatgaa ggtctgagcg gcgaccaaat gggccagatc gaaaaaattt     240
ttaaggtggt gtaccctgtg gatgatcatc actttaaggt gatcctgcac tatggcacac     300
tggtaatcga cggggttacg ccgaacatga tcgactattt cggacggccg tatgaaggca     360
tcgccgtgtt cgacggcaaa aagatcactg taacagggac cctgtggaac ggcaacaaaa     420
ttatcgacga gcgcctgatc aaccccgacg gctccctgct gttccgagta accatcaacg     480
gagtgaccgg ctggcggctg tgcgaacgca ttctggcggg atccggcggc ggcagcggcg     540
gcagcggcgg cagcggcggc gaattcgcag acaattttttc gctccatgat gcgttatctg     600
ggtctggaaa cccaaaccct caaggatggc ctggcgcatg ggggaaccag cctgctgggg     660 caggggggcta cccagggggct tcctatcctg gggcctaccc cgggcaggca cccccaggggg     720 cttatcctgg acaggcacct ccaggcgcct accctggagc acctggagct tatcccggag     780
cacctgcacc tggagtctac ccaggccac ccagcggccc tgggccctac ccatcttctg     840
gacagccaag tgcccccgga gcctaccctg ccactggccc ctatggcgcc cctgctgggc     900
cactgattgt gccttataac ctgcctttgc ctgggggagt ggtgcctcgc atgctgataa     960
caattctggg cacggtgaag cccaatgcaa acagaattgc tttagatttc caaagaggga    1020
atgatgttgc cttccacttt aacccacgct tcaatgagaa caacaggaga gtcattgttt    1080
gcaatacaaa gctggataat aactggggaa gggaagaaag acagtcggtt ttcccatttg    1140
aaagtgggaa accattcaaa atacaagtac tggttgaacc tgaccacttc aaggttgcag    1200
tgaatgatgc tcacttgttg cagtacaatc atcgggttaa aaaactcaat gaaatcagca    1260
aactgggaat ttctggtgac atagacctca ccagtgcttc atataacatg atactcgagc    1320
accaccacca ccaccactga                                                1340
```

```
<210> SEQ ID NO 3
<211> LENGTH: 545
<212> TYPE: DNA
<213> ORGANISM: Artificial Sequence
<220> FEATURE:
<223> OTHER INFORMATION: Synthetic polynucleotide
```

<400> SEQUENCE: 3

```
ccatggcggt cttcacactc gaagatttcg ttggggactg gcgacagaca gccggctaca      60
acctggacca agtccttgaa cagggaggtg tgtccagttt gtttcagaat ctcggggtgt     120
ccgtaactcc gatccaaagg attgtcctga gcggtgaaaa tgggctgaag atcgacatcc     180
atgtcatcat cccgtatgaa ggtctgagcg gcgaccaaat gggccagatc gaaaaaattt     240
ttaaggtggt gtaccctgtg gatgatcatc actttaaggt gatcctgcac tatggcacac     300
tggtaatcga cggggttacg ccgaacatga tcgactattt cggacggccg tatgaaggca     360
tcgccgtgtt cgacggcaaa aagatcactg taacagggac cctgtggaac ggcaacaaaa     420
ttatcgacga gcgcctgatc aaccccgacg gctccctgct gttccgagta accatcaacg     480
gagtgaccgg ctggcggctg tgcgaacgca ttctggcggg atcccaccac caccaccacc     540
actga                                                                 545
```

-continued

```
<210> SEQ ID NO 4
<211> LENGTH: 1690
<212> TYPE: DNA
<213> ORGANISM: Artificial Sequence
<220> FEATURE:
<223> OTHER INFORMATION: Synthetic polynucleotide

<400> SEQUENCE: 4
ccatgtccaa aggagaagag ctgttcactg gagtggtacc aatacttgtg gagttggacg      60
gagatgtgaa cggacacaaa ttttcagtcc gcggggaggg ggaaggggat gctactattg     120
gcaagctgac gctcaaattc atctgtacca ccggaaaaact ccctgtaccc tggcccacac     180
tggtgacaac tctgacttac ggcgtgcaat gttttagccg atacccagac cacatgaaga     240
ggcacgactt tttcaaaagc gcaatgcctg aaggatacgt acaggaaagg accatttctt     300
ttaaagacga cgggaagtac aaaacccggg cagtggtgaa gtttgagggc gataccctcg     360
tcaataggat cgaattgaag ggaactgact tcaaagaaga tggcaacatc ctgggtcaca     420
agcttgagta taactttaac tcccacaacg tgtatattac agccgacaaa cagaagaatg     480
gaattaaggc taacttcact gtcagacaca atgtcgaaga tggctccgtg cagctcgccg     540
atcactatca acagaatact cctatcgggg acggcccagt cctgctgccc gacaaccact     600
acctgagtac ccagactgtt ctgagcaaag atccgaacga gaagcgcgac cacatggtgc     660
tgcatgagta tgtcaacgct gcgggaatta ccctcggcat ggacgagctg tacaagggat     720
ccggcggcgg cagcggcggc agcggcggca gcggcggcat ggcgcgcatg aaacagctgg     780
aagataaagt ggaagaactg ctgagcaaaa actatcatct ggaaaaccgc gtggcgcgcc     840
tggaaaaact ggtgggcgaa cgcggcggcg gcagcggcgg cagcggcggc ggcggcagcg     900
gcggcagcgg cgaattcgca gacaattttt cgctccatga tgcgttatct gggtctggaa     960
acccaaaccc tcaaggatgc ctggcgcatg ggggaaccag cctgctgggg cagggggcta    1020 cccagggggct tcctatcctg gggcctaccc cgggcaggca cccccagggg cttatcctgg    1080
acaggcacct ccaggcgcct accctggagc acctggagct tatcccggag cacctgcacc    1140
tggagtctac ccagggccac ccagcggccc tggggcctac ccatcttctg gacagccaag    1200
tgcccccgga gcctaccctg ccactggccc ctatggcgcc cctgctgggc cactgattgt    1260
gccttataac ctgcctttgc ctgggggagt ggtgcctcgc atgctgataa caattctggg    1320
cacggtgaag cccaatgcaa acagaattgc tttagatttc caaagaggga atgatgttgc    1380
cttccacttt aacccacgct tcaatgagaa caacaggaga gtcattgttt gcaatacaaa    1440
gctggataat aactggggaa gggaagaaag acagtcggtt ttcccatttg aaagtgggaa    1500
accattcaaa atacaagtac tggttgaacc tgaccacttc aaggttgcag tgaatgatgc    1560
tcacttgttg cagtacaatc atcgggttaa aaaactcaat gaaatcagca aactgggaat    1620
ttctggtgac atagacctca ccagtgcttc atataacatg atactcgagc accaccacca    1680
ccaccactga                                                           1690

<210> SEQ ID NO 5
<211> LENGTH: 1537
<212> TYPE: DNA
<213> ORGANISM: Artificial Sequence
<220> FEATURE:
<223> OTHER INFORMATION: Synthetic polynucleotide

<400> SEQUENCE: 5
ccatgtccaa aggagaagag ctgttcactg gagtggtacc aatacttgtg gagttggacg      60
```

-continued

```
gagatgtgaa cggacacaaa ttttcagtcc gcggggaggg ggaaggggat gctactattg      120
gcaagctgac gctcaaattc atctgtacca ccggaaaact ccctgtaccc tggcccacac      180
tggtgacaac tctgacttac ggcgtgcaat gttttagccg atacccagac cacatgaaga      240
ggcacgactt tttcaaaagc gcaatgcctg aaggatacgt acaggaaagg accatttctt      300
ttaaagacga cgggaagtac aaaacccggg cagtggtgaa gtttgagggc gataccctcg      360
tcaataggat cgaattgaag ggaactgact tcaaagaaga tggcaacatc ctgggtcaca      420
agcttgagta taactttaac tcccacaacg tgtatattac agccgacaaa cagaagaatg      480
gaattaaggc taacttcact gtcagacaca atgtcgaaga tggctccgtg cagctcgccg      540
atcactatca acagaatact cctatcgggg acggcccagt cctgctgccc gacaaccact      600
acctgagtac ccagactgtt ctgagcaaag atccgaacga gaagcgcgac cacatggtgc      660
tgcatgagta tgtcaacgct gcgggaatta ccctcggcat ggacgagctg tacaagggat      720
ccggcggcgg cagcggcggc agcggcggca gcggcggcga attcgcagac aatttttcgc      780
tccatgatgc gttatctggg tctggaaacc caaaccctca aggatggcct ggcgcatggg      840
ggaaccagcc tgctggggca gggggctacc caggggcttc ctatcctggg gcctaccccg      900
ggcaggcacc cccagggggct tatcctggac aggcacctcc aggcgcctac cctggagcac      960
ctggagctta tcccggagca cctgcacctg gagtctaccc agggcaccc agcggccctg     1020 gggcctaccc atcttctgga cagccaagtg cccccggagc ctaccctgcc actggcccct     1080
atggcgcccc tgctgggcca ctgattgtgc cttataacct gccttttgcct ggggagtgg      1140 tgcctcgcat gctgataaca attctgggca cggtgaagcc caatgcaaca gaattgcttt     1200
agatttccaa agagggaatg atgttgcctt ccactttaac ccacgcttca atgagaacaa     1260
caggagagtc attgtttgca atacaaagct ggataataac tggggaaggg aagaaagaca     1320
gtcggttttc ccatttgaaa gtgggaaacc attcaaaata caagtactgg ttgaacctga     1380
ccacttcaag gttgcagtga atgatgctca cttgttgcag tacaatcatc gggttaaaaa     1440
actcaatgaa atcagcaaac tgggaatttc tggtgacata gacctcacca gtgcttcata     1500
taacatgata ctcgagcacc accaccacca ccactga                               1537
```

```
<210> SEQ ID NO 6
<211> LENGTH: 3970
<212> TYPE: DNA
<213> ORGANISM: Artificial Sequence
<220> FEATURE:
<223> OTHER INFORMATION: Synthetic polynucleotide

<400> SEQUENCE: 6
```

```
ccatggccac atcgaatccg gctttcgacc ccaaaaactt aatgcagagt gaaatctatc       60
attttgccca gaataaccca ttggcagact tttcaagcga taaaaactcc attctgacgt      120
tatctgacaa cgcgttccatt atgggaaatc aatccttact ttggaaatgg aaaggcggct      180
ccagttttac gttacataaa aaattaatcg tgccgaccga taaggaagca tctaaagcat      240
ggggacgcag tagtacgccg gtgttctcct tctggctgta caacgagaaa cctattgatg      300
ggtacttgac catcgacttc ggcgaaaaat tgatttcaac tagcgaagca caagctggct      360
ttaaggttaa attggacttc accgggtggc gtacggtcgg agtcagcctt aacaatgact      420
tagagaatcg cgaaatgacc ttgaatgcta cgaatacgtc cagcgatgga acccaggata      480
gcatcggtcg tagtctggga gcaaaggtgg acagtatccg cttcaaagct ccgagcaacg      540
```

-continued

```
tttcacaggg ggaaatttat atcgaccgta ttatgttcag tgtcgacgac gcccgttatc      600
aatggagtga ctatcaagta aagacccgtc tgtcagaacc tgagatccag tttcataatg      660
tgaagccgca gttgcccgta acgcccgaaa atttggcagc tattgatctt atccgccagc      720
gcctgatcaa tgagtttgtc ggcgggagaa agaaaccaa cctggcgctg gaagaaaata      780
tctcaaaact gaaaagtgac tttgatgcac ttaatatcca cacgctggcg aacgggggaa      840
cccaaggacg tcacttaatt actgacaagc aaattatcat ctatcaaccc gagaatctta      900
actcacaaga taaacagtta tttgacaatt atgtcatctt aggtaactac acgaccttga      960
tgtttaacat ctctcgcgcc tatgtttttgg aaaaagaccc cactcaaaag gcacaattaa     1020
agcagatgta ccttctgatg accaaacatc ttttggatca gggattcgtg aaaggtagtg     1080
cgttagtaac aacacaccat tggggggtaca gttcgcgctg gtggtatatc agtactttgt     1140
taatgtctga tgcattgaag gaggcgaatc ttcagacgca ggtttacgat tccctgctgt     1200
ggtattcgcg tgagttcaaa tcttcgttcg atatgaaggt cagcgctgac tcttcggatt     1260
tggattactt taatacccctt tcgcgccagc acttggcctt gttactgctg gagccagacg     1320
accagaaacg catcaacctt gtcaacacgt ttagtcacta tatcacagga gcgcttactc     1380
aagtaccgcc ggggggaaaa gatggtcttc gtccagatgg tacggcctgg cgccatgagg     1440
gtaactatcc gggctattcc tttccggcat ttaagaatgc gtcccaactg atttaccttc     1500
tgcgtgatac cccattttca gtgggagaat ctggatggaa caacttgaag aaagcgatgg     1560
tctctgcttg gatttactct aacccagaag ttggattacc attagcaggc cgtcacccat     1620
tcaatagtcc ctcccttaaa agtgtcgccc aggggtatta ttggttagct atgtctgcaa     1680
agtcgagtcc tgacaaaacc ctggcgtcta tctacttggc catctccgat aaaactcaaa     1740
acgaatcaac cgccattttt ggcgaaacca tcacgccggc ttctttgccg caggggttct     1800
acgcctttaa tggaggcgcc ttcggcattc atcgttggca ggataagatg gttacattga     1860
aagcgtacaa taccaacgta tggagttccg agatctataa caaggataat cgctatggcc     1920
gttatcagtc tcacggggtg gctcaaattg tctctaacgg tagtcaatta agtcaaggtt     1980
atcaacagga gggatgggac tggaaccgca tgcctggggc aacaactatc catctgccgc     2040
tgaaggattt agatagccct aagccacata cactgatgca gcgtggtgaa cgtggcttct     2100
cgggtactag ttcactggag gggcaatacg ggatgatggc atttgactta atctatccag     2160
ctaatttaga gcgcttcgac cccaatttta ctgctaagaa gagcgtcctg gcagcggata     2220
accacctgat ctttattgga agcaatatta atagctcgga caagaacaag aatgttgaga     2280
cgacactttt tcagcatgcc atcactccaa cttttgaatac gctgtggatc aatggacaaa     2340
agatcgaaaa tatgccatac cagacaacac ttcagcaggg tgactggttg attgactcga     2400
atgggaacgg gtacttaatt acacaagccg aaaaagtgaa tgtctcgcgc cagcaccaag     2460
tttcggcgga gaataaaaac cgtcaaccta ctgagggcaa cttcagctct gcctggattg     2520
atcacagtac tcgcccaaaa gacgcatcat atgagtacat ggtattcttg gatgctacgc     2580
ctgagaaaat gggagagatg gctcaaaagt tccgtgagaa caacggattg taccaagttc     2640
tgcgcaagga taaagatgtg catatcattt tagataaact ttccaatgta acggggtatg     2700 cctttttatca acccgccagt attgaggata aatggatcaa gaaagtgaat aagcccgcca     2760
tcgtaatgac tcatcgccag aaagacactc ttattgtctc ggcggtaaca cccgatctta     2820
atatgactcg ccagaaagca gctactcccg taacaatcaa cgttacgatc aatgggaagt     2880
ggcaaagtgc tgataagaac agtgaggtta aataccaggt gtccggcgat aatacggagt     2940
```

-continued

```
tgacgtttac atcttacttc ggcatcccac aagaaattaa gttgtcccct ttgccgggat    3000
ccggcggcgg cagcggcggc agcggcggca gcggcggcat ggcgcgcatg aaacagctgg    3060
aagataaagt ggaagaactg ctgagcaaaa actatcatct ggaaaaccgc gtggcgcgcc    3120
tggaaaaact ggtgggcgaa cgcggcggcg gcagcggcgg cagcggcggc ggcggcagcg    3180
gcggcagcgg cgaattcgca gacaatttt cgctccatga tgcgttatct gggtctggaa     3240
acccaaaccc tcaaggatgg cctggcgcat gggggaacca gcctgctggg gcaggggct     3300 acccaggggc ttcctatcct ggggcctacc ccgggcaggc accccaggg gcttatcctg      3360 gacaggcacc tccaggcgcc taccctggag cacctggagc ttatcccgga gcacctgcac    3420
ctggagtcta cccagggcca cccagcggcc ctggggccta cccatcttct ggacagccaa    3480
gtgcccccgg agcctaccct gccactggcc cctatggcgc ccctgctggg ccactgattg    3540
tgccttataa cctgcctttg cctgggggag tggtgcctcg catgctgata acaattctgg    3600
gcacggtgaa gcccaatgca aacagaattg ctttagattt ccaaagaggg aatgatgttg    3660
ccttccactt taacccacgc ttcaatgaga caacaggag agtcattgtt tgcaatacaa      3720
agctggataa taactgggga agggaagaaa gacagtcggt tttcccattt gaaagtggga    3780
aaccattcaa aatacaagta ctggttgaac ctgaccactt caaggtgcag tgaatgatgc    3840
tcacttgttg cagtacaatc atcgggttaa aaaactcaat gaaatcagca aactgggaat    3900
ttctggtgac atagacctca ccagtgcttc atataacatg atactcgagc accaccacca    3960
ccaccactga                                                           3970
```

<210> SEQ ID NO 7
<211> LENGTH: 3824
<212> TYPE: DNA
<213> ORGANISM: Artificial Sequence
<220> FEATURE:
<223> OTHER INFORMATION: Synthetic polynucleotide

<400> SEQUENCE: 7

```
ccatggccac atcgaatccg gctttcgacc ccaaaaactt aatgcagagt gaaatctatc      60
attttgccca gaataaccca ttggcagact tttcaagcga taaaaactcc attctgacgt     120
tatctgacaa gcgttccatt atgggaaatc aatccttact ttggaaatgg aaaggcggct     180
ccagttttac gttacataaa aaattaatcg tgccgaccga taaggaagca tctaaagcat     240
ggggacgcag tagtacgccg gtgttctcct tctggctgta caacgagaaa cctattgatg     300
ggtacttgac catcgacttc ggcgaaaaat tgatttcaac tagcgaagca caagctggct     360
ttaaggttaa attggacttc accgggtggc gtacggtcgg agtcagcctt aacaatgact     420
tagagaatcg cgaaatgacc ttgaatgcta cgaatacgtc cagcgatgga acccaggata    480
gcatcggtcg tagtctggga gcaaaggtgg acagtatccg cttcaaagct ccgagcaacg    540
tttcacaggg ggaaatttat atcgaccgta ttatgttcag tgtcgacgac gcccgttatc    600
aatggagtga ctatcaagta aagacccgtc tgtcagaacc tgagatccag tttcataatg    660
tgaagccgca gttgcccgta acgcccgaaa atttggcagc tattgatctt atccgccagc    720
gcctgatcaa tgagtttgtc ggcgggagaa agaaaccaa cctggcgctg aagaaaata     780 tctcaaaact gaaaagtgac tttgatgcac ttaatatcca cacgctggcg aacgggggaa    840
cccaaggacg tcacttaatt actgacaagc aaattatcat ctatcaaccc gagaatctta    900
actcacaaga taaacagtta tttgacaatt atgtcatctt aggtaactac acgaccttga    960
```

-continued

```
tgtttaacat ctctcgcgcc tatgtttttg aaaaagaccc cactcaaaag gcacaattaa   1020
agcagatgta ccttctgatg accaaacatc ttttggatca gggattcgtg aaaggtagtg   1080
cgttagtaac aacacaccat tggggggtaca gttcgcgctg gtggtataca gtactttgtt   1140
aatgtctgat gcattgaagg aggcgaatct tcagacgcag gtttacgatt ccctgctgtg   1200
gtattcgcgt gagttcaaat cttcgttcga tatgaaggtc agcgctgact cttcggattt   1260
ggattacttt aatacccttt cgcgccagca cttggccttg ttactgctgg agccagacga   1320
ccagaaacgc atcaaccttg tcaacacgtt tagtcactat atcacaggag cgcttactca   1380
agtaccgccg gggggaaaag atggtcttcg tccagatggt acggcctggc gccatgaggg   1440
taactatccg ggctattcct ttccggcatt taagaatgcg tcccaactga tttaccttct   1500
gcgtgatacc ccattttcag tgggagaatc tggatggaac aacttgaaga aagcgatggt   1560
ctctgcttgg atttactcta acccagaagt tggattacca ttagcaggcc gtcacccatt   1620
caatagtccc tcccttaaaa gtgtcgccca ggggtattat tggttagcta tgtctgcaaa   1680
gtcgagtcct gacaaaaccc tggcgtctat ctacttggcc atctccgata aaactcaaaa   1740
cgaatcaacc gccattttttg gcgaaaccat cacgccggct tctttgccgc aggggttcta   1800
cgcctttaat ggaggcgcct tcggcattca tcgttggcag gataagatgg ttacattgaa   1860
agcgtacaat accaacgtat ggagttccga gatctataac aaggataatc gctatggccg   1920
ttatcagtct cacggggtgg ctcaattgtc tctaacggta gtcaattaag tcaaggttat   1980
caacaggagg gatgggactg gaaccgcatg cctggggcaa caactatcca tctgccgctg   2040
aagatttaga tagccctaag ccacatacac tgatgcagcg tggtgaacgt ggcttctcgg   2100
gtactagttc actggagggg caatacggga tgatggcatt tgacttaatc tatccagcta   2160
atttagagcg cttcgacccc aattttactg ctaagaagag cgtcctggca gcggataacc   2220
acctgatctt tattggaagc aatattaata gctcggacaa gaacaagaat gttgagacga   2280 cacttttttca gcatgccatc actccaactt tgaatacgct gtggatcaat ggacaaaaga   2340
tcgaaaatat gccataccag acaacacttc agcagggtga ctggttgatt gactcgaatg   2400
ggaacgggta cttaattaca caagccgaaa aagtgaatgt ctcgcgccag caccaagttt   2460
cggcggagaa taaaaaccgt caacctactg agggcaactt cagctctgcc tggattgatc   2520
acagtactcg cccaaaagac gcatcatatg agtacatggt attcttggat gctacgcctg   2580
agaaaatggg agagatggct caaaagttcc gtgagaacaa cggattgtac caagttctgc   2640
gcaaggataa agatgtgcat atcatttttag ataaactttc caatgtaacg gggtatgcct   2700
tttatcaacc cgccagtatt gaggataaat ggatcaagaa agtgaataag cccgccatcg   2760
taatgactca tcgccagaaa gacactctta ttgtctcggc ggtaacaccc gatcttaata   2820
tgactcgcca gaaagcagct actcccgtaa caatcaacgt tacgatcaat gggaagtggc   2880
aaagtgctga taagaacagt gaggttaaat accaggtgtc cggcgataat acggagttga   2940
cgtttacatc ttacttcggc atcccacaag aaattaagtt gtccccttttg ccgggatccg   3000 gtggcggctc aggaggcagc ggaggttcag gtggggaatt catggctgac aacttcagtt   3060
tgcatgatgc tttaagtggc tccgggaacc cgaaccctca aggctggcca gggggcatggg   3120 gtaaccaacc ggcgggagca ggaggttatc ccggagcgag ctaccctgga gcctacccag   3180
gacaggctcc gcctggcgcg tatcctgggc aggctccacc aggtgcctac ccggggggcac   3240 ccggggcata tccgggagct cctgctcccg gagtttatcc gggtcctcct tcaggaccgg   3300
gagcgtatcc atcgagcggc cagcccagtg caacgggtgc gtacccagcc acgggcccct   3360
```

-continued

```
atggagcccc agcgggacca ttaattgtac cctataatct tccgcttcca ggcggcgtag    3420
ttcctcgtat gttaattacc attttaggaa cagtaaaacc aaatgctaat cgtattgcat    3480
tagactttca acgtggcaac gacgtagctt ttcattttaa cccacgtttt aacgaaaaca    3540
atcgtcgtgt cattgtatgc aatacaaaac tggataataa ttggggacgc gaggagcgcc    3600
agagtgtgtt cccattcgag tcgggcaaac cattcaaaat tcaggtattg gtcgagccag    3660
accatttcaa ggtcgcggtc aatgacgctc acttattaca gtacaatcat cgcgtaaaga    3720
aactgaatga gatcagtaag ttaggaatct ccggagacat tgatcttaca agtgcgagtt    3780
acacgatgat tcaccaccac caccaccact gaaagcttct cgag    3824
```

```
<210> SEQ ID NO 8
<211> LENGTH: 904
<212> TYPE: DNA
<213> ORGANISM: Artificial Sequence
<220> FEATURE:
<223> OTHER INFORMATION: Synthetic polynucleotide

<400> SEQUENCE: 8
```

```
ccatggcgcg catgaaacag ctggaagata aagtggaaga actgctgagc aaaaactatc      60
atctggaaaa ccgcgtggcg cgcctggaaa aactggtggg cgaacgcgga tccggcggcg     120
gcagcggcgg cagcggcggc ggcggcagcg cggcagcggg cgaattctcc aaaggagaag     180
agctgttcac tggagtggta ccaatacttg tggagttgga cggagatgtg aacggacaca     240
aattttcagt ccgcggggag ggggaagggg atgctactat tggcaagctg acgctcaaat     300
tcatctgtac caccggaaaa ctccctgtac cctggcccac actggtgaca actctgactt     360
acggcgtgca atgttttagc cgatacccag accacatgaa gaggcacgac ttttttcaaaa    420 gcgcaatgcc tgaaggatac gtacaggaaa ggaccatttc tttttaaagac gacgggaagt     480 acaaaacccg ggcagtggtg aagtttgagg gcgataccct cgtcaatagg atcgaattga     540
agggaactga cttcaaagaa gatggcaaca tcctgggtca caagcttgag tataacttta     600
actcccacaa cgtgtatatt acagccgaca aacagaagaa tggaattaag gctaacttca     660
ctgtcagaca caatgtcgaa gatggctccg tgcagctcgc cgatcactat caacagaata     720
ctcctatcgg gacggcccag tcctgctgcc cgacaaccac tacctgagta cccagactgt     780
tctgagcaaa gatccgaacg agaagcgcga ccacatggtg ctgcatgagt atgtcaacgc     840
tgcgggaatt accctcggca tggacgagct gtacaagctc gagcaccacc accaccacca     900
ctga    904
```

```
<210> SEQ ID NO 9
<211> LENGTH: 496
<212> TYPE: PRT
<213> ORGANISM: Artificial Sequence
<220> FEATURE:
<223> OTHER INFORMATION: Synthetic polypeptide

<400> SEQUENCE: 9
```

```
Met Ala Val Phe Thr Leu Glu Asp Phe Val Gly Asp Trp Arg Gln Thr
1               5                   10                  15

Ala Gly Tyr Asn Leu Asp Gln Val Leu Glu Gln Gly Gly Val Ser Ser
            20                  25                  30

Leu Phe Gln Asn Leu Gly Val Ser Val Thr Pro Ile Gln Arg Ile Val
        35                  40                  45

Leu Ser Gly Glu Asn Gly Leu Lys Ile Asp Ile His Val Ile Ile Pro
```

```
        50                  55                  60

Tyr Glu Gly Leu Ser Gly Asp Gln Met Gly Gln Ile Glu Lys Ile Phe
65                  70                  75                  80

Lys Val Val Tyr Pro Val Asp Asp His His Phe Lys Val Ile Leu His
                85                  90                  95

Tyr Gly Thr Leu Val Ile Asp Gly Val Thr Pro Asn Met Ile Asp Tyr
                100                 105                 110

Phe Gly Arg Pro Tyr Glu Gly Ile Ala Val Phe Asp Gly Lys Lys Ile
                115                 120                 125

Thr Val Thr Gly Thr Leu Trp Asn Gly Asn Lys Ile Ile Asp Glu Arg
                130                 135                 140

Leu Ile Asn Pro Asp Gly Ser Leu Leu Phe Arg Val Thr Ile Asn Gly
145                 150                 155                 160

Val Thr Gly Trp Arg Leu Cys Glu Arg Ile Leu Ala Gly Ser Gly Gly
                165                 170                 175

Gly Ser Gly Gly Ser Gly Gly Ser Gly Gly Met Ala Arg Met Lys Gln
                180                 185                 190

Leu Glu Asp Lys Val Glu Glu Leu Leu Ser Lys Asn Tyr His Leu Glu
                195                 200                 205

Asn Arg Val Ala Arg Leu Glu Lys Leu Val Gly Glu Arg Gly Gly Gly
                210                 215                 220

Ser Gly Gly Ser Gly Gly Gly Ser Gly Gly Ser Gly Glu Phe Ala
225                 230                 235                 240

Asp Asn Phe Ser Leu His Asp Ala Leu Ser Gly Ser Gly Asn Pro Asn
                245                 250                 255

Pro Gln Gly Trp Pro Gly Ala Trp Gly Asn Gln Pro Ala Gly Ala Gly
                260                 265                 270

Gly Tyr Pro Gly Ala Ser Tyr Pro Gly Ala Tyr Pro Gly Gln Ala Pro
                275                 280                 285

Pro Gly Ala Tyr Pro Gly Gln Ala Pro Pro Gly Ala Tyr Pro Gly Ala
                290                 295                 300

Pro Gly Ala Tyr Pro Gly Ala Pro Ala Pro Gly Val Tyr Pro Gly Pro
305                 310                 315                 320

Pro Ser Gly Pro Gly Ala Tyr Pro Ser Ser Gly Gln Pro Ser Ala Pro
                325                 330                 335

Gly Ala Tyr Pro Ala Thr Gly Pro Tyr Gly Ala Pro Ala Gly Pro Leu
                340                 345                 350

Ile Val Pro Tyr Asn Leu Pro Leu Pro Gly Gly Val Val Pro Arg Met
                355                 360                 365

Leu Ile Thr Ile Leu Gly Thr Val Lys Pro Asn Ala Asn Arg Ile Ala
                370                 375                 380

Leu Asp Phe Gln Arg Gly Asn Asp Val Ala Phe His Phe Asn Pro Arg
385                 390                 395                 400

Phe Asn Glu Asn Asn Arg Arg Val Ile Val Cys Asn Thr Lys Leu Asp
                405                 410                 415

Asn Asn Trp Gly Arg Glu Glu Arg Gln Ser Val Phe Pro Phe Glu Ser
                420                 425                 430

Gly Lys Pro Phe Lys Ile Gln Val Leu Val Glu Pro Asp His Phe Lys
                435                 440                 445

Val Ala Val Asn Asp Ala His Leu Leu Gln Tyr Asn His Arg Val Lys
                450                 455                 460

Lys Leu Asn Glu Ile Ser Lys Leu Gly Ile Ser Gly Asp Ile Asp Leu
465                 470                 475                 480
```

-continued

```
Thr Ser Ala Ser Tyr Asn Met Ile Leu Glu His His His His His
            485             490             495

<210> SEQ ID NO 10
<211> LENGTH: 445
<212> TYPE: PRT
<213> ORGANISM: Artificial Sequence
<220> FEATURE:
<223> OTHER INFORMATION: Synthetic polypeptide

<400> SEQUENCE: 10

Met Ala Val Phe Thr Leu Glu Asp Phe Val Gly Asp Trp Arg Gln Thr
1               5               10              15

Ala Gly Tyr Asn Leu Asp Gln Val Leu Glu Gln Gly Gly Val Ser Ser
            20              25              30

Leu Phe Gln Asn Leu Gly Val Ser Val Thr Pro Ile Gln Arg Ile Val
            35              40              45

Leu Ser Gly Glu Asn Gly Leu Lys Ile Asp Ile His Val Ile Ile Pro
        50              55              60

Tyr Glu Gly Leu Ser Gly Asp Gln Met Gly Gln Ile Glu Lys Ile Phe
65              70              75              80

Lys Val Val Tyr Pro Val Asp Asp His His Phe Lys Val Ile Leu His
            85              90              95

Tyr Gly Thr Leu Val Ile Asp Gly Val Thr Pro Asn Met Ile Asp Tyr
            100             105             110

Phe Gly Arg Pro Tyr Glu Gly Ile Ala Val Phe Asp Gly Lys Lys Ile
            115             120             125

Thr Val Thr Gly Thr Leu Trp Asn Gly Asn Lys Ile Ile Asp Glu Arg
            130             135             140

Leu Ile Asn Pro Asp Gly Ser Leu Leu Phe Arg Val Thr Ile Asn Gly
145             150             155             160

Val Thr Gly Trp Arg Leu Cys Glu Arg Ile Leu Ala Gly Ser Gly Gly
            165             170             175

Gly Ser Gly Gly Ser Gly Gly Ser Gly Gly Glu Phe Ala Asp Asn Phe
            180             185             190

Ser Leu His Asp Ala Leu Ser Gly Ser Gly Asn Pro Asn Pro Gln Gly
            195             200             205

Trp Pro Gly Ala Trp Gly Asn Gln Pro Ala Gly Ala Gly Gly Tyr Pro
            210             215             220

Gly Ala Ser Tyr Pro Gly Ala Tyr Pro Gly Gln Ala Pro Pro Gly Ala
225             230             235             240

Tyr Pro Gly Gln Ala Pro Pro Gly Ala Tyr Pro Gly Ala Pro Gly Ala
            245             250             255

Tyr Pro Gly Ala Pro Ala Pro Gly Val Tyr Pro Gly Pro Pro Ser Gly
            260             265             270

Pro Gly Ala Tyr Pro Ser Ser Gly Gln Pro Ser Ala Pro Gly Ala Tyr
            275             280             285

Pro Ala Thr Gly Pro Tyr Gly Ala Pro Ala Gly Pro Leu Ile Val Pro
            290             295             300

Tyr Asn Leu Pro Leu Pro Gly Gly Val Val Pro Arg Met Leu Ile Thr
305             310             315             320

Ile Leu Gly Thr Val Lys Pro Asn Ala Asn Arg Ile Ala Leu Asp Phe
            325             330             335

Gln Arg Gly Asn Asp Val Ala Phe His Phe Asn Pro Arg Phe Asn Glu
            340             345             350
```

-continued

Asn Asn Arg Arg Val Ile Val Cys Asn Thr Lys Leu Asp Asn Asn Trp
    355             360             365

Gly Arg Glu Glu Arg Gln Ser Val Phe Pro Phe Glu Ser Gly Lys Pro
    370             375             380

Phe Lys Ile Gln Val Leu Val Glu Pro Asp His Phe Lys Val Ala Val
385             390             395             400

Asn Asp Ala His Leu Leu Gln Tyr Asn His Arg Val Lys Lys Leu Asn
            405             410             415

Glu Ile Ser Lys Leu Gly Ile Ser Gly Asp Ile Asp Leu Thr Ser Ala
            420             425             430

Ser Tyr Asn Met Ile Leu Glu His His His His His His
            435             440             445

<210> SEQ ID NO 11
<211> LENGTH: 180
<212> TYPE: PRT
<213> ORGANISM: Artificial Sequence
<220> FEATURE:
<223> OTHER INFORMATION: Synthetic polypeptide

<400> SEQUENCE: 11

Met Ala Val Phe Thr Leu Glu Asp Phe Val Gly Asp Trp Arg Gln Thr
1               5               10              15

Ala Gly Tyr Asn Leu Asp Gln Val Leu Glu Gln Gly Gly Val Ser Ser
            20              25              30

Leu Phe Gln Asn Leu Gly Val Ser Val Thr Pro Ile Gln Arg Ile Val
            35              40              45

Leu Ser Gly Glu Asn Gly Leu Lys Ile Asp Ile His Val Ile Ile Pro
    50              55              60

Tyr Glu Gly Leu Ser Gly Asp Gln Met Gly Gln Ile Glu Lys Ile Phe
65              70              75              80

Lys Val Val Tyr Pro Val Asp Asp His His Phe Lys Val Ile Leu His
            85              90              95

Tyr Gly Thr Leu Val Ile Asp Gly Val Thr Pro Asn Met Ile Asp Tyr
            100             105             110

Phe Gly Arg Pro Tyr Glu Gly Ile Ala Val Phe Asp Gly Lys Lys Ile
            115             120             125

Thr Val Thr Gly Thr Leu Trp Asn Gly Asn Lys Ile Ile Asp Glu Arg
            130             135             140

Leu Ile Asn Pro Asp Gly Ser Leu Leu Phe Arg Val Thr Ile Asn Gly
145             150             155             160

Val Thr Gly Trp Arg Leu Cys Glu Arg Ile Leu Ala Gly Ser His His
            165             170             175

His His His His
            180

<210> SEQ ID NO 12
<211> LENGTH: 563
<212> TYPE: PRT
<213> ORGANISM: Artificial Sequence
<220> FEATURE:
<223> OTHER INFORMATION: Synthetic polypeptide

<400> SEQUENCE: 12

Met Ser Lys Gly Glu Glu Leu Phe Thr Gly Val Val Pro Ile Leu Val
1               5               10              15

Glu Leu Asp Gly Asp Val Asn Gly His Lys Phe Ser Val Arg Gly Glu

-continued

```
              20              25              30

Gly Glu Gly Asp Ala Thr Ile Gly Lys Leu Thr Leu Lys Phe Ile Cys
          35              40              45

Thr Thr Gly Lys Leu Pro Val Pro Trp Pro Thr Leu Val Thr Thr Leu
      50              55              60

Thr Tyr Gly Val Gln Cys Phe Ser Arg Tyr Pro Asp His Met Lys Arg
65              70              75              80

His Asp Phe Phe Lys Ser Ala Met Pro Glu Gly Tyr Val Gln Glu Arg
              85              90              95

Thr Ile Ser Phe Lys Asp Asp Gly Lys Tyr Lys Thr Arg Ala Val Val
          100             105             110

Lys Phe Glu Gly Asp Thr Leu Val Asn Arg Ile Glu Leu Lys Gly Thr
      115             120             125

Asp Phe Lys Glu Asp Gly Asn Ile Leu Gly His Lys Leu Glu Tyr Asn
      130             135             140

Phe Asn Ser His Asn Val Tyr Ile Thr Ala Asp Lys Gln Lys Asn Gly
145             150             155             160

Ile Lys Ala Asn Phe Thr Val Arg His Asn Val Glu Asp Gly Ser Val
          165             170             175

Gln Leu Ala Asp Asp His Tyr Gln Gln Asn Thr Pro Ile Gly Asp Gly
          180             185             190

Pro Val Leu Leu Pro Asp Asn His Tyr Leu Ser Thr Gln Thr Val Leu
          195             200             205

Ser Lys Asp Pro Asn Glu Lys Arg Asp His Met Val Leu His Glu Tyr
      210             215             220

Val Asn Ala Ala Gly Ile Thr Leu Gly Met Asp Glu Leu Tyr Lys Gly
225             230             235             240

Ser Gly Gly Gly Ser Gly Gly Ser Gly Gly Ser Gly Gly Met Ala Arg
          245             250             255

Met Lys Gln Leu Glu Asp Lys Val Glu Glu Leu Leu Ser Lys Asn Tyr
          260             265             270

His Leu Glu Asn Arg Val Ala Arg Leu Glu Lys Leu Val Gly Glu Arg
      275             280             285

Gly Gly Gly Ser Gly Gly Ser Gly Gly Gly Gly Ser Gly Gly Ser Gly
      290             295             300

Glu Phe Ala Asp Asn Phe Ser Leu His Asp Ala Leu Ser Gly Ser Gly
305             310             315             320

Asn Pro Asn Pro Gln Gly Trp Pro Gly Ala Trp Gly Asn Gln Pro Ala
          325             330             335

Gly Ala Gly Gly Tyr Pro Gly Ala Ser Tyr Pro Gly Ala Tyr Pro Gly
          340             345             350

Gln Ala Pro Pro Gly Ala Tyr Pro Gly Gln Ala Pro Pro Gly Ala Tyr
          355             360             365

Pro Gly Ala Pro Gly Ala Tyr Pro Gly Ala Pro Ala Pro Gly Val Tyr
      370             375             380

Pro Gly Pro Pro Ser Gly Pro Gly Ala Tyr Pro Ser Ser Gly Gln Pro
385             390             395             400

Ser Ala Pro Gly Ala Tyr Pro Ala Thr Gly Pro Tyr Gly Ala Pro Ala
          405             410             415

Gly Pro Leu Ile Val Pro Tyr Asn Leu Pro Leu Pro Gly Gly Val Val
          420             425             430

Pro Arg Met Leu Ile Thr Ile Leu Gly Thr Val Lys Pro Asn Ala Asn
      435             440             445
```

-continued

```
Arg Ile Ala Leu Asp Phe Gln Arg Gly Asn Asp Val Ala Phe His Phe
    450                 455                 460

Asn Pro Arg Phe Asn Glu Asn Asn Arg Arg Val Ile Val Cys Asn Thr
465                 470                 475                 480

Lys Leu Asp Asn Asn Trp Gly Arg Glu Glu Arg Gln Ser Val Phe Pro
                485                 490                 495

Phe Glu Ser Gly Lys Pro Phe Lys Ile Gln Val Leu Val Glu Pro Asp
                500                 505                 510

His Phe Lys Val Ala Val Asn Asp Ala His Leu Leu Gln Tyr Asn His
            515                 520                 525

Arg Val Lys Lys Leu Asn Glu Ile Ser Lys Leu Gly Ile Ser Gly Asp
        530                 535                 540

Ile Asp Leu Thr Ser Ala Ser Thr Asn Met Ile Leu Glu His His His
545                 550                 555                 560

His His His
```

```
<210> SEQ ID NO 13
<211> LENGTH: 510
<212> TYPE: PRT
<213> ORGANISM: Artificial Sequence
<220> FEATURE:
<223> OTHER INFORMATION: Synthetic polypeptide

<400> SEQUENCE: 13
```

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Ile Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Lys Tyr Lys Thr Arg Ala Val Val
                100                 105                 110

Lys Phe Glu Gly Asp Thr Leu Val Asn Arg Ile Glu Leu Lys Gly Thr
            115                 120                 125

Asp Phe Lys Glu Asp Gly Asn Ile Leu Gly His Lys Leu Glu Tyr Asn
        130                 135                 140

Phe Asn Ser His Val Val Tyr Ile Thr Ala Asp Lys Gln Lys Asn Gly
145                 150                 155                 160

Ile Lys Ala Asn Phe Thr Val Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
            195                 200                 205

Lys Asp Pro Asn Glu Lys Arg Asp His Met Val Leu His Glu Tyr Val
        210                 215                 220

Asn Ala Ala Gly Ile Thr Leu Gly Met Asp Glu Leu Tyr Lys Gly Ser
225                 230                 235                 240
```

```
Gly Gly Gly Ser Gly Gly Ser Gly Gly Ser Gly Gly Glu Phe Ala Asp
            245             250             255

Asn Phe Ser Leu His Asp Ala Leu Ser Gly Ser Gly Asn Pro Asn Pro
            260             265             270

Gln Gly Trp Pro Gly Ala Trp Gly Asn Gln Pro Ala Gly Ala Gly Gly
            275             280             285

Tyr Pro Gly Ala Ser Tyr Pro Gly Ala Tyr Pro Gly Gln Ala Pro Pro
            290             295             300

Gly Ala Tyr Pro Gly Gln Ala Pro Pro Gly Ala Tyr Pro Gly Ala Pro
305             310             315             320

Gly Ala Tyr Pro Gly Ala Pro Ala Pro Gly Val Tyr Pro Gly Pro Pro
            325             330             335

Ser Gly Pro Gly Ala Tyr Pro Ser Ser Gly Gln Pro Ser Ala Pro Gly
            340             345             350

Ala Tyr Pro Ala Thr Gly Pro Tyr Gly Ala Pro Ala Gly Pro Leu Ile
            355             360             365

Val Pro Tyr Asn Leu Pro Leu Pro Gly Gly Val Val Pro Arg Met Leu
            370             375             380

Ile Thr Ile Leu Gly Thr Val Lys Pro Asn Ala Asn Arg Ile Ala Leu
385             390             395             400

Asp Phe Gln Arg Gly Asn Asp Val Ala Phe His Phe Asn Pro Arg Phe
            405             410             415

Asn Glu Asn Asn Arg Arg Val Ile Val Cys Asn Thr Lys Leu Asp Asn
            420             425             430

Asn Trp Gly Arg Glu Glu Arg Gln Ser Val Phe Pro Phe Glu Ser Gly
            435             440             445

Lys Pro Phe Lys Ile Gln Val Leu Val Glu Pro Asp His Phe Lys Val
            450             455             460

Ala Val Asn Asp Ala His Leu Leu Gln Tyr Asn His Arg Val Lys Lys
465             470             475             480

Leu Asn Glu Ile Ser Lys Leu Gly Ile Ser Gly Asp Ile Asp Leu Thr
            485             490             495

Ser Ala Ser Tyr Asn Met Ile Leu Glu His His His His
            500             505             510
```

```
<210> SEQ ID NO 14
<211> LENGTH: 300
<212> TYPE: PRT
<213> ORGANISM: Artificial Sequence
<220> FEATURE:
<223> OTHER INFORMATION: Synthetic polypeptide

<400> SEQUENCE: 14
```

```
Met Ala Arg Met Lys Gln Leu Glu Asp Lys Val Glu Glu Leu Leu Ser
1               5               10              15

Lys Asn Tyr His Leu Glu Asn Arg Val Ala Arg Leu Glu Lys Leu Val
            20              25              30

Gly Glu Arg Gly Ser Gly Gly Ser Gly Gly Ser Gly Gly Gly Gly
            35              40              45

Ser Gly Gly Ser Gly Glu Phe Ser Lys Gly Glu Glu Leu Phe Thr Gly
            50              55              60

Val Val Pro Ile Leu Val Glu Leu Asp Gly Asp Val Asn Gly His Lys
65              70              75              80

Phe Ser Val Arg Gly Glu Gly Glu Gly Asp Ala Thr Ile Gly Lys Leu
            85              90              95
```

```
Thr Leu Lys Phe Ile Cys Thr Thr Gly Lys Leu Pro Val Pro Trp Pro
            100                 105                 110

Thr Leu Val Thr Thr Leu Thr Tyr Gly Val Gln Cys Phe Ser Arg Tyr
            115                 120                 125

Pro Asp His Met Lys Arg His Asp Phe Phe Lys Ser Ala Met Pro Glu
            130                 135                 140

Gly Tyr Val Gln Glu Arg Thr Ile Ser Phe Lys Asp Asp Gly Lys Tyr
145                 150                 155                 160

Lys Thr Arg Ala Val Val Lys Phe Glu Gly Asp Thr Leu Val Asn Arg
                165                 170                 175

Ile Glu Leu Lys Gly Thr Asp Phe Lys Glu Asp Gly Asn Ile Leu Gly
            180                 185                 190

His Lys Leu Glu Tyr Asn Phe Asn Ser His Asn Val Tyr Ile Thr Ala
            195                 200                 205

Asp Lys Gln Lys Asn Gly Ile Lys Ala Asn Phe Thr Val Arg His Asn
            210                 215                 220

Val Glu Asp Gly Ser Val Gln Leu Ala Asp His Tyr Gln Gln Asn Thr
225                 230                 235                 240

Pro Ile Gly Asp Gly Pro Val Leu Leu Pro Asp Asn His Tyr Leu Ser
                245                 250                 255

Thr Gln Thr Val Leu Ser Lys Asp Pro Asn Glu Lys Arg Asp His Met
            260                 265                 270

Val Leu His Glu Tyr Val Asn Ala Ala Gly Ile Thr Leu Gly Met Asp
            275                 280                 285

Glu Leu Tyr Lys Leu Glu His His His His His His
    290                 295                 300
```

```
<210> SEQ ID NO 15
<211> LENGTH: 1323
<212> TYPE: PRT
<213> ORGANISM: Artificial Sequence
<220> FEATURE:
<223> OTHER INFORMATION: Synthetic polypeptide

<400> SEQUENCE: 15
```

```
Met Ala Thr Ser Asn Pro Ala Phe Asp Pro Lys Asn Leu Met Gln Ser
1               5                   10                  15

Glu Ile Tyr His Phe Ala Gln Asn Asn Pro Leu Ala Asp Phe Ser Ser
            20                  25                  30

Asp Lys Asn Ser Ile Leu Thr Leu Ser Asp Lys Arg Ser Ile Met Gly
            35                  40                  45

Asn Gln Ser Leu Leu Trp Lys Trp Lys Gly Gly Ser Ser Phe Thr Leu
            50                  55                  60

His Lys Lys Leu Ile Val Pro Thr Asp Lys Glu Ala Ser Lys Ala Trp
65                  70                  75                  80

Gly Arg Ser Ser Thr Pro Val Phe Ser Phe Trp Leu Tyr Asn Glu Lys
                85                  90                  95

Pro Ile Asp Gly Tyr Leu Thr Ile Asp Phe Gly Glu Lys Leu Ile Ser
            100                 105                 110

Thr Ser Glu Ala Gln Ala Gly Phe Lys Val Lys Leu Asp Phe Thr Gly
            115                 120                 125

Trp Arg Thr Val Gly Val Ser Leu Asn Asn Asp Leu Glu Asn Arg Glu
            130                 135                 140

Met Thr Leu Asn Ala Thr Asn Thr Ser Ser Asp Gly Thr Gln Asp Ser
145                 150                 155                 160
```

-continued

Ile Gly Arg Ser Leu Gly Ala Lys Val Asp Ser Ile Arg Phe Lys Ala
                165                     170                     175

Pro Ser Asn Val Ser Gln Gly Glu Ile Tyr Ile Asp Arg Ile Met Phe
                180                     185                     190

Ser Val Asp Asp Ala Arg Tyr Gln Trp Ser Asp Tyr Gln Val Lys Thr
                195                     200                     205

Arg Leu Ser Glu Pro Glu Ile Gln Phe His Asn Val Lys Pro Gln Leu
        210                     215                     220

Pro Val Thr Pro Glu Asn Leu Ala Ala Ile Asp Leu Ile Arg Gln Arg
225                     230                     235                     240

Leu Ile Asn Glu Phe Val Gly Gly Glu Lys Glu Thr Asn Leu Ala Leu
                245                     250                     255

Glu Glu Asn Ile Ser Lys Leu Lys Ser Asp Phe Asp Ala Leu Asn Ile
                260                     265                     270

His Thr Leu Ala Asn Gly Gly Thr Gln Gly Arg His Leu Ile Thr Asp
        275                     280                     285

Lys Gln Ile Ile Ile Tyr Gln Pro Glu Asn Leu Asn Ser Gln Asp Lys
        290                     295                     300

Gln Leu Phe Asp Asn Tyr Val Ile Leu Gly Asn Tyr Thr Thr Leu Met
305                     310                     315                     320

Phe Asn Ile Ser Arg Ala Tyr Val Leu Glu Lys Asp Pro Thr Gln Lys
                325                     330                     335

Ala Gln Leu Lys Gln Met Tyr Leu Leu Met Thr Lys His Leu Leu Asp
                340                     345                     350

Gln Gly Phe Val Lys Gly Ser Ala Leu Val Thr Thr His His Trp Gly
        355                     360                     365

Tyr Ser Ser Arg Trp Trp Tyr Ile Ser Thr Leu Leu Met Ser Asp Ala
        370                     375                     380

Leu Lys Glu Ala Asn Leu Gln Thr Gln Val Tyr Asp Ser Leu Leu Trp
385                     390                     395                     400

Tyr Ser Arg Glu Phe Lys Ser Ser Phe Asp Met Lys Val Ser Ala Asp
                405                     410                     415

Ser Ser Asp Leu Asp Tyr Phe Asn Thr Leu Ser Arg Gln His Leu Ala
                420                     425                     430

Leu Leu Leu Leu Glu Pro Asp Asp Gln Lys Arg Ile Asn Leu Val Asn
        435                     440                     445

Thr Phe Ser His Tyr Ile Thr Gly Ala Leu Thr Gln Val Pro Pro Gly
        450                     455                     460

Gly Lys Asp Gly Leu Arg Pro Asp Gly Thr Ala Trp Arg His Glu Gly
465                     470                     475                     480

Asn Tyr Pro Gly Tyr Ser Phe Pro Ala Phe Lys Asn Ala Ser Gln Leu
                485                     490                     495

Ile Tyr Leu Leu Arg Asp Thr Pro Phe Ser Val Gly Glu Ser Gly Trp
                500                     505                     510

Asn Asn Leu Lys Lys Ala Met Val Ser Ala Trp Ile Tyr Ser Asn Pro
        515                     520                     525

Glu Val Gly Leu Pro Leu Ala Gly Arg His Pro Phe Asn Ser Pro Ser
        530                     535                     540

Leu Lys Ser Val Ala Gln Gly Tyr Tyr Trp Leu Ala Met Ser Ala Lys
545                     550                     555                     560

Ser Ser Pro Asp Lys Thr Leu Ala Ser Ile Tyr Leu Ala Ile Ser Asp
                565                     570                     575

Lys Thr Gln Asn Glu Ser Thr Ala Ile Phe Gly Glu Thr Ile Thr Pro

-continued

```
                   580              585              590

Ala Ser Leu Pro Gln Gly Phe Tyr Ala Phe Asn Gly Gly Ala Phe Gly
        595              600              605

Ile His Arg Trp Gln Asp Lys Met Val Thr Leu Lys Ala Tyr Asn Thr
    610              615              620

Asn Val Trp Ser Ser Glu Ile Tyr Asn Lys Asp Asn Arg Tyr Gly Arg
625              630              635              640

Tyr Gln Ser His Gly Val Ala Gln Ile Val Ser Asn Gly Ser Gln Leu
            645              650              655

Ser Gln Gly Tyr Gln Gln Glu Gly Trp Asp Trp Asn Arg Met Pro Gly
            660              665              670

Ala Thr Thr Ile His Leu Pro Leu Lys Asp Leu Asp Ser Pro Lys Pro
        675              680              685

His Thr Leu Met Gln Arg Gly Glu Arg Gly Phe Ser Gly Thr Ser Ser
    690              695              700

Leu Glu Gly Gln Tyr Gly Met Met Ala Phe Asp Leu Ile Tyr Pro Ala
705              710              715              720

Asn Leu Glu Arg Phe Asp Pro Asn Phe Thr Ala Lys Lys Ser Val Leu
            725              730              735

Ala Ala Asp Asn His Leu Ile Phe Ile Gly Ser Asn Ile Asn Ser Ser
            740              745              750

Asp Lys Asn Lys Asn Val Glu Thr Thr Leu Phe Gln His Ala Ile Thr
        755              760              765

Pro Thr Leu Asn Thr Leu Trp Ile Asn Gly Gln Lys Ile Glu Asn Met
    770              775              780

Pro Tyr Gln Thr Thr Leu Gln Gln Gly Asp Trp Leu Ile Asp Ser Asn
785              790              795              800

Gly Asn Gly Tyr Leu Ile Thr Gln Ala Glu Lys Val Asn Val Ser Arg
            805              810              815

Gln His Gln Val Ser Ala Glu Asn Lys Asn Arg Gln Pro Thr Glu Gly
        820              825              830

Asn Phe Ser Ser Ala Ala Trp Ile Asp His Ser Thr Arg Pro Lys Asp
        835              840              845

Ala Ser Tyr Glu Tyr Met Val Phe Leu Asp Ala Thr Pro Glu Lys Met
    850              855              860

Gly Glu Met Ala Gln Lys Phe Arg Glu Asn Asn Gly Leu Tyr Gln Val
865              870              875              880

Leu Arg Lys Asp Lys Asp Val His Ile Ile Leu Asp Lys Leu Ser Asn
            885              890              895

Val Thr Gly Tyr Ala Phe Tyr Gln Pro Ala Ser Ile Glu Asp Lys Trp
            900              905              910

Ile Lys Lys Val Asn Lys Pro Ala Ile Val Met Thr His Arg Gln Lys
        915              920              925

Asp Thr Leu Ile Val Ser Ala Val Thr Pro Asp Leu Asn Met Thr Arg
    930              935              940

Gln Lys Ala Ala Thr Pro Val Thr Ile Asn Val Thr Ile Asn Gly Lys
945              950              955              960

Trp Gln Ser Ala Asp Lys Asn Ser Glu Val Lys Tyr Gln Val Ser Gly
            965              970              975

Asp Asn Thr Glu Leu Thr Phe Thr Ser Tyr Phe Gly Ile Pro Gln Glu
            980              985              990

Ile Lys Leu Ser Pro Leu Pro Gly  Ser Gly Gly Gly Ser  Gly Gly Ser
        995              1000             1005
```

```
Gly Gly  Ser Gly Gly Met Ala  Arg Met Lys Gln Leu  Glu Asp Lys
    1010             1015             1020

Val Glu  Glu Leu Leu Ser Lys  Asn Tyr His Leu Glu  Asn Arg Val
    1025             1030             1035

Ala Arg  Leu Glu Lys Leu Val  Gly Glu Arg Gly Gly  Gly Ser Gly
    1040             1045             1050

Gly Ser  Gly Gly Gly Gly Ser  Gly Gly Ser Gly Glu  Phe Ala Asp
    1055             1060             1065

Asn Phe  Ser Leu His Asp Ala  Leu Ser Gly Ser Gly  Asn Pro Asn
    1070             1075             1080

Pro Gln  Gly Trp Pro Gly Ala  Trp Gly Asn Gln Pro  Ala Gly Ala
    1085             1090             1095

Gly Gly  Tyr Pro Gly Ala Ser  Tyr Pro Gly Ala Tyr  Pro Gly Gln
    1100             1105             1110

Ala Pro  Pro Gly Ala Tyr Pro  Gly Gln Ala Pro Pro  Gly Ala Tyr
    1115             1120             1125

Pro Gly  Ala Pro Gly Ala Tyr  Pro Gly Ala Pro Ala  Pro Gly Val
    1130             1135             1140

Tyr Pro  Gly Pro Pro Ser Gly  Pro Gly Ala Tyr Pro  Ser Ser Gly
    1145             1150             1155

Gln Pro  Ser Ala Pro Gly Ala  Tyr Pro Ala Thr Gly  Pro Tyr Gly
    1160             1165             1170

Ala Pro  Ala Gly Pro Leu Ile  Val Pro Tyr Asn Leu  Pro Leu Pro
    1175             1180             1185

Gly Gly  Val Val Pro Arg Met  Leu Ile Thr Ile Leu  Gly Thr Val
    1190             1195             1200

Lys Pro  Asn Ala Asn Arg Ile  Ala Leu Asp Phe Gln  Arg Gly Asn
    1205             1210             1215

Asp Val  Ala Phe His Phe Asn  Pro Arg Phe Asn Glu  Asn Asn Arg
    1220             1225             1230

Arg Val  Ile Val Cys Asn Thr  Lys Leu Asp Asn Asn  Trp Gly Arg
    1235             1240             1245

Glu Glu  Arg Gln Ser Val Phe  Pro Phe Glu Ser Gly  Lys Pro Phe
    1250             1255             1260

Lys Ile  Gln Val Leu Val Glu  Pro Asp His Phe Lys  Val Ala Val
    1265             1270             1275

Asn Asp  Ala His Leu Leu Gln  Tyr Asn His Arg Val  Lys Lys Leu
    1280             1285             1290

Asn Glu  Ile Ser Lys Leu Gly  Ile Ser Gly Asp Ile  Asp Leu Thr
    1295             1300             1305

Ser Ala  Ser Tyr Asn Met Ile  Leu Glu His His His  His His His
    1310             1315             1320
```

```
<210> SEQ ID NO 16
<211> LENGTH: 1270
<212> TYPE: PRT
<213> ORGANISM: Artificial Sequence
<220> FEATURE:
<223> OTHER INFORMATION: Synthetic polypeptide

<400> SEQUENCE: 16

Met Ala Thr Ser Asn Pro Ala Phe Asp Pro Lys Asn Leu Met Gln Ser
1               5                   10                  15

Glu Ile Tyr His Phe Ala Gln Asn Asn Pro Leu Ala Asp Phe Ser Ser
            20                  25                  30
```

```
Asp Lys Asn Ser Ile Leu Thr Leu Ser Asp Lys Arg Ser Ile Met Gly
        35                  40                  45

Asn Gln Ser Leu Leu Trp Lys Trp Lys Gly Gly Ser Ser Phe Thr Leu
        50                  55                  60

His Lys Lys Leu Ile Val Pro Thr Asp Lys Glu Ala Ser Lys Ala Trp
65                  70                  75                  80

Gly Arg Ser Ser Thr Pro Val Phe Ser Phe Trp Leu Tyr Asn Glu Lys
                85                  90                  95

Pro Ile Asp Gly Tyr Leu Thr Ile Asp Phe Gly Glu Lys Leu Ile Ser
                100                 105                 110

Thr Ser Glu Ala Gln Ala Gly Phe Lys Val Lys Leu Asp Phe Thr Gly
        115                 120                 125

Trp Arg Thr Val Gly Val Ser Leu Asn Asn Asp Leu Glu Asn Arg Glu
        130                 135                 140

Met Thr Leu Asn Ala Thr Asn Thr Ser Ser Asp Gly Thr Gln Asp Ser
145                 150                 155                 160

Ile Gly Arg Ser Leu Gly Ala Lys Val Asp Ser Ile Arg Phe Lys Ala
                165                 170                 175

Pro Ser Asn Val Ser Gln Gly Glu Ile Tyr Ile Asp Arg Ile Met Phe
                180                 185                 190

Ser Val Asp Asp Ala Arg Tyr Gln Trp Ser Asp Tyr Gln Val Lys Thr
                195                 200                 205

Arg Leu Ser Glu Pro Glu Ile Gln Phe His Asn Val Lys Pro Gln Leu
        210                 215                 220

Pro Val Thr Pro Glu Asn Leu Ala Ala Ile Asp Leu Ile Arg Gln Arg
225                 230                 235                 240

Leu Ile Asn Glu Phe Val Gly Gly Glu Lys Glu Thr Asn Leu Ala Leu
                245                 250                 255

Glu Glu Asn Ile Ser Lys Leu Lys Ser Asp Phe Asp Ala Leu Asn Ile
                260                 265                 270

His Thr Leu Ala Asn Gly Gly Thr Gln Gly Arg His Leu Ile Thr Asp
        275                 280                 285

Lys Gln Ile Ile Ile Tyr Gln Pro Glu Asn Leu Asn Ser Gln Asp Lys
        290                 295                 300

Gln Leu Phe Asp Asn Tyr Val Ile Leu Gly Asn Tyr Thr Thr Leu Met
305                 310                 315                 320

Phe Asn Ile Ser Arg Ala Tyr Val Leu Glu Lys Asp Pro Thr Gln Lys
                325                 330                 335

Ala Gln Leu Lys Gln Met Tyr Leu Leu Met Thr Lys His Leu Leu Asp
                340                 345                 350

Gln Gly Phe Val Lys Gly Ser Ala Leu Val Thr Thr His His Trp Gly
                355                 360                 365

Tyr Ser Ser Arg Trp Trp Tyr Ile Ser Thr Leu Leu Met Ser Asp Ala
        370                 375                 380

Leu Lys Glu Ala Asn Leu Gln Thr Gln Val Tyr Asp Ser Leu Leu Trp
385                 390                 395                 400

Tyr Ser Arg Glu Phe Lys Ser Ser Phe Asp Met Lys Val Ser Ala Asp
                405                 410                 415

Ser Ser Asp Leu Asp Tyr Phe Asn Thr Leu Ser Arg Gln His Leu Ala
                420                 425                 430

Leu Leu Leu Leu Glu Pro Asp Asp Gln Lys Arg Ile Asn Leu Val Asn
        435                 440                 445
```

-continued

```
Thr Phe Ser His Tyr Ile Thr Gly Ala Leu Thr Gln Pro Val Pro Gly
    450                 455                 460

Gly Lys Asp Gly Leu Arg Pro Asp Gly Thr Ala Trp Arg His Glu Gly
465                 470                 475                 480

Asn Tyr Pro Gly Tyr Ser Phe Pro Ala Phe Lys Asn Ala Ser Gln Leu
                485                 490                 495

Ile Tyr Leu Leu Arg Asp Thr Pro Phe Ser Val Gly Glu Ser Gly Trp
            500                 505                 510

Asn Asn Leu Lys Lys Ala Met Val Ser Ala Trp Ile Tyr Ser Asn Pro
        515                 520                 525

Glu Val Gly Leu Pro Leu Ala Gly Arg His Pro Phe Asn Ser Pro Ser
    530                 535                 540

Leu Lys Ser Val Ala Gln Gly Tyr Tyr Trp Leu Ala Met Ser Ala Lys
545                 550                 555                 560

Ser Ser Pro Asp Lys Thr Leu Ala Ser Ile Tyr Leu Ala Ile Ser Asp
                565                 570                 575

Lys Thr Gln Asn Glu Ser Thr Ala Ile Phe Gly Glu Thr Ile Thr Pro
            580                 585                 590

Ala Ser Leu Pro Gln Gly Phe Tyr Ala Phe Asn Gly Gly Ala Phe Gly
            595                 600                 605

Ile His Arg Trp Gln Asp Lys Met Val Thr Leu Lys Ala Tyr Asn Thr
    610                 615                 620

Asn Val Trp Ser Ser Glu Ile Tyr Asn Lys Asp Asn Arg Tyr Gly Arg
625                 630                 635                 640

Tyr Gln Ser His Gly Val Ala Gln Ile Val Ser Asn Gly Ser Gln Leu
                645                 650                 655

Ser Gln Gly Tyr Gln Gln Glu Gly Trp Asp Trp Asn Arg Met Pro Gly
            660                 665                 670

Ala Thr Thr Ile His Leu Pro Leu Lys Asp Leu Asp Ser Pro Lys Pro
            675                 680                 685

His Thr Leu Met Gln Arg Gly Glu Arg Gly Phe Ser Gly Thr Ser Ser
    690                 695                 700

Leu Glu Gly Gln Tyr Gly Met Met Ala Phe Asp Leu Ile Tyr Pro Ala
705                 710                 715                 720

Asn Leu Glu Arg Phe Asp Pro Asn Phe Thr Ala Lys Lys Ser Val Leu
                725                 730                 735

Ala Ala Asp Asn His Leu Ile Phe Ile Gly Ser Asn Ile Asn Ser Ser
            740                 745                 750

Asp Lys Asn Lys Asn Val Glu Thr Thr Leu Phe Gln His Ala Ile Thr
            755                 760                 765

Pro Thr Leu Asn Thr Leu Trp Ile Asn Gly Gln Lys Glu Ile Asn Met
    770                 775                 780

Pro Tyr Gln Thr Thr Leu Gln Gln Gly Asp Trp Leu Ile Asp Ser Asn
785                 790                 795                 800

Gly Asn Gly Tyr Leu Ile Thr Gln Ala Glu Lys Val Asn Val Ser Arg
                805                 810                 815

Gln His Gln Val Ser Ala Glu Asn Lys Asn Arg Gln Pro Thr Glu Gly
            820                 825                 830

Asn Phe Ser Ser Ala Trp Ile Asp His Ser Thr Arg Pro Lys Asp Ala
            835                 840                 845

Ser Tyr Glu Tyr Met Val Phe Leu Asp Ala Thr Pro Glu Lys Met Gly
    850                 855                 860

Glu Met Ala Gln Lys Phe Arg Glu Asn Asn Gly Leu Tyr Gln Val Leu
```

-continued

```
865                 870                 875                 880

Arg Lys Asp Lys Asp Val His Ile Ile Leu Asp Lys Leu Ser Asn Val
                885                 890             895

Thr Gly Tyr Ala Phe Tyr Gln Pro Ala Ser Ile Glu Asp Lys Trp Ile
            900             905                 910

Lys Lys Val Asn Lys Pro Ala Ile Val Met Thr His Arg Gln Lys Asp
        915             920                 925

Thr Leu Ile Val Ser Ala Val Thr Pro Asp Leu Asn Met Thr Arg Gln
    930             935             940

Lys Ala Ala Thr Pro Val Thr Ile Asn Val Thr Ile Asn Gly Lys Trp
945             950             955             960

Gln Ser Ala Asp Lys Asn Ser Glu Val Lys Tyr Gln Val Ser Gly Asp
            965             970             975

Asn Thr Glu Leu Thr Phe Thr Ser Tyr Phe Gly Ile Pro Gln Glu Ile
            980             985             990

Lys Leu Ser Pro Leu Pro Gly Ser  Gly Gly Gly Ser Gly  Gly Ser Gly
        995             1000                1005

Gly Ser  Gly Gly Glu Phe Met  Ala Asp Asn Phe Ser  Leu His Asp
    1010            1015            1020

Ala Leu  Ser Gly Ser Gly Asn  Pro Asn Pro Gln Gly  Trp Pro Gly
    1025            1030            1035

Ala Trp  Gly Asn Gln Pro Ala  Gly Ala Gly Gly Tyr  Pro Gly Ala
    1040            1045            1050

Ser Tyr  Pro Gly Ala Tyr Pro  Gly Gln Ala Pro Pro  Gly Ala Tyr
    1055            1060            1065

Pro Gly  Gln Ala Pro Pro Gly  Ala Tyr Pro Gly Ala  Pro Gly Ala
    1070            1075            1080

Tyr Pro  Gly Ala Pro Ala Pro  Gly Val Tyr Pro Gly  Pro Pro Ser
    1085            1090            1095

Gly Pro  Gly Ala Tyr Pro Ser  Ser Gly Gln Pro Ser  Ala Thr Gly
    1100            1105            1110

Ala Tyr  Pro Ala Thr Gly Pro  Tyr Gly Ala Pro Ala  Gly Pro Leu
    1115            1120            1125

Ile Val  Pro Tyr Asn Leu Pro  Leu Pro Gly Gly Val  Val Pro Arg
    1130            1135            1140

Met Leu  Ile Thr Ile Leu Gly  Thr Val Lys Pro Asn  Ala Asn Arg
    1145            1150            1155

Ile Ala  Leu Asp Phe Gln Arg  Gly Asn Asp Val Ala  Phe His Phe
    1160            1165            1170

Asn Pro  Arg Phe Asn Glu Asn  Asn Arg Arg Val Ile  Val Cys Asn
    1175            1180            1185

Thr Lys  Leu Asp Asn Asn Trp  Gly Arg Glu Glu Arg  Gln Ser Val
    1190            1195            1200

Phe Pro  Phe Glu Ser Gly Lys  Pro Phe Lys Ile Gln  Val Leu Val
    1205            1210            1215

Glu Pro  Asp His Phe Lys Val  Ala Val Asn Asp Ala  His Leu Leu
    1220            1225            1230

Gln Tyr  Asn His Arg Val Lys  Lys Leu Asn Glu Ile  Ser Lys Leu
    1235            1240            1245

Gly Ile  Ser Gly Asp Ile Asp  Leu Thr Ser Ala Ser  Tyr Thr Met
    1250            1255            1260

Ile His  His His His His His
    1265            1270
```

-continued

```
<210> SEQ ID NO 17
<211> LENGTH: 35
<212> TYPE: PRT
<213> ORGANISM: Artificial Sequence
<220> FEATURE:
<223> OTHER INFORMATION: Synthetic polypeptide

<400> SEQUENCE: 17

Met Ala Arg Met Lys Gln Leu Glu Asp Lys Val Glu Glu Leu Leu Ser
1               5                   10                  15

Lys Asn Tyr His Leu Glu Asn Arg Val Ala Arg Leu Glu Lys Leu Val
            20                  25                  30

Gly Glu Arg
        35

<210> SEQ ID NO 18
<211> LENGTH: 34
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 18

Xaa Arg Met Lys Gln Leu Glu Asp Lys Val Glu Glu Leu Leu Ser Lys
1               5                   10                  15

Asn Tyr His Leu Glu Asn Glu Val Ala Arg Leu Lys Lys Leu Val Gly
            20                  25                  30

Glu Arg

<210> SEQ ID NO 19
<211> LENGTH: 34
<212> TYPE: PRT
<213> ORGANISM: Artificial Sequence
<220> FEATURE:
<223> OTHER INFORMATION: Synthetic polypeptide

<400> SEQUENCE: 19

Met Lys Val Lys Gln Leu Val Asp Lys Val Glu Glu Leu Leu Ser Lys
1               5                   10                  15

Asn Tyr His Leu Val Asn Glu Val Ala Arg Leu Val Lys Leu Val Gly
            20                  25                  30

Glu Arg

<210> SEQ ID NO 20
<211> LENGTH: 34
<212> TYPE: PRT
<213> ORGANISM: Artificial Sequence
<220> FEATURE:
<223> OTHER INFORMATION: Synthetic polypeptide

<400> SEQUENCE: 20

Met Lys Val Lys Gln Leu Glu Asp Val Val Glu Glu Leu Leu Ser Val
1               5                   10                  15

Asn Tyr His Leu Glu Asn Val Val Ala Arg Leu Lys Lys Leu Val Gly
            20                  25                  30

Glu Arg
```

-continued

```
<210> SEQ ID NO 21
<211> LENGTH: 34
<212> TYPE: PRT
<213> ORGANISM: Artificial Sequence
<220> FEATURE:
<223> OTHER INFORMATION: Synthetic polypeptide

<400> SEQUENCE: 21

Met Lys Val Lys Gln Leu Ala Asp Lys Val Glu Glu Leu Leu Ser Lys
1               5                   10                  15

Asn Tyr His Leu Ala Asn Glu Val Ala Arg Leu Ala Lys Leu Val Gly
            20                  25                  30

Glu Arg

<210> SEQ ID NO 22
<211> LENGTH: 34
<212> TYPE: PRT
<213> ORGANISM: Artificial Sequence
<220> FEATURE:
<223> OTHER INFORMATION: Synthetic polypeptide

<400> SEQUENCE: 22

Met Lys Val Lys Gln Leu Glu Asp Ala Val Glu Glu Leu Leu Ser Ala
1               5                   10                  15

Asn Tyr His Leu Glu Asn Ala Val Ala Arg Leu Lys Lys Leu Val Gly
            20                  25                  30

Glu Arg

<210> SEQ ID NO 23
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 23

Xaa Gly Glu Ile Ala Gln Ala Leu Lys Glu Ile Ala Lys Ala Leu Lys
1               5                   10                  15

Glu Ile Ala Trp Ala Leu Lys Glu Ile Ala Gln Ala Leu Lys Gly
            20                  25                  30

<210> SEQ ID NO 24
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 24

Xaa Gly Glu Ile Ala Lys Ala Leu Arg Glu Ile Ala Lys Ala Leu Arg
1               5                   10                  15

Glu Xaa Ala Trp Ala His Arg Glu Glu Ala Lys Ala Leu Arg Gly
            20                  25                  30
```

-continued

```
<210> SEQ ID NO 25
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 25

Xaa Gly Glu Ile Ala Lys Ala Leu Arg Glu Ile Ala Lys Ala Leu Arg
1               5                   10                  15

Glu Cys Ala Trp Ala His Arg Glu Glu Ala Lys Ala Leu Arg Gly
            20                  25                  30

<210> SEQ ID NO 26
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 26

Xaa Gly Glu Ile Ala Lys Ala Leu Arg Glu Ile Ala Lys Ala Leu Arg
1               5                   10                  15

Glu Cys Ala Trp Ala His Arg Glu Glu Ala Lys Ala Leu Arg Gly
            20                  25                  30

<210> SEQ ID NO 27
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 27

Xaa Gly Glu Ile Ala Lys Ala Leu Arg Glu Ile Ala Lys Ala Leu Arg
1               5                   10                  15

Glu Cys Ala Trp Ala His Arg Glu Ile Ala Lys Ala Leu Arg Gly
            20                  25                  30

<210> SEQ ID NO 28
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 28

Xaa Gly Glu Ile Ala Lys Ala Leu Arg Glu Ile Ala Lys Ala Leu Arg
1               5                   10                  15

Glu Ile Ala Trp Ala His Arg Glu Ile Ala Lys Ala Leu Arg Gly
            20                  25                  30
```

<210> SEQ ID NO 29
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 29

Xaa Gly Glu Ile Ala Gln Ala Leu Lys Glu Ile Ala Lys Ala Leu Lys
1               5                   10                  15

Glu Ile Ala Trp Ala Cys Lys Glu Ile Ala Gln Ala Leu Lys Gly
            20                  25                  30

<210> SEQ ID NO 30
<211> LENGTH: 34
<212> TYPE: PRT
<213> ORGANISM: Artificial Sequence
<220> FEATURE:
<223> OTHER INFORMATION: Synthetic polypeptide

<400> SEQUENCE: 30

Met Lys Val Lys Gln Leu Ala Asp Ala Val Glu Glu Leu Ala Ser Ala
1               5                   10                  15

Asn Tyr His Leu Ala Asn Ala Val Ala Arg Leu Ala Lys Ala Val Gly
            20                  25                  30

Glu Arg

<210> SEQ ID NO 31
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 31

Gly Ser Gly Gly Gly Ser Gly Gly Ser Gly Gly Ser Gly Gly
1               5                   10

<210> SEQ ID NO 32
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 32

Gly Gly Gly Ser Gly Gly Ser Gly Gly Gly Gly Ser Gly Gly Ser Gly
1               5                   10                  15

<210> SEQ ID NO 33
<211> LENGTH: 249
<212> TYPE: PRT
<213> ORGANISM: Artificial Sequence
<220> FEATURE:
<223> OTHER INFORMATION: Synthetic Polypeptide

<400> SEQUENCE: 33

Ala Asp Asn Phe Ser Leu His Asp Ala Leu Ser Gly Ser Gly Asn Pro
1               5                   10                  15

Asn Pro Gln Gly Trp Pro Gly Ala Trp Gly Asn Gln Pro Ala Gly Ala

-continued

```
            20              25              30
Gly Gly Tyr Pro Gly Ala Ser Tyr Pro Gly Ala Tyr Pro Gly Gln Ala
        35              40              45

Pro Pro Gly Ala Tyr Pro Gly Gln Ala Pro Pro Gly Ala Tyr Pro Gly
    50              55              60

Ala Pro Gly Ala Tyr Pro Gly Ala Pro Ala Pro Gly Val Tyr Pro Gly
65              70              75              80

Pro Pro Ser Gly Pro Gly Ala Tyr Pro Ser Ser Gly Gln Pro Ser Ala
            85              90              95

Pro Gly Ala Tyr Pro Ala Thr Gly Pro Tyr Gly Ala Pro Ala Gly Pro
            100             105             110

Leu Ile Val Pro Tyr Asn Leu Pro Leu Pro Gly Gly Val Val Pro Arg
            115             120             125

Met Leu Ile Thr Ile Leu Gly Thr Val Lys Pro Asn Ala Asn Arg Ile
        130             135             140

Ala Leu Asp Phe Gln Arg Gly Asn Asp Val Ala Phe His Phe Asn Pro
145             150             155             160

Arg Phe Asn Glu Asn Asn Arg Arg Val Ile Val Cys Asn Thr Lys Leu
            165             170             175

Asp Asn Asn Trp Gly Arg Glu Glu Arg Gln Ser Val Phe Pro Phe Glu
            180             185             190

Ser Gly Lys Pro Phe Lys Ile Gln Val Leu Val Glu Pro Asp His Phe
            195             200             205

Lys Val Ala Val Asn Asp Ala His Leu Leu Gln Tyr Asn His Arg Val
        210             215             220

Lys Lys Leu Asn Glu Ile Ser Lys Leu Gly Ile Ser Gly Asp Ile Asp
225             230             235             240

Leu Thr Ser Ala Ser Tyr Asn Met Ile
            245

<210> SEQ ID NO 34
<211> LENGTH: 144
<212> TYPE: PRT
<213> ORGANISM: Artificial Sequence
<220> FEATURE:
<223> OTHER INFORMATION: Synthetic Polypeptide

<400> SEQUENCE: 34

Tyr Gly Ala Pro Ala Gly Pro Leu Ile Val Pro Tyr Asn Leu Pro Leu
1               5               10              15

Pro Gly Gly Val Val Pro Arg Met Leu Ile Thr Ile Leu Gly Thr Val
            20              25              30

Lys Pro Asn Ala Asn Arg Ile Ala Leu Asp Phe Gln Arg Gly Asn Asp
        35              40              45

Val Ala Phe His Phe Asn Pro Arg Phe Asn Glu Asn Asn Arg Arg Val
    50              55              60

Ile Val Cys Asn Thr Lys Leu Asp Asn Asn Trp Gly Arg Glu Glu Arg
65              70              75              80

Gln Ser Val Phe Pro Phe Glu Ser Gly Lys Pro Phe Lys Ile Gln Val
            85              90              95
```

-continued

```
Leu Val Glu Pro Asp His Phe Lys Val Ala Val Asn Asp Ala His Leu
            100                 105                 110

Leu Gln Tyr Asn His Arg Val Lys Lys Leu Asn Glu Ile Ser Lys Leu
        115                 120                 125

Gly Ile Ser Gly Asp Ile Asp Leu Thr Ser Ala Ser Tyr Asn Met Ile
    130                 135                 140
```